(12) United States Patent
Wang et al.

(10) Patent No.: US 10,899,738 B2
(45) Date of Patent: Jan. 26, 2021

(54) PIPERIDINES AS MENIN INHIBITORS

(71) Applicant: THE REGENTS OF THE UNIVERSITY OF MICHIGAN, Ann Arbor, MI (US)

(72) Inventors: Shaomeng Wang, Superior Township, MI (US); Angelo Aguilar, Ann Arbor, MI (US); Ke Zheng, Ann Arbor, MI (US); Shilin Xu, Ann Arbor, MI (US); Tianfeng Xu, Ypsilanti, MI (US); Denzil Bernard, Ann Arbor, MI (US); Liyue Huang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/098,147

(22) PCT Filed: May 2, 2017

(86) PCT No.: PCT/US2017/030577
§ 371 (c)(1),
(2) Date: Nov. 1, 2018

(87) PCT Pub. No.: WO2017/192543
PCT Pub. Date: Nov. 9, 2017

(65) Prior Publication Data
US 2019/0152947 A1 May 23, 2019

Related U.S. Application Data

(60) Provisional application No. 62/330,350, filed on May 2, 2016.

(51) Int. Cl.
| C07D 401/14 | (2006.01) |
| C07D 401/04 | (2006.01) |
| C07D 405/04 | (2006.01) |
| C07D 211/34 | (2006.01) |
| A61P 35/00  | (2006.01) |

(52) U.S. Cl.
CPC ............ *C07D 401/14* (2013.01); *A61P 35/00* (2018.01); *C07D 211/34* (2013.01); *C07D 401/04* (2013.01); *C07D 405/04* (2013.01)

(58) Field of Classification Search
CPC .................................................. C07D 401/14
See application file for complete search history.

(56) References Cited

U.S. PATENT DOCUMENTS

| 9,212,180 B2 | 12/2015 | Grembecka et al. |
| 9,216,993 B2 | 12/2015 | Grembecka et al. |
| 2009/0298772 A1 | 12/2009 | Thirman |
| 2011/0065690 A1 | 3/2011 | Grembecka et al. |
| 2014/0248240 A1 | 9/2014 | Bair et al. |
| 2014/0275070 A1 | 9/2014 | Grembecka et al. |
| 2014/0371239 A1 | 12/2014 | Grembecka et al. |
| 2016/0045504 A1 | 2/2016 | Grembecka et al. |
| 2016/0046647 A1 | 2/2016 | Grembecka et al. |
| 2020/0022953 A1 | 1/2020 | Wang et al. |

FOREIGN PATENT DOCUMENTS

| WO | WO-98/54167 A1 | 12/1998 |
| WO | WO-2006/136606 A2 | 12/2006 |
| WO | WO-2011/060321 A1 | 5/2011 |
| WO | WO-2014/200479 A1 | 12/2014 |
| WO | 2016/040330 A1 | 3/2016 |
| WO | 2016/195776 A1 | 12/2016 |
| WO | 2016/197027 A1 | 12/2016 |
| WO | 2017/112768 A1 | 6/2017 |
| WO | 2017/161002 A1 | 9/2017 |
| WO | 2017/161028 A1 | 9/2017 |
| WO | 2017/192543 A1 | 11/2017 |
| WO | 2017/214367 A1 | 12/2017 |
| WO | 2018/053267 | 3/2018 |

(Continued)

OTHER PUBLICATIONS

Simone, Oncology: Introduction, Cecil Textbook of Medicine, 20th Edition, 1996 vol. 1, pp. 1004-1010.*
Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e4195.*
Sanz-Garcia, "Current and advancing treatments for metastatic colorectal cancer" Expert Opinion on Biological Therapy, 16:1, 2016 , 93-110.*
Garson "Models of ovarian cancer—Are we there yet?" Molecular and Cellular Endocrinology 239 (2005) 15-26.*

(Continued)

*Primary Examiner* — David K O'Dell
(74) *Attorney, Agent, or Firm* — Marshall, Gerstein & Borun LLP

(57) ABSTRACT

The present disclosure provides compounds by Formula (I): (Formula (I)) and the pharmaceutically acceptable salts, hydrates, and solvates thereof, wherein $R^2$, $R^{3a}$, $R^{3b}$, A, G, X, and Y are as defined as set forth in the specification. The present disclosure also provides compounds of Formula (I) for use to treat a condition or disorder responsive to menin inhibition such as cancer.

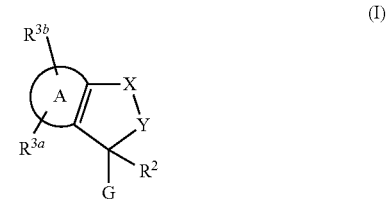

(I)

29 Claims, 5 Drawing Sheets

(56) References Cited

FOREIGN PATENT DOCUMENTS

Figure 1:
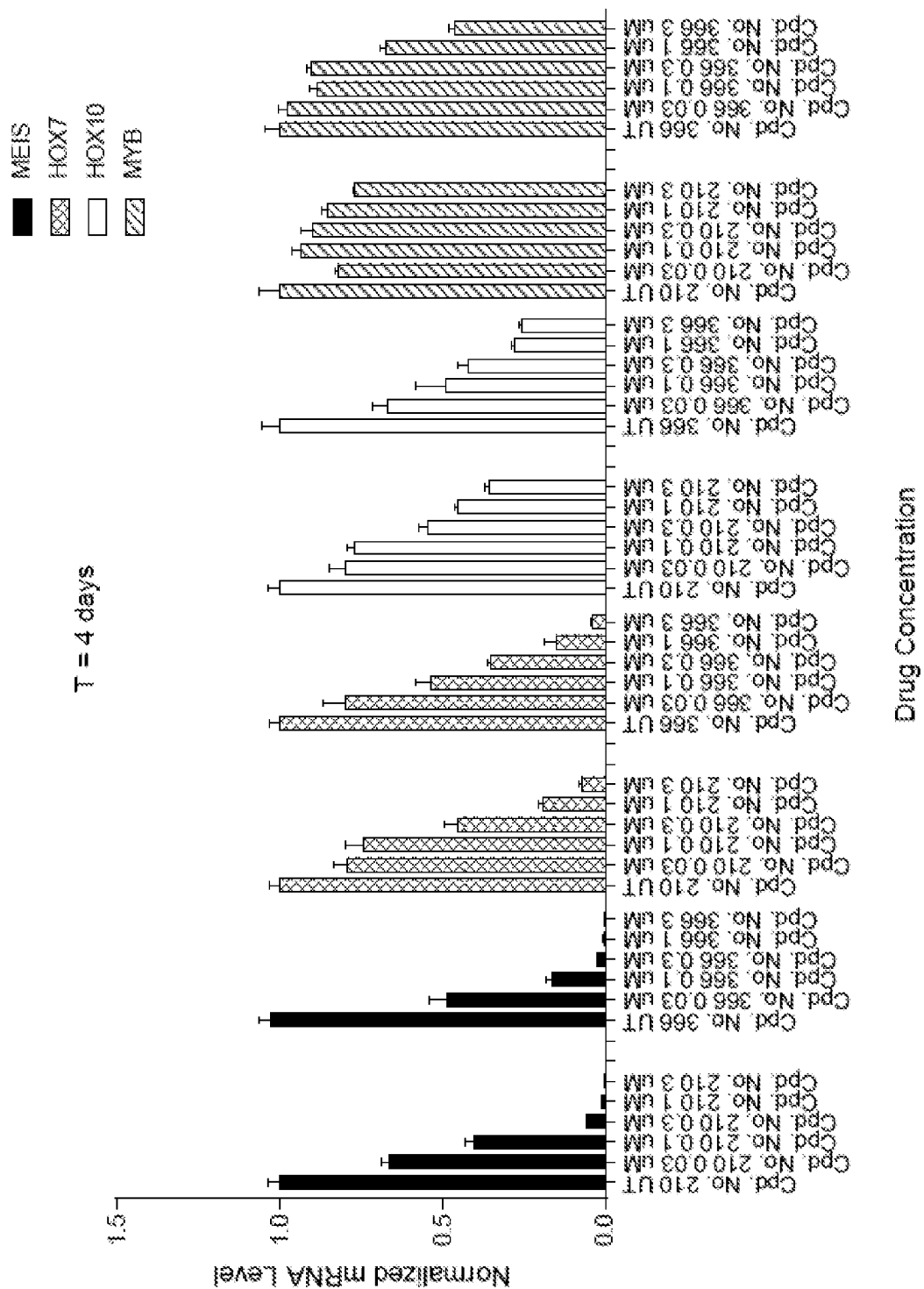

| WO | 2018/106818 A1 | 6/2018 |
| WO | 2018/175746 A1 | 9/2018 |
| WO | 2018/226976 A1 | 12/2018 |
| WO | 2019/060365 A1 | 3/2019 |
| WO | 2019/189732 A1 | 10/2019 |
| WO | 2020/069027 A1 | 4/2020 |

OTHER PUBLICATIONS

Sale "Models of ovarian cancer metastasis: Murine models" Drug Discovery Today: Disease Models 2006, 3, 150-154.*
Schober "New Advances in the Treatment of Metastatic Pancreatic Cancer" Digestion 2015;92:175-184.*
Boniface "Multidisciplinary management for esophageal and gastric cancer" Cancer Management and Research 2016:8 39-44.*
Gerratana "Do platinum salts fit all triple negative breast cancers?" Cancer Treatment Reviews 48 (2016) 34-41.*
Yoo "New drugs in prostate cancer" Prostate Int 4 (2016) 37-42.*
Vardiman "The World Health Organization (WHO) classification of the myeloid neoplasms" Blood (2002), 100(7), 2292-2302.*
Pui "Treatment of Acute Lymphoblastic Leukemia" New England Journal of Medicine 2006, 354, 166-78.*
Krishnan "Multiple myeloma and persistence of drug resistance in the age of novel drugs (Review)" International Journal of Oncology 49: 33-50, 2016.*
Stewart "Novel therapeutics in multiple myeloma" Hematology 2012, 17(51), s105-s108.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
He "High-Affinity Small-Molecule Inhibitors of the Menin-Mixed Lineage Leukemia (MLL) Interaction Closely Mimic a Natural Protein—Protein Interaction"| J. Med. Chem. 2014, 57, 1543-1556.*
Georg Pilz, "Modern multiple sclerosis treatment—what is approved, what is on the horizon" Drug Discovery Today Dec. 2008 , vol. 13, Nos. 23/24 1013-1025.*
A.M. Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*
Argollo "Novel therapeutic targets for inflammatory bowel disease" Journal of Autoimmunity (2017), 85, 103-116.*
Poli-de-Figueiredo "Experimental Models of Sepsis and Their Clinical Relevance" Shock, vol. 30, Supplement 1, pp. 53-59, 2008.*
Gentile "HMGB1 as a therapeutic target for sepsis: it's all in the timing!" Expert Opinion on Therapeutic Targets, 2014, 18:3, 243-245.*
Marshall "Why have clinical trials in sepsis failed?" Trends in Molecular Medicine, Apr. 2014, vol. 20, No. 4 195-203.*
Muller and Kräusslich in "Antiviral Strategies" Handbook of Experimental Pharmacology vol. 189 Chapter 1, pp. 1-24.*
Burm, B., et al.,"Synthesis of New Bridged Tetrahydro-β-Carbolines and Spiro-Fused Quinuclidines," *Tetrahedron*, vol. 57, No. 10 (2001), pp. 2039-2049.
Kita, Y., et al., "Enhancing Effects of Salt Formation on Catalytic Activity and Enantioselectivity for Asymmetric Hydrogenation of Isoquinolinium Salts by Dinuclear Halide-Bridged Iridium Complexes Bearing Chiral Diphosphine Ligands," *Chemistry—A European Journal*, vol. 21, No. 5 (2015), pp. 1915-1927.
Pitta, B.R., et al., "Metalated Nitrile and Enolate Chlorinations," *Organic Letters*, vol. 12, No. 12 (2010), pp. 2810-2813.
Prat, L., et al.,"Synthesis of N-Methyl-4-Pyridyl-1, 2, 3, 4-Tetrahydroisoquinolines Via a Pictet-Spengler Cyclisation," *Journal of Heterocyclic Chemistry*, vol. 37, No. 4 (2000), pp. 767-771.
Senter, T., et al.,"Progress Towards Small Molecule Menin-Mixed Lineage Leukemia (MLL) Interaction Inhibitors With in Vivo Utility," *Bioorganic & Medicinal Chemistry Letters*, vol. 25, No. 13 (2015), pp. 2720-2725.
Xu, Y., et al.,"Discovery of Novel Inhibitors Targeting the Menin-Mixed Lineage Leukemia Interface Using Pharmacophore-and Docking-Based Virtual Screening," *Journal of Chemical Information and Modeling*, vol. 56, No. 9 (2016), pp. 1847-1855.
He, S., et al., "High-Affinity Small-Molecule Inhibitors of the Menin-Mixed Lineage Leukemia (MLL) Interaction Closely Mimic a Natural Protein-Protein Interaction," Journal of Medicinal Chemistry, vol. 57, No. 4 (2014), pp. 1543-1556.
International Search Report for Patent Application No. PCT/US2017/030577, dated Jun. 30, 2017.
Aguilar, et al: Structure-Based Discovery of M-89 as a Highly Potent Inhibitor of the Menin-Mixed Lineage Leukemia (Menin-MLL) Protein-Protein Interaction; J. Med. Chem. 2019, 62, 6015-6034.
Borkin et al., Pharmacologic inhibition of the Menin-MLL interaction blocks progression of MLL leukemia in vivo, Cancer Cell, 27(4):589-602 (Apr. 2015).
Brzezinka, et al: Functional diversity of inhibitors tackling the differentiation blockage of MLLrearranged leukemia; Journal of Hematology & Oncology, 2019, 12:66, 1-14.
Cierpicki et al., Challenges and opportunities in targeting the menin-MLL interaction, Future Med. Chem., 6(4):447-62 (Mar. 2014).
International Application No. PCT/US2018/025417, International Preliminary Report on Patentability, dated Oct. 10, 2019.
International Application No. PCT/US2018/025417, International Search Report and Written Opinion, dated Jun. 20, 2018.
Klossowski, et al: Menin inhibitor MI-3454 induces remission in MLL 1-rearranged and NPM1-mutated models of leukemia; J Clin Invest. 2020;130(2):981-997.
Krivtsov, et al: A Menin-MLL Inhibitor Induces Specific Chromatin Changes and Eradicates Disease in Models of MLLRearranged Leukemia; 2019, Cancer Cell 36, 660-673.
Kühn, et al: Targeting Chromatin Regulators Inhibits Leukemogenic Gene Expression in NPM1 Mutant Leukemia, Cancer Discovery Oct. 2016, 1166-1181.
Kurmasheva, et al: Evaluation of VTP-50469, a menin-MLL1 inhibitor, against Ewing sarcoma xenograft models by the pediatric preclinical testing consortium; Pediatr Blood Cancer. 2020;e28284; 1-4.
Lambert, et al: Direct and Indirect Targeting of HOXA9 Transcription Factor in Acute Myeloid Leukemia, Cancers 2019, 11,837; 1-38.
Secker et al., Cancers 2020, MAT2AasKeyRegulatorandTherapeuticTargetin MLLr Leukemogenesis, 12, 1342, 39 pages.
Uckelmann, et al: Therapeutic targeting of preleukemia cells in a mouse model of NPMI mutant acute myeloid leukemia; Science 367, 2020, 586-590.
Xu, et al: Design of the First-in-Class, Highly Potent Irreversible Inhibitor Targeting the Menin-MLL Protein-Protein Interaction; Angew. Chem. Int. Ed. 2018, 57, 1601-1605.
Xu, et al: Discovery of M-808 as a Highly Potent, Covalent, Small-Molecule Inhibitor of the Menin-MLL Interaction with Strong In Vivo Antitumor Activity; J. Med. Chem. 2020, 63, 4997-5010.

* cited by examiner

PIPERIDINES AS MENIN INHIBITORS

BACKGROUND OF THE INVENTION

Field of the Invention

The present disclosure provides compounds as menin inhibitors and therapeutic methods of treating conditions and diseases wherein inhibition of menin provides a benefit.

Background Art

Mixed-lineage leukemia (MLL) is a proto-oncogene that was originally discovered at the site of chromosomal translocations in human leukemias. Due to chromosomal translocations, MLL is fused with more than 40 different partner proteins to yield a diverse collection of chimeric fusion proteins. The MLL protein is a histone methyltransferase that covalently modifies chromatin and is mutated in certain subsets of acute leukemia. Many of the fusion partners constitutively activate novel transcriptional effector properties of MLL that often correlate with its oncogenic potential in animal models of acute leukemia. MLL normally associates with a group of highly conserved cofactors to form a macromolecular complex that includes menin, a product of the MEN1 tumor suppressor gene. The MEN1 gene is mutated in heritable and sporadic endocrine tumors.

Menin is in involved in a diverse network of protein-protein interactions. Cierpicki and Grembecka, *Future Med. Chem.* 6:447-462 (2014). Overexpression of menin leads to inhibition of Ras-transformed cells. Menin interacts with the transcription factors JunD and NF-κB and represses their activation of gene transcription. Studies on these interacting proteins suggest that menin exerts its effects predominantly through inhibitory effects on transcription. But an alternative possibility is that menin mediates its effects through transcriptional activation of target genes. Additionally, menin interacts with RPA2, a component of a single-stranded DNA-binding protein involved in DNA repair and replication. Menin also interacts with FANCD2, a nuclear protein that plays a critical role in maintaining genome stability with breast cancer 1 gene (Brea1) product.

The mechanisms by which menin, which does not have significant homology with other proteins, functions as a tumor suppressor are not completely known. Menin plays a role in regulating cellular proliferation because Men1 knockout mice show increased proliferation in neuroendocrine tissues, down-modulation of menin in epithelial cells increases proliferation, and Men1 knockout fibroblasts proliferate more rapidly than wild-type cells as assayed by tritiated thymidine incorporation. MEN1 cells also have increased sensitivity to DNA-damaging agents. Menin interacts with promoters of HOX genes.

Certain oncogenic MLL fusion proteins stably associate with menin through a high-affinity interaction that is required for the initiation of MLL-mediated leukemogenesis. Menin is essential for maintenance of MLL-associated but not other oncogene induced myeloid transformation. Acute genetic ablation of menin reverses Hox gene expression mediated by MLL-menin promoter-associated complexes, and specifically eliminates the differentiation arrest and oncogenic properties of MLL-transformed leukemic blasts.

MLL fusion proteins, a consequence of acquired genetic aberrations, transform hematopoietic cells through two alternate mechanisms, by either constitutive transcriptional effector activity or inducing forced MLL dimerization and oligomerization. Both mechanisms result in the inappropriate expression of a subset of HOX genes, particularly HOXA9, whose consistent expression is a characteristic feature of human MLL leukemias.

Menin interacts with transcription activators, e.g., sc-Myb, MLL1, SMAD 1,3,5, Pem, Runx2, Hlbx9,ER, PPARγ, vitamin D receptor, transcription repressors, e.g., JunD, Sin3A, HDAC, EZH2, PRMT5, NFκB, Sirt1, CHES1, cell signaling proteins, e.g., AKT, SOS1/GEF, β-catenin, SMAD 1,3,5, NFκB,ER, PPARγ, vitamin D receptor, and other proteins, e.g., cell cycle: RPA2, ASK; DNA repair: FANCD2; cell structure: GFAP, vimenten, NMMHCIIA, IQGAP1; Others: HSP70, CHIP, ("menin-interacting proteins") involved in regulating gene transcription and cell signaling. Matkar, *Trends in Biochemical Sciences* 38: 394-402 (2013). Targeting menin interactions, e.g., menin-MLL interaction, with small molecules represents an attractive strategy to develop new anticancer agents. See, e.g., Cierpicki and Grembecka, *Future Med. Chem.* 6:447-462 (2014); He et al., *J. Med. Chem.* 57:1543-1556 (2014); and Borkin et al., *Cancer Cell* 27:589-602 (2015).

Small molecules that disrupt the interaction of MLL and menin are disclosed in U.S. Pat. Nos. 9,212,180 and 9,216,993; and U.S. Patent Application Publication Nos. 2011/0065690; 2014/0275070; 2016/0045504; and 2016/0046647. Peptides that disrupt the interaction of MLL and menin are disclosed in U.S. Patent Application Publication No. 2009/0298772.

There is an ongoing need for new agents, e.g., small molecules, for treating cancer and other diseases responsive to menin inhibition.

BRIEF SUMMARY OF THE INVENTION

In one aspect, the present disclosure provides piperidines, and related analogs, represented by any one or more of Formulae I-VI, VIi, VIII, VIII-A, VIII-B, VIII-C, VIII-D, VIII-E, VIII-F, VIII-G, VIII-H, IX, IX-A, IX-B, IX-C, IX-D, IX-E, IX-F, IX-G, IX-H, X, X-A, X-B, X-C, X-D, X-E, X-F, X-G, X-H, Xi, Xi-A, Xi-B, Xi-C, Xi-D, Xi-E, Xi-F, Xi-G, or Xi-H below, and the pharmaceutically acceptable salts, hydrates, and solvates thereof, collectively referred to herein as "Compounds of the Disclosure." Compounds of the Disclosure are inhibitors of menin and/or synthetic intermediates that can be used to prepare inhibitors of menin. Compounds of the Disclosure are useful in treating diseases or conditions wherein inhibition of menin provides a therapeutic benefit to a patient.

In another aspect, the present disclosure provides methods of treating a condition or disease by administering a therapeutically effective amount of a Compound of the Disclosure to a patient, e.g., a human, in need thereof. The disease or condition is treatable by inhibition menin, for example, a cancer, e.g., leukemia, a chronic autoimmune disorder, an inflammatory condition, a proliferative disorder, sepsis, or a viral infection. Also provided are methods of preventing the proliferation of unwanted proliferating cells, such as cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis and/or differentiation in those cells.

In another aspect, the present disclosure provides a method of inhibiting menin in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein inhibition of menin provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

It is to be understood that both the foregoing summary and the following detailed description are exemplary and explanatory only, and are not restrictive of the invention as claimed.

DETAILED DESCRIPTION OF DRAWINGS

FIG. 1 is bar graph showing the effect of Cpd. No. 210 and Cpd. No. 366 on MOLM-13 genes MEIS1, HOX7, HOX10, and MYB after 4 days of treatment.

Figure 2:
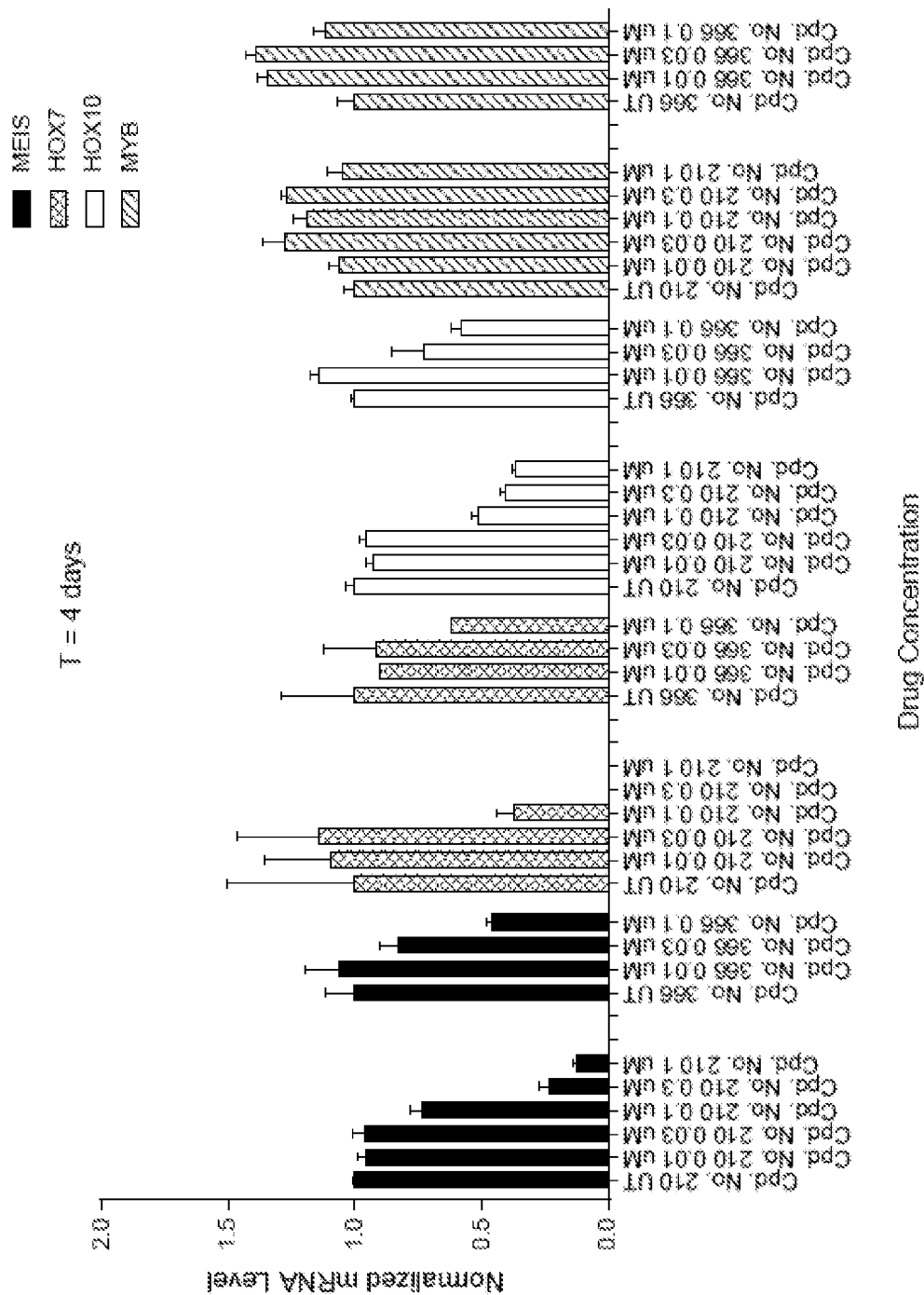

FIG. 2 is bar graph showing the effect of Cpd. No. 210 and Cpd. No. 366 on MV4-11 genes MEIS1, HOX7, HOX10, and MYB after 4 days of treatment.

Figure 3:
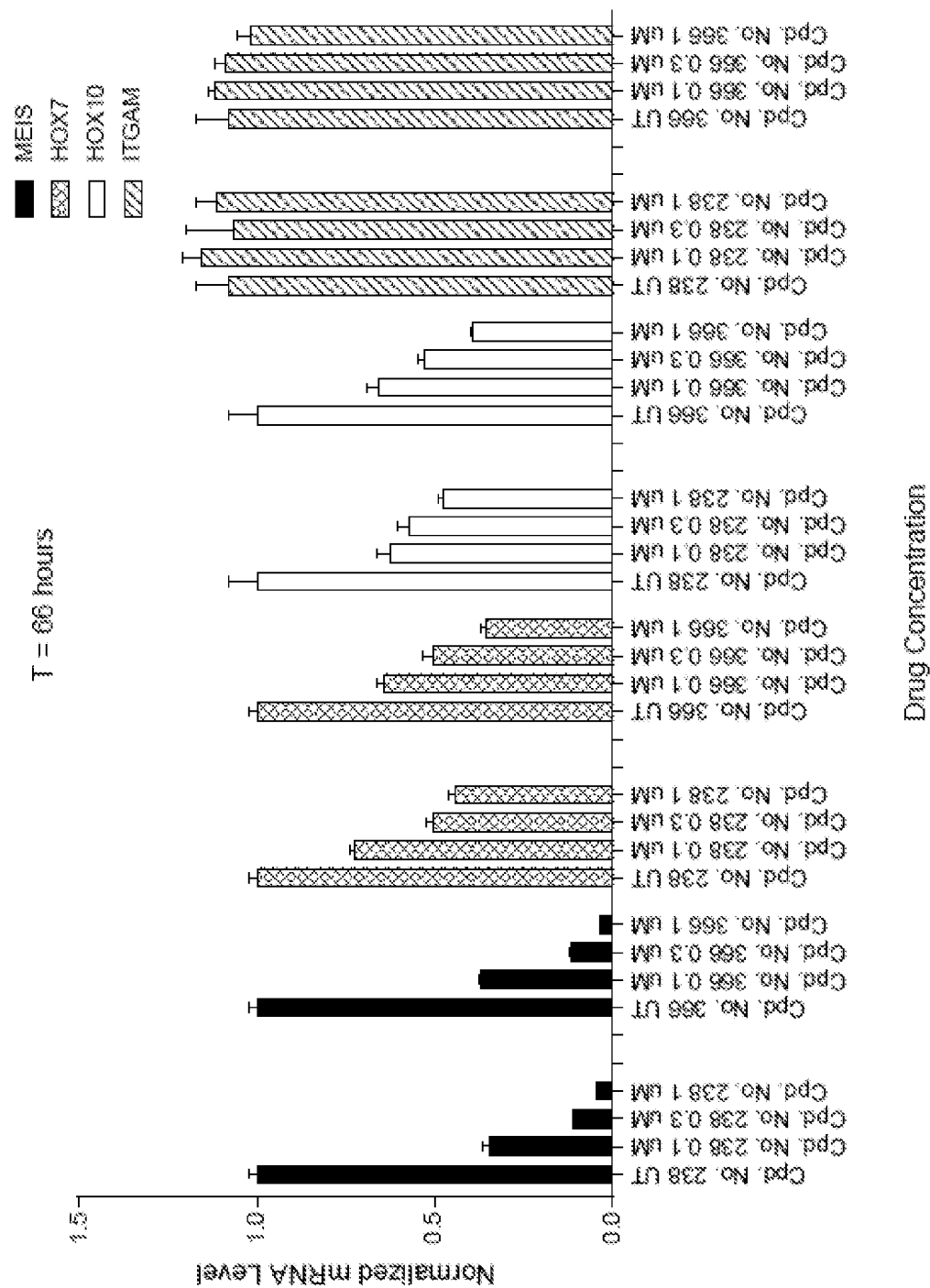

FIG. 3 is bar graph showing the effect of Cpd. No. 366 and Cpd. No. 238 on MOLM-13 genes MEIS1, HOX7, HOX10, and ITGAM after 66 hours of treatment.

Figure 4:
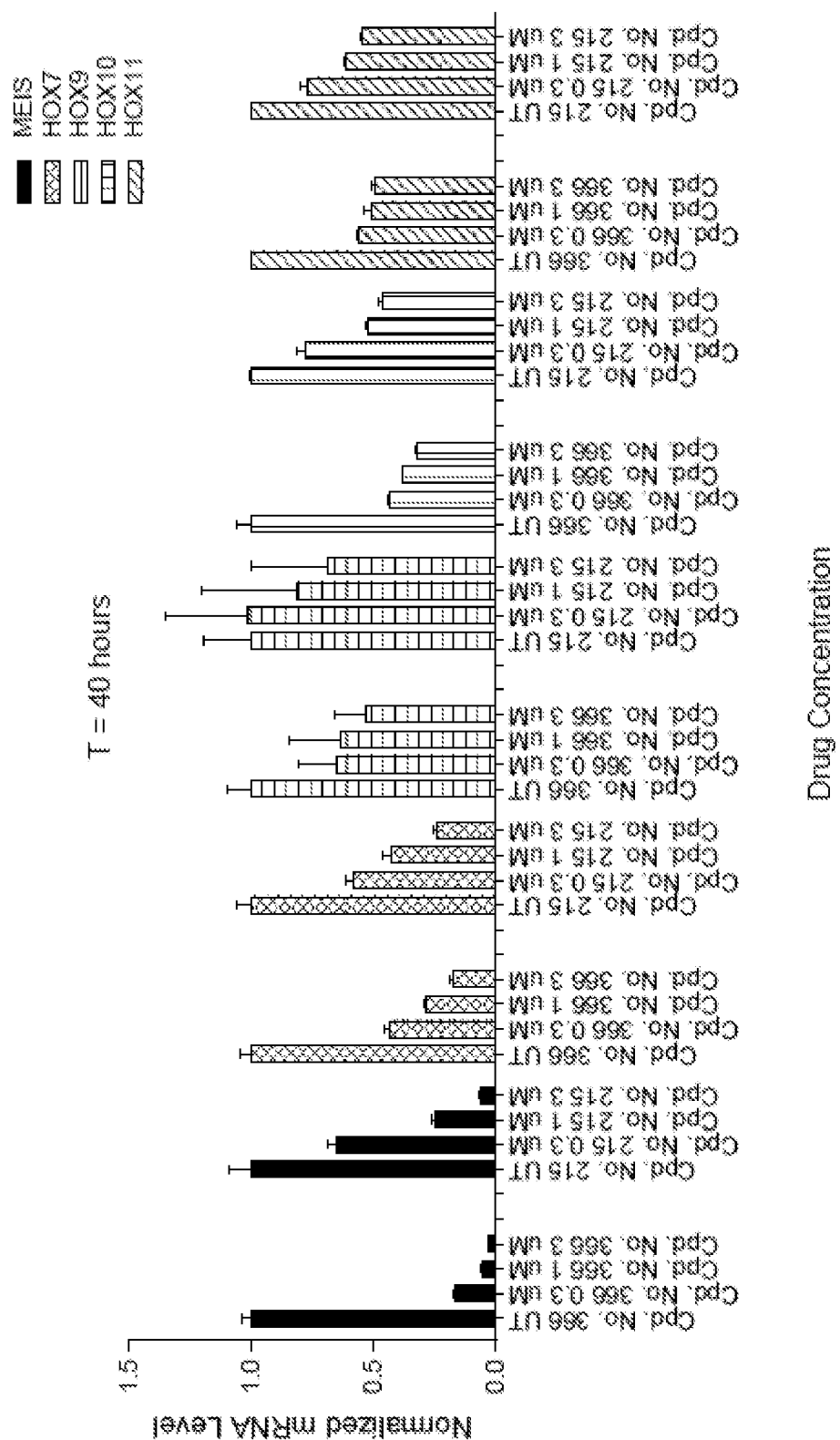

FIG. 4 is bar graph showing the effect Cpd. No. 366 and Cpd. No. 215 on MOLM-13 genes MEIS1, HOX7, HOX9, HOX10, and HOX11 after 40 hours of treatment.

Figure 5:
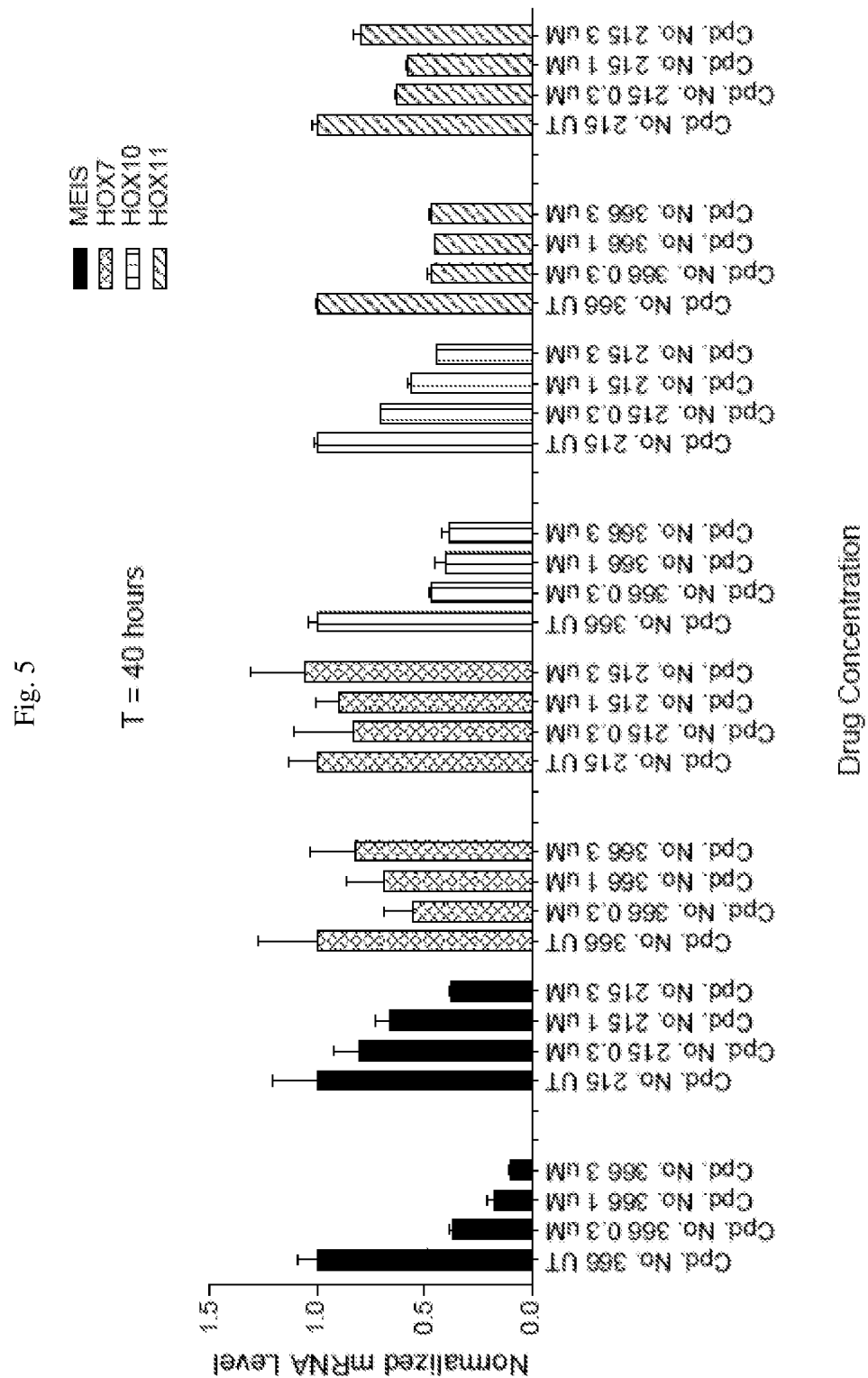

FIG. 5 is bar graph showing the effect Cpd. No. 366 and Cpd. No. 215 on MV4-11 genes MEIS1, HOX7, HOX10, and HOX11 after 40 hours of treatment.

DETAILED DESCRIPTION OF THE INVENTION

Compounds of the Disclosure are menin inhibitors and/or synthetic intermediates used to prepare menin inhibitors.

In one embodiment, Compounds of the Disclosure are compounds represented by Formula I:

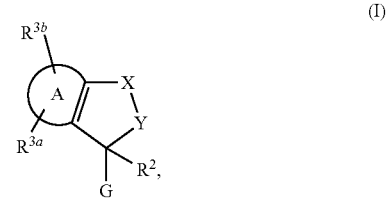

and the pharmaceutically acceptable salts, hydrates, and solvates thereof, wherein:

is a fused thienyl or fused phenyl group,

G is selected from the group consisting of:

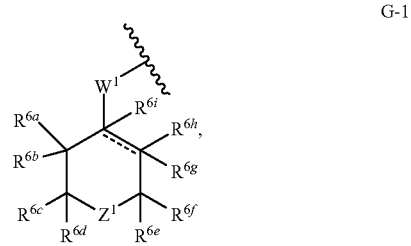

G-1

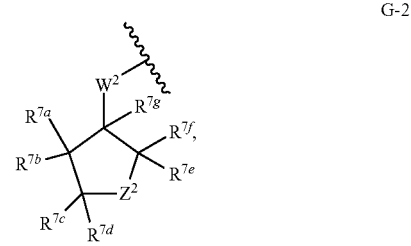

G-2

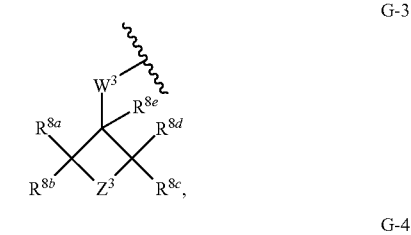

G-3

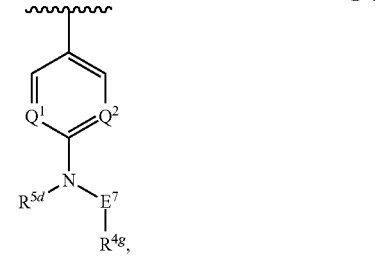

G-4

-continued

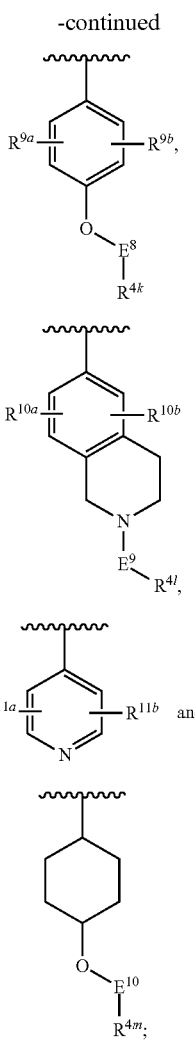

G-5

G-6

G-7

G-8

$W^1$ is absent or —$CH_2$—;

$Z^1$ is selected from the group consisting of —C(R)(-$E^1$-$R^{4a}$)—, —N(-$E^1$-$R^{4a}$)— and —C[—N(-$E^2$-$R^{4b}$)($R^{4h}$)]($R^{5a}$)—, i.e., $Z^1$ is:

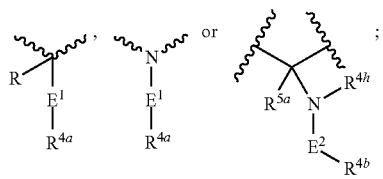

$W^2$ is absent or —$CH_2$—;

$Z^2$ is selected from the group consisting of —N(-$E^3$-$R^{4c}$)— and —C[—N(-$E^4$-$R^{4d}$)($R^{4i}$)]($R^{5b}$)—;

$W^3$ is absent or —$CH_2$—;

$Z^3$ is selected from the group consisting of —N(-$E^5$-$R^{4e}$)— and —C[—N(-$E^6$-$R^{4f}$)($R^{4j}$)]($R^{5c}$)—;

═══ is a single or double bond, with the proviso that when ═══ is a double bond, $R^{6h}$ and $R^{6i}$ are absent;

$Q^1$ and $Q^2$ are each independently CH or N;

X—Y is selected from the group consisting of:
—N($R^{1a}$)—C(═O)—;
—C(═O)—O—;
—C(═O)—N($R^{1b}$)—;
—$CH_2$N($R^{1c}$)—$CH_2$—;
—C(═O)N($R^{1d}$)—$CH_2$—;
—$CH_2CH_2$—N($R^{1e}$)—;
—$CH_2$N($R^{1f}$)—C(═O)—; and
—$CH_2$O—$CH_2$—; or X and Y do not form a chemical bond, and X is selected from the group consisting of hydrogen, alkyl, halo, hydroxy, cyano, amino, alkylamino, dialkylamino, haloalkyl, alkoxy, and haloalkoxy; and Y is selected from the group consisting of cyano, hydroxy, and —$CH_2$—$R^{12}$;

$E^1$, $E^2$, $E^3$, $E^4$, $E^5$, $E^6$, $E^7$, $E^8$, $E^9$, and $E^{10}$ are each independently selected from the group consisting of:
—C(═O)—;
—C(═O)N($R^{13}$)—;
[C($R^{14a}$)($R^{14b}$)]$_m$O—;
[C($R^{14a}$)($R^{14b}$)]$_m$N($R^{15}$)—;
[C($R^{14c}$)($R^{14d}$)]$_n$—;
—$CH_2$(═O)—; and
—S(═O)$_2$—; or $E^1$, $E^2$, $E^3$, $E^4$, $E^5$, $E^6$, $E^7$, $E^8$, $E^9$, and $E^{10}$ are each independently absent;

R is selected from the group consisting of hydrogen and alkyl;

$R^{1a}$ is selected from the group consisting of hydrogen and alkyl;

$R^{1b}$ is selected from the group consisting of hydrogen, alkyl, and aralkyl;

$R^{1c}$ is selected from the group consisting of hydrogen, alkyl, haloalkyl, optionally substituted cycloalkyl, optionally substituted heterocyclo, (cycloalkyl)alkyl, (heterocycloalkyl)alkyl, aralkyl, (heteroaryl)alkyl, alkylcarbonyl, arylcarbonyl, and alkoxycarbonyl;

$R^{1d}$ is selected from the group consisting of hydrogen, alkyl, and aralkyl;

$R^{1e}$ is selected from the group consisting of hydrogen, alkyl, and (aryloxy)alkyl;

$R^{1f}$ is selected from the group consisting of hydrogen and alkyl;

$R^2$ is selected from the group consisting of hydrogen, alkyl, alkenyl, optionally substituted cycloalkyl, optionally substituted aryl, optionally substituted heterocyclo, optionally substituted heteroaryl, and aralkyl;

$R^{3a}$ and $R^{3b}$ are each independently selected from the group consisting of hydrogen, alkyl, halo, hydroxy, cyano, amino, alkylamino, dialkylamino, haloalkyl, alkoxy, and haloalkoxy;

$R^{4a}$, $R^{4b}$, $R^{4c}$, $R^{4d}$, $R^{4e}$, $R^{4f}$, $R^{4g}$, $R^{4k}$, $R^{4l}$, and $R^{4m}$ are each independently selected from the group consisting of hydrogen, alkyl, optionally substituted alkenyl, optionally substituted alkynyl, optionally substituted cycloalkyl, optionally substituted aryl, optionally substituted heterocyclo, optionally substituted heteroaryl, aralkyl, (heterocyclo)alkyl, and (heteroaryl)alkyl;

$R^{4h}$, $R^{4i}$, and $R^{4j}$ are each independently selected from the group consisting of hydrogen and alkyl;

$R^{5a}$, $R^{5b}$, $R^{5c}$, and $R^{5d}$ are each independently selected from the group consisting of hydrogen and alkyl;

$R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen and alkyl;

$R^{6i}$ is selected from the group consisting of hydrogen, alkyl, and halo;

$R^{7a}$, $R^{7b}$, $R^{7c}$, $R^{7d}$, $R^{7e}$, and $R^{7f}$ are each independently selected from the group consisting of hydrogen and alkyl;

$R^{7g}$ is selected from the group consisting of hydrogen, alkyl, and halo;

$R^{8a}$, $R^{8b}$, $R^{8c}$, and $R^{8d}$ are each independently selected from the group consisting of hydrogen and alkyl;

$R^{8e}$ is selected from the group consisting of hydrogen, alkyl, and halo;

$R^{9a}$ and $R^{9b}$ are each independently selected from the group consisting of hydrogen, alkyl, halo, hydroxy, cyano, amino, alkylamino, dialkylamino, haloalkyl, alkoxy, and haloalkoxy;

$R^{10a}$ and $R^{10b}$ are each independently selected from the group consisting of hydrogen, alkyl, halo, hydroxy, cyano, amino, alkylamino, dialkylamino, haloalkyl, alkoxy, and haloalkoxy;

$R^{11a}$ and $R^{11b}$ are each independently selected from the group consisting of hydrogen, alkyl, halo, hydroxy, cyano, amino, alkylamino, dialkylamino, haloalkyl, alkoxy, and haloalkoxy;

$R^{12}$ is selected from the group consisting of hydroxy, amino, optionally substituted heteroaryl, optionally substituted heterocyclo, and —NHC(=O)—$R^{16}$;

m is 2, 3, 4, or 5, n is 1, 2, 3, 4, or 5

$R^{13}$ is selected from the group consisting of hydrogen and alkyl;

$R^{14a}$ and $R^{14b}$ are each independently selected from the group consisting of hydrogen and alkyl;

$R^{14c}$ and $R^{14d}$ are each independently selected from the group consisting of hydrogen and alkyl;

$R^{15}$ is selected from the group consisting of hydrogen and alkyl; and $R^{16}$ is selected from the group consisting of alkyl, optionally substituted aryl, optionally substituted heteroaryl, and optionally substituted cycloalkyl.

In another embodiment, Compounds of the Disclosure are compounds represented by Formula II:

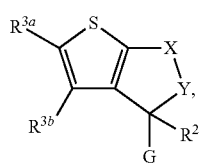

II and the pharmaceutically acceptable salts, hydrates, and solvates thereof, wherein $R^2$, $R^{3a}$, $R^{3b}$, G, X, and Y are as defined in connection with Formula I.

In another embodiment, Compounds of the Disclosure are compounds represented by Formula III:

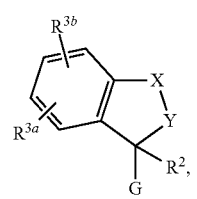

III and the pharmaceutically acceptable salts, hydrates, and solvates thereof, wherein $R^2$, $R^{3a}$, $R^{3b}$, G, X, and Y are as defined in connection with Formula I.

In another embodiment, Compounds of the Disclosure are compounds represented by any one of Formulae I-III, and the pharmaceutically acceptable salts, hydrates, and solvates thereof, wherein G is G-1. In another embodiment, $W^1$ is absent. In another embodiment, ═ is a single bond and $R^{6a}$, $R^{6b}$, $R^{6c}$, $R^{6d}$, $R^{6e}$, $R^{6f}$, $R^{6g}$, $R^{6h}$, and $R^{6i}$ are each independently selected from the group consisting of hydrogen and $C_{1-3}$ alkyl. In another embodiment, $W^1$ is absent, ═ is a single bond, and $R^{6a}$, $R^{6b}$, $R^{6c}$, $R^{6d}$, $R^{6e}$, $R^{6f}$, $R^{6g}$, $R^{6h}$, and $R^{6i}$ are each independently selected from the group consisting of hydrogen and $C_{1-3}$ alkyl. In another embodiment, $R^{6a}$, $R^{6b}$, $R^{6c}$, $R^{6d}$, $R^{6e}$, $R^{6f}$, $R^{6g}$, $R^{6h}$, and $R^{6i}$ are each hydrogen.

In another embodiment, $E^1$ is —C(═O)—. In another embodiment, $E^1$ is —C(═O)N($R^{13}$)—. In another embodiment, $E^1$ is —[C($R^{14a}$)($R^{14b}$)]$_m$O—. In another embodiment, $E^1$ is —[C($R^{14a}$)($R^{14b}$)]$_m$N($R^{15}$)—. In another embodiment, $E^1$ is —[C($R^{14c}$)($R^{14d}$)]$_n$—. In another embodiment, $E^1$ is —[C($R^{14c}$)($R^{14d}$)]$_n$— and n is 1 or 2 and $R^{14c}$ and $R^{14d}$ are each hydrogen. In another embodiment, $E^1$ is —CH$_2$(═O)—. In another embodiment, $E^1$ is —S(═O)$_2$—. In another embodiment, $E^1$ is absent.

In another embodiment, Compounds of the Disclosure are compounds represented by any one of Formulae I-III, and the pharmaceutically acceptable salts, hydrates, and solvates thereof, wherein G is G-2. In another embodiment, $W^2$ is absent. In another embodiment, $R^{7a}$, $R^{7b}$, $R^{7c}$, $R^{7d}$, $R^{7e}$, $R^{7f}$, and $R^{7g}$ are each independently selected from the group consisting of hydrogen and $C_{1-3}$ alkyl. In another embodiment, $W^2$ is absent and $R^{7a}$, $R^{7b}$, $R^{7c}$, $R^{7d}$, $R^{7e}$, $R^{7f}$, and $R^{7g}$ are each independently selected from the group consisting of hydrogen and $C_{1-3}$ alkyl. In another embodiment, $R^{7a}$, $R^{7b}$, $R^{7c}$, $R^{7d}$, $R^{7e}$, $R^{7f}$, and $R^{7g}$ are each hydrogen.

In another embodiment, Compounds of the Disclosure are compounds represented by any one of Formulae I-III, and the pharmaceutically acceptable salts, hydrates, and solvates thereof, wherein G is G-3. In another embodiment, $W^3$ is absent. In another embodiment, $R^{8a}$, $R^{8b}$, $R^{8c}$, $R^{8d}$, and $R^{8e}$ are each independently selected from the group consisting of hydrogen and $C_{1-3}$ alkyl. In another embodiment, $W^3$ is absent and $R^{8a}$, $R^{8b}$, $R^{8c}$, $R^{8d}$, and $R^{8e}$ are each independently selected from the group consisting of hydrogen and $C_{1-3}$ alkyl. In another embodiment, $R^{8a}$, $R^{8b}$, $R^{8c}$, $R^{8d}$, and $R^{8e}$ are each hydrogen.

In another embodiment, Compounds of the Disclosure are compounds represented by any one of Formulae I-III, and the pharmaceutically acceptable salts, hydrates, and solvates thereof, wherein G is G-4.

In another embodiment, Compounds of the Disclosure are compounds represented by any one of Formulae I-III, and the pharmaceutically acceptable salts, hydrates, and solvates thereof, wherein G is G-5.

In another embodiment, Compounds of the Disclosure are compounds represented by any one of Formulae I-III, and the pharmaceutically acceptable salts, hydrates, and solvates thereof, wherein G is G-6.

In another embodiment, Compounds of the Disclosure are compounds represented by any one of Formulae I-III, and the pharmaceutically acceptable salts, hydrates, and solvates thereof, wherein G is G-7.

In another embodiment, Compounds of the Disclosure are compounds represented by any one of Formulae I-III, and the pharmaceutically acceptable salts, hydrates, and solvates thereof, wherein G is selected from the group consisting of:

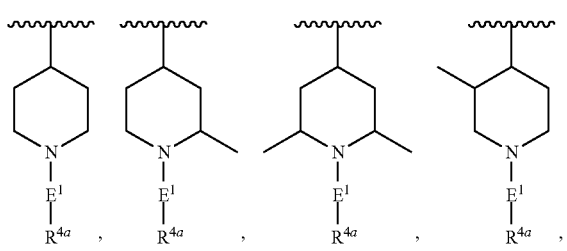

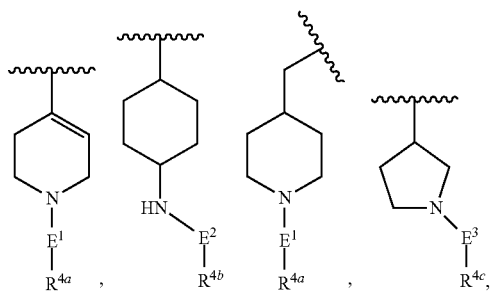

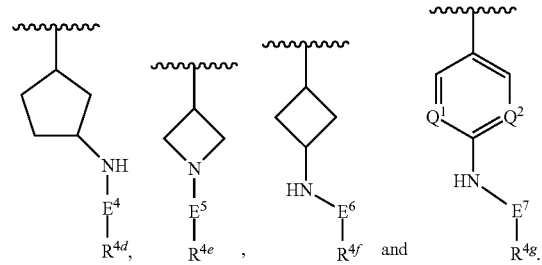

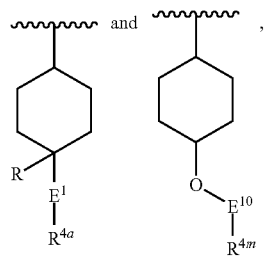

with the proviso that $Q^1$ is N and $Q^2$ is selected from the group consisting of CH and N, and $R^{4a}$, $R^{4b}$, $R^{4c}$, $R^{4d}$, $R^{4e}$, $R^{4f}$, $R^{4g}$, $E^1$, $E^2$, $E^3$, $E^4$, $E^5$, $E^6$, and $E^7$ are as defined in connection with Formula I. In another embodiment, $E^1$, $E^2$, $E^3$, $E^4$, $E^5$, $E^6$, and $E^7$ are each independently selected from the group consisting of —C(=O)—, —C(=O)N($R^{13}$)—, —[C($R^{14a}$)($R^{14b}$)]$_m$O—, —[C($R^{14a}$)($R^{14b}$)]$_m$N($R^{15}$)—, —[C($R^{14c}$)($R^{14d}$)]$_n$—, —CH$_2$(=O)—, and —S(=O)$_2$—. In another embodiment, $E^1$, $E^2$, $E^3$, $E^4$, $E^5$, $E^6$, and $E^7$ are each absent.

In another embodiment, Compounds of the Disclosure are compounds represented by any one of Formulae I-III, and the pharmaceutically acceptable salts, hydrates, and solvates thereof, wherein G is selected from the group consisting of:

R, $R^{4a}$, $R^{4m}$, $E^1$, and $E^{10}$ are as defined in connection with Formula I. In another embodiment, $E^1$ is —[C($R^{14c}$)($R^{14d}$)]$_n$—, $R^{14c}$ and $R^{14d}$ are hydrogen, and n is 1 or 2. In another embodiment, $E^{10}$ is —[C($R^{14a}$)($R^{14b}$)]$_m$O—, $R^{14c}$ and $R^{14d}$ are hydrogen, and m is 2, 3, or 4.

In another embodiment, Compounds of the Disclosure are compounds represented by any one of Formulae I-III, and the pharmaceutically acceptable salts, hydrates, and solvates thereof, wherein G is $G^1$, $G^2$, $G^3$, or $G^4$, $R^{4a}$, $R^{4b}$, $R^{4c}$, $R^{4d}$, $R^{4e}$, $R^{4f}$, and $R^{4g}$ are each independently selected from the group consisting of alkyl, optionally substituted cycloalkyl, optionally substituted aryl, optionally substituted heterocyclo, optionally substituted heteroaryl, aralkyl, and (heteroaryl)alkyl; and $R^2$, $R^{3a}$, $R^{3b}$, $E^1$, $E^2$, $E^3$, $E^4$, $E^5$, $E^6$, $E^7$, X, and Y are as defined in connection with Formula I. In another embodiment, $R^{4a}$, $R^{4b}$, $R^{4c}$, $R^{4d}$, $R^{4e}$, $R^{4f}$, and $R^{4g}$ are each alkyl. In another embodiment, $R^{4a}$, $R^{4b}$, $R^{4c}$, $R^{4d}$, $R^{4e}$, $R^{4f}$, and $R^{4g}$ are each optionally substituted cycloalkyl. In another embodiment, $R^{4a}$, $R^{4b}$, $R^{4c}$, $R^{4d}$, $R^{4e}$, $R^{4f}$, and $R^{4g}$ are each optionally substituted aryl. In another embodiment, $R^{4a}$, $R^{4b}$, $R^{4c}$, $R^{4d}$, $R^{4e}$, $R^{4f}$, and $R^{4g}$ are each optionally substituted heterocyclo. In another embodiment, $R^{4a}$, $R^{4b}$, $R^{4c}$, $R^{4d}$, $R^{4e}$, $R^{4f}$, and $R^{4g}$ are each optionally substituted heteroaryl. In another embodiment, $R^{4a}$, $R^{4b}$, $R^{4c}$, $R^{4d}$, $R^{4e}$, $R^{4f}$, and $R^{4g}$ are each aralkyl. In another embodiment, $R^{4a}$, $R^{4b}$, $R^{4c}$, $R^{4d}$, $R^{4e}$, $R^{4f}$, and $R^{4g}$ are each (heteroaryl)alkyl.

In another embodiment, Compounds of the Disclosure are compounds represented by Formula IV:

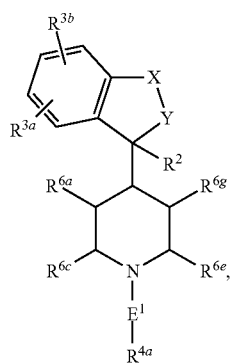

IV and the pharmaceutically acceptable salts, hydrates, and solvates thereof, wherein $R^2$, $R^{3a}$, $R^{3b}$, $R^{4a}$, $R^{6a}$, $R^{6c}$, $R^{6e}$, $R^{6g}$, $E^1$, X, and Y are as defined in connection with Formula I. In another embodiment, $E^1$ is —[C($R^{14a}$)($R^{14b}$)]$_m$O— and $R^{4a}$ is selected from the group consisting of optionally substituted aryl and optionally substituted heteroaryl.

In another embodiment, Compounds of the Disclosure are compounds represented by Formula V:

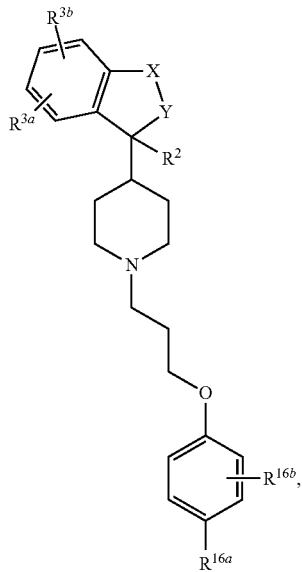

and the pharmaceutically acceptable salts, hydrates, and solvates thereof, wherein $R^{16a}$ is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl; $R^{16b}$ is selected from the group consisting of hydrogen, alkyl, halo, hydroxy, cyano, amino, alkylamino, dialkylamino, haloalkyl, alkoxy, and haloalkoxy; and $R^2$, $R^{3a}$, $R^{3b}$, X, and Y are as defined in connection with Formula I.

In another embodiment, Compounds of the Disclosure are compounds represented by Formula VIi:

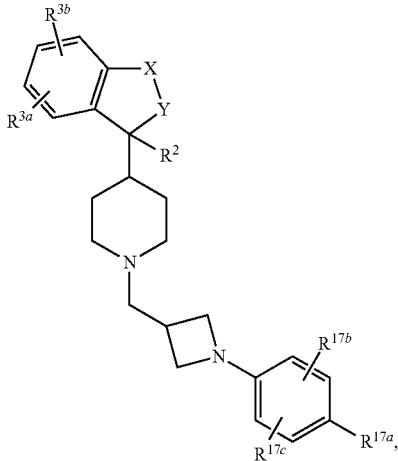

and the pharmaceutically acceptable salts, hydrates, and solvates thereof, wherein $R^{17a}$ is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl; $R^{17b}$ and $R^{17c}$ are independently selected from the group consisting of hydrogen, alkyl, halo, hydroxy, cyano, amino, alkylamino, dialkylamino, haloalkyl, alkoxy, and haloalkoxy; and $R^2$, $R^{3a}$, $R^{3b}$, X, and Y are as defined in connection with Formula I. In another embodiment, $R^{17a}$ is selected from the group consisting of alkylsulfonyl, cycloalkylsulfonyl, arylsulfonyl, and heteroarylsulfonyl; $R^{17b}$ is hydrogen; and $R^{17c}$ is hydrogen.

In another embodiment, Compounds of the Disclosure are compounds represented by any one of Formulae I-VI, and the pharmaceutically acceptable salts, hydrates, and solvates thereof, wherein $R^2$ is selected from the group consisting of alkyl, alkenyl, optionally substituted cycloalkyl, optionally substituted aryl, optionally substituted heterocyclo, optionally substituted heteroaryl, and aralkyl. In another embodiment, $R^2$ is unsubstituted cycloalkyl. In another embodiment, $R^2$ is substituted cycloalkyl.

In another embodiment, Compounds of the Disclosure are compounds represented by any one of Formulae I-VI, and the pharmaceutically acceptable salts, hydrates, and solvates thereof, wherein $R^2$ is a radical, i.e., a substituted cycloalkyl, having Formula VII:

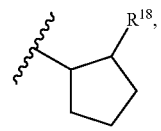

$R^{18}$ is selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N($R^{19a}$)C(=O)—$R^{19b}$, and —N($R^{20a}$)SO$_2$—$R^{20b}$; $R^{19a}$ is selected from the group consisting of hydrogen and alkyl; $R^{19b}$ is selected from the group consisting of amino, alkoxy, alkyl, and optionally substituted aryl; and $R^{20a}$ is selected from the group consisting of hydrogen and alkyl; and $R^{20b}$ is selected from the group consisting of amino, alkyl, and optionally substituted aryl. In another embodiment, $R^{18}$ is selected from the group consisting of alkylcarbonyloxy, cycloalkylcarbonyloxy, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, and (heterocyclo)alkyl. In another embodiment, $R^{18}$ is selected from the group consisting of —OC(=O)-amino and —NHC(=O)—$R^{19b}$.

In another embodiment, Compounds of the Disclosure are compounds represented by any one of Formulae I-VI, and the pharmaceutically acceptable salts, hydrates, and solvates thereof, wherein $R^2$ is selected from the group consisting of:
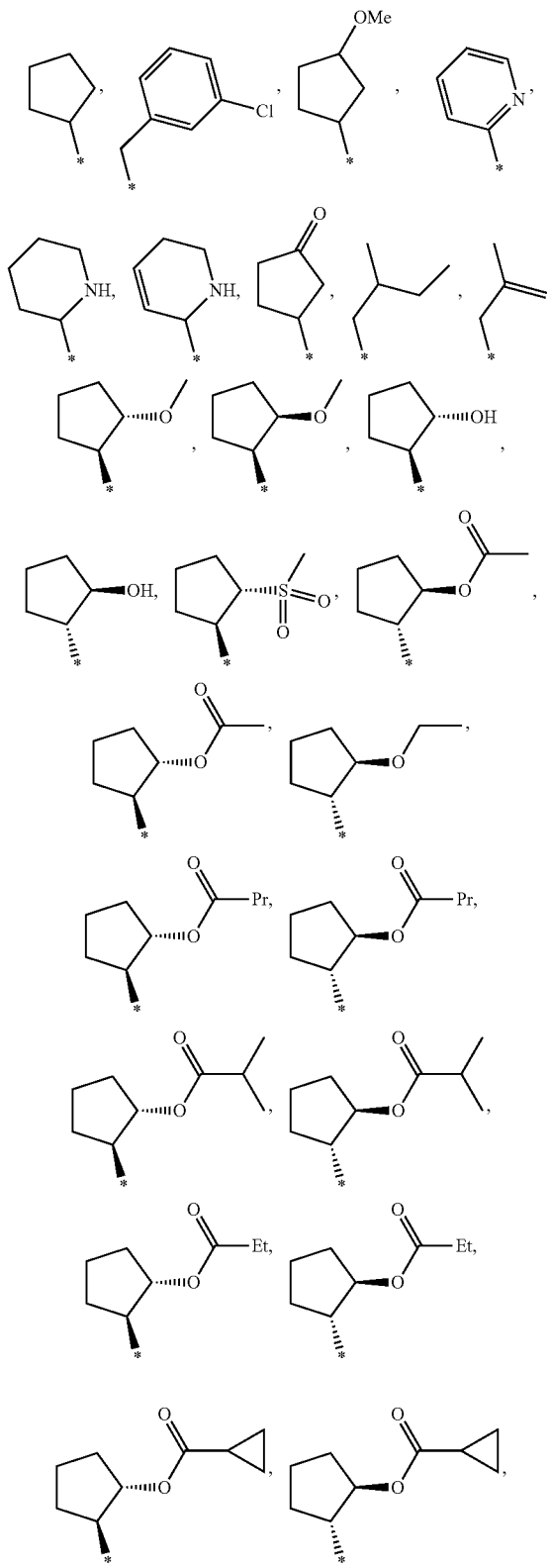
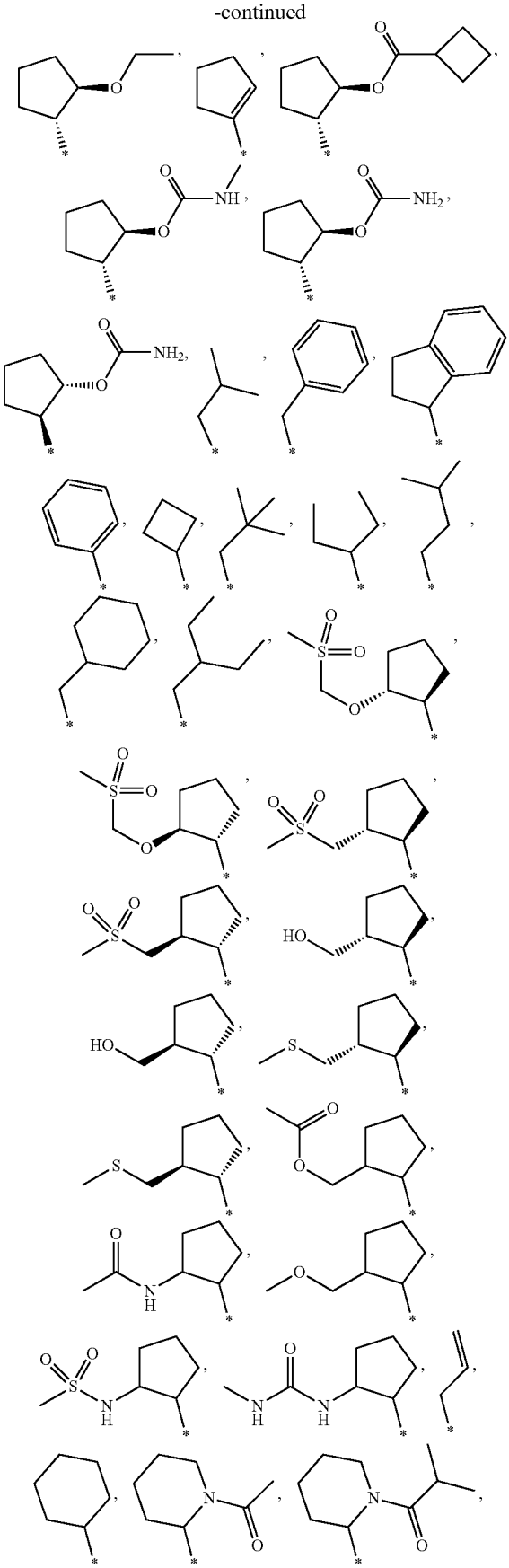

-continued

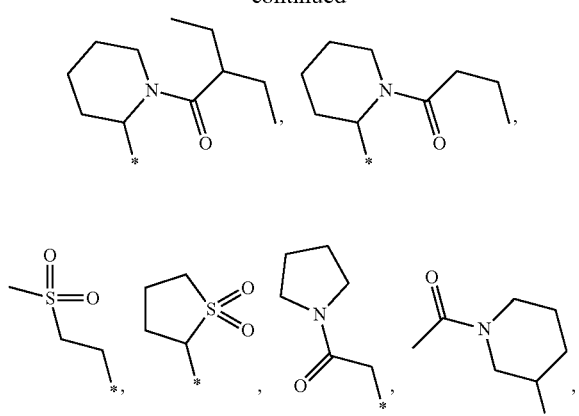

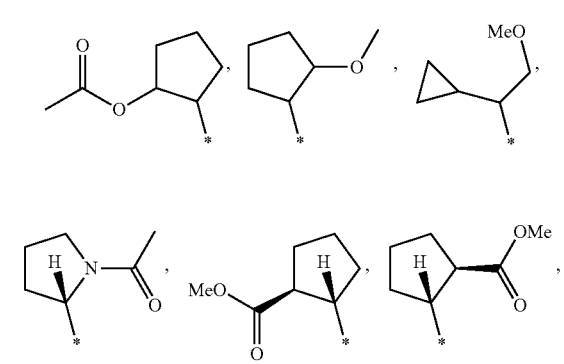

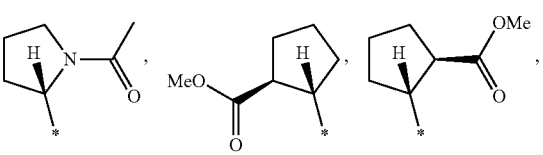

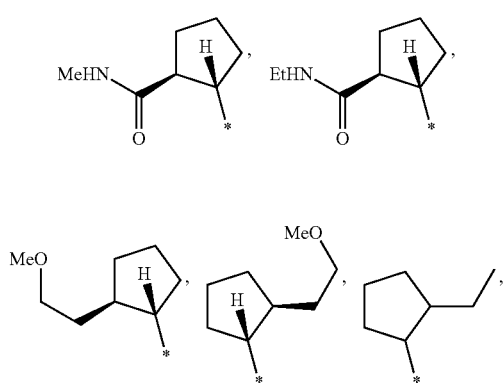

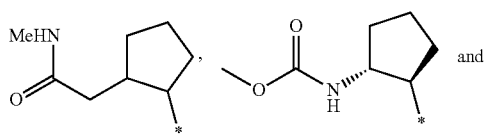

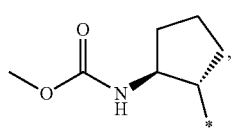

wherein "*" indicates the point of attachment to the remainder of the molecule.

In another embodiment, Compounds of the Disclosure are compounds represented by Formula VIII:

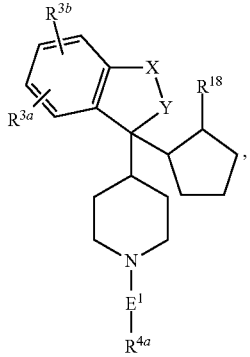

VIII and the pharmaceutically acceptable salts, hydrates, and solvates thereof, wherein $R^{3a}$, $R^{3b}$, $R^{4a}$, $R^{18}$, $E^1$, X, and Y are as defined in connection with Formula I. In another embodiment, $R^{18}$ is selected from the group consisting of —OC(=O)-amino and —NHC(=O)—$R^{19b}$, wherein $R^{19b}$ is selected from the group consisting of amino, alkoxy, and alkyl.

In another embodiment, Compounds of the Disclosure are compounds represented by any one or more of Formulae VIII-A, VIII-B, VIII-C, VIII-D, VIII-E, VIII-F, VIII-G, or VIII-H:

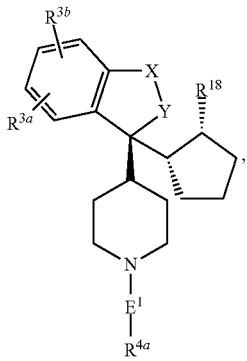

Formula VIII-A

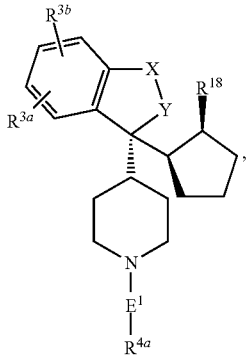

Formula VIII-B

-continued

Formula VIII-C

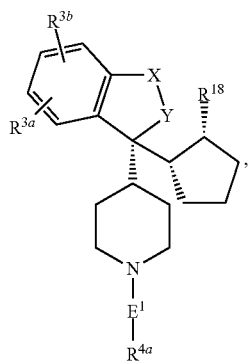

Formula VIII-D

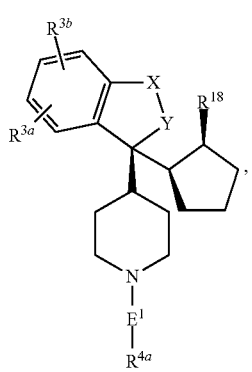

Formula VIII-E

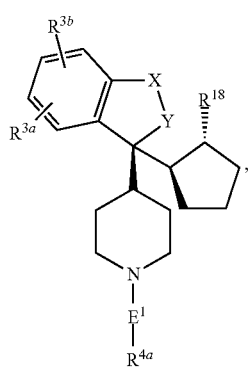

Formula VIII-F

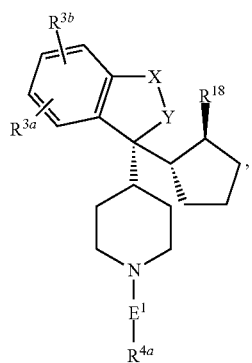

-continued

Formula VIII-G

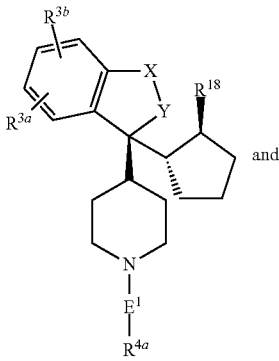

and

Formula VIII-H

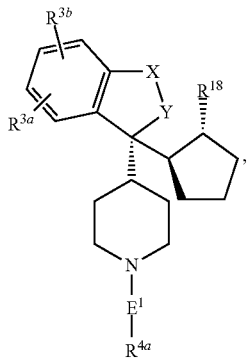

and the pharmaceutically acceptable salts, hydrates, and solvates thereof, wherein $R^{3a}$, $R^{3b}$, $R^{4a}$, $R^{18}$, $E^1$, X, and Y are as defined in connection with Formula VIII. In another embodiment, $R^{18}$ is selected from the group consisting of —OC(=O)-amino and —NHC(=O)—$R^{19b}$, wherein $R^{19b}$ is selected from the group consisting of amino, alkoxy, and alkyl.

In another embodiment, Compounds of the Disclosure are compounds represented by any one of Formulae I-VI, VIII, VIII-A, VIII-B, VIII-C, VIII-D, VIII-E, VIII-F, VIII-G, or VIII-H, and the pharmaceutically acceptable salts, hydrates, and solvates thereof, wherein X—Y is selected from the group consisting of —N($R^{1a}$)—C(=O)—, —C(=O)—O—, —C(=O)—N($R^{1b}$)—, —CH$_2$N($R^{1c}$)—CH$_2$—, —C(=O)N($R^{1d}$)—CH$_2$—, —CH$_2$CH$_2$—N($R^{1e}$)—, —CH$_2$N($R^{1f}$)—C(=O)—, and —CH$_2$O—CH$_2$—. In this embodiment, X and Y are taken together to form a chemical bond, and the radial listed to the left of the chemical bond corresponds to X, and is attached to the A-ring, and the radical listed to the right corresponds to Y and is attached to —C($R^2$)(G)-. For example, when X—Y is —N($R^{1a}$)—C(=O)—, X is —N($R^{1a}$)—, and is attached to the A-ring and Y is —C(=O)—, and is attached to —C($R^2$)(G)-; when X—Y is —C(=O)—O—, X is —C(=O)—, and is attached to the A-ring and Y is —O—, and is attached to —C($R^2$)(G)-; when X—Y is —C(=O)—N($R^{1b}$)—, X is —C(=O)—, and is attached to the A-ring and Y is —N($R^{1b}$)—, and is attached to —C($R^2$)(G)-; etc.

In another embodiment, Compounds of the Disclosure are compounds represented by any one of Formulae I-VI, VIII, VIII-A, VIII-B, VIII-C, VIII-D, VIII-E, VIII-F, VIII-G, or VIII-H, and the pharmaceutically acceptable salts, hydrates, and solvates thereof, wherein X and Y do not form a chemical bond and X is hydrogen. In another embodiment, Y is selected from the group consisting of cyano and —CH$_2$—R$^{12}$. In another embodiment, Y is cyano. In another embodiment, Y is —CH$_2$—R$^{12}$.

In another embodiment, Compounds of the Disclosure are compounds represented by Formula IX:

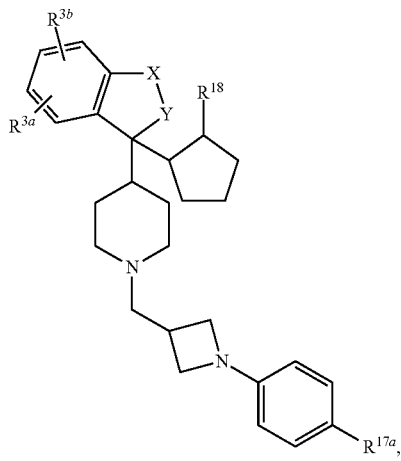

IX and the pharmaceutically acceptable salts, hydrates, and solvates thereof, wherein X—Y is —CH$_2$N(R$^{1c}$)—CH$_2$—, or X and Y do not form a chemical bond, and X is hydrogen; and Y is selected from the group consisting of —CN and —CH$_2$—R$^{12}$; R$^{1c}$ is C$_{1-3}$ alkyl; R$^{12}$ is selected from the group consisting of amino and heteroaryl; R$^{17a}$ is selected from the group consisting of chloro, cyano, alkylsulfonyl, haloalkylsulfonyl, cycloalkylsulfonyl, arylsulfonyl, and heteroarylsulfonyl; R$^{18}$ is selected from the group consisting of —OC(=O)-amino and —NHC(=O)—R$^{19b}$; and R$^{19b}$ is selected from the group consisting of amino, alkoxy, alkyl, and optionally substituted aryl, and R$^{3a}$ and R$^{3b}$ are as defined are as defined in connection with Formula I. In another embodiment, X—Y is —CH$_2$N(R$^{1c}$)—CH$_2$—; and R$^{1c}$ is selected from the group consisting of hydrogen and C$_{1-6}$ alkyl.

In another embodiment, Compounds of the Disclosure are compounds represented by one or more of Formulae IX-A, IX-B, IX-C, IX-D, IX-E, IX-F, IX-G, or IX-H:

Formula IX-A

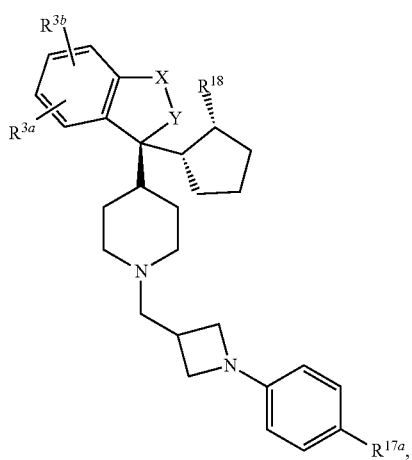

Formula IX-B

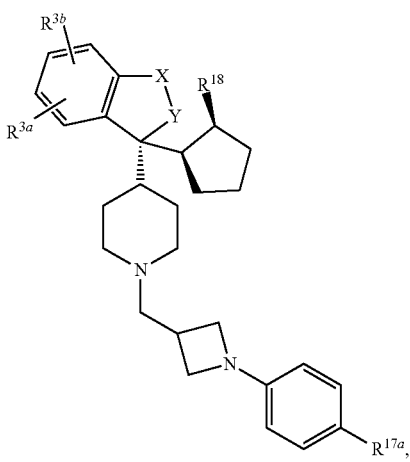

Formula IX-C

Formula IX-D

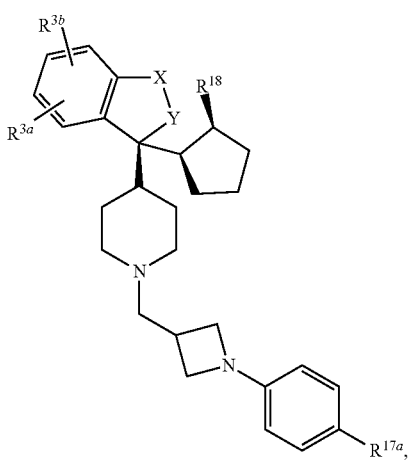

Formula IX-E

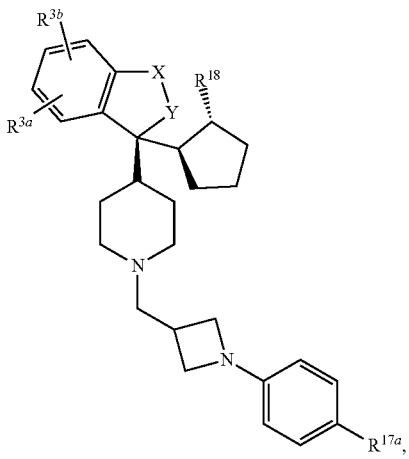

Formula IX-F

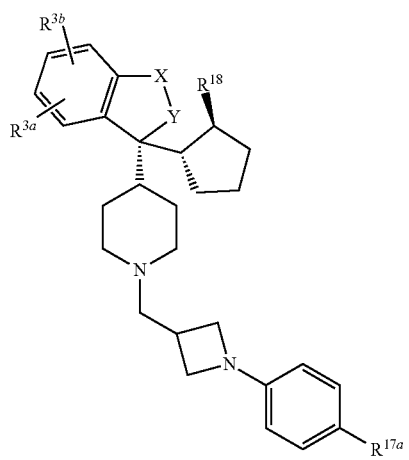

Formula IX-G

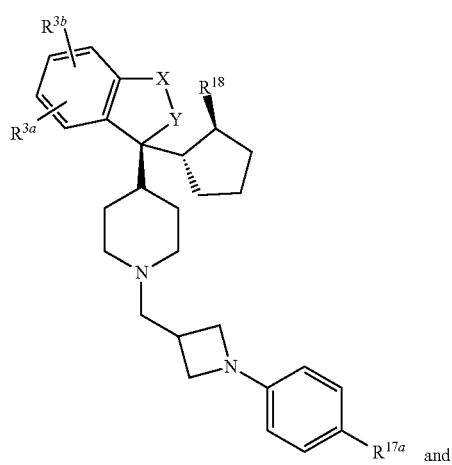
and

Formula IX-H

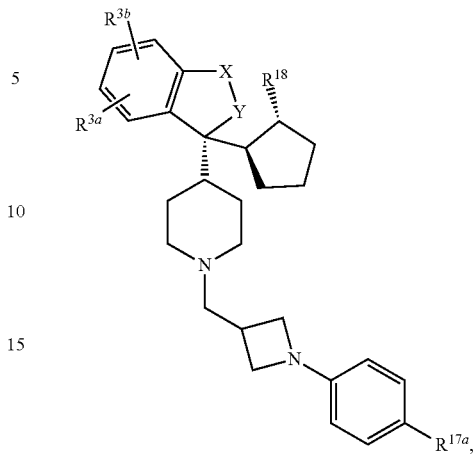

and the pharmaceutically acceptable salts, hydrates, and solvates thereof, wherein X—Y is —CH$_2$N(R$^{1c}$)—CH$_2$—, or X and Y do not form a chemical bond, and X is hydrogen and Y is selected from the group consisting of —CN and —CH$_2$—R$^{12}$; R$^{1c}$ is C$_{1-3}$ alkyl; R$^{12}$ is selected from the group consisting of amino and heteroaryl; R$^{17a}$ is selected from the group consisting of alkylsulfonyl, cycloalkylsulfonyl, arylsulfonyl, and heteroarylsulfonyl; R$^{18}$ is selected from the group consisting of —OC(=O)-amino and —NHC(=O)—R$^{19b}$; and R$^{19b}$ is selected from the group consisting of amino, alkoxy, alkyl, and optionally substituted aryl, and R$^{3a}$ and R$^{3b}$ are as defined are as defined in connection with Formula I. In another embodiment, X—Y is —CH$_2$N(R$^{1c}$)—CH$_2$—; and R$^{1c}$ is selected from the group consisting of hydrogen and C$_{1-6}$ alkyl.

In another embodiment, Compounds of the Disclosure are compounds represented by Formula Xi:

Xi

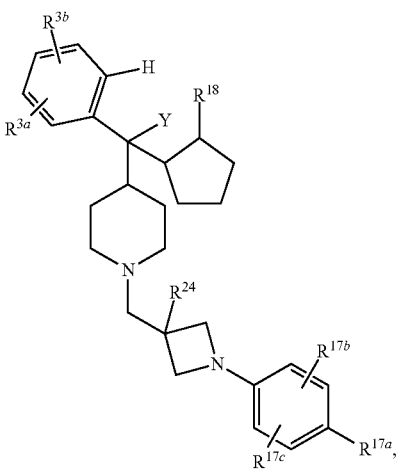

and the pharmaceutically acceptable salts, hydrates, and solvates thereof, wherein Y is selected from the group consisting of cyano and —CH$_2$—R$^{12}$; R$^{12}$ is selected from the group consisting of amino and heteroaryl; R$^{17a}$ is selected from the group consisting of chloro, cyano, alkylsulfonyl, haloalkylsulfonyl, cycloalkylsulfonyl, arylsulfonyl, and heteroarylsulfonyl; R$^{17b}$ and R$^{17c}$ are independently selected from the group consisting of hydrogen and halo; $R^{18}$ is selected from the group consisting of —OC(=O)-amino, e.g., —OC(=O)N(H)CH$_3$, and —NHC(=O)—$R^{19b}$, e.g., —NHC(=O)OCH$_3$; $R^{19b}$ is selected from the group consisting of amino, alkoxy, alkyl, and optionally substituted aryl; $R^{24}$ is selected from the group consisting of hydrogen and fluoro, and $R^{3a}$ and $R^{3b}$ are as defined are as defined in connection with Formula I. In another embodiment, $R^{12}$ is optionally substituted 5-membered heteroaryl. In another embodiment, $R^{12}$ is optionally substituted imidazol-1-yl, e.g.,

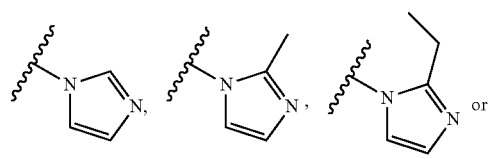

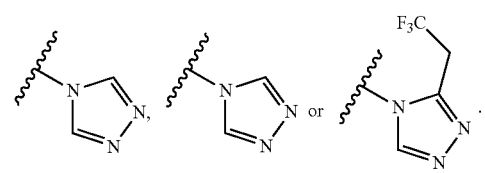 [SMILES: *n1cnnc1 ; *n1cnnc1 ; "or" ; *n1cnnc1CC(F)(F)F ; "."]

In another embodiment, $R^{12}$ is optionally substituted 1,3,4-triazole, e.g.,

In another embodiment, $R^{12}$ is optionally substituted 1,2,3-triazole, e.g.,

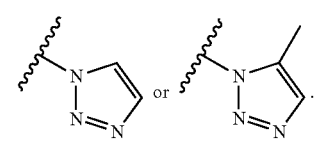

In another embodiment, Compounds of the Disclosure are compounds represented by one or more of Formulae Xi-A, Xi-B, Xi-C, Xi-D, Xi-E, Xi-F, Xi-G, or Xi-H:

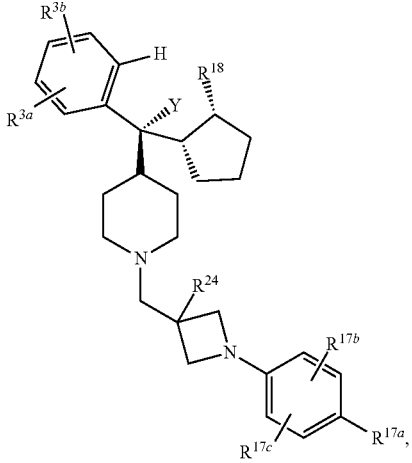

Formula Xi-A

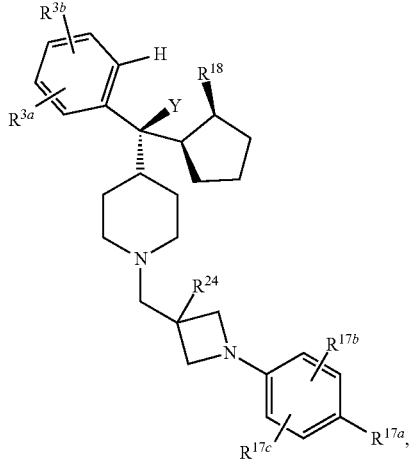

Formula Xi-B

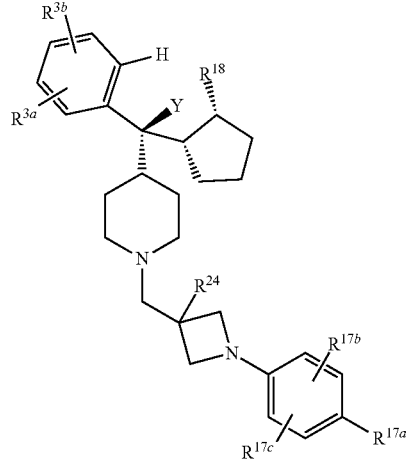

Formula Xi-C

-continued

Formula Xi-D

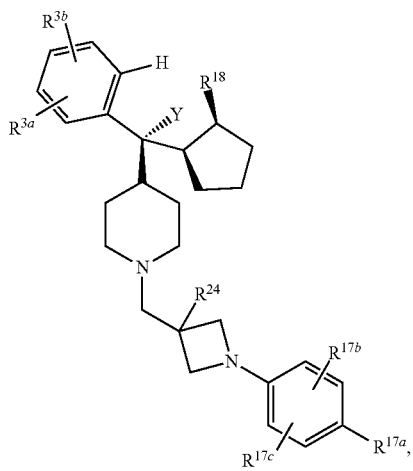

Formula Xi-E

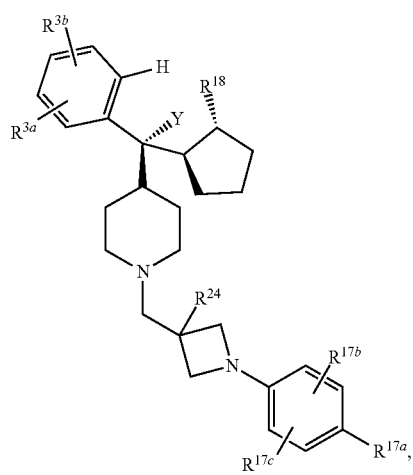

Formula Xi-F

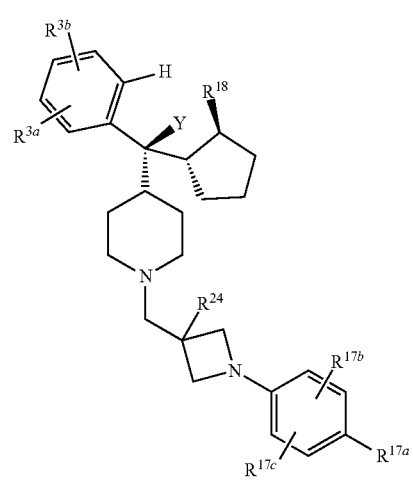

-continued

Formula Xi-G

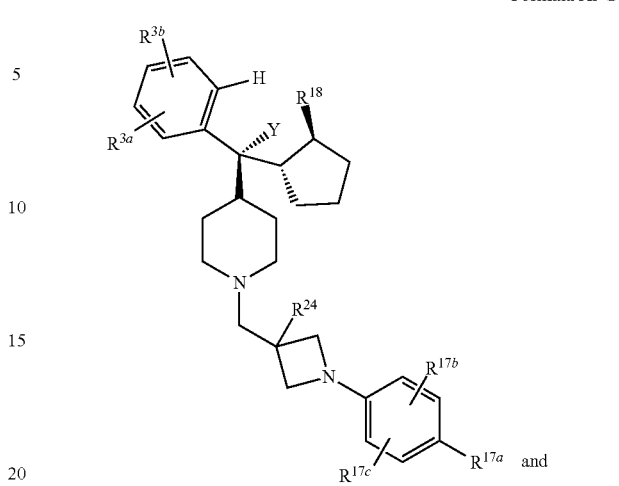

and

Formula Xi-H

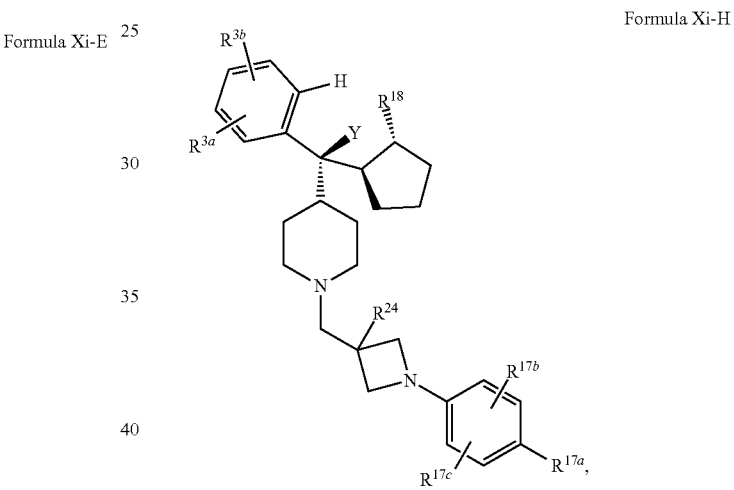

and the pharmaceutically acceptable salts, hydrates, and solvates thereof, wherein Y is selected from the group consisting of cyano and —CH$_2$—R$^{12}$; R$^{12}$ is selected from the group consisting of amino and heteroaryl; R$^{17a}$ is selected from the group consisting of chloro, cyano, alkylsulfonyl, haloalkylsulfonyl, cycloalkylsulfonyl, arylsulfonyl, and heteroarylsulfonyl; R$^{17b}$ and R$^{17c}$ are independently selected from the group consisting of hydrogen and halo; R$^{18}$ is selected from the group consisting of —OC(=O)-amino and —NHC(=O)—R$^{19b}$; R$^{19b}$ is selected from the group consisting of amino, alkoxy, alkyl, and optionally substituted aryl; R$^{24}$ is selected from the group consisting of hydrogen and fluoro, and R$^{3a}$ and R$^{3b}$ are as defined are as defined in connection with Formula I. In another embodiment, R$^{12}$ is an optionally substituted 5-membered heteroaryl. In another embodiment, R$^{12}$ is an optionally substituted imidazol-1-yl. In another embodiment, R$^{12}$ is optionally substituted 1,3,4-triazole. In another embodiment, R$^{12}$ is optionally substituted 1,2,3-triazole.

In another embodiment, Compounds of the Disclosure are one or more of the compounds of Table 1, and the pharmaceutically acceptable salts, hydrates, and solvates

TABLE 1

| Cpd. No. | Chemical Structure | Chemical Name |
|---|---|---|
| 1 | 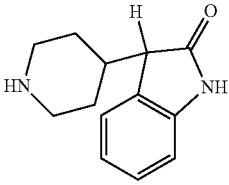 [SMILES: O=C1Nc2ccccc2C1C1CCNCC1] | 3-(piperidin-4-yl)indolin-2-one |
| 2 | 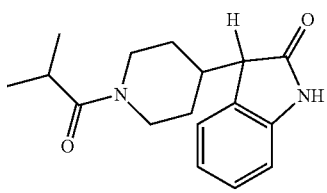 [SMILES: CC(C)C(=O)N1CCC(C2C(=O)Nc3ccccc32)CC1] | 3-(1-isobutyrylpiperidin-4-yl)indolin-2-one |
| 3 | 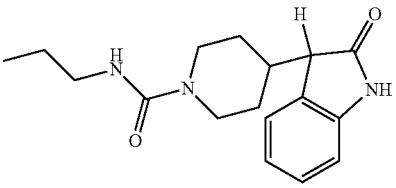 [SMILES: CCCNC(=O)N1CCC(C2C(=O)Nc3ccccc32)CC1] | 4-(2-oxoindolin-3-yl)-N-propylpiperidine-1-carboxamide |
| 4 | 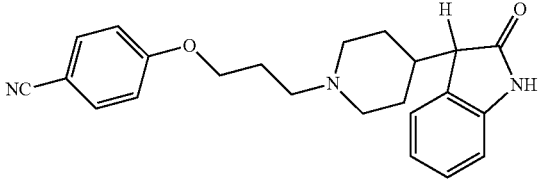 [SMILES: N#Cc1ccc(OCCCN2CCC(C3C(=O)Nc4ccccc43)CC2)cc1] | 4-(3-(4-(2-oxoindolin-3-yl)piperidin-1-yl)propoxy)benzonitrile |
| 5 | 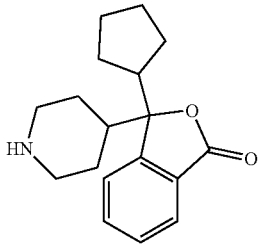 [SMILES: O=C1OC(C2CCCC2)(C2CCNCC2)c2ccccc21] | 3-cyclopentyl-3-(piperidin-4-yl)isobenzofuran-1(3H)-one |
| 6 | 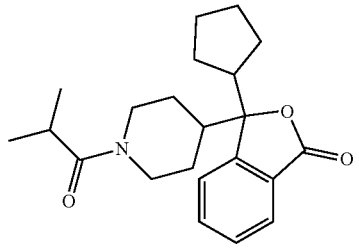 [SMILES: CC(C)C(=O)N1CCC(C2(C3CCCC3)OC(=O)c3ccccc32)CC1] | 3-cyclopentyl-3-(1-isobutyrylpiperidin-4-yl)isobenzofuran-1(3H)-one |
| 7 | 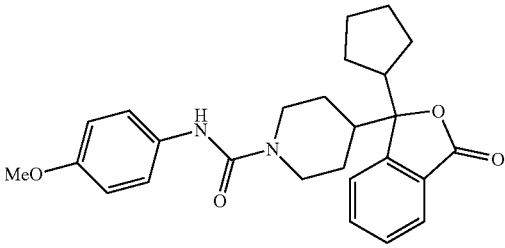 [SMILES: COc1ccc(NC(=O)N2CCC(C3(C4CCCC4)OC(=O)c4ccccc43)CC2)cc1] | 4-(1-cyclopentyl-3-oxo-1,3-dihydroisobenzofuran-1-yl)-N-(4-methoxyphenyl)piperidine-1-carboxamide |

TABLE 1-continued

| Cpd. No. | Chemical Structure | Chemical Name |
|---|---|---|
| 8 | 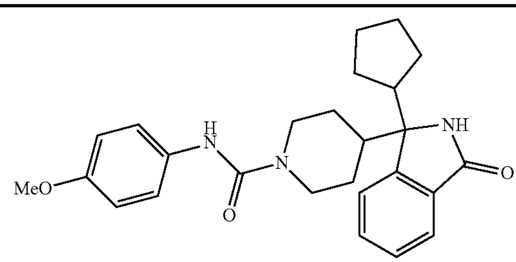 | 4-(1-cyclopentyl-3-oxoisoindolin-1-yl)-N-(4-methoxyphenyl)piperidine-1-carboxamide |
| 9 | 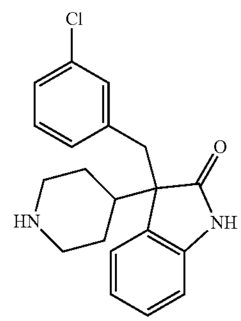 [SMILES: O=C1Nc2ccccc2C1(Cc1cccc(Cl)c1)C1CCNCC1] | 3-(3-chlorobenzyl)-3-(piperidin-4-yl)indolin-2-one |
| 10 | 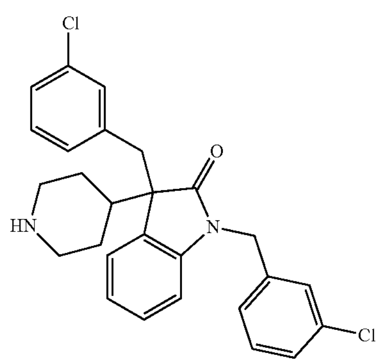 [SMILES: O=C1N(Cc2cccc(Cl)c2)c2ccccc2C1(Cc1cccc(Cl)c1)C1CCNCC1] | 1,3-bis(3-chlorobenzyl)-3-(piperidin-4-yl)indolin-2-one |
| 11 | 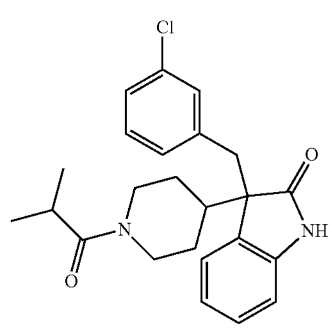 [SMILES: CC(C)C(=O)N1CCC(C2(Cc3cccc(Cl)c3)C(=O)Nc3ccccc32)CC1] | 3-(3-chlorobenzyl)-3-(1-isobutyrylpiperidin-4-yl)indolin-2-one |
| 12 | 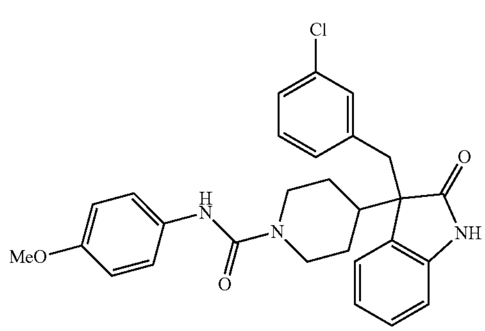 [SMILES: COc1ccc(NC(=O)N2CCC(C3(Cc4cccc(Cl)c4)C(=O)Nc4ccccc43)CC2)cc1] | 4-(3-(3-chlorobenzyl)-2-oxoindolin-3-yl)-N-(4-methoxyphenyl)piperidine-1-carboxamide |

TABLE 1-continued

| Cpd. No. | Chemical Structure | Chemical Name |
|---|---|---|
| 13 | 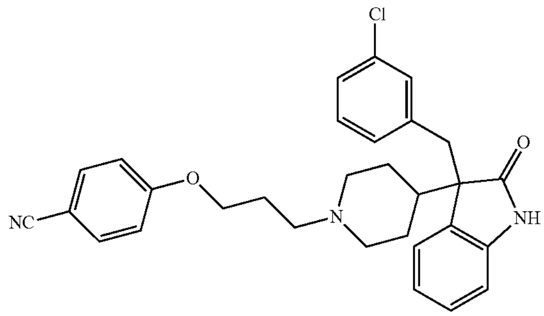 [SMILES: N#Cc1ccc(OCCCN2CCC(C3(Cc4cccc(Cl)c4)C(=O)Nc4ccccc43)CC2)cc1] | 4-(3-(4-(3-(3-chlorobenzyl)-2-oxoindolin-3-yl)piperidin-1-yl)propoxy)benzonitrile |
| 14 | 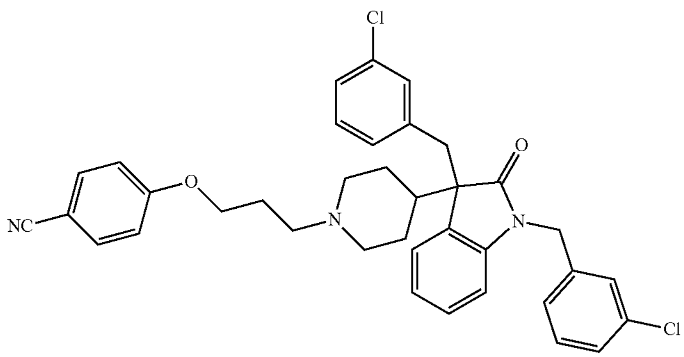 [SMILES: N#Cc1ccc(OCCCN2CCC(C3(Cc4cccc(Cl)c4)C(=O)N(Cc4cccc(Cl)c4)c4ccccc43)CC2)cc1] | 4-(3-(4-(1,3-bis(3-chlorobenzyl)-2-oxoindolin-3-yl)piperidin-1-yl)propoxy)benzonitrile |
| 15 | 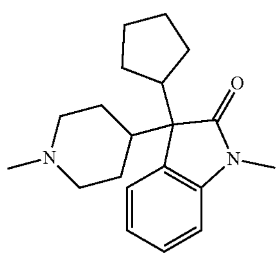 | 3-cyclopentyl-1-methyl-3-(1-methylpiperidin-4-yl)indolin-2-one |
| 16 | 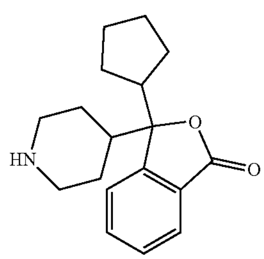 [SMILES: O=C1OC(C2CCCC2)(C2CCNCC2)c2ccccc21] | 3-cyclopentyl-3-(piperidin-4-yl)isobenzofuran-1(3H)-one |
| 17 | 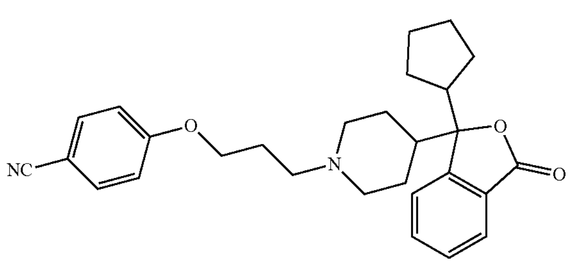 [SMILES: N#Cc1ccc(OCCCN2CCC(C3(C4CCCC4)OC(=O)c4ccccc43)CC2)cc1] | 4-(3-(4-(1-cyclopentyl-3-oxo-1,3-dihydroisobenzofuran-1-yl)piperidin-1-yl)propoxy)benzonitrile |

TABLE 1-continued

| Cpd. No. | Chemical Structure | Chemical Name |
|---|---|---|
| 18 | 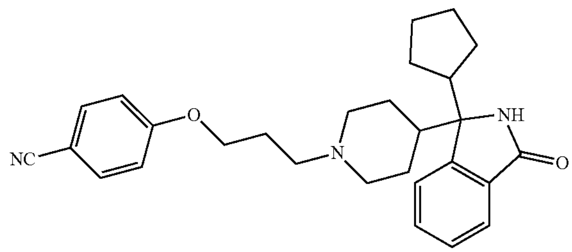 [SMILES: N#Cc1ccc(OCCCN2CCC(C3(C4CCCC4)NC(=O)c4ccccc43)CC2)cc1] | 4-(3-(4-(1-cyclopentyl-3-oxoisoindolin-1-yl)piperidin-1-yl)propoxy)benzonitrile |
| 19 | 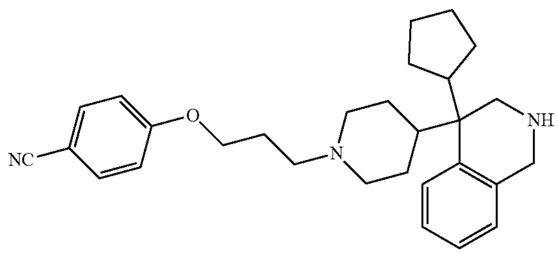 [SMILES: N#Cc1ccc(OCCCN2CCC(C3(C4CCCC4)CNCc4ccccc43)CC2)cc1] | 4-(3-(4-(4-cyclopentyl-1,2,3,4-tetrahydroisoquinolin-4-yl)piperidin-1-yl)propoxy)benzonitrile |
| 20 | 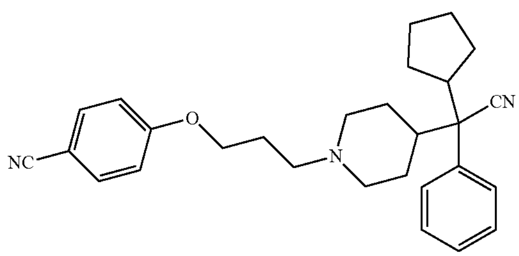 [SMILES: N#Cc1ccc(OCCCN2CCC(C(C#N)(c3ccccc3)C3CCCC3)CC2)cc1] | 4-(3-(4-(cyano(cyclopentyl)(phenyl)methyl)piperidin-1-yl)propoxy)benzonitrile |
| 21 | 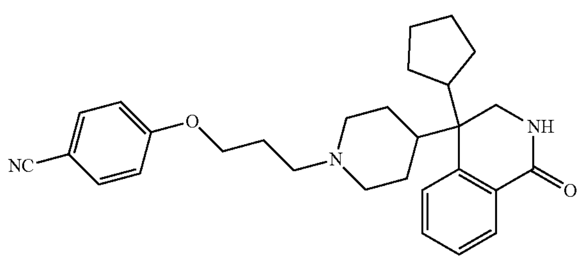 [SMILES: N#Cc1ccc(OCCCN2CCC(C3(C4CCCC4)CNC(=O)c4ccccc43)CC2)cc1] | 4-(3-(4-(4-cyclopentyl-1-oxo-1,2,3,4-tetrahydroisoquinolin-4-yl)piperidin-1-yl)propoxy)benzonitrile |
| 22 | 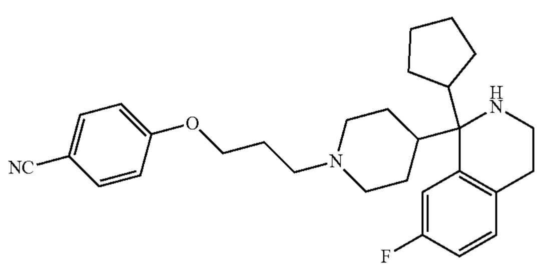 [SMILES: N#Cc1ccc(OCCCN2CCC(C3(C4CCCC4)NCCc4ccc(F)cc43)CC2)cc1] | 4-(3-(4-(1-cyclopentyl-7-fluoro-1,2,3,4-tetrahydroisoquinolin-1-yl)piperidin-1-yl)propoxy)benzonitrile |
| 23 | 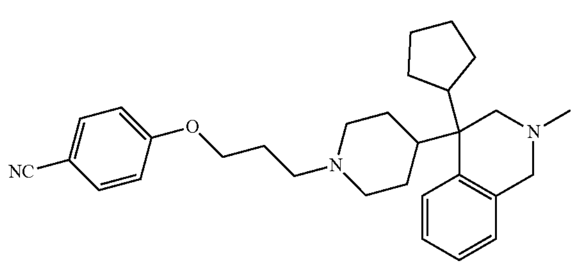 [SMILES: CN1Cc2ccccc2C(C2CCCC2)(C2CCN(CCCOc3ccc(C#N)cc3)CC2)C1] | 4-(3-(4-(4-cyclopentyl-2-methyl-1,2,3,4-tetrahydroisoquinolin-4-yl)piperidin-1-yl)propoxy)benzonitrile |

TABLE 1-continued

| Cpd. No. | Chemical Structure | Chemical Name |
|---|---|---|
| 24 | 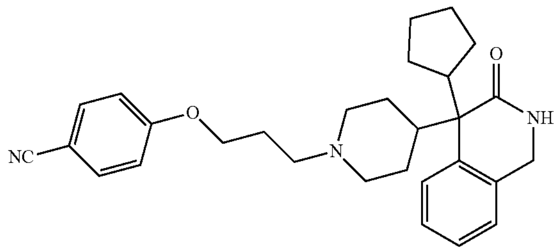 [SMILES: N#Cc1ccc(OCCCN2CCC(C3(C4CCCC4)C(=O)NCc4ccccc43)CC2)cc1] | 4-(3-(4-(4-cyclopentyl-3-oxo-1,2,3,4-tetrahydroisoquinolin-4-yl)piperidin-1-yl)propoxy)benzonitrile |
| 25 | 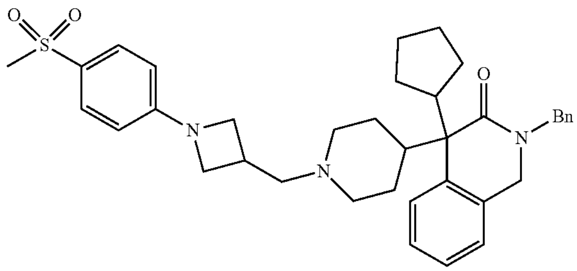 [SMILES: CS(=O)(=O)c1ccc(N2CC(CN3CCC(C4(C5CCCC5)C(=O)N(Cc5ccccc5)Cc5ccccc54)CC3)C2)cc1] | 2-benzyl-4-cyclopentyl-4-(1-((1-(4-(methylsulfonyl)phenyl)azetidin-3-yl)methyl)piperidin-4-yl)-1,4-dihydroisoquinolin-3(2H)-one |
| 26 | 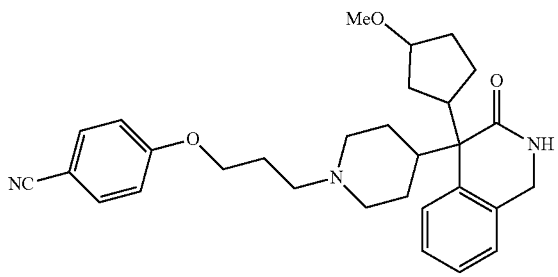 [SMILES: COC1CCC(C2(C3CCN(CCCOc4ccc(C#N)cc4)CC3)C(=O)NCc3ccccc32)C1] | 4-(3-(4-(4-(3-methoxycyclopentyl)-3-oxo-1,2,3,4-tetrahydroisoquinolin-4-yl)piperidin-1-yl)propoxy)benzonitrile |
| 27 | 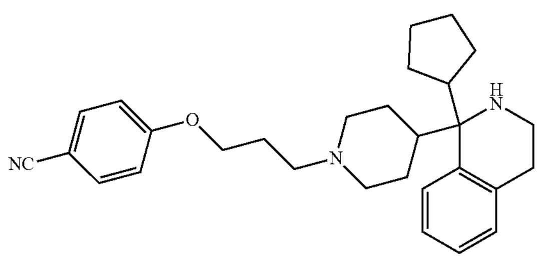 [SMILES: N#Cc1ccc(OCCCN2CCC(C3(C4CCCC4)NCCc4ccccc43)CC2)cc1] | 4-(3-(4-(1-cyclopentyl-1,2,3,4-tetrahydroisoquinolin-1-yl)piperidin-1-yl)propoxy)benzonitrile |
| 28 | 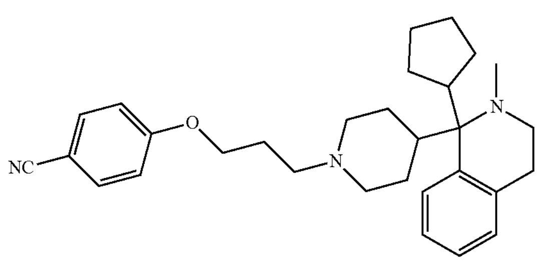 [SMILES: CN1CCc2ccccc2C1(C1CCCC1)C1CCN(CCCOc2ccc(C#N)cc2)CC1] | 4-(3-(4-(1-cyclopentyl-2-methyl-1,2,3,4-tetrahydroisoquinolin-1-yl)piperidin-1-yl)propoxy)benzonitrile |
| 29 | 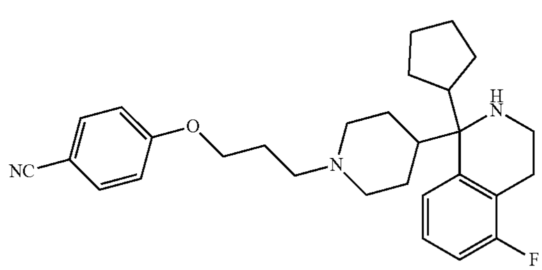 [SMILES: N#Cc1ccc(OCCCN2CCC(C3(C4CCCC4)NCCc4c(F)cccc43)CC2)cc1] | 4-(3-(4-(1-cyclopentyl-5-fluoro-1,2,3,4-tetrahydroisoquinolin-1-yl)piperidin-1-yl)propoxy)benzonitrile |

TABLE 1-continued

| Cpd. No. | Chemical Structure | Chemical Name |
|---|---|---|
| 30 | 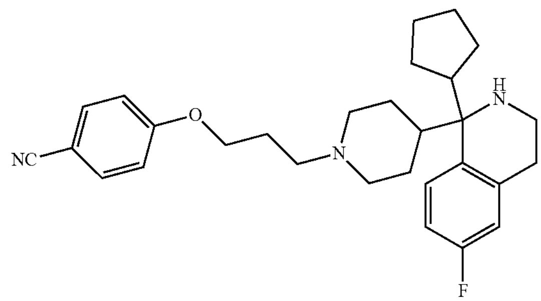 [SMILES: N#Cc1ccc(OCCCN2CCC(C3(C4CCCC4)NCCc4cc(F)ccc43)CC2)cc1] | 4-(3-(4-(1-cyclopentyl-6-fluoro-1,2,3,4-tetrahydroisoquinolin-1-yl)piperidin-1-yl)propoxy)benzonitrile |
| 31 | 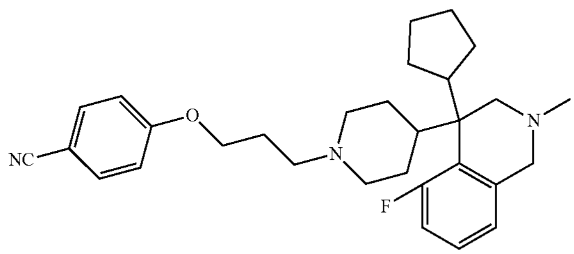 [SMILES: CN1Cc2cccc(F)c2C(C2CCCC2)(C2CCN(CCCOc3ccc(C#N)cc3)CC2)C1] | 4-(3-(4-(4-cyclopentyl-5-fluoro-2-methyl-1,2,3,4-tetrahydroisoquinolin-4-yl)piperidin-1-yl)propoxy)benzonitrile |
| 32 | 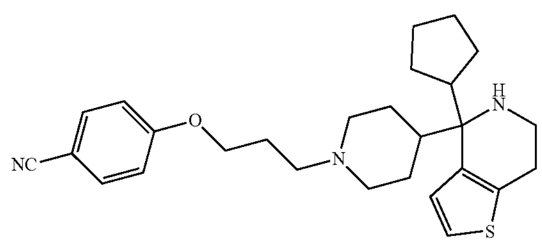 [SMILES: N#Cc1ccc(OCCCN2CCC(C3(C4CCCC4)NCCc4sccc43)CC2)cc1] | 4-(3-(4-(4-cyclopentyl-4,5,6,7-tetrahydrothieno[3,2-c]pyridin-4-yl)piperidin-1-yl)propoxy)benzonitrile |
| 33 | 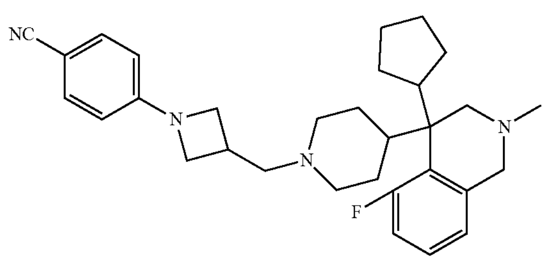 [SMILES: CN1Cc2cccc(F)c2C(C2CCCC2)(C2CCN(CC3CN(c4ccc(C#N)cc4)C3)CC2)C1] | 4-(3-((4-(4-cyclopentyl-5-fluoro-2-methyl-1,2,3,4-tetrahydroisoquinolin-4-yl)piperidin-1-yl)methyl)azetidin-1-yl)benzonitrile |
| 34 | 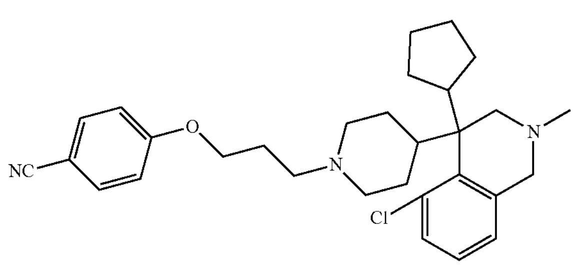 [SMILES: CN1Cc2cccc(Cl)c2C(C2CCCC2)(C2CCN(CCCOc3ccc(C#N)cc3)CC2)C1] | 4-(3-(4-(5-chloro-4-cyclopentyl-2-methyl-1,2,3,4-tetrahydroisoquinolin-4-yl)piperidin-1-yl)propoxy)benzonitrile |
| 35 | 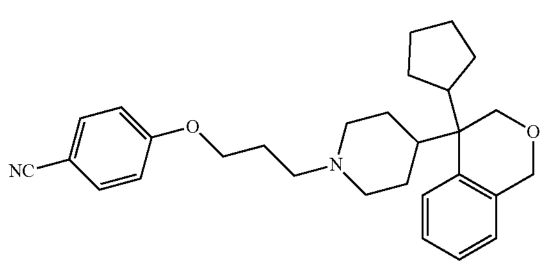 [SMILES: N#Cc1ccc(OCCCN2CCC(C3(C4CCCC4)COCc4ccccc43)CC2)cc1] | 4-(3-(4-(4-cyclopentylisochroman-4-yl)piperidin-1-yl)propoxy)benzonitrile |

TABLE 1-continued

| Cpd. No. | Chemical Structure | Chemical Name |
|---|---|---|
| 37 | 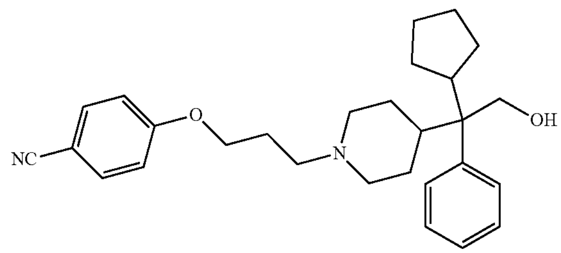 [SMILES: N#Cc1ccc(OCCCN2CCC(C(CO)(c3ccccc3)C3CCCC3)CC2)cc1] | 4-(3-(4-(1-cyclopentyl-2-hydroxy-1-phenylethyl)piperidin-1-yl)propoxy)benzonitrile |
| 38 | 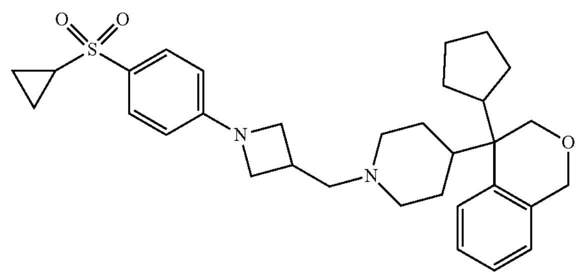 [SMILES: O=S(=O)(c1ccc(N2CC(CN3CCC(C4(C5CCCC5)COCc5ccccc54)CC3)C2)cc1)C1CC1] | 4-(4-cyclopentylisochroman-4-yl)-1-((1-(4-(cyclopropylsulfonyl)phenyl)azetidin-3-yl)methyl)piperidine |
| 39 | 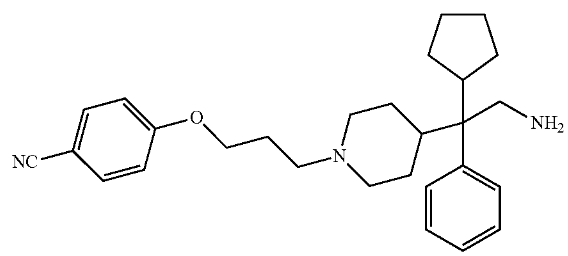 [SMILES: N#Cc1ccc(OCCCN2CCC(C(CN)(c3ccccc3)C3CCCC3)CC2)cc1] | 4-(3-(4-(2-amino-1-cyclopentyl-1-phenylethyl)piperidin-1-yl)propoxy)benzonitrile |
| 40 | 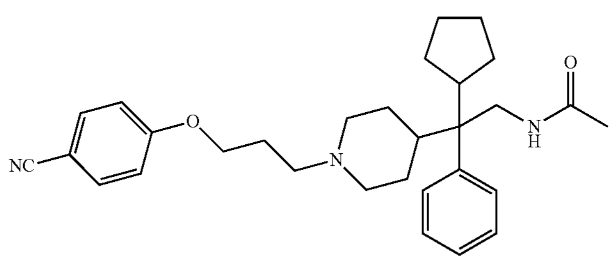 [SMILES: CC(=O)NCC(c1ccccc1)(C1CCCC1)C1CCN(CCCOc2ccc(C#N)cc2)CC1] | N-(2-(1-(3-(4-cyanophenoxy)propyl)piperidin-4-yl)-2-cyclopentyl-2-phenylethyl)acetamide |
| 41 | 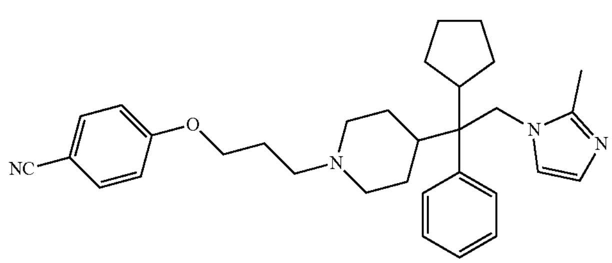 [SMILES: Cc1nccn1CC(c1ccccc1)(C1CCCC1)C1CCN(CCCOc2ccc(C#N)cc2)CC1] | 4-(3-(4-(1-cyclopentyl-2-(2-methyl-1H-imidazol-1-yl)-1-phenylethyl)piperidin-1-yl)propoxy)benzonitrile |

TABLE 1-continued

| Cpd. No. | Chemical Structure | Chemical Name |
|---|---|---|
| 42 | 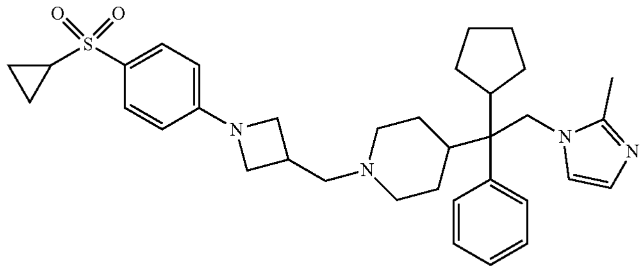 [SMILES: Cc1nccn1CC(c1ccccc1)(C1CCCC1)C1CCN(CC2CN(c3ccc(S(=O)(=O)C4CC4)cc3)C2)CC1] | 4-(1-cyclopentyl-2-(2-methyl-1H-imidazol-1-yl)-1-phenylethyl)-1-((1-(4-(cyclopropylsulfonyl)phenyl)azetidin-3-yl)methyl)piperidine |
| 43 | 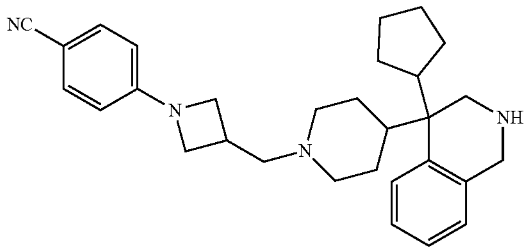 [SMILES: N#Cc1ccc(N2CC(CN3CCC(C4(C5CCCC5)CNCc5ccccc54)CC3)C2)cc1] | 4-(3-((4-(4-cyclopentyl-1,2,3,4-tetrahydroisoquinolin-4-yl)piperidin-1-yl)methyl)azetidin-1-yl)benzonitrile |
| 44 | 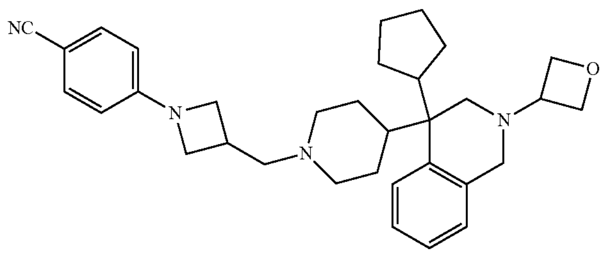 [SMILES: N#Cc1ccc(N2CC(CN3CCC(C4(C5CCCC5)CN(C5COC5)Cc5ccccc54)CC3)C2)cc1] | 4-(3-((4-(4-cyclopentyl-2-(oxetan-3-yl)-1,2,3,4-tetrahydroisoquinolin-4-yl)piperidin-1-yl)methyl)azetidin-1-yl)benzonitrile |
| 45 | 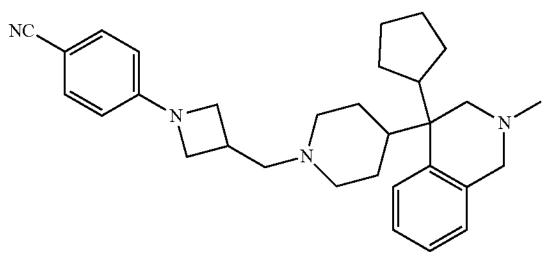 [SMILES: CN1Cc2ccccc2C(C2CCCC2)(C2CCN(CC3CN(c4ccc(C#N)cc4)C3)CC2)C1] | 4-(3-((4-(4-cyclopentyl-2-methyl-1,2,3,4-tetrahydroisoquinolin-4-yl)piperidin-1-yl)methyl)azetidin-1-yl)benzonitrile |
| 46 | 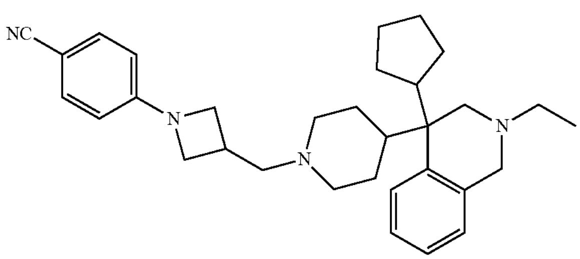 [SMILES: CCN1Cc2ccccc2C(C2CCCC2)(C2CCN(CC3CN(c4ccc(C#N)cc4)C3)CC2)C1] | 4-(3-((4-(4-cyclopentyl-2-ethyl-1,2,3,4-tetrahydroisoquinolin-4-yl)piperidin-1-yl)methyl)azetidin-1-yl)benzonitrile |
| 47 | 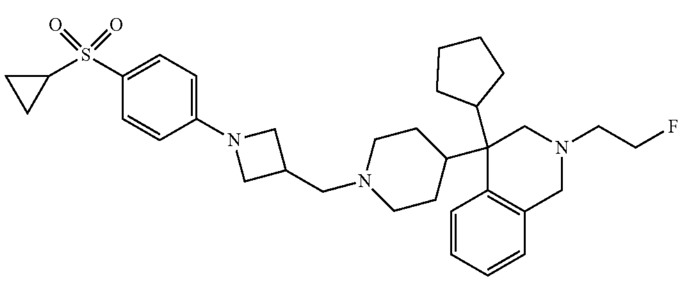 [SMILES: O=S(=O)(c1ccc(N2CC(CN3CCC(C4(C5CCCC5)CN(CCF)Cc5ccccc54)CC3)C2)cc1)C1CC1] | 4-cyclopentyl-4-(1-((1-(4-(cyclopropylsulfonyl)phenyl)azetidin-3-yl)methyl)piperidin-4-yl)-2-(2-fluoroethyl)-1,2,3,4-tetrahydroisoquinoline |

TABLE 1-continued

| Cpd. No. | Chemical Structure | Chemical Name |
|---|---|---|
| 48 | 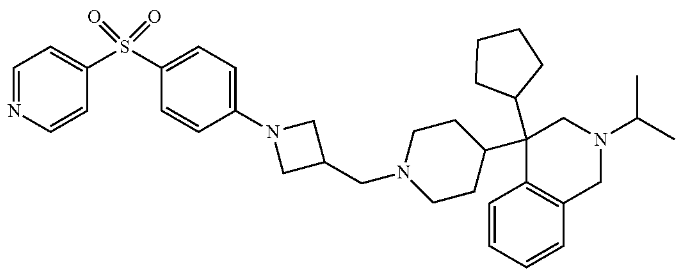 [SMILES: CC(C)N1Cc2ccccc2C(C2CCCC2)(C2CCN(CC3CN(c4ccc(S(=O)(=O)c5ccncc5)cc4)C3)CC2)C1] | 4-cyclopentyl-2-isopropyl-4-(1-((1-(4-(pyridin-4-ylsulfonyl)phenyl)azetidin-3-yl)methyl)piperidin-4-yl)-1,2,3,4-tetrahydroisoquinoline |
| 49 | 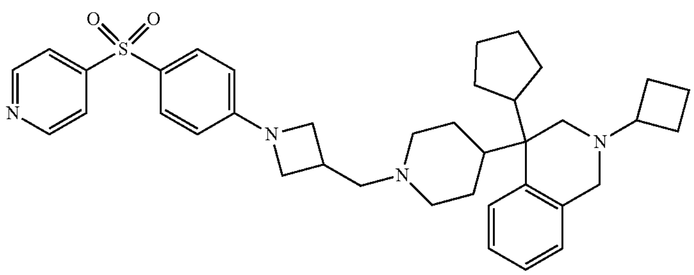 [SMILES: O=S(=O)(c1ccncc1)c1ccc(N2CC(CN3CCC(C4(C5CCCC5)CN(C5CCC5)Cc5ccccc54)CC3)C2)cc1] | 2-cyclobutyl-4-cyclopentyl-4-(1-((1-(4-(pyridin-4-ylsulfonyl)phenyl)azetidin-3-yl)methyl)piperidin-4-yl)-1,2,3,4-tetrahydroisoquinoline |
| 50 | 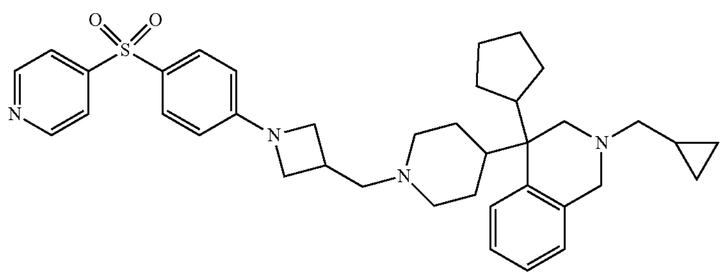 [SMILES: O=S(=O)(c1ccncc1)c1ccc(N2CC(CN3CCC(C4(C5CCCC5)CN(CC5CC5)Cc5ccccc54)CC3)C2)cc1] | 4-cyclopentyl-2-(cyclopropylmethyl)-4-(1-((1-(4-(pyridin-4-ylsulfonyl)phenyl)azetidin-3-yl)methyl)piperidin-4-yl)-1,2,3,4-tetrahydroisoquinoline |
| 51 | 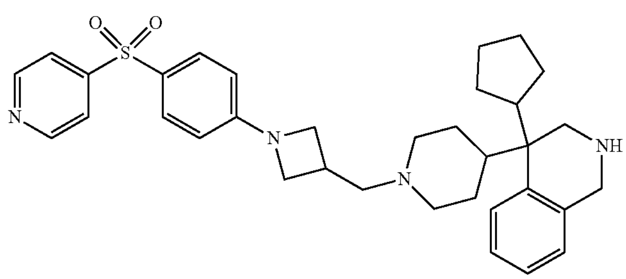 [SMILES: O=S(=O)(c1ccncc1)c1ccc(N2CC(CN3CCC(C4(C5CCCC5)CNCc5ccccc54)CC3)C2)cc1] | 4-cyclopentyl-4-(1-((1-(4-(pyridin-4-ylsulfonyl)phenyl)azetidin-3-yl)methyl)piperidin-4-yl)-1,2,3,4-tetrahydroisoquinoline |
| 52 | 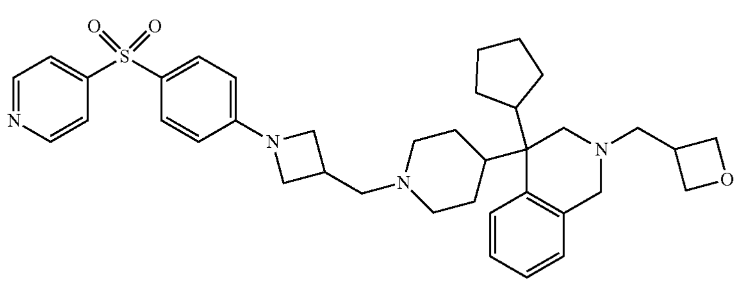 [SMILES: O=S(=O)(c1ccncc1)c1ccc(N2CC(CN3CCC(C4(C5CCCC5)CN(CC5COC5)Cc5ccccc54)CC3)C2)cc1] | 4-cyclopentyl-2-(oxetan-3-ylmethyl)-4-(1-((1-(4-(pyridin-4-ylsulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 53 | 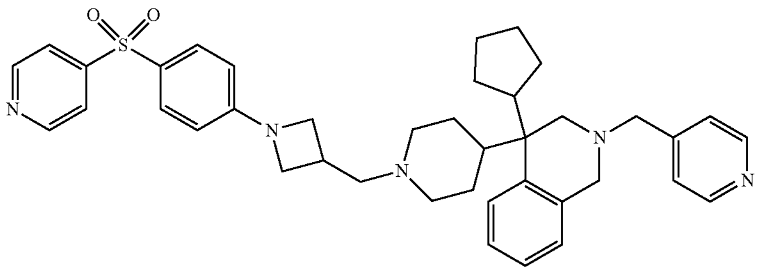 [SMILES: O=S(=O)(c1ccncc1)c1ccc(N2CC(CN3CCC(C4(C5CCCC5)CN(Cc5ccncc5)Cc5ccccc54)CC3)C2)cc1] | 4-cyclopentyl-2-(pyridin-4-ylmethyl)-4-(1-((1-(4-(pyridin-4-ylsulfonyl)phenyl)azetidin-3-yl)methyl)piperidin-4-yl)-1,2,3,4-tetrahydroisoquinoline |
| 54 | 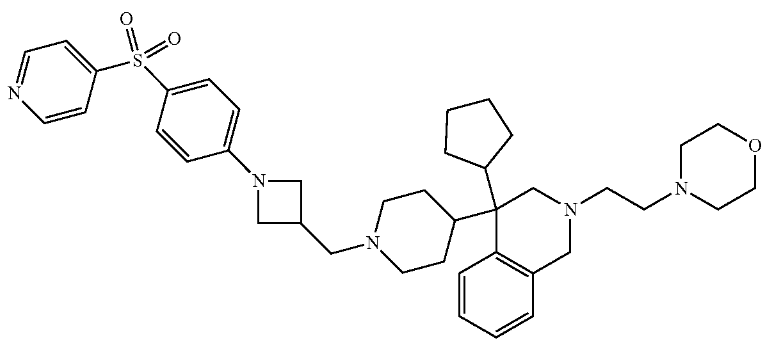 [SMILES: O=S(=O)(c1ccncc1)c1ccc(N2CC(CN3CCC(C4(C5CCCC5)CN(CCN5CCOCC5)Cc5ccccc54)CC3)C2)cc1] | 4-(2-(4-cyclopentyl-4-(1-((1-(4-(pyridin-4-ylsulfonyl)phenyl)azetidin-3-yl)methyl)piperidin-4-yl)-3,4-dihydroisoquinolin-2(1H)-yl)ethyl)morpholine |
| 55 | 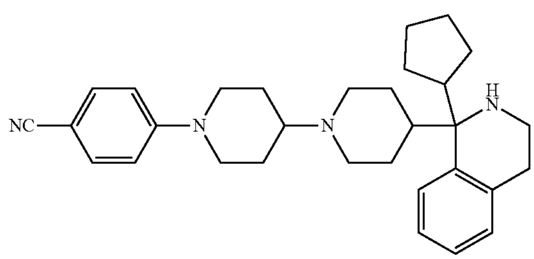 [SMILES: N#Cc1ccc(N2CCC(N3CCC(C4(C5CCCC5)NCCc5ccccc54)CC3)CC2)cc1] | 4-(4-(1-cyclopentyl-1,2,3,4-tetrahydroisoquinolin-1-yl)-[1,4'-bipiperidin]-1'-yl)benzonitrile |
| 56 | 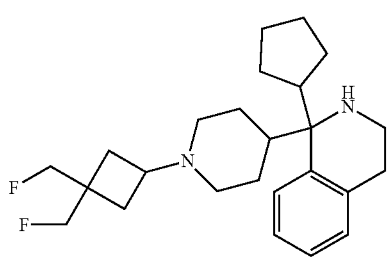 [SMILES: FCC1(CF)CC(N2CCC(C3(C4CCCC4)NCCc4ccccc43)CC2)C1] | 1-(1-(3,3-bis(fluoromethyl)cyclobutyl)piperidin-4-yl)-1-cyclopentyl-1,2,3,4-tetrahydroisoquinoline |
| 57 | 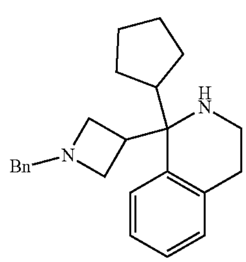 [SMILES: c1ccc(CN2CC(C3(C4CCCC4)NCCc4ccccc43)C2)cc1] | 1-(1-benzylazetidin-3-yl)-1-cyclopentyl-1,2,3,4-tetrahydroisoquinoline |

TABLE 1-continued

| Cpd. No. | Chemical Structure | Chemical Name |
|---|---|---|
| 58 | 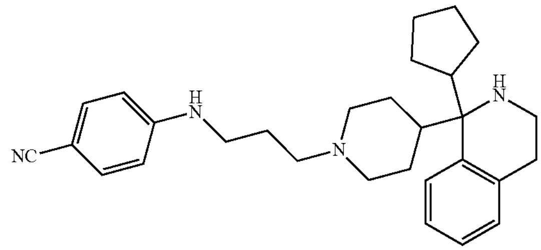 [SMILES: N#Cc1ccc(NCCCN2CCC(C3(C4CCCC4)NCCc4ccccc43)CC2)cc1] | 4-((3-(4-(1-cyclopentyl-1,2,3,4-tetrahydroisoquinolin-1-yl)piperidin-1-yl)propyl)amino)benzonitrile |
| 59 | 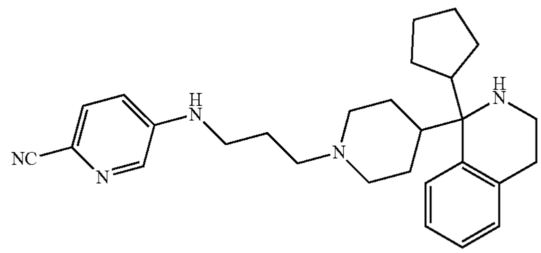 [SMILES: N#Cc1ccc(NCCCN2CCC(C3(C4CCCC4)NCCc4ccccc43)CC2)cn1] | 5-((3-(4-(1-cyclopentyl-1,2,3,4-tetrahydroisoquinolin-1-yl)piperidin-1-yl)propyl)amino)picolinonitrile |
| 60 | 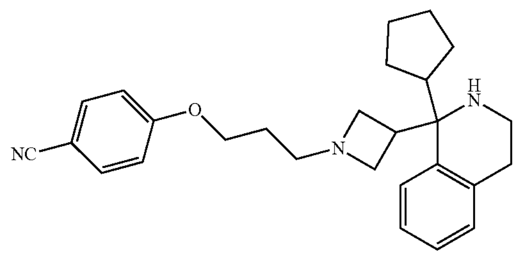 [SMILES: N#Cc1ccc(OCCCN2CC(C3(C4CCCC4)NCCc4ccccc43)C2)cc1] | 4-(3-(3-(1-cyclopentyl-1,2,3,4-tetrahydroisoquinolin-1-yl)azetidin-1-yl)propoxy)benzonitrile |
| 61 | 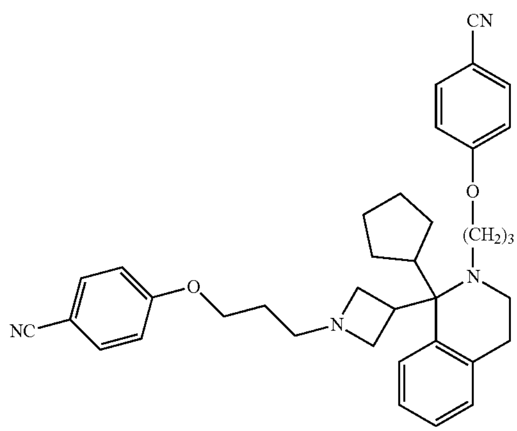 | 4-(3-(3-(2-((4-cyanophenoxy)methyl)-1-cyclopentyl-1,2,3,4-tetrahydroisoquinolin-1-yl)azetidin-1-yl)propoxy)benzonitrile compound with ethene (1:1) |
| 62 | 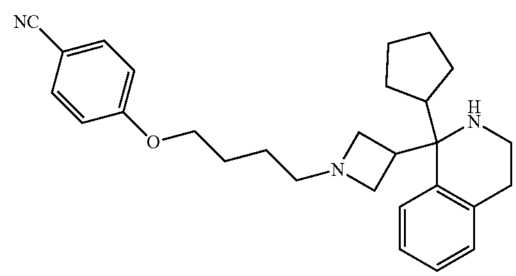 [SMILES: N#Cc1ccc(OCCCCN2CC(C3(C4CCCC4)NCCc4ccccc43)C2)cc1] | 4-(4-(3-(1-cyclopentyl-1,2,3,4-tetrahydroisoquinolin-1-yl)azetidin-1-yl)butoxy)benzonitrile |

TABLE 1-continued

| Cpd. No. | Chemical Structure | Chemical Name |
|---|---|---|
| 63 | 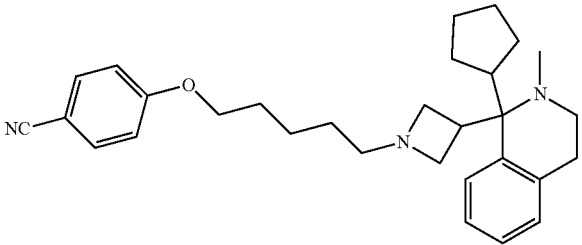 [SMILES: CN1CCc2ccccc2C1(C1CCCC1)C1CN(CCCCCOc2ccc(C#N)cc2)C1] | 4-((5-(3-(1-cyclopentyl-2-methyl-1,2,3,4-tetrahydroisoquinolin-1-yl)azetidin-1-yl)pentyl)oxy)benzonitrile |
| 64 | 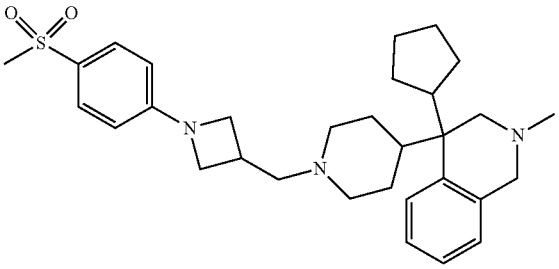 | 4-cyclopentyl-2-methyl-4-(1-((1-(4-(methylsulfonyl)phenyl)azetidin-3-yl)methyl)piperidin-4-yl)-1,2,3,4-tetrahydroisoquinoline |
| 65 | 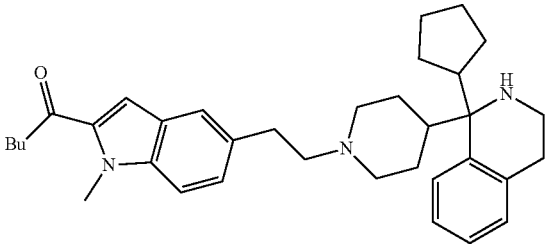 | 1-(5-(2-(4-(1-cyclopentyl-1,2,3,4-tetrahydroisoquinolin-1-yl)piperidin-1-yl)ethyl)-1-methyl-1H-indol-2-yl)pentan-1-one |
| 66 | 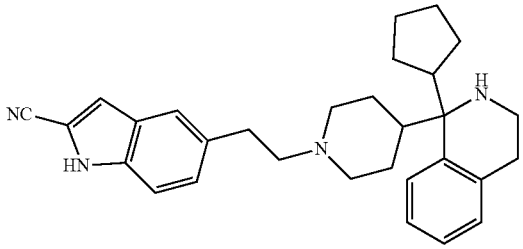 [SMILES: N#Cc1cc2cc(CCN3CCC(C4(C5CCCC5)NCCc5ccccc54)CC3)ccc2[nH]1] | 5-(2-(4-(1-cyclopentyl-1,2,3,4-tetrahydroisoquinolin-1-yl)piperidin-1-yl)ethyl)-1H-indole-2-carbonitrile |
| 67 | 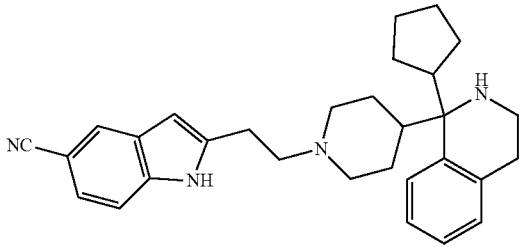 [SMILES: N#Cc1ccc2[nH]c(CCN3CCC(C4(C5CCCC5)NCCc5ccccc54)CC3)cc2c1] | 2-(2-(4-(1-cyclopentyl-1,2,3,4-tetrahydroisoquinolin-1-yl)piperidin-1-yl)ethyl)-1H-indole-5-carbonitrile |
| 68 | 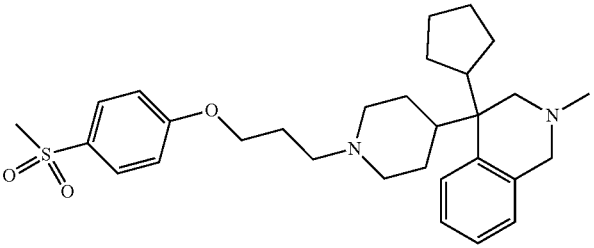 [SMILES: CN1Cc2ccccc2C(C2CCCC2)(C2CCN(CCCOc3ccc(S(C)(=O)=O)cc3)CC2)C1] | 4-cyclopentyl-2-methyl-4-(1-(3-(4-(methylsulfonyl)phenoxy)propyl)piperidin-4-yl)-1,2,3,4-tetrahydroisoquinoline |

TABLE 1-continued

| Cpd. No. | Chemical Structure | Chemical Name |
|---|---|---|
| 69 | 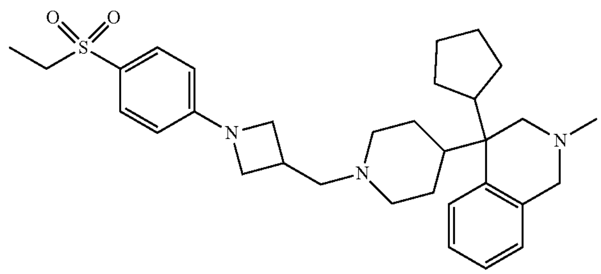 [SMILES: CCS(=O)(=O)c1ccc(N2CC(CN3CCC(C4(C5CCCC5)CN(C)Cc5ccccc54)CC3)C2)cc1] | 4-cyclopentyl-4-(1-((1-(4-(ethylsulfonyl)phenyl)azetidin-3-yl)methyl)piperidin-4-yl)-2-methyl-1,2,3,4-tetrahydroisoquinoline |
| 70 | 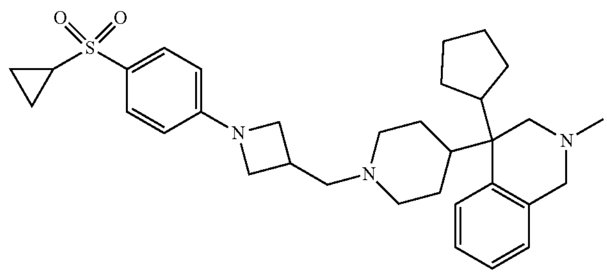 [SMILES: CN1Cc2ccccc2C(C2CCCC2)(C2CCN(CC3CN(c4ccc(S(=O)(=O)C5CC5)cc4)C3)CC2)C1] | 4-cyclopentyl-4-(1-((1-(4-(cyclopropylsulfonyl)phenyl)azetidin-3-yl)methyl)piperidin-4-yl)-2-methyl-1,2,3,4-tetrahydroisoquinoline |
| 71 | 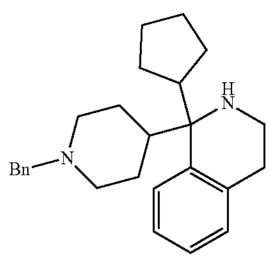 [SMILES: c1ccc(CN2CCC(C3(C4CCCC4)NCCc4ccccc43)CC2)cc1] | 1-(1-benzylpiperidin-4-yl)-1-cyclopentyl-1,2,3,4-tetrahydroisoquinoline |
| 72 | 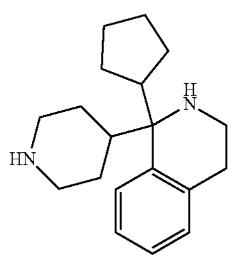 [SMILES: c1ccc2c(c1)CCNC2(C1CCCC1)C1CCNCC1] | 1-cyclopentyl-1-(piperidin-4-yl)-1,2,3,4-tetrahydroisoquinoline |
| 73 | 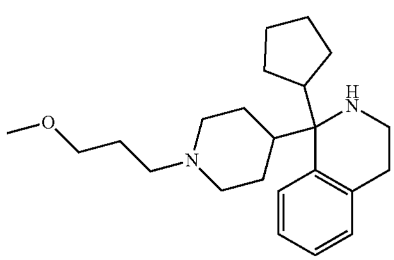 [SMILES: COCCCN1CCC(C2(C3CCCC3)NCCc3ccccc32)CC1] | 1-cyclopentyl-1-(1-(3-methoxypropyl)piperidin-4-yl)-1,2,3,4-tetrahydroisoquinoline |
| 74 | 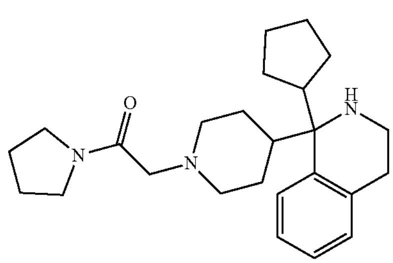 [SMILES: O=C(CN1CCC(C2(C3CCCC3)NCCc3ccccc32)CC1)N1CCCC1] | 2-(4-(1-cyclopentyl-1,2,3,4-tetrahydroisoquinolin-1-yl)piperidin-1-yl)-1-(pyrrolidin-1-yl)ethan-1-one |

TABLE 1-continued

| Cpd. No. | Chemical Structure | Chemical Name |
|---|---|---|
| 75 | 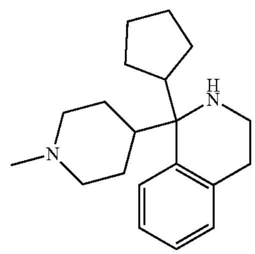 [SMILES: CN1CCC(C2(C3CCCC3)NCCc3ccccc32)CC1] | 1-cyclopentyl-1-(1-methylpiperidin-4-yl)-1,2,3,4-tetrahydroisoquinoline |
| 76 | 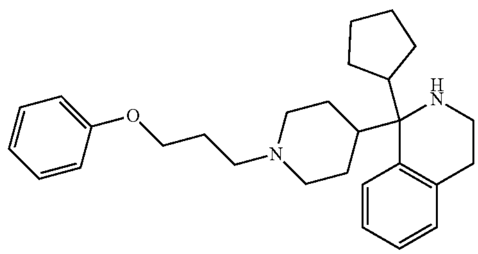 [SMILES: c1ccc(OCCCN2CCC(C3(C4CCCC4)NCCc4ccccc43)CC2)cc1] | 1-cyclopentyl-1-(1-(3-phenoxypropyl)piperidin-4-yl)-1,2,3,4-tetrahydroisoquinoline |
| 77 | 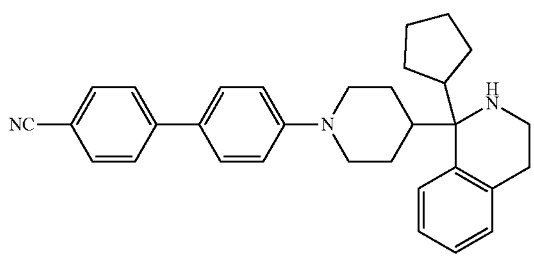 [SMILES: N#Cc1ccc(-c2ccc(N3CCC(C4(C5CCCC5)NCCc5ccccc54)CC3)cc2)cc1] | 4'-(4-(1-cyclopentyl-1,2,3,4-tetrahydroisoquinolin-1-yl)piperidin-1-yl)-[1,1'-biphenyl]-4-carbonitrile |
| 78 | 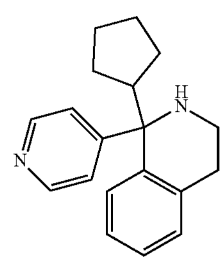 [SMILES: c1ccc2c(c1)CCNC2(c1ccncc1)C1CCCC1] | 1-cyclopentyl-1-(pyridin-4-yl)-1,2,3,4-tetrahydroisoquinoline |
| 79 | 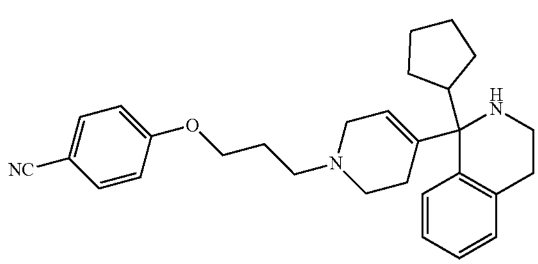 [SMILES: N#Cc1ccc(OCCCN2CC=C(C3(C4CCCC4)NCCc4ccccc43)CC2)cc1] | 4-(3-(4-(1-cyclopentyl-1,2,3,4-tetrahydroisoquinolin-1-yl)-3,6-dihydropyridin-1(2H)-yl)propoxy)benzonitrile |
| 80 | 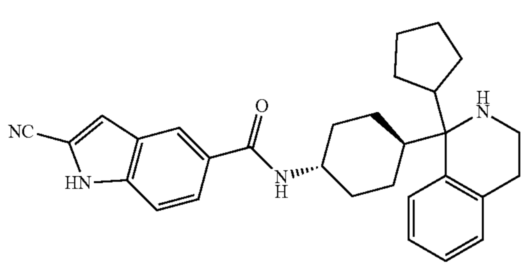 [SMILES: N#Cc1cc2cc(C(=O)N[C@H]3CC[C@H](C4(C5CCCC5)NCCc5ccccc54)CC3)ccc2[nH]1] | 2-cyano-N-((1r,4r)-4-(1-cyclopentyl-1,2,3,4-tetrahydroisoquinolin-1-yl)cyclohexyl)-1H-indole-5-carboxamide |

TABLE 1-continued

| Cpd. No. | Chemical Structure | Chemical Name |
|---|---|---|
| 81 | 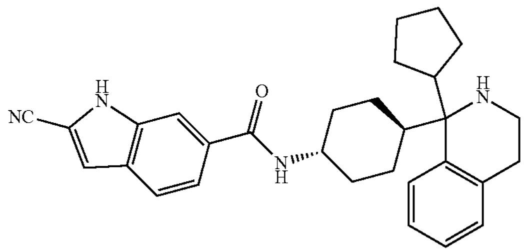 [SMILES: N#Cc1cc2ccc(C(=O)N[C@H]3CC[C@H](C4(C5CCCC5)NCCc5ccccc54)CC3)cc2[nH]1] | 2-cyano-N-((1r,4r)-4-(1-cyclopentyl-1,2,3,4-tetrahydroisoquinolin-1-yl)cyclohexyl)-1H-indole-6-carboxamide |
| 82 | 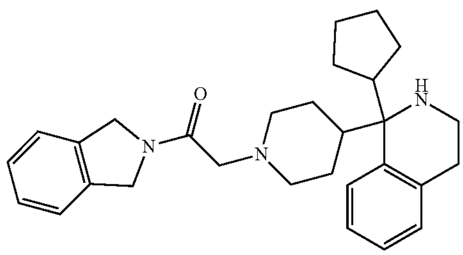 [SMILES: O=C(CN1CCC(C2(C3CCCC3)NCCc3ccccc32)CC1)N1Cc2ccccc2C1] | 2-(4-(1-cyclopentyl-1,2,3,4-tetrahydroisoquinolin-1-yl)piperidin-1-yl)-1-(isoindolin-2-yl)ethan-1-one |
| 83 | 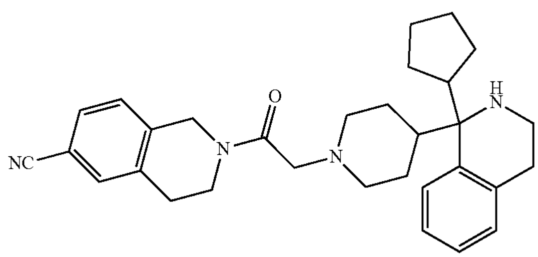 [SMILES: N#Cc1ccc2c(c1)CCN(C(=O)CN1CCC(C3(C4CCCC4)NCCc4ccccc43)CC1)C2] | 2-(2-(4-(1-cyclopentyl-1,2,3,4-tetrahydroisoquinolin-1-yl)piperidin-1-yl)acetyl)-1,2,3,4-tetrahydroisoquinoline-6-carbonitrile |
| 84 | 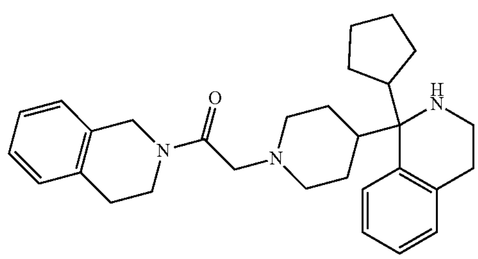 [SMILES: O=C(CN1CCC(C2(C3CCCC3)NCCc3ccccc32)CC1)N1CCc2ccccc2C1] | 2-(4-(1-cyclopentyl-1,2,3,4-tetrahydroisoquinolin-1-yl)piperidin-1-yl)-1-(3,4-dihydroisoquinolin-2(1H)-yl)ethan-1-one |
| 85 | 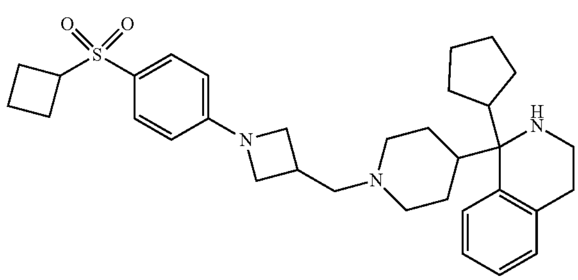 [SMILES: O=S(=O)(c1ccc(N2CC(CN3CCC(C4(C5CCCC5)NCCc5ccccc54)CC3)C2)cc1)C1CCC1] | 1-(1-((1-(4-(cyclobutylsulfonyl)phenyl)azetidin-3-yl)methyl)piperidin-4-yl)-1-cyclopentyl-1,2,3,4-tetrahydroisoquinoline |
| 86 | 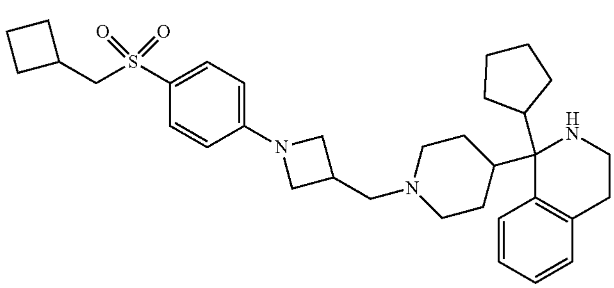 [SMILES: O=S(=O)(CC1CCC1)c1ccc(N2CC(CN3CCC(C4(C5CCCC5)NCCc5ccccc54)CC3)C2)cc1] | 1-(1-((1-(4-((cyclobutylmethyl)sulfonyl)phenyl)azetidin-3-yl)methyl)piperidin-4-yl)-1-cyclopentyl-1,2,3,4-tetrahydroisoquinoline |

TABLE 1-continued

| Cpd. No. | Chemical Structure | Chemical Name |
|---|---|---|
| 87 | 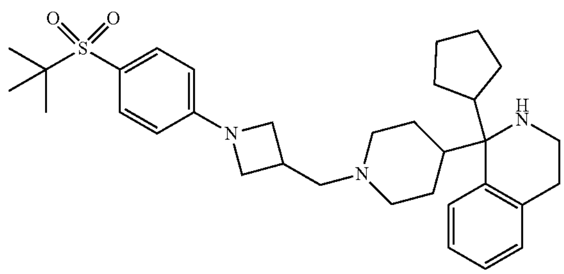 [SMILES: CC(C)(C)S(=O)(=O)c1ccc(N2CC(CN3CCC(C4(C5CCCC5)NCCc5ccccc54)CC3)C2)cc1] | 1-(1-((1-(4-(tert-butylsulfonyl)phenyl)azetidin-3-yl)methyl)piperidin-4-yl)-1-cyclopentyl-1,2,3,4-tetrahydroisoquinoline |
| 88 | 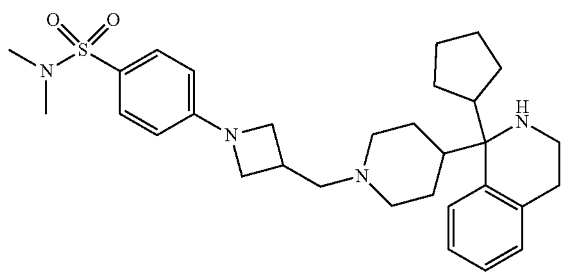 [SMILES: CN(C)S(=O)(=O)c1ccc(N2CC(CN3CCC(C4(C5CCCC5)NCCc5ccccc54)CC3)C2)cc1] | 4-(3-((4-(1-cyclopentyl-1,2,3,4-tetrahydroisoquinolin-1-yl)piperidin-1-yl)methyl)azetidin-1-yl)-N,N-dimethylbenzenesulfonamide |
| 89 | 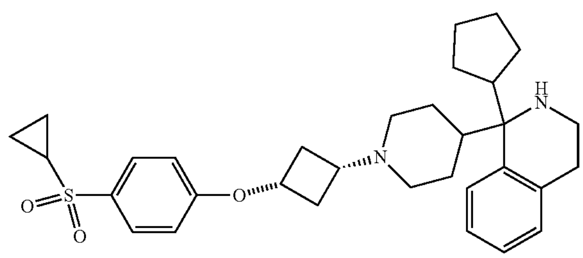 [SMILES: O=S(=O)(c1ccc(O[C@H]2C[C@@H](N3CCC(C4(C5CCCC5)NCCc5ccccc54)CC3)C2)cc1)C1CC1] | 1-cyclopentyl-1-(1-((1s,3s)-3-(4-(cyclopropylsulfonyl)phenoxy)cyclobutyl)piperidin-4-yl)-1,2,3,4-tetrahydroisoquinoline |
| 90 | 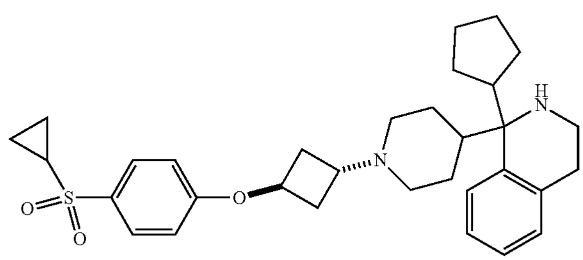 | 1-cyclopentyl-1-(1-((1r,3r)-3-(4-(cyclopropylsulfonyl)phenoxy)cyclobutyl)piperidin-4-yl)-1,2,3,4-tetrahydroisoquinoline |
| 91 | 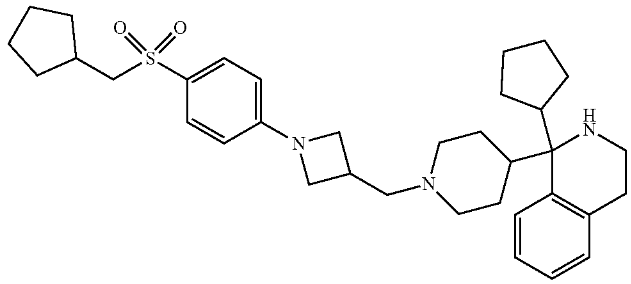 [SMILES: O=S(=O)(CC1CCCC1)c1ccc(N2CC(CN3CCC(C4(C5CCCC5)NCCc5ccccc54)CC3)C2)cc1] | 1-cyclopentyl-1-(1-((1-(4-((cyclopentylmethyl)sulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 92 | 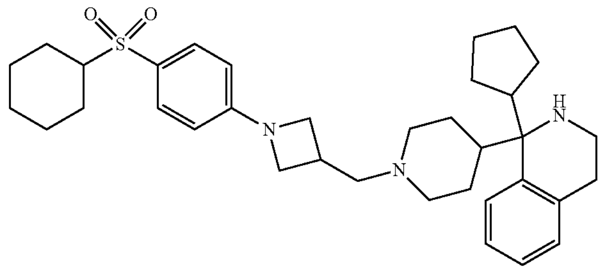 [SMILES: O=S(=O)(c1ccc(N2CC(CN3CCC(C4(C5CCCC5)NCCc5ccccc54)CC3)C2)cc1)C1CCCCC1] | 1-(1-((1-(4-(cyclohexylsulfonyl)phenyl)azetidin-3-yl)methyl)piperidin-4-yl)-1-cyclopentyl-1,2,3,4-tetrahydroisoquinoline |
| 93 | 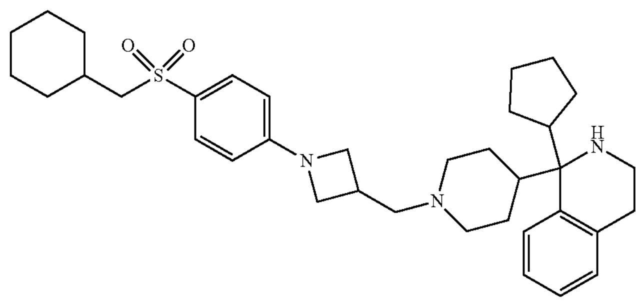 [SMILES: O=S(=O)(CC1CCCCC1)c1ccc(N2CC(CN3CCC(C4(C5CCCC5)NCCc5ccccc54)CC3)C2)cc1] | 1-(1-((1-(4-((cyclohexylmethyl)sulfonyl)phenyl)azetidin-3-yl)methyl)piperidin-4-yl)-1-cyclopentyl-1,2,3,4-tetrahydroisoquinoline |
| 94 | 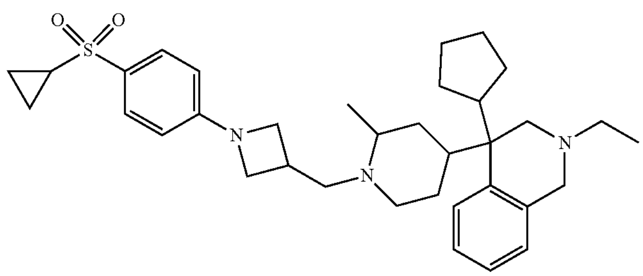 [SMILES: CCN1Cc2ccccc2C(C2CCCC2)(C2CCN(CC3CN(c4ccc(S(=O)(=O)C5CC5)cc4)C3)C(C)C2)C1] | 4-cyclopentyl-4-(1-((1-(4-(cyclopropylsulfonyl)phenyl)azetidin-3-yl)methyl)-2-methylpiperidin-4-yl)-2-ethyl-1,2,3,4-tetrahydroisoquinoline |
| 95 | 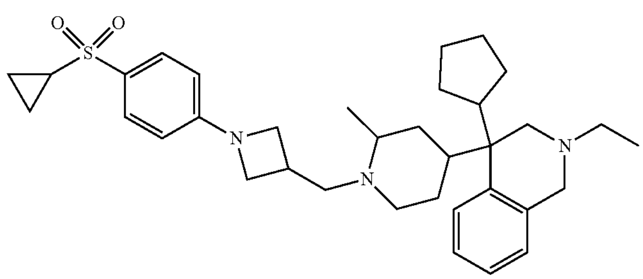 [SMILES: CCN1Cc2ccccc2C(C2CCCC2)(C2CCN(CC3CN(c4ccc(S(=O)(=O)C5CC5)cc4)C3)C(C)C2)C1] | 4-cyclopentyl-4-(1-((1-(4-(cyclopropylsulfonyl)phenyl)azetidin-3-yl)methyl)-2-methylpiperidin-4-yl)-2-ethyl-1,2,3,4-tetrahydroisoquinoline |
| 96 | 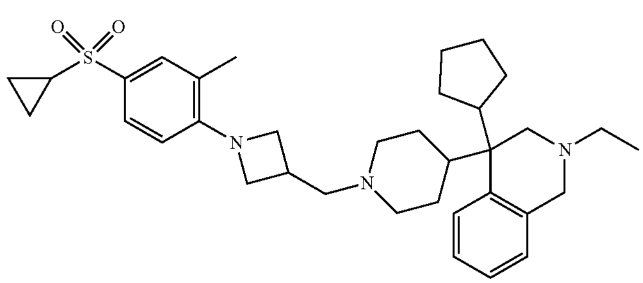 [SMILES: CCN1Cc2ccccc2C(C2CCCC2)(C2CCN(CC3CN(c4ccc(S(=O)(=O)C5CC5)cc4C)C3)CC2)C1] | 4-cyclopentyl-4-(1-((1-(4-(cyclopropylsulfonyl)-2-methylphenyl)azetidin-3-yl)methyl)piperidin-4-yl)-2-ethyl-1,2,3,4-tetrahydroisoquinoline |

TABLE 1-continued

| Cpd. No. | Chemical Structure | Chemical Name |
|---|---|---|
| 97 | 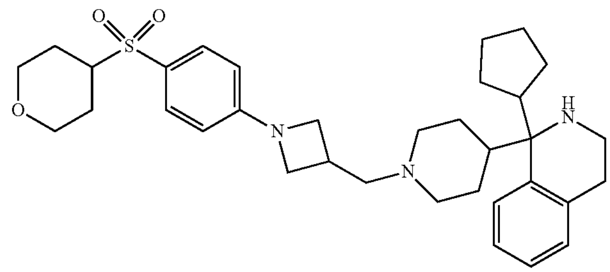 [SMILES: O=S(=O)(c1ccc(N2CC(CN3CCC(C4(C5CCCC5)NCCc5ccccc54)CC3)C2)cc1)C1CCOCC1] | 1-cyclopentyl-1-(1-((1-(4-((tetrahydro-2H-pyran-4-yl)sulfonyl)phenyl)azetidin-3-yl)methyl)piperidin-4-yl)-1,2,3,4-tetrahydroisoquinoline |
| 98 | 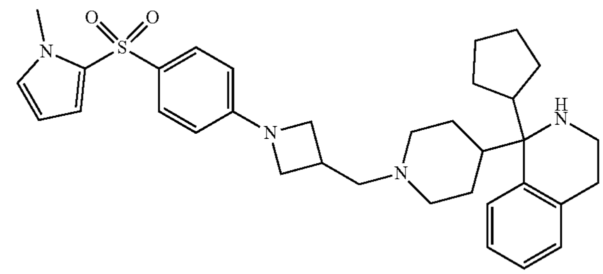 [SMILES: Cn1cccc1S(=O)(=O)c1ccc(N2CC(CN3CCC(C4(C5CCCC5)NCCc5ccccc54)CC3)C2)cc1] | 1-cyclopentyl-1-(1-((1-(4-((1-methyl-1H-pyrrol-2-yl)sulfonyl)phenyl)azetidin-3-yl)methyl)piperidin-4-yl)-1,2,3,4-tetrahydroisoquinoline |
| 99 | 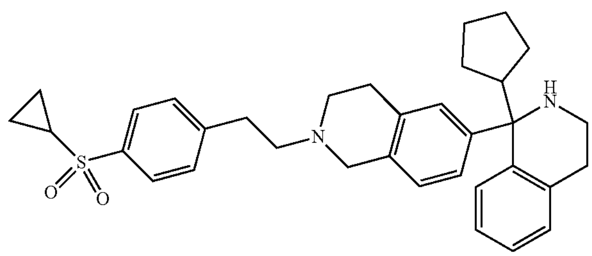 [SMILES: O=S(=O)(c1ccc(CCN2CCc3cc(C4(C5CCCC5)NCCc5ccccc54)ccc3C2)cc1)C1CC1] | 1-cyclopentyl-2'-(4-(cyclopropylsulfonyl)phenethyl)-1,1',2,2',3,3',4,4'-octahydro-1,6'-biisoquinoline |
| 100 | 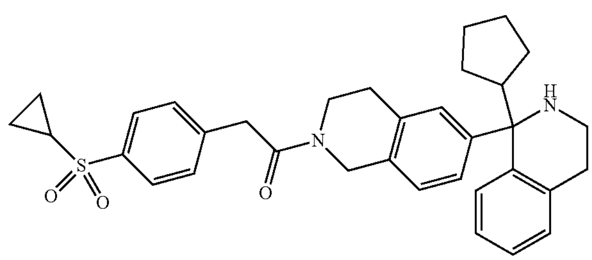 [SMILES: O=C(Cc1ccc(S(=O)(=O)C2CC2)cc1)N1CCc2cc(C3(C4CCCC4)NCCc4ccccc43)ccc2C1] | 1-(1-cyclopentyl-1,2,3,3',4,4'-hexahydro-[1,6'-biisoquinolin]-2'-(1'H)-yl)-2-(4-(cyclopropylsulfonyl)phenyl)ethan-1-one |
| 101 | 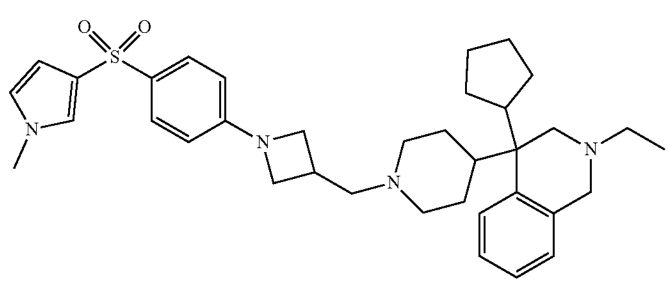 [SMILES: CCN1Cc2ccccc2C(C2CCCC2)(C2CCN(CC3CN(c4ccc(S(=O)(=O)c5ccn(C)c5)cc4)C3)CC2)C1] | 4-cyclopentyl-2-ethyl-4-(1-((1-(4-((1-methyl-1H-pyrrol-3-yl)sulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 102 | 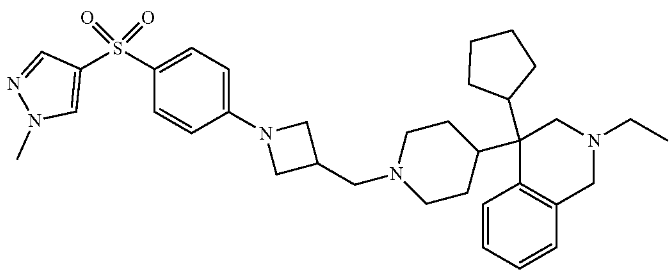 [SMILES: CCN1Cc2ccccc2C(C2CCCC2)(C2CCN(CC3CN(c4ccc(S(=O)(=O)c5cnn(C)c5)cc4)C3)CC2)C1] | 4-cyclopentyl-2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinoline |
| 103 | 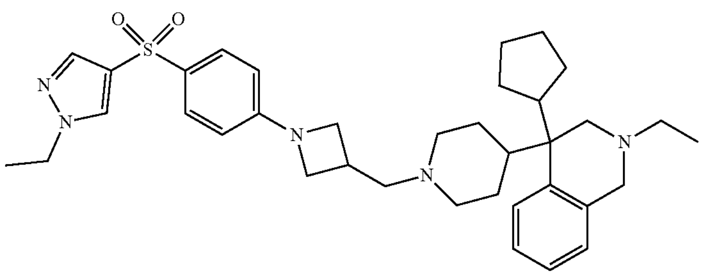 [SMILES: CCN1Cc2ccccc2C(C2CCCC2)(C2CCN(CC3CN(c4ccc(S(=O)(=O)c5cnn(CC)c5)cc4)C3)CC2)C1] | 4-cyclopentyl-2-ethyl-4-(1-((1-(4-((1-ethyl-1H-pyrazol-4-yl)sulfonyl)phenyl)azetidin-3-yl)methyl)piperidin-4-yl)-1,2,3,4-tetrahydroisoquinoline |
| 104 | 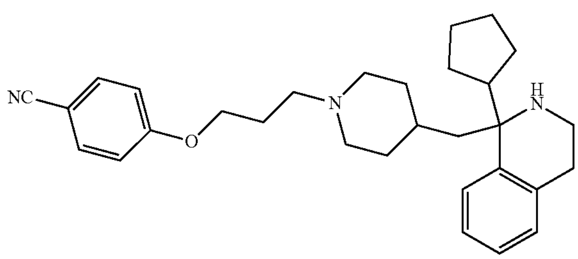 [SMILES: N#Cc1ccc(OCCCN2CCC(CC3(C4CCCC4)NCCc4ccccc43)CC2)cc1] | 4-(3-(4-((1-cyclopentyl-1,2,3,4-tetrahydroisoquinolin-1-yl)methyl)piperidin-1-yl)propoxy)benzonitrile |
| 105 | 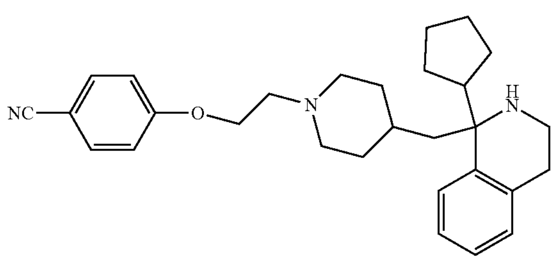 [SMILES: N#Cc1ccc(OCCN2CCC(CC3(C4CCCC4)NCCc4ccccc43)CC2)cc1] | 4-(2-(4-((1-cyclopentyl-1,2,3,4-tetrahydroisoquinolin-1-yl)methyl)piperidin-1-yl)ethoxy)benzonitrile |
| 106 | 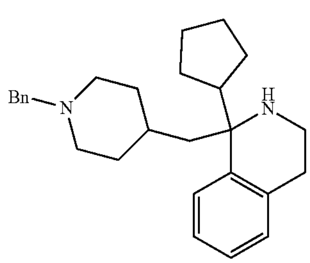 [SMILES: c1ccc(CN2CCC(CC3(C4CCCC4)NCCc4ccccc43)CC2)cc1] | 1-((1-benzylpiperidin-4-yl)methyl)-1-cyclopentyl-1,2,3,4-tetrahydroisoquinoline |
| 107 | 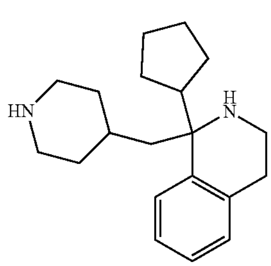 [SMILES: c1ccc2c(c1)CCNC2(CC1CCNCC1)C1CCCC1] | 1-cyclopentyl-1-(piperidin-4-ylmethyl)-1,2,3,4-tetrahydroisoquinoline |

TABLE 1-continued

| Cpd. No. | Chemical Structure | Chemical Name |
|---|---|---|
| 108 | 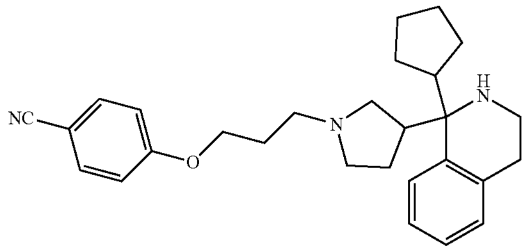 [SMILES: N#Cc1ccc(OCCCN2CCC(C3(C4CCCC4)NCCc4ccccc43)C2)cc1] | 4-(3-(3-(1-cyclopentyl-1,2,3,4-tetrahydroisoquinolin-1-yl)pyrrolidin-1-yl)propoxy)benzonitrile |
| 109 | 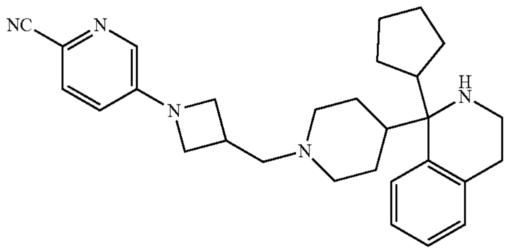 [SMILES: N#Cc1ccc(N2CC(CN3CCC(C4(C5CCCC5)NCCc5ccccc54)CC3)C2)cn1] | 5-(3-((4-(1-cyclopentyl-1,2,3,4-tetrahydroisoquinolin-1-yl)piperidin-1-yl)methyl)azetidin-1-yl)picolinonitrile |
| 110 | 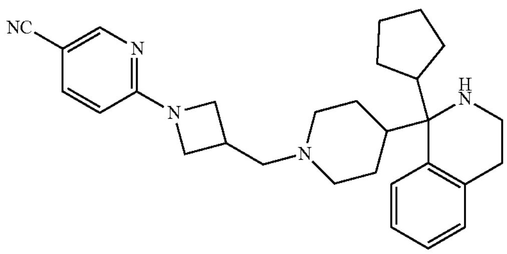 [SMILES: N#Cc1ccc(N2CC(CN3CCC(C4(C5CCCC5)NCCc5ccccc54)CC3)C2)nc1] | 6-(3-((4-(1-cyclopentyl-1,2,3,4-tetrahydroisoquinolin-1-yl)piperidin-1-yl)methyl)azetidin-1-yl)nicotinonitrile |
| 111 | 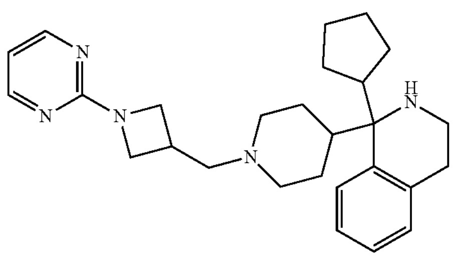 [SMILES: c1cnc(N2CC(CN3CCC(C4(C5CCCC5)NCCc5ccccc54)CC3)C2)nc1] | 1-cyclopentyl-1-(1-((1-(pyrimidin-2-yl)azetidin-3-yl)methyl)piperidin-4-yl)-1,2,3,4-tetrahydroisoquinoline |
| 112 | 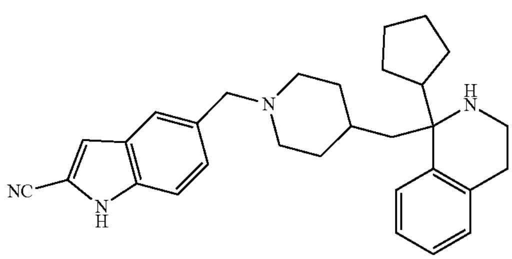 [SMILES: N#Cc1cc2cc(CN3CCC(CC4(C5CCCC5)NCCc5ccccc54)CC3)ccc2[nH]1] | 5-((4-((1-cyclopentyl-1,2,3,4-tetrahydroisoquinolin-1-yl)methyl)piperidin-1-yl)methyl)-1H-indole-2-carbonitrile |
| 113 | 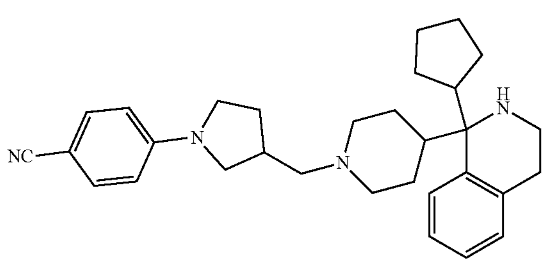 [SMILES: N#Cc1ccc(N2CCC(CN3CCC(C4(C5CCCC5)NCCc5ccccc54)CC3)C2)cc1] | 4-(3-((4-(1-cyclopentyl-1,2,3,4-tetrahydroisoquinolin-1-yl)piperidin-1-yl)methyl)pyrrolidin-1-yl)benzonitrile |

TABLE 1-continued

| Cpd. No. | Chemical Structure | Chemical Name |
|---|---|---|
| 114 | 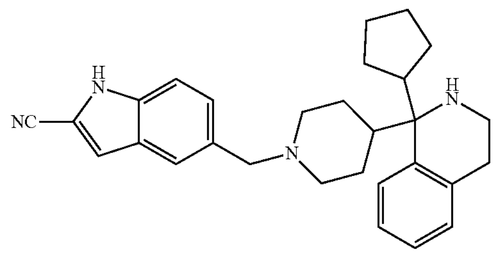 [SMILES: N#Cc1cc2cc(CN3CCC(C4(C5CCCC5)NCCc5ccccc54)CC3)ccc2[nH]1] | 5-((4-(1-cyclopentyl-1,2,3,4-tetrahydroisoquinolin-1-yl)piperidin-1-yl)methyl)-1H-indol-2-carbonitrile |
| 115 | 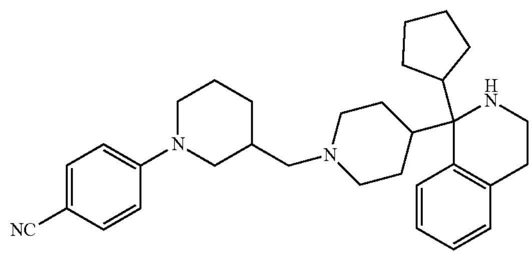 [SMILES: N#Cc1ccc(N2CCCC(CN3CCC(C4(C5CCCC5)NCCc5ccccc54)CC3)C2)cc1] | 4-(3-((4-(1-cyclopentyl-1,2,3,4-tetrahydroisoquinolin-1-yl)piperidin-1-yl)methyl)piperidin-1-yl)benzonitrile |
| 116 | 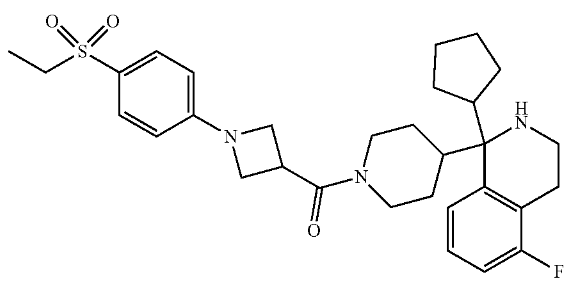 [SMILES: CCS(=O)(=O)c1ccc(N2CC(C(=O)N3CCC(C4(C5CCCC5)NCCc5c(F)cccc54)CC3)C2)cc1] | (4-(1-cyclopentyl-5-fluoro-1,2,3,4-tetrahydroisoquinolin-1-yl)piperidin-1-yl)(1-(4-(ethylsulfonyl)phenyl)azetidin-3-yl)methanone |
| 117 | 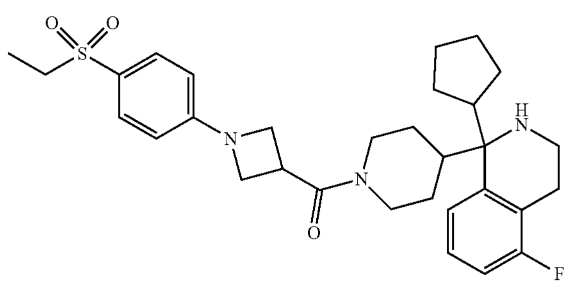 [SMILES: CCS(=O)(=O)c1ccc(N2CC(C(=O)N3CCC(C4(C5CCCC5)NCCc5c(F)cccc54)CC3)C2)cc1] | (4-(1-cyclopentyl-5-fluoro-1,2,3,4-tetrahydroisoquinolin-1-yl)piperidin-1-yl)(1-(4-(ethylsulfonyl)phenyl)piperidin-4-yl)methanone |
| 118 | 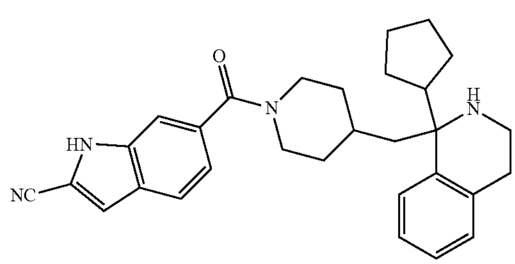 [SMILES: N#Cc1cc2ccc(C(=O)N3CCC(CC4(C5CCCC5)NCCc5ccccc54)CC3)cc2[nH]1] | 6-(4-((1-cyclopentyl-1,2,3,4-tetrahydroisoquinolin-1-yl)methyl)piperidine-1-carbonyl)-1H-indole-2-carbonitrile |

TABLE 1-continued

| Cpd. No. | Chemical Structure | Chemical Name |
|---|---|---|
| 119 | 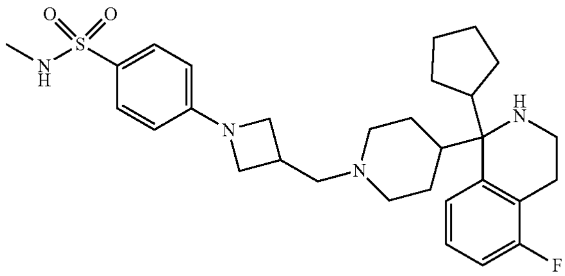 [SMILES: CNS(=O)(=O)c1ccc(N2CC(CN3CCC(C4(C5CCCC5)NCCc5c(F)cccc54)CC3)C2)cc1] | 4-(3-((4-(1-cyclopentyl-5-fluoro-1,2,3,4-tetrahydroisoquinolin-1-yl)piperidin-1-yl)methyl)azetidin-1-yl)-N-methylbenzenesulfonamide |
| 120 | 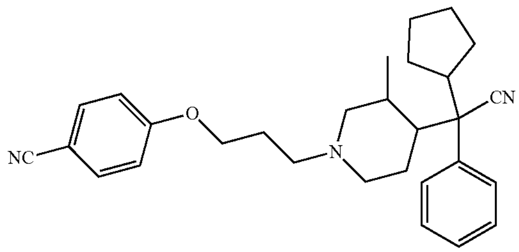 [SMILES: CC1CN(CCCOc2ccc(C#N)cc2)CCC1C(C#N)(c1ccccc1)C1CCCC1] | 4-(3-(4-(cyano(cyclopentyl)(phenyl)methyl)-3-methylpiperidin-1-yl)propoxy)benzonitrile |
| 121 | 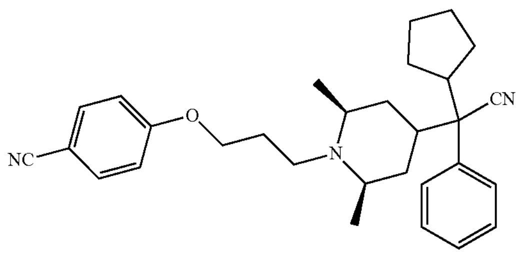 [SMILES: C[C@@H]1CC(C(C#N)(c2ccccc2)C2CCCC2)C[C@H](C)N1CCCOc1ccc(C#N)cc1] | 4-(3-((2S,6R)-4-(cyano(cyclopentyl)(phenyl)methyl)-2,6-dimethylpiperidin-1-yl)propoxy)benzonitrile |
| 122 | 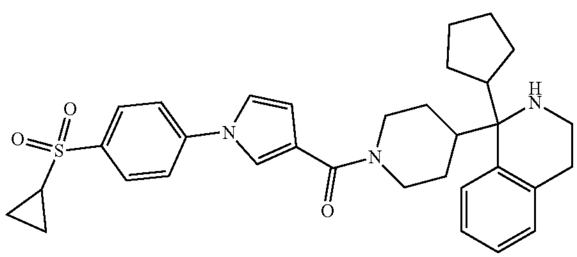 [SMILES: O=C(c1ccn(-c2ccc(S(=O)(=O)C3CC3)cc2)c1)N1CCC(C2(C3CCCC3)NCCc3ccccc32)CC1] | (4-(1-cyclopentyl-1,2,3,4-tetrahydroisoquinolin-1-yl)piperidin-1-yl)(1-(4-(cyclopropylsulfonyl)phenyl)-1H-pyrrol-3-yl)methanone |
| 123 | 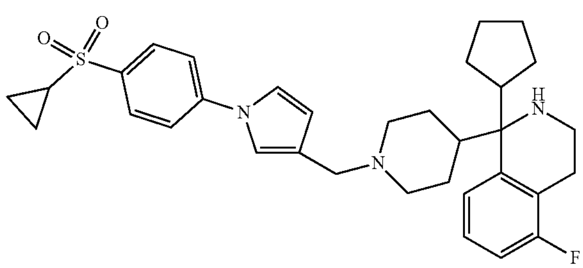 [SMILES: O=S(=O)(c1ccc(-n2ccc(CN3CCC(C4(C5CCCC5)NCCc5c(F)cccc54)CC3)c2)cc1)C1CC1] | 1-cyclopentyl-1-(1-((1-(4-(cyclopropylsulfonyl)phenyl)-1H-pyrrol-3-yl)methyl)piperidin-4-yl)-5-fluoro-1,2,3,4-tetrahydroisoquinoline |
| 124 | 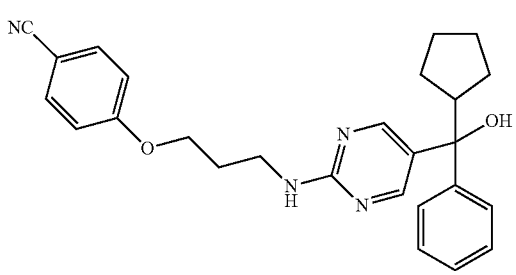 [SMILES: N#Cc1ccc(OCCCNc2ncc(C(O)(c3ccccc3)C3CCCC3)cn2)cc1] | 4-(3-((5-(cyclopentyl(hydroxy)(phenyl)methyl)pyrimidin-2-yl)amino)propoxy)benzonitrile |

TABLE 1-continued

| Cpd. No. | Chemical Structure | Chemical Name |
|---|---|---|
| 125 | 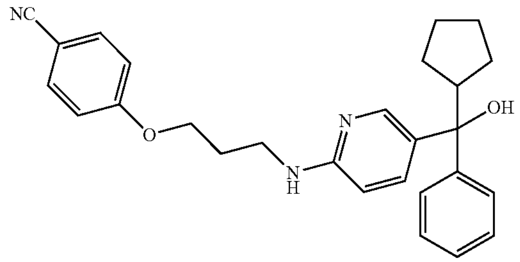 [SMILES: N#Cc1ccc(OCCCNc2ccc(C(O)(c3ccccc3)C3CCCC3)cn2)cc1] | 4-(3-((5-(cyclopentyl(hydroxy)(phenyl)methyl)pyridin-2-yl)amino)propoxy)benzonitrile |
| 126 | 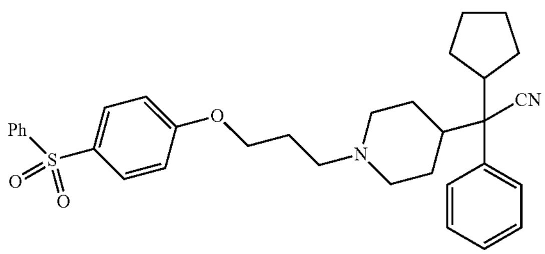 [SMILES: N#CC(c1ccccc1)(C1CCCC1)C1CCN(CCCOc2ccc(S(=O)(=O)c3ccccc3)cc2)CC1] | 2-cyclopentyl-2-phenyl-2-(1-(3-(4-(phenylsulfonyl)phenoxy)propyl)piperidin-4-yl)acetonitrile |
| 127 | 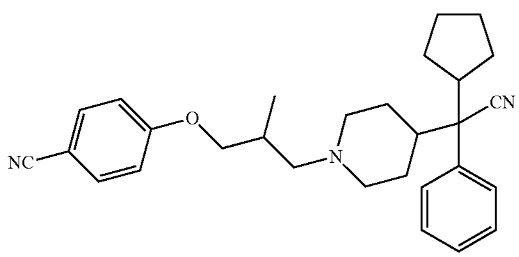 [SMILES: CC(COc1ccc(C#N)cc1)CN1CCC(C(C#N)(c2ccccc2)C2CCCC2)CC1] | 4-(3-(4-(cyano(cyclopentyl)(phenyl)methyl)piperidin-1-yl)-2-methylpropoxy)benzonitrile |
| 128 | 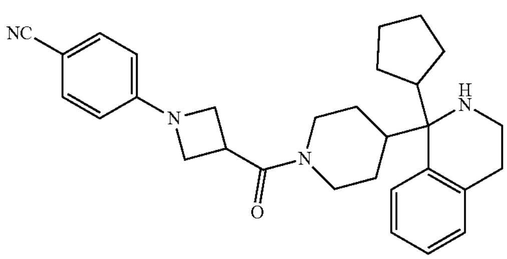 [SMILES: N#Cc1ccc(N2CC(C(=O)N3CCC(C4(C5CCCC5)NCCc5ccccc54)CC3)C2)cc1] | 4-(3-(4-(1-cyclopentyl-1,2,3,4-tetrahydroisoquinolin-1-yl)piperidine-1-carbonyl)azetidin-1-yl)benzonitrile |
| 129 | 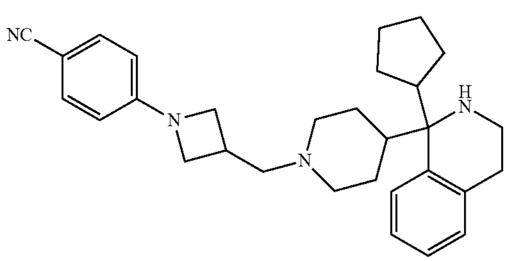 | 4-(3-((4-(1-cyclopentyl-1,2,3,4-tetrahydroisoquinolin-1-yl)piperidin-1-yl)methyl)azetidin-1-yl)benzonitrile |
| 130 | 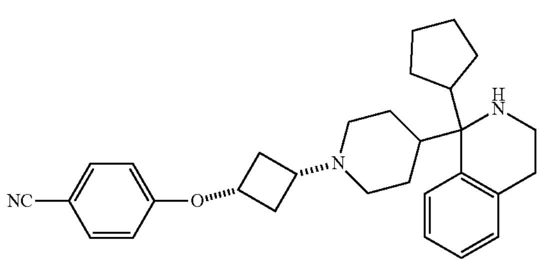 | 4-((1s,3s)-3-(4-(1-cyclopentyl-1,2,3,4-tetrahydroisoquinolin-1-yl)piperidin-1-yl)cyclobutoxy)benzonitrile |

US 10,899,738 B2

TABLE 1-continued

| Cpd. No. | Chemical Structure | Chemical Name |
|---|---|---|
| 131 | 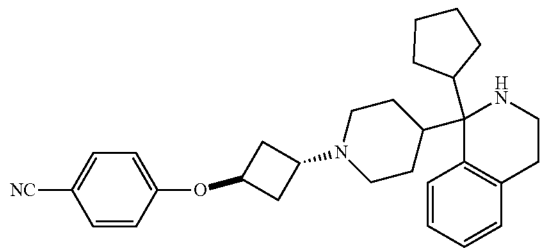 | 4-((1r,3r)-3-(4-(1-cyclopentyl-1,2,3,4-tetrahydroisoquinolin-1-yl)piperidin-1-yl)cyclobutoxy)benzonitrile |
| 132 | 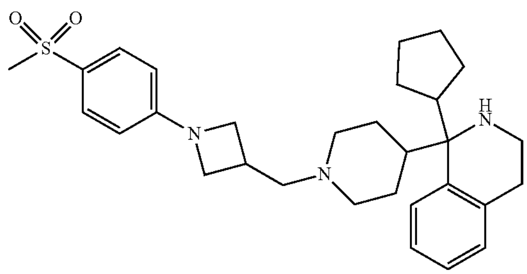 [SMILES: CS(=O)(=O)c1ccc(N2CC(CN3CCC(C4(C5CCCC5)NCCc5ccccc54)CC3)C2)cc1] | 1-cyclopentyl-1-(1-((1-(4-(methylsulfonyl)phenyl)azetidin-3-yl)methyl)piperidin-4-yl)-1,2,3,4-tetrahydroisoquinoline |
| 133 | 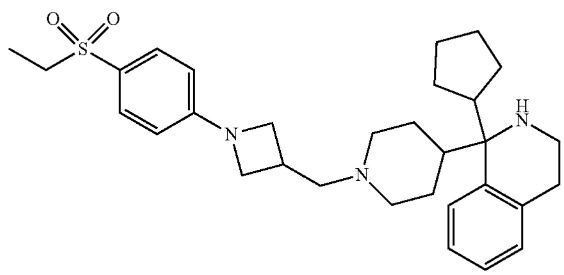 [SMILES: CCS(=O)(=O)c1ccc(N2CC(CN3CCC(C4(C5CCCC5)NCCc5ccccc54)CC3)C2)cc1] | 1-cyclopentyl-1-(1-((1-(4-(ethylsulfonyl)phenyl)azetidin-3-yl)methyl)piperidin-4-yl)-1,2,3,4-tetrahydroisoquinoline |
| 134 | 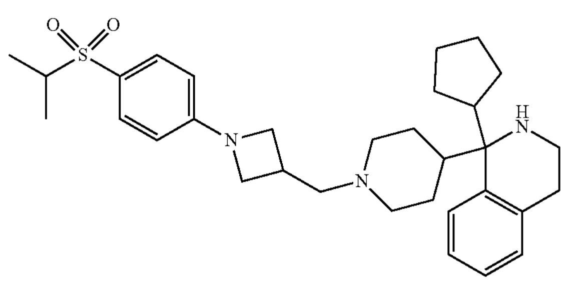 [SMILES: CC(C)S(=O)(=O)c1ccc(N2CC(CN3CCC(C4(C5CCCC5)NCCc5ccccc54)CC3)C2)cc1] | 1-cyclopentyl-1-(1-((1-(4-(isopropylsulfonyl)phenyl)azetidin-3-yl)methyl)piperidin-4-yl)-1,2,3,4-tetrahydroisoquinoline |
| 135 | 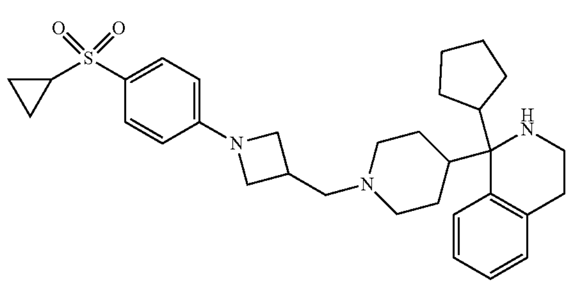 [SMILES: O=S(=O)(c1ccc(N2CC(CN3CCC(C4(C5CCCC5)NCCc5ccccc54)CC3)C2)cc1)C1CC1] | 1-cyclopentyl-1-(1-((1-(4-(cyclopropylsulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 136 | 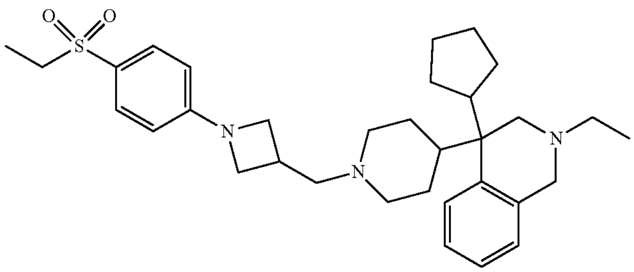 [SMILES: CCN1Cc2ccccc2C(C2CCCC2)(C2CCN(CC3CN(c4ccc(S(=O)(=O)CC)cc4)C3)CC2)C1] | 4-cyclopentyl-2-ethyl-4-(1-((1-(4-(ethylsulfonyl)phenyl)azetidin-3-yl)methyl)piperidin-4-yl)-1,2,3,4-tetrahydroisoquinoline |
| 137 | 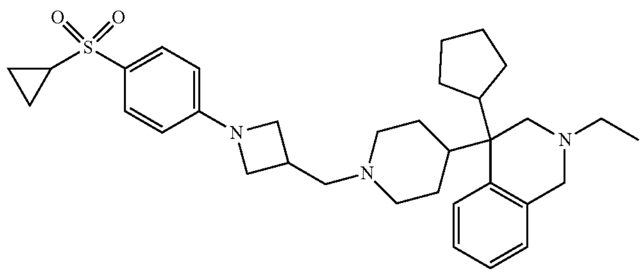 [SMILES: CCN1Cc2ccccc2C(C2CCCC2)(C2CCN(CC3CN(c4ccc(S(=O)(=O)C5CC5)cc4)C3)CC2)C1] | 4-cyclopentyl-4-(1-((1-(4-(cyclopropylsulfonyl)phenyl)azetidin-3-yl)methyl)piperidin-4-yl)-2-ethyl-1,2,3,4-tetrahydroisoquinoline |
| 138 | 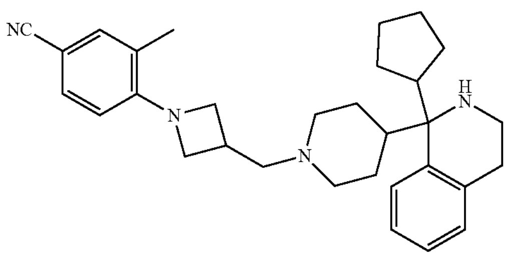 [SMILES: Cc1cc(C#N)ccc1N1CC(CN2CCC(C3(C4CCCC4)NCCc4ccccc43)CC2)C1] | 4-(3-((4-(1-cyclopentyl-1,2,3,4-tetrahydroisoquinolin-1-yl)piperidin-1-yl)methyl)azetidin-1-yl)-3-methylbenzonitrile |
| 139 | 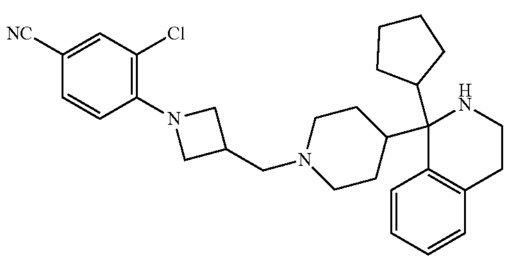 [SMILES: N#Cc1ccc(N2CC(CN3CCC(C4(C5CCCC5)NCCc5ccccc54)CC3)C2)c(Cl)c1] | 3-chloro-4-(3-((4-(1-cyclopentyl-1,2,3,4-tetrahydroisoquinolin-1-yl)piperidin-1-yl)methyl)azetidin-1-yl)benzonitrile |
| 140 | 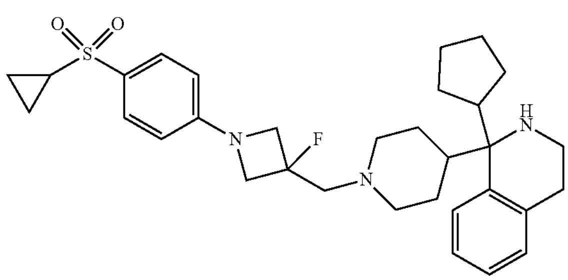 [SMILES: O=S(=O)(c1ccc(N2CC(F)(CN3CCC(C4(C5CCCC5)NCCc5ccccc54)CC3)C2)cc1)C1CC1] | 1-cyclopentyl-1-(1-((1-(4-(cyclopropylsulfonyl)phenyl)-3-fluoroazetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 141 | 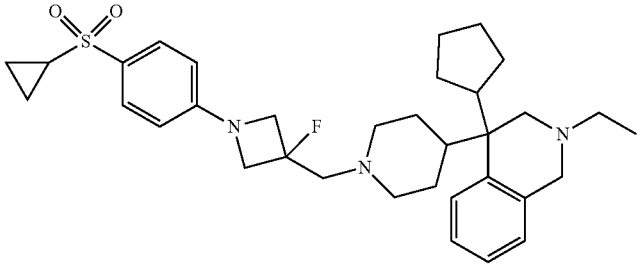 [SMILES: CCN1Cc2ccccc2C(C2CCCC2)(C2CCN(CC3(F)CN(c4ccc(S(=O)(=O)C5CC5)cc4)C3)CC2)C1] | 4-cyclopentyl-4-(1-((1-(4-(cyclopropylsulfonyl)phenyl)-3-fluoroazetidin-3-yl)methyl)piperidin-4-yl)-2-ethyl-1,2,3,4-tetrahy36droisoquinoline |
| 142 | 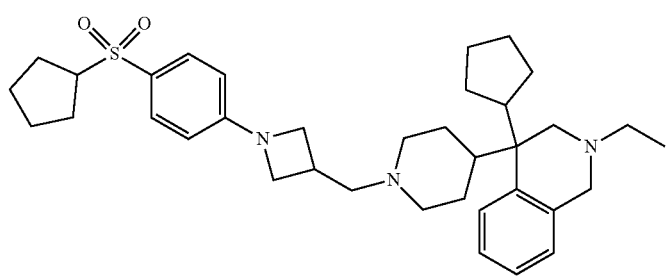 [SMILES: CCN1Cc2ccccc2C(C2CCCC2)(C2CCN(CC3CN(c4ccc(S(=O)(=O)C5CCCC5)cc4)C3)CC2)C1] | 4-cyclopentyl-4-(1-((1-(4-(cyclopentylsulfonyl)phenyl)azetidin-3-yl)methyl)piperidin-4-yl)-2-ethyl-1,2,3,4-tetrahydroisoquinoline |
| 143 | 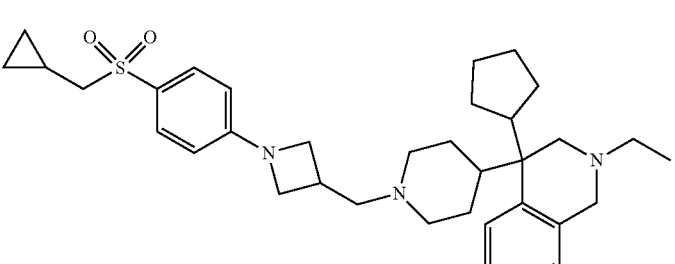 | 4-cyclopentyl-4-(1-((1-(4-((cyclopropylmethyl)sulfonyl)phenyl)azetidin-3-yl)methyl)piperidin-4-yl)-2-ethyl-1,2,3,4-tetrahydroisoquinoline |
| 144 | 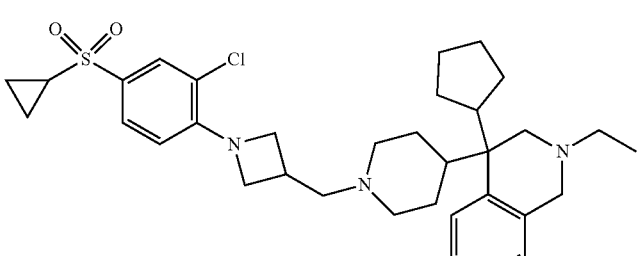 | 4-(1-((1-(2-chloro-4-(cyclopropylsulfonyl)phenyl)azetidin-3-yl)methyl)piperidin-4-yl)-4-cyclopentyl-2-ethyl-1,2,3,4-tetrahydroisoquinoline |
| 145 | 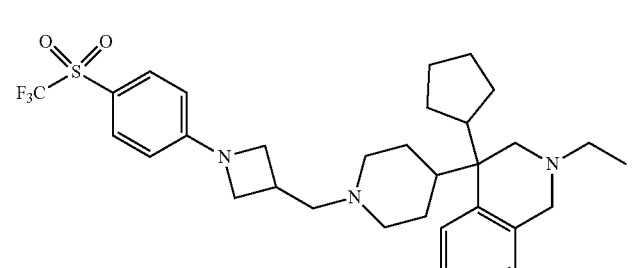 | 4-cyclopentyl-2-ethyl-4-(1-((1-(4-((trifluoromethyl)sulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 146 | 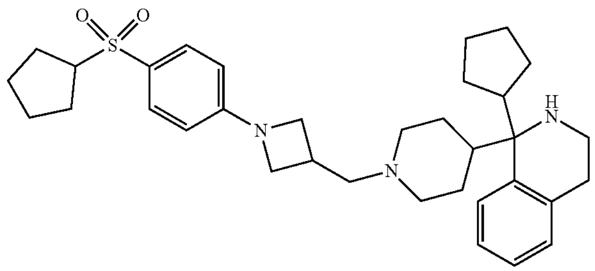 [SMILES: O=S(=O)(c1ccc(N2CC(CN3CCC(C4(C5CCCC5)NCCc5ccccc54)CC3)C2)cc1)C1CCCC1] | 1-cyclopentyl-1-(1-((1-(4-(cyclopentylsulfonyl)phenyl)azetidin-3-yl)methyl)piperidin-4-yl)-1,2,3,4-tetrahydroisoquinoline |
| 147 | 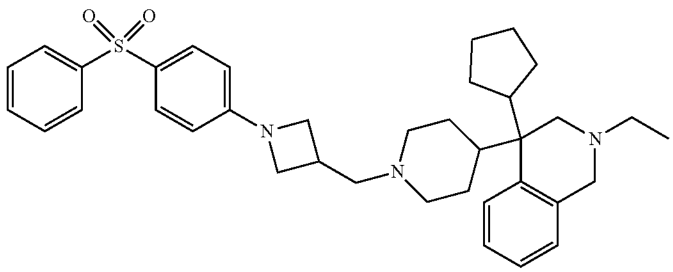 [SMILES: CCN1Cc2ccccc2C(C2CCCC2)(C2CCN(CC3CN(c4ccc(S(=O)(=O)c5ccccc5)cc4)C3)CC2)C1] | 4-cyclopentyl-2-ethyl-4-(1-((1-(4-(phenylsulfonyl)phenyl)azetidin-3-yl)methyl)piperidin-4-yl)-1,2,3,4-tetrahydroisoquinoline |
| 148 | 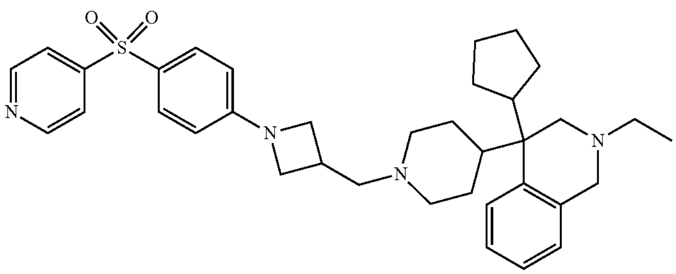 [SMILES: CCN1Cc2ccccc2C(C2CCCC2)(C2CCN(CC3CN(c4ccc(S(=O)(=O)c5ccncc5)cc4)C3)CC2)C1] | 4-cyclopentyl-2-ethyl-4-(1-((1-(4-(pyridin-4-ylsulfonyl)phenyl)azetidin-3-yl)methyl)piperidin-4-yl)-1,2,3,4-tetrahydroisoquinoline |
| 149 | 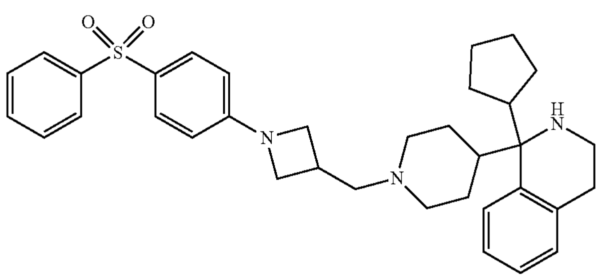 [SMILES: O=S(=O)(c1ccccc1)c1ccc(N2CC(CN3CCC(C4(C5CCCC5)NCCc5ccccc54)CC3)C2)cc1] | 1-cyclopentyl-1-(1-((1-(4-(phenylsulfonyl)phenyl)azetidin-3-yl)methyl)piperidin-4-yl)-1,2,3,4-tetrahydroisoquinoline |
| 151 | 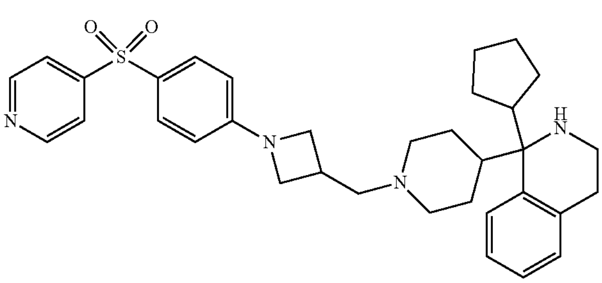 [SMILES: O=S(=O)(c1ccncc1)c1ccc(N2CC(CN3CCC(C4(C5CCCC5)NCCc5ccccc54)CC3)C2)cc1] | 1-cyclopentyl-1-(1-((1-(4-(pyridin-4-ylsulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 152 | 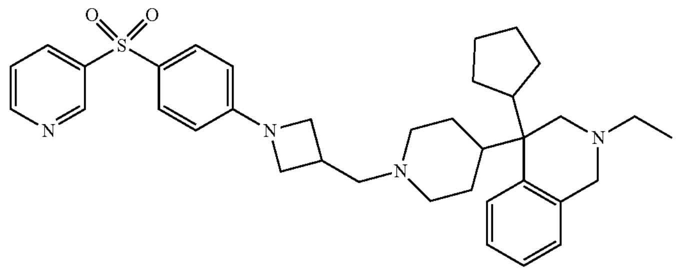 [SMILES: CCN1Cc2ccccc2C(C2CCCC2)(C2CCN(CC3CN(c4ccc(S(=O)(=O)c5cccnc5)cc4)C3)CC2)C1] | 4-cyclopentyl-2-ethyl-4-(1-((1-(4-(pyridin-3-ylsulfonyl)phenyl)azetidin-3-yl)methyl)piperidin-4-yl)-1,2,3,4-tetrahydroisoquinoline |
| 153 | 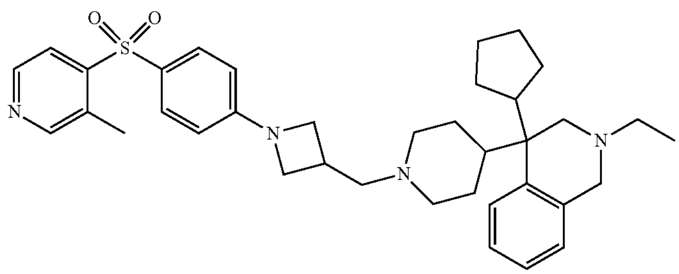 [SMILES: CCN1Cc2ccccc2C(C2CCCC2)(C2CCN(CC3CN(c4ccc(S(=O)(=O)c5ccncc5C)cc4)C3)CC2)C1] | 4-cyclopentyl-2-ethyl-4-(1-((1-(4-((3-methylpyridin-4-yl)sulfonyl)phenyl)azetidin-3-yl)methyl)piperidin-4-yl)-1,2,3,4-tetrahydroisoquinoline |
| 154 | 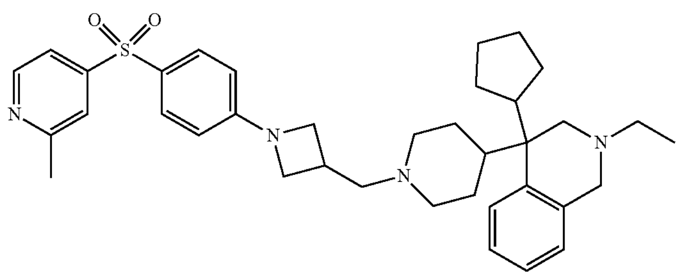 [SMILES: CCN1Cc2ccccc2C(C2CCCC2)(C2CCN(CC3CN(c4ccc(S(=O)(=O)c5ccnc(C)c5)cc4)C3)CC2)C1] | 4-cyclopentyl-2-ethyl-4-(1-((1-(4-((2-methylpyridin-4-yl)sulfonyl)phenyl)azetidin-3-yl)methyl)piperidin-4-yl)-1,2,3,4-tetrahydroisoquinoline |
| 155 | 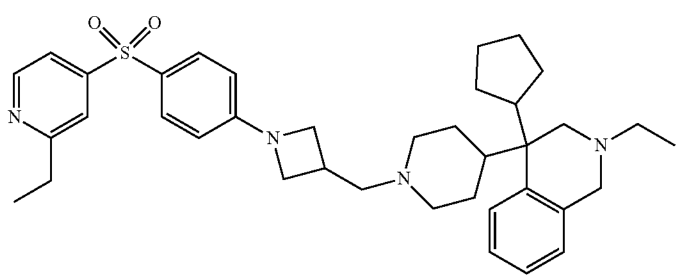 [SMILES: CCc1cc(S(=O)(=O)c2ccc(N3CC(CN4CCC(C5(C6CCCC6)CN(CC)Cc6ccccc65)CC4)C3)cc2)ccn1] | 4-cyclopentyl-2-ethyl-4-(1-((1-(4-((2-ethylpyridin-4-yl)sulfonyl)phenyl)azetidin-3-yl)methyl)piperidin-4-yl)-1,2,3,4-tetrahydroisoquinoline |
| 156 | 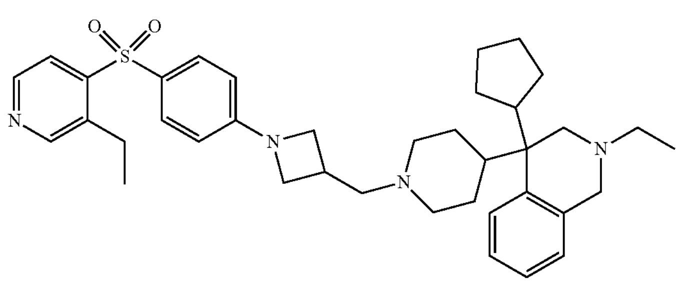 [SMILES: CCc1cnccc1S(=O)(=O)c1ccc(N2CC(CN3CCC(C4(C5CCCC5)CN(CC)Cc5ccccc54)CC3)C2)cc1] | 4-cyclopentyl-2-ethyl-4-(1-((1-(4-((3-ethylpyridin-4-yl)sulfonyl)phenyl)azetidin-3-yl)methyl)piperidin-4-yl)-1,2,3,4-tetrahydroisoquinoline |

| Cpd. No. | Chemical Structure | Chemical Name |
|---|---|---|
| 157 | 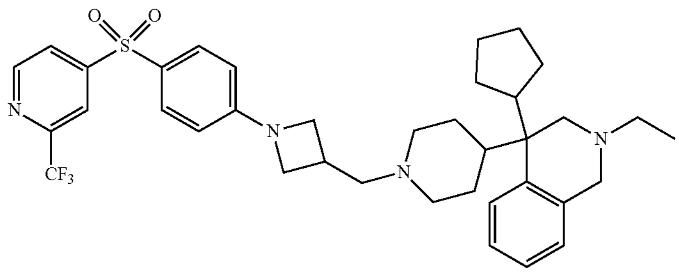 [SMILES: CCN1Cc2ccccc2C(C2CCCC2)(C2CCN(CC3CN(c4ccc(S(=O)(=O)c5ccnc(C(F)(F)F)c5)cc4)C3)CC2)C1] | 4-cyclopentyl-2-ethyl-4-(1-((1-(4-((2-(trifluoromethyl)pyridin-4-yl)sulfonyl)phenyl)azetidin-3-yl)methyl)piperidin-4-yl)-1,2,3,4-tetrahydroisoquinoline |
| 158 | 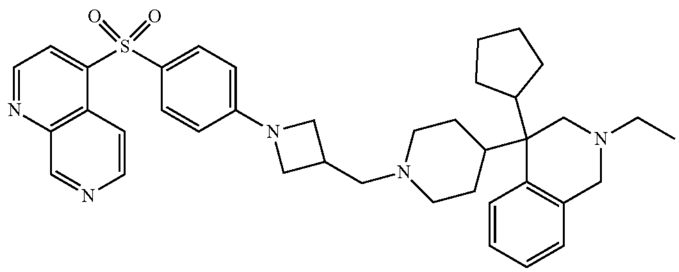 [SMILES: CCN1Cc2ccccc2C(C2CCCC2)(C2CCN(CC3CN(c4ccc(S(=O)(=O)c5ccnc6cnccc56)cc4)C3)CC2)C1] | 4-((4-(3-((4-(4-cyclopentyl-2-ethyl-1,2,3,4-tetrahydroisoquinolin-4-yl)piperidin-1-yl)methyl)azetidin-1-yl)phenyl)sulfonyl)-1,7-naphthyridine |
| 159 | 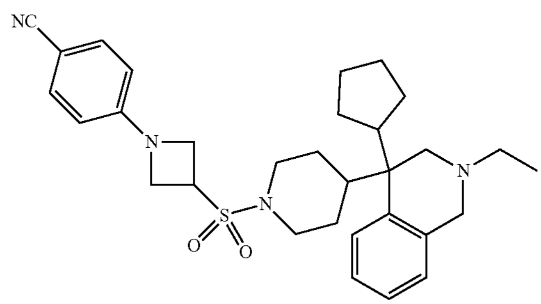 [SMILES: CCN1Cc2ccccc2C(C2CCCC2)(C2CCN(S(=O)(=O)C3CN(c4ccc(C#N)cc4)C3)CC2)C1] | 4-(3-((4-(4-cyclopentyl-2-ethyl-1,2,3,4-tetrahydroisoquinolin-4-yl)piperidin-1-yl)sulfonyl)azetidin-1-yl)benzonitrile |
| 160 | 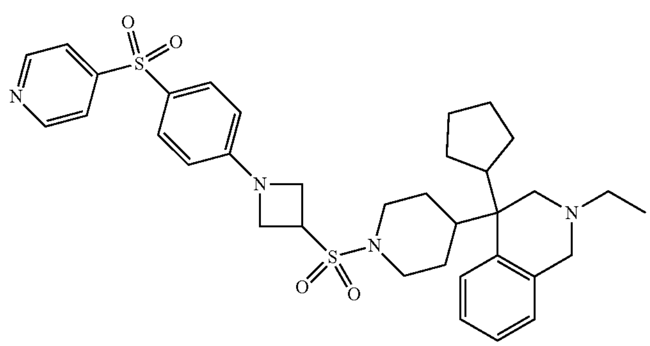 [SMILES: CCN1Cc2ccccc2C(C2CCCC2)(C2CCN(S(=O)(=O)C3CN(c4ccc(S(=O)(=O)c5ccncc5)cc4)C3)CC2)C1] | 4-cyclopentyl-2-ethyl-4-(1-((1-(4-(pyridin-4-ylsulfonyl)phenyl)azetidin-3-yl)sulfonyl)piperidin-4-yl)-1,2,3,4-tetrahydroisoquinoline |
| 161 | 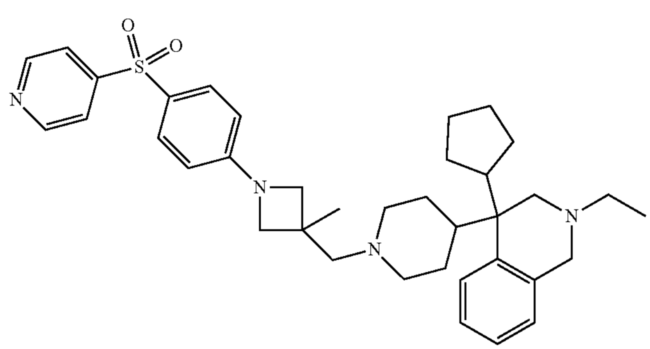 [SMILES: CCN1Cc2ccccc2C(C2CCCC2)(C2CCN(CC3(C)CN(c4ccc(S(=O)(=O)c5ccncc5)cc4)C3)CC2)C1] | 4-cyclopentyl-2-ethyl-4-(1-((3-methyl-1-(4-(pyridin-4-ylsulfonyl)phenyl)azetidin-3-yl)methyl)piperidin-4-yl)-1,2,3,4-tetrahydroisoquinoline |

TABLE 1-continued

| Cpd. No. | Chemical Structure | Chemical Name |
|---|---|---|
| 162 | 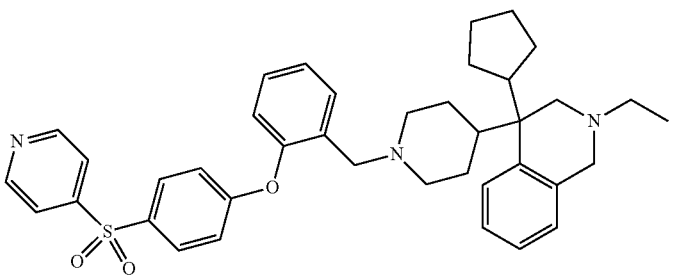 [SMILES: CCN1Cc2ccccc2C(C2CCCC2)(C2CCN(Cc3ccccc3Oc3ccc(S(=O)(=O)c4ccncc4)cc3)CC2)C1] | 4-cyclopentyl-2-ethyl-4-(1-(2-(4-(pyridin-4-ylsulfonyl)phenoxy)benzyl)piperidin-4-yl)-1,2,3,4-tetrahydroisoquinoline |
| 163 | 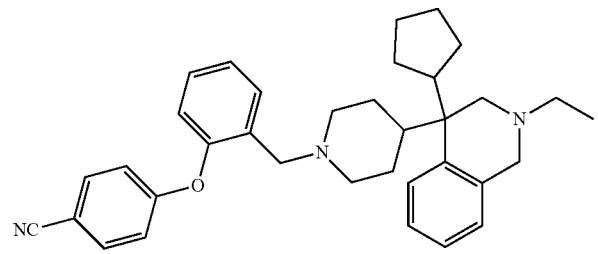 [SMILES: CCN1Cc2ccccc2C(C2CCCC2)(C2CCN(Cc3ccccc3Oc3ccc(C#N)cc3)CC2)C1] | 4-(2-((4-(4-cyclopentyl-2-ethyl-1,2,3,4-tetrahydroisoquinolin-4-yl)piperidin-1-yl)methyl)phenoxy)benzonitrile |
| 164 | 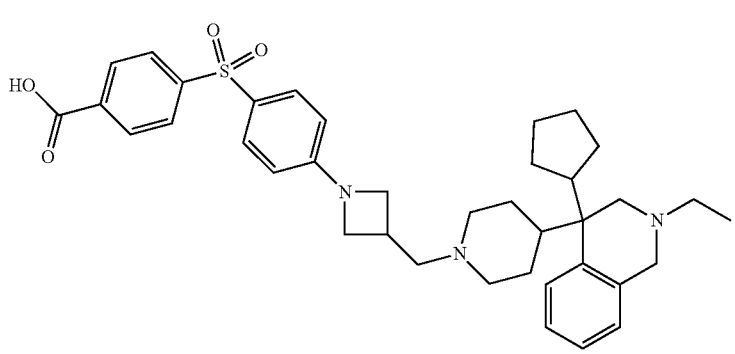 [SMILES: CCN1Cc2ccccc2C(C2CCCC2)(C2CCN(CC3CN(c4ccc(S(=O)(=O)c5ccc(C(=O)O)cc5)cc4)C3)CC2)C1] | 4-((4-(3-((4-(4-cyclopentyl-2-ethyl-1,2,3,4-tetrahydroisoquinolin-4-yl)piperidin-1-yl)methyl)azetidin-1-yl)phenyl)sulfonyl)benzoic acid |
| 165 | 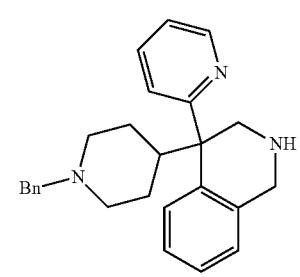 [SMILES: c1ccc(CN2CCC(C3(c4ccccn4)CNCc4ccccc43)CC2)cc1] | 4-(1-benzylpiperidin-4-yl)-4-(pyridin-2-yl)-1,2,3,4-tetrahydroisoquinoline |
| 166 | 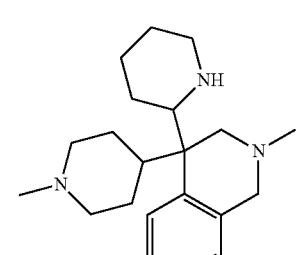 | 2-methyl-4-(1-methylpiperidin-4-yl)-4-(piperidin-2-yl)-1,2,3,4-tetrahydroisoquinoline |

TABLE 1-continued

| Cpd. No. | Chemical Structure | Chemical Name |
|---|---|---|
| 167 | 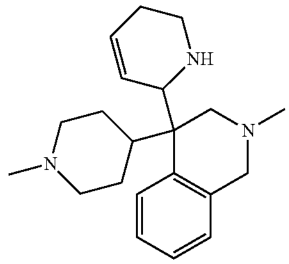 | 2-methyl-4-(1-methylpiperidin-4-yl)-4-(1,2,5,6-tetrahydropyridin-2-yl)-1,2,3,4-tetrahydroisoquinoline |
| 168 | 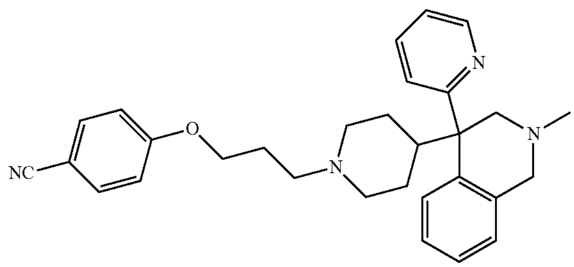 [SMILES: CN1Cc2ccccc2C(c2ccccn2)(C2CCN(CCCOc3ccc(C#N)cc3)CC2)C1] | 4-(3-(4-(2-methyl-4-(pyridin-2-yl)-1,2,3,4-tetrahydroisoquinolin-4-yl)pyridin-1-yl)propoxy)benzonitrile |
| 169 | 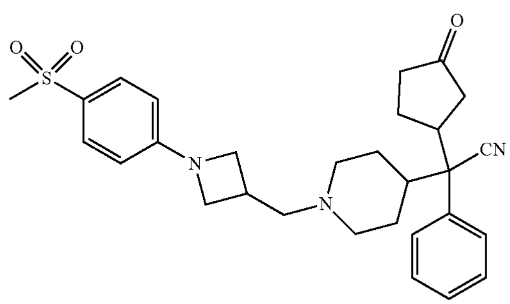 [SMILES: CS(=O)(=O)c1ccc(N2CC(CN3CCC(C(C#N)(c4ccccc4)C4CCC(=O)C4)CC3)C2)cc1] | 2-(1-((1-(4-(methylsulfonyl)phenyl)azetidin-3-yl)methyl)piperidin-4-yl)-2-(3-oxocyclopentyl)-2-phenylacetonitrile |
| 170 | 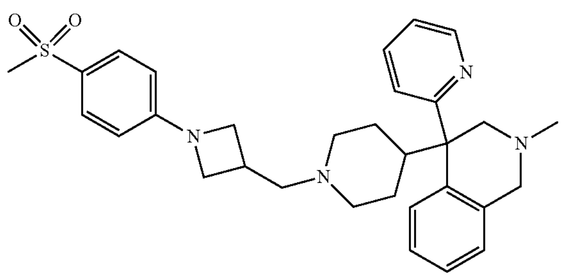 | 2-methyl-4-(1-((1-(4-(methylsulfonyl)phenyl)azetidin-3-yl)methyl)piperidin-4-yl)-4-(pyridin-2-yl)-1,2,3,4-tetrahydroisoquinoline |
| 171 | 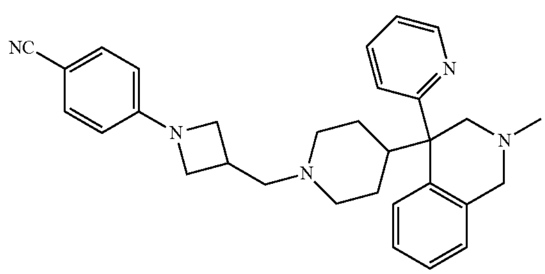 [SMILES: CN1Cc2ccccc2C(c2ccccn2)(C2CCN(CC3CN(c4ccc(C#N)cc4)C3)CC2)C1] | 4-(3-((4-(2-methyl-4-(pyridin-2-yl)-1,2,3,4-tetrahydroisoquinolin-4-yl)piperidin-1-yl)methyl)azetidin-1-yl)benzonitrile |

TABLE 1-continued

| Cpd. No. | Chemical Structure | Chemical Name |
|---|---|---|
| 172 | 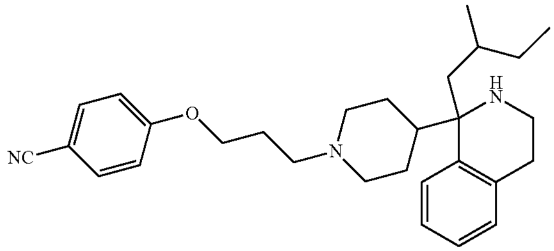 [SMILES: CCC(C)CC1(C2CCN(CCCOc3ccc(C#N)cc3)CC2)NCCc2ccccc21] | 4-(3-(4-(1-(2-methylbutyl)-1,2,3,4-tetrahydroisoquinolin-1-yl)piperidin-1-yl)propoxy)benzonitrile |
| 173 | 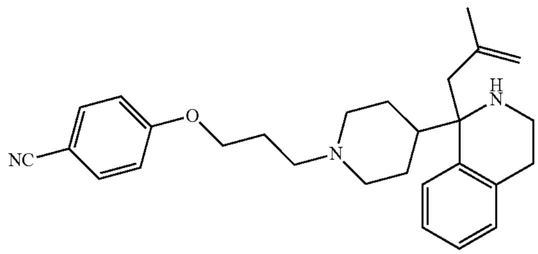 [SMILES: C=C(C)CC1(C2CCN(CCCOc3ccc(C#N)cc3)CC2)NCCc2ccccc21] | 4-(3-(4-(1-(2-methylallyl)-1,2,3,4-tetrahydroisoquinolin-1-yl)piperidin-1-yl)propoxy)benzonitrile |
| 174 | 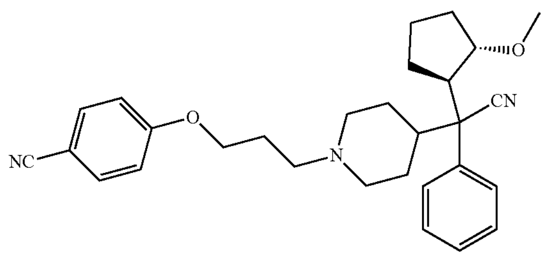 [SMILES: CO[C@H]1CCC[C@@H]1C(C#N)(c1ccccc1)C1CCN(CCCOc2ccc(C#N)cc2)CC1] | 4-(3-(4-(cyano((1R,2S)-2-methoxycyclopentyl)(phenyl)methyl)piperidin-1-yl)propoxy)benzonitrile |
| 175 | 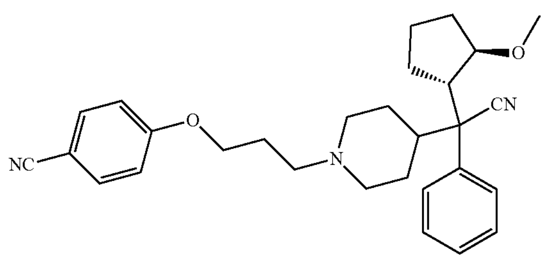 [SMILES: CO[C@@H]1CCC[C@H]1C(C#N)(c1ccccc1)C1CCN(CCCOc2ccc(C#N)cc2)CC1] | rac-4-(3-(4-(cyano((1S,2R)-2-methoxycyclopentyl)(phenyl)methyl)piperidin-1-yl)propoxy)benzonitrile |
| 176 | 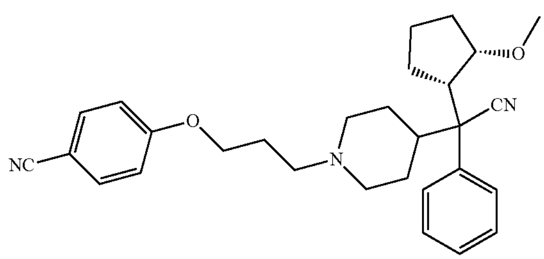 [SMILES: CO[C@H]1CCC[C@H]1C(C#N)(c1ccccc1)C1CCN(CCCOc2ccc(C#N)cc2)CC1] | rac-4-(3-(4-(cyano((1S,2S)-2-methoxycyclopentyl)(phenyl)methyl)piperidin-1-yl)propoxy)benzonitrile |
| 177 | 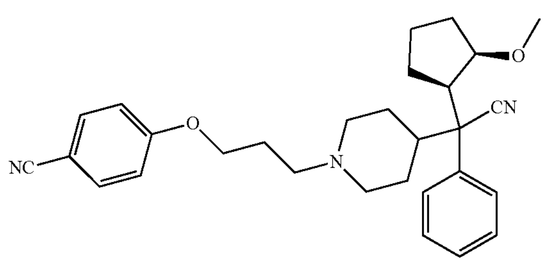 [SMILES: CO[C@@H]1CCC[C@@H]1C(C#N)(c1ccccc1)C1CCN(CCCOc2ccc(C#N)cc2)CC1] | rac-4-(3-(4-(cyano((1R,2R)-2-methoxycyclopentyl)(phenyl)methyl)piperidin-1-yl)propoxy)benzonitrile |

TABLE 1-continued

| Cpd. No. | Chemical Structure | Chemical Name |
|---|---|---|
| 178 | 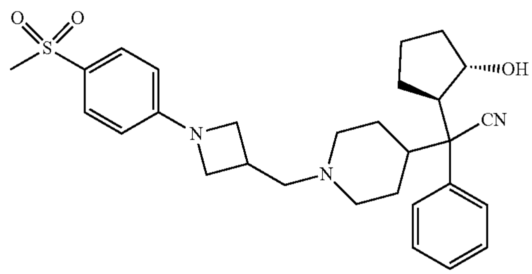 [SMILES: CS(=O)(=O)c1ccc(N2CC(CN3CCC(C(C#N)(c4ccccc4)[C@H]4CCC[C@@H]4O)CC3)C2)cc1] | rac-2-((1R,2S)-2-hydroxycyclopentyl)-2-(1-((1-(4-(methylsulfonyl)phenyl)azitidin-3-yl)methyl)piperidin-4-yl)-2-phenylacetonitrile |
| 179 | 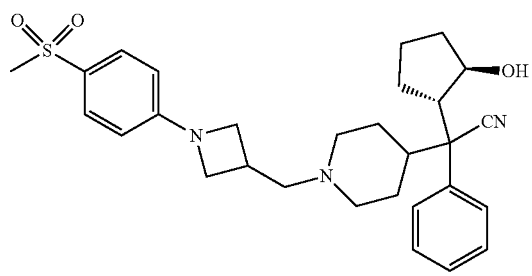 [SMILES: CS(=O)(=O)c1ccc(N2CC(CN3CCC(C(C#N)(c4ccccc4)[C@@H]4CCC[C@H]4O)CC3)C2)cc1] | rac-2-((1S,2R)-2-hydroxycyclopentyl)-2-(1-((1-(4-(methylsulfonyl)phenyl)azetidin-3-yl)methyl)piperidin-4-yl)-2-phenylacetonitrile |
| 180 | 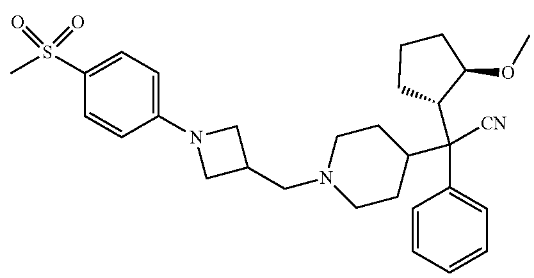 | rac-2-((1S,2R)-2-methoxycyclopentyl)-2-(1-((1-(4-(methylsulfonyl)phenyl)azetidin-3-yl)methyl)piperidin-4-yl)-2-phenylacetonitrile |
| 181 | 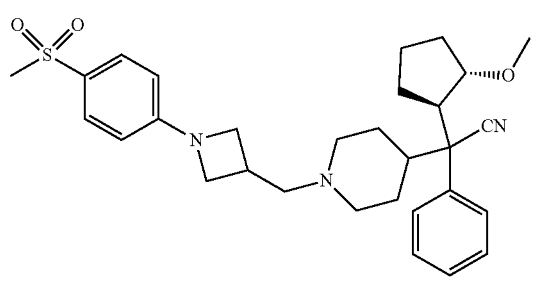 | rac-2-((1R,2S)-2-methoxycyclopentyl)-2-(1-((1-(4-(methylsulfonyl)phneyl)azetidin-3-yl)methyl)piperidin-4-yl)-2-phenylacetonitrile |
| 182 | 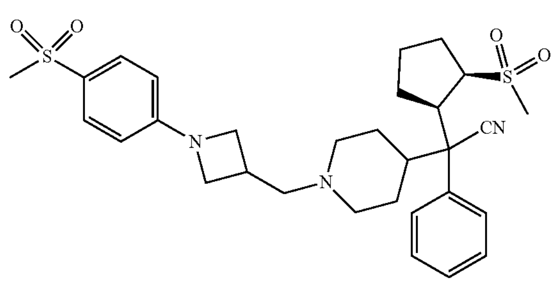 [SMILES: CS(=O)(=O)c1ccc(N2CC(CN3CCC(C(C#N)(c4ccccc4)[C@H]4CCC[C@H]4S(C)(=O)=O)CC3)C2)cc1] | rac-2-((1R,2R)-2-(methylsulfonyl)cyclopentyl)-2-(1-((1-(4-(methylsulfonyl)phenyl)azetidin-3-yl)methyl)piperidin-4-yl)-2-phenylacetonitrile |

TABLE 1-continued

| Cpd. No. | Chemical Structure | Chemical Name |
|---|---|---|
| 183 | 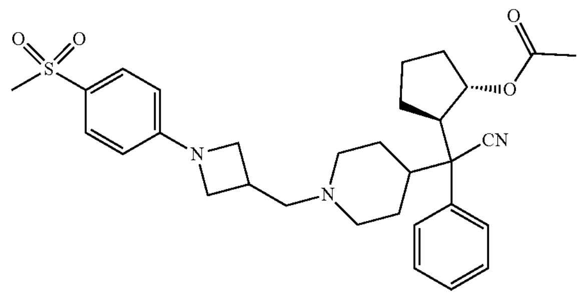 [SMILES: CC(=O)O[C@H]1CCC[C@@H]1C(C#N)(c1ccccc1)C1CCN(CC2CN(c3ccc(S(C)(=O)=O)cc3)C2)CC1] | rac-(1S,2R)-2-(cyano(1-((1-(4-(methylsulfonyl)phenyl)azetidin-3-yl)methyl)piperidin-4-yl)(phenyl)methyl)cyclopentyl acetate |
| 184 | 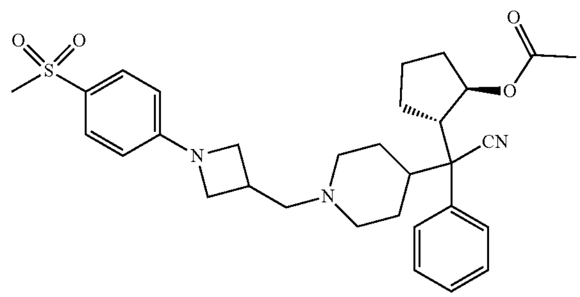 [SMILES: CC(=O)O[C@@H]1CCC[C@H]1C(C#N)(c1ccccc1)C1CCN(CC2CN(c3ccc(S(C)(=O)=O)cc3)C2)CC1] | rac-(1R,2S)-2-(cyano(1-((1-(4-(methylsulfonyl)phenyl)azetidin-3-yl)methyl)piperidin-4-yl)(phenyl)methyl)cyclopentyl actate |
| 185 | 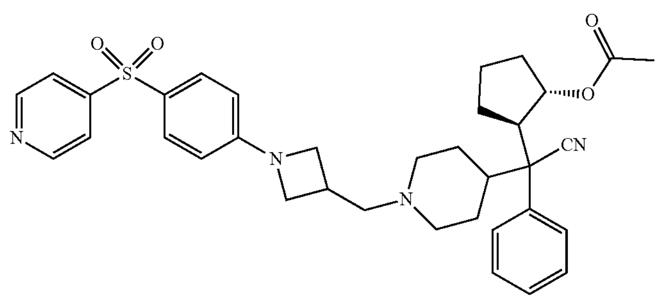 [SMILES: CC(=O)O[C@H]1CCC[C@@H]1C(C#N)(c1ccccc1)C1CCN(CC2CN(c3ccc(S(=O)(=O)c4ccncc4)cc3)C2)CC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl acetate |
| 186 | 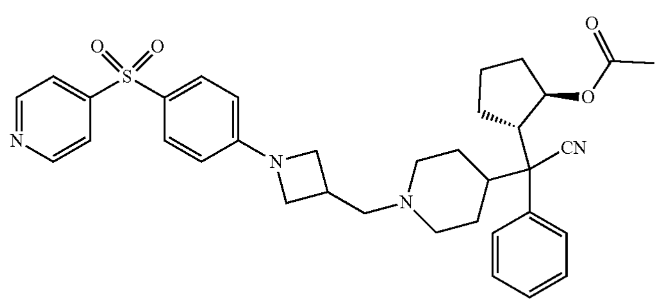 [SMILES: CC(=O)O[C@@H]1CCC[C@H]1C(C#N)(c1ccccc1)C1CCN(CC2CN(c3ccc(S(=O)(=O)c4ccncc4)cc3)C2)CC1] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl acetate |
| 187 | 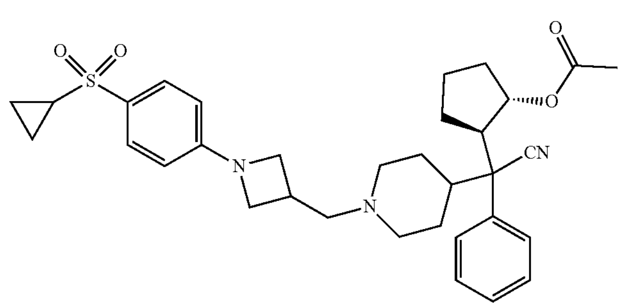 [SMILES: CC(=O)O[C@H]1CCC[C@@H]1C(C#N)(c1ccccc1)C1CCN(CC2CN(c3ccc(S(=O)(=O)C4CC4)cc3)C2)CC1] | rac-(1S,2R)-2-(cyano(1-((1-(4-(cyclopropylsulfonyl)phenyl)azetidin-3-yl)methyl)piperidin-4-yl)(phenyl)methyl)cyclopentyl acetate |

TABLE 1-continued

| Cpd. No. | Chemical Structure | Chemical Name |
|---|---|---|
| 188 | 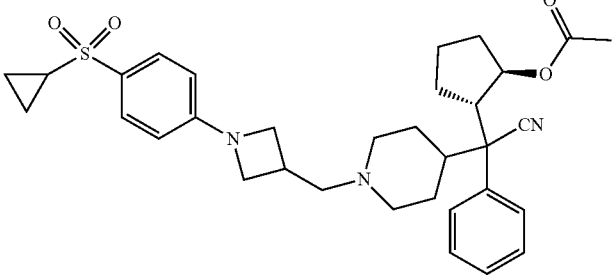 | rac-((1R,2S)-2-(cyano(1-((1-(4-(cyclopropylsulfonyl)phenyl)azetidin-3-yl)methyl)piperidin-4-yl)(phenyl)methyl)cyclopentyl acetate |
| 189 | 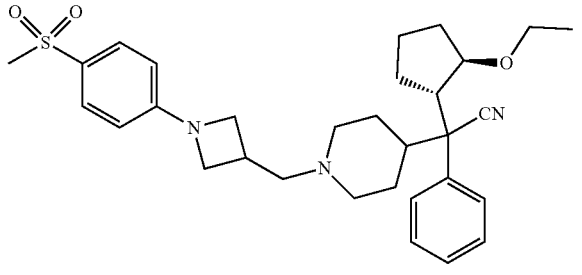 [SMILES: CCO[C@@H]1CCC[C@H]1C(C#N)(c1ccccc1)C1CCN(CC2CN(c3ccc(S(C)(=O)=O)cc3)C2)CC1] | rac-2-((1S,2R)-2-ethoxycyclopentyl)-2-(1-((1-(4-(methylsulfonyl)phenyl)azetidin-3-yl)methyl)piperidin-4-yl)-2-phenylacetonitrile |
| 190 | 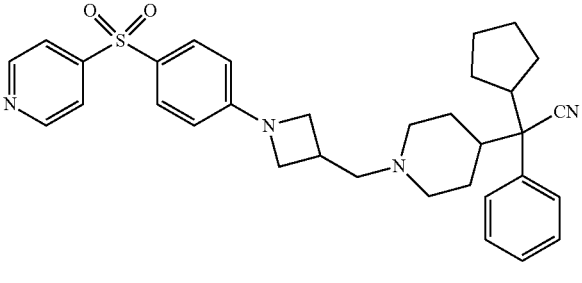 [SMILES: N#CC(c1ccccc1)(C1CCCC1)C1CCN(CC2CN(c3ccc(S(=O)(=O)c4ccncc4)cc3)C2)CC1] | 2-cyclopentyl-2-phenyl-2-(1-((1-(4-(pyridin-4-ylsulfonyl)phenyl)azetidin-3-yl)methyl)piperidin-4-yl)acetonitrile |
| 191 | 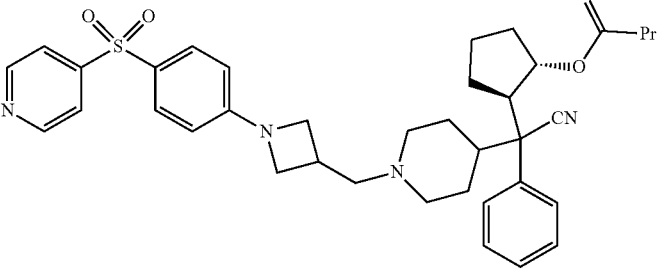 | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl butyrate |
| 192 | 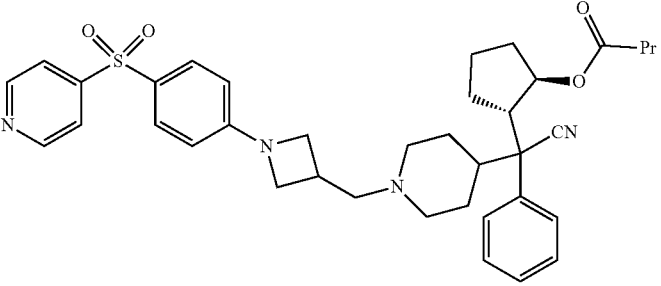 | rac-(1R,2S)-2-(cyano(phenyl)(1-((1-(4-(pyridin-4-ylsulfonyl)phenyl)azetidin-3-yl)methyl)pyridin-4-yl)methyl)cyclopentyl butyrate |

TABLE 1-continued

| Cpd. No. | Chemical Structure | Chemical Name |
|---|---|---|
| 193 | 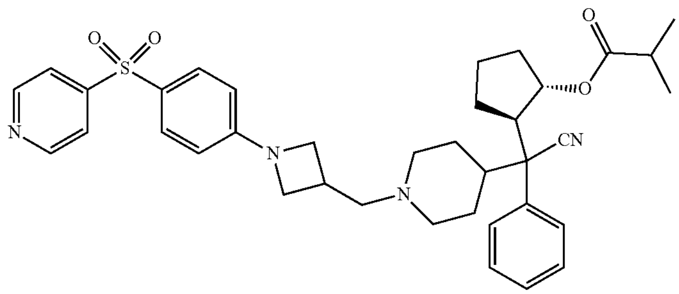 [SMILES: CC(C)C(=O)O[C@H]1CCC[C@@H]1C(C#N)(c1ccccc1)C1CCN(CC2CN(c3ccc(S(=O)(=O)c4ccncc4)cc3)C2)CC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl isobutyrate |
| 194 | 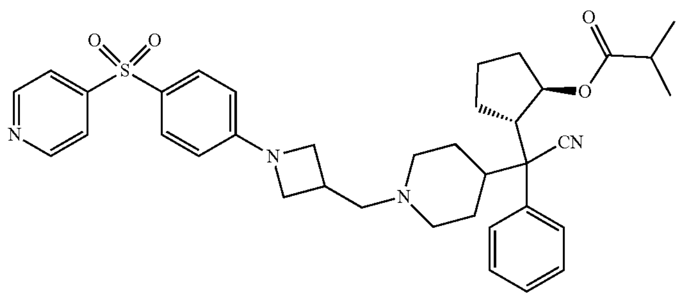 [SMILES: CC(C)C(=O)O[C@@H]1CCC[C@H]1C(C#N)(c1ccccc1)C1CCN(CC2CN(c3ccc(S(=O)(=O)c4ccncc4)cc3)C2)CC1] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl isobutyrate |
| 195 | 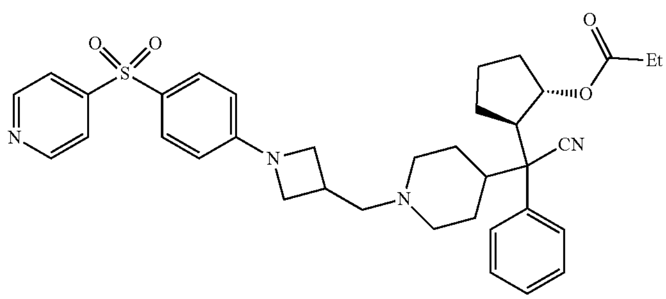 | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl propionate |
| 196 | 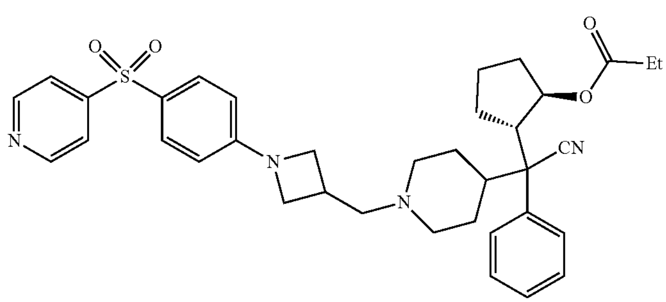 | rac-(1R,2S)-2-(cyano(phenyl)(1-((1-(4-(pyridin-4-ylsulfonyl)phenyl)azetidin-3-yl)methyl)piperidin-4-yl)methylcyclopentyl propionate |
| 197 | 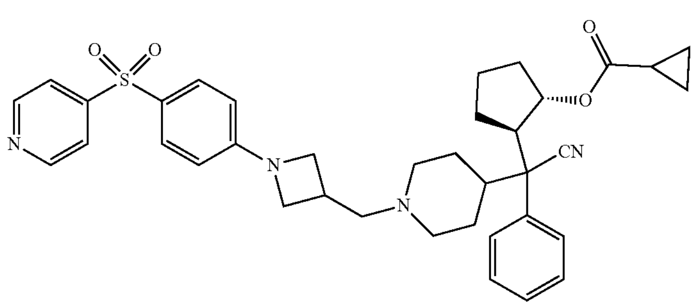 [SMILES: N#CC(c1ccccc1)(C1CCN(CC2CN(c3ccc(S(=O)(=O)c4ccncc4)cc3)C2)CC1)[C@H]1CCC[C@@H]1OC(=O)C1CC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl cyclopropanecarboxylate |

TABLE 1-continued

| Cpd. No. | Chemical Structure | Chemical Name |
|---|---|---|
| 198 | 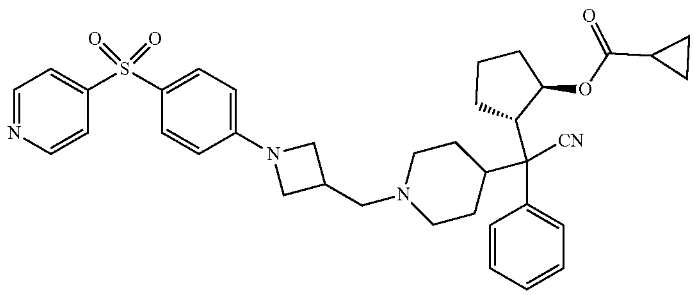 [SMILES: N#CC(c1ccccc1)(C1CCN(CC2CN(c3ccc(S(=O)(=O)c4ccncc4)cc3)C2)CC1)[C@@H]1CCC[C@H]1OC(=O)C1CC1] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl cyclopropanecarboxylate |
| 199 | 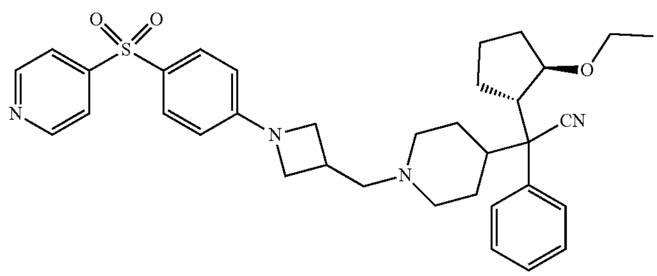 [SMILES: CCO[C@@H]1CCC[C@H]1C(C#N)(c1ccccc1)C1CCN(CC2CN(c3ccc(S(=O)(=O)c4ccncc4)cc3)C2)CC1] | rac-2-((1S,2R)-2-ethoxycyclopentyl)-2-phenyl-2-(1-((1-(4-(pyridin-4-ylsulfonyl)phenyl)azetidin-3-yl)methyl)piperidin-4-yl)acetonitrile |
| 200 | 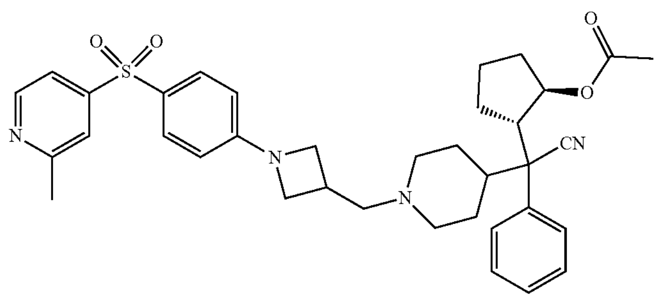 [SMILES: CC(=O)O[C@@H]1CCC[C@H]1C(C#N)(c1ccccc1)C1CCN(CC2CN(c3ccc(S(=O)(=O)c4ccnc(C)c4)cc3)C2)CC1] | rac-(1R,2S)-2-(cyano(1-((1-(4-((2-methylpyridin-4-yl)sulfonyl)phenyl)azetidin-3-yl)methyl)piperidin-4-yl)(phenyl)methyl)cyclopentyl acetate |
| 201 | 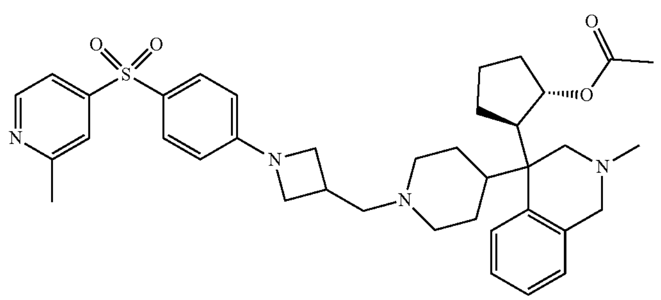 [SMILES: CC(=O)O[C@H]1CCC[C@@H]1C1(C2CCN(CC3CN(c4ccc(S(=O)(=O)c5ccnc(C)c5)cc4)C3)CC2)CN(C)Cc2ccccc21] | rac-(1S,2R)-2-(2-methyl-4-(1-((1-(4-((2-methylpyridin-4-yl)sulfonyl)phenyl)azetidin-3-yl)methyl)piperidin-4-yl)-1,2,3,4-tetrahydroisoquinolin-4-yl)cyclopentyl acetate |
| 202 | 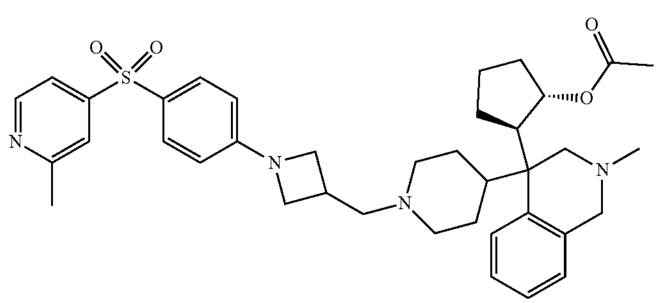 [SMILES: CC(=O)O[C@H]1CCC[C@@H]1C1(C2CCN(CC3CN(c4ccc(S(=O)(=O)c5ccnc(C)c5)cc4)C3)CC2)CN(C)Cc2ccccc21] | rac-(1R,2S)-2-(2-methyl-4-(1-((1-(4-((2-methylpyridin-4-yl)sulfonyl)phenyl)azetidin-3-yl)methyl)piperidin-4-yl)-1,2,3,4-tetrahydroisoquinolin-4-yl)cyclopentyl acetate |

TABLE 1-continued

| Cpd. No. | Chemical Structure | Chemical Name |
|---|---|---|
| 203 | 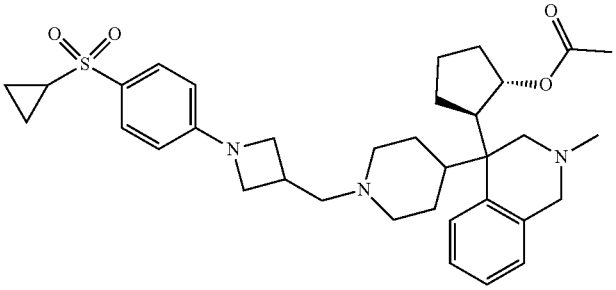 [SMILES: CC(=O)O[C@H]1CCC[C@@H]1C1(C2CCN(CC3CN(c4ccc(S(=O)(=O)C5CC5)cc4)C3)CC2)CN(C)Cc2ccccc21] | rac-(1S,2R)-2-(4-(1-((1-(4-(cyclopropylsulfonyl)phenyl)azetidin-3-yl)methyl)piperidin-4-yl)-2-methyl-1,2,3,4-tetrahydroisoquinolin-4-yl)cyclopentyl acetate |
| 204 | 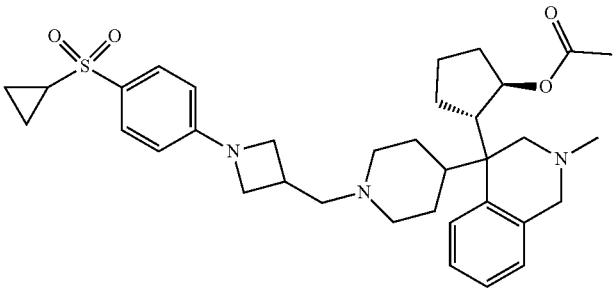 [SMILES: CC(=O)O[C@@H]1CCC[C@H]1C1(C2CCN(CC3CN(c4ccc(S(=O)(=O)C5CC5)cc4)C3)CC2)CN(C)Cc2ccccc21] | rac-(1R,2S)-2-(4-(1-((1-(4-(cyclopropylsulfonyl)phenyl)azetidin-3-yl)methyl)piperidin-4-yl)-2-methyl-1,2,3,4-tetrahydroisoquinolin-4-yl)cyclopentyl acetate |
| 205 | 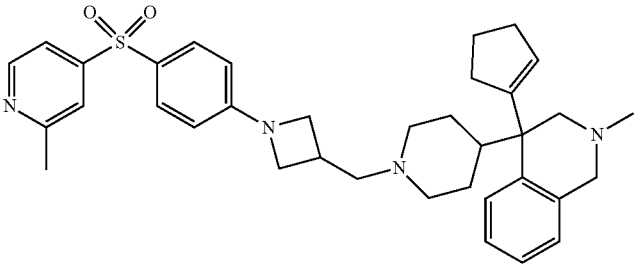 [SMILES: Cc1cc(S(=O)(=O)c2ccc(N3CC(CN4CCC(C5(C6=CCCC6)CN(C)Cc6ccccc65)CC4)C3)cc2)ccn1] | 4-(cyclopent-1-en-1-yl)-2-methyl-4-(1-((1-(4-((2-methylpyridin-4-yl)sulfonyl)phenyl)azetidin-3-yl)methyl)piperidin-4-yl)-1,2,3,4-tetrahydroisoquinoline |
| 206 | 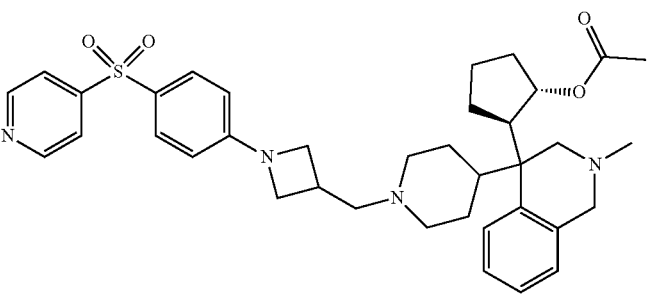 [SMILES: CC(=O)O[C@H]1CCC[C@@H]1C1(C2CCN(CC3CN(c4ccc(S(=O)(=O)c5ccncc5)cc4)C3)CC2)CN(C)Cc2ccccc21] | rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl acetate |
| 207 | 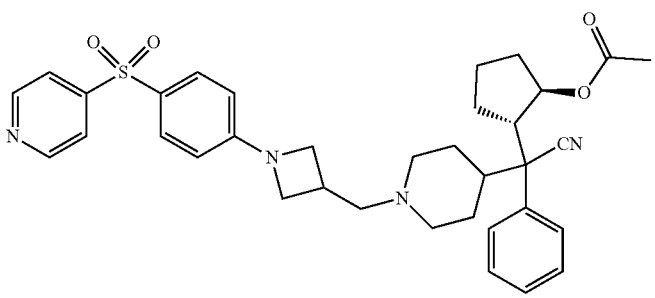 [SMILES: CC(=O)O[C@@H]1CCC[C@H]1C(C#N)(c1ccccc1)C1CCN(CC2CN(c3ccc(S(=O)(=O)c4ccncc4)cc3)C2)CC1] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl acetate |

TABLE 1-continued

| Cpd. No. | Chemical Structure | Chemical Name |
|---|---|---|
| 208 | 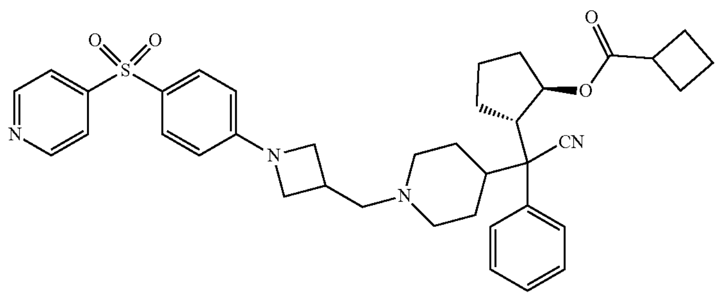 | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl cyclobutanecarboxylate |
| 209 | 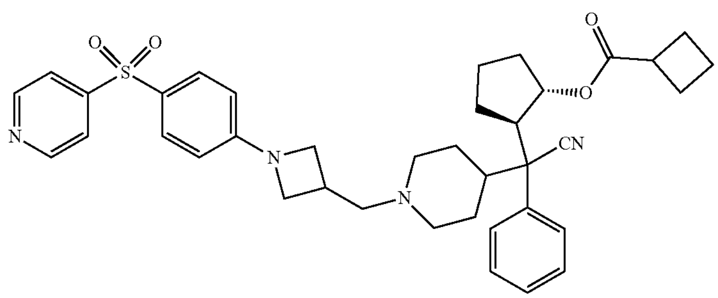 [SMILES: N#CC(c1ccccc1)(C1CCN(CC2CN(c3ccc(S(=O)(=O)c4ccncc4)cc3)C2)CC1)[C@H]1CCC[C@@H]1OC(=O)C1CCC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl cyclobutanecarboxylate |
| 210 | 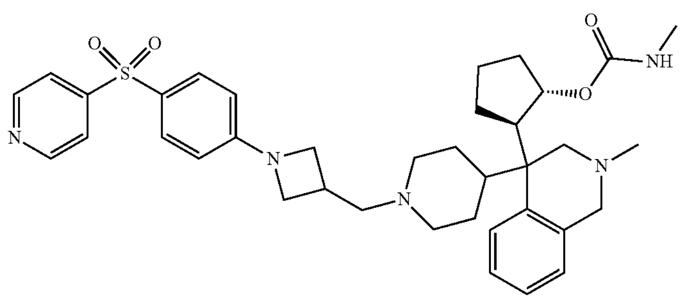 [SMILES: CNC(=O)O[C@H]1CCC[C@@H]1C1(C2CCN(CC3CN(c4ccc(S(=O)(=O)c5ccncc5)cc4)C3)CC2)CN(C)Cc2ccccc21] | rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl methylcarbamate |
| 211 | 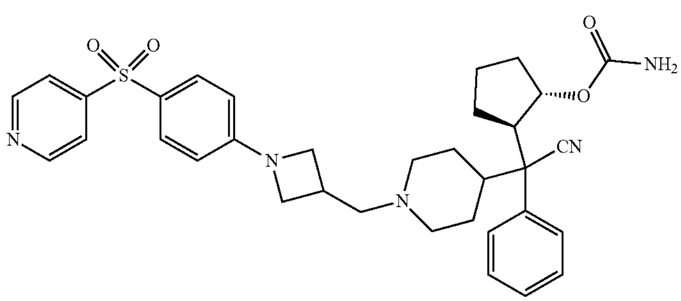 [SMILES: N#CC(c1ccccc1)(C1CCN(CC2CN(c3ccc(S(=O)(=O)c4ccncc4)cc3)C2)CC1)[C@H]1CCC[C@@H]1OC(N)=O] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl carbamate |
| 212 | 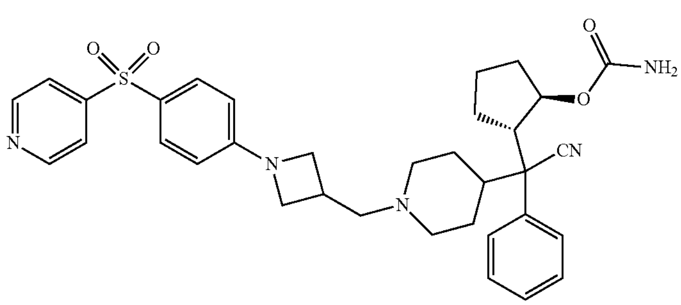 [SMILES: N#CC(c1ccccc1)(C1CCN(CC2CN(c3ccc(S(=O)(=O)c4ccncc4)cc3)C2)CC1)[C@@H]1CCC[C@H]1OC(N)=O] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl carbamate |

TABLE 1-continued

| Cpd. No. | Chemical Structure | Chemical Name |
|---|---|---|
| 213 | 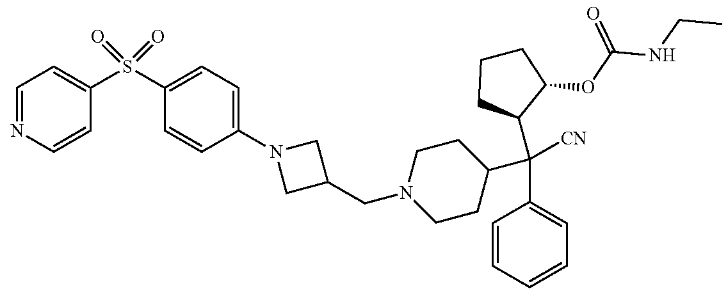 [SMILES: CCNC(=O)O[C@H]1CCC[C@@H]1C(C#N)(c1ccccc1)C1CCN(CC2CN(c3ccc(S(=O)(=O)c4ccncc4)cc3)C2)CC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl ethylcarbamate |
| 214 | 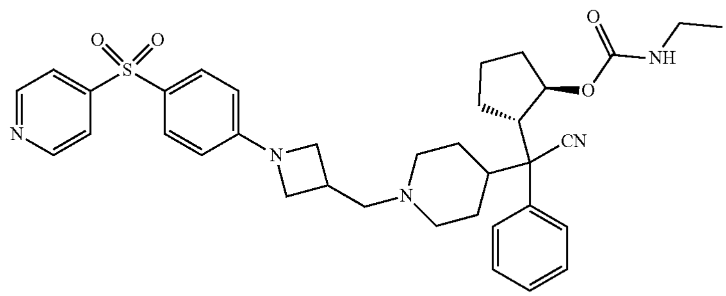 [SMILES: CCNC(=O)O[C@@H]1CCC[C@H]1C(C#N)(c1ccccc1)C1CCN(CC2CN(c3ccc(S(=O)(=O)c4ccncc4)cc3)C2)CC1] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl ethylcarbamate |
| 215 | 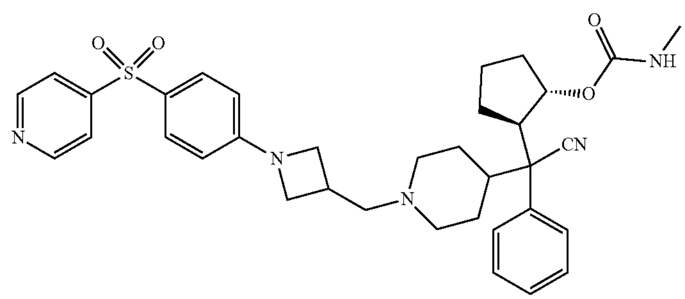 [SMILES: CNC(=O)O[C@H]1CCC[C@@H]1C(C#N)(c1ccccc1)C1CCN(CC2CN(c3ccc(S(=O)(=O)c4ccncc4)cc3)C2)CC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl methylcarbamate |
| 216 | 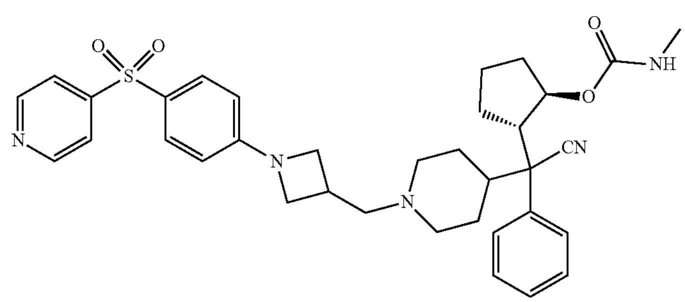 [SMILES: CNC(=O)O[C@@H]1CCC[C@H]1C(C#N)(c1ccccc1)C1CCN(CC2CN(c3ccc(S(=O)(=O)c4ccncc4)cc3)C2)CC1] | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl methylcarbamate |
| 217 | 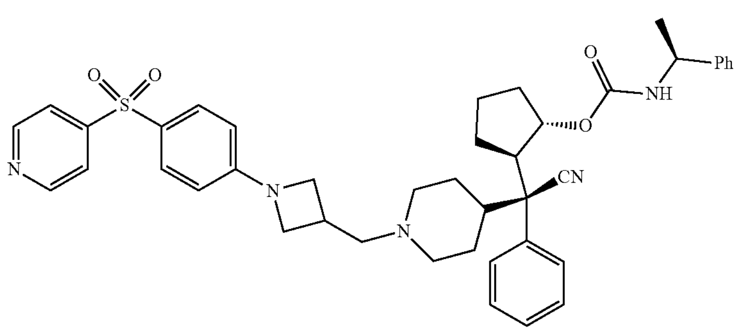 [SMILES: C[C@H](NC(=O)O[C@H]1CCC[C@@H]1[C@](C#N)(c1ccccc1)C1CCN(CC2CN(c3ccc(S(=O)(=O)c4ccncc4)cc3)C2)CC1)c1ccccc1] | (1S,2R)-2-((S)-cyano(phenyl)(1-((1-(4-(pyridin-4-ylsulfonyl)phenyl)azetidin-3-yl)methyl)piperidin-4-yl)methyl)cyclopentyl ((S)-1-phenylethyl)carbamate |

TABLE 1-continued

| Cpd. No. | Chemical Structure | Chemical Name |
|---|---|---|
| 218 | 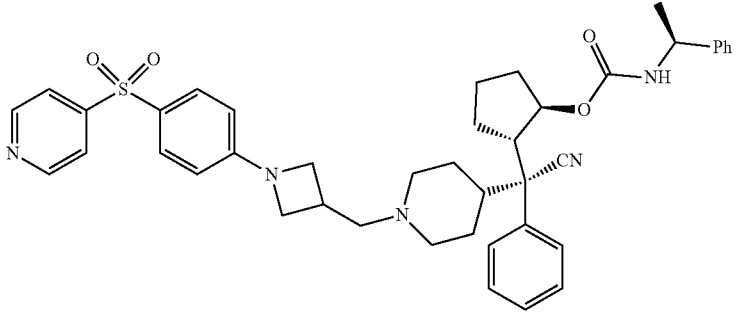 [SMILES: C[C@H](NC(=O)O[C@@H]1CCC[C@H]1[C@@](C#N)(c1ccccc1)C1CCN(CC2CN(c3ccc(S(=O)(=O)c4ccncc4)cc3)C2)CC1)c1ccccc1] | (1R,2S)-2-((R)-cyano(phenyl)(1-((1-(4-(pyridin-4-ylsulfonyl)phenyl)azetidin-3-yl)methyl)piperidin-4-yl)methyl)cyclopentyl ((S)-1-phenylethyl)carbamate |
| 219 | 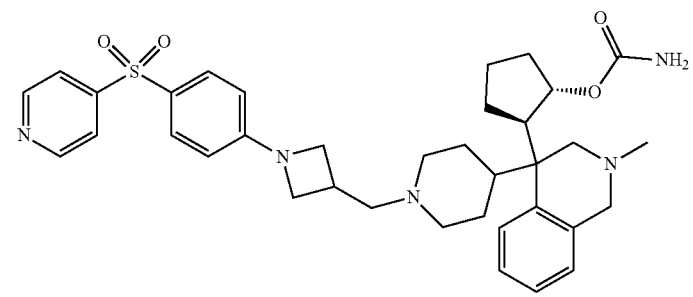 [SMILES: CN1Cc2ccccc2C(C2CCN(CC3CN(c4ccc(S(=O)(=O)c5ccncc5)cc4)C3)CC2)([C@H]2CCC[C@@H]2OC(N)=O)C1] | rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl carbamate |
| 220 | 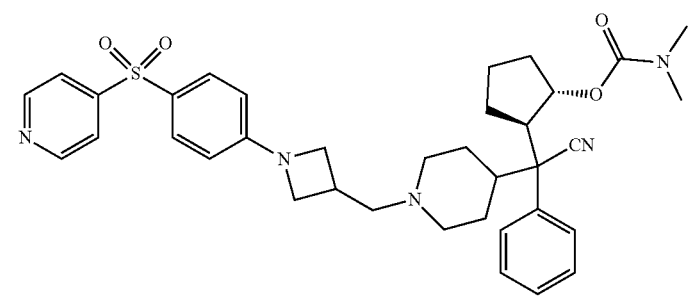 [SMILES: CN(C)C(=O)O[C@H]1CCC[C@@H]1C(C#N)(c1ccccc1)C1CCN(CC2CN(c3ccc(S(=O)(=O)c4ccncc4)cc3)C2)CC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl dimethylcarbamate |
| 221 | 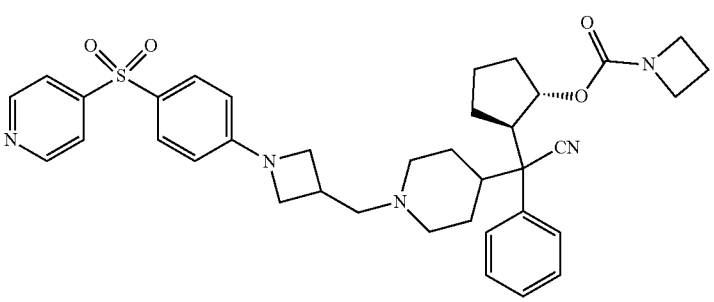 [SMILES: N#CC(c1ccccc1)(C1CCN(CC2CN(c3ccc(S(=O)(=O)c4ccncc4)cc3)C2)CC1)[C@H]1CCC[C@@H]1OC(=O)N1CCC1] | rac-(1S,2R)-2-(cyano(phenyl)(1-((1-(4-(pyridin-4-ylsulfonyl)phenyl)azetidin-3-yl)methyl)piperidin-4-yl)methyl)cyclopentyl azetidine-1-carboxylate |
| 222 | 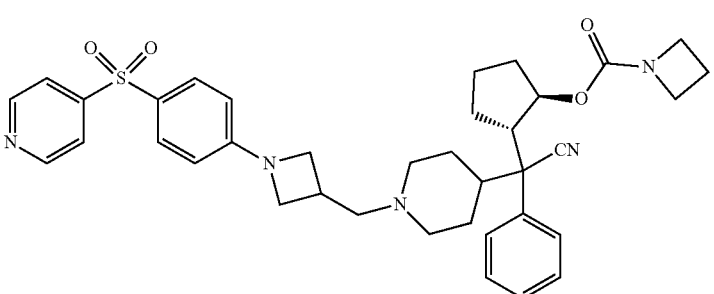 | rac-(1R,2S)-2-(cyano(phenyl)(1-((1-(4-(pyridin-4-ylsulfonyl)phenyl)azetidin-3-yl)methyl)piperidin-4-yl)methyl)cyclopentyl azetidine-1-carboxylate |

TABLE 1-continued

| Cpd. No. | Chemical Structure | Chemical Name |
|---|---|---|
| 223 | 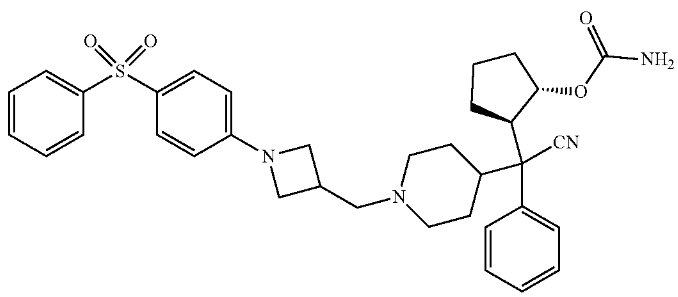 [SMILES: N#CC(c1ccccc1)(C1CCN(CC2CN(c3ccc(S(=O)(=O)c4ccccc4)cc3)C2)CC1)[C@H]1CCC[C@@H]1OC(N)=O] | rac-(1S,2R)-2-(cyano(phenyl)(1-((1-(4-(phenylsulfonyl)phenyl)azetidin-3-yl)methyl)piperidin-4-yl)methyl)cyclopentyl carbamate |
| 224 | 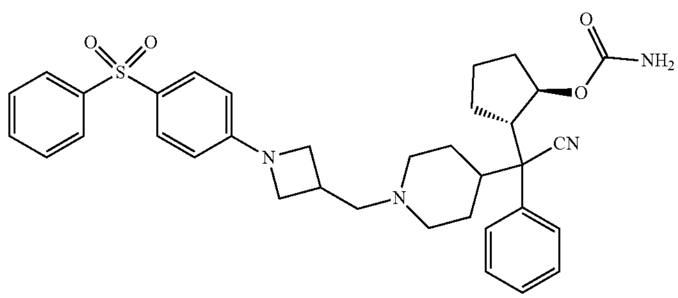 [SMILES: N#CC(c1ccccc1)(C1CCN(CC2CN(c3ccc(S(=O)(=O)c4ccccc4)cc3)C2)CC1)[C@@H]1CCC[C@H]1OC(N)=O] | rac-(1R,2S)-2-(cyano(phenyl)(1-((1-(4-(phenylsulfonyl)phenyl)azetidin-3-yl)methyl)piperidin-4-yl)methyl)cyclopentyl carbamate |
| 225 | 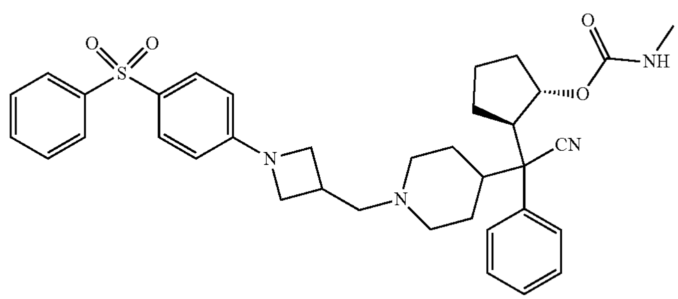 [SMILES: CNC(=O)O[C@H]1CCC[C@@H]1C(C#N)(c1ccccc1)C1CCN(CC2CN(c3ccc(S(=O)(=O)c4ccccc4)cc3)C2)CC1] | rac-(1S,2R)-2-(cyano(phenyl)(1-((1-(4-(phenylsulfonyl)phenyl)azetidin-3-yl)methyl)piperidin-4-yl)methyl)cyclopentyl methylcarbamate |
| 226 | 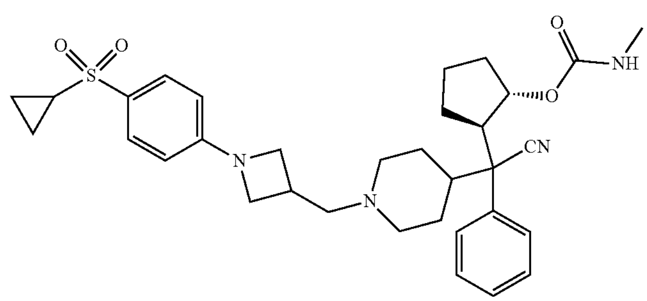 [SMILES: CNC(=O)O[C@H]1CCC[C@@H]1C(C#N)(c1ccccc1)C1CCN(CC2CN(c3ccc(S(=O)(=O)C4CC4)cc3)C2)CC1] | rac-(1S,2R)-2-(cyano(1-((1-(4-(cyclopropylsulfonyl)phenyl)azetidin-3-yl)methyl)piperidin-4-yl)(phenyl)methyl)cyclopentyl methylcarbamate |
| 227 | 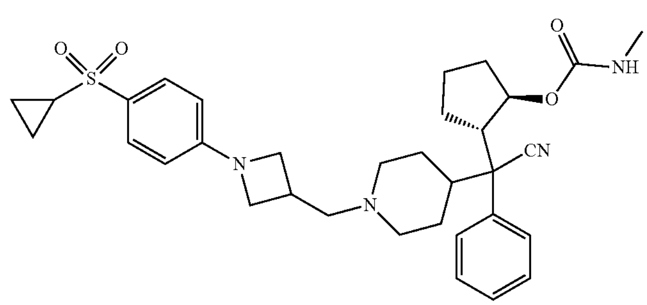 [SMILES: CNC(=O)O[C@@H]1CCC[C@H]1C(C#N)(c1ccccc1)C1CCN(CC2CN(c3ccc(S(=O)(=O)C4CC4)cc3)C2)CC1] | rac-(1R,2S)-2-(cyano(1-((1-(4-(cyclopropylsulfonyl)phenyl)azetidin-3-yl)methyl)piperidin-4-yl)(phenyl)methyl)cyclopentyl methylcarbamate |

TABLE 1-continued

| Cpd. No. | Chemical Structure | Chemical Name |
|---|---|---|
| 228 | 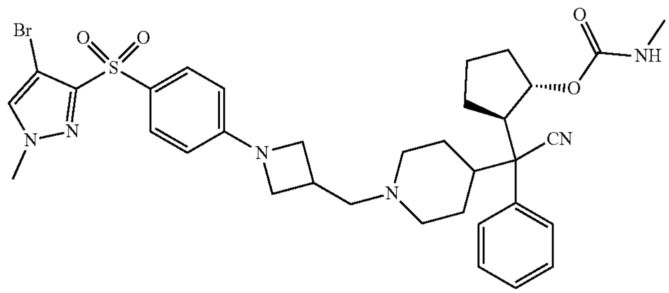 [SMILES: CNC(=O)O[C@H]1CCC[C@@H]1C(C#N)(c1ccccc1)C1CCN(CC2CN(c3ccc(S(=O)(=O)c4nn(C)cc4Br)cc3)C2)CC1] | rac-(1S,2R)-2-((1-((1-(4-((4-bromo-1-methyl-1H-pyrazol-3-yl)sulfonyl)phenyl)azetidin-3-yl)methyl)piperidin-4-yl)(cyano)(phenyl)methyl) cyclopentyl methylcarbamate |
| 229 | 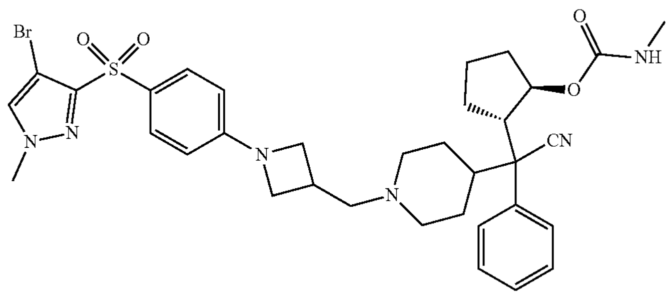 [SMILES: CNC(=O)O[C@@H]1CCC[C@H]1C(C#N)(c1ccccc1)C1CCN(CC2CN(c3ccc(S(=O)(=O)c4nn(C)cc4Br)cc3)C2)CC1] | rac-(1R,2S)-2-((1-((1-(4-((4-bromo-1-methyl-1H-pyrazol-3-yl)sulfonyl)phenyl)azetidin-3-yl)methyl)piperidin-4-yl)(cyano)(phenyl)methyl) cyclopentyl methylcarbamate |
| 230 | 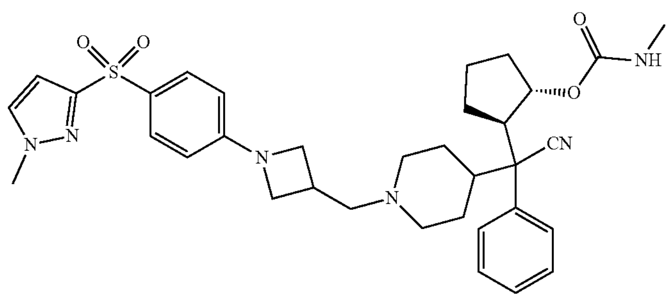 [SMILES: CNC(=O)O[C@H]1CCC[C@@H]1C(C#N)(c1ccccc1)C1CCN(CC2CN(c3ccc(S(=O)(=O)c4ccn(C)n4)cc3)C2)CC1] | rac-(1S,2R)-2-(cyano(1-((1-(4-((1-methyl-1H-pyrazol-3-yl)sulfonyl)phenyl)azetidin-3-yl)methyl)piperidin-4-yl)(phenyl)methyl)cyclopentyl methylcarbamate |
| 231 | 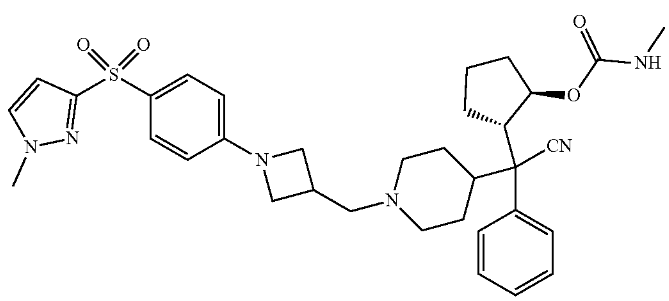 [SMILES: CNC(=O)O[C@@H]1CCC[C@H]1C(C#N)(c1ccccc1)C1CCN(CC2CN(c3ccc(S(=O)(=O)c4ccn(C)n4)cc3)C2)CC1] | rac-(1R,2S)-2-((1-((1-(4-((4-bromo-1-methyl-1H-pyrazol-3-yl)sulfonyl)phenyl)azetidin-3-yl)methyl)piperidin-4-yl)(cyano)(phenyl)methyl) cyclopentyl methylcarbamate |
| 232 | 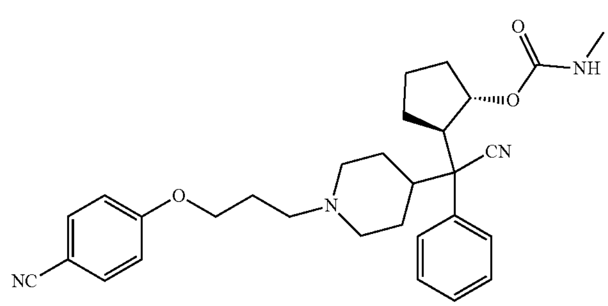 [SMILES: CNC(=O)O[C@H]1CCC[C@@H]1C(C#N)(c1ccccc1)C1CCN(CCCOc2ccc(C#N)cc2)CC1] | rac-(1S,2R)-2-(cyano(1-(3-(4-cyanophenoxy)propyl) piperidin-4-yl)(phenyl)methyl)cyclopentyl methylcarbamate |

TABLE 1-continued

| Cpd. No. | Chemical Structure | Chemical Name |
|---|---|---|
| 233 | 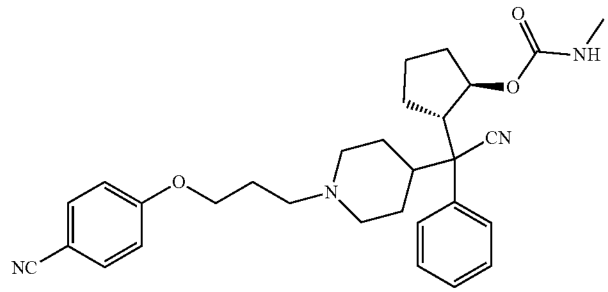 [SMILES: CNC(=O)O[C@@H]1CCC[C@H]1C(C#N)(c1ccccc1)C1CCN(CCCOc2ccc(C#N)cc2)CC1] | rac-(1R,2S)-2-(cyano(1-(3-(4-cyanophenoxy)propyl)piperidin-4-yl)(phenyl)methyl)cyclopentyl methylcarbamate |
| 234 | 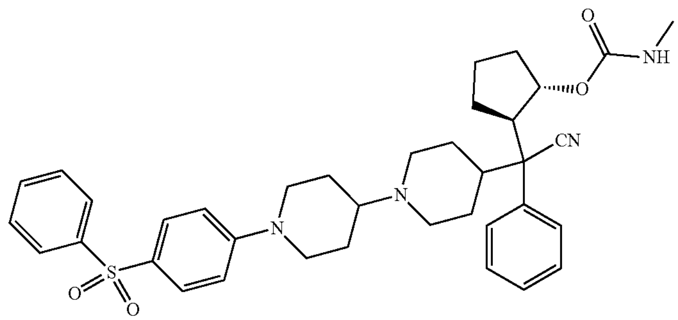 [SMILES: CNC(=O)O[C@H]1CCC[C@@H]1C(C#N)(c1ccccc1)C1CCN(C2CCN(c3ccc(S(=O)(=O)c4ccccc4)cc3)CC2)CC1] | rac-(1S,2R)-2-(cyano(phenyl)(1'-(4-(phenylsulfonyl)phenyl)-[1,4'-bipiperidin]-4-yl)methyl)cyclopentyl methylcarbamate |
| 235 | 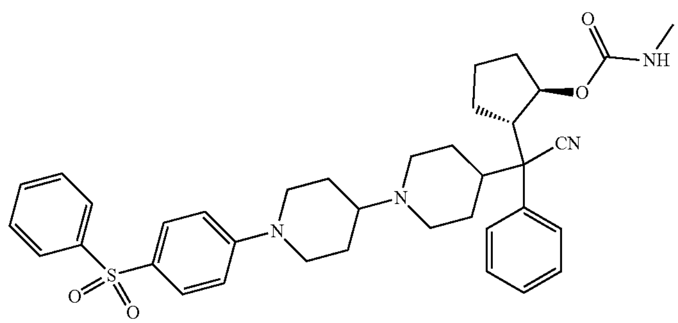 [SMILES: CNC(=O)O[C@@H]1CCC[C@H]1C(C#N)(c1ccccc1)C1CCN(C2CCN(c3ccc(S(=O)(=O)c4ccccc4)cc3)CC2)CC1] | rac-(1R,2S)-2-(cyano(phenyl)(1'-(4-(phenylsulfonyl)phenyl)-[1,4'-bipiperidin]-4-yl)methyl)cyclopentyl methylcarbamate |
| 236 | 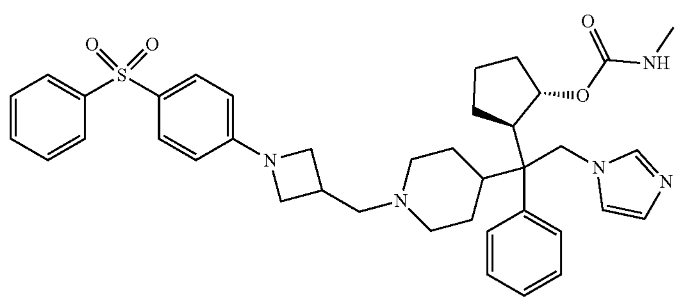 [SMILES: CNC(=O)O[C@H]1CCC[C@@H]1C(Cn1ccnc1)(c1ccccc1)C1CCN(CC2CN(c3ccc(S(=O)(=O)c4ccccc4)cc3)C2)CC1] | rac-(1S,2R)-2-(2-(1H-imidazol-1-yl)-1-phenyl-1-(1-((1-(4-(phenylsulfonyl)phenyl)azetidin-3-yl)methyl)piperidin-4-yl)ethyl)cyclopentyl methylcarbamate |
| 237 | 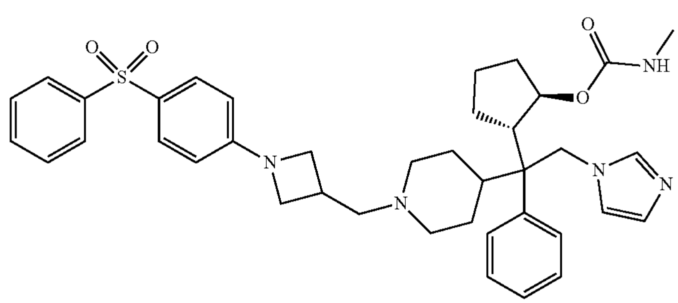 [SMILES: CNC(=O)O[C@@H]1CCC[C@H]1C(Cn1ccnc1)(c1ccccc1)C1CCN(CC2CN(c3ccc(S(=O)(=O)c4ccccc4)cc3)C2)CC1] | rac-(1R,2S)-2-(2-(1H-imidazol-1-yl)-1-phenyl-1-(1-((1-(4-(phenylsulfonyl)phenyl)azetidin-3-yl)methyl)piperidin-4-yl)ethyl)cyclopentyl methylcarbamate |

TABLE 1-continued

| Cpd. No. | Chemical Structure | Chemical Name |
|---|---|---|
| 238 | 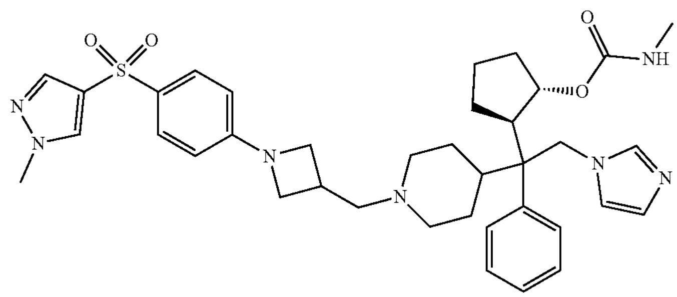 [SMILES: CNC(=O)O[C@H]1CCC[C@@H]1C(Cn1ccnc1)(c1ccccc1)C1CCN(CC2CN(c3ccc(S(=O)(=O)c4cnn(C)c4)cc3)C2)CC1] | rac-(1S,2R)-2-(2-(1H-imidazol-1-yl)-1-(1-((1-(4-((1-methyl-1H-pyrazol-4-yl)sulfonyl)phenyl)azetidin-3-yl)methyl)piperidin-4-yl)-1-phenylethyl)cyclopentyl methylcarbamate |
| 239 | 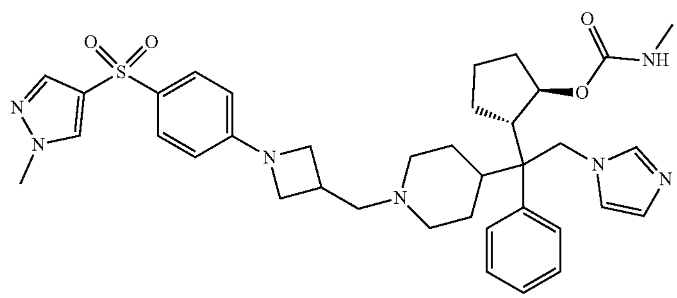 [SMILES: CNC(=O)O[C@@H]1CCC[C@H]1C(Cn1ccnc1)(c1ccccc1)C1CCN(CC2CN(c3ccc(S(=O)(=O)c4cnn(C)c4)cc3)C2)CC1] | rac-(1R,2S)-2-(2-(1H-imidazol-1-yl)-1-(1-((1-(4-((1-methyl-1H-pyrazol-4-yl)sulfonyl)phenyl)azetidin-3-yl)methyl)piperidin-4-yl)-1-phenethyl)cyclopentyl methylcarbamate |
| 240 | 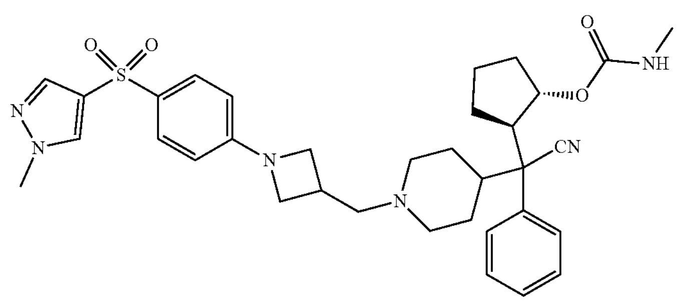 [SMILES: CNC(=O)O[C@H]1CCC[C@@H]1C(C#N)(c1ccccc1)C1CCN(CC2CN(c3ccc(S(=O)(=O)c4cnn(C)c4)cc3)C2)CC1] | rac-(1S,2R)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl methylcarbamate |
| 241 | 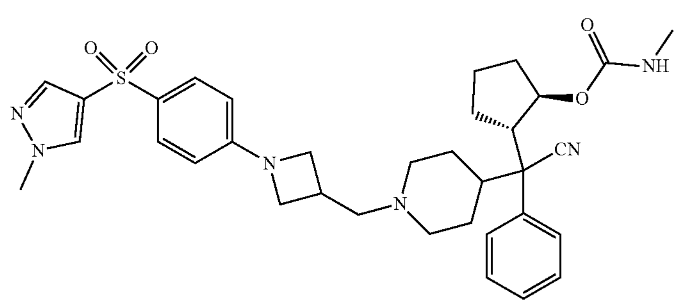 [SMILES: CNC(=O)O[C@@H]1CCC[C@H]1C(C#N)(c1ccccc1)C1CCN(CC2CN(c3ccc(S(=O)(=O)c4cnn(C)c4)cc3)C2)CC1] | rac-(1R,2S)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl methylcarbamate |
| 242 | 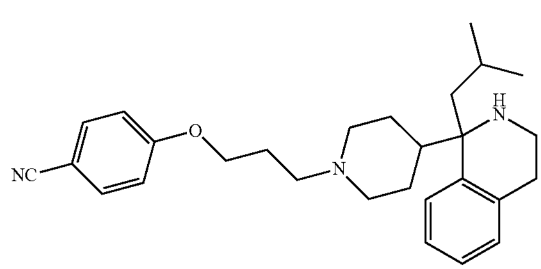 [SMILES: CC(C)CC1(C2CCN(CCCOc3ccc(C#N)cc3)CC2)NCCc2ccccc21] | 4-(3-(4-(1-isobutyl-1,2,3,4-tetrahydroisoquinolin-1-yl)piperidin-1-yl)propoxy)benzonitrile |

TABLE 1-continued

| Cpd. No. | Chemical Structure | Chemical Name |
|---|---|---|
| 243 | 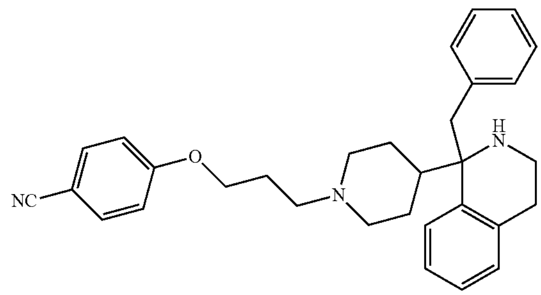 [SMILES: N#Cc1ccc(OCCCN2CCC(C3(Cc4ccccc4)NCCc4ccccc43)CC2)cc1] | 4-(3-(4-(1-benzyl-1,2,3,4-tetrahydroisoquinolin-1-yl)piperidin-1-yl)propoxy)benzonitrile |
| 244 | 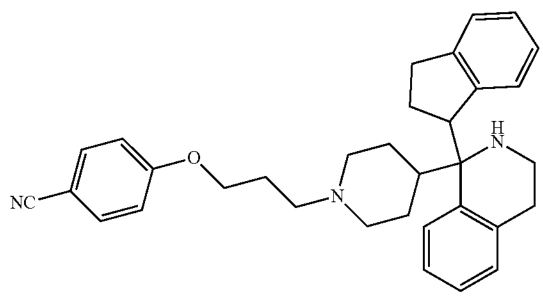 [SMILES: N#Cc1ccc(OCCCN2CCC(C3(C4CCc5ccccc54)NCCc4ccccc43)CC2)cc1] | 4-(3-(4-(1-(2,3-dihydro-1H-inden-1-yl)-1,2,3,4-tetrahydroisoquinolin-1-yl)piperidin-1-yl)propoxy)benzonitrile |
| 245 | 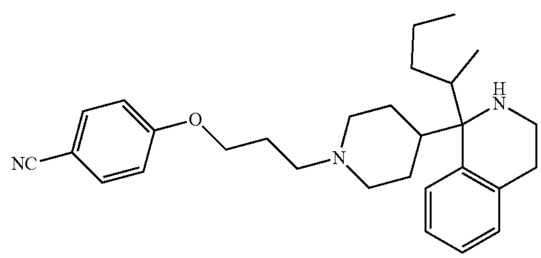 [SMILES: CCCC(C)C1(C2CCN(CCCOc3ccc(C#N)cc3)CC2)NCCc2ccccc21] | 4-(3-(4-(1-(pentan-2-yl)-1,2,3,4-tetrahydroisoquinolin-1-yl)piperidin-1-yl)propoxy)benzonitrile |
| 246 | 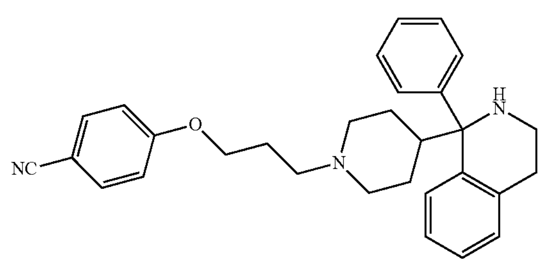 [SMILES: N#Cc1ccc(OCCCN2CCC(C3(c4ccccc4)NCCc4ccccc43)CC2)cc1] | 4-(3-(4-(1-phenyl-1,2,3,4-tetrahydroisoquinolin-1-yl)piperidin-1-yl)propoxy)benzonitrile |
| 247 | 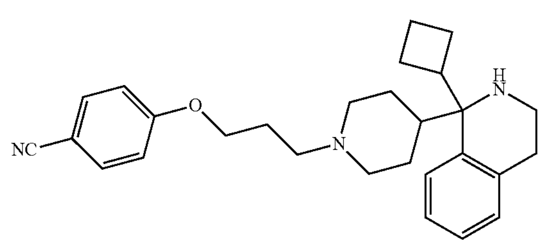 [SMILES: N#Cc1ccc(OCCCN2CCC(C3(C4CCC4)NCCc4ccccc43)CC2)cc1] | 4-(3-(4-(1-cyclobutyl-1,2,3,4-tetrahydroisoquinolin-1-yl)piperidin-1-yl)propoxy)benzonitrile |

TABLE 1-continued

| Cpd. No. | Chemical Structure | Chemical Name |
|---|---|---|
| 248 | 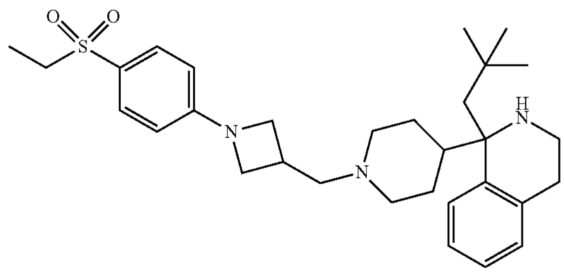 [SMILES: CCS(=O)(=O)c1ccc(N2CC(CN3CCC(C4(CC(C)(C)C)NCCc5ccccc54)CC3)C2)cc1] | 1-(1-((1-(4-(ethylsulfonyl)phenyl)azetidin-3-yl)methyl)piperidin-4-yl)-1-neopentyl-1,2,3,4-tetrahydroisoquinoline |
| 249 | 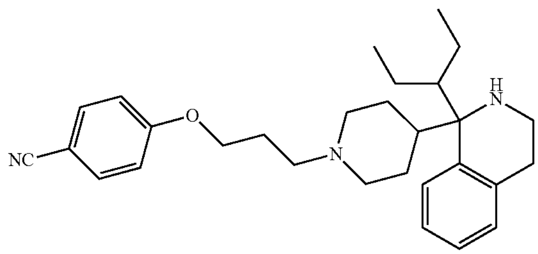 [SMILES: CCC(CC)C1(C2CCN(CCCOc3ccc(C#N)cc3)CC2)NCCc2ccccc21] | 4-(3-(4-(1-(pentan-3-yl)-1,2,3,4-tetrahydroisoquinolin-1-yl)piperidin-1-yl)propoxy)benzonitrile |
| 250 | 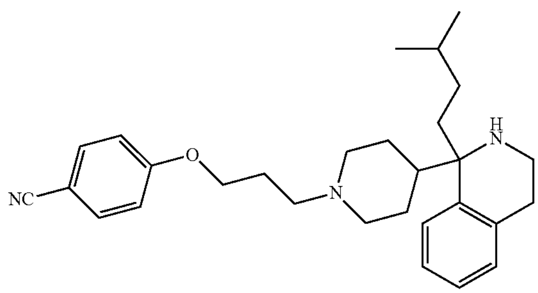 [SMILES: CC(C)CCC1(C2CCN(CCCOc3ccc(C#N)cc3)CC2)NCCc2ccccc21] | 4-(3-(4-(1-isopentyl-1,2,3,4-tetrahydroisoquinolin-1-yl)piperidin-1-yl)propoxy)benzonitrile |
| 251 | 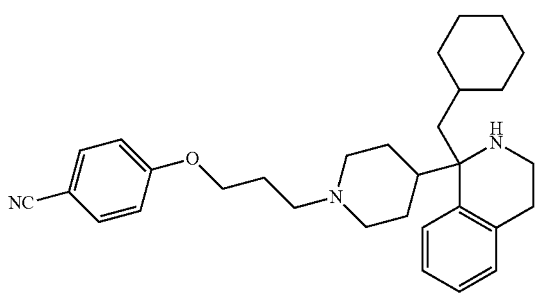 [SMILES: N#Cc1ccc(OCCCN2CCC(C3(CC4CCCCC4)NCCc4ccccc43)CC2)cc1] | 4-(3-(4-(1-(cyclohexylmethyl)-1,2,3,4-tetrahydroisoquinolin-1-yl)piperidin-1-yl)propoxy)benzonitrile |
| 252 | 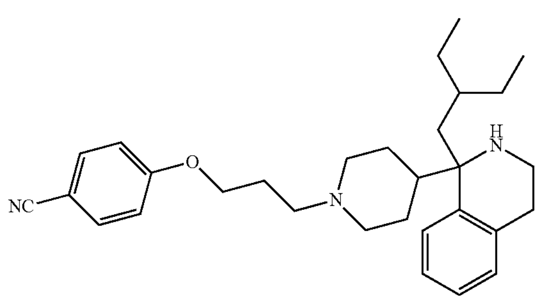 [SMILES: CCC(CC)CC1(C2CCN(CCCOc3ccc(C#N)cc3)CC2)NCCc2ccccc21] | 4-(3-(4-(1-(2-ethylbutyl)-1,2,3,4-tetrahydroisoquinolin-1-yl)piperidin-1-yl)propoxy)benzonitrile |

TABLE 1-continued

| Cpd. No. | Chemical Structure | Chemical Name |
|---|---|---|
| 253 | 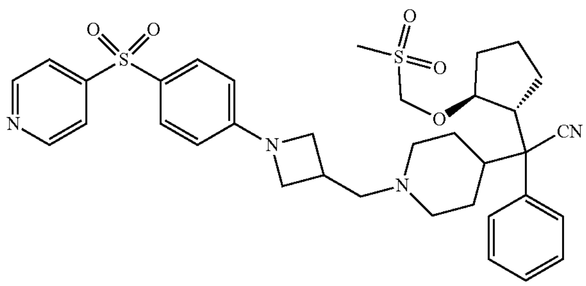 [SMILES: CS(=O)(=O)CO[C@H]1CCC[C@@H]1C(C#N)(c1ccccc1)C1CCN(CC2CN(c3ccc(S(=O)(=O)c4ccncc4)cc3)C2)CC1] | rac-2-((1R,2S)-2-((methylsulfonyl)methoxy)cyclopentyl)-2-phenyl-2-(1-((1-(4-(pyridin-4-ylsulfonyl)phenyl)azetidin-3-yl)methyl)piperidin-4-yl)acetonitrile |
| 254 | 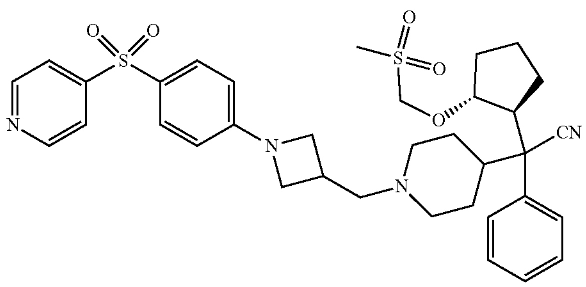 [SMILES: CS(=O)(=O)CO[C@@H]1CCC[C@H]1C(C#N)(c1ccccc1)C1CCN(CC2CN(c3ccc(S(=O)(=O)c4ccncc4)cc3)C2)CC1] | rac-2-((1S,2R)-2-((methylsulfonyl)methoxy)cyclopentyl)-2-phenyl-2-(1-((1-(4-(pyridin-4-ylsulfonyl)phenyl)azetidin-3-yl)methyl)piperidin-4-yl)acetonitrile |
| 255 | 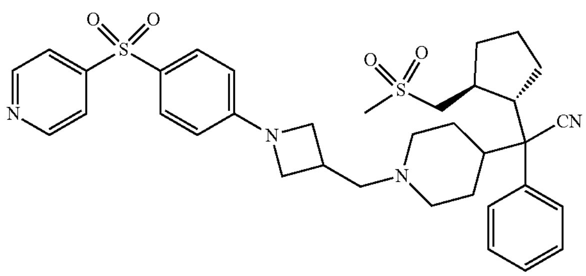 [SMILES: CS(=O)(=O)C[C@H]1CCC[C@@H]1C(C#N)(c1ccccc1)C1CCN(CC2CN(c3ccc(S(=O)(=O)c4ccncc4)cc3)C2)CC1] | rac-2-((1S,2S)-2-((methylsulfonyl)methyl)cyclopentyl)-2-phenyl-2-(1-((1-(4-(pyridin-4-ylsulfonyl)phenyl)azetidin-3-yl)methyl)piperidin-4-yl)acetonitrile |
| 256 | 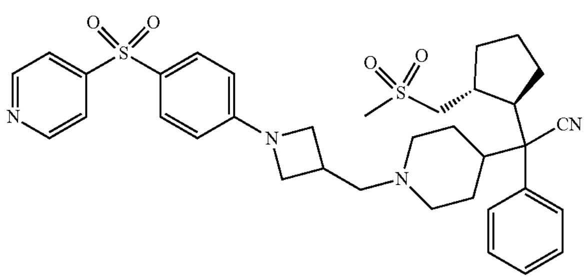 [SMILES: CS(=O)(=O)C[C@@H]1CCC[C@H]1C(C#N)(c1ccccc1)C1CCN(CC2CN(c3ccc(S(=O)(=O)c4ccncc4)cc3)C2)CC1] | rac-2-((1R,2R)-2-((methylsulfonyl)methyl)cyclopentyl)-2-phenyl-2-(1-((1-(4-(pyridin-4-ylsulfonyl)phenyl)azetidin-3-yl)methyl)piperidin-4-yl)acetonitrile |
| 257 | 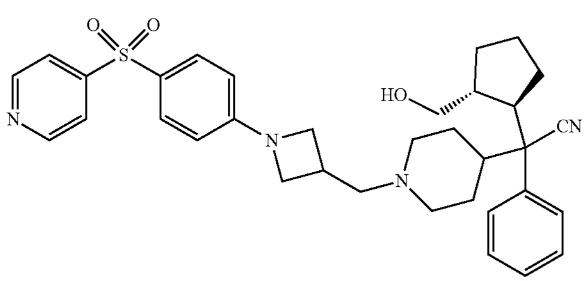 [SMILES: N#CC(c1ccccc1)(C1CCN(CC2CN(c3ccc(S(=O)(=O)c4ccncc4)cc3)C2)CC1)[C@@H]1CCC[C@H]1CO] | rac-2-((1R,2R)-2-(hydroxymethyl)cyclopentyl)-2-phenyl-2-(1-((1-(4-(pyridin-4-ylsulfonyl)phenyl)azetidin-3-yl)methyl)piperidin-4-yl)acetonitrile |

TABLE 1-continued

| Cpd. No. | Chemical Structure | Chemical Name |
|---|---|---|
| 258 | 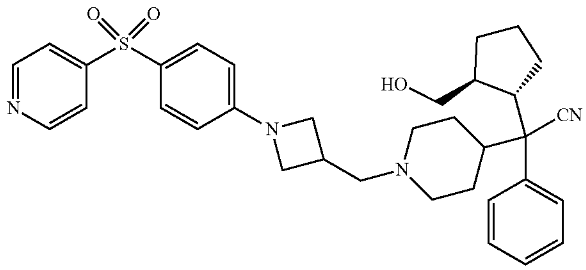 [SMILES: N#CC(c1ccccc1)(C1CCN(CC2CN(c3ccc(S(=O)(=O)c4ccncc4)cc3)C2)CC1)[C@H]1CCC[C@@H]1CO] | rac-2-((1S,2S)-2-(hydroxymethyl)cyclopentyl)-2-phenyl-2-(1-((1-(4-(pyridin-4-ylsulfonyl)phenyl)azetidin-3-yl)methyl)piperidin-4-yl)acetonitrile |
| 259 | 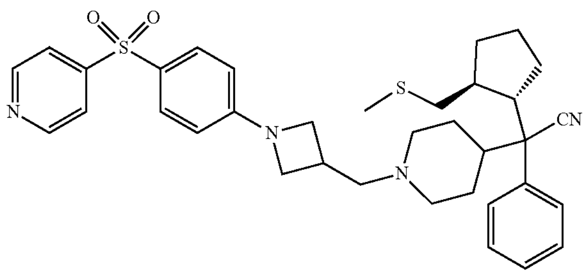 [SMILES: CSC[C@H]1CCC[C@@H]1C(C#N)(c1ccccc1)C1CCN(CC2CN(c3ccc(S(=O)(=O)c4ccncc4)cc3)C2)CC1] | rac-2-((1S,2S)-2-((methylthio)methyl)cyclopentyl)-2-phenyl-2-(1-((1-(4-(pyridin-4-ylsulfonyl)phenyl)azetidin-3-yl)methyl)piperidin-4-yl)acetonitrile |
| 260 | 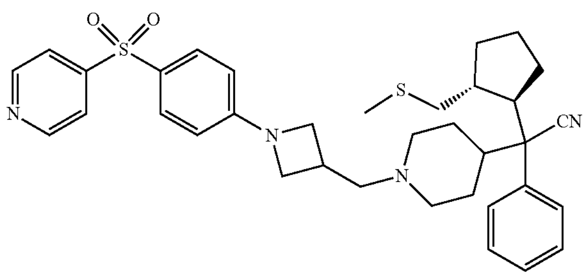 [SMILES: CSC[C@@H]1CCC[C@H]1C(C#N)(c1ccccc1)C1CCN(CC2CN(c3ccc(S(=O)(=O)c4ccncc4)cc3)C2)CC1] | rac-2-((1R,2R)-2-((methylthio)methyl)cyclopentyl)-2-phenyl-2-(1-((1-(4-(pyridin-4-ylsulfonyl)phenyl)azetidin-3-yl)methyl)piperidin-4-yl)acetonitrile |
| 261 | 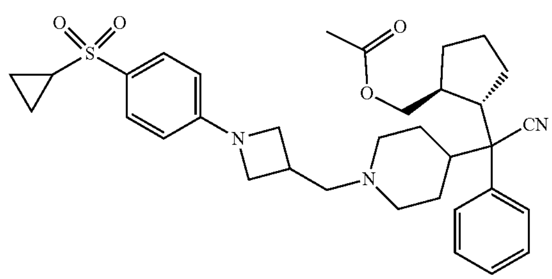 [SMILES: CC(=O)OC[C@H]1CCC[C@@H]1C(C#N)(c1ccccc1)C1CCN(CC2CN(c3ccc(S(=O)(=O)C4CC4)cc3)C2)CC1] | rac-((1S,2S)-2-(cyano(1-((1-(4-(cyclopropylsulfonyl)phenyl)azetidin-3-yl)methyl)piperidin-4-yl)(phenyl)methyl)cyclopentyl)methyl acetate |
| 262 | 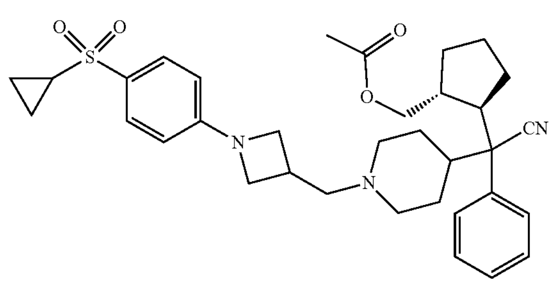 [SMILES: CC(=O)OC[C@@H]1CCC[C@H]1C(C#N)(c1ccccc1)C1CCN(CC2CN(c3ccc(S(=O)(=O)C4CC4)cc3)C2)CC1] | rac-((1R,2R)-2-(cyano(1-((1-(4-(cyclopropylsulfonyl)phenyl)azetidin-3-yl)methyl)piperidin-4-yl)(phenyl)methyl)cyclopentyl)methyl acetate |

TABLE 1-continued

| Cpd. No. | Chemical Structure | Chemical Name |
|---|---|---|
| 263 | 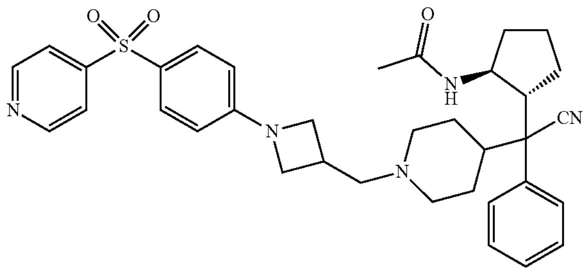 [SMILES: CC(=O)N[C@H]1CCC[C@@H]1C(C#N)(c1ccccc1)C1CCN(CC2CN(c3ccc(S(=O)(=O)c4ccncc4)cc3)C2)CC1] | rac-N-((1S,2R)-2-(cyano(phenyl)(1-((1-(4-(pyridin-4-ylsulfonyl)phenyl)azetidin-3-yl)methyl)piperidin-4-yl)methyl)cyclopentyl) acetamide |
| 264 | 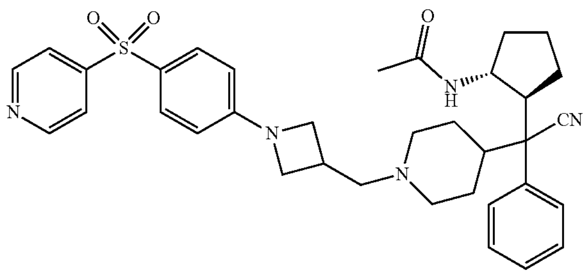 [SMILES: CC(=O)N[C@@H]1CCC[C@H]1C(C#N)(c1ccccc1)C1CCN(CC2CN(c3ccc(S(=O)(=O)c4ccncc4)cc3)C2)CC1] | rac-N-((1R,2S)-2-(cyano(phenyl)(1-((1-(4-(pyridin-4-ylsulfonyl)phenyl)azetidin-3-yl)methyl)piperidin-4-yl)methyl)cyclopentyl) acetamide |
| 265 | 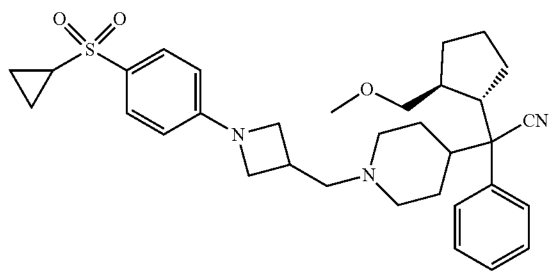 [SMILES: COC[C@H]1CCC[C@@H]1C(C#N)(c1ccccc1)C1CCN(CC2CN(c3ccc(S(=O)(=O)C4CC4)cc3)C2)CC1] | rac-2-(1-((1-(4-(cyclopropylsulfonyl)phenyl) azetidin-3-yl)methyl)piperidin-4-yl)-2-((1S,2S)-2-(methoxymethyl)cyclopentyl)-2-phenylacetonitrile |
| 266 | 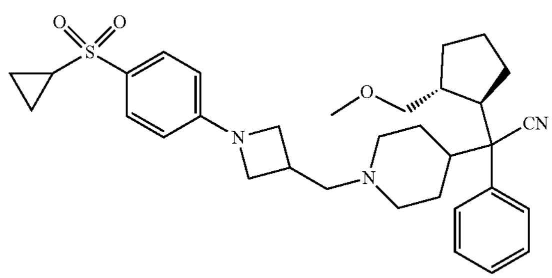 [SMILES: COC[C@@H]1CCC[C@H]1C(C#N)(c1ccccc1)C1CCN(CC2CN(c3ccc(S(=O)(=O)C4CC4)cc3)C2)CC1] | rac-2-(1-((1-(4-(cyclopropylsulfonyl)phenyl) azetidin-3-yl)methyl)piperidin-4-yl)-2-((1R,2R)-2-(methoxymethyl)cyclopentyl)-2-phenylacetonitrile |
| 267 | 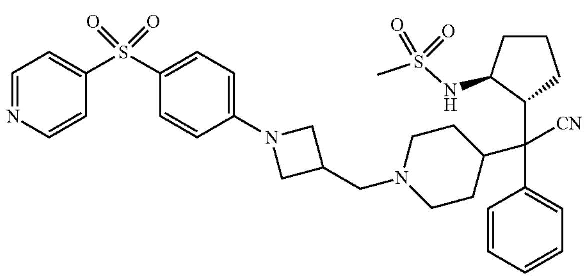 [SMILES: CS(=O)(=O)N[C@H]1CCC[C@@H]1C(C#N)(c1ccccc1)C1CCN(CC2CN(c3ccc(S(=O)(=O)c4ccncc4)cc3)C2)CC1] | rac-N-((1S,2R)-2-(cyano(phenyl)(1-((1-(4-(pyridin-4-ylsulfony)phenyl)azetidin-3-yl)methyl)piperidin-4-yl)methyl)cyclopentyl) methanesulfonamide |

TABLE 1-continued

| Cpd. No. | Chemical Structure | Chemical Name |
|---|---|---|
| 268 | 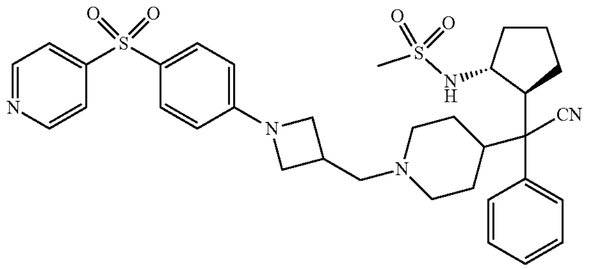 [SMILES: CS(=O)(=O)N[C@@H]1CCC[C@H]1C(C#N)(c1ccccc1)C1CCN(CC2CN(c3ccc(S(=O)(=O)c4ccncc4)cc3)C2)CC1] | rac-N-((1R,2S)-2-(cyano(phenyl)(1-((1-(4-(pyridin-4-ylsulfonyl)phenyl)azetidin-3-yl)methyl)piperidin-4-yl)methyl)cyclopentyl)methanesulfonamide |
| 269 | 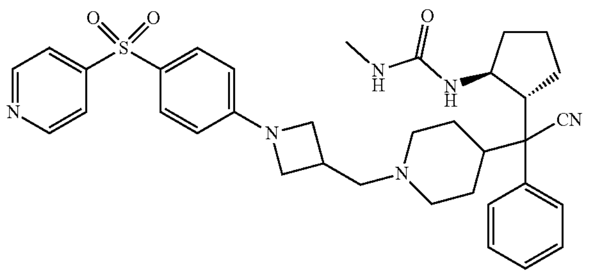 [SMILES: CNC(=O)N[C@H]1CCC[C@@H]1C(C#N)(c1ccccc1)C1CCN(CC2CN(c3ccc(S(=O)(=O)c4ccncc4)cc3)C2)CC1] | rac-1-((1S,2R)-2-(cyano(phenyl)(1-((1-(4-(pyridin-4-ylsulfonyl)phenyl)azetidin-3-yl)methyl)piperidin-4-yl)methyl)cyclopentyl)-3-methylurea |
| 270 | 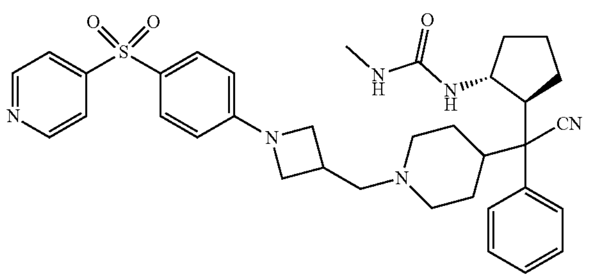 | rac-1-((1R,2S)-2-(cyano(phenyl)(1-((1-(4-(pyridin-4-ylsulfonyl)phenyl)azetidin-3-yl)methyl)piperidin-4-yl)methyl)cyclopentyl)-3-methylurea |
| 271 | 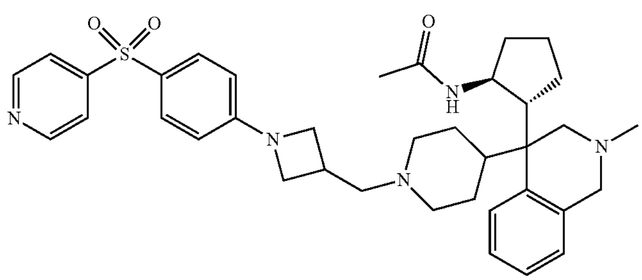 [SMILES: CC(=O)N[C@H]1CCC[C@@H]1C1(C2CCN(CC3CN(c4ccc(S(=O)(=O)c5ccncc5)cc4)C3)CC2)CN(C)Cc2ccccc21] | rac-N-((1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl)acetamide |
| 272 | 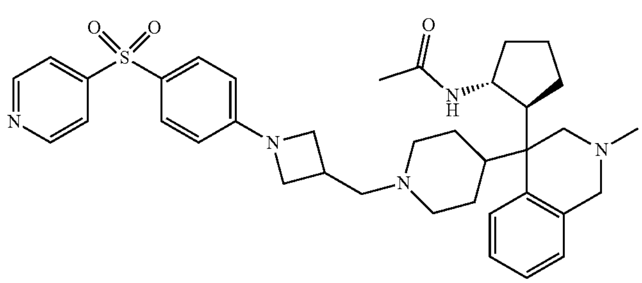 [SMILES: CC(=O)N[C@@H]1CCC[C@H]1C1(C2CCN(CC3CN(c4ccc(S(=O)(=O)c5ccncc5)cc4)C3)CC2)CN(C)Cc2ccccc21] | rac-N-((1R,2S)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl)acetamide |

TABLE 1-continued

| Cpd. No. | Chemical Structure | Chemical Name |
|---|---|---|
| 273 | 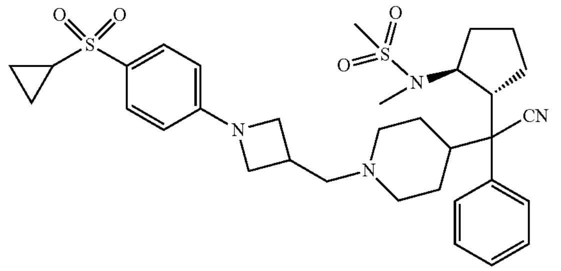 [SMILES: CN([C@H]1CCC[C@@H]1C(C#N)(c1ccccc1)C1CCN(CC2CN(c3ccc(S(=O)(=O)C4CC4)cc3)C2)CC1)S(C)(=O)=O] | rac-N-((1S,2R)-2-(cyano(1-((1-(4-(cyclopropylsulfonyl)phenyl)azetidin-3-yl)methyl)piperidin-4-yl)(phenyl)methyl)cyclopentyl)-N-methylmethanesulfonamide |
| 274 | 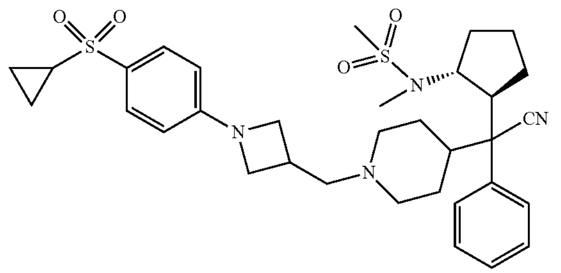 [SMILES: CN([C@@H]1CCC[C@H]1C(C#N)(c1ccccc1)C1CCN(CC2CN(c3ccc(S(=O)(=O)C4CC4)cc3)C2)CC1)S(C)(=O)=O] | rac-N-((1R,2S)-2-(cyano(1-((1-(4-(cyclopropylsulfonyl)phenyl)azetidin-3-yl)methyl)piperidin-4-yl)(phenyl)methyl)cyclopentyl)-N-methanesulfonamide |
| 275 | 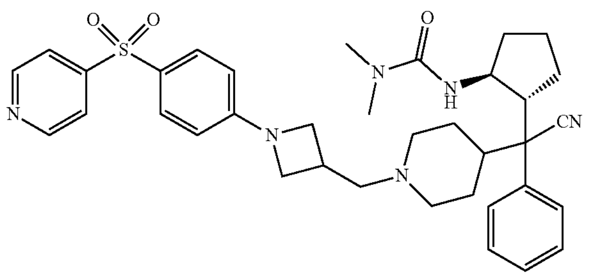 [SMILES: CN(C)C(=O)N[C@H]1CCC[C@@H]1C(C#N)(c1ccccc1)C1CCN(CC2CN(c3ccc(S(=O)(=O)c4ccncc4)cc3)C2)CC1] | rac-3-((1S,2R)-2-(cyano(phenyl)(1-((1-(4-(pyridin-4-ylsulfonyl)phenyl)azetidin-3-yl)methyl)piperidin-4-yl)methyl)cyclopentyl)-1,1-dimethylurea |
| 276 | 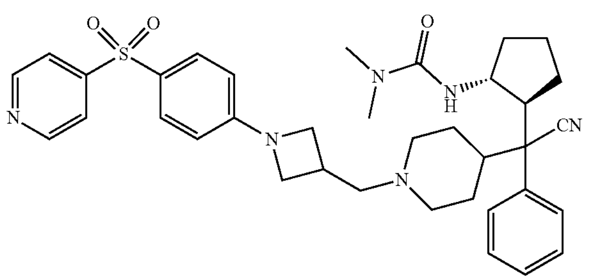 | rac-3-((1R,2S)-2-(cyano(phenyl)(1-((1-(4-(pyridin-4-ylsulfonyl)phenyl)azetidin-3-yl)methyl)piperidin-4-yl)methyl)cyclopentyl)-1,1-dimethylurea |
| 277 | 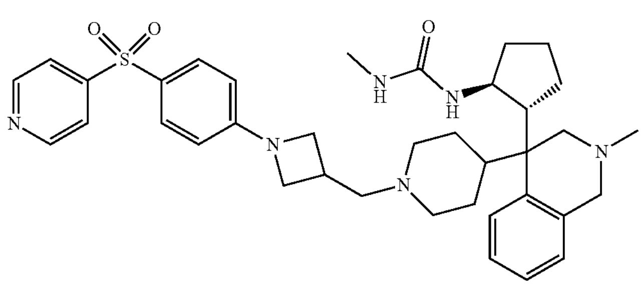 [SMILES: CNC(=O)N[C@H]1CCC[C@@H]1C1(C2CCN(CC3CN(c4ccc(S(=O)(=O)c5ccncc5)cc4)C3)CC2)CN(C)Cc2ccccc21] | rac-1-methyl-3-((1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl)urea |

TABLE 1-continued

| Cpd. No. | Chemical Structure | Chemical Name |
|---|---|---|
| 278 | 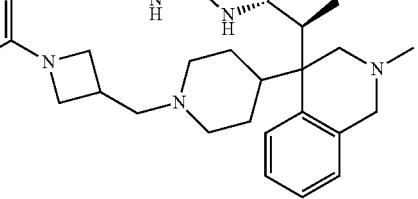 | rac-1-methyl-3-((1R,2S)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl)urea |
| 279 | 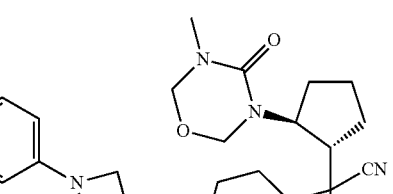 | rac-2-((1R,2S)-2-(5-methyl-4-oxo-1,3,5-oxadiazinan-3-yl)cyclopentyl)-2-phenyl-2-(1-((1-(4-(pyridin-4-ylsulfonyl)phenyl)azetidin-3-yl)methyl)piperidin-4-yl)acetonitrile |
| 280 | 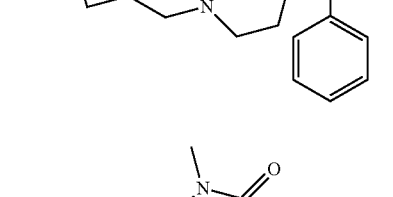 | rac-2-((1S,2R)-2-(5-methyl-4-oxo-1,3,5-oxadiazinan-3-yl)cyclopentyl)-2-phenyl-2-(1-((1-(4-(pyridin-4-ylsulfonyl)phenyl)azetidin-3-yl)methyl)piperidin-4-yl)acetonitrile |
| 281 | 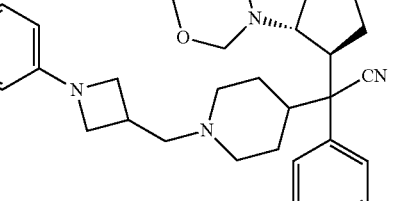 | rac-N-((1S,2R)-2-(cyano(1-((1-(4-(cyclopropylsulfonyl)phenyl)azetidin-3-yl)methyl)piperidin-4-yl)(phenyl)methyl)cyclopentyl)acetamide |
| 282 | 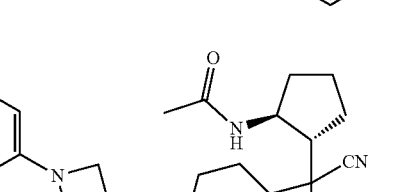 | rac-N-((1R,2S)-2-(cyano(1-((1-(4-(cyclopropylsulfonyl)phenyl)azetidin-3-yl)methyl)piperidin-4-yl)(phenyl)methyl)cyclopentyl)acetamide |

TABLE 1-continued

| Cpd. No. | Chemical Structure | Chemical Name |
|---|---|---|
| 283 | 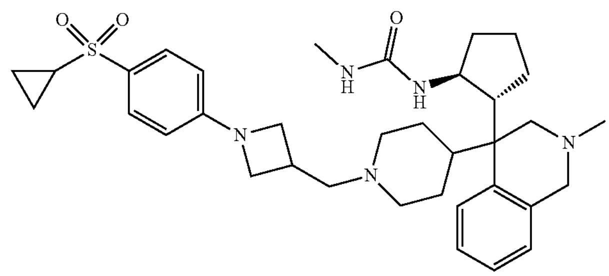 [SMILES: CNC(=O)N[C@H]1CCC[C@@H]1C1(C2CCN(CC3CN(c4ccc(S(=O)(=O)C5CC5)cc4)C3)CC2)CN(C)Cc2ccccc21] | rac-1-((1S,2R)-2-(4-(1-((1-(4-(cyclopropylsulfonyl)phenyl)azetidin-3-yl)methyl)piperidin-4-yl)-2-methyl-1,2,3,4-tetrahydroisoquinolin-4-yl)cyclopentyl)-3-methylurea |
| 284 | 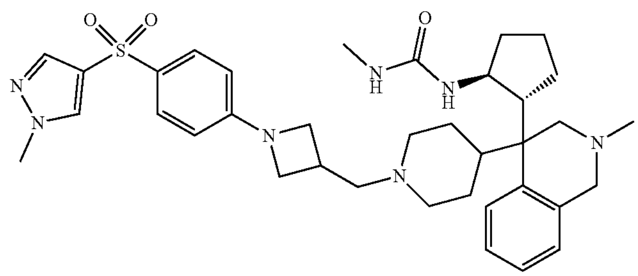 [SMILES: CNC(=O)N[C@H]1CCC[C@@H]1C1(C2CCN(CC3CN(c4ccc(S(=O)(=O)c5cnn(C)c5)cc4)C3)CC2)CN(C)Cc2ccccc21] | rac-1-methyl-3-((1S,2R)-2-(2-methyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)urea |
| 285 | 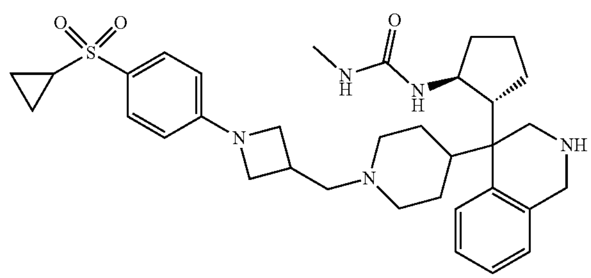 [SMILES: CNC(=O)N[C@H]1CCC[C@@H]1C1(C2CCN(CC3CN(c4ccc(S(=O)(=O)C5CC5)cc4)C3)CC2)CNCc2ccccc21] | rac-1-((1S,2R)-2-(4-(1-((1-(4-(cyclopropylsulfonyl)phenyl)azetidin-3-yl)methyl)piperidin-4-yl)-1,2,3,4-tetrahydroisoquinolin-4-yl)cyclopentyl)-3-methylurea |
| 286 | 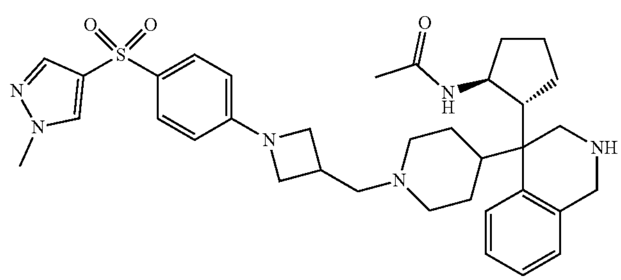 [SMILES: CC(=O)N[C@H]1CCC[C@@H]1C1(C2CCN(CC3CN(c4ccc(S(=O)(=O)c5cnn(C)c5)cc4)C3)CC2)CNCc2ccccc21] | rac-N-((1S,2R)-2-(4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)acetamide |
| 287 | 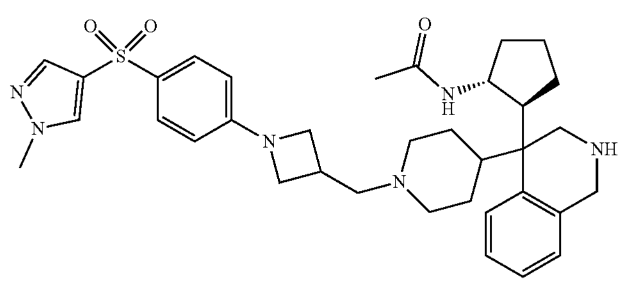 [SMILES: CC(=O)N[C@@H]1CCC[C@H]1C1(C2CCN(CC3CN(c4ccc(S(=O)(=O)c5cnn(C)c5)cc4)C3)CC2)CNCc2ccccc21] | rac-N-((1R,2S)-2-(4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)acetamide |

TABLE 1-continued

| Cpd. No. | Chemical Structure | Chemical Name |
|---|---|---|
| 288 | 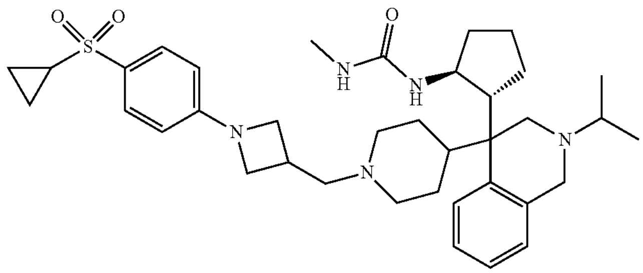 [SMILES: CNC(=O)N[C@H]1CCC[C@@H]1C1(C2CCN(CC3CN(c4ccc(S(=O)(=O)C5CC5)cc4)C3)CC2)CN(C(C)C)Cc2ccccc21] | rac-1-((1S,2R)-2-(4-(1-((1-(4-(cyclopropylsulfonyl)phenyl)azetidin-3-yl)methyl)piperidin-4-yl)-2-isopropyl-1,2,3,4-tetrahydroisoquinolin-4-yl)cyclopentyl)-3-methylurea |
| 289 | 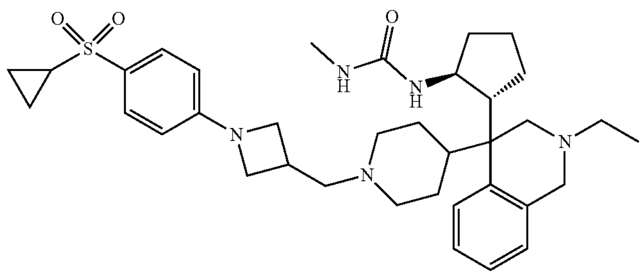 [SMILES: CCN1Cc2ccccc2C(C2CCN(CC3CN(c4ccc(S(=O)(=O)C5CC5)cc4)C3)CC2)([C@H]2CCC[C@@H]2NC(=O)NC)C1] | rac-1-((1S,2R)-2-(4-(1-((1-(4-(cyclopropylsulfonyl)phenyl)azetidin-3-yl)methyl)piperidin-4-yl)-2-ethyl-1,2,3,4-tetrahydroisoquinolin-4-yl)cyclopentyl)-3-methylurea |
| 290 | 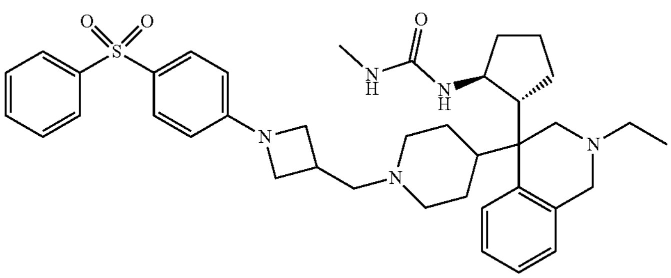 [SMILES: CCN1Cc2ccccc2C(C2CCN(CC3CN(c4ccc(S(=O)(=O)c5ccccc5)cc4)C3)CC2)([C@H]2CCC[C@@H]2NC(=O)NC)C1] | rac-1-((1S,2R)-2-(2-ethyl-4-(1-((1-(4-(phenylsulfonyl)phenyl)azetidin-3-yl)methyl)piperidin-4-yl)-1,2,3,4-tetrahydroisoquinolin-4-yl)cyclopentyl)-3-methylurea |
| 291 | 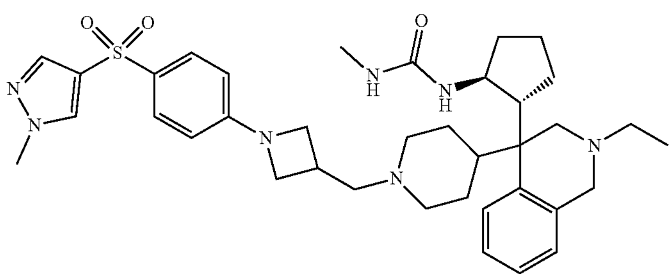 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(=O)NC)C1] | rac-1-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)-3-methylurea |
| 292 | 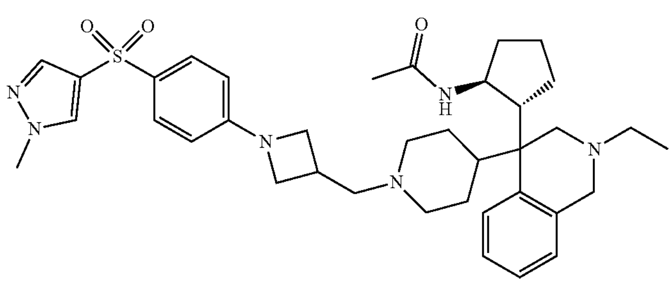 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(C)=O)C1] | rac-N-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)acetamide |

TABLE 1-continued

| Cpd. No. | Chemical Structure | Chemical Name |
|---|---|---|
| 293 | 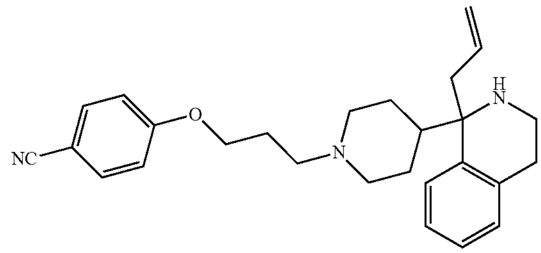 [SMILES: C=CCC1(C2CCN(CCCOc3ccc(C#N)cc3)CC2)NCCc2ccccc21] | 4-(3-(4-(1-allyl-1,2,3,4-tetrahydroisoquinolin-1-yl)piperidin-1-yl)propoxy)benzonitrile |
| 294 | 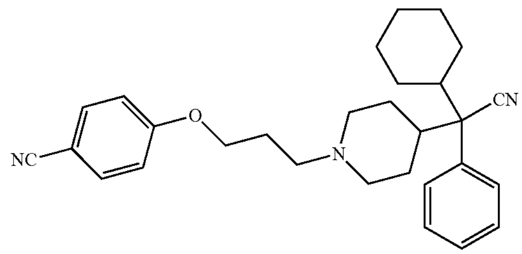 [SMILES: N#Cc1ccc(OCCCN2CCC(C(C#N)(c3ccccc3)C3CCCCC3)CC2)cc1] | 4-(3-(4-(cyano(cyclohexyl)(phenyl)methyl)piperidin-1-yl)propoxy)benzonitrile |
| 295 | 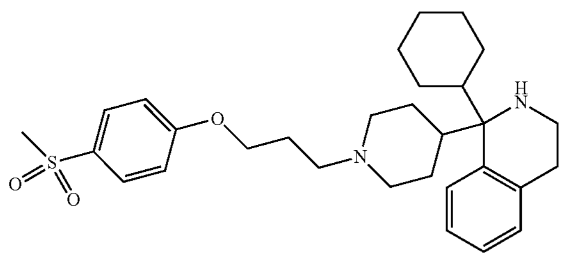 [SMILES: CS(=O)(=O)c1ccc(OCCCN2CCC(C3(C4CCCCC4)NCCc4ccccc43)CC2)cc1] | 1-cyclohexyl-1-(1-(3-(4-(methylsulfonyl)phenoxy)propyl)piperidin-4-yl)-1,2,3,4-tetrahydroisoquinoline |
| 296 | 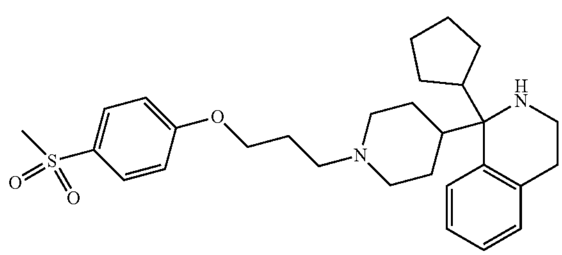 [SMILES: CS(=O)(=O)c1ccc(OCCCN2CCC(C3(C4CCCC4)NCCc4ccccc43)CC2)cc1] | 1-cyclopentyl-1-(1-(3-(4-(methylsulfonyl)phenoxy)propyl)piperidin-4-yl)-1,2,3,4-tetrahydroisoquinoline |
| 297 | 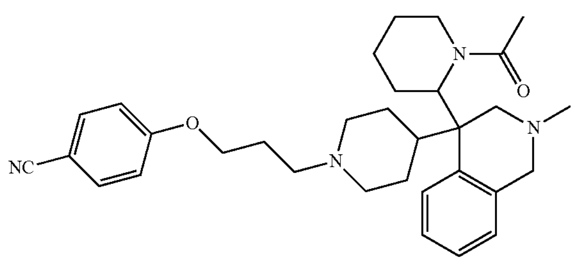 [SMILES: CC(=O)N1CCCCC1C1(C2CCN(CCCOc3ccc(C#N)cc3)CC2)CN(C)Cc2ccccc21] | 4-(3-(4-(4-(1-acetylpiperidin-2-yl)-2-methyl-1,2,3,4-tetrahydroisoquinolin-4-yl)piperidin-1-yl)propoxy)benzonitrile |
| 298 | 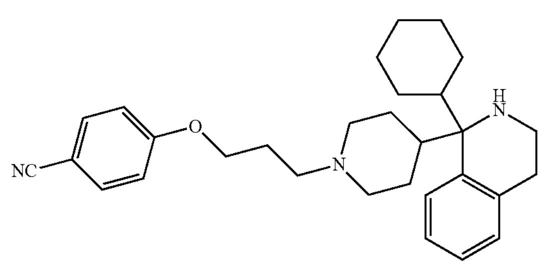 [SMILES: N#Cc1ccc(OCCCN2CCC(C3(C4CCCCC4)NCCc4ccccc43)CC2)cc1] | 4-(3-(4-(1-cyclohexyl-1,2,3,4-tetrahydroisoquinolin-1-yl)piperidin-1-yl)propoxy)benzonitrile |

TABLE 1-continued

| Cpd. No. | Chemical Structure | Chemical Name |
|---|---|---|
| 299 | 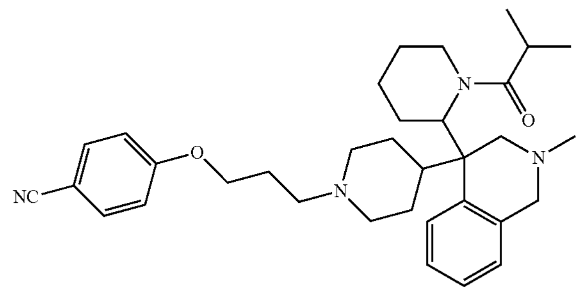 [SMILES: CC(C)C(=O)N1CCCCC1C1(C2CCN(CCCOc3ccc(C#N)cc3)CC2)CN(C)Cc2ccccc21] | 4-(3-(4-(4-(1-isobutyrylpiperidin-2-yl)-2-methyl-1,2,3,4-tetrahydroisoquinolin-4-yl)piperidin-1-yl)propoxy)benzonitrile |
| 300 | 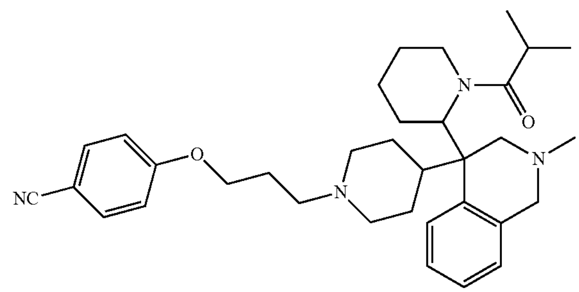 [SMILES: CC(C)C(=O)N1CCCCC1C1(C2CCN(CCCOc3ccc(C#N)cc3)CC2)CN(C)Cc2ccccc21] | 4-(3-(4-(4-(1-isobutyrylpiperidin-2-yl)-2-methyl-1,2,3,4-tetrahydroisoquinolin-4-yl)piperidin-1-yl)propoxy)benzonitrile |
| 301 | 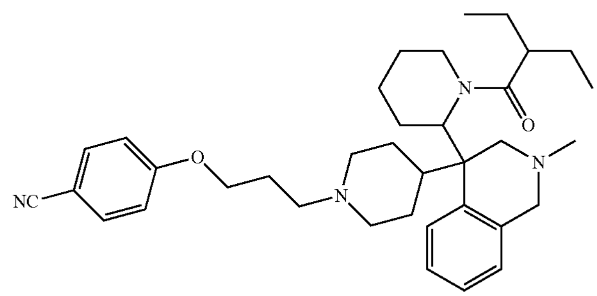 [SMILES: CCC(CC)C(=O)N1CCCCC1C1(C2CCN(CCCOc3ccc(C#N)cc3)CC2)CN(C)Cc2ccccc21] | 4-(3-(4-(4-(1-(2-ethylbutanoyl)piperidin-2-yl)-2-methyl-1,2,3,4-tetrahydroisoquinolin-4-yl)piperidin-1-yl)propoxy)benzonitrile |
| 302 | 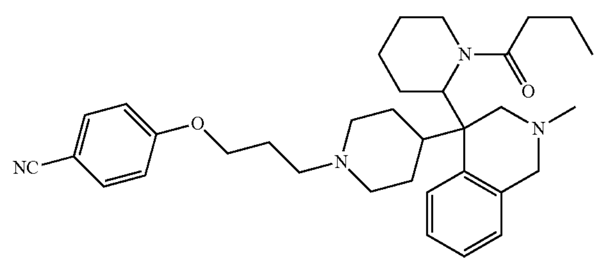 [SMILES: CCCC(=O)N1CCCCC1C1(C2CCN(CCCOc3ccc(C#N)cc3)CC2)CN(C)Cc2ccccc21] | 4-(3-(4-(4-(1-butyrylpiperidin-2-yl)-2-methyl-1,2,3,4-tetrahydroisoquinolin-4-yl)piperidin-1-yl)propoxy)benzonitrile |
| 303 | 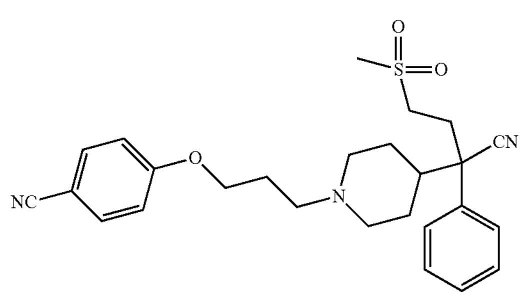 [SMILES: CS(=O)(=O)CCC(C#N)(c1ccccc1)C1CCN(CCCOc2ccc(C#N)cc2)CC1] | 4-(3-(4-(4-(1-cyano-3-(methylsulfonyl)-1-phenylpropyl)piperidin-1-yl)propoxy)benzonitrile |

TABLE 1-continued

| Cpd. No. | Chemical Structure | Chemical Name |
| --- | --- | --- |
| 304 | 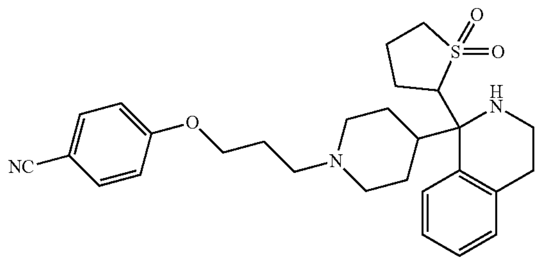 [SMILES: N#Cc1ccc(OCCCN2CCC(C3(C4CCCS4(=O)=O)NCCc4ccccc43)CC2)cc1] | 4-(3-(4-(1-(1,1-dioxidotetrahydrothiophen-2-yl)-1,2,3,4-tetrahydroisoquinolin-1-yl)piperidin-1-yl)propoxy)benzonitrile |
| 305 | 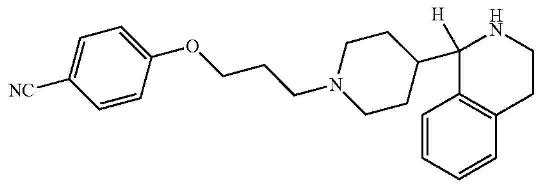 [SMILES: N#Cc1ccc(OCCCN2CCC(C3NCCc4ccccc43)CC2)cc1] | 4-(3-(4-(1,2,3,4-tetrahydroisoquinolin-1-yl)piperidin-1-yl)propoxy)benzonitrile |
| 306 | 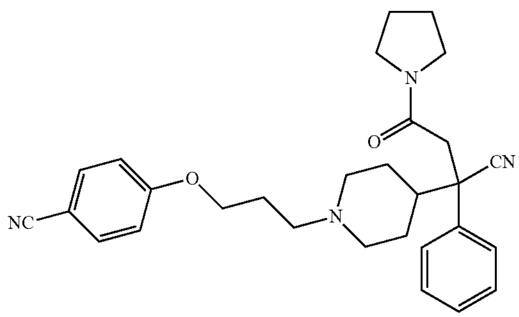 [SMILES: N#Cc1ccc(OCCCN2CCC(C(C#N)(CC(=O)N3CCCC3)c3ccccc3)CC2)cc1] | 4-(3-(4-(1-cyano-3-oxo-1-phenyl-3-(pyrrolidin-1-yl)propyl)piperidin-1-yl)propoxy)benzonitrile |
| 307 | 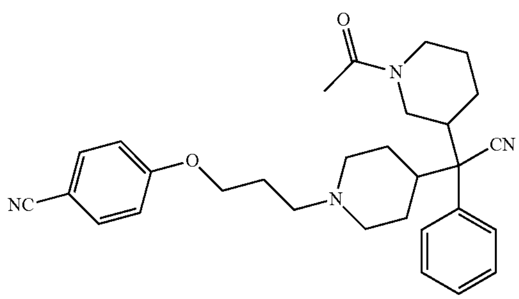 [SMILES: CC(=O)N1CCCC(C(C#N)(c2ccccc2)C2CCN(CCCOc3ccc(C#N)cc3)CC2)C1] | 4-(3-(4-((1-acetylpiperidin-3-yl)(cyano)(phenyl)methyl)piperidin-1-yl)propoxy)benzontrile |
| 308 | 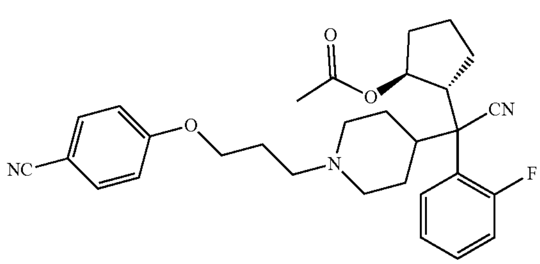 [SMILES: CC(=O)O[C@H]1CCC[C@@H]1C(C#N)(c1ccccc1F)C1CCN(CCCOc2ccc(C#N)cc2)CC1] | rac-(1S,2R)-2-(cyano(1-(3-(4-cyanophenoxy)propyl)piperidin-4-yl)(2-fluorophenyl)methyl)cyclopentyl acetate |
| 309 | 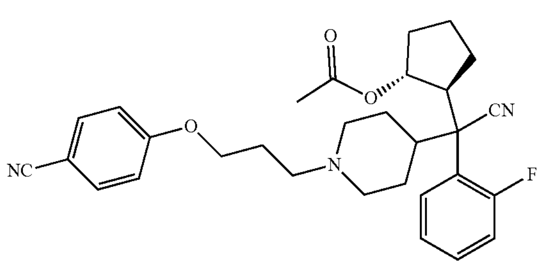 [SMILES: CC(=O)O[C@@H]1CCC[C@H]1C(C#N)(c1ccccc1F)C1CCN(CCCOc2ccc(C#N)cc2)CC1] | rac-(1R,2S)-2-(cyano(1-(3-(4-cyanophenoxy)propyl)piperidin-4-yl)(2-fluorophenyl)methyl) cyclopentyl acetate |

TABLE 1-continued

| Cpd. No. | Chemical Structure | Chemical Name |
|---|---|---|
| 310 | 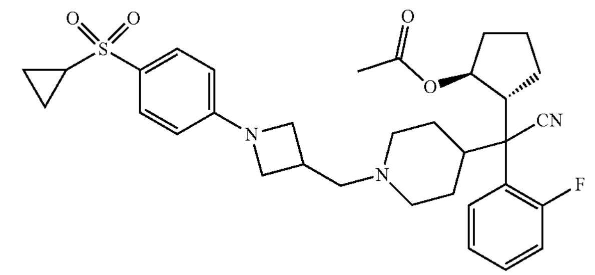 [SMILES: CC(=O)O[C@H]1CCC[C@@H]1C(C#N)(c1ccccc1F)C1CCN(CC2CN(c3ccc(S(=O)(=O)C4CC4)cc3)C2)CC1] | rac-(1S,2R)-2-(cyano(1-((1-(4-(cyclopropylsulfonyl)phenyl)azetidin-3-yl)methyl)piperidin-4-yl)(2-fluorophenyl)methyl)cyclopentyl acetate |
| 311 | 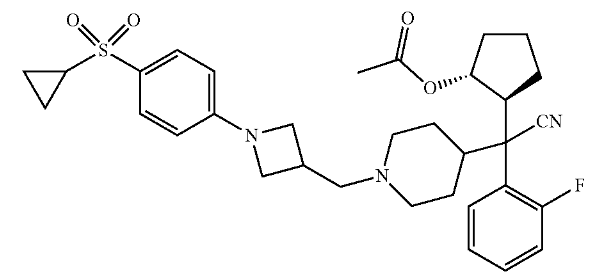 [SMILES: CC(=O)O[C@@H]1CCC[C@H]1C(C#N)(c1ccccc1F)C1CCN(CC2CN(c3ccc(S(=O)(=O)C4CC4)cc3)C2)CC1] | rac-(1R,2S)-2-(cyano(1-((1-(4-(cyclopropylsulfonyl)phenyl)azetidin-3-yl)methyl)piperidin-4-yl)(2-fluorophenyl)methyl)cyclopentyl acetate |
| 312 | 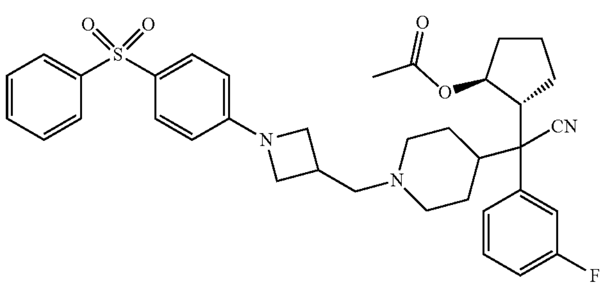 [SMILES: CC(=O)O[C@H]1CCC[C@@H]1C(C#N)(c1cccc(F)c1)C1CCN(CC2CN(c3ccc(S(=O)(=O)c4ccccc4)cc3)C2)CC1] | rac-(1S,2R)-2-(cyano(3-fluorophenyl)(1-((1-(4-(phenylsulfonyl)phenyl)azetidin-3-yl)methyl)piperidin-4-yl)methyl)cyclopentyl acetate |
| 313 | 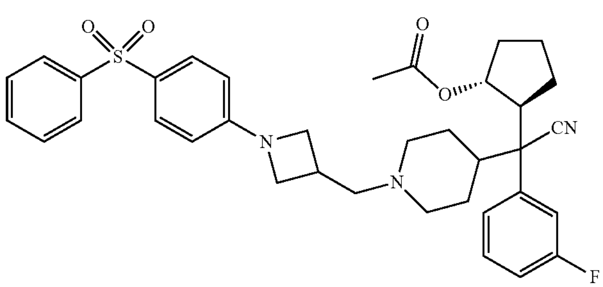 [SMILES: CC(=O)O[C@@H]1CCC[C@H]1C(C#N)(c1cccc(F)c1)C1CCN(CC2CN(c3ccc(S(=O)(=O)c4ccccc4)cc3)C2)CC1] | rac-(1R,2S)-2-(cyano(3-fluorophenyl)(1-((1-(4-(phenylsulfonyl)phenyl)azetidin-3-yl)methyl)piperidin-4-yl)methyl)cyclopentyl acetate |
| 314 | 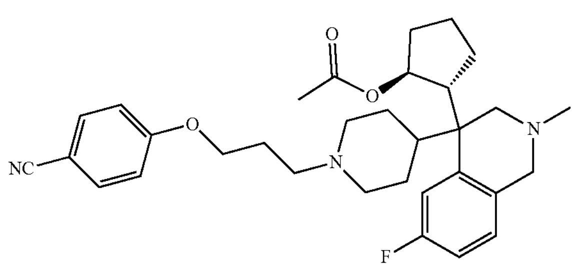 [SMILES: CC(=O)O[C@H]1CCC[C@@H]1C1(C2CCN(CCCOc3ccc(C#N)cc3)CC2)CN(C)Cc2ccc(F)cc21] | rac-(1S,2R)-2-(4-(1-(3-(4-cyanophenoxy)propyl)piperidin-4-yl)-6-fluoro-2-methyl-1,2,3,4-tetrahydroisoquinolin-4-yl)cyclopentyl acetate |

TABLE 1-continued

| Cpd. No. | Chemical Structure | Chemical Name |
|---|---|---|
| 315 | 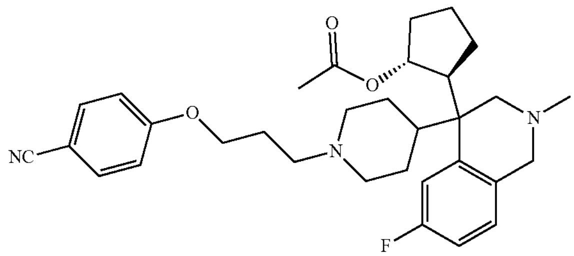 [SMILES: CC(=O)O[C@@H]1CCC[C@H]1C1(C2CCN(CCCOc3ccc(C#N)cc3)CC2)CN(C)Cc2ccc(F)cc21] | rac-(1R,2S)-2-(4-(1-(3-(4-cyanophenoxy)propyl)piperidin-4-yl)-6-fluoro-2-methyl-1,2,3,4-tetrahydroisoquinolin-4-yl)cyclopentyl acetate |
| 316 | 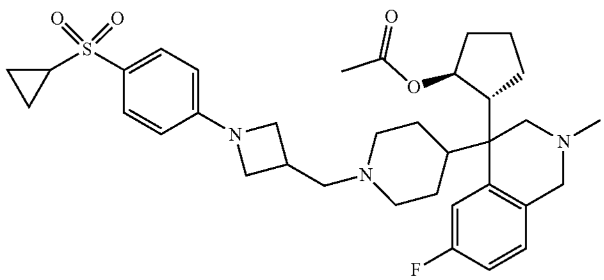 [SMILES: CC(=O)O[C@H]1CCC[C@@H]1C1(C2CCN(CC3CN(c4ccc(S(=O)(=O)C5CC5)cc4)C3)CC2)CN(C)Cc2ccc(F)cc21] | rac-(1S,2R)-2-(4-(1-((1-(4-(cyclopropylsulfonyl)phenyl)azetidin-3-yl)methyl)piperidin-4-yl)-6-fluoro-2-methyl-1,2,3,4-tetrahydroisoquinolin-4-yl)cyclopentyl acetate |
| 317 | 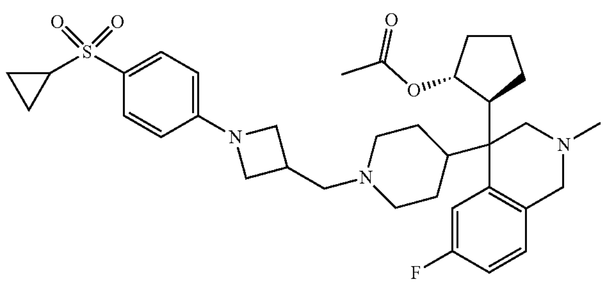 [SMILES: CC(=O)O[C@@H]1CCC[C@H]1C1(C2CCN(CC3CN(c4ccc(S(=O)(=O)C5CC5)cc4)C3)CC2)CN(C)Cc2ccc(F)cc21] | rac-(1R,2S)-2-(4-(1-((1-(4-(cyclopropylsulfonyl)phenyl)azetidin-3-yl)methyl)piperidin-4-yl)-6-fluoro-2-methyl-1,2,3,4-tetrahydroisoquinolin-4-yl)cyclopentyl acetate |
| 318 | 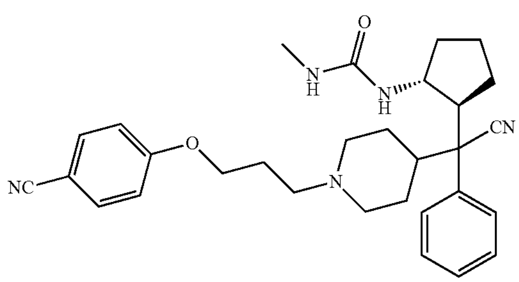 [SMILES: CNC(=O)N[C@@H]1CCC[C@H]1C(C#N)(c1ccccc1)C1CCN(CCCOc2ccc(C#N)cc2)CC1] | rac-1-((1R,2S)-2-(cyano(1-(3-(4-cyanophenoxy)propyl)piperidin-4-yl)(phenyl)methyl)cyclopentyl)-3-methylurea |
| 319 | 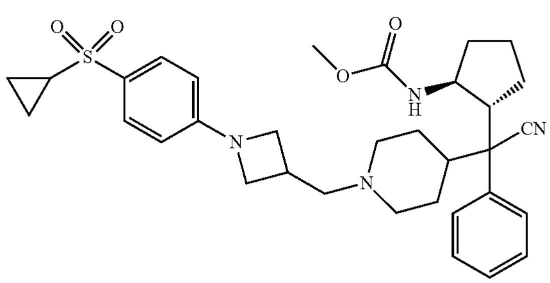 [SMILES: COC(=O)N[C@H]1CCC[C@@H]1C(C#N)(c1ccccc1)C1CCN(CC2CN(c3ccc(S(=O)(=O)C4CC4)cc3)C2)CC1] | rac-methyl ((1S,2R)-2-(cyano(1-((1-(4-(cyclopropylsulfonyl)phenyl)azetidin-3-yl)methyl)piperidin-4-yl)(phenyl)methyl)cyclopentyl)carbamate |

TABLE 1-continued

| Cpd. No. | Chemical Structure | Chemical Name |
|---|---|---|
| 320 | 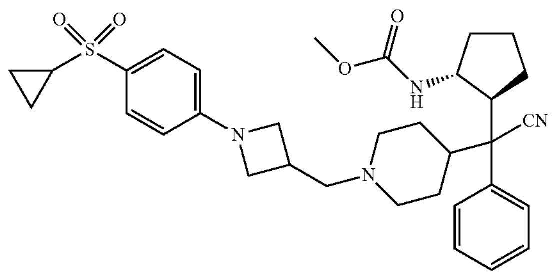 [SMILES: COC(=O)N[C@@H]1CCC[C@H]1C(C#N)(c1ccccc1)C1CCN(CC2CN(c3ccc(S(=O)(=O)C4CC4)cc3)C2)CC1] | rac-methyl ((1R,2S)-2-(cyano(1-((1-(4-(cyclopropylsulfonyl)phenyl)azetidin-3-yl)methyl)piperidin-4-yl)(phenyl)methyl)cyclopentyl)carbamate |
| 321 | 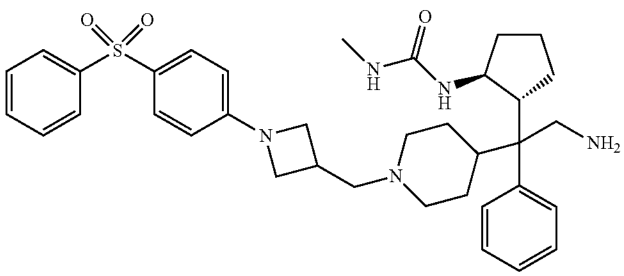 [SMILES: CNC(=O)N[C@H]1CCC[C@@H]1C(CN)(c1ccccc1)C1CCN(CC2CN(c3ccc(S(=O)(=O)c4ccccc4)cc3)C2)CC1] | rac-1-((1S,2R)-2-(2-amino-1-phenyl-1-(1-((1-(4-(phenylsulfonyl)phenyl)azetidin-3-yl)methyl)piperidin-4-yl)ethyl)cyclopentyl)-3-methylurea |
| 322 | 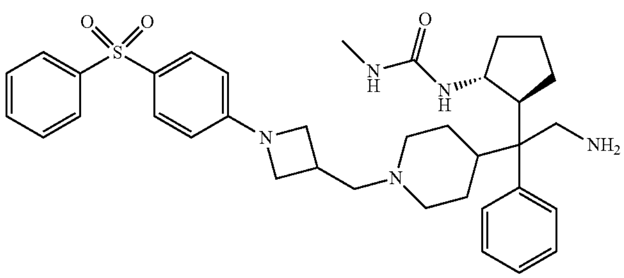 [SMILES: CNC(=O)N[C@@H]1CCC[C@H]1C(CN)(c1ccccc1)C1CCN(CC2CN(c3ccc(S(=O)(=O)c4ccccc4)cc3)C2)CC1] | rac-1-((1R,2S)-2-(2-amino-1-phenyl-1-(1-((1-(4-(phenylsulfonyl)phenyl)azetidin-3-yl)methyl)piperidin-4-yl)ethyl)cyclopentyl)-3-methylurea |
| 323 | 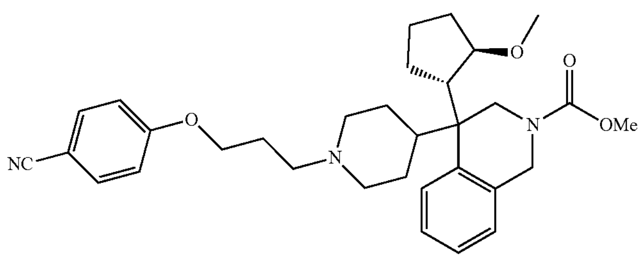 [SMILES: COC(=O)N1Cc2ccccc2C(C2CCN(CCCOc3ccc(C#N)cc3)CC2)([C@@H]2CCC[C@H]2OC)C1] | methyl rac-4-(1-(3-(4-cyanophenoxy)propyl)piperidin-4-yl)-4-((1S,2R)-2-methoxycyclopentyl)-3,4-dihydroisoquinoline-2(1H)-carboxylate |
| 324 | 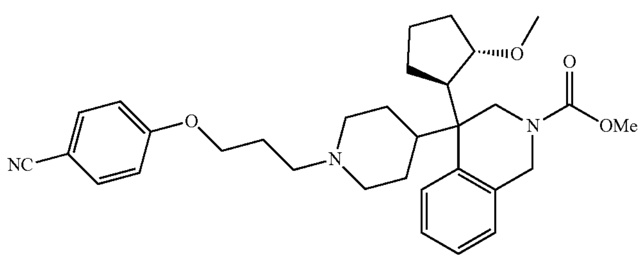 [SMILES: COC(=O)N1Cc2ccccc2C(C2CCN(CCCOc3ccc(C#N)cc3)CC2)([C@H]2CCC[C@@H]2OC)C1] | methyl rac-4-(1-(3-(4-cyanophenoxy)propyl)piperidin-4-yl)-4-((1R,2S)-2-methoxycyclopentyl)-3,4-dihydroisoquinoline-2(1H)-carboxylate |

TABLE 1-continued

| Cpd. No. | Chemical Structure | Chemical Name |
|---|---|---|
| 325 | 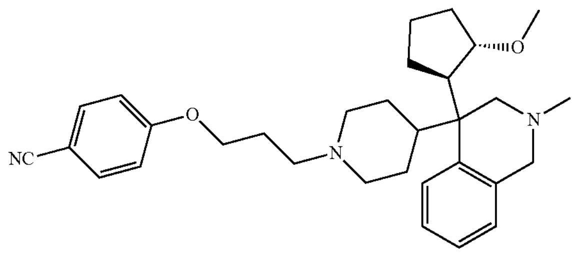 [SMILES: CO[C@H]1CCC[C@@H]1C1(C2CCN(CCCOc3ccc(C#N)cc3)CC2)CN(C)Cc2ccccc21] | rac-4-(3-(4-(4-((1R,2S)-2-methoxycyclopentyl)-2-methyl-1,2,3,4-tetrahydroisoquinolin-4-yl)piperidin-1-yl)propoxy)benzonitrile |
| 326 | 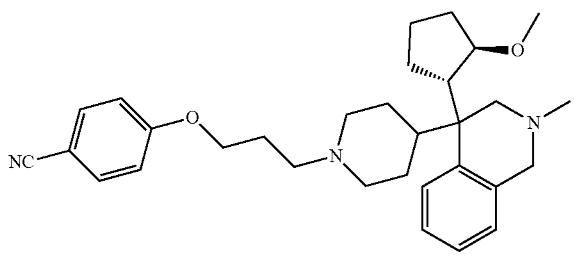 [SMILES: CO[C@@H]1CCC[C@H]1C1(C2CCN(CCCOc3ccc(C#N)cc3)CC2)CN(C)Cc2ccccc21] | rac-4-(3-(4-(4-((1S,2R)-2-methoxycyclopentyl)-2-methyl-1,2,3,4-tetrahydroisoquinolin-4-yl)piperidin-1-yl)propoxy)benzonitrile |
| 327 | 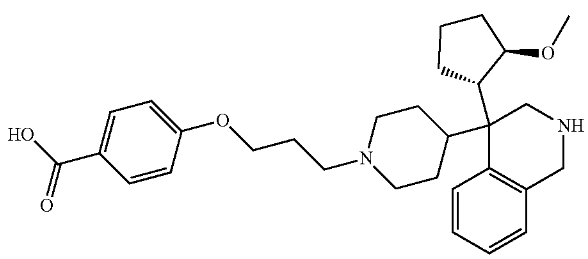 [SMILES: CO[C@@H]1CCC[C@H]1C1(C2CCN(CCCOc3ccc(C(=O)O)cc3)CC2)CNCc2ccccc21] | rac-4-(3-(4-(4-((1S,2R)-2-methoxycyclopentyl)-1,2,3,4-tetrahydroisoquinolin-4-yl)piperidin-1-yl)propoxy)benzoic acid |
| 328 | 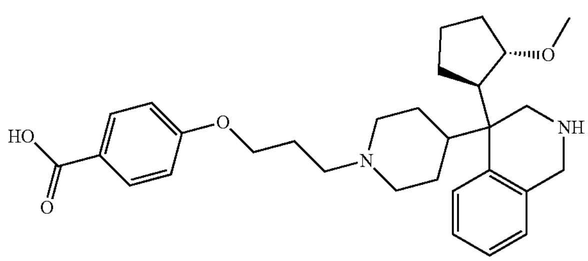 [SMILES: CO[C@H]1CCC[C@@H]1C1(C2CCN(CCCOc3ccc(C(=O)O)cc3)CC2)CNCc2ccccc21] | rac-4-(3-(4-(4-((1R,2S)-2-methoxycyclopentyl)-1,2,3,4-tetrahydroisoquinolin-4-yl)piperidin-1-yl)propoxy)benzoic acid |
| 329 | 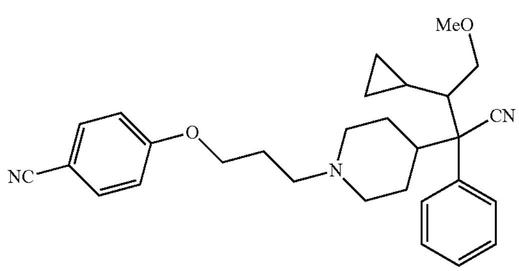 [SMILES: COCC(C1CC1)C(C#N)(c1ccccc1)C1CCN(CCCOc2ccc(C#N)cc2)CC1] | 4-(3-(4-(1-cyano-2-cyclopropyl)-3-methoxy-1-phenylpropyl)piperidin-1-yl)propoxy)benzonitrile |
| 330 | 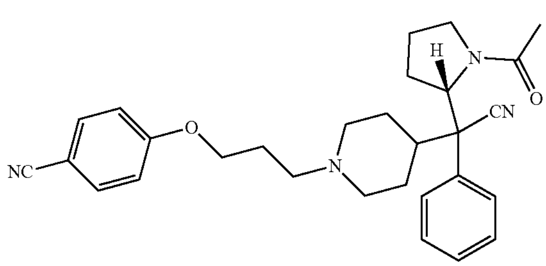 | 4-(3-(4-(((S)-1-acetylpyrrolidin-2-yl)(cyano)(phenyl)methyl)piperidin-1-yl)propoxy)benzonitrile |

TABLE 1-continued

| Cpd. No. | Chemical Structure | Chemical Name |
|---|---|---|
| 331 | 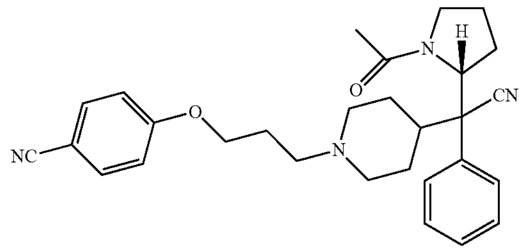 | 4-(3-(4-(((R)-1-acetylpyrrolidin-2-yl)(cyano)(phenyl)methyl)piperidin-1-yl)propoxy)benzonitrile |
| 332 | 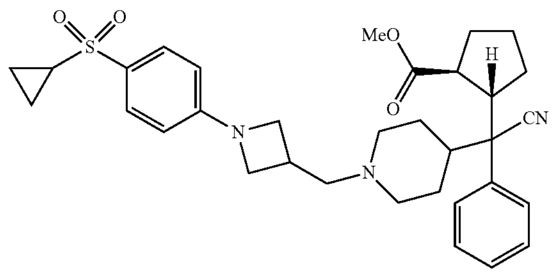 | methyl rac-(1S,2S)-2-(cyano(1-((1-(4-(cyclopropylsulfonyl)phenyl)azetidin-3-yl)methyl)piperidin-4-yl)(phenyl)methyl)cyclopentane-1-carboxylate |
| 333 | 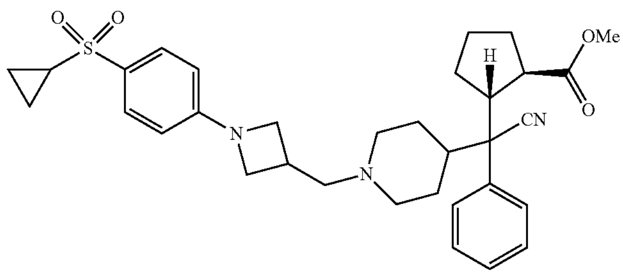 | methyl rac-(1R,2R)-2-(cyano(1-((1-(4-(cyclopropylsulfonyl)phenyl)azetidin-3-yl)methyl)piperidin-4-yl)(phenyl)methyl)cyclopentane-1-carboxylate |
| 334 | 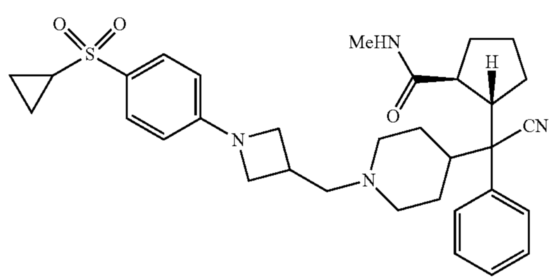 | rac-(1S,2S)-2-(cyano(1-((1-(4-(cyclopropylsulfonyl)phenyl)azetidin-3-yl)methyl)piperidin-4-yl)(phenyl)methyl)-N-methylcyclopentane-1-carboxylate |
| 335 | 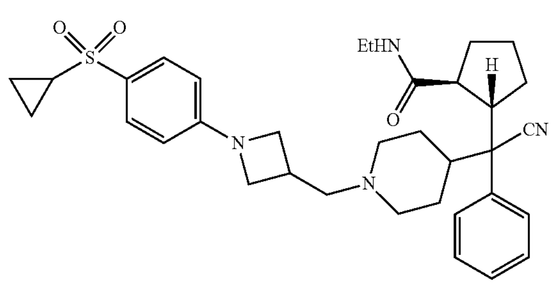 | rac-(1S,2S)-2-(cyano(1-((1-(4-(cyclopropylsulfonyl)phenyl)azetidin-3-yl)methyl)piperidin-4-yl)(phenyl)methyl)-N-ethylcyclopentane-1-carboxamide |

TABLE 1-continued

| Cpd. No. | Chemical Structure | Chemical Name |
|---|---|---|
| 336 | 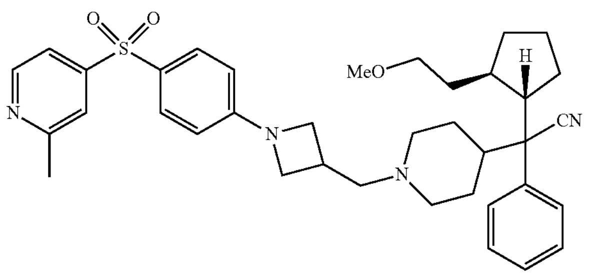 | rac-2-((1S,2R)-2-(2-methoxyethyl)cyclopentyl)-2-(1-((1-(4-((2-methylpyridin-4-yl)sulfonyl)phenyl)azetidin-3-yl)methyl)piperidin-4-yl)-2-phenylacetonitrile |
| 337 | 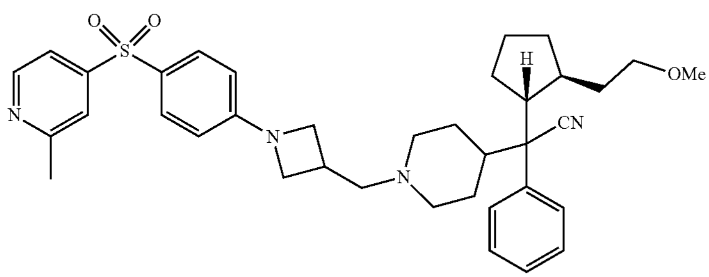 | rac-2-((1R,2S)-2-(2-methoxyethyl)cyclopentyl)-2-(1-((1-(4-((2-methylpyridin-4-yl)sulfonyl)phenyl)azetidin-3-yl)methyl)piperidin-4-yl)-2-phenylacetonitrile |
| 338 | 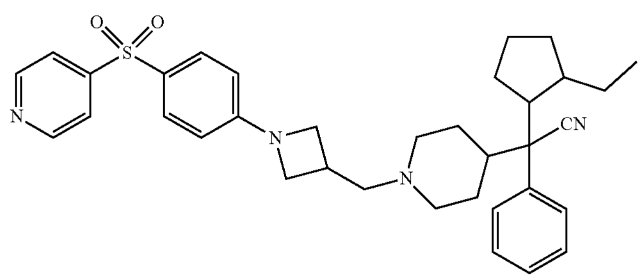 [SMILES: CCC1CCCC1C(C#N)(c1ccccc1)C1CCN(CC2CN(c3ccc(S(=O)(=O)c4ccncc4)cc3)C2)CC1] | 2-(2-ethylcyclopentyl)-2-phenyl-2-(1-((1-(4-(pyridin-4-ylsulfonyl)phenyl)azetidin-3-yl)methyl)piperidin-4-yl)acetonitrile |
| 339 | 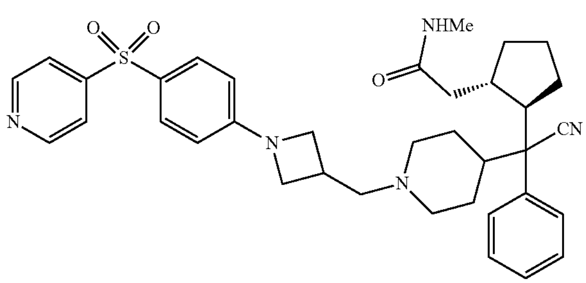 [SMILES: CNC(=O)C[C@@H]1CCC[C@H]1C(C#N)(c1ccccc1)C1CCN(CC2CN(c3ccc(S(=O)(=O)c4ccncc4)cc3)C2)CC1] | rac-2-((1S,2R)-2-(cyano(phenyl)(1-((1-(4-(pyridin-4-ylsulfonyl)phenyl)azetidin-3-yl)methyl)piperidin-4-yl)methyl)cyclopentyl)-N-methylacetamide |
| 340 | 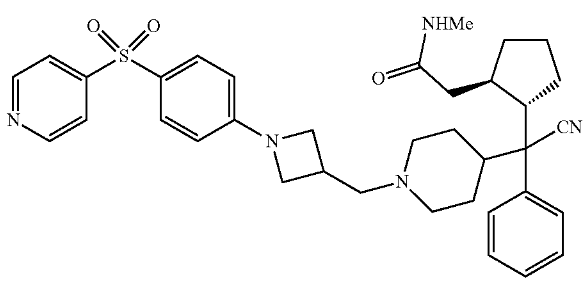 [SMILES: CNC(=O)C[C@H]1CCC[C@@H]1C(C#N)(c1ccccc1)C1CCN(CC2CN(c3ccc(S(=O)(=O)c4ccncc4)cc3)C2)CC1] | rac-2-((1R,2S)-2-(cyano(phenyl)(1-((1-(4-(pyridin-4-ylsulfonyl)phenyl)azetidin-3-yl)methyl)piperidin-4-yl)methyl)cyclopentyl)-N-methylacetamide |

TABLE 1-continued

| Cpd. No. | Chemical Structure | Chemical Name |
|---|---|---|
| 341 | 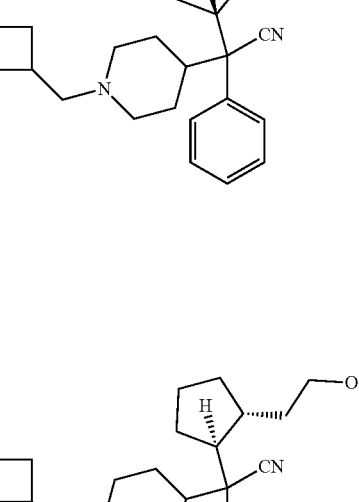 | rac-2-((1R,2S)-2-(2-hydroxyethyl)cyclopentyl)-2-phenyl-2-(1-((1-(4-(pyridin-4-ylsulfonyl)phenyl)azetidin-3-yl)methyl)piperidin-4-yl)acetonitrile |
| 342 | 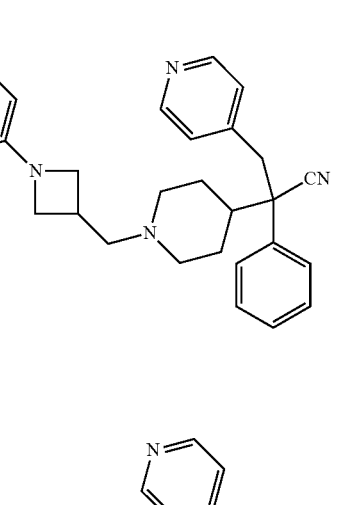 | rac-2-((1S,2R)-2-(2-hydroxyethyl)cyclopentyl)-2-phenyl-2-(1-((1-(4-(pyridin-4-ylsulfonyl)phenyl)azetidin-3-yl)methyl)piperidin-4-yl)acetonitrile |
| 343 | 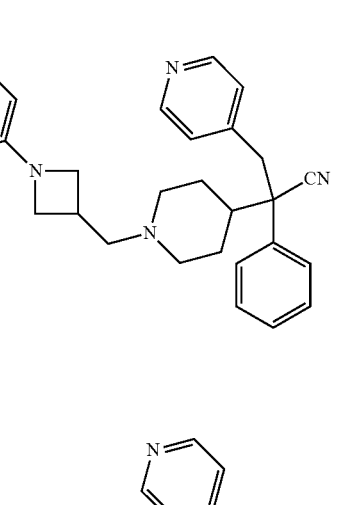 | 2-phenyl-3-(pyridin-4-yl)-2-(1-((1-(4-(pyridin-4-ylsulfonyl)phenyl)azetidin-3-yl)methyl)piperidin-4-yl)propanenitrile |
| 344 | 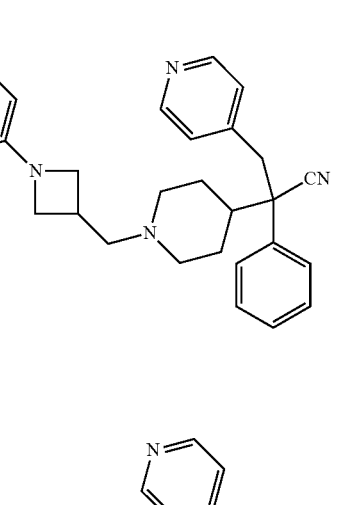 | 4-(3-(4-(1-cyano-1-phenyl-2-(pyridin-4-yl)ethyl)piperidin-1-yl)propoxy)benzonitrile |

TABLE 1-continued

| Cpd. No. | Chemical Structure | Chemical Name |
|---|---|---|
| 345 | 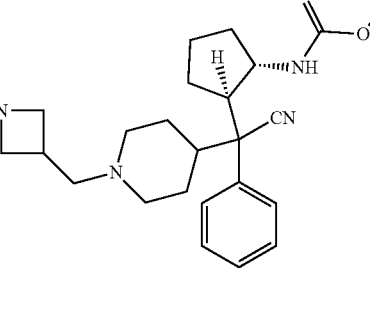 | methyl (rac-(1S,2R)-2-(cyano(phenyl)(1-((1-(4-(pyridin-4-ylsulfonyl)phenyl)azetidin-3-yl)methyl)piperidin-4-yl)methyl)cyclopentyl) carbamate |
| 346 | 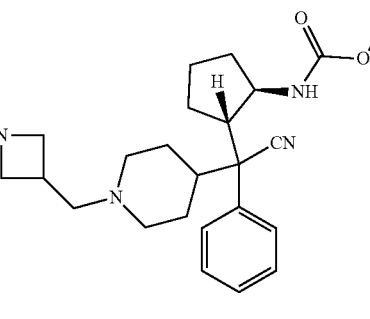 | methyl (rac-(1R,2S)-2-(cyano(phenyl)(1-((1-(4-(pyridin-4-ylsulfonyl)phenyl)azetidin-3-yl)methyl)piperidin-4-yl)methyl)cyclopentyl) carbamate |
| 347 | 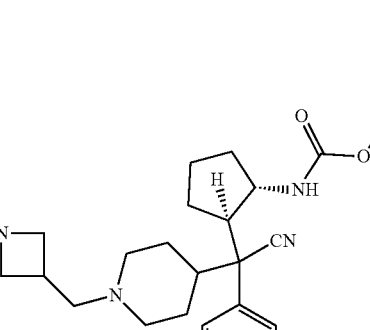 | methyl (rac-(1S,2R)-2-(cyano(phenyl)(1-((1-(4-(phenylsulfonyl)phenyl)azetidin-3-yl)methyl)piperidin-4-yl)methyl)cyclopentyl) carbamate |
| 348 | 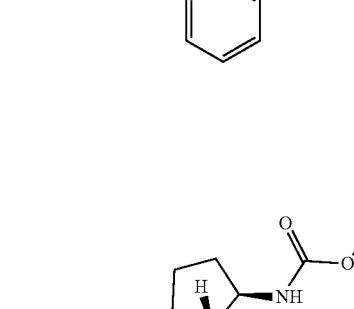 | methyl (rac-(1R,2S)-2-(cyano(phenyl)(1-((1-(4-(phenylsulfonyl)phenyl)azetidin-3-yl)methyl)piperidin-4-yl)methyl)cyclopentyl) carbamate |

TABLE 1-continued

| Cpd. No. | Chemical Structure | Chemical Name |
|---|---|---|
| 349 | 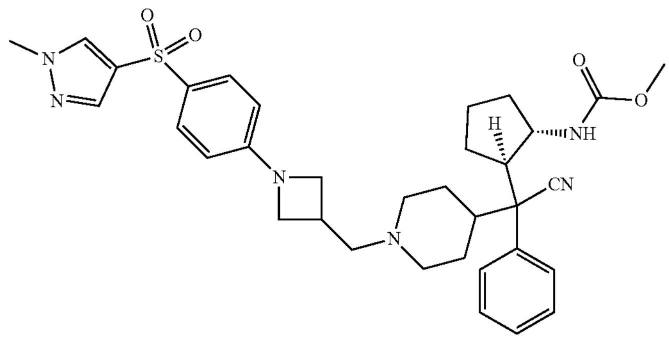 | methyl (rac-(1S,2R)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl)carbamate |
| 350 | 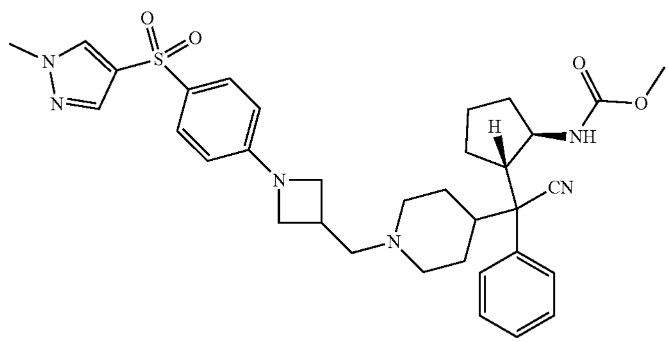 | methyl (rac-(1R,2S)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl)carbamate |
| 351 | 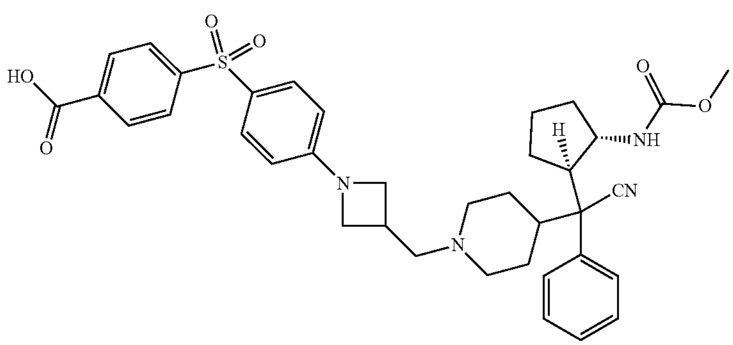 | rac-4-((4-(3-((4-(cyano((1R,2S)-2-((methoxycarbonyl)amino)cyclopentyl)(phenyl)methyl)piperidin-1-yl)methyl)azetidin-1-yl)phenyl)sulfonyl)benzoic acid |
| 352 | 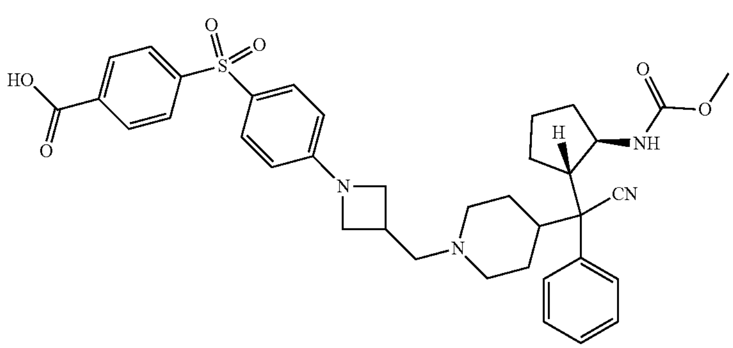 | rac-4-((4-(3-((4-(cyano((1S,2R)-2-((methoxycarbonyl)amino)cyclopentyl)(phenyl)methyl)piperidin-1-yl)methyl)azetidin-1-yl)phenyl)sulfonyl)benzoic acid |

TABLE 1-continued

| Cpd. No. | Chemical Structure | Chemical Name |
|---|---|---|
| 353 | 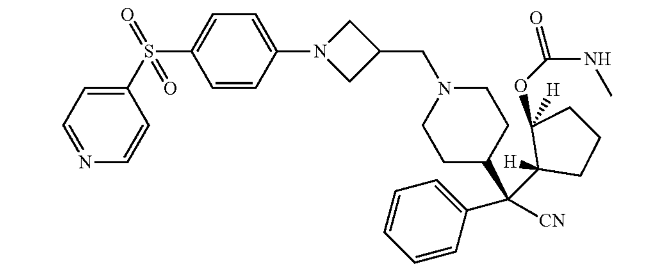 [SMILES: CNC(=O)O[C@H]1CCC[C@@H]1[C@](C#N)(c1ccccc1)C1CCN(CC2CN(c3ccc(S(=O)(=O)c4ccncc4)cc3)C2)CC1] | rac-(1S,2R)-2-((S)-cyano(phenyl)(1-((1-(4-(pyridin-4-ylsulfonyl)phenyl)azetidin-3-yl)methyl)piperidin-4-yl)methyl)cyclopentyl methylcarbamate |
| 354 | 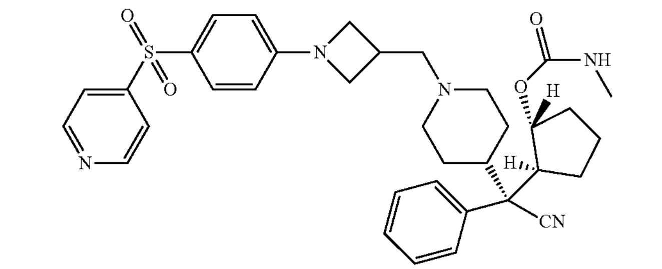 [SMILES: CNC(=O)O[C@@H]1CCC[C@H]1[C@@](C#N)(c1ccccc1)C1CCN(CC2CN(c3ccc(S(=O)(=O)c4ccncc4)cc3)C2)CC1] | rac-(1R,2S)-2-((R)-cyano(phenyl)(1-((1-(4-(pyridin-4-ylsulfonyl)phenyl)azetidin-3-yl)methyl)piperidin-4-yl)methyl)cyclopentyl methylcarbamate |
| 355 | 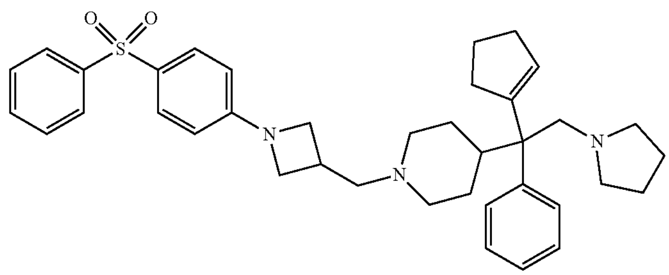 [SMILES: O=S(=O)(c1ccccc1)c1ccc(N2CC(CN3CCC(C(CN4CCCC4)(C4=CCCC4)c4ccccc4)CC3)C2)cc1] | 4-(1-(cyclopent-1-en-1-yl)-1-phenyl-2-(pyrrolidin-1-yl)ethyl)-1-((1-(4-(phenylsulfonyl)phenyl)azetidin-3-yl)methyl)piperidine |
| 356 | 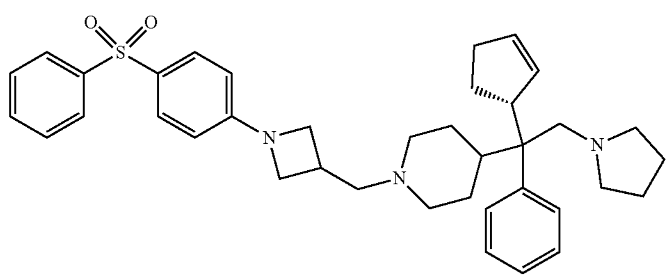 [SMILES: O=S(=O)(c1ccccc1)c1ccc(N2CC(CN3CCC(C(CN4CCCC4)(c4ccccc4)[C@H]4C=CCC4)CC3)C2)cc1] | 4-(1-((R)-cyclopent-2-en-1-yl)-1-phenyl-2-(pyrrolidin-1-yl)ethyl)-1-((1-(4-(phenylsulfonyl)phenyl)azetidin-3-yl)methyl)piperidine |
| 357 | 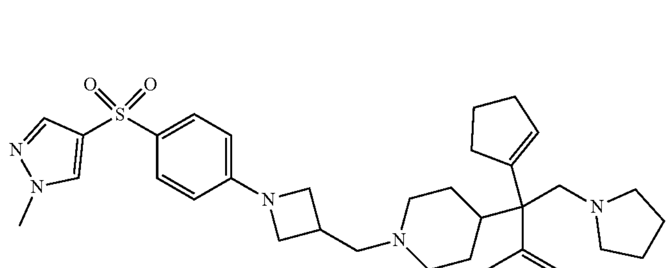 | 4-(1-(cyclopent-1-en-1-yl)-1-phenyl-2-(pyrrolidin-1-yl)ethyl)-1-((1-(4-((1-methyl-1H-pyrazol-4-yl)sulfonyl)phenyl)azetidin-3-yl)methyl)piperidine |

TABLE 1-continued

| Cpd. No. | Chemical Structure | Chemical Name |
|---|---|---|
| 358 | 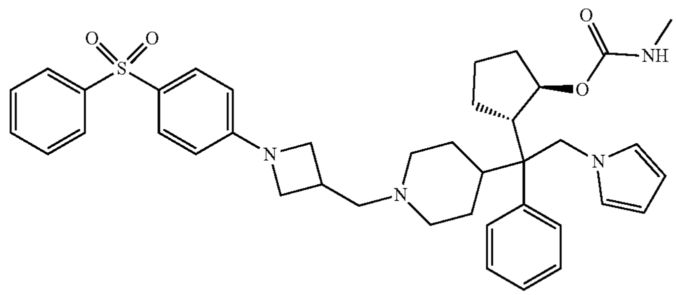 [SMILES: CNC(=O)O[C@@H]1CCC[C@H]1C(Cn1cccc1)(c1ccccc1)C1CCN(CC2CN(c3ccc(S(=O)(=O)c4ccccc4)cc3)C2)CC1] | rac-(1R,2S)-2-(1-phenyl-1-(1-((1-(4-(phenylsulfonyl)phenyl)azetidin-3-yl)methyl)piperidin-4-yl)-2-(1H-pyrrol-1-yl)ethyl)cyclopentyl methylcarbamate |
| 359 | 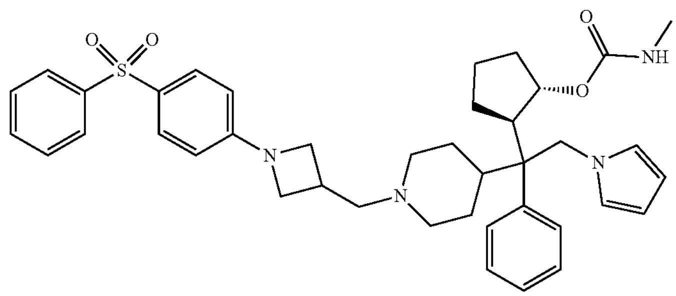 [SMILES: CNC(=O)O[C@H]1CCC[C@@H]1C(Cn1cccc1)(c1ccccc1)C1CCN(CC2CN(c3ccc(S(=O)(=O)c4ccccc4)cc3)C2)CC1] | rac-(1S,2R)-2-(1-phenyl-1-(1-((1-(4-(phenylsulfonyl)phenyl) azetidin-3-yl) methyl)piperidin-4-yl)-2-(1H-pyrrol-1-yl)ethyl)cyclopentyl methylcarbamate |
| 360 | 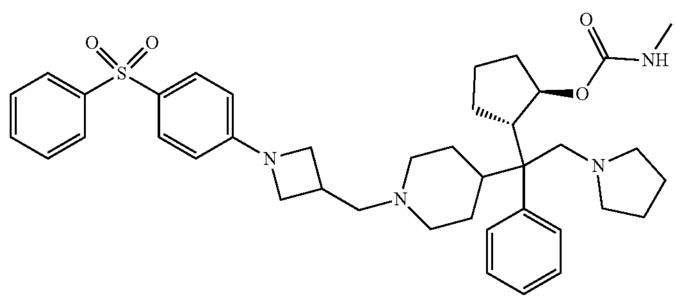 [SMILES: CNC(=O)O[C@@H]1CCC[C@H]1C(CN1CCCC1)(c1ccccc1)C1CCN(CC2CN(c3ccc(S(=O)(=O)c4ccccc4)cc3)C2)CC1] | rac-(1R,2S)-2-(1-phenyl-1-(1-((1-(4-(phenylsulfonyl)phenyl) azetidin-3-yl)methyl)piperidin-4-yl)-2-(pyrrolidin-1-yl)ethyl)cyclopentyl methylcarbamate |
| 361 | 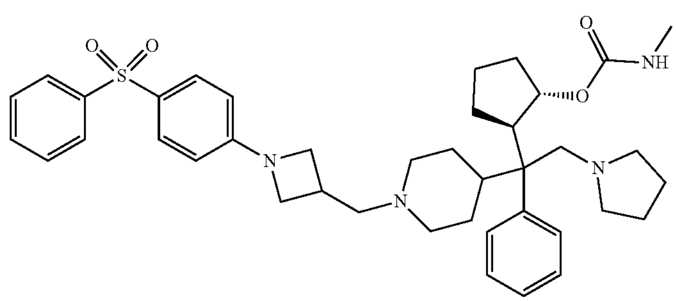 [SMILES: CNC(=O)O[C@H]1CCC[C@@H]1C(CN1CCCC1)(c1ccccc1)C1CCN(CC2CN(c3ccc(S(=O)(=O)c4ccccc4)cc3)C2)CC1] | rac-(1S,2R)-2-(1-phenyl-1-(1-((1-(4-(phenylsulfonyl)phenyl) azetidin-3-yl)methyl)piperidin-4-yl)-2-(pyrrolidin-1-yl)ethyl)cyclopentyl methylcarbamate |
| 362 | 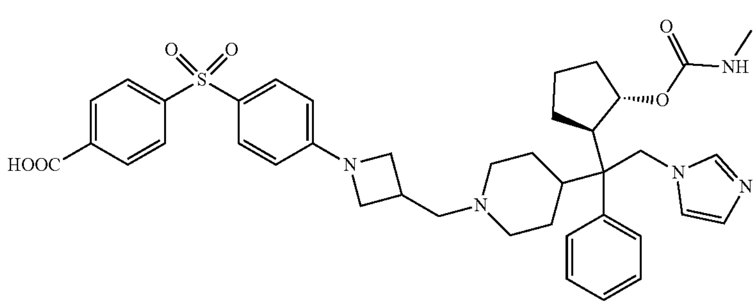 [SMILES: CNC(=O)O[C@H]1CCC[C@@H]1C(Cn1ccnc1)(c1ccccc1)C1CCN(CC2CN(c3ccc(S(=O)(=O)c4ccc(C(=O)O)cc4)cc3)C2)CC1] | rac-4-((4-(3-((4-(2-(1H-imidazol-1-yl)-1-((1R,2S)-2-((methylcarbamoyl)oxy) cyclopentyl)-1-phenylethyl)piperidin-1-yl)methyl)azetidin-1-yl)phenyl)sulfonyl)benzoic acid |

TABLE 1-continued

| Cpd. No. | Chemical Structure | Chemical Name |
|---|---|---|
| 363 | 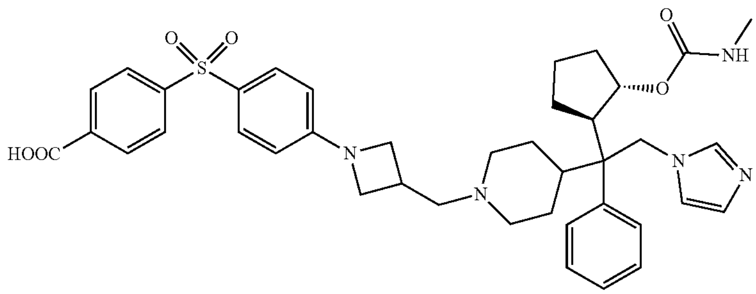 [SMILES: CNC(=O)O[C@H]1CCC[C@@H]1C(Cn1ccnc1)(c1ccccc1)C1CCN(CC2CN(c3ccc(S(=O)(=O)c4ccc(C(=O)O)cc4)cc3)C2)CC1] | rac-4-((4-(3-((4-(2-(1H-imidazol-1-yl)-1-((1R,2S)-2-((methylcarbamoyl)oxy)cyclopentyl)-1-phenylethyl)piperidin-1-yl)methyl)azetidin-1-yl)phenyl)sulfonyl)benzoic acid |
| 364 | 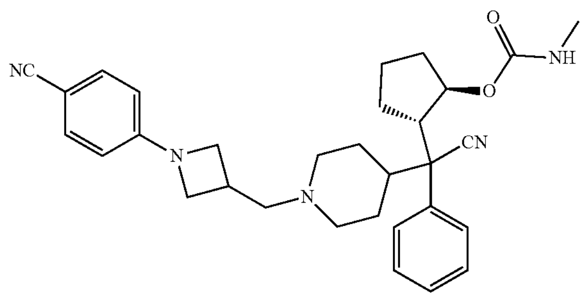 [SMILES: CNC(=O)O[C@@H]1CCC[C@H]1C(C#N)(c1ccccc1)C1CCN(CC2CN(c3ccc(C#N)cc3)C2)CC1] | rac-(1R,2S)-2-(cyano(1-((1-(4-cyanophenyl)azetidin-3-yl)methyl)piperidin-4-yl)(phenyl)methyl)cyclopentyl methylcarbamate |
| 365 | 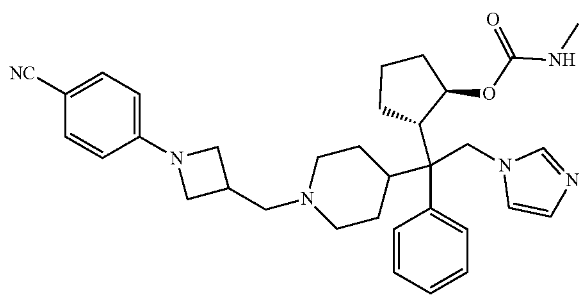 [SMILES: CNC(=O)O[C@@H]1CCC[C@H]1C(Cn1ccnc1)(c1ccccc1)C1CCN(CC2CN(c3ccc(C#N)cc3)C2)CC1] | rac-(1R,2S)-2-(1-(1-((1-(4-cyanophenyl)azetidin-3-yl)methyl)piperidin-4-yl)-2-(1H-imidazol-1-yl)-1-phenylethyl)cyclopentyl methylcarbamate |
| 366 | 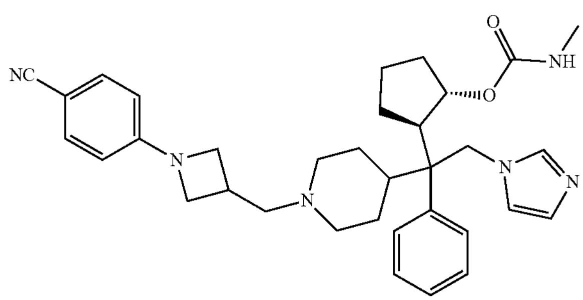 [SMILES: CNC(=O)O[C@H]1CCC[C@@H]1C(Cn1ccnc1)(c1ccccc1)C1CCN(CC2CN(c3ccc(C#N)cc3)C2)CC1] | rac-(1S,2R)-2-(1-(1-((1-(4-cyanophenyl)azetidin-3-yl)methyl)piperidin-4-yl)-2-(1H-imidazol-1-yl)-1-phenylethyl)cyclopentyl methylcarbamate |
| 367 | 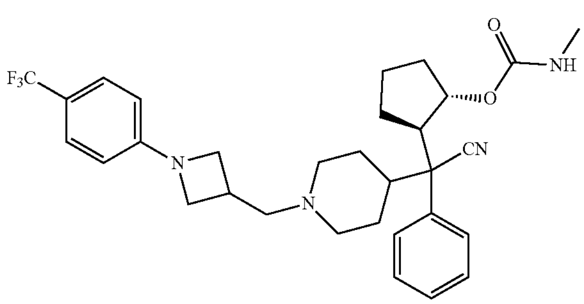 [SMILES: CNC(=O)O[C@H]1CCC[C@@H]1C(C#N)(c1ccccc1)C1CCN(CC2CN(c3ccc(C(F)(F)F)cc3)C2)CC1] | rac-(1S,2R)-2-(cyano(phenyl)(1-((1-(4-(trifluoromethyl)phenyl)azetidin-3-yl)methyl)piperidin-4-yl)methyl)cyclopentyl methylcarbamate |

TABLE 1-continued

| Cpd. No. | Chemical Structure | Chemical Name |
|---|---|---|
| 368 | 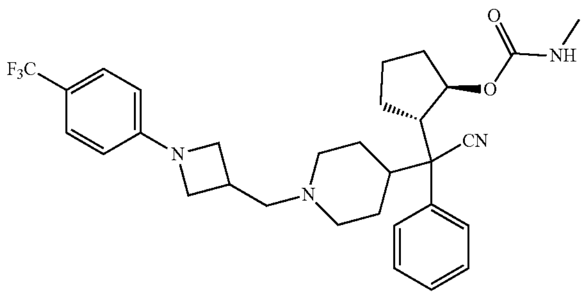 [SMILES: CNC(=O)O[C@@H]1CCC[C@H]1C(C#N)(c1ccccc1)C1CCN(CC2CN(c3ccc(C(F)(F)F)cc3)C2)CC1] | rac-(1R,2S)-2-(cyano(phenyl)(1-((1-(4-(trifluoromethyl)phenyl)azetidin-3-yl)methyl)piperidin-4-yl)methyl)cyclopentyl methylcarbamate |
| 369 | 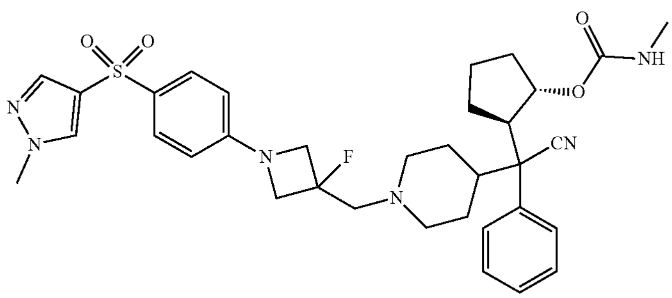 [SMILES: CNC(=O)O[C@H]1CCC[C@@H]1C(C#N)(c1ccccc1)C1CCN(CC2(F)CN(c3ccc(S(=O)(=O)c4cnn(C)c4)cc3)C2)CC1] | rac-(1S,2R)-2-(cyano(1-((3-fluoro-1-(4-((1-methyl-1H-pyrazol-4-yl)sulfonyl)phenyl)azetidin-3-yl)methyl)piperidin-4-yl)(phenyl)methyl)cyclopentyl methylcarbamate |
| 370 | 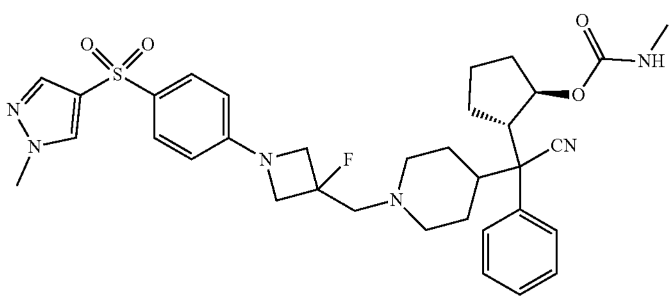 [SMILES: CNC(=O)O[C@@H]1CCC[C@H]1C(C#N)(c1ccccc1)C1CCN(CC2(F)CN(c3ccc(S(=O)(=O)c4cnn(C)c4)cc3)C2)CC1] | rac-(1R,2S)-2-(cyano(1-((3-fluoro-1-(4-((1-methyl-1H-pyrazol-4-yl)sulfonyl)phenyl)azetidin-3-yl)methyl)piperidin-4-yl)(phenyl)methyl)cyclopentyl methylcarbamate |
| 371 | 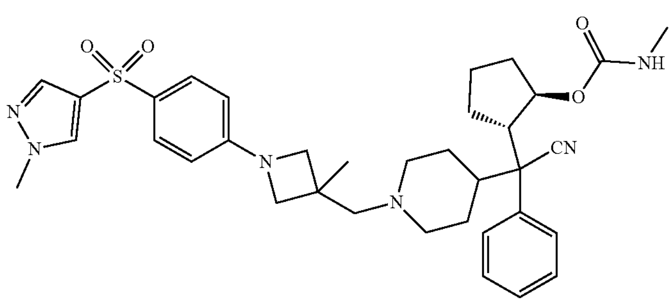 [SMILES: CNC(=O)O[C@@H]1CCC[C@H]1C(C#N)(c1ccccc1)C1CCN(CC2(C)CN(c3ccc(S(=O)(=O)c4cnn(C)c4)cc3)C2)CC1] | rac-(1R,2S)-2-(cyano(1-((3-methyl-1-(4-((1-methyl-1H-pyrazol-4-yl)sulfonyl)phenyl)azetidin-3-yl)methyl)piperidin-4-yl)(phenyl)methyl)cyclopentyl methylcarbamate |
| 372 | 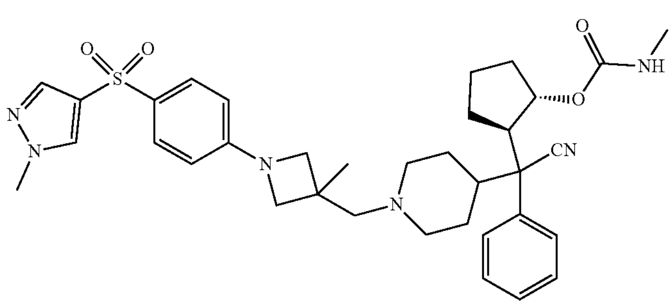 [SMILES: CNC(=O)O[C@H]1CCC[C@@H]1C(C#N)(c1ccccc1)C1CCN(CC2(C)CN(c3ccc(S(=O)(=O)c4cnn(C)c4)cc3)C2)CC1] | rac-(1S,2R)-2-(cyano(1-((3-methyl-1-(4-((1-methyl-1H-pyrazol-4-yl)sulfonyl)phenyl)azetidin-3-yl)methyl)piperidin-4-yl)(phenyl)methyl)cyclopentyl methylcarbamate |

TABLE 1-continued

| Cpd. No. | Chemical Structure | Chemical Name |
|---|---|---|
| 373 | 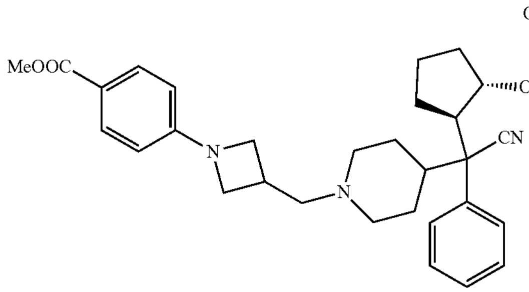 | methyl rac-4-(3-((4-(cyano((1R,2S)-2-((methylcarbamoyl)oxy)cyclopentyl)(phenyl)methyl)piperidin-1-yl)methyl)azetidin-1-yl)benzoate |
| 374 | 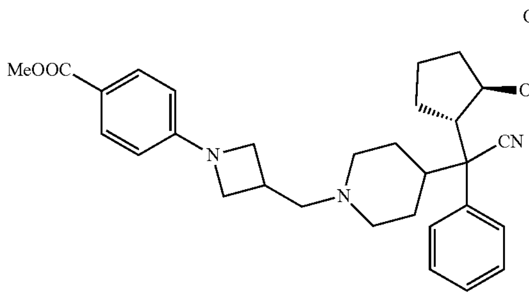 | methyl rac-4-(3-((4-(cyano((1S,2R)-2-((methylcarbamoyl)oxy)cyclopentyl)(phenyl)methyl)piperidin-1-yl)methyl)azetidin-1-yl)benzoate |
| 375 | 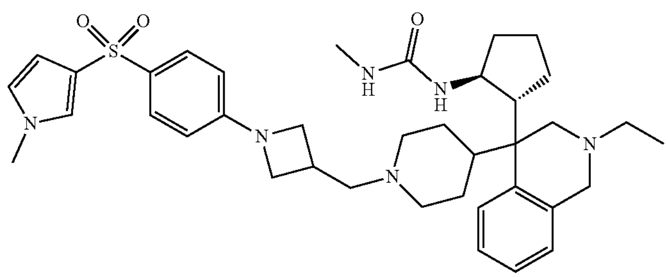 [SMILES: CCN1Cc2ccccc2C(C2CCN(CC3CN(c4ccc(S(=O)(=O)c5ccn(C)c5)cc4)C3)CC2)([C@H]2CCC[C@@H]2NC(=O)NC)C1] | rac-1-((1S,2R)-2-(2-ethyl-4-(1-((1-(4-((1-methyl-1H-pyrrol-3-yl)sulfonyl)phenyl)azetidin-3-yl)methyl)piperidin-4-yl)-1,2,3,4-tetrahydroisoquinolin-4-yl)cyclopentyl)-3-methylurea |
| 376 | 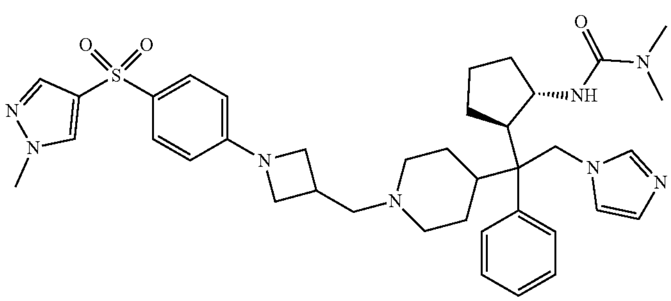 [SMILES: CN(C)C(=O)N[C@H]1CCC[C@@H]1C(Cn1ccnc1)(c1ccccc1)C1CCN(CC2CN(c3ccc(S(=O)(=O)c4cnn(C)c4)cc3)C2)CC1] | rac-3-((1S,2R)-2-(2-(1H-imidazol-1-yl)-1-(1-((1-(4-((1-methyl-1H-pyrazol-4-yl)sulfonyl)phenyl)azetidin-3-yl)methyl)piperidin-4-yl)-1-phenylethyl)cyclopentyl)-1,1-dimethylurea |
| 377 | 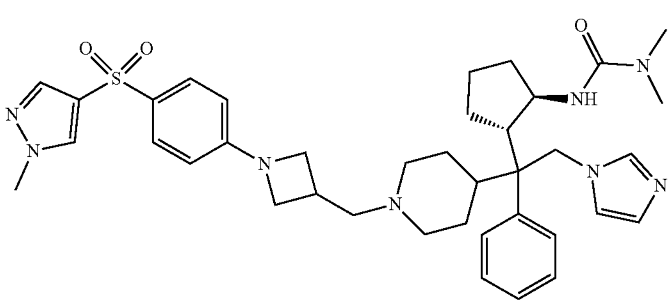 [SMILES: CN(C)C(=O)N[C@@H]1CCC[C@H]1C(Cn1ccnc1)(c1ccccc1)C1CCN(CC2CN(c3ccc(S(=O)(=O)c4cnn(C)c4)cc3)C2)CC1] | rac-3-((1R,2S)-2-(2-(1H-imidazol-1-yl)-1-(1-((1-(4-((1-methyl-1H-pyrazol-4-yl)sulfonyl)phenyl)azetidin-3-yl)methyl)piperidin-4-yl)-1-phenylethyl)cyclopentyl)-1,1-dimethylurea |

TABLE 1-continued

| Cpd. No. | Chemical Structure | Chemical Name |
|---|---|---|
| 378 | 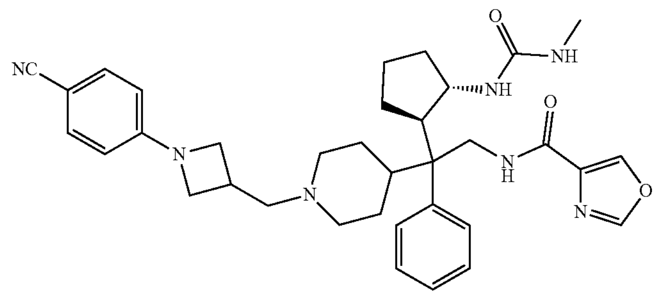 [SMILES: CNC(=O)N[C@H]1CCC[C@@H]1C(CNC(=O)c1cocn1)(c1ccccc1)C1CCN(CC2CN(c3ccc(C#N)cc3)C2)CC1] | rac-N-(2-(1-((1-(4-cyanophenyl)azetidin-3-yl)methyl)piperidin-4-yl)-2-((1R,2S)-2-(3-methylureido)cyclopentyl)-2-phenylethyl)oxazole-4-carboxamide |
| 379 | 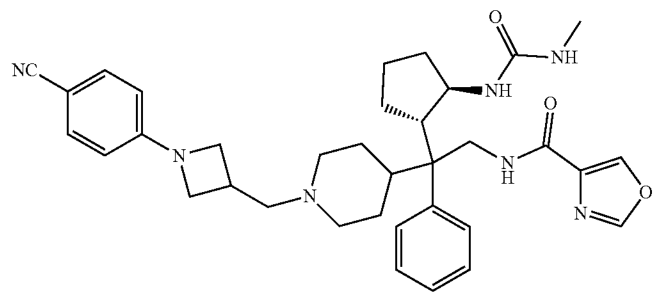 [SMILES: CNC(=O)N[C@@H]1CCC[C@H]1C(CNC(=O)c1cocn1)(c1ccccc1)C1CCN(CC2CN(c3ccc(C#N)cc3)C2)CC1] | rac-N-(2-(1-((1-(4-cyanophenyl)azetidin-3-yl)methyl)piperidin-4-yl)-2-((1S,2R)-2-(3-methylureido)cyclopentyl)-2-phenylethyl)oxazole-4-carboxamide |
| 380 | 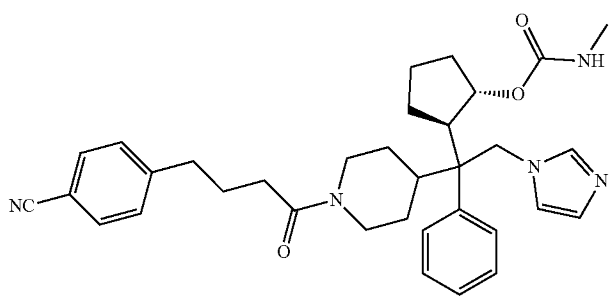 [SMILES: CNC(=O)O[C@H]1CCC[C@@H]1C(Cn1ccnc1)(c1ccccc1)C1CCN(C(=O)CCCc2ccc(C#N)cc2)CC1] | rac-(1S,2R)-2-(1-(1-(4-(4-cyanophenyl)butanoyl)piperidin-4-yl)-2-(1H-imidazol-1-yl)-1-phenylethyl)cyclopentyl methylcarbamate |
| 381 | 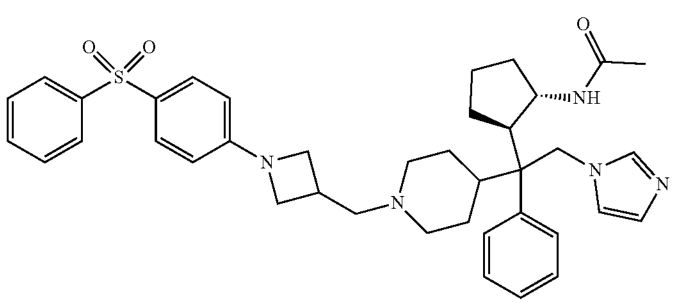 [SMILES: CC(=O)N[C@H]1CCC[C@@H]1C(Cn1ccnc1)(c1ccccc1)C1CCN(CC2CN(c3ccc(S(=O)(=O)c4ccccc4)cc3)C2)CC1] | rac-N-((1S,2R)-2-(2-(1H-imidazol-1-yl)-1-phenyl-1-(1-((1-(4-(phenylsulfonyl)phenyl)azetidin-3-yl)methyl)piperidin-4-yl)ethyl)cyclopentyl)acetamide |
| 382 | 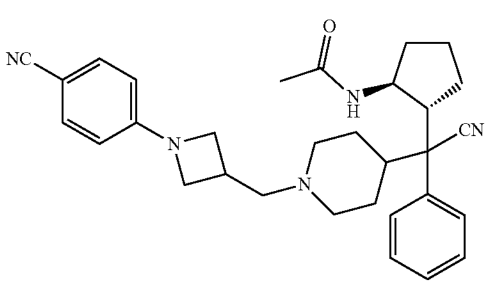 [SMILES: CC(=O)N[C@H]1CCC[C@@H]1C(C#N)(c1ccccc1)C1CCN(CC2CN(c3ccc(C#N)cc3)C2)CC1] | rac-N-((1S,2R)-2-(cyano(1-((1-(4-cyanophenyl)azetidin-3-yl)methyl)piperidin-4-yl)(phenyl)methyl)cyclopentyl)acetamide |

TABLE 1-continued

| Cpd. No. | Chemical Structure | Chemical Name |
|---|---|---|
| 383 | 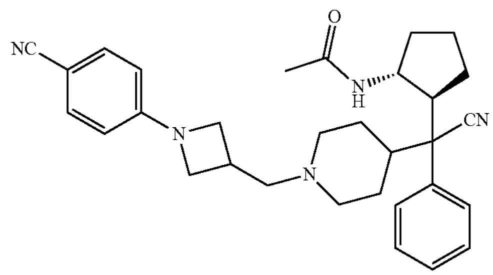 [SMILES: CC(=O)N[C@@H]1CCC[C@H]1C(C#N)(c1ccccc1)C1CCN(CC2CN(c3ccc(C#N)cc3)C2)CC1] | rac-N-((1R,2S)-2-(cyano(1-((1-(4-cyanophenyl)azetidin-3-yl)methyl)piperidin-4-yl)(phenyl)methyl)cyclopentyl)acetamide |
| 384 | 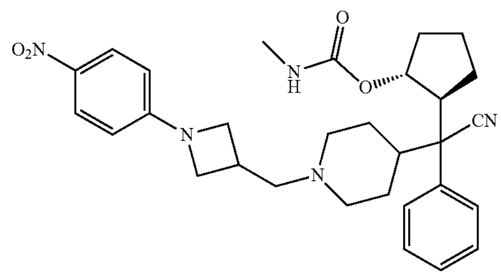 [SMILES: CNC(=O)O[C@@H]1CCC[C@H]1C(C#N)(c1ccccc1)C1CCN(CC2CN(c3ccc([N+](=O)[O-])cc3)C2)CC1] | rac-(1R,2S)-2-(cyano(1-((1-(4-nitrophenyl)azetidin-3-yl)methyl)piperidin-4-yl)(phenyl)methyl)cyclopentyl methylcarbamate |
| 385 | 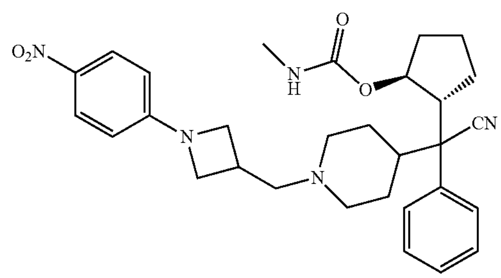 [SMILES: CNC(=O)O[C@H]1CCC[C@@H]1C(C#N)(c1ccccc1)C1CCN(CC2CN(c3ccc([N+](=O)[O-])cc3)C2)CC1] | rac-(1S,2R)-2-(cyano(1-((1-(4-nitrophenyl)azetidin-3-yl)methyl)piperidin-4-yl)(phenyl)methyl)cyclopentyl methylcarbamate |
| 386 | 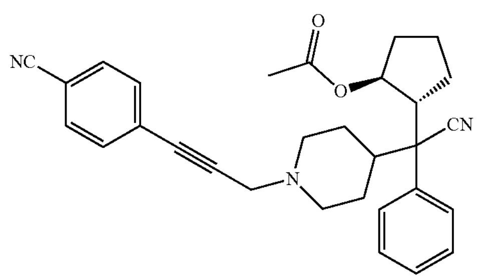 [SMILES: CC(=O)O[C@H]1CCC[C@@H]1C(C#N)(c1ccccc1)C1CCN(CC#Cc2ccc(C#N)cc2)CC1] | rac-(1S,2R)-2-(cyano(1-(3-(4-cyanophenyl)prop-2-yn-1-yl)piperidin-4-yl)(phenyl)methyl)cyclopentyl acetate |
| 387 | 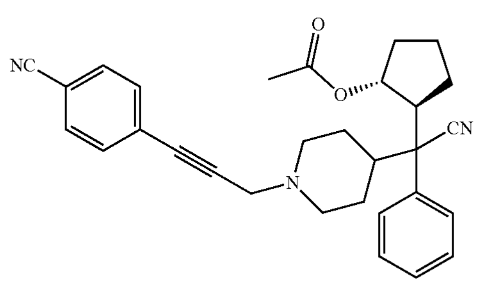 [SMILES: CC(=O)O[C@@H]1CCC[C@H]1C(C#N)(c1ccccc1)C1CCN(CC#Cc2ccc(C#N)cc2)CC1] | rac-(1R,2S)-2-(cyano(1-(3-(4-cyanophenyl)prop-2-yn-1-yl)piperidin-4-yl)(phenyl)methyl)cyclopentyl acetate |

TABLE 1-continued

| Cpd. No. | Chemical Structure | Chemical Name |
|---|---|---|
| 388 | 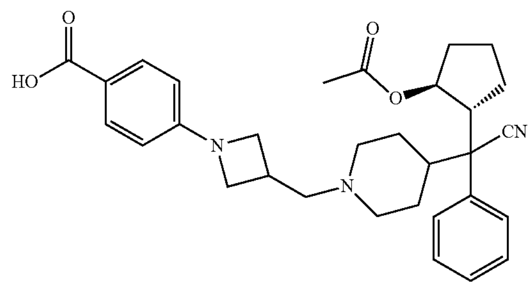 [SMILES: CC(=O)O[C@H]1CCC[C@@H]1C(C#N)(c1ccccc1)C1CCN(CC2CN(c3ccc(C(=O)O)cc3)C2)CC1] | rac-4-(3-((4-(((1R,2S)-2-acetoxycyclopentyl)(cyano)(phenyl)methyl)piperidin-1-yl)methyl)azetidin-1-yl)benzoic acid |
| 389 | 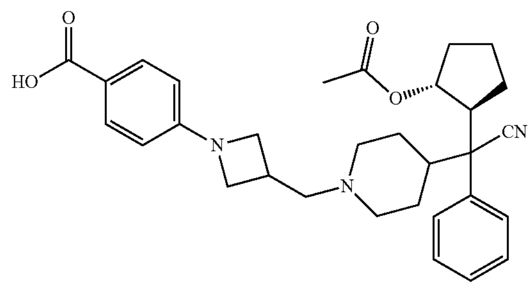 [SMILES: CC(=O)O[C@@H]1CCC[C@H]1C(C#N)(c1ccccc1)C1CCN(CC2CN(c3ccc(C(=O)O)cc3)C2)CC1] | rac-4-(3-((4-(((1S,2R)-2-acetoxycyclopentyl)(cyano)(phenyl)methyl)piperidin-1-yl)methyl)azetidin-1-yl)benzoic acid |
| 390 | 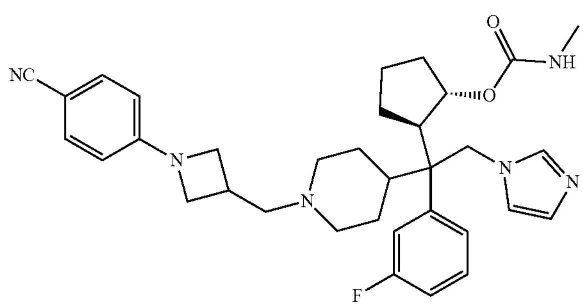 [SMILES: CNC(=O)O[C@H]1CCC[C@@H]1C(Cn1ccnc1)(c1cccc(F)c1)C1CCN(CC2CN(c3ccc(C#N)cc3)C2)CC1] | rac-(1S,2R)-2-(1-(1-((1-(4-cyanophenyl)azetidin-3-yl)methyl)piperidin-4-yl)-1-(3-fluorophenyl)-2-(1H-imidazol-1-yl)ethyl)cyclopentyl methylcarbamate |
| 391 | 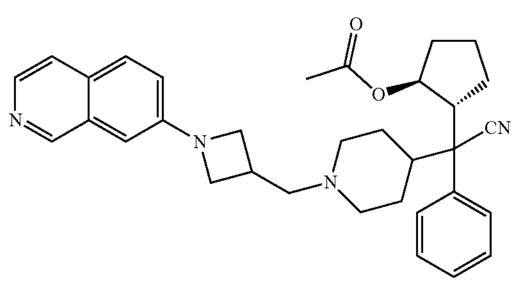 [SMILES: CC(=O)O[C@H]1CCC[C@@H]1C(C#N)(c1ccccc1)C1CCN(CC2CN(c3ccc4ccncc4c3)C2)CC1] | rac-(1S,2R)-2-(cyano(1-((1-(isoquinolin-7-yl)azetidin-3-yl)methyl)piperidin-4-yl)(phenyl)methyl)cyclopentyl acetate |
| 392 | 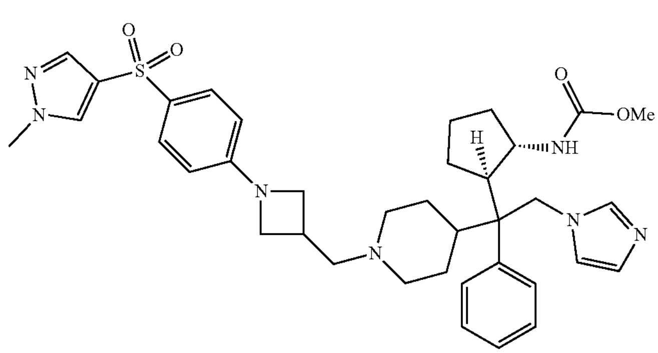 | methyl rac-((1S,2R)-2-(2-(1H-imidazol-1-yl)-1-(1-((1-(4-((1-methyl-1H-pyrazol-4-yl)sulfonyl)phenyl)azetidin-3-yl)methyl)piperidin-4-yl)-1-phenylethyl)cyclopentyl)carbamate |

TABLE 1-continued

| Cpd. No. | Chemical Structure | Chemical Name |
|---|---|---|
| 393 | 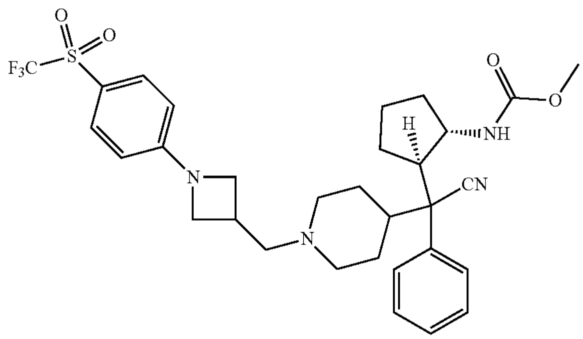 | methyl rac-((1S,2R)-2-(cyano(phenyl)(1-((1-(4-((trifluoromethyl)sulfonyl)phenyl)azetidin-3-yl)methyl)piperidin-4-yl)methyl)cyclopentyl)carbamate |
| 394 | 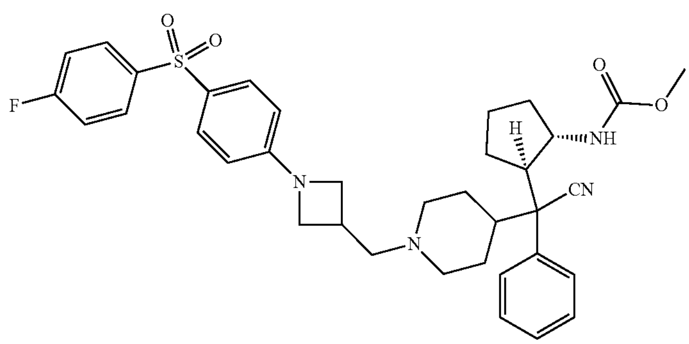 | methyl rac((1S,2R)-2-(cyano(1-((1-(4-((4-fluorophenyl)sulfonyl)phenyl)azetidin-3-yl)methyl)piperidin-4-yl)(phenyl)methyl)cyclopentyl)carbamate |
| 395 | 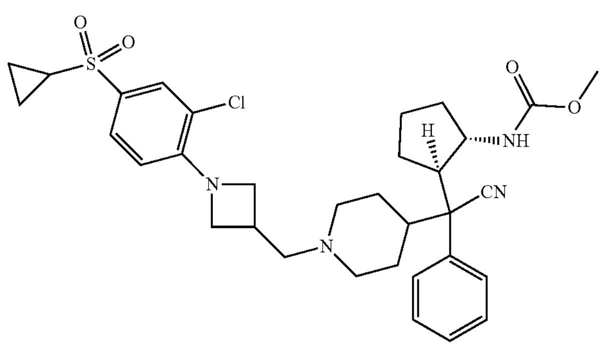 | methyl rac-((1S,2R)-2-((1-((1-(2-chloro-4-(cyclopropylsulfonyl)phenyl)azetidin-3-yl)methyl)piperidin-4-yl)(cyano)(phenyl)methyl)cyclopentyl)carbamate |
| 396 | 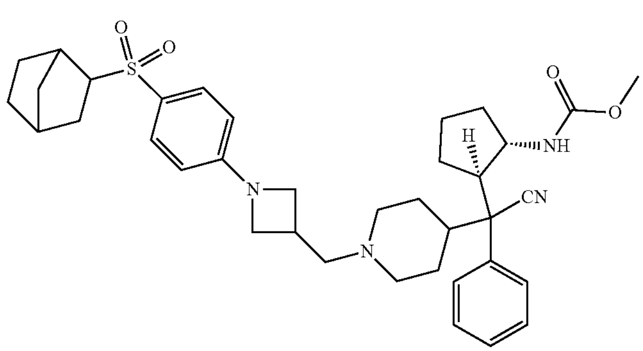 | methyl rac-((1S,2R)-2-((1-((1-(4-(bicyclo[2.2.1]heptan-2-ylsulfonyl)phenyl)azetidin-3-yl)methyl)piperidin-4-yl)(cyano)(phenyl)methyl)cyclopentyl)carbamate |

TABLE 1-continued

| Cpd. No. | Chemical Structure | Chemical Name |
|---|---|---|
| 397 | 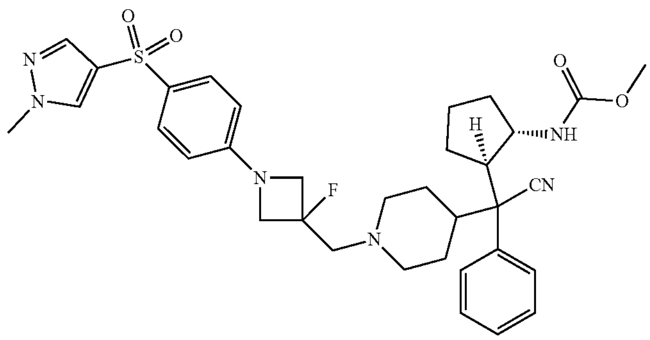 | methyl rac-((1S,2R)-2-(cyano(1-((3-fluoro-1-(4-((1-methyl-1H-pyrazol-4-yl)sulfonyl)phenyl)azetidin-3-yl)methyl)piperidin-4-yl)(phenyl)methyl)cyclopentyl)carbamate |
| 398 | 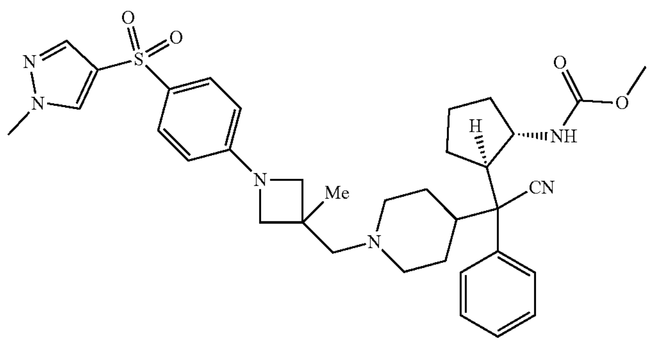 | methyl rac-((1S,2R)-2-(cyano(1-((3-methyl-1-(4-((1-methyl-1H-pyrazol-4-yl)sulfonyl)phenyl)azetidin-3-yl)methyl)piperidin-4-yl)(phenyl)methyl)cyclopentyl)carbamate |
| 399 | 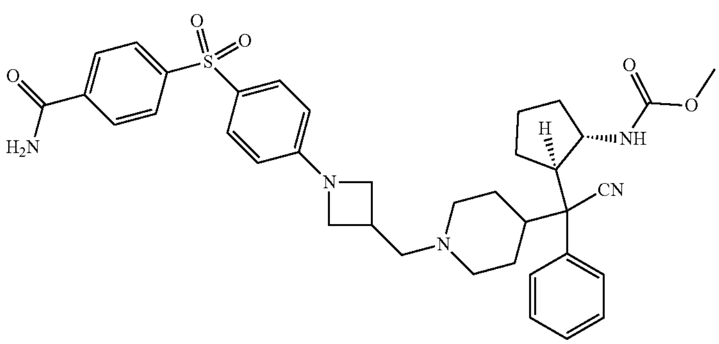 | methyl rac-((1S,2R)-2-((1-((1-(4-((4-carbamoylphenyl)sulfonyl)phenyl)azetidin-3-yl)methyl)piperidin-4-yl)(cyano)(phenyl)methyl)cyclopentyl)carbamate |
| 400 | 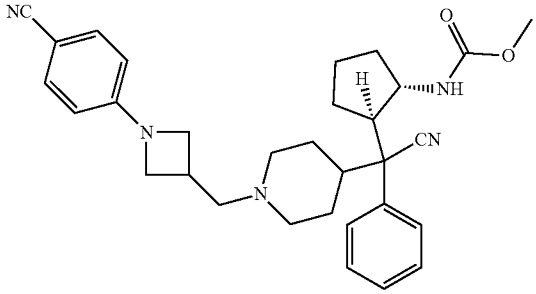 | methyl rac-((1S,2R)-2-(cyano(1-((1-(4-cyanophenyl)azetidin-3-yl)methyl)piperidin-4-yl)(phenyl)methyl)cyclopentyl)carbamate |

TABLE 1-continued

| Cpd. No. | Chemical Structure | Chemical Name |
|---|---|---|
| 401 | 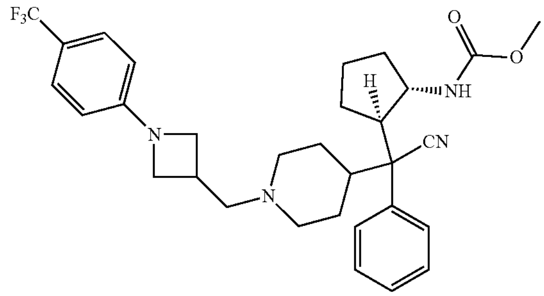 | methyl rac-((1S,2R)-2-(cyano(phenyl)(1-((1-(4-(trifluoromethyl)phenyl)azetidin-3-yl)methyl)piperidin-4-yl)methyl)cyclopentyl)carbamate |
| 402 | 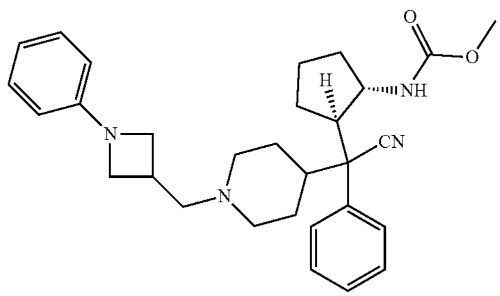 | methyl rac-((1S,2R)-2-(cyano(phenyl)(1-((1-phenylazetidin-3-yl)methyl)piperidin-4-yl)methyl)cyclopentyl)carbamate |
| 403 | 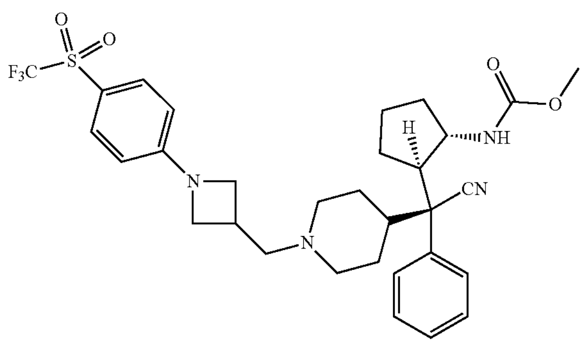 | methyl ((1S,2R)-2-((S)-cyano(phenyl)(1-((1-(4-((trifluoromethyl)sulfonyl)phenyl)azetidin-3-yl)methyl)piperidin-4-yl)methyl)cyclopentyl)carbamate |
| 404 | 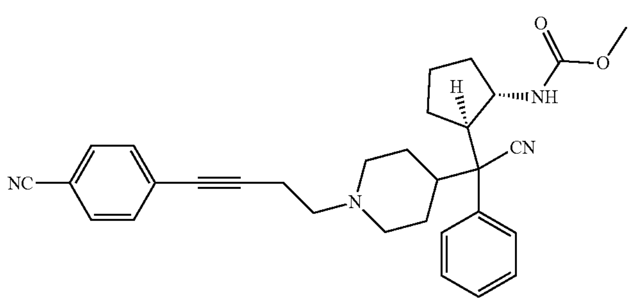 | methyl rac-((1S,2R)-2-(cyano(1-(4-(4-cyanophenyl)but-3-yn-1-yl)piperidin-4-yl)(phenyl)methyl)cyclopentyl)carbamate |
| 405 | 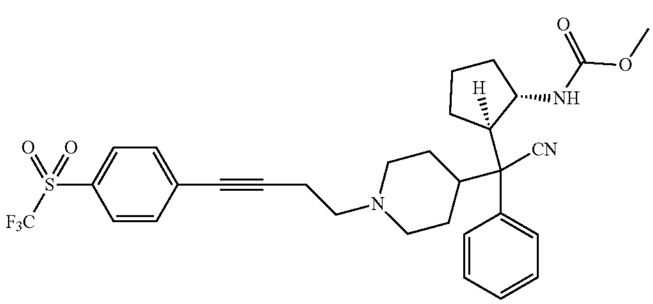 | methyl rac-((1S,2R)-2-(cyano(phenyl)(1-(4-(4-((trifluoromethyl)sulfonyl)phenyl)but-3-yn-1-yl)piperidin-4-yl)methyl)cyclopentyl)carbamate |

TABLE 1-continued

| Cpd. No. | Chemical Structure | Chemical Name |
|---|---|---|
| 406 | 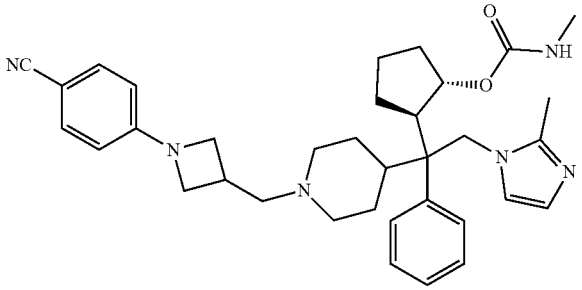 | rac-(1S,2R)-2-(1-(1-((1-(4-cyanophenyl)azetidin-3-yl)methyl)piperidin-4-yl)-2-(2-methyl-1H-imidazol-1-yl)-1-phenylethyl)cyclopentyl methylcarbamate |
| 407 | 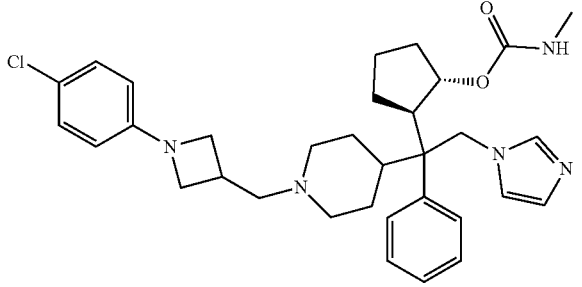 [SMILES: CNC(=O)O[C@H]1CCC[C@@H]1C(Cn1ccnc1)(c1ccccc1)C1CCN(CC2CN(c3ccc(Cl)cc3)C2)CC1] | rac-(1S,2R)-2-(1-(1-((1-(4-chlorophenyl)azetidin-3-yl)methyl)piperidin-4-yl)-2-(1H-imidazol-1-yl)-1-phenylethyl)cyclopentyl methylcarbamate |
| 408 | 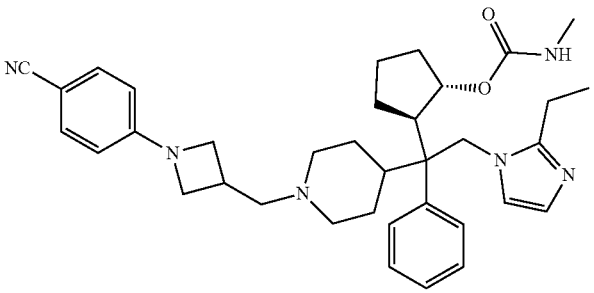 [SMILES: CCc1nccn1CC(c1ccccc1)(C1CCN(CC2CN(c3ccc(C#N)cc3)C2)CC1)[C@H]1CCC[C@@H]1OC(=O)NC] | rac-(1S,2R)-2-(1-(1-((1-(4-cyanophenyl)azetidin-3-yl)methyl)piperidin-4-yl)-2-(2-ethyl-1H-imidazol-1-yl)-1-phenylethyl)cyclopentyl methylcarbamate |
| 409 | 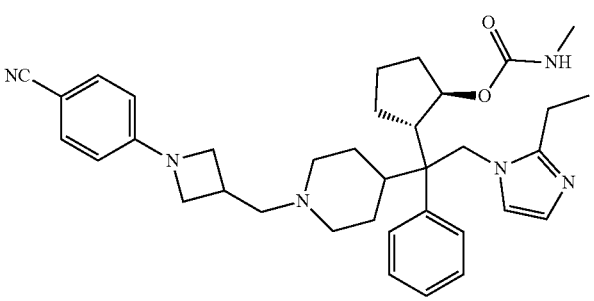 [SMILES: CCc1nccn1CC(c1ccccc1)(C1CCN(CC2CN(c3ccc(C#N)cc3)C2)CC1)[C@@H]1CCC[C@H]1OC(=O)NC] | rac-(1R,2S)-2-(1-(1-((1-(4-cyanophenyl)azetidin-3-yl)methyl)piperidin-4-yl)-2-(2-ethyl-1H-imidazol-1-yl)-1-phenylethyl)cyclopentyl methylcarbamate |
| 410 | 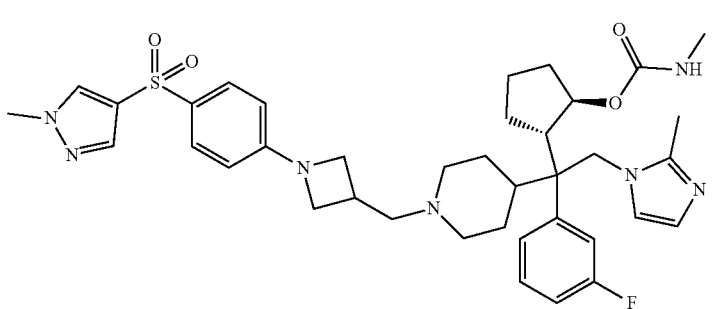 | rac-(1R,2S)-2-(1-(3-fluorophenyl)-2-(2-methyl-1H-imidazol-1-yl)-1-((1-(4-((1-methyl-1H-pyrazol-4-yl)sulfonyl)phenyl)azetidin-3-yl)methyl)piperidin-4-yl)ethyl)cyclopentyl methylcarbamate |

TABLE 1-continued

| Cpd. No. | Chemical Structure | Chemical Name |
|---|---|---|
| 411 | 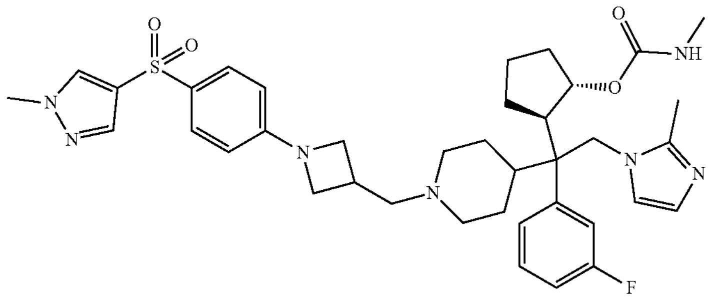 | rac-(1S,2R)-2-(1-(3-fluorophenyl)-2-(2-methyl-1H-imidazol-1-yl)-1-(1-((1-(4-((1-methyl-1H-pyrazol-4-yl)sulfonyl)phenyl)azetidin-3-yl)methyl)piperidin-4-3-yl)ethyl)cyclopentyl methylcarbamate |
| 412 | 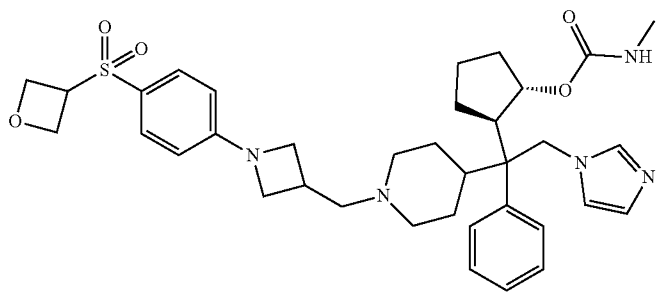 [SMILES: CNC(=O)O[C@H]1CCC[C@@H]1C(Cn1ccnc1)(c1ccccc1)C1CCN(CC2CN(c3ccc(S(=O)(=O)C4COC4)cc3)C2)CC1] | rac-(1S,2R)-2-(2-(1H-imidazol-1-yl)-1-(1-((1-(4-(oxetan-3-ylsulfonyl)phenyl)azetidin-3-yl)methyl)piperidin-4-yl)-1-phenylethyl)cyclopentyl methylcarbamate |
| 413 | 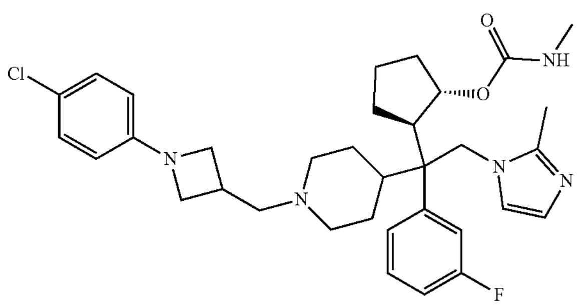 [SMILES: CNC(=O)O[C@H]1CCC[C@@H]1C(Cn1ccnc1C)(c1cccc(F)c1)C1CCN(CC2CN(c3ccc(Cl)cc3)C2)CC1] | rac-(1S,2R)-2-(1-(1-((1-(4-chlorophenyl)azetidin-3-yl)methyl)piperidin-4-yl)-1-(3-fluorophenyl)-2-(2-methyl-1H-imidazol-1-yl)ethyl)cyclopentyl methylcarbamate |
| 414 | 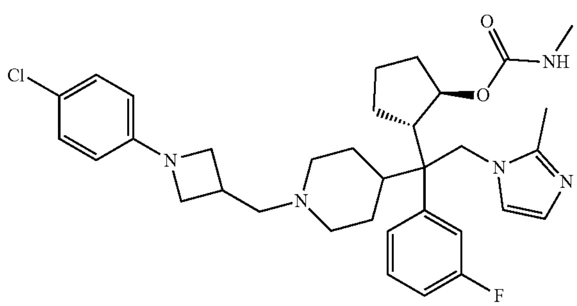 [SMILES: CNC(=O)O[C@@H]1CCC[C@H]1C(Cn1ccnc1C)(c1cccc(F)c1)C1CCN(CC2CN(c3ccc(Cl)cc3)C2)CC1] | rac-(1R,2S)-2-(1-(1-((1-(4-chlorophenyl)azetidin-3-yl)methyl)piperidin-4-yl)-1-(3-fluorophenyl)-2-(2-methyl-1H-imidazol-1-yl)ethyl)cyclopentyl methylcarbamate |
| 415 | 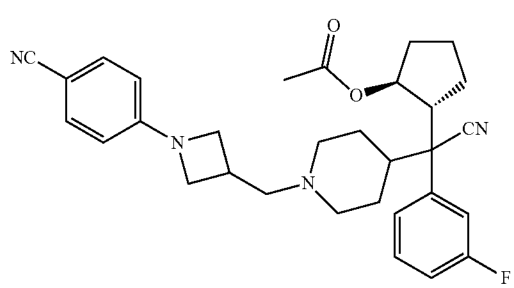 [SMILES: CC(=O)O[C@H]1CCC[C@@H]1C(C#N)(c1cccc(F)c1)C1CCN(CC2CN(c3ccc(C#N)cc3)C2)CC1] | rac-(1S,2R)-2-(cyano(1-((1-(4-cyanophenyl)azetidin-3-yl)methyl)piperidin-4-yl)(3-fluorophenyl)methyl)cyclopentyl acetate |

TABLE 1-continued

| Cpd. No. | Chemical Structure | Chemical Name |
|---|---|---|
| 416 | 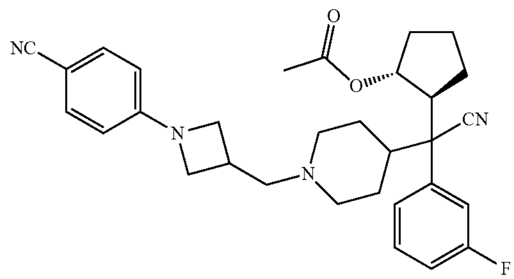 [SMILES: CC(=O)O[C@@H]1CCC[C@H]1C(C#N)(c1cccc(F)c1)C1CCN(CC2CN(c3ccc(C#N)cc3)C2)CC1] | rac-(1R,2S)-2-(cyano(1-((1-(4-cyanophenyl)azetidin-3-yl)methyl)piperidin-4-yl)(3-fluorophenyl)methyl)cyclopentyl acetate |
| 417 | 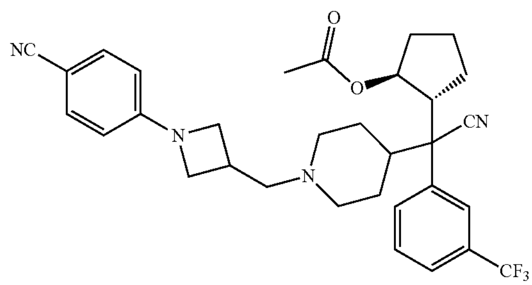 [SMILES: CC(=O)O[C@H]1CCC[C@@H]1C(C#N)(c1cccc(C(F)(F)F)c1)C1CCN(CC2CN(c3ccc(C#N)cc3)C2)CC1] | rac-(1S,2R)-2-(cyano(1-((1-(4-cyanophenyl)azetidin-3-yl)methyl)piperidin-4-yl)(3-(trifluoromethyl)phenyl)methyl)cyclopentyl acetate |
| 418 | 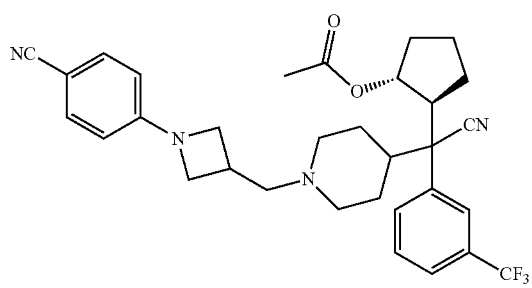 [SMILES: CC(=O)O[C@@H]1CCC[C@H]1C(C#N)(c1cccc(C(F)(F)F)c1)C1CCN(CC2CN(c3ccc(C#N)cc3)C2)CC1] | rac-(1R,2S)-2-(cyano(1-((1-(4-cyanophenyl)azetidin-3-yl)methyl)piperidin-4-yl)(3-(trifluoromethyl)phenyl)methyl)cyclopentyl acetate |
| 419 | 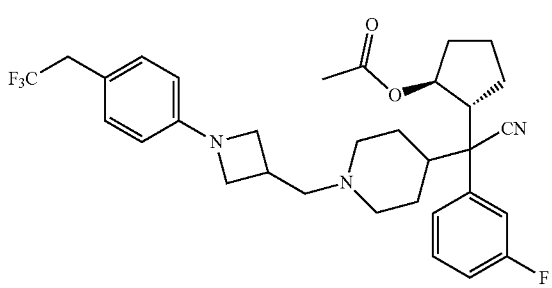 [SMILES: CC(=O)O[C@H]1CCC[C@@H]1C(C#N)(c1cccc(F)c1)C1CCN(CC2CN(c3ccc(CC(F)(F)F)cc3)C2)CC1] | rac-(1S,2R)-2-(cyano(3-fluorophenyl)(1-((1-(4-(2,2,2-trifluoroethyl)phenyl)azetidin-3-yl)methyl)piperidin-4-yl)methyl)cyclopentyl acetate |
| 420 | 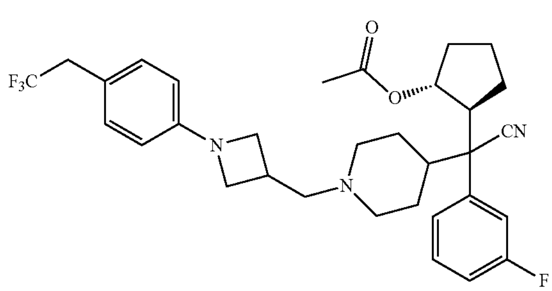 [SMILES: CC(=O)O[C@@H]1CCC[C@H]1C(C#N)(c1cccc(F)c1)C1CCN(CC2CN(c3ccc(CC(F)(F)F)cc3)C2)CC1] | rac-(1R,2S)-2-(cyano(3-fluorophenyl)(1-((1-(4-(2,2,2-trifluoroethyl)phenyl)azetidin-3-yl)methyl)piperidin-4-yl)methyl)cyclopentyl acetate |

TABLE 1-continued

| Cpd. No. | Chemical Structure | Chemical Name |
|---|---|---|
| 421 | 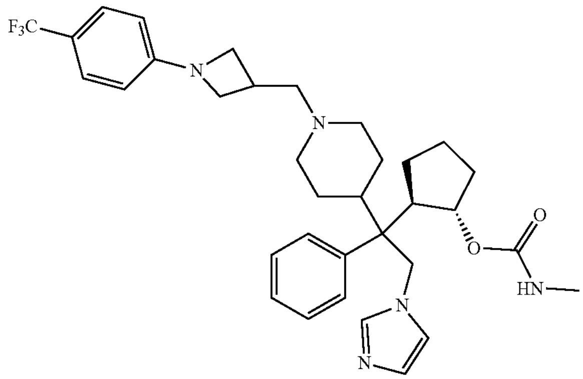 [SMILES: CNC(=O)O[C@H]1CCC[C@@H]1C(Cn1ccnc1)(c1ccccc1)C1CCN(CC2CN(c3ccc(C(F)(F)F)cc3)C2)CC1] | rac-(1S,2R)-2-(2-(1H-imidazol-1-yl)-1-phenyl-1-(1-((1-(4-(trifluoromethyl)phenyl)azetidin-3-yl)methyl)piperidin-4-yl)ethyl)cyclopentyl methylcarbamate |
| 422 | 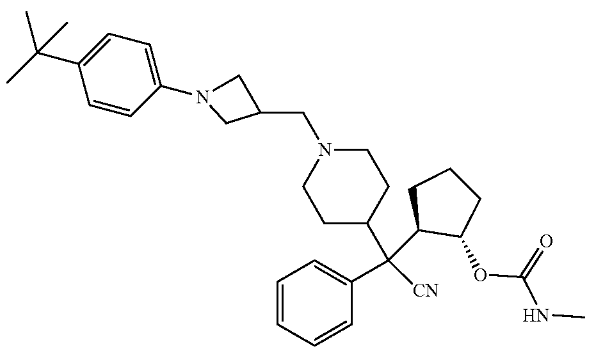 [SMILES: CNC(=O)O[C@H]1CCC[C@@H]1C(C#N)(c1ccccc1)C1CCN(CC2CN(c3ccc(C(C)(C)C)cc3)C2)CC1] | rac-(1S,2R)-2-((1-((1-(4-(tert-butyl)phenyl)azetidin-3-yl)methyl)piperidin-4-yl)(cyano)(phenyl)methyl) cyclopentyl methylcarbamate |
| 423 | 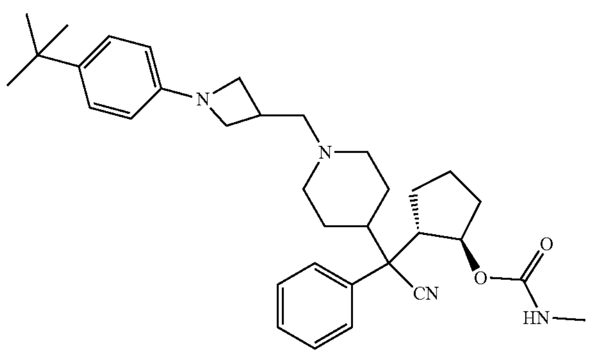 [SMILES: CNC(=O)O[C@@H]1CCC[C@H]1C(C#N)(c1ccccc1)C1CCN(CC2CN(c3ccc(C(C)(C)C)cc3)C2)CC1] | rac-(1R,2S)-2-((1-((1-(4-(tert-butyl)phenyl)azetidin-3-yl)methyl)piperidin-4-yl)(cyano)(phenyl)methyl) cyclopentyl methylcarbamate |
| 424 | 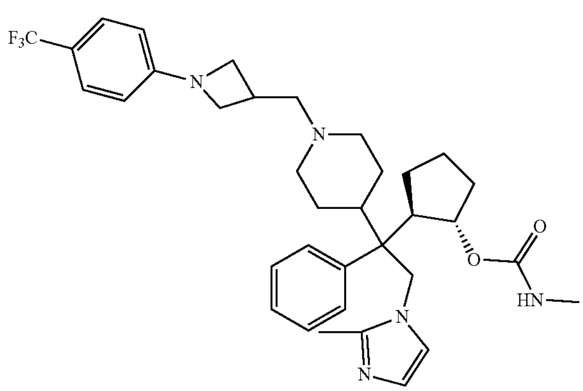 [SMILES: CNC(=O)O[C@H]1CCC[C@@H]1C(Cn1ccnc1C)(c1ccccc1)C1CCN(CC2CN(c3ccc(C(F)(F)F)cc3)C2)CC1] | rac-(1S,2R)-2-(2-(2-methyl-1H-imidazol-1-yl)-1-phenyl-1-(1-((1-(4-(trifluoromethyl)phenyl)azetidin-3-yl)methyl)piperidin-4-yl)ethyl)cyclopentyl methylcarbamate |

TABLE 1-continued

| Cpd. No. | Chemical Structure | Chemical Name |
|---|---|---|
| 425 | 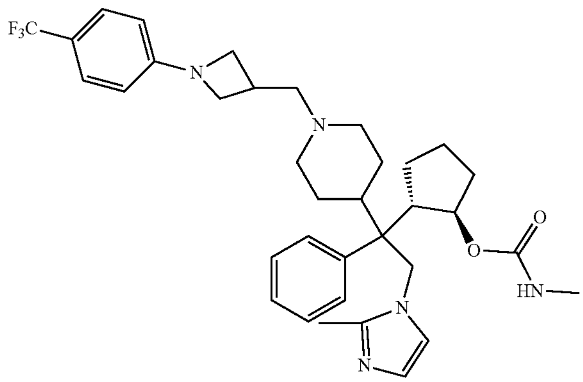 [SMILES: CNC(=O)O[C@@H]1CCC[C@H]1C(Cn1ccnc1C)(c1ccccc1)C1CCN(CC2CN(c3ccc(C(F)(F)F)cc3)C2)CC1] | rac-(1R,2S)-2-(2-(2-methyl-1H-imidazol-1-yl)-1-phenyl-1-(1-((1-(4-(trifluoromethyl)phenyl)azetidin-3-yl)methyl)piperidin-4-yl)ethyl)cyclopentyl methylcarbamate |

In another embodiment, Compounds of the Disclosure are one or more of the compounds of Table 2, and the pharmaceutically acceptable salts, hydrates, and solvates thereof.

TABLE 2

| Cpd No. | Chemical Structure | Chemical Name |
|---|---|---|
| 238 | 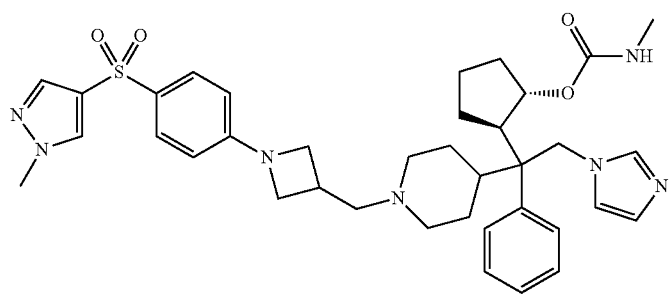 [SMILES: CNC(=O)O[C@H]1CCC[C@@H]1C(Cn1ccnc1)(c1ccccc1)C1CCN(CC2CN(c3ccc(S(=O)(=O)c4cnn(C)c4)cc3)C2)CC1] | rac-(1S,2R)-2-(2-(1H-imidazol-1-yl)-1-(1-((1-(4-((1-methyl-1H-pyrazol-4-yl)sulfonyl)phenyl)azetidin-3-yl)methyl)piperidin-4-yl)-1-phenylethyl)cyclopentyl methylcarbamate |
| 236 | 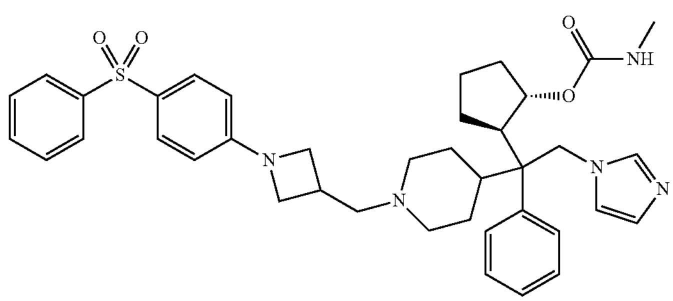 [SMILES: CNC(=O)O[C@H]1CCC[C@@H]1C(Cn1ccnc1)(c1ccccc1)C1CCN(CC2CN(c3ccc(S(=O)(=O)c4ccccc4)cc3)C2)CC1] | rac-(1S,2R)-2-(2-(1H-imidazol-1-yl)-1-phenyl-1-(1-((1-(4-(phenylsulfonyl)phenyl)azetidin-3-yl)methyl)piperidin-4-yl)ethyl)cyclopentyl methylcarbamate |
| 240 | 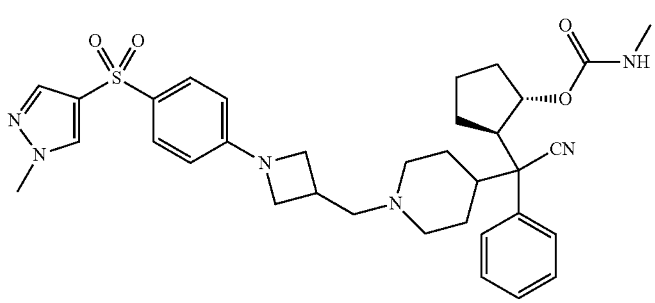 [SMILES: CNC(=O)O[C@H]1CCC[C@@H]1C(C#N)(c1ccccc1)C1CCN(CC2CN(c3ccc(S(=O)(=O)c4cnn(C)c4)cc3)C2)CC1] | rac-(1S,2R)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl methylcarbamate |

TABLE 2-continued

| Cpd No. | Chemical Structure | Chemical Name |
|---|---|---|
| 230 | 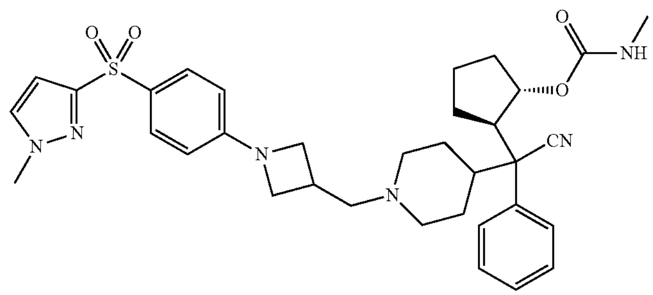 [SMILES: CNC(=O)O[C@H]1CCC[C@@H]1C(C#N)(c1ccccc1)C1CCN(CC2CN(c3ccc(S(=O)(=O)c4ccn(C)n4)cc3)C2)CC1] | rac-(1S,2R)-2-(cyano(1-((1-(4-((1-methyl-1H-pyrazol-3-yl)sulfonyl)phenyl)azetidin-3-yl)methyl)piperidin-4-yl)(phenyl)methyl)cyclopentyl methylcarbamate |
| 210 | 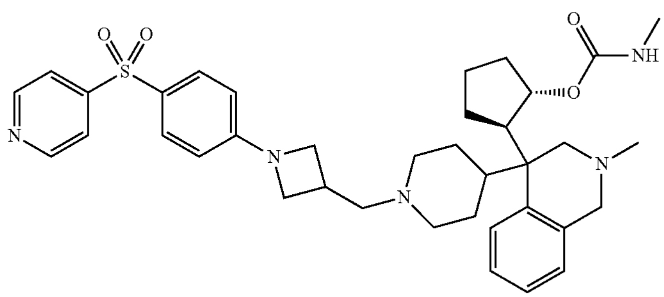 [SMILES: CNC(=O)O[C@H]1CCC[C@@H]1C1(C2CCN(CC3CN(c4ccc(S(=O)(=O)c5ccncc5)cc4)C3)CC2)CN(C)Cc2ccccc21] | rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl methylcarbamate |
| 290 | 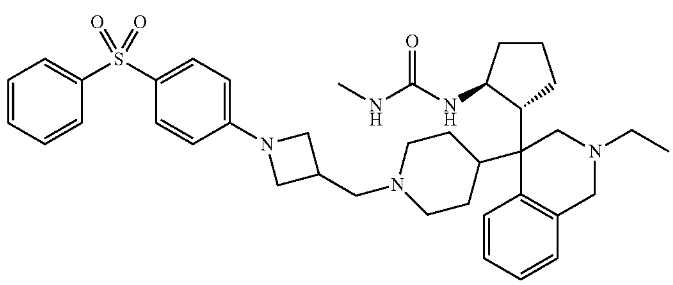 [SMILES: CCN1Cc2ccccc2C(C2CCN(CC3CN(c4ccc(S(=O)(=O)c5ccccc5)cc4)C3)CC2)([C@H]2CCC[C@@H]2NC(=O)NC)C1] | rac-1-((1S,2R)-2-(2-ethyl-4-(1-((1-(4-(phenylsulfonyl)phenyl)azetidin-3-yl)methyl)piperidin-4-yl)-1,2,3,4-tetrahydroisoquinolin-4-yl)cyclopentyl)-3-methylurea |
| 291 | 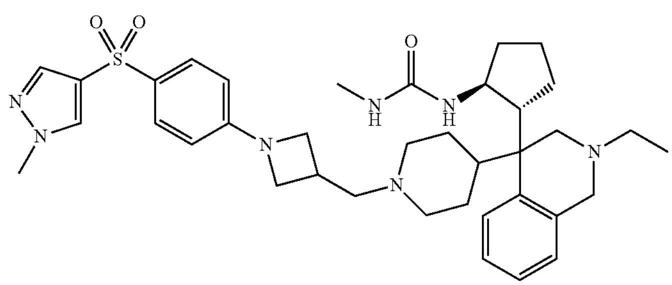 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(=O)NC)C1] | rac-1-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)-3-methylurea |
| 292 | 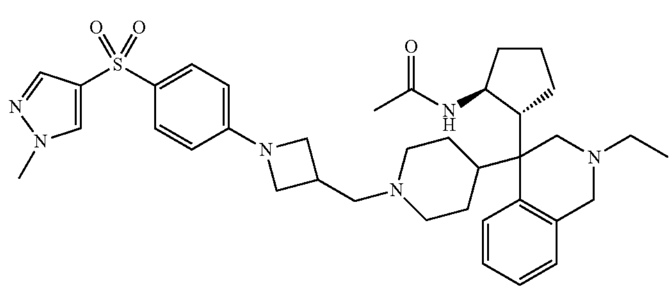 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(C)=O)C1] | rac-N-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)acetamide |

TABLE 2-continued

| Cpd No. | Chemical Structure | Chemical Name |
|---|---|---|
| 271 | 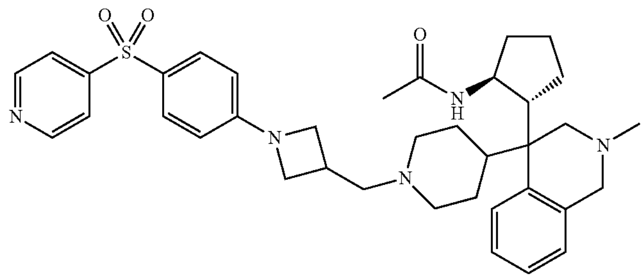 [SMILES: CC(=O)N[C@H]1CCC[C@@H]1C1(C2CCN(CC3CN(c4ccc(S(=O)(=O)c5ccncc5)cc4)C3)CC2)CN(C)Cc2ccccc21] | rac-N-((1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl)acetamide |
| 289 | 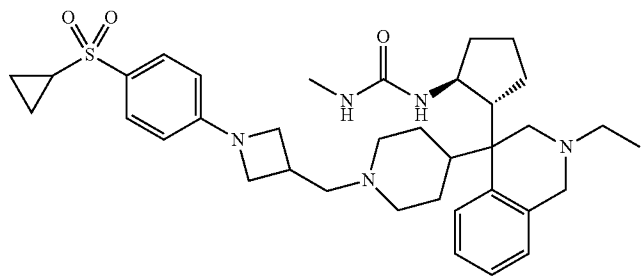 [SMILES: CCN1Cc2ccccc2C(C2CCN(CC3CN(c4ccc(S(=O)(=O)C5CC5)cc4)C3)CC2)([C@H]2CCC[C@@H]2NC(=O)NC)C1] | rac-1-((1S,2R)-2-(4-(1-((1-(4-(cyclopropylsulfonyl)phenyl)azetidin-3-yl)methyl)piperidin-4-yl)-2-ethyl-1,2,3,4-tetrahydroisoquinolin-4-yl)cyclopentyl)-3-methylurea |
| 321 | 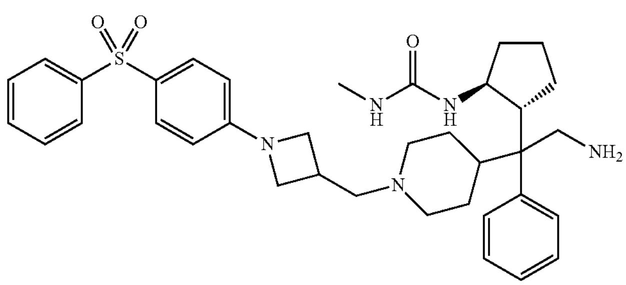 [SMILES: CNC(=O)N[C@H]1CCC[C@@H]1C(CN)(c1ccccc1)C1CCN(CC2CN(c3ccc(S(=O)(=O)c4ccccc4)cc3)C2)CC1] | rac-1-((1S,2R)-2-(2-amino-1-phenyl-1-(1-((1-(4-(phenylsulfonyl)phenyl)azetidin-3-yl)methyl)piperidin-4-yl)ethyl)cyclopentyl)-3-methylurea |
| 349 | 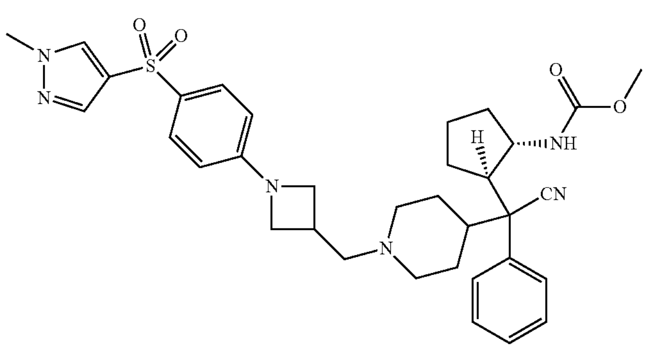 | methyl (rac-(1S,2R)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl)carbamate |

In another embodiment, Compounds of the Disclosure are one or more of the compounds of Table 5, and the pharmaceutically acceptable salts, hydrates, and solvates thereof.
TABLE 5
| Cpd. No. | Chemical Structure |
| --- | --- |
| 426 | 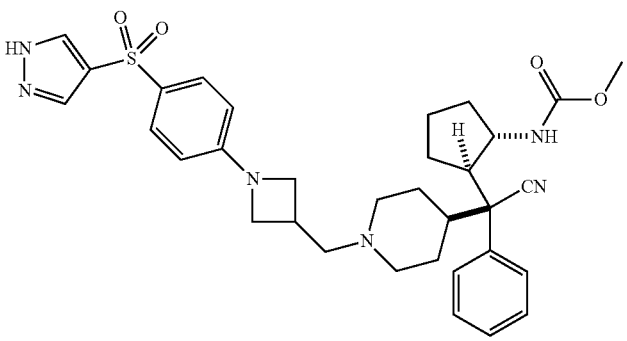 |
| 427 | 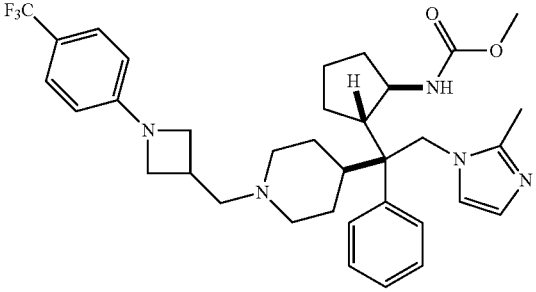 |
| 428 | 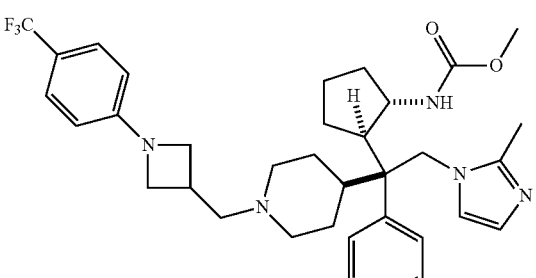 |
| 429 | 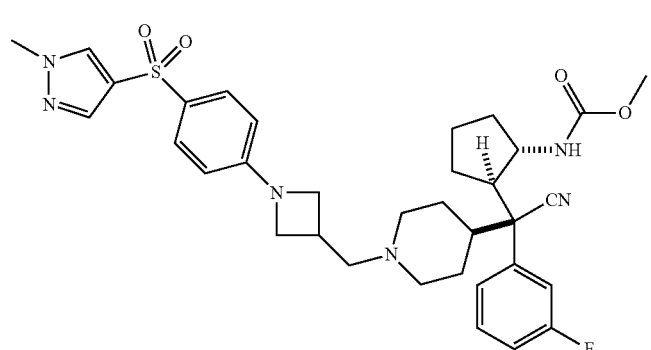 |

TABLE 5-continued

| Cpd. No. | Chemical Structure |
|---|---|
| 430 | 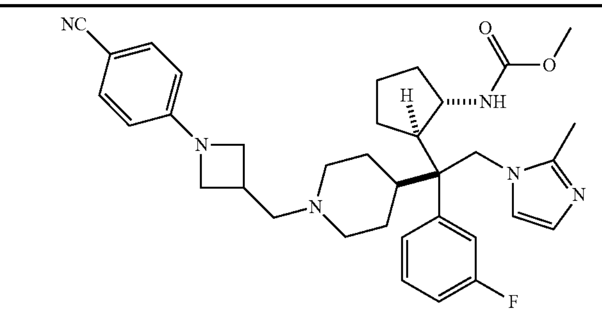 |
| 431 | 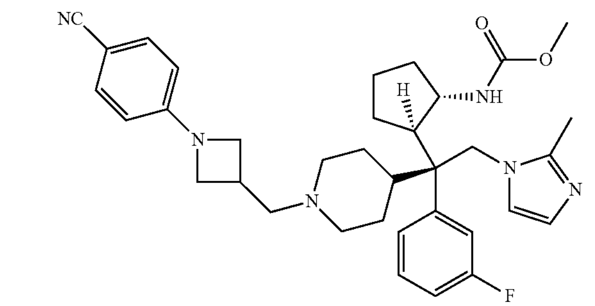 |
| 432 | 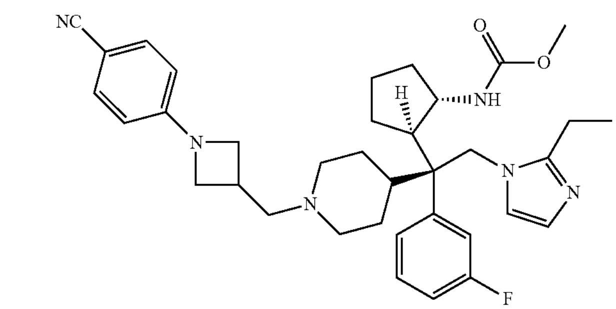 |
| 433 | 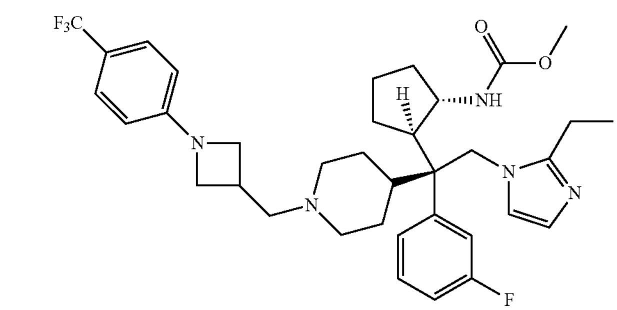 |
| 434 | 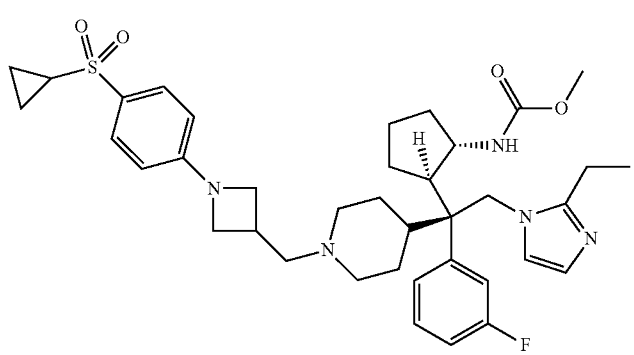 |

TABLE 5-continued
| Cpd. No. | Chemical Structure |
|---|---|
| 435 | 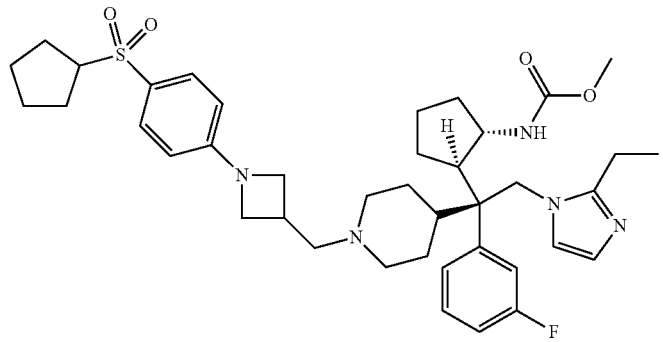 |
| 436 | 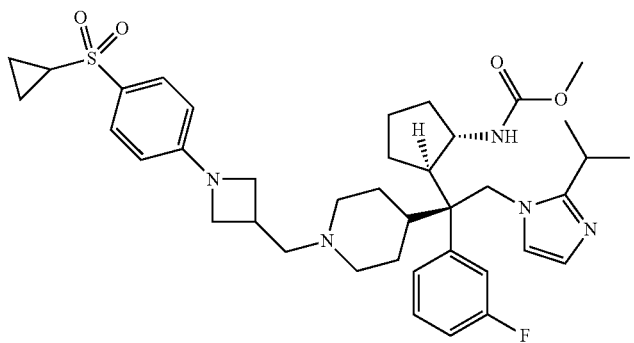 |
| 437 | 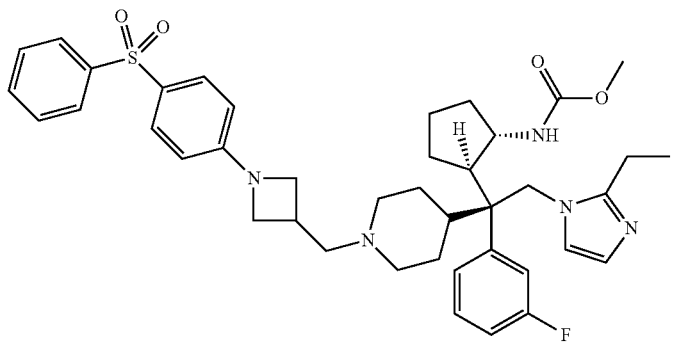 |
| 438 | 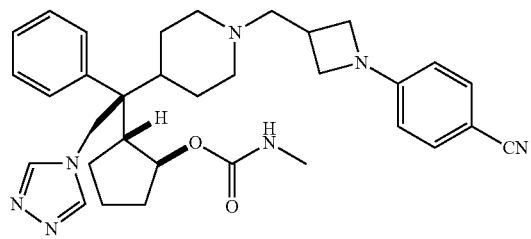 [SMILES: CNC(=O)O[C@H]1CCC[C@@H]1[C@](Cn1cnnc1)(c1ccccc1)C1CCN(CC2CN(c3ccc(C#N)cc3)C2)CC1] |
| 439 | 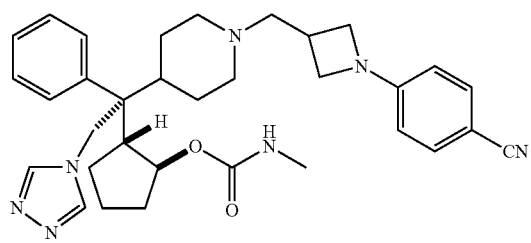 [SMILES: CNC(=O)O[C@H]1CCC[C@@H]1[C@@](Cn1cnnc1)(c1ccccc1)C1CCN(CC2CN(c3ccc(C#N)cc3)C2)CC1] |

TABLE 5-continued
| Cpd. No. | Chemical Structure |
|---|---|
| 440 | 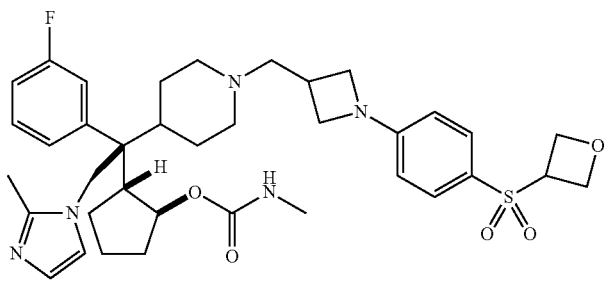 [SMILES: CNC(=O)O[C@H]1CCC[C@@H]1[C@](Cn1ccnc1C)(c1cccc(F)c1)C1CCN(CC2CN(c3ccc(S(=O)(=O)C4COC4)cc3)C2)CC1] |
| 441 | 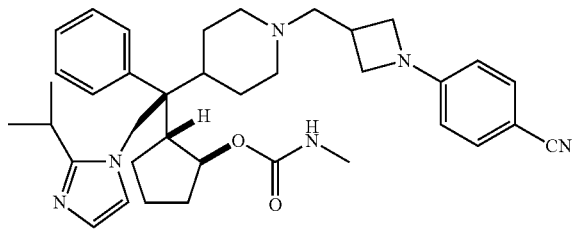 [SMILES: CNC(=O)O[C@H]1CCC[C@@H]1[C@](Cn1ccnc1C(C)C)(c1ccccc1)C1CCN(CC2CN(c3ccc(C#N)cc3)C2)CC1] |
| 442 | 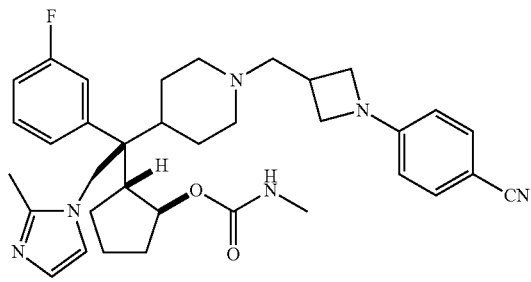 [SMILES: CNC(=O)O[C@H]1CCC[C@@H]1[C@](Cn1ccnc1C)(c1cccc(F)c1)C1CCN(CC2CN(c3ccc(C#N)cc3)C2)CC1] |
| 443 | 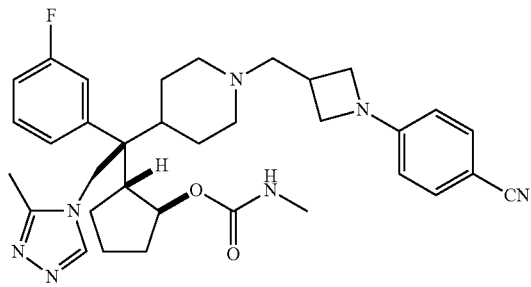 [SMILES: CNC(=O)O[C@H]1CCC[C@@H]1[C@](Cn1cnnc1C)(c1cccc(F)c1)C1CCN(CC2CN(c3ccc(C#N)cc3)C2)CC1] |
| 444 | 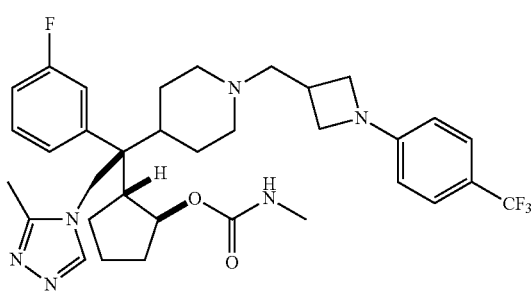 [SMILES: CNC(=O)O[C@H]1CCC[C@@H]1[C@](Cn1cnnc1C)(c1cccc(F)c1)C1CCN(CC2CN(c3ccc(C(F)(F)F)cc3)C2)CC1] |

TABLE 5-continued
| Cpd. No. | Chemical Structure |
|---|---|
| 445 | 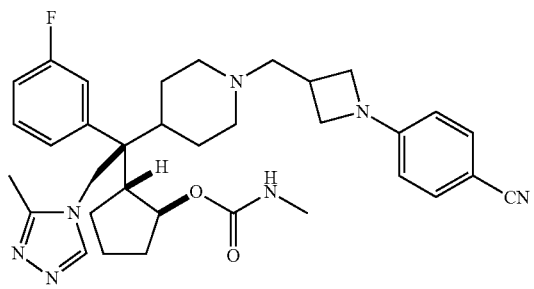 [SMILES: CNC(=O)O[C@H]1CCC[C@@H]1[C@](Cn1cnnc1C)(c1cccc(F)c1)C1CCN(CC2CN(c3ccc(C#N)cc3)C2)CC1] |
| 446 | 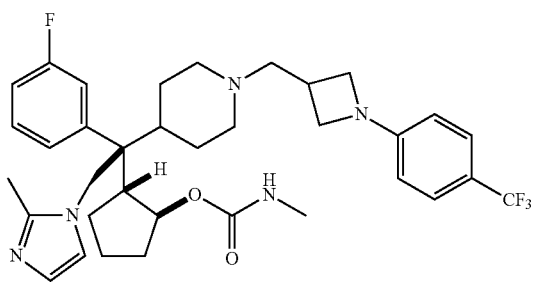 [SMILES: CNC(=O)O[C@H]1CCC[C@@H]1[C@](Cn1ccnc1C)(c1cccc(F)c1)C1CCN(CC2CN(c3ccc(C(F)(F)F)cc3)C2)CC1] |
| 447 | 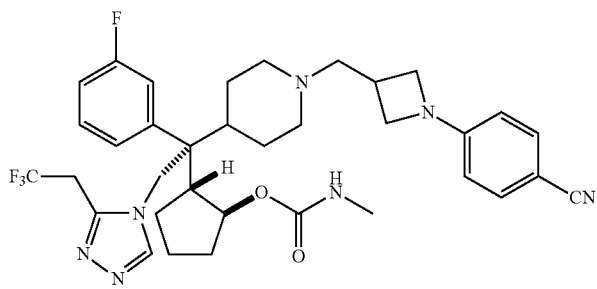 [SMILES: CNC(=O)O[C@H]1CCC[C@@H]1[C@@](Cn1cnnc1CC(F)(F)F)(c1cccc(F)c1)C1CCN(CC2CN(c3ccc(C#N)cc3)C2)CC1] |
| 448 | 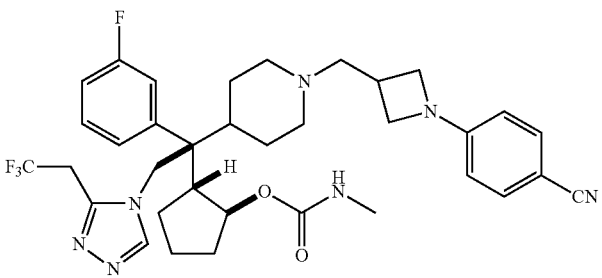 [SMILES: CNC(=O)O[C@H]1CCC[C@@H]1[C@](Cn1cnnc1CC(F)(F)F)(c1cccc(F)c1)C1CCN(CC2CN(c3ccc(C#N)cc3)C2)CC1] |
| 449 | 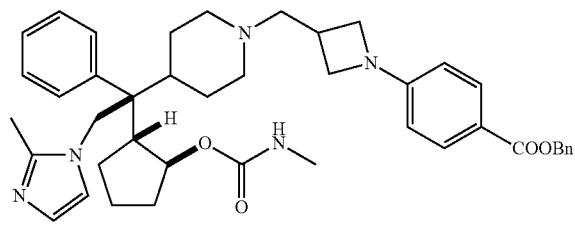 |

TABLE 5-continued
| Cpd. No. | Chemical Structure |
|---|---|
| 450 | 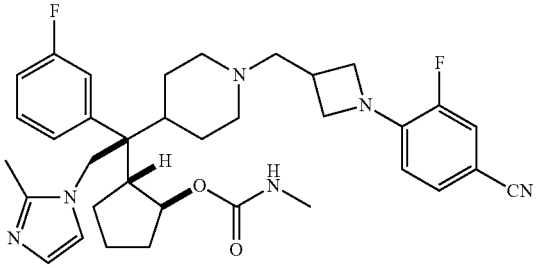 [SMILES: CNC(=O)O[C@H]1CCC[C@@H]1[C@](Cn1ccnc1C)(c1cccc(F)c1)C1CCN(CC2CN(c3ccc(C#N)cc3F)C2)CC1] |
| 451 | 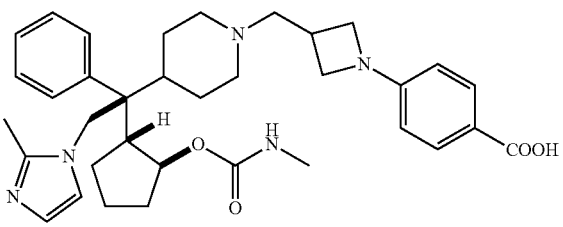 [SMILES: CNC(=O)O[C@H]1CCC[C@@H]1[C@](Cn1ccnc1C)(c1ccccc1)C1CCN(CC2CN(c3ccc(C(=O)O)cc3)C2)CC1] |
| 452 | 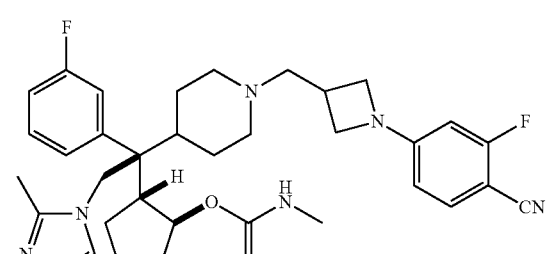 |
| 453 | 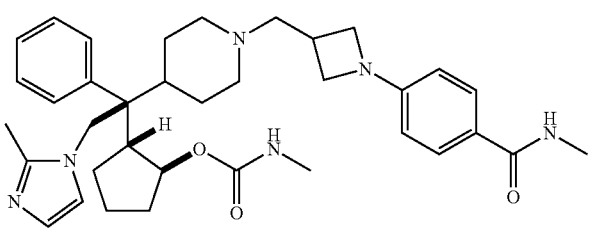 |
| 454 | 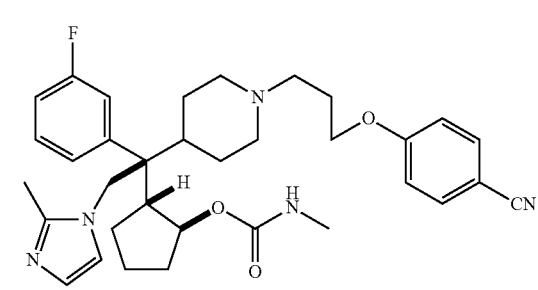 [SMILES: CNC(=O)O[C@H]1CCC[C@@H]1[C@](Cn1ccnc1C)(c1cccc(F)c1)C1CCN(CCCOc2ccc(C#N)cc2)CC1] |
| 455 | 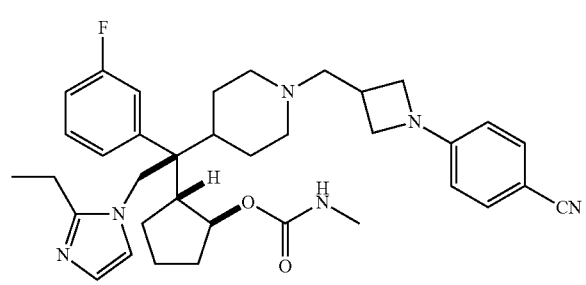 [SMILES: CCc1nccn1C[C@@](c1cccc(F)c1)(C1CCN(CC2CN(c3ccc(C#N)cc3)C2)CC1)[C@H]1CCC[C@@H]1OC(=O)NC] |

TABLE 5-continued
| Cpd. No. | Chemical Structure |
|---|---|
| 456 | 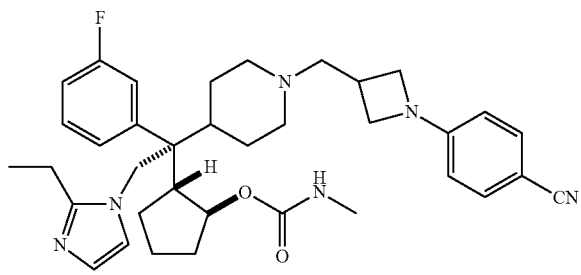 [SMILES: CCc1nccn1C[C@](c1cccc(F)c1)(C1CCN(CC2CN(c3ccc(C#N)cc3)C2)CC1)[C@H]1CCC[C@@H]1OC(=O)NC] |
| 457 | 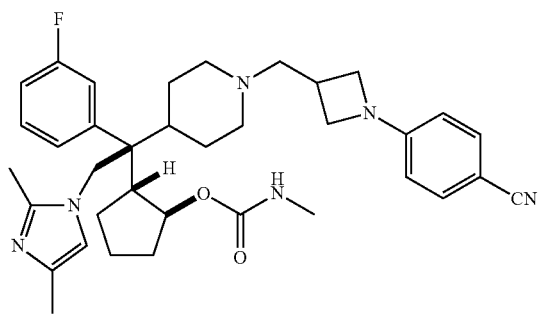 [SMILES: CNC(=O)O[C@H]1CCC[C@@H]1[C@](Cn1cc(C)nc1C)(c1cccc(F)c1)C1CCN(CC2CN(c3ccc(C#N)cc3)C2)CC1] |
| 458 | 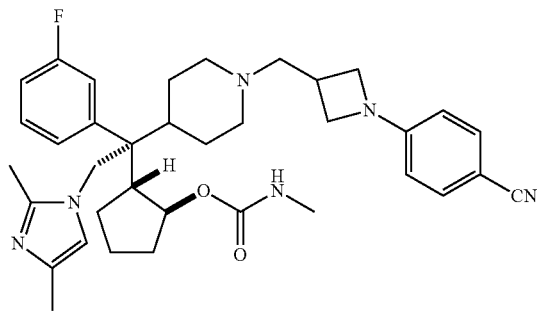 [SMILES: CNC(=O)O[C@H]1CCC[C@@H]1[C@@](Cn1cc(C)nc1C)(c1cccc(F)c1)C1CCN(CC2CN(c3ccc(C#N)cc3)C2)CC1] |
| 459 | 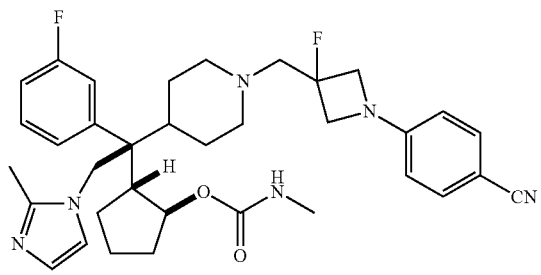 [SMILES: CNC(=O)O[C@H]1CCC[C@@H]1[C@](Cn1ccnc1C)(c1cccc(F)c1)C1CCN(CC2(F)CN(c3ccc(C#N)cc3)C2)CC1] |
| 460 | 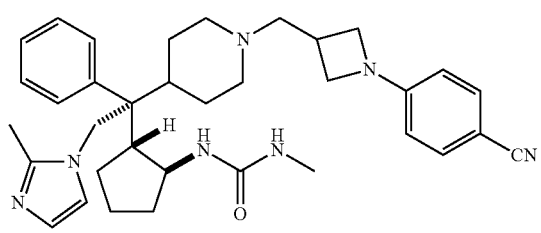 [SMILES: CNC(=O)N[C@H]1CCC[C@@H]1[C@@](Cn1ccnc1C)(c1ccccc1)C1CCN(CC2CN(c3ccc(C#N)cc3)C2)CC1] |

TABLE 5-continued
| Cpd. No. | Chemical Structure |
|---|---|
| 461 | 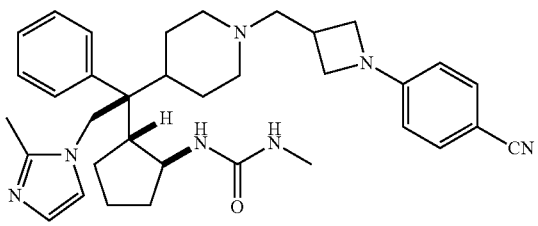 [SMILES: CNC(=O)N[C@H]1CCC[C@@H]1[C@](Cn1ccnc1C)(c1ccccc1)C1CCN(CC2CN(c3ccc(C#N)cc3)C2)CC1] |
| 462 | 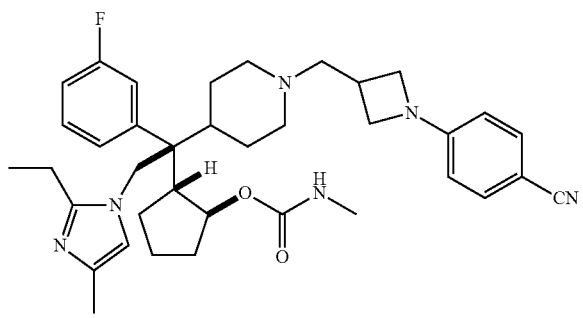 [SMILES: CCc1nc(C)cn1C[C@@](c1cccc(F)c1)(C1CCN(CC2CN(c3ccc(C#N)cc3)C2)CC1)[C@H]1CCC[C@@H]1OC(=O)NC] |
| 463 | 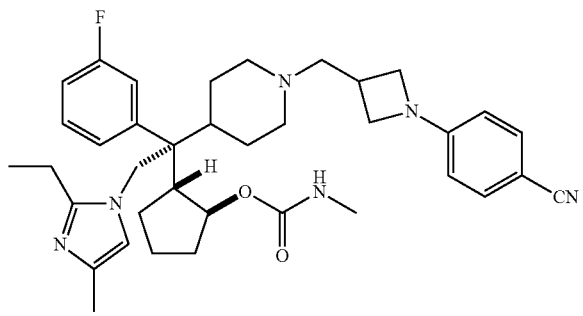 [SMILES: CCc1nc(C)cn1C[C@](c1cccc(F)c1)(C1CCN(CC2CN(c3ccc(C#N)cc3)C2)CC1)[C@H]1CCC[C@@H]1OC(=O)NC] |
| 464 | 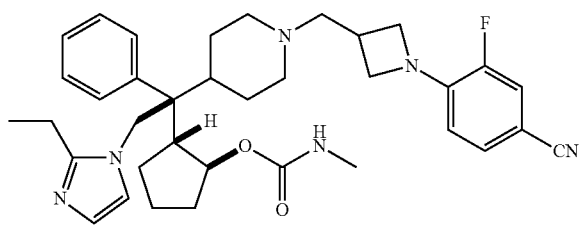 [SMILES: CCc1nccn1C[C@@](c1ccccc1)(C1CCN(CC2CN(c3ccc(C#N)cc3F)C2)CC1)[C@H]1CCC[C@@H]1OC(=O)NC] |
| 465 | 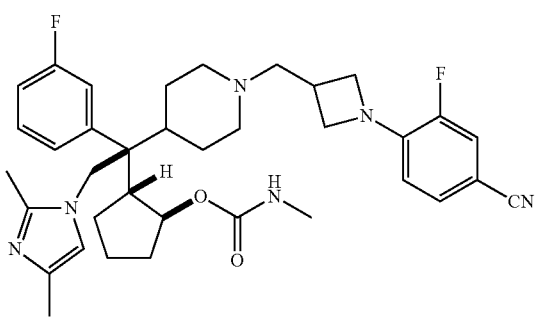 [SMILES: CNC(=O)O[C@H]1CCC[C@@H]1[C@](Cn1cc(C)nc1C)(c1cccc(F)c1)C1CCN(CC2CN(c3ccc(C#N)cc3F)C2)CC1] |

TABLE 5-continued
| Cpd. No. | Chemical Structure |
|---|---|
| 466 | 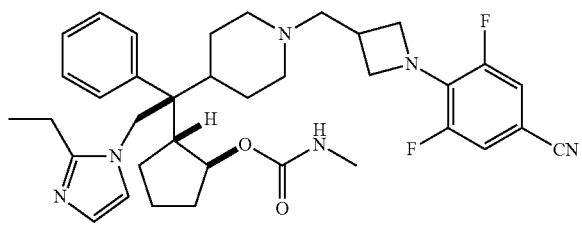 [SMILES: CCc1nccn1C[C@@](c1ccccc1)(C1CCN(CC2CN(c3c(F)cc(C#N)cc3F)C2)CC1)[C@H]1CCC[C@@H]1OC(=O)NC] |
| 467 | 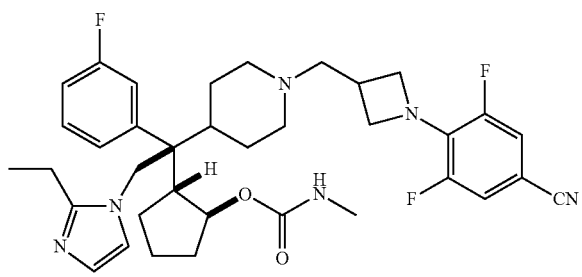 [SMILES: CCc1nccn1C[C@@](c1cccc(F)c1)(C1CCN(CC2CN(c3c(F)cc(C#N)cc3F)C2)CC1)[C@H]1CCC[C@@H]1OC(=O)NC] |
| 468 | 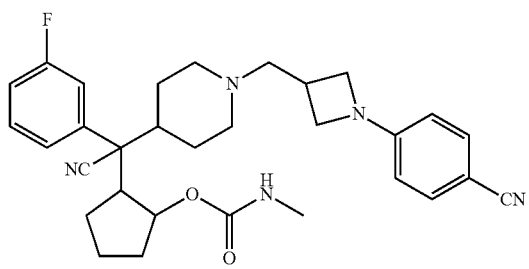 [SMILES: CNC(=O)OC1CCCC1C(C#N)(c1cccc(F)c1)C1CCN(CC2CN(c3ccc(C#N)cc3)C2)CC1] |
| 469 | 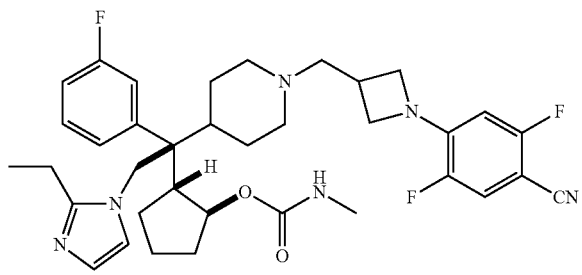 [SMILES: CCc1nccn1C[C@@](c1cccc(F)c1)(C1CCN(CC2CN(c3cc(F)c(C#N)cc3F)C2)CC1)[C@H]1CCC[C@@H]1OC(=O)NC] |
| 470 | 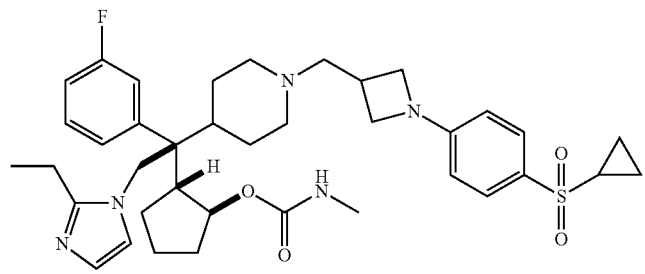 [SMILES: CCc1nccn1C[C@@](c1cccc(F)c1)(C1CCN(CC2CN(c3ccc(S(=O)(=O)C4CC4)cc3)C2)CC1)[C@H]1CCC[C@@H]1OC(=O)NC] |

TABLE 5-continued
| Cpd. No. | Chemical Structure |
|---|---|
| 471 | 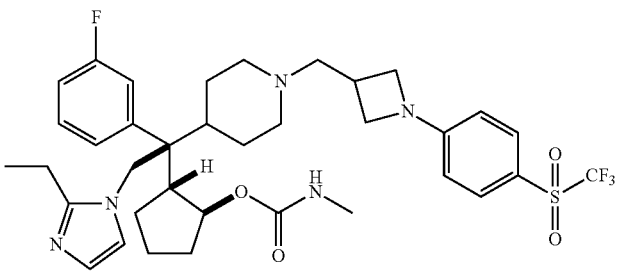 [SMILES: CCc1nccn1C[C@@](c1cccc(F)c1)(C1CCN(CC2CN(c3ccc(S(=O)(=O)C(F)(F)F)cc3)C2)CC1)[C@H]1CCC[C@@H]1OC(=O)NC] |
| 472 | 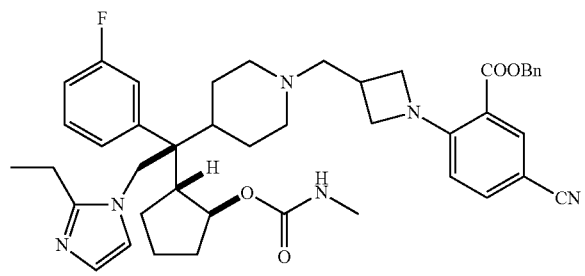 |
| 473 | 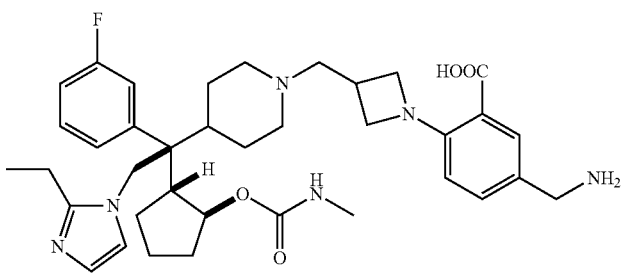 [SMILES: CCc1nccn1C[C@@](c1cccc(F)c1)(C1CCN(CC2CN(c3ccc(CN)cc3C(=O)O)C2)CC1)[C@H]1CCC[C@@H]1OC(=O)NC] |
| 474 | 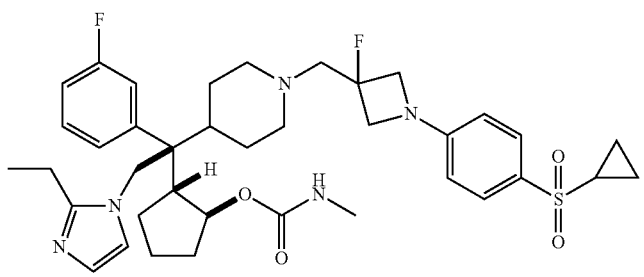 |
| 475 | 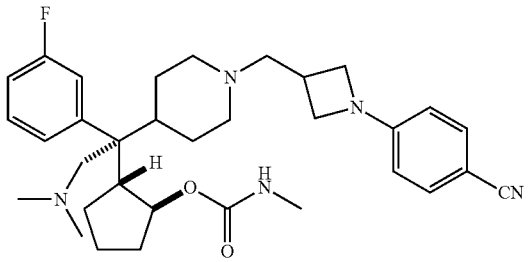 [SMILES: CNC(=O)O[C@H]1CCC[C@@H]1[C@@](CN(C)C)(c1cccc(F)c1)C1CCN(CC2CN(c3ccc(C#N)cc3)C2)CC1] |

TABLE 5-continued
| Cpd. No. | Chemical Structure |
| --- | --- |
| 476 | 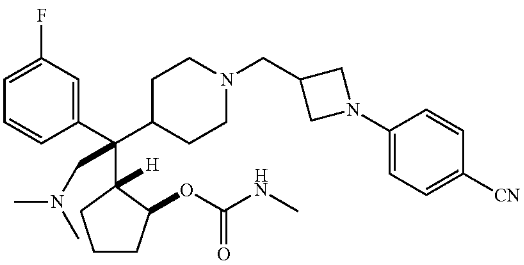 [SMILES: CNC(=O)O[C@H]1CCC[C@@H]1[C@](CN(C)C)(c1cccc(F)c1)C1CCN(CC2CN(c3ccc(C#N)cc3)C2)CC1] |
| 477 | 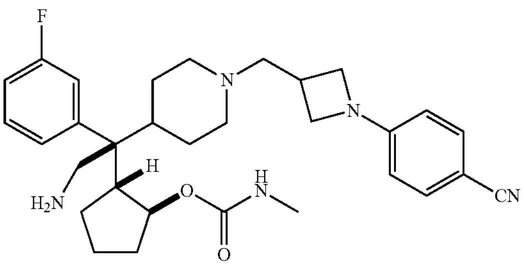 [SMILES: CNC(=O)O[C@H]1CCC[C@@H]1[C@](CN)(c1cccc(F)c1)C1CCN(CC2CN(c3ccc(C#N)cc3)C2)CC1] |
| 478 | 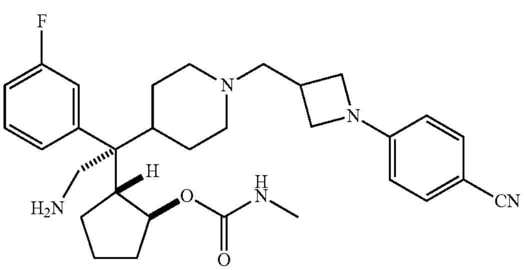 [SMILES: CNC(=O)O[C@H]1CCC[C@@H]1[C@@](CN)(c1cccc(F)c1)C1CCN(CC2CN(c3ccc(C#N)cc3)C2)CC1] |
| 479 | 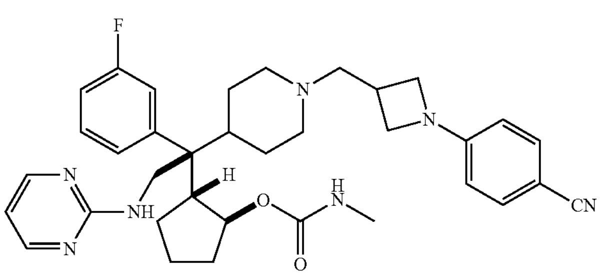 [SMILES: CNC(=O)O[C@H]1CCC[C@@H]1[C@](CNc1ncccn1)(c1cccc(F)c1)C1CCN(CC2CN(c3ccc(C#N)cc3)C2)CC1] |
| 480 | 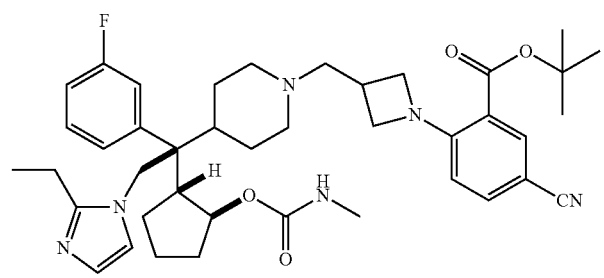 [SMILES: CCc1nccn1C[C@@](c1cccc(F)c1)(C1CCN(CC2CN(c3ccc(C#N)cc3C(=O)OC(C)(C)C)C2)CC1)[C@H]1CCC[C@@H]1OC(=O)NC] |

TABLE 5-continued
| Cpd. No. | Chemical Structure |
|---|---|
| 481 | 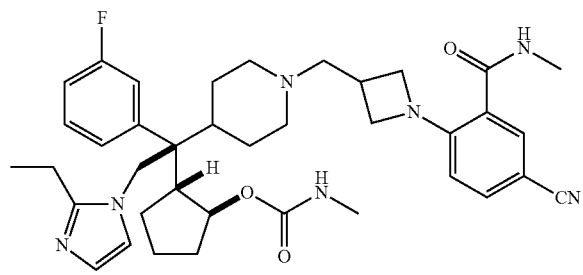 [SMILES: CCc1nccn1C[C@@](c1cccc(F)c1)(C1CCN(CC2CN(c3ccc(C#N)cc3C(=O)NC)C2)CC1)[C@H]1CCC[C@@H]1OC(=O)NC] |
| 482 | 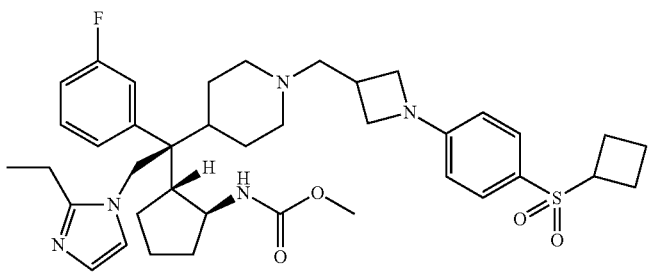 [SMILES: CCc1nccn1C[C@@](c1cccc(F)c1)(C1CCN(CC2CN(c3ccc(S(=O)(=O)C4CCC4)cc3)C2)CC1)[C@H]1CCC[C@@H]1NC(=O)OC] |
| 483 | 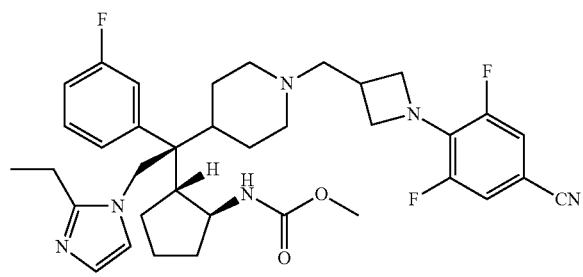 [SMILES: CCc1nccn1C[C@@](c1cccc(F)c1)(C1CCN(CC2CN(c3c(F)cc(C#N)cc3F)C2)CC1)[C@H]1CCC[C@@H]1NC(=O)OC] |
| 484 | 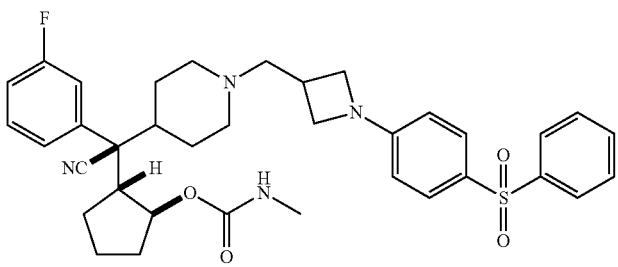 [SMILES: CNC(=O)O[C@H]1CCC[C@@H]1[C@](C#N)(c1cccc(F)c1)C1CCN(CC2CN(c3ccc(S(=O)(=O)c4ccccc4)cc3)C2)CC1] |
| 485 | 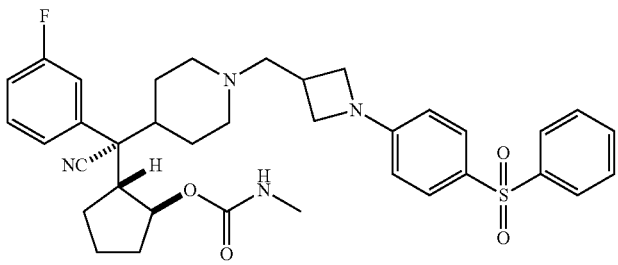 [SMILES: CNC(=O)O[C@H]1CCC[C@@H]1[C@@](C#N)(c1cccc(F)c1)C1CCN(CC2CN(c3ccc(S(=O)(=O)c4ccccc4)cc3)C2)CC1] |

TABLE 5-continued

| Cpd. No. | Chemical Structure |
|---|---|
| 486 | 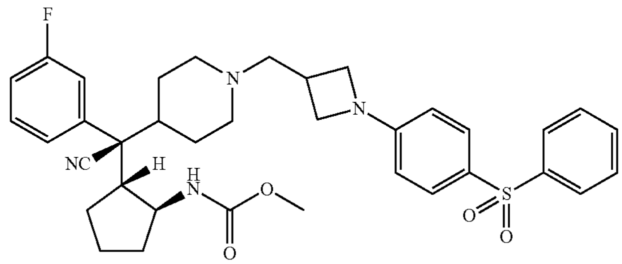 [SMILES: COC(=O)N[C@H]1CCC[C@@H]1[C@](C#N)(c1cccc(F)c1)C1CCN(CC2CN(c3ccc(S(=O)(=O)c4ccccc4)cc3)C2)CC1] |
| 487 | 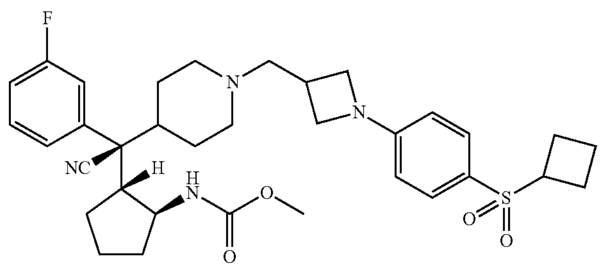 [SMILES: COC(=O)N[C@H]1CCC[C@@H]1[C@](C#N)(c1cccc(F)c1)C1CCN(CC2CN(c3ccc(S(=O)(=O)C4CCC4)cc3)C2)CC1] |
| 488 | 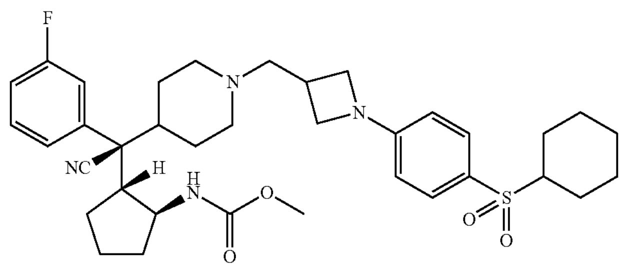 [SMILES: COC(=O)N[C@H]1CCC[C@@H]1[C@](C#N)(c1cccc(F)c1)C1CCN(CC2CN(c3ccc(S(=O)(=O)C4CCCCC4)cc3)C2)CC1] |
| 489 | 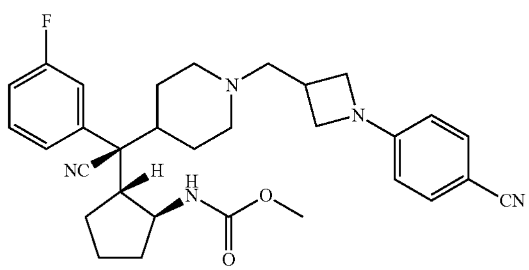 [SMILES: COC(=O)N[C@H]1CCC[C@@H]1[C@](C#N)(c1cccc(F)c1)C1CCN(CC2CN(c3ccc(C#N)cc3)C2)CC1] |
| 490 | 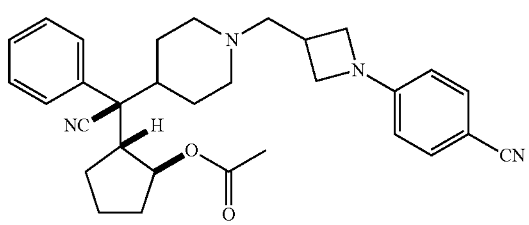 [SMILES: CC(=O)O[C@H]1CCC[C@@H]1[C@](C#N)(c1ccccc1)C1CCN(CC2CN(c3ccc(C#N)cc3)C2)CC1] |
| 491 | 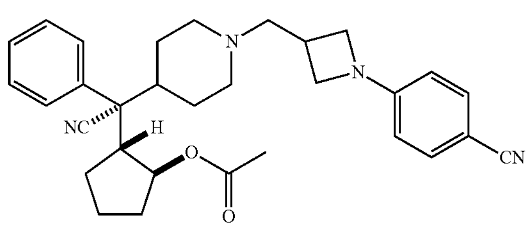 [SMILES: CC(=O)O[C@H]1CCC[C@@H]1[C@@](C#N)(c1ccccc1)C1CCN(CC2CN(c3ccc(C#N)cc3)C2)CC1] |

TABLE 5-continued
| Cpd. No. | Chemical Structure |
|---|---|
| 492 | 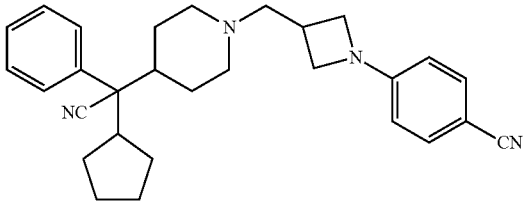 [SMILES: N#Cc1ccc(N2CC(CN3CCC(C(C#N)(c4ccccc4)C4CCCC4)CC3)C2)cc1] |
| 493 | 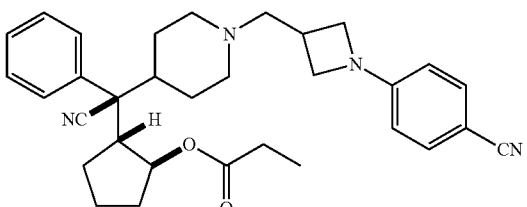 [SMILES: CCO[C@H]1CCC[C@@H]1[C@](C#N)(c1ccccc1)C1CCN(CC2CN(c3ccc(C#N)cc3)C2)CC1] |
| 494 | 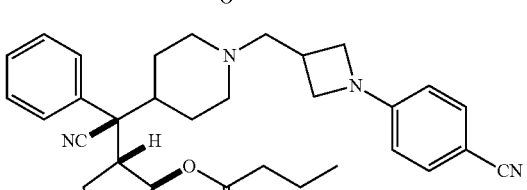 |
| 495 | 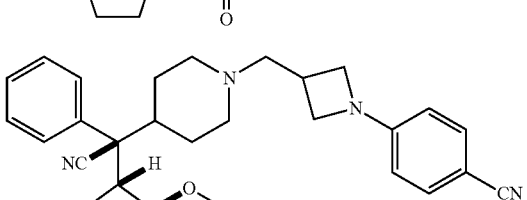 |
| 496 | 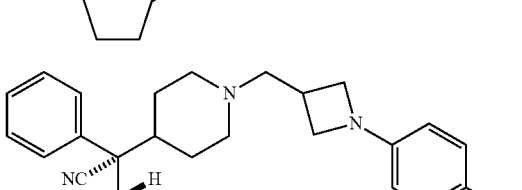 |
| 497 | 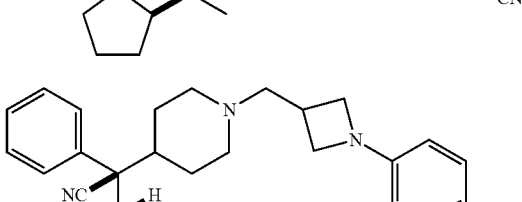 |
| 498 | 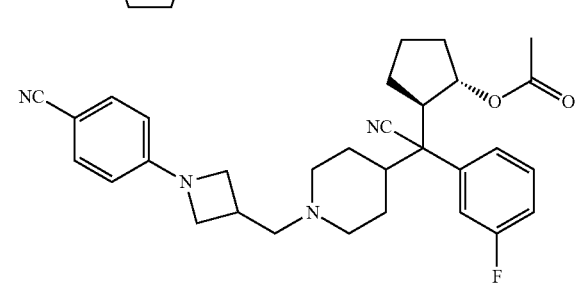 |

TABLE 5-continued
| Cpd. No. | Chemical Structure |
|---|---|
| 499 | 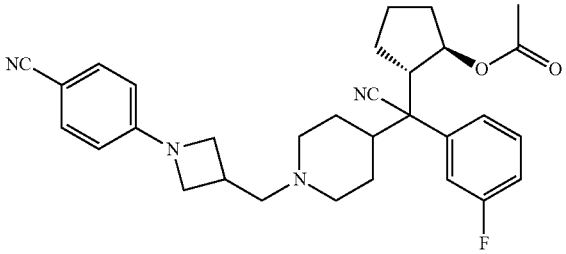 |
| 500 | 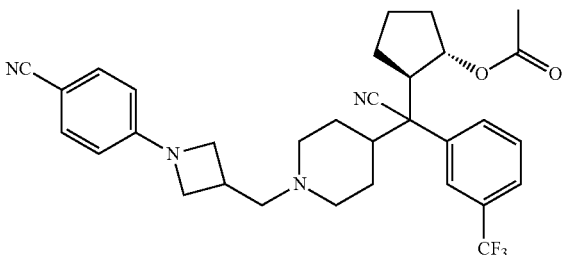 [SMILES: CC(=O)O[C@H]1CCC[C@@H]1C(C#N)(c1cccc(F)c1)C1CCN(CC2CN(c3ccc(C#N)cc3)C2)CC1] |
| 501 | 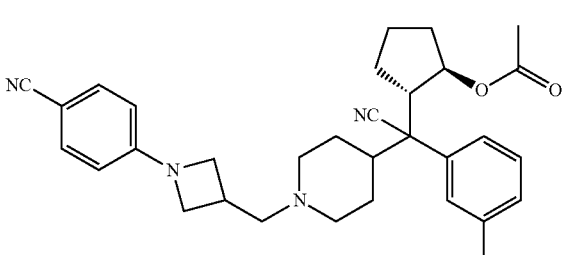 |
| 502 | 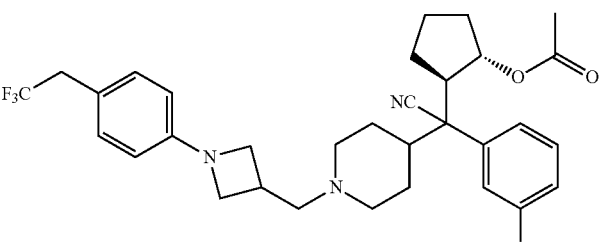 |
| 503 | 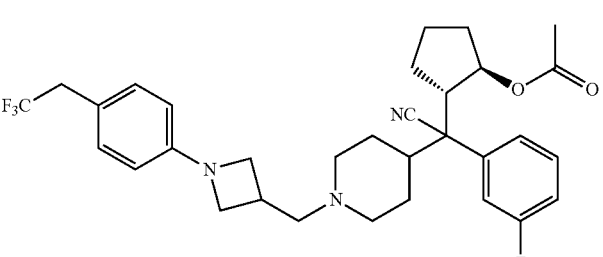 |
| 504 | 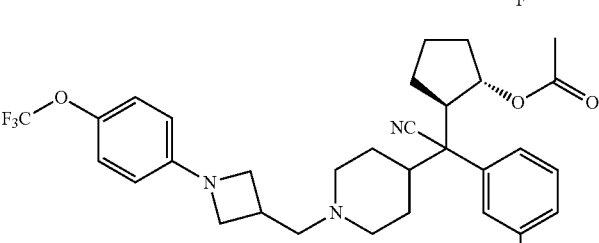 |

TABLE 5-continued
| Cpd. No. | Chemical Structure |
| --- | --- |
| 505 | 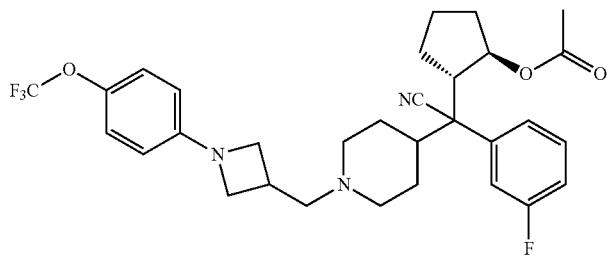 [SMILES: CC(=O)O[C@@H]1CCC[C@H]1C(C#N)(c1cccc(F)c1)C1CCN(CC2CN(c3ccc(OC(F)(F)F)cc3)C2)CC1] |
| 506 | 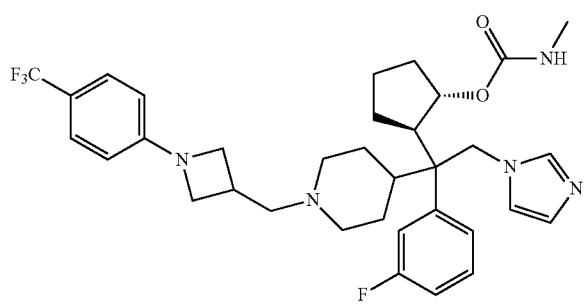 [SMILES: CNC(=O)O[C@H]1CCC[C@@H]1C(Cn1ccnc1)(c1cccc(F)c1)C1CCN(CC2CN(c3ccc(C(F)(F)F)cc3)C2)CC1] |
| 507 | 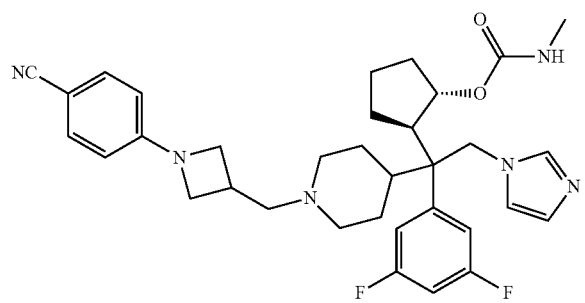 [SMILES: CNC(=O)O[C@H]1CCC[C@@H]1C(Cn1ccnc1)(c1cc(F)cc(F)c1)C1CCN(CC2CN(c3ccc(C#N)cc3)C2)CC1] |
| 508 | 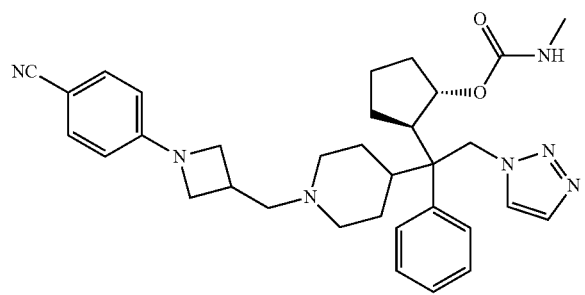 [SMILES: CNC(=O)O[C@H]1CCC[C@@H]1C(Cn1ccnn1)(c1ccccc1)C1CCN(CC2CN(c3ccc(C#N)cc3)C2)CC1] |
| 509 | 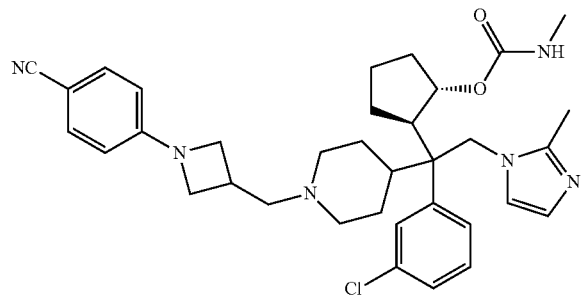 [SMILES: CNC(=O)O[C@H]1CCC[C@@H]1C(Cn1ccnc1C)(c1cccc(Cl)c1)C1CCN(CC2CN(c3ccc(C#N)cc3)C2)CC1] |

TABLE 5-continued
| Cpd. No. | Chemical Structure |
|---|---|
| 510 | 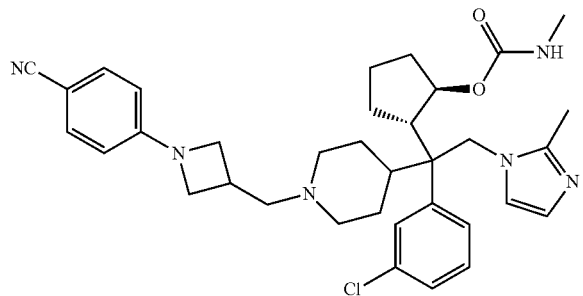 [SMILES: CNC(=O)O[C@@H]1CCC[C@H]1C(Cn1ccnc1C)(c1cccc(Cl)c1)C1CCN(CC2CN(c3ccc(C#N)cc3)C2)CC1] |
| 511 | 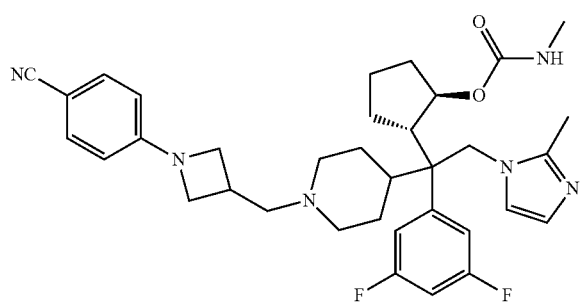 [SMILES: CNC(=O)O[C@@H]1CCC[C@H]1C(Cn1ccnc1C)(c1cc(F)cc(F)c1)C1CCN(CC2CN(c3ccc(C#N)cc3)C2)CC1] |
| 512 | 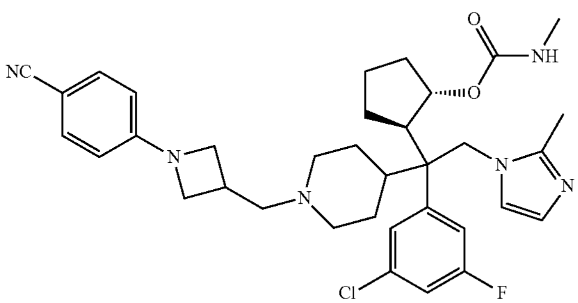 [SMILES: CNC(=O)O[C@H]1CCC[C@@H]1C(Cn1ccnc1C)(c1cc(F)cc(Cl)c1)C1CCN(CC2CN(c3ccc(C#N)cc3)C2)CC1] |
| 513 | 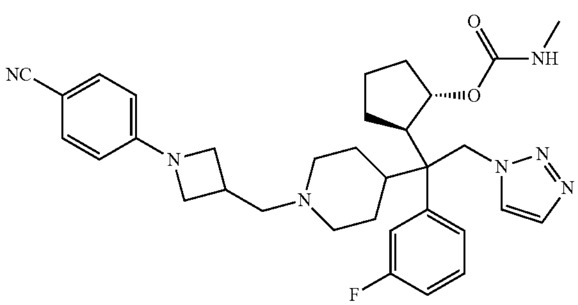 [SMILES: CNC(=O)O[C@H]1CCC[C@@H]1C(Cn1ccnn1)(c1cccc(F)c1)C1CCN(CC2CN(c3ccc(C#N)cc3)C2)CC1] |
| 514 | 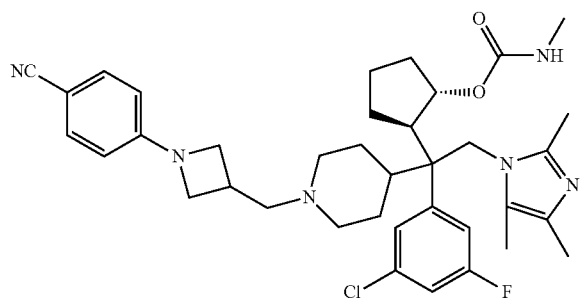 [SMILES: CNC(=O)O[C@H]1CCC[C@@H]1C(Cn1c(C)nc(C)c1C)(c1cc(F)cc(Cl)c1)C1CCN(CC2CN(c3ccc(C#N)cc3)C2)CC1] |

TABLE 5-continued
| Cpd. No. | Chemical Structure |
|---|---|
| 515 | 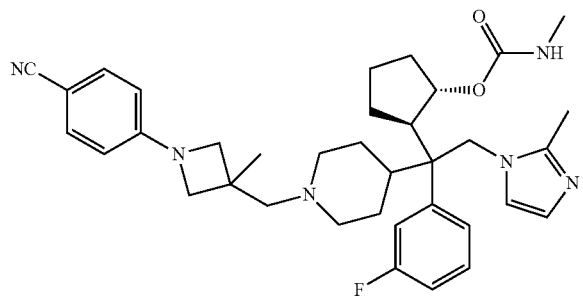 |
| 516 | 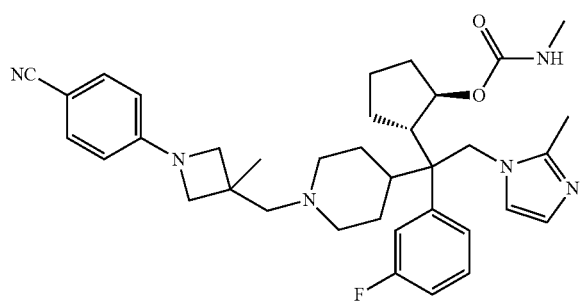 |
| 517 | 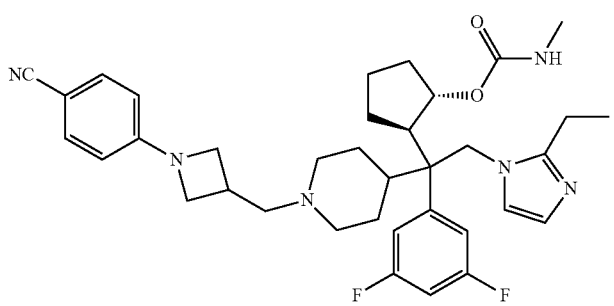 [SMILES: CCc1nccn1CC(c1cc(F)cc(F)c1)(C1CCN(CC2CN(c3ccc(C#N)cc3)C2)CC1)[C@H]1CCC[C@@H]1OC(=O)NC] |
| 518 | 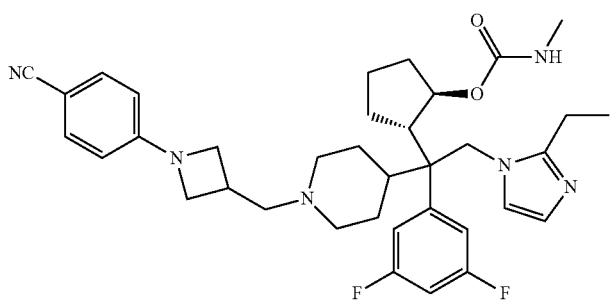 [SMILES: CCc1nccn1CC(c1cc(F)cc(F)c1)(C1CCN(CC2CN(c3ccc(C#N)cc3)C2)CC1)[C@@H]1CCC[C@H]1OC(=O)NC] |
| 519 | 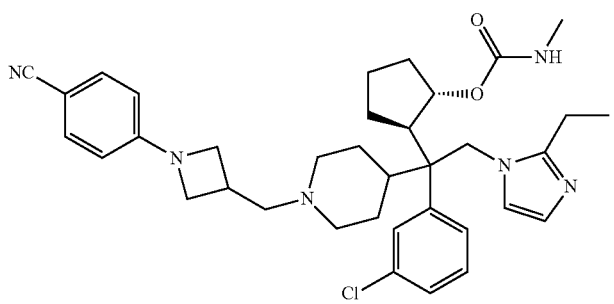 [SMILES: CCc1nccn1CC(c1cccc(Cl)c1)(C1CCN(CC2CN(c3ccc(C#N)cc3)C2)CC1)[C@H]1CCC[C@@H]1OC(=O)NC] |

TABLE 5-continued

| Cpd. No. | Chemical Structure |
|---|---|
| 520 | 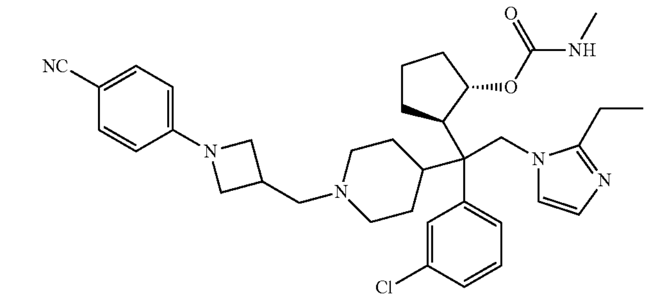 [SMILES: CCc1nccn1CC(c1cccc(Cl)c1)(C1CCN(CC2CN(c3ccc(C#N)cc3)C2)CC1)[C@H]1CCC[C@@H]1OC(=O)NC] |
| 521 | 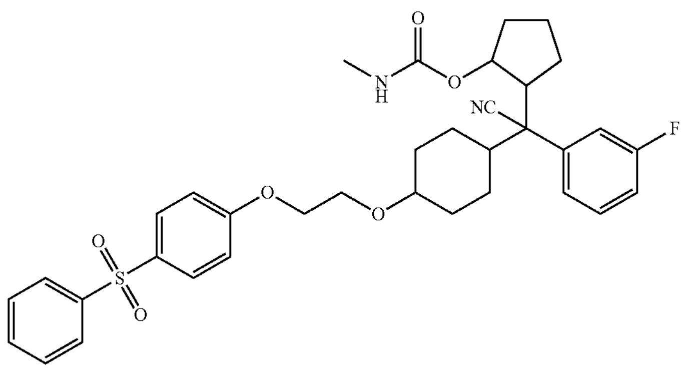 [SMILES: CNC(=O)OC1CCCC1C(C#N)(c1cccc(F)c1)C1CCC(OCCOc2ccc(S(=O)(=O)c3ccccc3)cc2)CC1] |
| 522 | 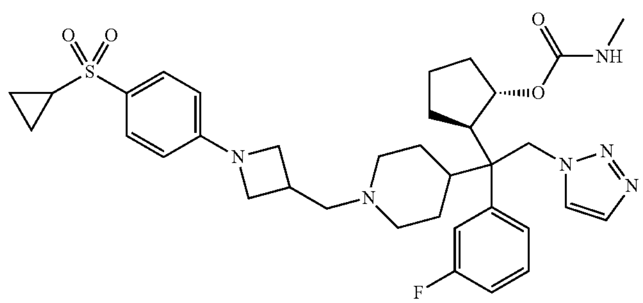 [SMILES: CNC(=O)O[C@H]1CCC[C@@H]1C(Cn1ccnn1)(c1cccc(F)c1)C1CCN(CC2CN(c3ccc(S(=O)(=O)C4CC4)cc3)C2)CC1] |

Compounds of the Disclosure inhibit menin and are useful in the treatment of a variety of diseases and conditions. In particular, Compounds of the Disclosure are useful in methods of treating a disease or condition wherein inhibition of menin provides a benefit, for example, cancers and proliferative diseases. Methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric.

Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate, or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as menin inhibitors for the treatment of diseases and conditions wherein inhibition of menin has a beneficial effect. Compounds of the Disclosure typically have a binding affinity ($IC_{50}$) to menin of less than 100 µM, e.g., less than 50 µM, less than 25 µM, and less than 5 µM, less than about 1 µM, less than about 0.5 µM, less than about 0.1 µM, less than about 0.05 µM, or less than about 0.01 µM. In one embodiment, the present disclosure relates to a method of treating an individual suffering from a disease or condition wherein inhibition of menin provides a benefit comprising administering a therapeutically effective amount of a Compound of the Disclosure to an individual in need thereof.

Diseases and conditions mediated by menin can be treated by administering Compounds of the Disclosure because these compounds are inhibitors of menin. The present disclosure is thus directed generally to a method for treating a condition or disorder responsive to inhibition of menin, in an animal, e.g., a human, suffering from, or at risk of suffering from, the condition or disorder, the method comprising administering to the animal an effective amount of one or more Compounds of the Disclosure.

The present disclosure is further directed to a method of inhibiting menin in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent, packaged separately or together, and an insert having instructions for using these active agents.

In one embodiment, a Compound of the Disclosure is administered in conjunction with a second therapeutic agent useful in the treatment of a disease or condition wherein inhibition of menin provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit menin activity in the patient.

In one embodiment, the disease to be treated by the Compound of the Disclosure is cancer. Examples of treatable cancers include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the menin inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as κ-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransyl-cytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU1O1, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Ax1 receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-[{(2,5-dihydroxyphenyl)methyl] amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

In another aspect, the present disclosure is drawn to the following particular embodiments:

Embodiment I. A compound having Formula I:

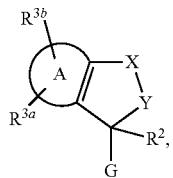

I or a pharmaceutically acceptable salt, hydrate, or solvate thereof, wherein:

A is

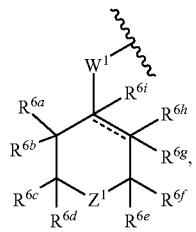

is a fused thienyl or fused phenyl group,

G is selected from the group consisting of:

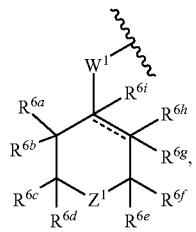
G-1

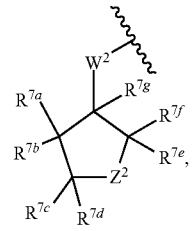
G-2

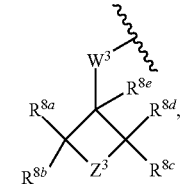
G-3

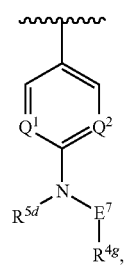
G-4

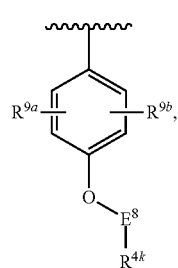
G-5

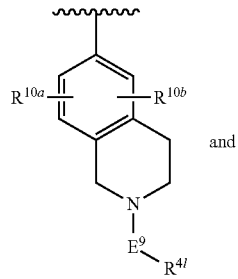
G-6 and

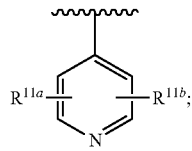
G-7

$W^1$ is absent or —CH$_2$—;
$Z^1$ is selected from the group consisting of —N(-E$^1$-R$^{4a}$)— and —C[—N(-E$^2$-R$^{4b}$)(R$^{4h}$)](R$^{5a}$)—;
$W^2$ is absent or —CH$_2$—;
$Z^2$ is selected from the group consisting of —N(-E$^3$-R$^{4c}$)— and —C[—N(-E$^4$-R$^{4d}$)(R$^{4i}$)](R$^{5b}$)—;
$W^3$ is absent or —CH$_2$—;
$Z^3$ is selected from the group consisting of —N(-E$^5$-R$^{4e}$)— and —C[—N(-E$^6$-R$^{4f}$)(R$^{4j}$)](R$^{5c}$)—;
═══ is a single or double bond, with the proviso that when ═══ is a double bond, $R^{6h}$ and $R^{6i}$ are absent;
$Q^1$ and $Q^2$ are each independently CH or N;
X—Y is selected from the group consisting of
—N(R$^{1a}$)—C(═O)—;
—C(═O)—O—;
—C(═O)—N(R$^{1b}$)—;
—CH$_2$N(R$^{1c}$)—CH$_2$—;
—C(═O)N(R$^{1d}$)—CH$_2$—;
—CH$_2$CH$_2$—N(R$^{1e}$)—;
—CH$_2$N(R$^{1f}$)—C(═O)—; and
—CH$_2$O—CH$_2$—; or X and Y do not form a chemical bond, and
X is selected from the group consisting of hydrogen, alkyl, halo, hydroxy, cyano, amino, alkylamino, dialkylamino, haloalkyl, alkoxy, and haloalkoxy; and
Y is selected from the group consisting of cyano, hydroxy, and —CH$_2$—R$^{12}$;

$E^1$, $E^2$, $E^3$, $E^4$, $E^5$, $E^6$, $E^7$, $E^8$, and $E^9$ are each independently selected from the group consisting of —C(═O)—, —C(═O)N(R$^{13}$)—, —[C(R$^{14a}$)(R$^{14b}$)]$_m$O—, —[C(R$^{14a}$)(R$^{14b}$)]$_m$N(R$^{15}$)—, —[C(R$^{14c}$)(R$^{14d}$)]$_n$—, —CH$_2$(═O)—, and —S(═O)$_2$—; or $E^1$, $E^2$, $E^3$, $E^4$, $E^5$, $E^6$, $E^7$, $E^8$, and $E^9$ are each independently absent;

$R^{1a}$ is selected from the group consisting of hydrogen and alkyl;

$R^{1b}$ is selected from the group consisting of hydrogen, alkyl, and aralkyl;

$R^{1c}$ is selected from the group consisting of hydrogen, alkyl, haloalkyl, optionally substituted cycloalkyl, optionally substituted heterocyclo, (cycloalkyl)alkyl, (heterocycloalkyl)alkyl, aralkyl, (heteroaryl)alkyl, alkylcarbonyl, arylcarbonyl, and alkoxycarbonyl;

$R^{1d}$ is selected from the group consisting of hydrogen, alkyl, and aralkyl;

$R^{1e}$ is selected from the group consisting of hydrogen, alkyl, and (aryloxy)alkyl;

$R^{1f}$ is selected from the group consisting of hydrogen and alkyl;

$R^2$ is selected from the group consisting of hydrogen, alkyl, alkenyl, optionally substituted cycloalkyl, optionally substituted aryl, optionally substituted heterocyclo, optionally substituted heteroaryl, and aralkyl;

$R^{3a}$ and $R^{3b}$ are each independently selected from the group consisting of hydrogen, alkyl, halo, hydroxy, cyano, amino, alkylamino, dialkylamino, haloalkyl, alkoxy, and haloalkoxy;

$R^{4a}$, $R^{4b}$, $R^{4c}$, $R^{4d}$, $R^{4e}$, $R^{4f}$, $R^{4g}$, $R^{4k}$, and $R^{4l}$ are each independently selected from the group consisting of hydrogen, alkyl, optionally substituted alkenyl, optionally substituted alkynyl, optionally substituted cycloalkyl, optionally substituted aryl, optionally substituted heterocyclo, optionally substituted heteroaryl, aralkyl, and (heteroaryl)alkyl;

$R_{4h}$, $R^{4i}$, and $R^{4j}$ are each independently selected from the group consisting of hydrogen and alkyl;

$R^{5a}$, $R^{5b}$, $R^{5c}$, and $R^{5d}$ are each independently selected from the group consisting of hydrogen and alkyl;

$R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen and alkyl;

$R^{6i}$ is selected from the group consisting of hydrogen, alkyl, and halo;

$R^{7a}$, $R^{7b}$, $R^{7c}$, $R^{7d}$, $R^{7e}$, and $R^{7f}$ are each independently selected from the group consisting of hydrogen and alkyl;

$R^{7g}$ is selected from the group consisting of hydrogen, alkyl, and halo;

$R^{8a}$, $R^{8b}$, $R^{8c}$, and $R^{8d}$ are each independently selected from the group consisting of hydrogen and alkyl;

$R^{8e}$ is selected from the group consisting of hydrogen, alkyl, and halo;

$R^{9a}$ and $R^{9b}$ are each independently selected from the group consisting of hydrogen, alkyl, halo, hydroxy, cyano, amino, alkylamino, dialkylamino, haloalkyl, alkoxy, and haloalkoxy;

$R^{10a}$ and $R^{10b}$ are each independently selected from the group consisting of hydrogen, alkyl, halo, hydroxy, cyano, amino, alkylamino, dialkylamino, haloalkyl, alkoxy, and haloalkoxy;

$R^{11a}$ and $R^{11b}$ are each independently selected from the group consisting of hydrogen, alkyl, halo, hydroxy, cyano, amino, alkylamino, dialkylamino, haloalkyl, alkoxy, and haloalkoxy;

$R^{12}$ is selected from the group consisting of hydroxy, amino, optionally substituted heteroaryl, optionally substituted heterocyclo, and —NHC(=O)—$R^{16}$;

m is 2, 3, 4, or 5, n is 1, 2, 3, 4, or 5

$R^{13}$ is selected from the group consisting of hydrogen and alkyl;

$R^{14a}$ and $R^{14b}$ are each independently selected from the group consisting of hydrogen and alkyl;

$R^{14c}$ and $R^{14d}$ are each independently selected from the group consisting of hydrogen and alkyl;

$R^{15}$ is selected from the group consisting of hydrogen and alkyl; and $R^{16}$ is selected from the group consisting of alkyl, optionally substituted aryl, optionally substituted heteroaryl, and optionally substituted cycloalkyl.

Embodiment II. The compound of Embodiment I, or a pharmaceutically acceptable salt, hydrate, or solvate thereof, having Formula II:

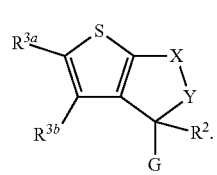

Embodiment III. The compound of Embodiment I, or a pharmaceutically acceptable salt, hydrate, or solvate thereof, having Formula III:

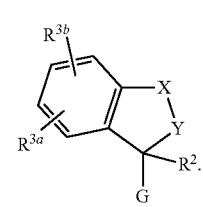

Embodiment IV. The compound of any one of Embodiments I-III, or a pharmaceutically acceptable salt, hydrate, or solvate thereof, wherein G is G-1.

Embodiment V. The compound of any one of Embodiments I-III, or a pharmaceutically acceptable salt, hydrate, or solvate thereof, wherein G is G-2.

Embodiment VI. The compound of any one of Embodiments I-III, or a pharmaceutically acceptable salt, hydrate, or solvate thereof, wherein G is G-3.

Embodiment VII. The compound of any one of Embodiments I-III, or a pharmaceutically acceptable salt, hydrate, or solvate thereof, wherein G is G-4.

Embodiment VIII. The compound of any one of Embodiments I-III, or a pharmaceutically acceptable salt, hydrate, or solvate thereof, wherein G is G-5.

Embodiment IX. The compound of any one of Embodiments I-III, or a pharmaceutically acceptable salt, hydrate, or solvate thereof, wherein G is G-6.

Embodiment X. The compound of any one of Embodiments I-III, or a pharmaceutically acceptable salt, hydrate, or solvate thereof, wherein G is G-7.

Embodiment XI. The compound of Embodiment IV, or a pharmaceutically acceptable salt, hydrate, or solvate thereof, wherein $W^1$ is absent.

Embodiment XII. The compound of Embodiment V, or a pharmaceutically acceptable salt, hydrate, or solvate thereof, wherein $W^2$ is absent.

Embodiment XIII The compound of Embodiment VI, or a pharmaceutically acceptable salt, hydrate, or solvate thereof, wherein $W^3$ is absent.

Embodiment XIV. The compound of Embodiments IX or XI, or a pharmaceutically acceptable salt, hydrate, or solvate thereof, wherein === is a single bond and $R^{6a}$, $R^{6b}$, $R^{6c}$, $R^{6d}$, $R^{6e}$, $R^{6f}$, $R^{6g}$, $R^{6h}$, and $R^{6i}$ are each independently selected from the group consisting of hydrogen and $C_{1-3}$ alkyl.

Embodiment XV. The compound of Embodiment XIV, or a pharmaceutically acceptable salt, hydrate, or solvate thereof, wherein $R^{6a}$, $R^{6b}$, $R^{6c}$, $R^{6d}$, $R^{6e}$, $R^{6f}$, $R^{6g}$, $R^{6h}$, and $R^{6i}$ are each hydrogen.

Embodiment XVI. The compound of Embodiments V or XII, or a pharmaceutically acceptable salt, hydrate, or solvate thereof, wherein $R^{7a}$, $R^{7b}$, $R^{7c}$, $R^{7d}$, $R^{7e}$, $R^{7f}$, and $R^{7g}$ are each independently selected from the group consisting of hydrogen and $C_{1-3}$ alkyl.

Embodiment XVII. The compound of Embodiment XVI, or a pharmaceutically acceptable salt, hydrate, or solvate thereof, wherein $R^{7a}$, $R^{7b}$, $R^{7c}$, $R^{7d}$, $R^{7e}$, $R^{7f}$, and $R^{7g}$ are each hydrogen.

Embodiment XVIII. The compound of Embodiments VI or XIII, or a pharmaceutically acceptable salt, hydrate, or solvate thereof, wherein $R^{8a}$, $R^{8b}$, $R^{8c}$, $R^{8d}$, and $R^{8e}$ are each independently selected from the group consisting of hydrogen and $C_{1-3}$ alkyl.

Embodiment XIX. The compound of Embodiment XVIII, or a pharmaceutically acceptable salt, hydrate, or solvate thereof, wherein $R^{8a}$, $R^{8b}$, $R^{8c}$, $R^{8d}$, and $R^{8e}$ are each hydrogen.

Embodiment XX. The compound of any one of Embodiments I-III, or a pharmaceutically acceptable salt, hydrate, or solvate thereof, wherein G is selected from the group consisting of:

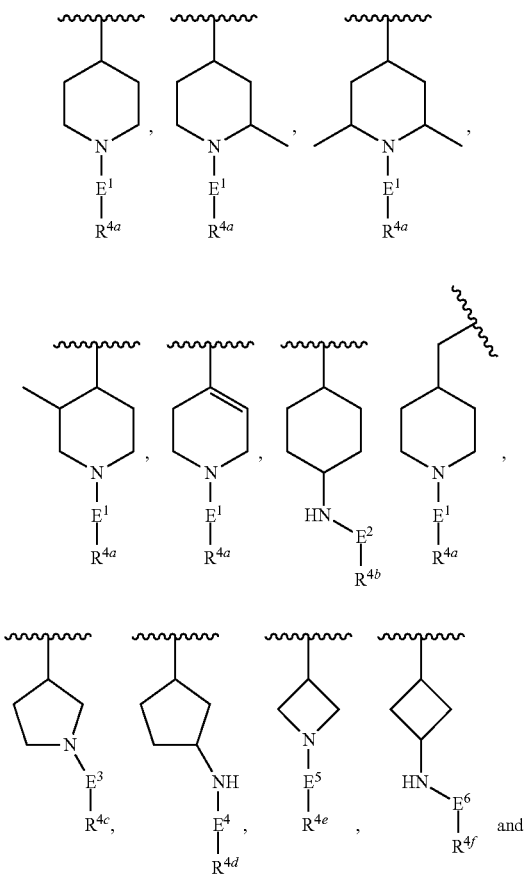

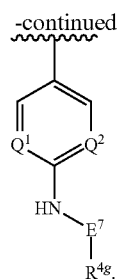

with the proviso that $Q^1$ is N and $Q^2$ is selected from the group consisting of CH and N.

Embodiment XXI. The compound of any one of Embodiments I-III or XX, or a pharmaceutically acceptable salt, hydrate, or solvate thereof, wherein $E^1$, $E^2$, $E^3$, $E^4$, $E^5$, $E^6$, and $E^7$ are each independently selected from the group consisting of —C(=O)—, —C(=O)N($R^{13}$)—, —[C($R^{14a}$)($R^{14b}$)]$_m$O—, —[C($R^{14a}$)($R^{14b}$)]$_m$N($R^{15}$)—, —[C($R^{14c}$)($R^{14d}$)]$_n$—, —CH$_2$(=O)—, and —S(=O)$_2$—.

Embodiment XXII. The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —C(=O)—.

Embodiment XXIII The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —C(=O)N($R^{13}$)—.

Embodiment XXIV. The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —[C($R^{14a}$)($R^{14b}$)]$_m$O—.

Embodiment XXV. The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —[C($R^{14a}$)($R^{14b}$)]$_m$N($R^{15}$)—.

Embodiment XXVI. The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —[C($R^{14c}$)($R^{14d}$)]$_n$—.

Embodiment XXVII. The compound of Embodiment XXVI, or a pharmaceutically acceptable salt, hydrate, or solvate thereof, wherein n is 1 and $R^{14c}$ and $R^{14d}$ are each hydrogen.

Embodiment XXVIII. The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —CH$_2$(=O)—.

Embodiment XXIX. The compound of Embodiment XXI, or a pharmaceutically acceptable salt, hydrate, or solvate thereof, wherein $E^1$, $E^2$, $E^3$, $E^4$, $E^5$, $E^6$, and $E^7$ are each —S(=O)$_2$—.

Embodiment XXX. The compound of any one of Embodiments I-III and XX, or a pharmaceutically acceptable salt, hydrate, or solvate thereof, wherein $E^1$, $E^2$, $E^3$, $E^4$, $E^5$, $E^6$, and $E^7$ are each absent.

Embodiment XXXI. The compound of any one of Embodiments I-III and XX-XXX, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each independently selected from the group consisting of alkyl, optionally substituted cycloalkyl, optionally substituted aryl, optionally substituted heterocyclo, optionally substituted heteroaryl, aralkyl, (heterocyclo)alkyl, and (heteroaryl)alkyl.

Embodiment XXXII. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each alkyl.

Embodiment XXXIII. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each optionally substituted cycloalkyl.

Embodiment XXXIV. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each optionally substituted aryl.

Embodiment XXXV. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each optionally substituted heterocyclo.

Embodiment XXXVI. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each optionally substituted heteroaryl.

Embodiment XXXVII. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each aralkyl.

Embodiment XXXVIII. The compound of Embodiment XXXI, or a pharmaceutically acceptable salt, hydrate, or solvate thereof, wherein $R^{4a}$, $R^{4b}$, $R^{4c}$, $R^{4d}$, $R^{4e}$, $R^{4f}$, and $R^{4g}$ are each (heteroaryl)alkyl.

Embodiment XXXIX. The compound of Embodiment I, or a pharmaceutically acceptable salt, hydrate, or solvate thereof, having Formula IV:

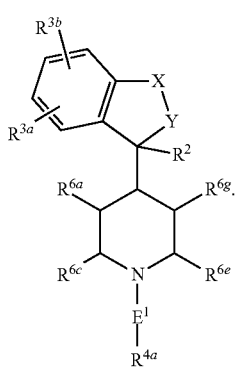

IV

Embodiment XL. The compound of Embodiment XXXIX, or a pharmaceutically acceptable salt, hydrate, or solvate thereof, wherein $E^1$ is —[C($R^{14a}$)($R^{14b}$)]$_m$O— and $R^{4a}$ is selected from the group consisting of optionally substituted aryl and optionally substituted heteroaryl.

Embodiment XLI. The compound of Embodiment XL, or a pharmaceutically acceptable salt, hydrate, or solvate thereof, having Formula V:

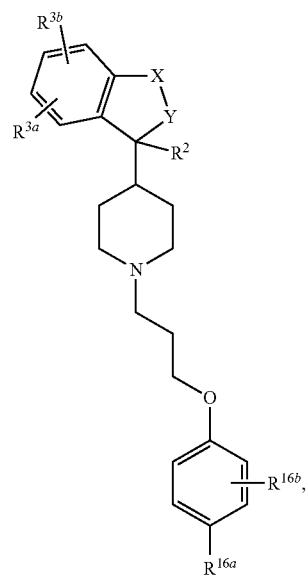

V wherein:

$R^{16a}$ is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl; and $R^{16b}$ is selected from the group consisting of hydrogen, alkyl, halo, hydroxy, cyano, amino, alkylamino, dialkylamino, haloalkyl, alkoxy, and haloalkoxy.

Embodiment XLII. The compound of Embodiment XXXIX, or a pharmaceutically acceptable salt, hydrate, or solvate thereof, wherein $E^1$ is —C($R^{14c}$)($R^{14d}$)$_n$— and $R^{4a}$ is substituted $C_{4-6}$ heterocyclo.

Embodiment XLIII. The compound of Embodiment XLII, or a pharmaceutically acceptable salt, hydrate, or solvate thereof, wherein n is 1 and $R^{14c}$ and $R^{14d}$ are hydrogen.

Embodiment XLIV. The compound of Embodiment XLIII, or a pharmaceutically acceptable salt, hydrate, or solvate thereof, having Formula VI:

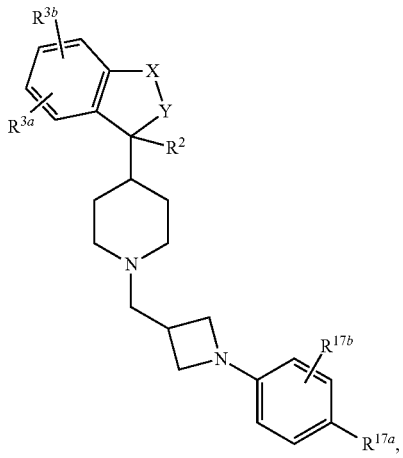

VI wherein:

$R^{17a}$ is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl; and $R^{17b}$ is selected from the group consisting of hydrogen, alkyl, halo, hydroxy, cyano, amino, alkylamino, dialkylamino, haloalkyl, alkoxy, and haloalkoxy.

Embodiment XLV. The compound of Embodiment XLIV, or a pharmaceutically acceptable salt, hydrate, or solvate thereof, wherein:

$R^{17a}$ is selected from the group consisting of alkylsulfonyl, cycloalkylsulfonyl, arylsulfonyl, and heteroarylsulfonyl; and $R^{17b}$ is hydrogen.

Embodiment XLVI. The compound of any one of Embodiments I-XLV, or a pharmaceutically acceptable salt, hydrate, or solvate thereof, wherein $R^2$ is selected from the group consisting of alkyl, alkenyl, optionally substituted cycloalkyl, optionally substituted aryl, optionally substituted heterocyclo, optionally substituted heteroaryl, and aralkyl.

Embodiment XLVII. The compound of Embodiment XLVI, or a pharmaceutically acceptable salt, hydrate, or solvate thereof, wherein $R^2$ is unsubstituted cycloalkyl.

Embodiment XLVIII. The compound of Embodiment XLVI, or a pharmaceutically acceptable salt, hydrate, or solvate thereof, wherein $R^2$ is substituted cycloalkyl.

Embodiment XLIX. The compound of Embodiment XLVIII, or a pharmaceutically acceptable salt, hydrate, or solvate thereof, wherein $R^2$ is substituted cycloalkyl having Formula VII:

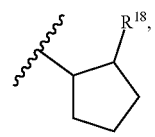

VII wherein:

$R^{18}$ is selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N($R^{19a}$)C(=O)—$R^{19b}$, and —N($R^{20a}$)SO$_2$—$R^{20b}$;

$R^{19a}$ is selected from the group consisting of hydrogen and alkyl;

$R^{19b}$ is selected from the group consisting of amino, alkoxy, alkyl, and optionally substituted aryl;

$R^{20a}$ is selected from the group consisting of hydrogen and alkyl; and $R^{20b}$ is selected from the group consisting of amino, alkyl, and optionally substituted aryl.

Embodiment L. The compound of Embodiment XLIX, or a pharmaceutically acceptable salt, hydrate, or solvate thereof, wherein $R^{18}$ is selected from the group consisting of alkylcarbonyloxy, cycloalkylcarbonyloxy, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, and (heterocyclo)alkyl.

Embodiment LI. The compound of Embodiment L, or a pharmaceutically acceptable salt, hydrate, or solvate thereof, wherein $R^{18}$ is selected from the group consisting of —OC(=O)-amino and —NHC(=O)—$R^{19b}$.

Embodiment LII. The compound of Embodiment XLVI, or a pharmaceutically acceptable salt, hydrate, or solvate thereof, wherein $R^2$ is selected from the group consisting of:

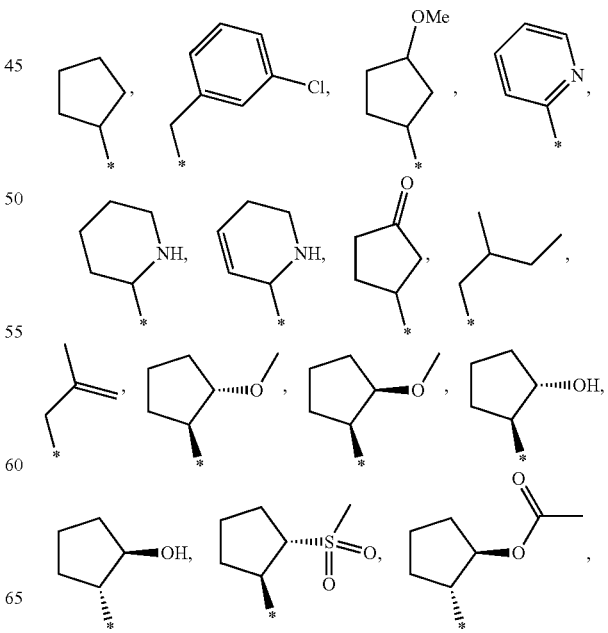

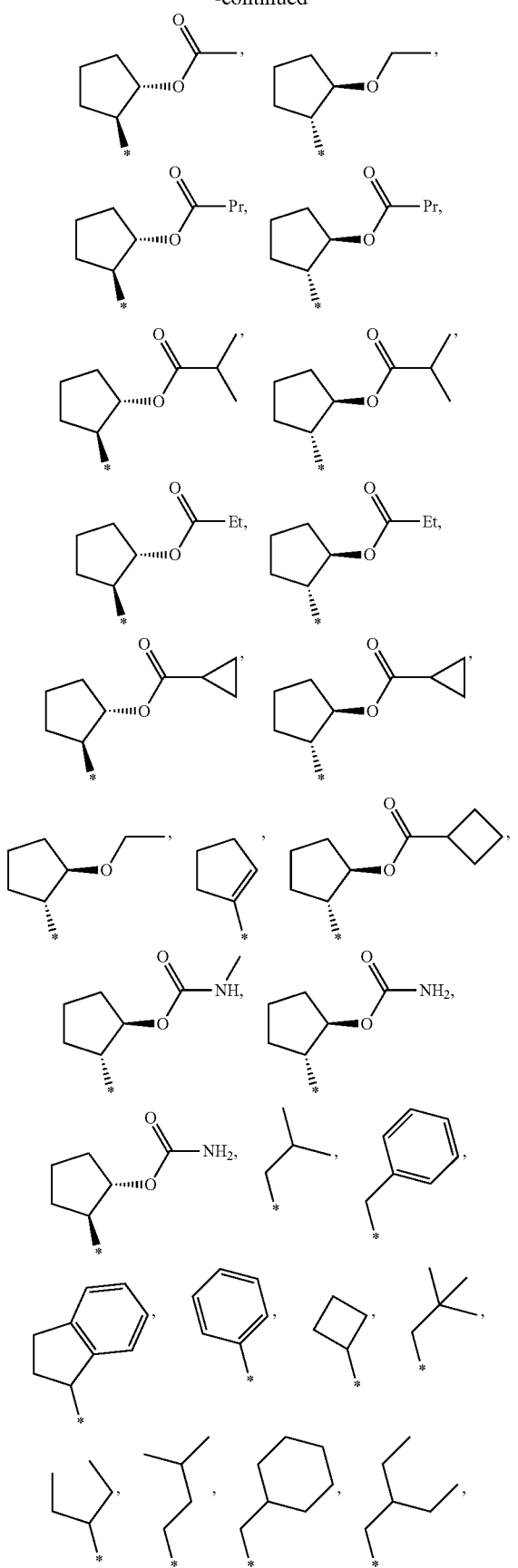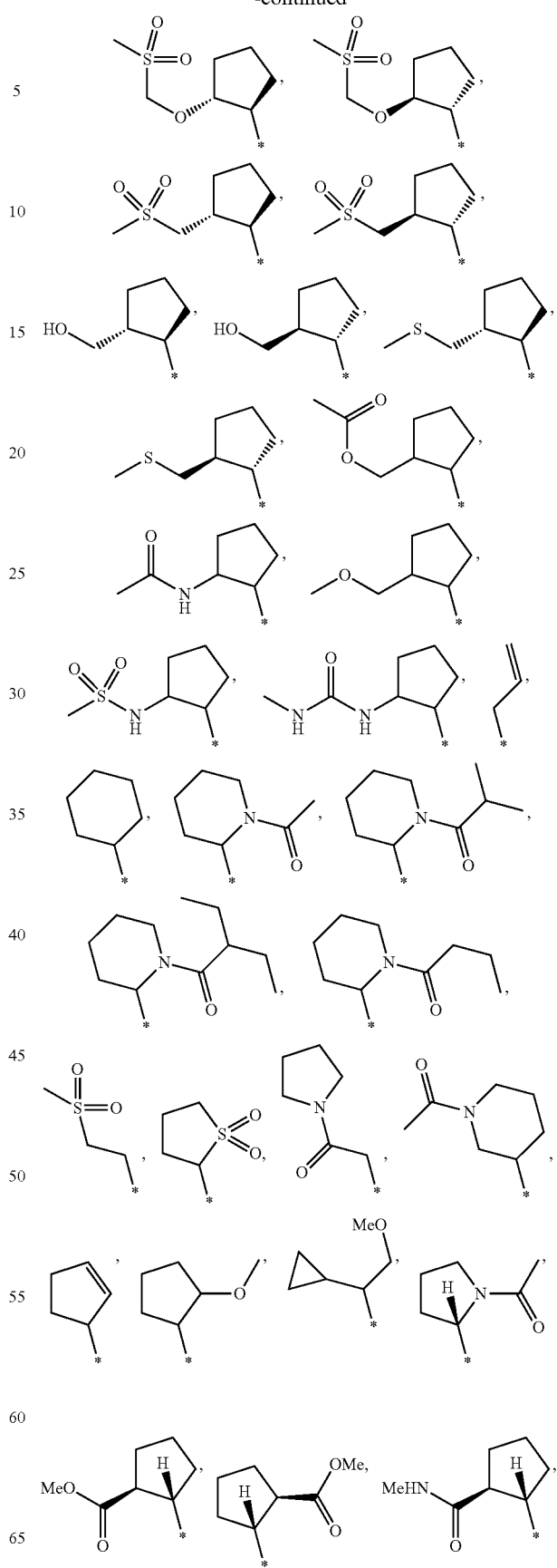

-continued

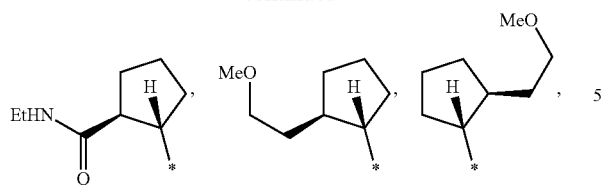

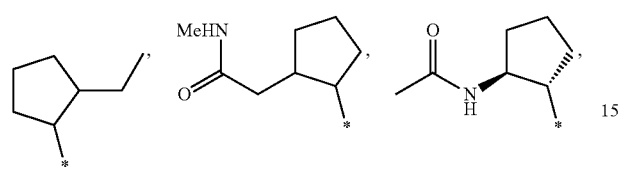

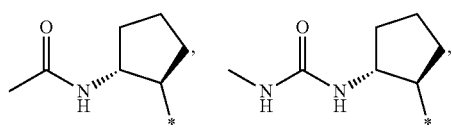

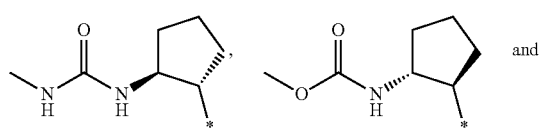 and

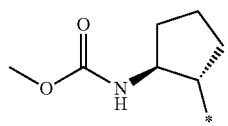

wherein "*" indicates the point of attachment to the remainder of the molecule.

Embodiment LIII. The compound of Embodiment I, or a pharmaceutically acceptable salt, hydrate, or solvate thereof, having Formula VIII:

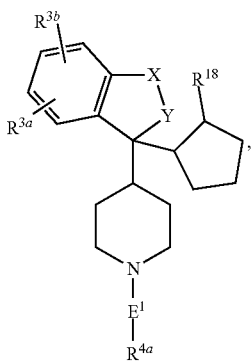

VIII

Embodiment LIV. The compound of Embodiment LIII, or a pharmaceutically acceptable salt, hydrate, or solvate thereof, having any one or more of the following formulae:

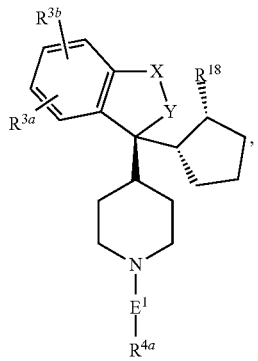

Formula VIII-A

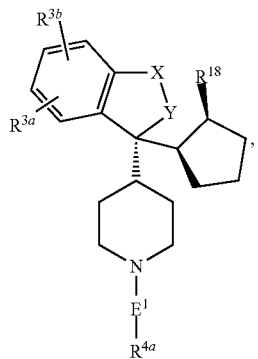

Formula VIII-B

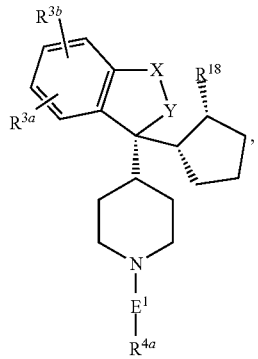

Formula VIII-C

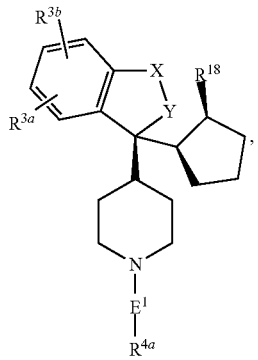

Formula VIII-D

-continued

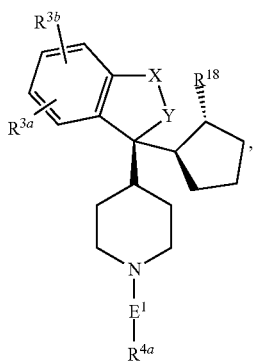

Formula VIII-E

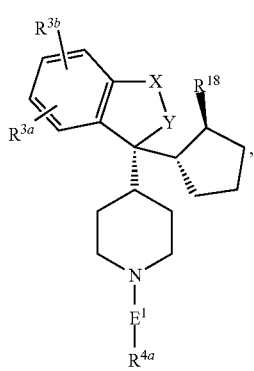

Formula VIII-F

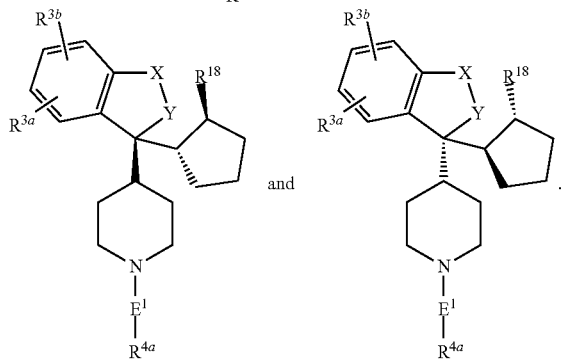

and

Embodiment LV. The compound of any one of Embodiments I-LIV, or a pharmaceutically acceptable salt, hydrate, or solvate thereof, wherein X—Y is selected from the group consisting of —N($R^{1a}$)—C(=O)—; —C(=O)—O—; —C(=O)—N($R^{1b}$)—; —CH$_2$N($R^{1c}$)—CH$_2$—; —C(=O)N($R^{1d}$)—CH$_2$—; —CH$_2$CH$_2$—N($R^{1e}$)—; —CH$_2$N($R^{1f}$)—C(=O)—; and —CH$_2$O—CH$_2$—.

Embodiment LVI. The compound of Embodiment LV, or a pharmaceutically acceptable salt, hydrate, or solvate thereof, wherein X—Y is —N($R^{1a}$)—C(=O)—.

Embodiment LVII. The compound of Embodiment LV, or a pharmaceutically acceptable salt, hydrate, or solvate thereof, wherein X—Y is —C(=O)—O—.

Embodiment LVIII. The compound of Embodiment LV, or a pharmaceutically acceptable salt, hydrate, or solvate thereof, wherein X—Y is —C(=O)—N($R^{1b}$)—.

Embodiment LIX. The compound of Embodiment LV, or a pharmaceutically acceptable salt, hydrate, or solvate thereof, wherein X—Y is —CH$_2$N($R^{1c}$)—CH$_2$—.

Embodiment LX. The compound of Embodiment LV, or a pharmaceutically acceptable salt, hydrate, or solvate thereof, wherein X—Y is —C(=O)N($R^{1d}$)—CH$_2$—.

Embodiment LXI. The compound of Embodiment LV, or a pharmaceutically acceptable salt, hydrate, or solvate thereof, wherein X—Y is —CH—$_2$CH$_2$—N($R^{1e}$)—.

Embodiment LXII. The compound of Embodiment LV, or a pharmaceutically acceptable salt, hydrate, or solvate thereof, wherein X—Y is —CH$_2$N($R^{1f}$)—C(=O)—.

Embodiment LXIII The compound of Embodiment LV, or a pharmaceutically acceptable salt, hydrate, or solvate thereof, wherein X—Y is —CH$_2$O—CH$_2$—.

Embodiment LXIV. The compound of any one of Embodiments I-LIV, or a pharmaceutically acceptable salt, hydrate, or solvate thereof, wherein X and Y do not form a chemical bond and X is hydrogen.

Embodiment LXV. The compound of Embodiment LXIV, or a pharmaceutically acceptable salt, hydrate, or solvate thereof, wherein Y is selected from the group consisting of cyano and —CH$_2$—$R^{12}$.

Embodiment LXVI. The compound of Embodiment LXV, or a pharmaceutically acceptable salt, hydrate, or solvate thereof, wherein Y is cyano.

Embodiment LXVII. The compound of Embodiment LXV, or a pharmaceutically acceptable salt, hydrate, or solvate thereof, wherein Y is —CH$_2$—$R^{12}$.

Embodiment LXVIII. The compound of Embodiment I, or a pharmaceutically acceptable salt, hydrate, or solvate thereof, having Formula IX:

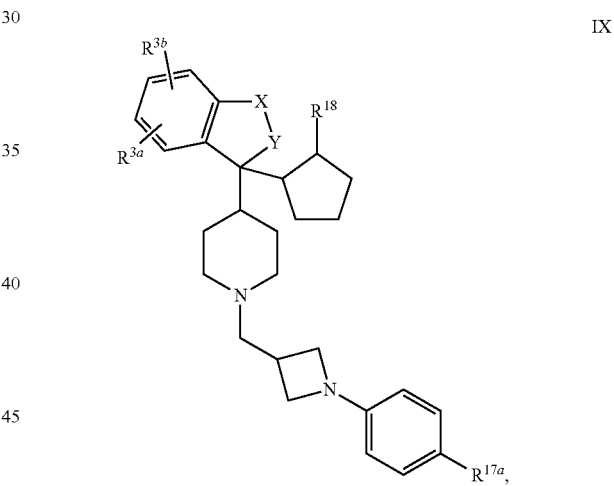

IX wherein:

X—Y is —CH$_2$N($R^{1c}$)—CH$_2$—, or

X and Y do not form a chemical bond, and

X is hydrogen; and

Y is selected from the group consisting of —CN and —CH$_2$—$R^{12}$;

$R^{1c}$ is $C_{1-3}$ alkyl;

$R^{12}$ is selected from the group consisting of amino and heteroaryl;

$R^{17a}$ is selected from the group consisting of alkylsulfonyl, cycloalkylsulfonyl, arylsulfonyl, and heteroarylsulfonyl;

$R^{18}$ is selected from the group consisting of —OC(=O)-amino and —NHC(=O)—$R^{19b}$; and $R^{19b}$ is selected from the group consisting of amino, alkoxy, alkyl, and optionally substituted aryl.

Embodiment LXIX: The compound of Embodiment LXVIII, or a pharmaceutically acceptable salt, hydrate, or solvate thereof, having any one or more of the following formulae:
Formula IX-A
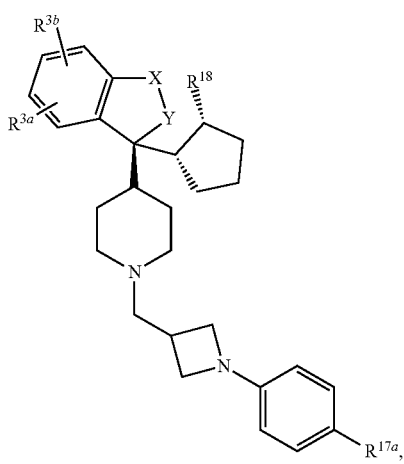
Formula IX-B
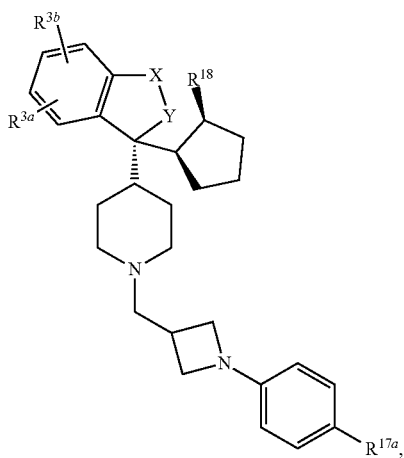
Formula IX-C
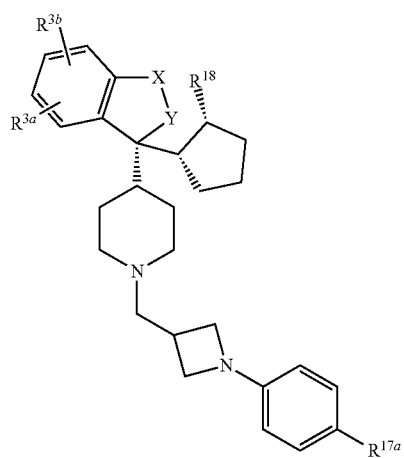
Formula IX-D
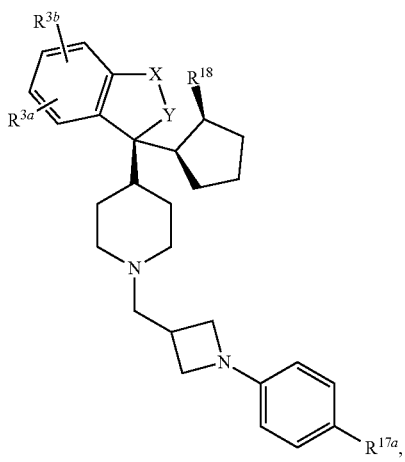
Formula IX-E
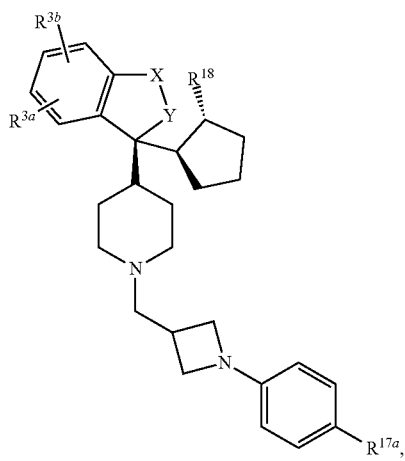
Formula IX-F
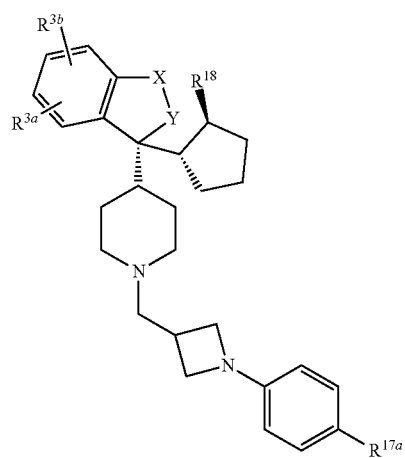

Formula IX-G

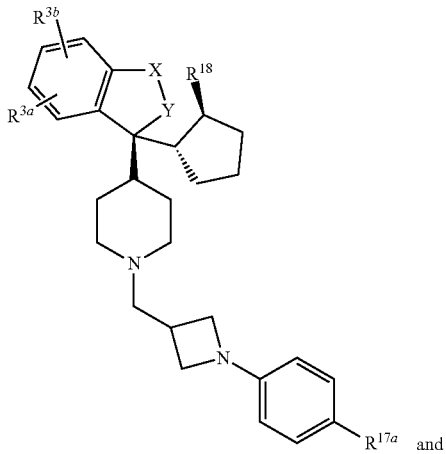 and

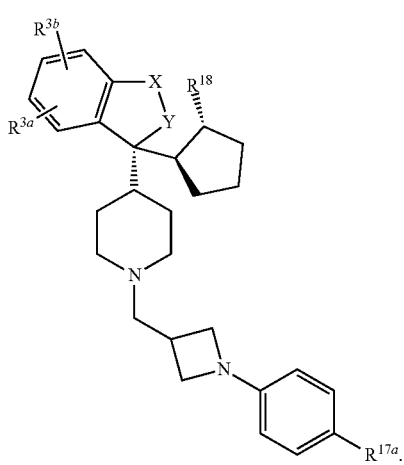

Formula IX-H

Embodiment LXX. The compound of Embodiment LXVIII or LXIX, or a pharmaceutically acceptable salt, hydrate, or solvate thereof, wherein:

X—Y is —CH$_2$N(R$^{1c}$)—CH$_2$—; and

R$^{1c}$ is selected from the group consisting of hydrogen and C$_{1-6}$ alkyl.

Embodiment LXXI. The compound of Embodiment I, or a pharmaceutically acceptable salt, hydrate, or solvate thereof, having Formula X:

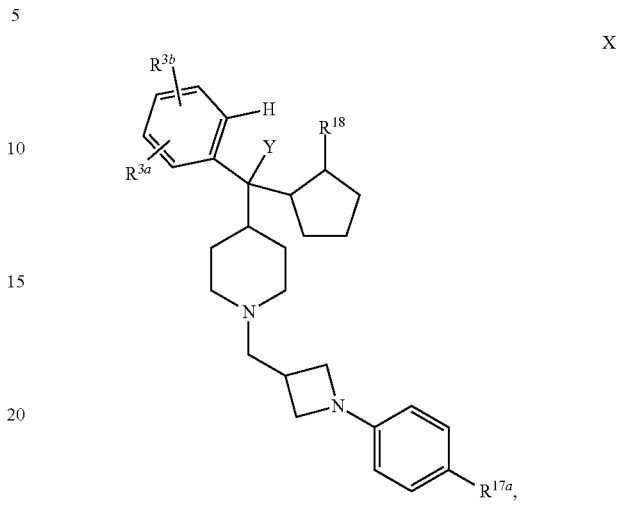

X wherein:

R$^{17a}$ is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl;

R$^{18}$ is selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N(R$^{19a}$)C(=O)—R$^{19b}$, and —N(R$^{20a}$)SO$_2$—R$^{20b}$;

R$^{19a}$ is selected from the group consisting of hydrogen and alkyl;

R$^{19b}$ is selected from the group consisting of amino, alkoxy, alkyl, and optionally substituted aryl;

R$^{20a}$ is selected from the group consisting of hydrogen and alkyl; and

R$^{20b}$ is selected from the group consisting of amino, alkyl, and optionally substituted aryl. In another embodiment, R18 is selected from the group consisting of alkylcarbonyloxy, cycloalkylcarbonyloxy, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, and (heterocyclo)alkyl.

Embodiment LXXII. The compound of Embodiment LXXI, or a pharmaceutically acceptable salt, hydrate, or solvate thereof, wherein:

Y is selected from the group consisting of cyano and —CH$_2$—R$^{12}$;

$R^{12}$ is selected from the group consisting of amino and heteroaryl;

$R^{18}$ is is selected from the group consisting of —OC(=O)-amino and —NHC(=O)—$R^{19b}$; and $R^{19b}$ is selected from the group consisting of amino, alkoxy, alkyl, and optionally substituted aryl.

Embodiment LXXIII. The compound of Embodiments LXXI or LXXII, or a pharmaceutically acceptable salt, hydrate, or solvate thereof, wherein $R^{17a}$ is selected from the group consisting of chloro, cyano, alkylsulfonyl, haloalkylsulfonyl, cycloalkylsulfonyl, arylsulfonyl, and heteroarylsulfonyl.

Embodiment LXXIV. The compound of any one of Embodiments LXXI-LXXIII, or a pharmaceutically acceptable salt, hydrate, or solvate thereof, having any one or more of the following formulae:

Formula X-A

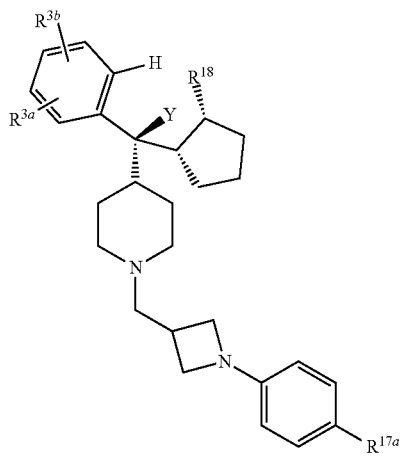

Formula X-B

Formula X-C

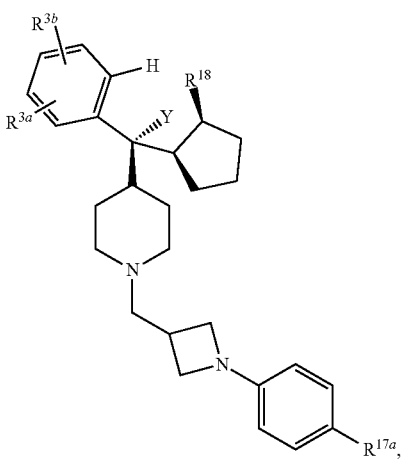

Formula X-D

Formula X-E

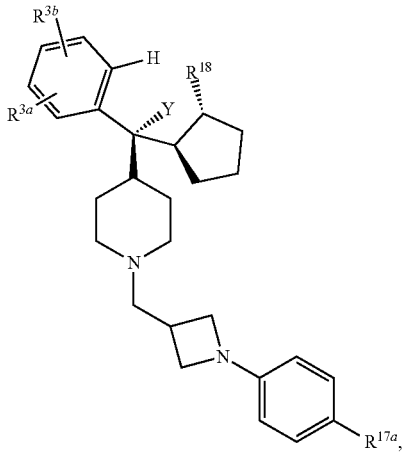

-continued

Formula X-F

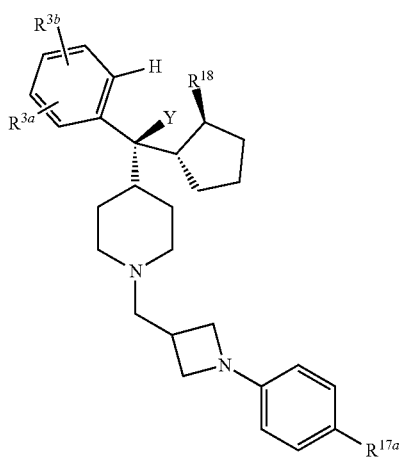

Formula X-G

and Formula X-H

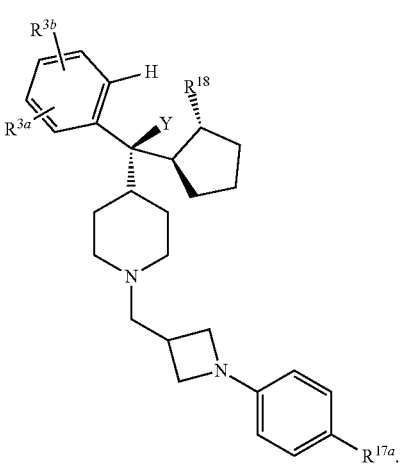

Embodiment LXXV. The compound of any one of Embodiments LXXI-LXXIV, or a pharmaceutically acceptable salt, hydrate, or solvate thereof, wherein Y is —CH$_2$—R$^{12}$.

Embodiment LXXVI. The compound of any one of Embodiments LXXI-LXXV, or a pharmaceutically acceptable salt, hydrate, or solvate thereof, wherein R$^{12}$ is 5-membered heteroaryl.

Embodiment LXXVII. The compound of any one of Embodiments LXXI-LXXVI or a pharmaceutically acceptable salt, hydrate, or solvate thereof, wherein R$^{12}$ is optionally substituted imidazol-1-yl.

To facilitate an understanding of the present disclosure, a number of terms and phrases are defined below.

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., C$_{1-12}$ alkyl, or the number of carbon atoms designated, e.g., a C$_1$ alkyl such as methyl, a C$_2$ alkyl such as ethyl, a C$_3$ alkyl such as propyl or isopropyl, a C$_{1-3}$ alkyl such as methyl, ethyl, propyl, or isopropyl, and so on. In one embodiment, the alkyl is a C$_{1-10}$ alkyl. In another embodiment, the alkyl is a C$_{1-6}$ alkyl. In another embodiment, the alkyl is a C$_{1-4}$ alkyl. In another embodiment, the alkyl is a straight chain C$_{1-10}$ alkyl. In another embodiment, the alkyl is a branched chain C$_{3-10}$ alkyl. In another embodiment, the alkyl is a straight chain C$_{1-6}$ alkyl. In another embodiment, the alkyl is a branched chain C$_{3-6}$ alkyl. In another embodiment, the alkyl is a straight chain C$_{1-4}$ alkyl. In another embodiment, the alkyl is a branched chain C$_{3-4}$ alkyl. In another embodiment, the alkyl is a straight or branched chain C$_{3-4}$ alkyl. Non-limiting exemplary C$_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary C$_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group refers to an alkyl that is either unsubstituted or substituted with one, two, or three substituents independently selected from the group consisting of nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and alkylcarbonyloxy. In one embodiment, the optionally substituted alkyl is substituted with two substituents. In another embodiment, the optionally substituted alkyl is substituted with one substituent. In another embodiment, the optionally substituted alkyl is unsubstituted. Non-limiting exemplary substituted alkyl groups include —CH$_2$CH$_2$NO$_2$, —CH$_2$SO$_2$CH$_3$, CH$_2$CH$_2$SO$_2$CH$_3$, —CH$_2$CH$_2$CO$_2$H, —CH$_2$SCH$_3$, —CH$_2$CH$_2$SO$_2$CH$_3$, —CH$_2$CH$_2$COPh, and —CH$_2$OC(=O)CH$_3$.

In the present disclosure, the term "cycloalkyl" as used by itself or as part of another group refers to unsubstituted saturated or partially unsaturated, e.g., containing one or two double bonds, cyclic aliphatic hydrocarbons containing one to three rings having from three to twelve carbon atoms, i.e., C$_{3-12}$ cycloalkyl, or the number of carbons designated. In one embodiment, the cycloalkyl has two rings. In another embodiment, the cycloalkyl has one ring. In another embodiment, the cycloalkyl is saturated. In another embodiment, the cycloalkyl is unsaturated. In another embodiment, the cycloalkyl is a C$_{3-8}$ cycloalkyl. In another embodiment, the cycloalkyl is a C$_{3-6}$ cycloalkyl. The term "cycloalkyl" is meant to include groups wherein a ring —CH$_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclopentanone.

In the present disclosure, the term "optionally substituted cycloalkyl" as used by itself or as part of another group refers to a cycloalkyl that is either unsubstituted or substituted with one, two, or three substituents independently selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N(R$^{19a}$)C(=O)—R$^{19b}$, and —N(R$^{20a}$)SO$_2$—R$^{20b}$, wherein R$^{19a}$ is selected from the group consisting of hydrogen and alkyl, R$^{19b}$ is selected from the group consisting of amino, alkoxy, alkyl, and optionally substituted aryl, R$^{20a}$ is selected from the group consisting of hydrogen and alkyl, and R$^{20b}$ is selected from the group consisting of amino, alkyl, and optionally substituted aryl. The term optionally substituted cycloalkyl includes cycloalkyl groups having a fused optionally substituted aryl, e.g., phenyl, or fused optionally substituted heteroaryl, e.g., pyridyl. An optionally substituted cycloalkyl having a fused optionally substituted aryl or fused optionally substituted heteroaryl group may be attached to the remainder of the molecule at any available carbon atom on the cycloalkyl ring. In one embodiment, the optionally substituted cycloalkyl is substituted with two substituents. In another embodiment, the optionally substituted cycloalkyl is substituted with one substituent. In another embodiment, the optionally substituted cycloalkyl is unsubstituted. Non-limiting exemplary substituted cycloalkyl groups include:

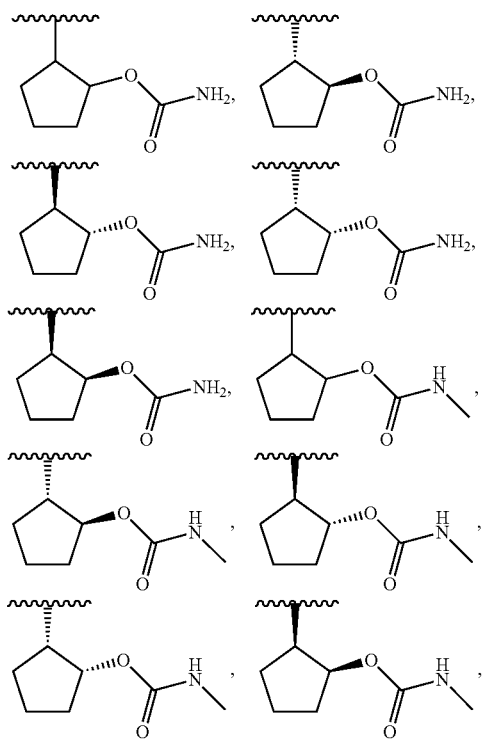

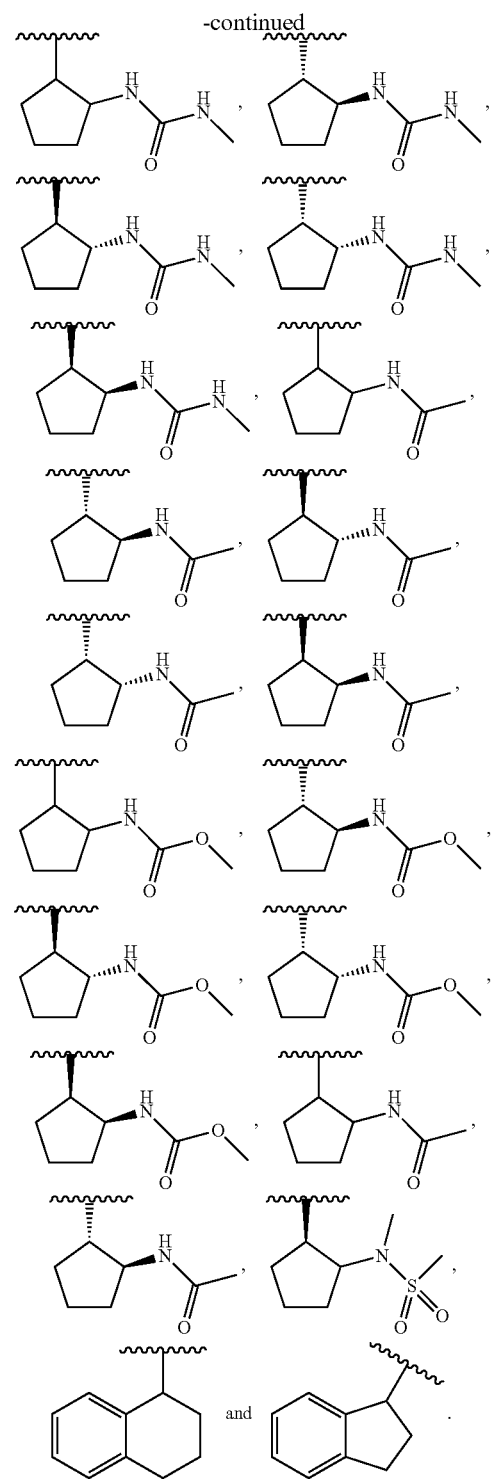

In the present disclosure, the term "aryl" as used by itself or as part of another group refers to unsubstituted monocyclic or bicyclic aromatic ring systems having from six to fourteen carbon atoms, i.e., a C$_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, amino, —CO$_2$CH$_2$Ph, alkylamino, dialkylamino, optionally substituted alkyl, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, haloalkylsulfonyl cycloalkylsulfonyl, (cycloalkyl)alkylsulfonyl, arylsulfonyl, heteroarylsulfonyl, heterocyclosulfonyl, carboxy, carboxyalkyl, optionally substituted cycloalkyl, alkenyl, alkynyl, optionally substituted aryl, optionally substituted heteroaryl, optionally substituted heterocyclo, alkoxycarbonyl, alkoxyalkyl, (amino)alkyl, (carboxamido)alkyl, and (heterocyclo)alkyl.

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. In another embodiment, the optionally substituted phenyl is unsubstituted. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, 4-(pyridin-4-ylsulfonyl) phenyl The term optionally substituted aryl includes phenyl groups having a fused optionally substituted cycloalkyl or fused optionally substituted heterocyclo group. An optionally substituted phenyl having a fused optionally substituted cycloalkyl or fused optionally substituted heterocyclo group may be attached to the remainder of the molecule at any available carbon atom on the phenyl ring. Non-limiting examples include:

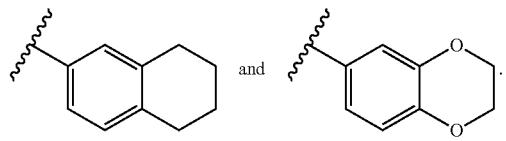 [SMILES: *c1ccc2c(c1)CCCC2 ; *c1ccc2c(c1)OCCO2]

In the present disclosure, the term "alkenyl" as used by itself or as part of another group refers to an alkyl containing one, two or three carbon-to-carbon double bonds. In one embodiment, the alkenyl has one carbon-to-carbon double bond. In another embodiment, the alkenyl is a C$_{2-6}$ alkenyl. In another embodiment, the alkenyl is a C$_{2-4}$ alkenyl. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group refers to an alkenyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, heteroaryl, and optionally substituted heterocyclo.

In the present disclosure, the term "alkynyl" as used by itself or as part of another group refers to an alkyl containing one to three carbon-to-carbon triple bonds. In one embodiment, the alkynyl has one carbon-to-carbon triple bond. In another embodiment, the alkynyl is a C$_{2-6}$ alkynyl. In another embodiment, the alkynyl is a C$_{2-4}$ alkynyl. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part refers to an alkynyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, cycloalkyl, alkenyl, alkynyl, optionally substituted aryl, optionally substituted heteroaryl, and heterocyclo.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a C$_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl substituted with one, two, or three hydroxy groups. In one embodiment, the hydroxyalkyl is a monohydroxyalkyl, i.e., a hydroxyalkyl substituted with one hydroxy group. In another embodiment, the hydroxyalkyl is a dihydroxyalkyl, i.e., a hydroxyalkyl substituted with two hydroxy groups. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "(cycloalkyl)alkyl," as used by itself or as part of another group refers to an alkyl substituted with an optionally substituted cycloalkyl. In one embodiment, the (cycloalkyl) alkyl, is a "(C$_{3-6}$ cycloalkyl) C$_{1-4}$ alkyl," i.e., a C$_{1-4}$ alkyl substituted with an optionally substituted C$_{3-6}$ cycloalkyl. Non-limiting exemplary (cycloalkyl) alkyl groups include:

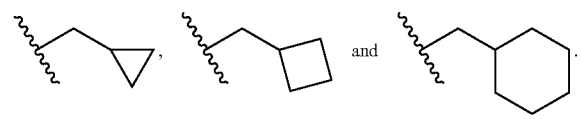

In the present disclosure, the term "alkylsulfonyl" as used by itself or as part of another group refers to a sulfonyl, i.e., —SO$_2$—, substituted with an optionally substituted alkyl. A non-limiting exemplary alkylsulfonyl group is —SO$_2$CH$_3$.

In the present disclosure, the term "haloalkylsulfonyl" as used by itself or as part of another group refers to a sulfonyl, i.e., —SO₂—, substituted with a haloalkyl. A non-limiting exemplary alkylsulfonyl group is —SO₂CF₃.

In the present disclosure, the term "cycloalkylsulfonyl" as used by itself or as part of another group refers to a sulfonyl, i.e., —SO₂—, substituted with an optionally substituted cycloalkyl. Non-limiting exemplary alkylsulfonyl group include —SO₂-cyclopropyl and —SO₂-cyclopenyl.

In the present disclosure, the term "(cycloalkyl)alkylsulfonyl" as used by itself or as part of another group refers to a sulfonyl, i.e., —SO₂—, substituted with a (cycloalkyl)alkyl. Non-limiting exemplary (cycloalkyl)alkylsulfonyl groups include:

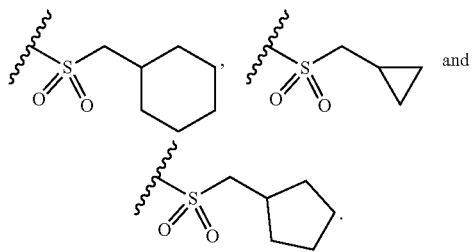

In the present disclosure, the term "arylsulfonyl" as used by itself or as part of another group refers to a sulfonyl, i.e., —SO₂—, substituted with an optionally substituted aryl. A non-limiting exemplary arylsulfonyl group is —SO₂Ph.

In the present disclosure, the term "heteroarylsulfonyl" as used by itself or as part of another group refers to a sulfonyl, i.e., —SO₂—, substituted with an optionally substituted heteroaryl group. Non-limiting exemplary heteroarylsulfonyl groups include:

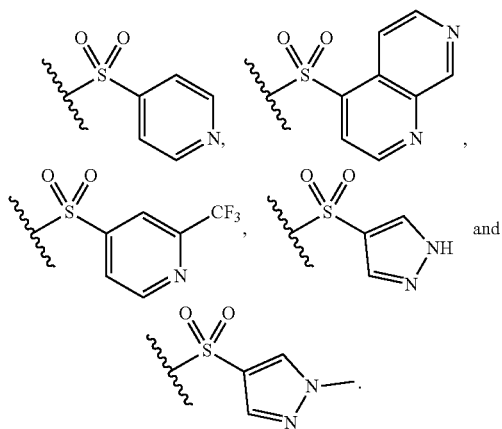

In the present disclosure, the term "heterocyclosulfonyl" as used by itself or as part of another group refers to a sulfonyl, i.e., —SO₂—, substituted with an optionally substituted heterocyclo group. A non-limiting exemplary heterocyclosulfonyl group is:

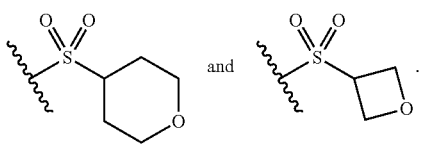 [SMILES: *S(=O)(=O)C1CCOCC1 ; *S(=O)(=O)C1COC1]

In the present disclosure, the term "sulfonamido" as used by itself or as part of another group refers to a radical of the formula —SO₂NR²¹ᵃR²¹ᵇ, wherein R²¹ᵃ and R²¹ᵇ are each independently selected from the group consisting of hydrogen, optionally substituted alkyl, and optionally substituted aryl, or R²¹ᵃ and R²¹ᵇ taken together with the nitrogen to which they are attached from a 3- to 8-membered heterocyclo group. Non-limiting exemplary sulfonamido groups include —SO₂NH₂, —SO₂N(H)CH₃, —SO₂N(CH₃)₂, and —SO₂N(H)Ph.

In the present disclosure, the term "alkoxy" as used by itself or as part of another group refers to an optionally substituted alkyl, optionally substituted cycloalkyl, optionally substituted alkenyl, or optionally substituted alkynyl attached to a terminal oxygen atom. In one embodiment, the alkoxy is an optionally substituted alkyl attached to a terminal oxygen atom. In one embodiment, the alkoxy group is a $C_{1-6}$ alkyl attached to a terminal oxygen atom. In another embodiment, the alkoxy group is a $C_{1-4}$ alkyl attached to a terminal oxygen atom. Non-limiting exemplary alkoxy groups include methoxy, ethoxy, tert-butoxy, and —OCH₂SO₂CH₃.

In the present disclosure, the term "alkylthio" as used by itself or as part of another group refers to an optionally substituted alkyl attached to a terminal sulfur atom. In one embodiment, the alkylthio group is a $C_{1-4}$ alkylthio group. Non-limiting exemplary alkylthio groups include —SCH₃ and —SCH₂CH₃.

In the present disclosure, the term "alkoxyalkyl" as used by itself or as part of another group refers to an optionally alkyl substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl attached to a terminal oxygen atom. Non-limiting exemplary aralkyloxy groups include PhCH₂O— and PhCH₂CH₂O—.

In the present disclosure, the term "heteroaryl" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is selected from the group consisting of thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl. In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group refers to a heteroaryl that is either unsubstituted or substituted with one two, three, or four substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, haloalkylsulfonyl cycloalkylsulfonyl, (cycloalkyl)alkylsulfonyl, arylsulfonyl, heteroarylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, and (heterocyclo)alkyl. In one embodiment, the optionally substituted heteroaryl has one substituent. In another embodiment, the optionally substituted heteroaryl is unsubstituted. Any available carbon or nitrogen atom can be substituted. The term optionally substituted heteroaryl includes heteroaryl groups having a fused optionally substituted cycloalkyl or fused optionally substituted heterocyclo group. An optionally substituted heteroaryl having a fused optionally substituted cycloalkyl or fused optionally substituted heterocyclo group may be attached to the remainder of the molecule at any available carbon atom on the heteroaryl ring.

In the present disclosure, the term "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" includes groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" also includes groups having fused optionally substituted aryl groups, e.g., indolinyl or chroman-4-yl. In one embodiment, the heterocyclo group is a C$_{4-6}$ heterocyclo, i.e., a 4-, 5- or 6-membered cyclic group, containing one ring and one or two oxygen and/or nitrogen atoms. In one embodiment, the heterocyclo group is a C$_{4-6}$ heterocyclo containing one ring and one nitrogen atom. The heterocyclo can be optionally linked to the rest of the molecule through any available carbon or nitrogen atom. Non-limiting exemplary heterocyclo groups include azetidinyl, dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group refers to a heterocyclo that is either unsubstituted or substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, cycloalkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, or (heterocyclo)alkyl. Substitution may occur on any available carbon or nitrogen atom, or both. Non-limiting exemplary substituted heterocyclo groups include:

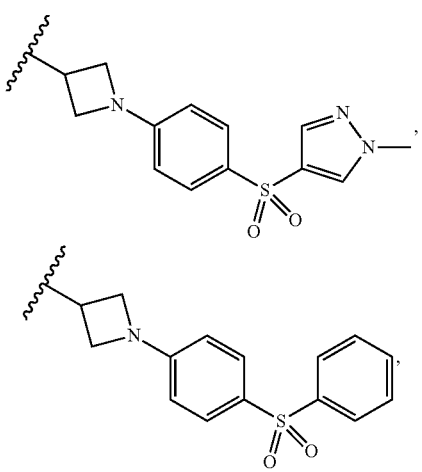

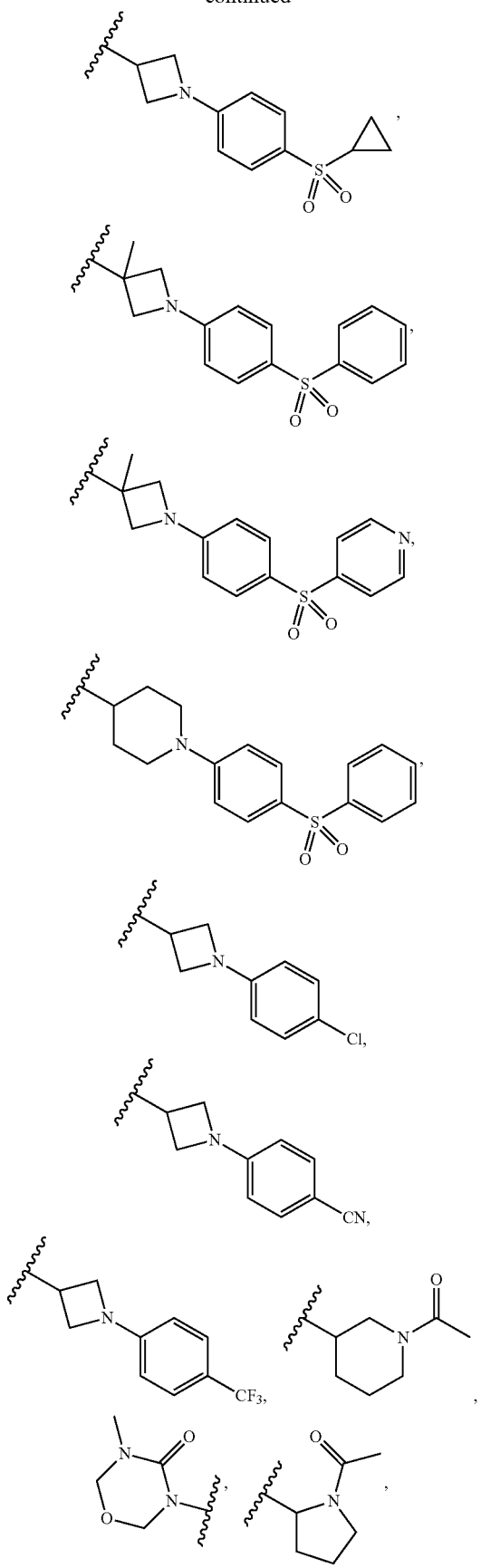

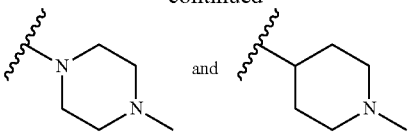

In the present disclosure, the term "amino" as used by itself or as part of another group refers to a radical of the formula —NR$^{22a}$R$^{22b}$, wherein R$^{22a}$ and R$^{22b}$ are each independently selected from the group consisting of hydrogen, alkyl, aralkyl, hydroxyalkyl, optionally substituted cycloalkyl, optionally substituted aryl, optionally substituted heterocyclo, and optionally substituted heteroaryl, or R$^{22a}$ and R$^{22b}$ are taken together to form a 3- to 8-membered optionally substituted heterocyclo. Non-limiting exemplary amino groups include —NH$_2$ and —N(H)(CH$_3$).

In the present disclosure, the term "(amino)alkyl" as used by itself or as part of another group refers to an alkyl substituted with an amino. Non-limiting exemplary (amino)alkyl groups include —CH$_2$CH$_2$NH$_2$, and —CH$_2$CH$_2$N(H)CH$_3$, —CH$_2$CH$_2$N(CH$_3$)$_2$, and —CH$_2$N(H)-cyclopropyl.

In the present disclosure, the term "carboxamido" as used by itself or as part of another group refers to a radical of formula —C(=O)NR$^{23a}$R$^{23b}$, wherein R$^{23a}$ and R$^{23b}$ are each independently selected from the group consisting of hydrogen, optionally substituted alkyl, hydroxyalkyl, optionally substituted cycloalkyl, optionally substituted aryl, optionally substituted heterocyclo, and optionally substituted heteroaryl, or R$^{23a}$ and R$^{23b}$ taken together with the nitrogen to which they are attached form a 3- to 8-membered optionally substituted heterocyclo group. In one embodiment, R$^{23a}$ and R$^{23b}$ are each independently hydrogen or optionally substituted alkyl. In one embodiment, R$^{23a}$ and R$^{23b}$ are taken together to taken together with the nitrogen to which they are attached form a 3- to 8-membered optionally substituted heterocyclo group. Non-limiting exemplary carboxamido groups include —CONH$_2$, —CON(H)CH$_3$, —CON(CH$_3$)$_2$, —CON(H)Ph,

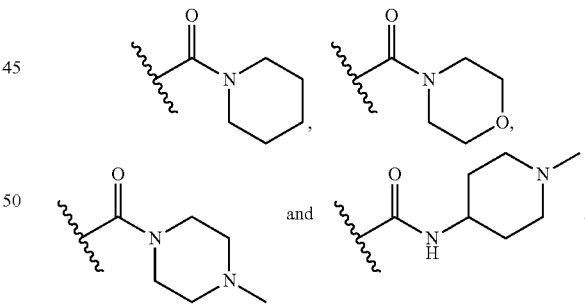

In the present disclosure, the term "alkylcarbonyl" as used by itself or as part of another group refers to a carbonyl group, i.e., —C(=O)—, substituted with an alkyl. Non-limiting exemplary alkylcarbonyl groups include —C(=O)CH$_3$ and —C(=O)CH$_2$CH$_2$CH$_2$CH$_3$.

In the present disclosure, the term "cycloalkylcarbonyl" as used by itself or as part of another group refers to a carbonyl group, i.e., —C(=O)—, substituted with a cycloalkyl. A non-limiting exemplary cycloalkylcarbonyl group is —C(=O)-cyclopropyl.

In the present disclosure, the term "arylcarbonyl" as used by itself or as part of another group refers to a carbonyl group, i.e., —C(=O)—, substituted with an optionally substituted aryl. A non-limiting exemplary arylcarbonyl group is —COPh.

In the present disclosure, the term "alkoxycarbonyl" as used by itself or as part of another group refers to a carbonyl group, i.e., —C(=O)—, substituted with an alkoxy. In one embodiment, the alkoxy is a $C_{1-4}$ alkoxy. Non-limiting exemplary alkoxycarbonyl groups include —C(=O)OMe, —C(=O)OEt, and —C(=O)OtBu.

In the present disclosure, the term "(alkoxycarbonyl)alkyl" as used by itself or as part of another group refers to an alkyl substituted by an alkoxycarbonyl group. Non-limiting exemplary (alkoxycarbonyl)alkyl groups include —CH$_2$C(=O)OMe, —CH$_2$C(=O)OEt, and —CH$_2$C(=O)OtBu.

In the present disclosure, the term "carboxy" as used by itself or as part of another group refers to a radical of the formula —CO$_2$H.

In the present disclosure, the term "carboxyalkyl" as used by itself or as part of another group refers to an alkyl substituted with a —CO$_2$H. A non-limiting exemplary carboxyalkyl group is —CH$_2$CO$_2$H.

In the present disclosure, the term "aralkyl" as used by itself or as part of another group refers to an alkyl substituted with one, two, or three optionally substituted aryl groups. In one embodiment, aralkyl is a $C_{1-4}$ alkyl substituted with one optionally substituted $C_5$ or $C_6$ aryl group. In another embodiment, the aralkyl is a $C_1$ alkyl substituted with one optionally substituted aryl group. In another embodiment, the aralkyl is a $C_2$ alkyl substituted with one optionally substituted aryl group. In another embodiment, the aralkyl is a $C_3$ alkyl substituted with one optionally substituted aryl group. In one embodiment, the aralkyl is a $C_1$ or $C_2$ alkyl substituted with one optionally substituted phenyl group. Non-limiting exemplary aralkyl groups include benzyl, phenethyl, —CHPh$_2$, —CH(CH$_3$)Ph, —CH$_2$(4-F-Ph), —CH$_2$(4-Me-Ph), —CH—$_2$(4-CF$_3$-Ph), and —CH(4-F-Ph)$_2$.

In the present disclosure, the term "(heterocyclo)alkyl" as used by itself or part of another group refers to an alkyl substituted with an optionally substituted heterocyclo group. In one embodiment, the (heterocyclo)alkyl is a $C_{1-4}$ alkyl substituted with one optionally substituted heterocyclo group. Non-limiting exemplary (heterocyclo)alkyl groups include:

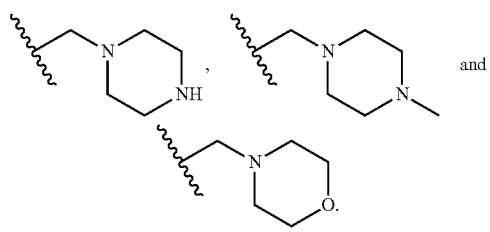

In the present disclosure, the term "(heteroaryl)alkyl" as used by itself or part of another group refers to an alkyl substituted with an optionally substituted heteroaryl group. In one embodiment, the (heteroaryl)alkyl is a $C_{1-4}$ alkyl substituted with one optionally substituted heteroaryl group. In another embodiment, the (heteroaryl)alkyl is a $C_1$ alkyl substituted with one optionally substituted heteroaryl group. Non-limiting exemplary (heteroaryl)alkyl groups include:

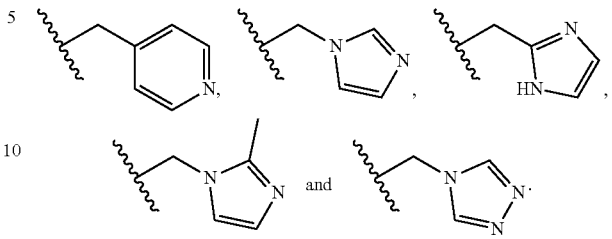

In the present disclosure, the term "(carboxamido)alkyl" as used by itself or as part of another group refers to an alkyl substituted with one or two carboxamido groups. In one embodiment, the (carboxamido)alkyl is a $C_{1-4}$ alkyl substituted with one carboxamido group, i.e., a (carboxamido)$C_{1-4}$ alkyl. In another embodiment, the (carboxamido)alkyl is a $C_{1-4}$ alkyl substituted with two carboxamido groups. Non-limiting exemplary (carboxamido)alkyl groups include —CH$_2$CONH$_2$, —C(H)CH$_3$—CONH$_2$, and —CH$_2$CON(H)CH$_3$.

In the present disclosure, the term "(aryloxy)alkyl" as used by itself or as part of another group refers to an alkyl substituted with an aryloxy group. In one embodiment, the "(aryloxy)alkyl" is a $C_{1-4}$ alkyl substituted with an aryloxy. In one embodiment, the "(aryloxy)alkyl" is a $C_{2-4}$ alkyl substituted with an aryloxy. Non-limiting exemplary (aryloxy)alkyl groups include —CH$_2$CH$_2$OPh and —CH$_2$CH$_2$CH$_2$OPh.

In the present disclosure, the term "alkylcarbonyloxy" as used by itself or as part of another group refers to an oxy, e.g., —O—, substituted with an alkylcarbonyl group. Non-limiting exemplary "alkylcarbonyloxy" groups include —OC(=O)CH$_2$CH$_3$, —OC(=O)CH$_3$, i.e., acetoxy, —OC(=O)CH$_2$CH$_2$CH$_3$, and —OC(=O)CH(CH$_3$)$_2$.

In the present disclosure, the term "cycloalkylcarbonyloxy" as used by itself or as part of another group refers to an oxy, e.g., —O—, substituted with an cycloalkylcarbonyl group. Non-limiting exemplary "cycloalkylcarbonyloxy" groups include —OC(=O)-cyclopropyl and —OC(=O)-cyclopenyl.

The term "menin inhibitor" or "inhibitor of menin" as used herein refers to a compound that disrupts, e.g., inhibits, the menin-MLL fusion protein interaction.

The term "a disease or condition wherein inhibition of menin provides a benefit" pertains to a disease or condition in which menin and/or the interaction of menin with a menin-interacting protein is important or necessary, e.g., for the onset, progress, or expression of that disease or condition, or a disease or a condition which is known to be treated by a menin inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by menin for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are menin inhibitors and can be used in treating diseases and conditions wherein menin inhibition provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce menin interactions in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of this disclosure (especially in the context of the claims) are to be construed to cover both the singular and the plural, unless otherwise indicated. Recitation of ranges of values herein are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

EXAMPLES

Example 1

Synthesis of 4-(1-(azetidin-3-ylmethyl)piperidin-4-yl)-4-cyclopentyl-2-ethyl-1,2,3,4-tetrahydroisoquinoline (S9)

Scheme 1

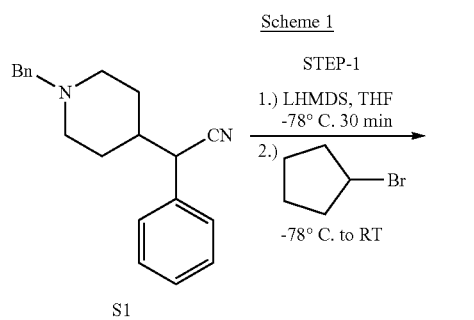

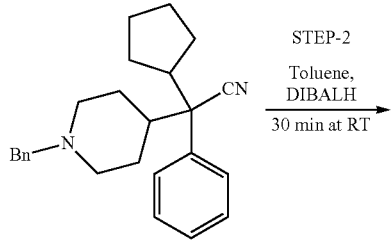

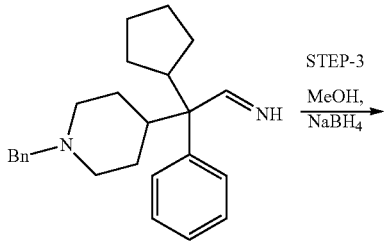

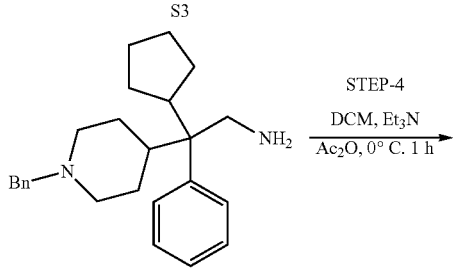

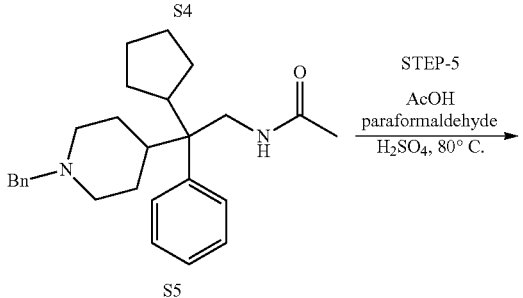

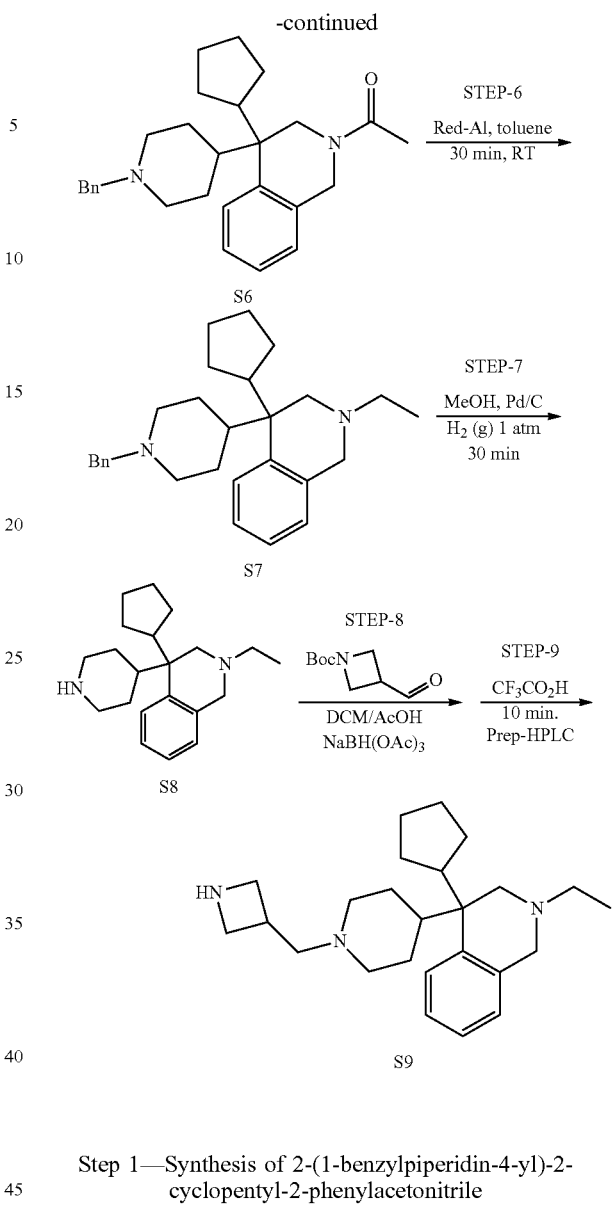

Step 1—Synthesis of 2-(1-benzylpiperidin-4-yl)-2-cyclopentyl-2-phenylacetonitrile LHMDS (1M in THF, 20.66 mL, 20.66 mmol) was added dropwise to a −78° C. stirred solution of 51 (3 g, 10.33 mmol) dissolved in dry THF (100 mL). After 30 minutes at −78° C., cyclopentylbromide (3.32 mL, 30.99 mmol) was added dropwise and the reaction was allowed to slowly warm to room temperature. After stirring overnight at RT, the reaction was quenched with saturated NH$_4$Cl, extracted with EtOAc, concentrated and purified by column chromatography on silica gel to produce 3.64 g of compound S2 as an oil.

Step 2—Synthesis of 2-(1-benzylpiperidin-4-yl)-2-cyclopentyl-2-phenylethan-1-imine DIBALH (0.5 M in toluene, 4.01 mL, 7.06 mmol) was added dropwise to a solution of S2 (506 mg, 1.41 mmol) from STEP 1 in toluene (20 mL) and stirred at RT. After one hour, the reaction was quenched by dropwise addition of 2M NaOH, and the aqueous layer was extracted with EtOAc and concentrated.

Step 3—Synthesis of 2-(1-benzylpiperidin-4-yl)-2-cyclopentyl-2-phenylethan-1-amine The crude product from STEP 2 was dissolved in MeOH and NaBH$_4$ (107 mg, 2.82 mmol) was slowly added and the reaction was stirred. After stirring overnight, the reaction was quenched with water, extracted with EtOAc, dried over Na$_2$SO$_4$, filtered through celite, and concentrated to produce S4 that was used in the next step without further purification.

Step 4—Synthesis of N-(2-(1-benzylpiperidin-4-yl)-2-cyclopentyl-2-phenylethyl)acetamide Acetic anhydride (108 mg, 1.06 mmol) was added to a solution, at 0° C., of crude S4 (0.705 mmol) and Et$_3$N (0.2 mL, 1.41 mmol) in DCM (3 mL) and stirred. After 30 minutes at 0° C., the reaction was put at RT and stirred. After 30 min at RT, the reaction was quenched with water and brine, extracted with EtOAc, dried over Na$_2$SO$_4$, filtered and concentrated to give 272 mg of crude S5 that was used without further purification.

Step 5—Synthesis of 1-(4-(1-benzylpiperidin-4-yl)-4-cyclopentyl-3,4-dihydroisoquinolin-2(1H)-yl)ethan-1-one Crude S5 was dissolved in AcOH (6 mL), paraformaldehyde (100 mg) and concentrated H$_2$SO$_4$ (0.3 mL) were added and the reaction was heated to 80° C. After stirring overnight, the reaction was cooled to RT, slowly quenched with saturated NaHCO$_3$, extracted with EtOAc, dried over Na$_2$SO$_4$, filtered and concentrated to give crude S6 that was used without further purification.

Step 6—Synthesis of 4-(1-benzylpiperidin-4-yl)-4-cyclopentyl-2-ethyl-1,2,3,4-tetrahydroisoquinoline Red-Al (3.2 M in toluene, 0.7 mL) was added dropwise to a solution, at RT, of crude S6 in toluene (5 mL) and stirred. After 30 minutes, the reaction was quenched by dropwise addition of 2M NaOH and the aqueous was extracted with EtOAc and concentrated. The crude S7 was purified by reverse phase prep HPLC and the pure compound was lyophilized to produce S7-TFA salt as a white powder.

Step 7—Synthesis of 4-cyclopentyl-2-ethyl-4-(piperidin-4-yl)-1,2,3,4-tetrahydroisoquinoline S7 (280 mg) was dissolved in MeOH (5 mL) and the solution was vacuumed briefly then put under N$_2$ atmosphere—this was repeated 3 times. Pd/C (10% wt/wt, 200 mg) was quickly added to the solution that was vacuumed and put under N$_2$ atmosphere. The solution was briefly vacuumed to remove the N$_2$ atmosphere then put under H$_2$ atmosphere—this was repeated 3 times. After 30 minutes, the reaction was filtered through celite and concentrated to give crude S8 (200 mg) that was used without further purification.

Step 8—Synthesis of tert-butyl 3-((4-(4-cyclopentyl-2-ethyl-1,2,3,4-tetrahydroisoquinolin-4-yl)piperidin-1-yl)methyl)azetidine-1-carboxylate 1-Boc-azetidine-3-carboxaldehyde (475 mg, 2.56 mmol) was added to a solution of crude S8 (200 mg, 0.641 mmol) in DCM/AcOH (1:1, 6 mL) and stirred. After 10 minutes, NaBH(OAc)$_3$ (1.08 g, 5.12 mmol) was slowly added to the reaction. After overnight, the reaction was slowly quenched with saturated NaHCO$_3$, extracted with EtOAc, dried over Na$_2$SO$_4$, filtered, and concentrated to produce crude Boc-protected-S9.

Step 9—Synthesis of 4-(1-(azetidin-3-ylmethyl)piperidin-4-yl)-4-cyclopentyl-2-ethyl-1,2,3,4-tetrahydroisoquinoline The crude product from STEP 8 was dissolved in trifluoroacetic acid and stirred. After 10 minutes, the TFA was removed in vacuo, the crude purified by reverse phase prep HPLC, and the pure product was lyophilized to give S9-TFA salt (169 mg) as white solid.

Example 2

Synthesis of 4-cyclopentyl-2-ethyl-4-(1-((1-(4-(pyridin-4-ylsulfonyl)phenyl)azetidin-3-yl)methyl)piperidin-4-yl)-1,2,3,4-tetrahydroisoquinoline (Cpd. No. 148)

Step 1—Synthesis of S11

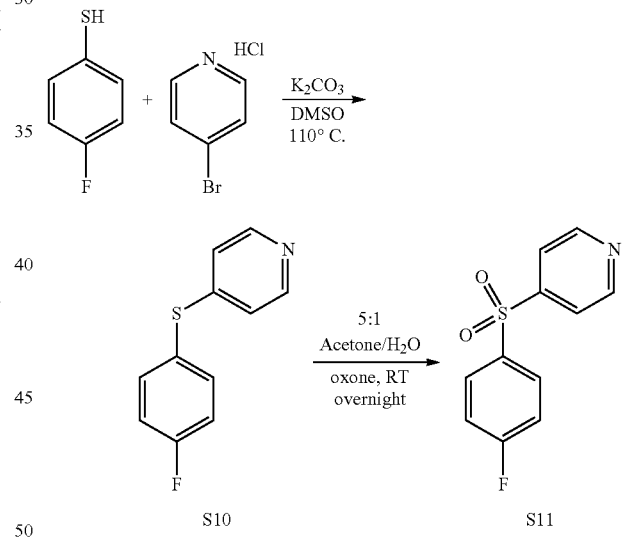

4-Bromopyridine.HCl (4.02 g, 20.68 mmol) was added to a solution of 4-fluorobenzenethiol (2.41 g, 18.80 mmol) and K$_2$CO$_3$ (7.78 g, 56.4 mmol) in DMSO (20 mL) and the reaction was heated to 110° C. After overnight, the reaction was cooled, quenched with saturated NH$_4$Cl and extracted with EtOAc. The combined organic layers were washed twice with saturated NaHCO$_3$, once with brine, dried over Na$_2$SO$_4$, filtered, and concentrated to produce crude S10 (4.01 g, quantitative yield) that was used without further purification. Oxone monopersulfate (15.03 g, 48.90 mmol) was added to a solution of crude S10 in Acetone/H$_2$O (5:1, 84 mL). After overnight, the reaction was quenched with saturated NaHCO$_3$, extracted with EtOAc, and purified by column chromatography to give S11 (quantitative yield) as a white solid.

289

Step 2—Synthesis of Cpd. No. 148

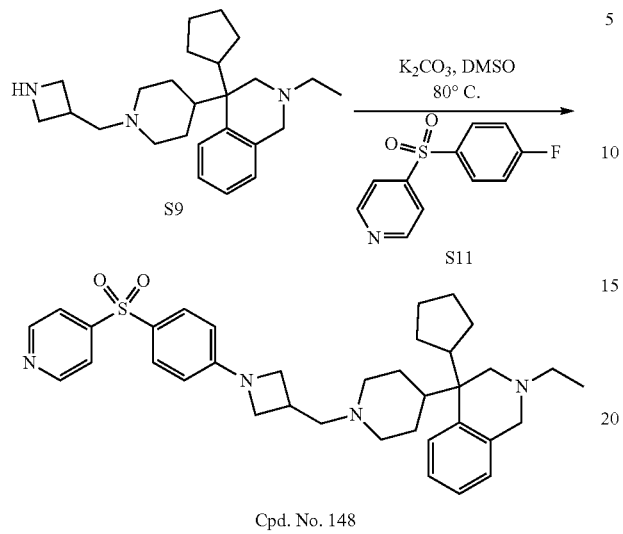

S11 (74 mg, 0.314 mmol) was added to a solution of Compound S9 (60 mg, 0.157 mmol) and $K_2CO_3$ (87 mg, 0.628 mmol) in DMSO (2 mL) then stirred and heated to 80° C. After overnight, the reaction was quenched with TFA (0.5 mL), diluted with 3:1 MeOH/$H_2O$ and purified by prep HPLC. The pure fractions were combined, concentrated, diluted with water, frozen and lyophilized to give Cpd. No. 148 as a yellow powder. $^1$H-NMR (400 MHz, $CD_3OD$) δ ppm 8.75 (d, 2H, J=5.8 Hz), 7.82 (dd, 2H, J=1.5 Hz, J=4.6 Hz), 7.76 (d, 2H, J=8.8 Hz), 7.57 (d, 1H, J=7.7 Hz), 7.47 (t, 1H, J=7.9 Hz), 7.40-7.29 (m, 2H), 6.50 (d, 2H, J=8.9 Hz), 4.53-4.08 (m, 4H), 3.85-3.68 (m, 3H), 3.58-3.38 (m, 7H), 3.10-2.89 (m, 2H), 2.87-2.67 (m, 1H), 2.57-2.26 (m, 1H), 2.16 (d, 1H, J=12.7 Hz), 1.93-1.80 (m, 2H), 1.80-1.53 (m, 6H), 1.48 (t, 3H, J=7.3 Hz), 1.36-1.19 (m, 2H), 1.17-0.99 (m, 1H), 0.96-0.71 (m, 1H); ESI-MS m/z 599.67 (M+H)$^+$.

Example 3

Synthesis of 4-(3-((4-(1-cyclopentyl-1,2,3,4-tetrahydroisoquinolin-1-yl)piperidin-1-yl)methyl)azetidin-1-yl)benzonitrile (Cpd. No. 129)

Step 1—Synthesis of S12

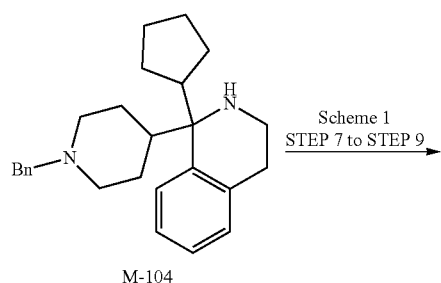

290

-continued

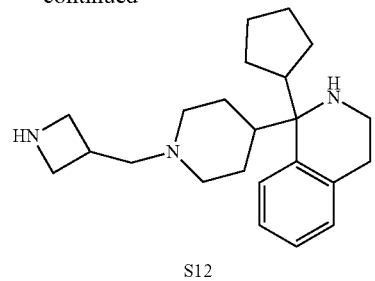

S12 was obtained using STEP7 to STEP 9 described for the synthesis of S9 in Scheme 1.

Step 2—Synthesis of Cpd. No. 129

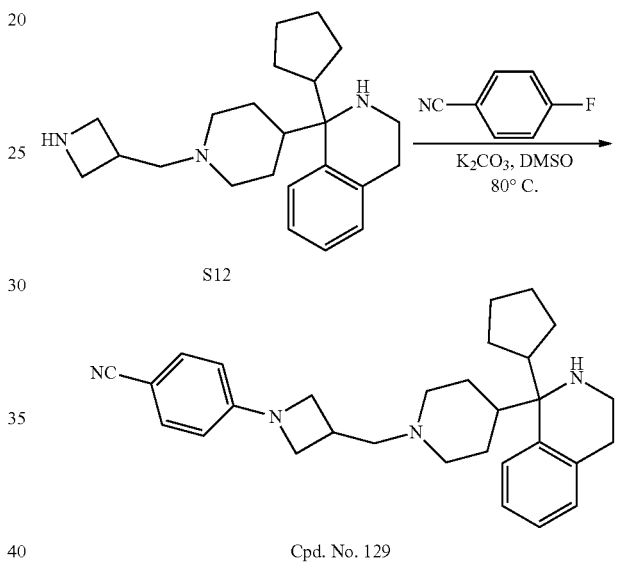

Starting with compound S12 and 4-fluorobenzonitrile, Cpd. No. 129 was synthesized using a similar procedure described for the synthesis of Cpd. No. 148. ESI-MS m/z 455.83 (M+H)$^+$

Example 4

Synthesis of methyl (rac-(1S,2R)-2-(cyano(phenyl) (1-((1-(4-(pyridin-4-ylsulfonyl)phenyl) azetidin-3-yl)methyl)piperidin-4-yl)methyl)cyclopentyl)carbamate (Cpd. No. 345) and methyl (rac-(1R,2S)-2-(cyano(phenyl)(1-((1-(4-(pyridin-4-ylsulfonyl) phenyl)azetidin-3-yl)methyl)piperidin-4-yl)methyl) cyclopentyl)carbamate (Cpd. No. 346)

Step 1—Synthesis of S14

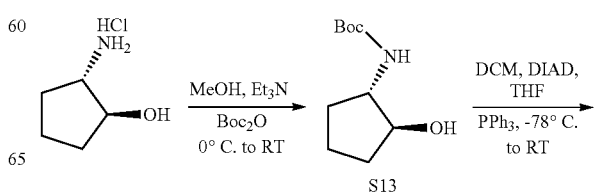

-continued

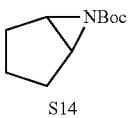

S14

Boc$_2$O (3.49 g, 15.98 mmol) was added to a solution, at 0° C., of (1S,2S)-2-aminocyclopentan-1-ol-HCl (2.0 g, 14.53 mmol) and Et$_3$N (4.05 mL, 29.06 mmol) in methanol (20 mL) and stirred. The reaction was allowed to warm to room temperature and after overnight the reaction was concentrated and the crude was purified by column chromatography to give S13 (2.87 g) as a white solid.

At −78° C., DIAD (4.17 mL, 21.25 mmol) was added to a solution of PPh$_3$ (5.57 g, 21.25 mmol) in THF (40 mL). After 1 hour at −78° C., a solution of compound S13 (2.87 g, 14.16 mmol) in THF (40 mL) was added to the reaction. After overnight at RT, the reaction was concentrated and then diluted with Et$_2$O. The white precipitate was filtered off and the oil was purified by column chromatography to produce compound S14 (2.21 g) as an oil.

Step 2—Synthesis of S17

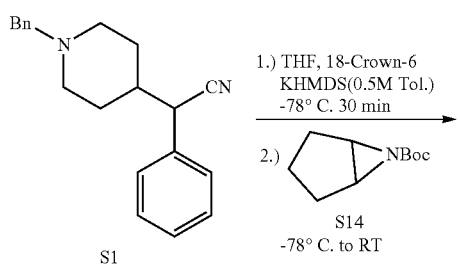

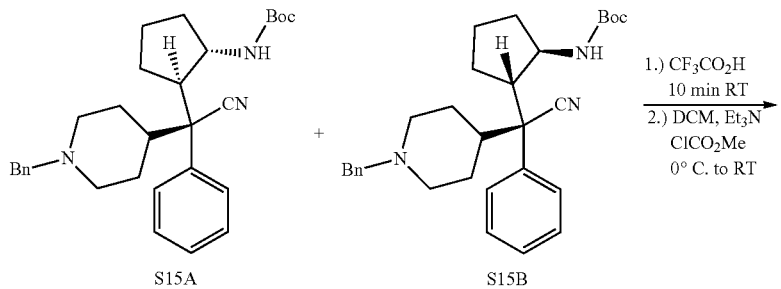

1:1 ratio of diatereomers were produced with the following relative stereochemistry

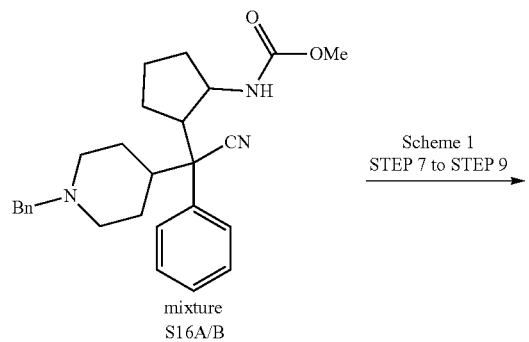

mixture
S16A/B

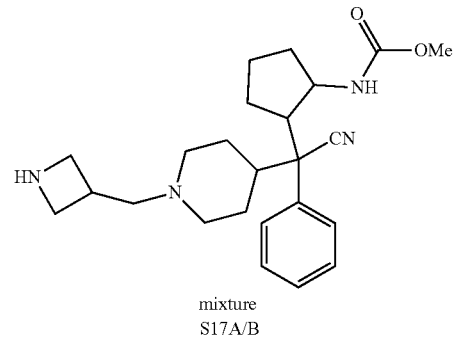

mixture
S17A/B

S1 (1.0 g, 3.45 mmol), 18-Crown-6 (2.73 g, 10.34 mmol) were added to a dry 100 mL RB-flask and the system was vacuumed. After 30 minutes under vacuum, $N_2$ atmosphere was slowly introduced, dry THF (30 mL) was added, and the system was vacuumed briefly then put under $N_2$ atmosphere—this purging was repeated three times. The reaction was cooled to −78° C., KHMDS (0.5M in toluene, 20.69 mL, 10.34 mmol) was added dropwise and the reaction stirred. After 30 minutes, at −78° C., compound S14 (2.52 g, 13.79 mmol) was added dropwise then the reaction system was vacuumed and put under $N_2$ atmosphere three times and allowed to slowly warm to RT. After overnight at RT, the reaction was quenched with saturated $NH_4Cl$, extracted with EtOAc, and purified by column chromatography to give a 1:1 diastereomer mixture of S15A and S15B (1.1 g) as a white solid.

The mixture of S15A and S15B (1.0 g, 2.11 mmol) was stirred in TFA (5 mL). After 30 minutes, the TFA was removed in vacuo. The crude product was dissolved in DCM (10 mL), $Et_3N$ (1.15 mL, 8.46 mmol) was added and the reaction was stirred and cooled to 0° C. Methyl chloroformate (0.327 mL, 4.23 mmol) was added dropwise to the reaction and stirred at 0° C. for 30 minutes then at RT for 30 minutes. The reaction was quenched with MeOH, concentrated, and purified by column chromatography to produce compound a mixture of S16A and S16B (0.910 g) that was dissolved in acetonitrile and lyophilized to give a solid.

A mixture S17A and S17B was obtained following STEP 7 to STEP 9 described in Scheme 1 for the synthesis of S9.

Step 3—Synthesis of Cpd. Nos. 345 and 346

Starting with a mixture of S17A and S17B and using a similar procedure described for the synthesis of Cpd. No. 148, a mixture of Cpd. No. 345 and Cpd. No. 346 was obtained and separated by prep HPLC.

Cpd. No. 345: $^1$H-NMR (400 MHz, $CD_3OD$) δ ppm 8.76 (s, 2H), 7.82 (d, 2H, J=5.2 Hz), 7.75 (d, 2H, J=8.8 Hz), 7.52 (d, 2H, J=7.0 Hz), 7.46-7.33 (m, 3H), 6.50 (d, 2H, J=8.8 Hz), 4.16 (dt, 2H, J=1.8 Hz, J=7.7 Hz), 3.96-3.85 (m, 1H), 3.73 (dd, 2H, J=5.9 Hz, J=7.8 Hz), 3.60-3.38 (m, 8H), 3.24-3.12 (m, 1H), 3.09-2.94 (m, 2H), 2.91-2.79 (m, 1H), 2.49 (t, 1H, J=12.2 Hz), 2.27 (d, 1H, J=14.4 Hz), 2.18-2.05 (m, 1H), 1.94 (d, 1H, J=14.4 Hz), 1.82-1.39 (m, 7H); ESI-MS m/z 628.50 $(M+H)^+$.

Cpd. No. 346: $^1$H-NMR (400 MHz, $CD_3OD$) δ ppm 8.75 (d, 2H, J=4.7 Hz), 7.81 (d, 2H, J=4.7 Hz), 7.75 (d, 2H, J=7.7 Hz), 7.53-7.35 (m, 5H), 6.49 (d, 2H, J=7.8 Hz), 4.21-4.05 (m, 3H), 3.79-3.65 (m, 5H), 3.55 (t, 2H, J=13.3 Hz), 3.41 (d, 2H, J=6.9 Hz), 3.23-3.02 (m, 2H), 2.99-2.76 (m, 2H), 2.59 (t, 1H, J=11.7 Hz), 2.28 (d, 1H, J=14.1 Hz), 2.07-1.88 (m, 2H), 1.87-1.74 (m, 1H), 1.71-1.53 (m, 3H), 1.53-1.35 (m, 2H), 1.34-1.18 (m, 1H); ESI-MS m/z 628.50 $(M+H)^+$.

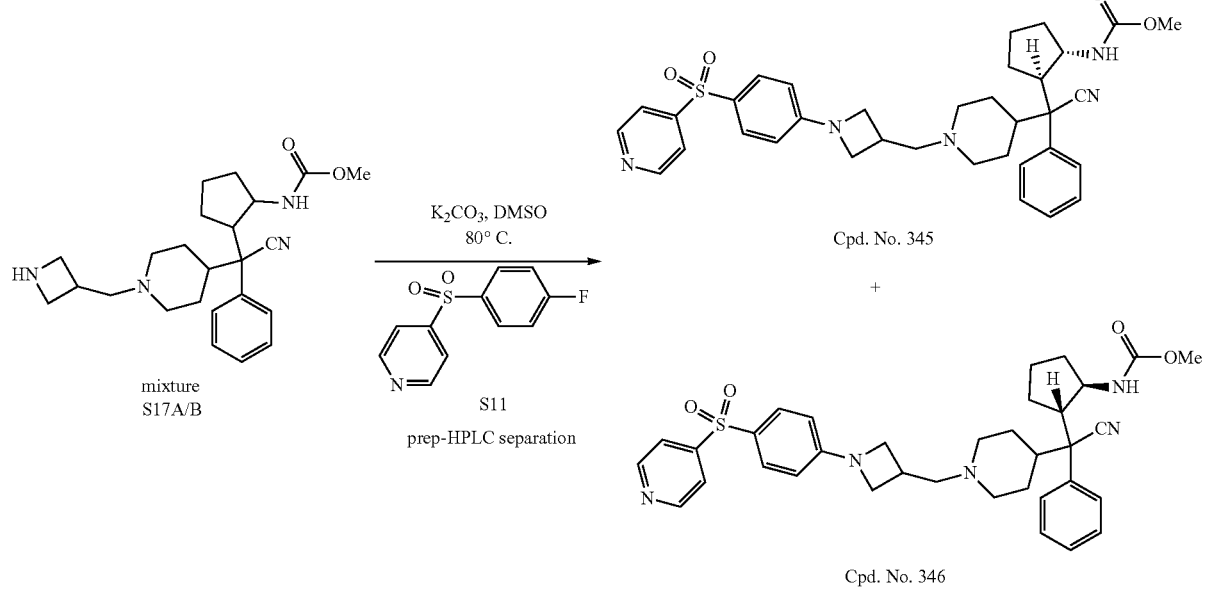

Example 5

Synthesis of methyl (rac-(1S,2R)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl)carbamate (Cpd. No. 349) and methyl (rac-(1R,2S)-2-(cyano(1-((1-(4-((1-methyl-1H-pyrazol-4-yl)sulfonyl)phenyl)azetidin-3-yl)methyl)piperidin-4-yl)(phenyl)methyl)cyclopentyl)carbamate (Cpd. No. 350)

Cpd. No. 349

Cpd. No. 350

Cpd. Nos. 349 and 350 were obtained using the synthetic strategy described for Cpd Nos. 345 and 346.

Cpd. No. 349: $^1$H-NMR (400 MHz, CD$_3$OD) δ ppm 8.09 (s, 1H), 7.74-7.68 (m, 3H), 7.52 (d, 2H, J=7.1 Hz), 7.47-7.34 (m, 3H), 6.48 (d, 2H, J=7.6 Hz), 4.14 (t, 2H, J=7.7 Hz), 3.88 (s, 3H), 3.74-3.66 (m, 2H), 3.64-3.39 (m, 8H), 3.24-3.11 (m, 1H), 3.10-2.95 (m, 2H), 2.90-2.80 (m, 1H), 2.50 (t, 1H, J=11.6 Hz), 2.28 (d, 1H, J=14.2 Hz), 2.18-2.08 (m, 1H), 1.94 (d, 1H, J=13.9 Hz), 1.83-1.39 (m, 8H); ESI-MS m/z 631.42 (M+H)$^+$.

Cpd. No. 350: Was obtained using the synthetic strategy described for Cpd. Nos. 345 and 346. $^1$H NMR (400 MHz, CD$_3$OD) δ ppm 8.09 (s, 1H), 7.74-7.68 (m, 3H), 7.50-7.34 (m, 5H), 6.47 (d, 2H, J=8.8 Hz), 4.16-4.06 (m, 3H), 3.88 (s, 3H), 3.78-3.63 (m, 5H), 3.63-3.49 (m, 2H), 3.41 (d, 2H, J=7.1 Hz), 3.24-3.03 (m, 2H), 2.97-2.75 (m, 2H), 2.64-2.51 (m, 1H), 2.33-2.17 (m, 1H), 2.08-1.87 (m, 2H), 1.87-1.73 (m, 1H), 1.73-1.52 (m, 3H), 1.52-1.36 (m, 2H), 1.36-1.16 (m, 1H); ESI-MS m/z 631.83 (M+H)$^+$.

Example 6

Synthesis of methyl ((1S,2R)-2-((S)-cyano(phenyl)(1-((1-(4-((trifluoromethyl)sulfonyl)phenyl)azetidin-3-yl)methyl)piperidin-4-yl)methyl)cyclopentyl)carbamate (Cpd. No. 403)

Step 1—Synthesis of Chiral S19

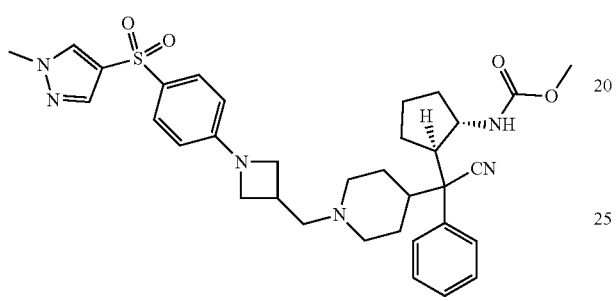

S19 was synthesized using the method described in J. Org. Chem. 2010, 75, 937-940.

Step 2—Chiral Synthesis of S22

297
-continued

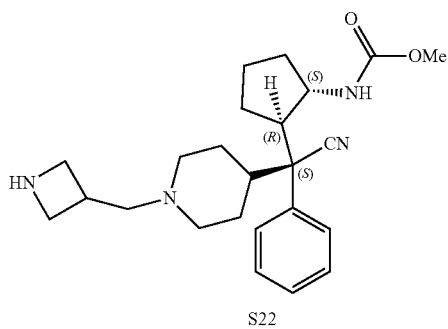

S22

S1 (50 mg, 0.172 mmol) and 18-Crown-6 (137 mg, 0.517 mmol) were added to a dry 50 mL RB flask and the system was vacuumed. After 30 minutes under vacuum, N₂ atmosphere was slowly introduced, dry THF (1.5 mL) was added, and the system was vacuumed briefly then put under N₂ atmosphere—this purging was repeated three times. The reaction was cooled to −78° C., KHMDS (0.5M in toluene, 1.03 mL, 0.517 mmol) was added dropwise and the reaction stirred. After 30 minutes, at −78° C., compound S19 (227 g, 0.82 mmol) was added dropwise then the reaction system was vacuumed and put under N₂ atmosphere three times and allowed to slowly warm to RT. After overnight at RT, the reaction was quenched with saturated NH₄Cl, extracted with EtOAc, and concentrated to give a 5:1 mixture of S20:S21. The 5:1 mixture was separated by prep HPLC. Pure S22 (10 mg) was obtained from pure S20 using the same synthetic strategy described for the synthesis of S17 from S15.

Step 3—Synthesis of Cpd. No. 403

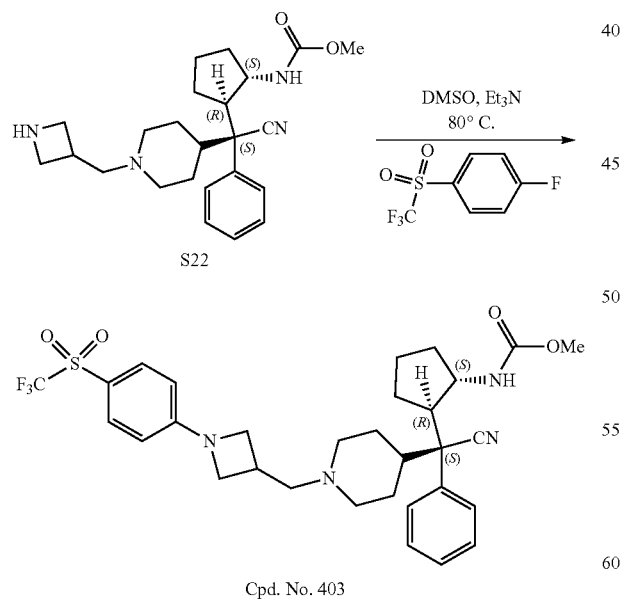

Cpd. No. 403

Starting with S22 and using Et₃N as the base, Cpd. No. 403 (as a single isomer) was obtained using a similar procedure described for the synthesis of Cpd. No. 148. ESI-MS m/z 619.50 (M+H)⁺.

298

Example 7

Synthesis of rac-(1S,2R)-2-(cyano(phenyl)(1-((1-(4-(pyridin-4-ylsulfonyl)phenyl)azetidin-3-yl)methyl)piperidin-4-yl)methyl)cyclopentyl methylcarbamate (Cpd. No. 215)

Scheme 2

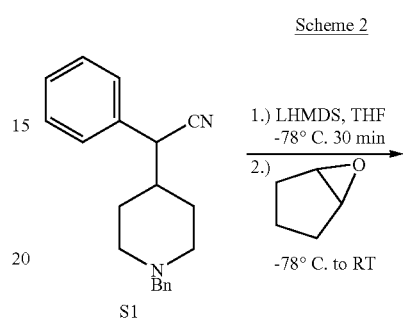

S1

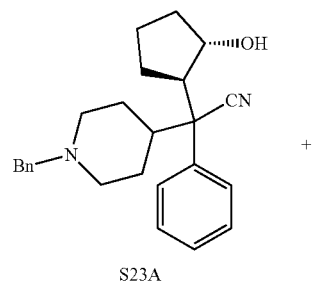

S23A
+

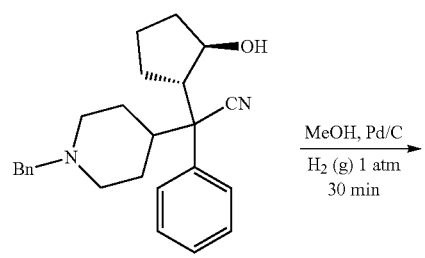

S23B

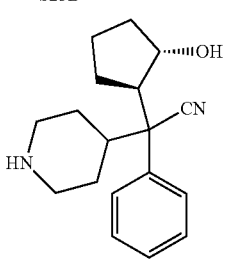

S24A
+

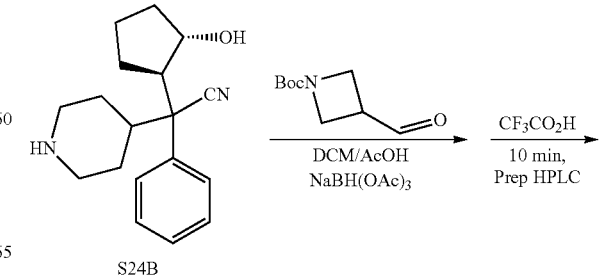

S24B

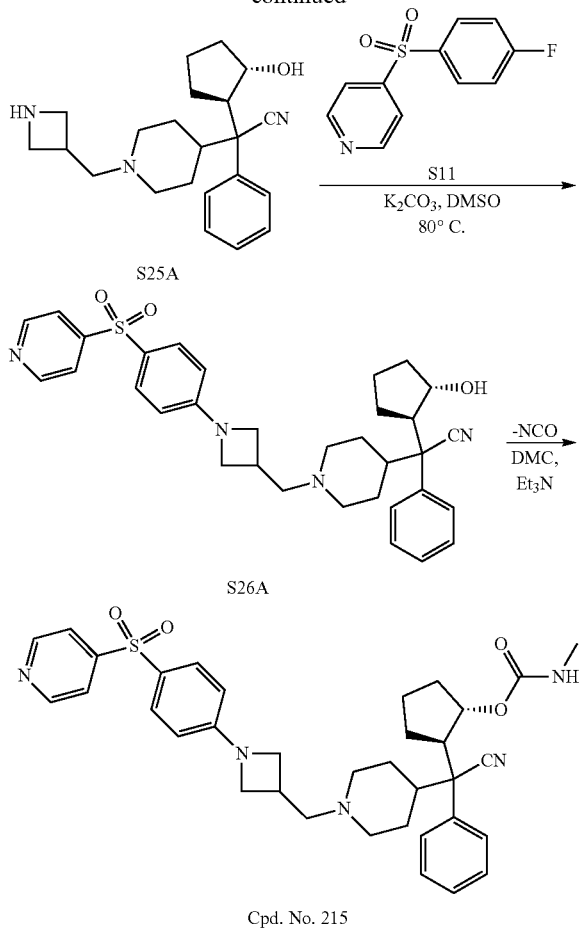

Step 1—Synthesis of a mixture of rac-2-(1-benzylpiperidin-4-yl)-2-((1R,2S)-2-hydroxycyclopentyl)-2-phenylacetonitrile (S23A) and rac-2-(1-benzylpiperidin-4-yl)-2-((1S,2R)-2-hydroxycyclopentyl)-2-phenylacetonitrile (S23B)

LHMDS (1M in THF, 20 mmol) was added dropwise to a solution of S1 (10 mmol) dissolved in dry THF (100 mL) at −78° C. and stirred. After 30 minutes, cyclopentene oxide (20 mmol) was added dropwise at −78° C. and the reaction was allowed to slowly warm to room temperature. After overnight at RT, the reaction was quenched with saturated NH₄Cl, extracted with EtOAc, concentrated and purified by column chromatography to produce 3.58 g (96% yield) of a mixture of S23A and S23B.

Step 2—Synthesis of a mixture of rac-2-((1R,2S)-2-hydroxycyclopentyl)-2-phenyl-2-(piperidin-4-yl)acetonitrile (S24A) and rac-2-((1S,2R)-2-hydroxycyclopentyl)-2-phenyl-2-(piperidin-4-yl)acetonitrile (S24B)

The S23A/B mixture (2.7 mmol) from STEP 1 was dissolved in MeOH (5 mL) and the solution was vacuumed briefly then put under $N_2$ atmosphere—this was repeated 3 times. Pd/C (10% wt/wt, 500 mg) was quickly added to the solution that was vacuumed and put under $N_2$ atmosphere. The solution was briefly vacuumed to remove the $N_2$ atmosphere then put under $H_2$ atmosphere—this was repeated 3 times. After 4 h, the reaction was filtered through celite and concentrated to give 750 mg a mixture of S24A and S24B (98% yield) that was used without further purification.

Step 3—Synthesis of rac-2-(1-(azetidin-3-ylmethyl)piperidin-4-yl)-2-((1R,2S)-2-hydroxycyclopentyl)-2-phenylacetonitrile (S25)

1-Boc-azetidine-3-carboxaldehyde (3.5 mmol) was added to a solution of a mixture of S24A and S24B (2.65 mmol) from STEP 2 in DCM/AcOH (1:1, 15 mL) and stirred. After 10 minutes, NaBH(OAc)₃ (8.0 mmol) was slowly added to the reaction. After stirring overnight, the reaction was slowly quenched with saturated NaHCO₃, extracted with EtOAc, dried over Na₂SO₄, filtered, and concentrated to produce crude Boc-protected-product. The crude product was dissolved in trifluoroacetic acid and stirred. After 10 minutes, the TFA was removed in vacuo, the crude product purified by reverse phase prep HPLC, and the pure product was lyophilized to give 1.05 g of S25A-TFA (85% yield) salt as white solid.

Step 4—Synthesis of rac-2-((1R,2S)-2-hydroxycyclopentyl)-2-phenyl-2-(1-((1-(4-(pyridin-4-ylsulfonyl)phenyl)azetidin-3-yl)methyl)piperidin-4-yl)acetonitrile (S26A)

S11 (1.0 mmol) was added to a solution of S25A from STEP 3 (0.5 mmol) and K₂CO₃ (1.6 mmol) in DMSO (3 mL) then stirred and heated to 80° C. After stirring overnight, the reaction was quenched with TFA (0.5 mL), diluted with 3:1 MeOH/H₂O and purified by prep HPLC. The pure fractions were combined, concentrated, diluted with water, frozen and lyophilized to give S26A as a white powder.

Step 5—Synthesis of rac-(1S,2R)-2-(cyano(phenyl)(1-((1-(4-(pyridin-4-ylsulfonyl)phenyl)azetidin-3-yl)methyl)piperidin-4-yl)methyl)cyclopentyl methylcarbamate (Cpd. No. 215)

Methylisocyanate (0.6 mmol) was added to a solution of S26A from STEP 4 (0.2 mmol) and NEt₃ (0.8 mmol) in DCM (2 mL) then stirred at RT for 4 h. The reaction was quenched with TFA (0.5 mL), diluted with 3:1 MeOH/H₂O and purified by prep-HPLC. The pure fractions were combined, concentrated, diluted with water, frozen and lyophilized to give Cpd. No. 215 as a white powder. ¹H NMR (400 MHz, MeOD) δ 8.76 (s, 2H), 7.83 (dd, J=4.4, 1.7 Hz, 2H), 7.76 (dd, J=8.9, 2.6 Hz, 2H), 7.44 (m, 5H), 6.50 (dd, J=8.9, 2.6 Hz, 2H), 4.16 (t, J=8.0 Hz, 2H), 3.74 (d, J=5.8 Hz, 2H), 3.54 (t, J=11.4 Hz, 2H), 3.41 (d, J=6.9 Hz, 2H), 3.31 (dd, J=3.1, 1.5 Hz, 2H), 3.18 (dd, J=17.8, 9.8 Hz, 2H), 3.05 (d, J=11.8 Hz, 2H), 2.54 (s, 3H), 2.48 (t, J=12.2 Hz, 1H), 2.37 (d, J=15.0 Hz, 1H), 2.28-2.11 (m, 2H), 2.02 (d, J=14.1 Hz, 1H), 1.82-1.62 (m, 4H), 1.53 (dd, J=26.5, 13.4 Hz, 2H). MS (ESI) m/z: [M+H]⁺ calcd, 627.3; found, 628.4.

Example 8

Synthesis of rac-(1S,2R)-2-(1-(1-((1-(4-cyanophenyl)azetidin-3-yl)methyl)piperidin-4-yl)-2-(1H-imidazol-1-yl)-1-phenylethyl)cyclopentyl methylcarbamate (Cpd. No. 366)

Scheme 3

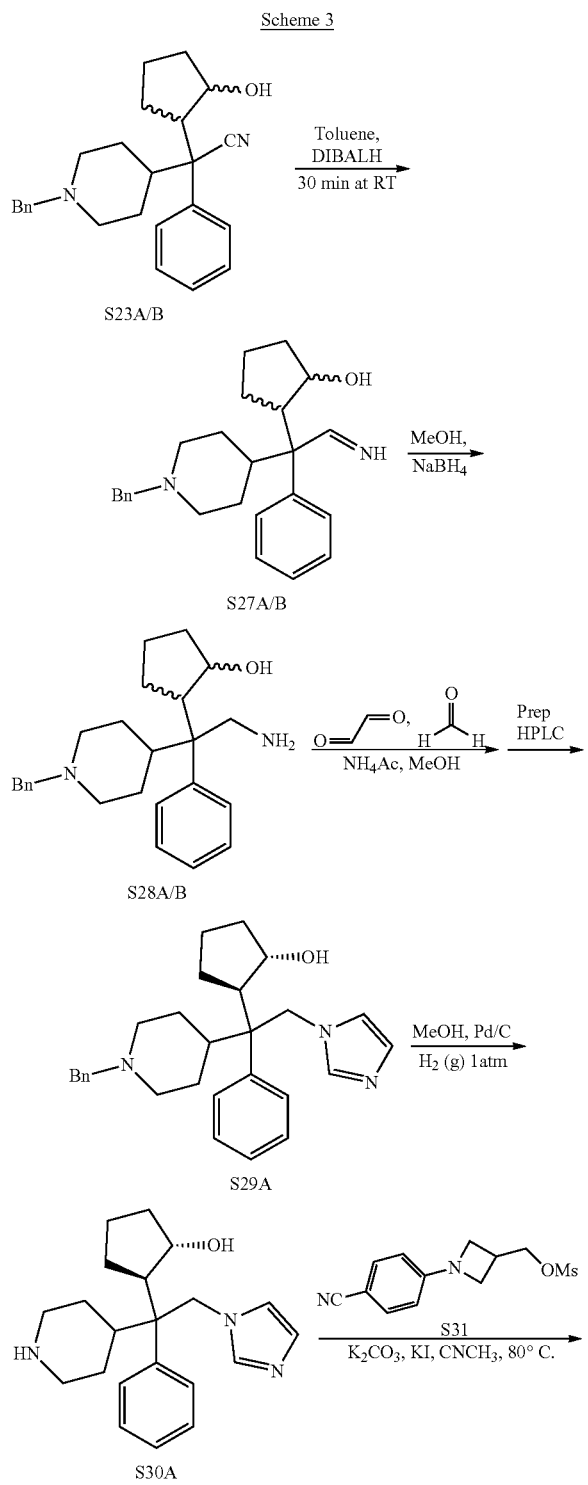

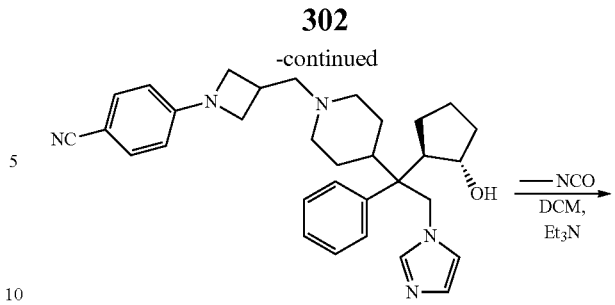

Step 1—Synthesis of a mixture of rac-(1S,2R)-2-(2-amino-1-(1-benzylpiperidin-4-yl)-1-phenylethyl)cyclopentan-1-ol (S28A) and rac-(1R,2S)-2-(2-amino-1-(1-benzylpiperidin-4-yl)-1-phenylethyl)cyclopentan-1-ol (S28B)

DIBALH (40 mmol) was added dropwise to a solution of a mixture of S23A/B (10 mmol), see Example 7, in toluene (40 mL) and stirred at RT. After one hour, the reaction was quenched by dropwise addition of 2M NaOH and the aqueous was extracted with EtOAc and concentrated. The crude S27A/B mixture thus obtained was dissolved in MeOH and NaBH$_4$ (15 mmol) was slowly added and the reaction was stirred. After stirring overnight, the reaction was quenched with water, extracted with EtOAc, dried over Na$_2$SO$_4$, filtered through celite, and concentrated to produce a mixture of S28A and S28B that was used in the next step without further purification.

Step 2—Synthesis of rac-(1S,2R)-2-(1-(1-benzylpiperidin-4-yl)-2-(1H-imidazol-1-yl)-1-phenylethyl)cyclopentan-1-ol (S29A)

NH$_4$Ac (40 mmol) was added to a solution of crude S28A/B mixture from Step 1 (10 mmol), oxalaldehyde (40 mmol), paraformaldehyde (40 mmol) in MeOH (15 mL) and stirred at 50° C. for 2 h or microwave 50° C. for 30 min. The crude product was purified by reverse phase prep HPLC, and the pure product was lyophilized to give S29A-TFA (active isomer, 35% yield in three steps) salt as a white solid.

Step 3—Synthesis of rac-(1S,2R)-2-(2-(1H-imidazol-1-yl)-1-phenyl-1-(piperidin-4-yl)ethyl)cyclopentan-1-ol (S30A)

Compound S29A (active isomer, 2 mmol) from STEP 2 was dissolved in MeOH (10 mL) and the solution was vacuumed briefly then put under N$_2$ atmosphere—this was repeated 3 times. Pd/C (10% wt/wt, 500 mg) was quickly added to the solution that was vacuumed and put under N$_2$ atmosphere. The solution was briefly vacuumed to remove the N$_2$ atmosphere then put under H$_2$ atmosphere—this was

Step 4—Synthesis of rac-4-(3-((4-(1-((1R,2S)-2-hydroxycyclopentyl)-2-(1H-imidazol-1-yl)-1-phenylethyl)piperidin-1-yl)methyl)azetidin-1-yl)benzonitrile (S32A)

To a solution of S30A (0.05 mmol) from STEP 3 in acetonitrile (2 mL) was added S31 (0.06 mmol), K₂CO₃ (0.15 mmol) and KI (0.005 mmol). The mixture was stirred at 80° C. overnight. Then, the mixture was extracted with ethyl acetate, washed with brine, dried (Na₂SO₄), and the solvent was evaporated. The residue was purified with prep HPLC to give S32A-TFA (75% yield) salt as white solid.

Step 5—Synthesis of rac-(1S,2R)-2-(1-(1-((1-(4-cyanophenyl)azetidin-3-yl)methyl)piperidin-4-yl)-2-(1H-imidazol-1-yl)-1-phenylethyl)cyclopentyl methylcarbamate (Cpd. No. 366)

Methylisocyanate (0.3 mmol) was added to a solution of S32A from STEP 4 (0.05 mmol) and NEt₃ (0.2 mmol) in DCM (1 mL) then stirred at RT for 4 h. The reaction was diluted with 3:1 MeOH/H₂O (10% TFA) and purified by prep-HPLC. The pure fractions were combined, concentrated, diluted with water, frozen and lyophilized to give Cpd. No. 366 as a white powder. $^1$H NMR (400 MHz, MeOD) δ 8.81 (s, 1H), 7.69 (d, J=7.7 Hz, 2H), 7.54 (t, J=7.5 Hz, 2H), 7.51-7.42 (m, 4H), 7.40 (s, 1H), 6.47 (d, J=8.2 Hz, 2H), 4.22-4.11 (m, 2H), 3.74 (s, 2H), 3.64 (d, J=11.7 Hz, 1H), 3.52-3.40 (m, 3H), 3.25 (dd, J=13.5, 6.9 Hz, 1H), 3.05 (t, J=12.0 Hz, 1H), 2.96 (t, J=11.9 Hz, 1H), 2.85 (s, 1H), 2.70 (s, 3H), 2.55 (d, J=11.2 Hz, 1H), 2.29 (d, J=13.4 Hz, 1H), 2.17 (s, 1H), 2.08-1.90 (m, 3H), 1.75-1.58 (m, 2H), 1.50 (dd, J=30.5, 12.1 Hz, 3H), 1.31 (d, J=0.8 Hz, 3H), 1.14 (d, J=11.0 Hz, 1H), 0.91 (d, J=11.6 Hz, 1H). MS (ESI) m/z: [M+H]⁺ calcd, 566.3; found, 567.5.

Example 8

Synthesis of rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl methylcarbamate (Cpd. No. 210)

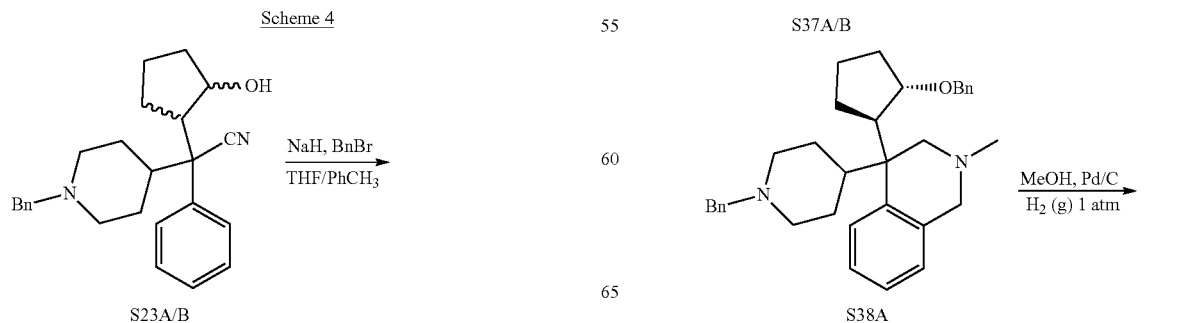

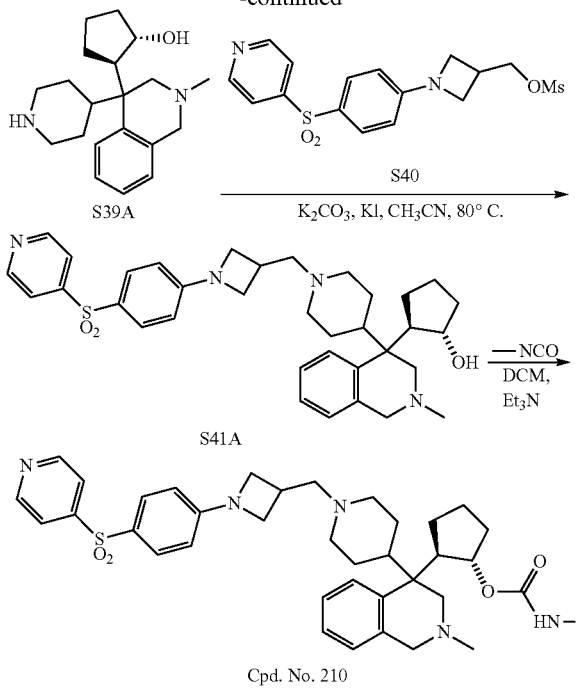

Step 1—Synthesis of rac-2-((1R,2S)-2-(benzyloxy)cyclopentyl)-2-(1-benzylpiperidin-4-yl)-2-phenylacetonitrile (S33A) and rac-2-((1S,2R)-2-(benzyloxy)cyclopentyl)-2-(1-benzylpiperidin-4-yl)-2-phenylacetonitrile (S33B)

NaH (65%, 30 mmol) was added to a solution of S23A/B (15 mmol) dissolved in dry THF/PhCH₃ (1:1, 100 mL) at 0° C. and stirred. After 30 minutes at 0° C., BnBr (16 mmol) was added dropwise and the reaction was allowed to warm to room temperature. After overnight at RT, the reaction was quenched with saturated NH₄Cl, extracted with EtOAc, concentrated and purified by column chromatography to produce a mixture of S33A and S33B (96% yield).

Step 2—Synthesis of rac-2-((1R,2S)-2-(benzyloxy)cyclopentyl)-2-(1-benzylpiperidin-4-yl)-2-phenylethan-1-amine (S35A) and rac-2-((1S,2R)-2-(benzyloxy)cyclopentyl)-2-(1-benzylpiperidin-4-yl)-2-phenylethan-1-amine (S35B)

DIBALH (40 mmol) was added dropwise to a solution S33A/B (10 mmol) from Step 1 in toluene (40 mL) and stirred at RT. After one hour, the reaction was quenched by dropwise addition of 2M NaOH and the aqueous was extracted with EtOAc and concentrated. The crude S34A/B was dissolved in MeOH and NaBH₄ (15 mmol) was slowly added and the reaction was stirred. After overnight, the reaction was quenched with water, extracted with EtOAc, dried over Na₂SO₄, filtered through celite, and concentrated to produce a mixture of S35A and S35B that was used in the next step without further purification.

Step 3—Synthesis of rac-4-((1R,2S)-2-(benzyloxy)cyclopentyl)-4-(1-benzylpiperidin-4-yl)-2-methyl-1,2,3,4-tetrahydroisoquinoline (S38A)

Methyl chloroformate (6 mmol) was added to a solution, at 0° C., of crude S35A/B (5 mmol) from STEP 2 and Et₃N (15 mmol) in DCM (20 mL) and stirred. After 30 minutes at 0° C., the reaction was put at RT and stirred. After 30 min at RT, the reaction was quenched with water and brine, extracted with EtOAc, dried over Na₂SO₄, filtered and concentrated to give crude S36A/B that was used without further purification.

Crude S36A/B was dissolved in AcOH (5 mL), paraformaldehyde (3 eq. base on S35A/B) and concentrated TFA (2 mL) were added at RT. After overnight, the reaction was slowly quenched with saturated NaHCO₃, extracted with EtOAc, dried over Na₂SO₄, filtered and concentrated to give crude S37A/B that was used without further purification.

Red-Al (3.2 M in toluene, 3 eq. base on S35A/B) was added dropwise to a solution, at RT, of crude S37A/B in toluene (15 mL) and stirred. After 30 minutes, the reaction was quenched by dropwise addition of 2M NaOH and the aqueous was extracted with EtOAc and concentrated. The crude S38A/B was purified by reverse phase prep HPLC and the pure compound was lyophilized to produce S38A-TFA (12% yield in 5 steps) salt as a white powder.

Step 4—Synthesis of rac-(1S,2R)-2-(2-methyl-4-(piperidin-4-yl)-1,2,3,4-tetrahydroisoquinolin-4-yl)cyclopentan-1-ol (S39A)

Compound S38A (0.5 mmol) from STEP 3 was dissolved in MeOH (5 mL) and the solution was vacuumed briefly then put under N₂ atmosphere—this was repeated 3 times. Pd/C (10% wt/wt, 100 mg) was quickly added to the solution that was vacuumed and put under N₂ atmosphere. The solution was briefly vacuumed to remove the N₂ atmosphere then put under H₂ atmosphere—this was repeated 3 times. After 4 h, the reaction was filtered through celite and concentrated to give crude S39A (96% yield) that was used without further purification.

Step 5—Synthesis of rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentan-1-ol (S41A)

To a solution of the intermediate S39A (0.05 mmol) from STEP 4 in acetonitrile (2 mL) was added S40 (0.06 mmol), K₂CO₃ (0.15 mmol) and KI (0.005 mmol). The mixture was stirred at 80° C. overnight. Then, the reaction was extracted with ethyl acetate, washed with brine, dried (Na₂SO₄), and the solvent was evaporated. The residue was purified by prep HPLC to give S41A-TFA (75% yield) salt as white solid.

Step 6—Synthesis of rac-(1S,2R)-2-(2-methyl-4-(1-((1-(4-(pyridin-4-ylsulfonyl)phenyl)azetidin-3-yl)methyl)piperidin-4-yl)-1,2,3,4-tetrahydroisoquinolin-4-yl)cyclopentyl methylcarbamate (Cpd. No. 210)

Methylisocyanate (0.3 mmol) was added to a solution of compound S41A (0.05 mmol) from STEP 5 and NEt₃ (0.2 mmol) in DCM (1 mL) then stirred at RT for 4 h. The reaction was diluted with 3:1 MeOH/H₂O (10% TFA) and purified by prep HPLC. The pure fractions were combined, concentrated, diluted with water, frozen and lyophilized to give Cpd. No. 210 as a white powder. ¹H NMR (400 MHz, MeOD) δ 8.66 (d, J=5.6 Hz, 2H), 7.73 (d, J=5.9 Hz, 2H), 7.63 (dd, J=20.6, 8.6 Hz, 2H), 7.44 (d, J=7.8 Hz, 1H), 7.31 (t, J=7.7 Hz, 1H), 7.23 (d, J=7.3 Hz, 1H), 7.14 (d, J=7.4 Hz, 1H), 6.38 (d, J=8.7 Hz, 2H), 4.99 (d, J=7.4 Hz, 2H), 4.25 (d, J=18.7 Hz, 2H), 4.05 (t, J=8.0 Hz, 2H), 3.63 (s, 3H), 3.45 (d, J=11.7 Hz, 1H), 3.28 (d, J=6.6 Hz, 4H), 3.14 (d, J=16.5 Hz, 4H), 2.97-2.71 (m, 2H), 2.18 (s, 3H), 1.94 (d, J=19.7 Hz, 3H), 1.69 (d, J=39.4 Hz, 6H). MS (ESI) m/z: [M+H]⁺ calcd, 657.3; found, 658.4.
Example 9
Synthesis of rac-N-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)acetamide (Cpd. No. 292)
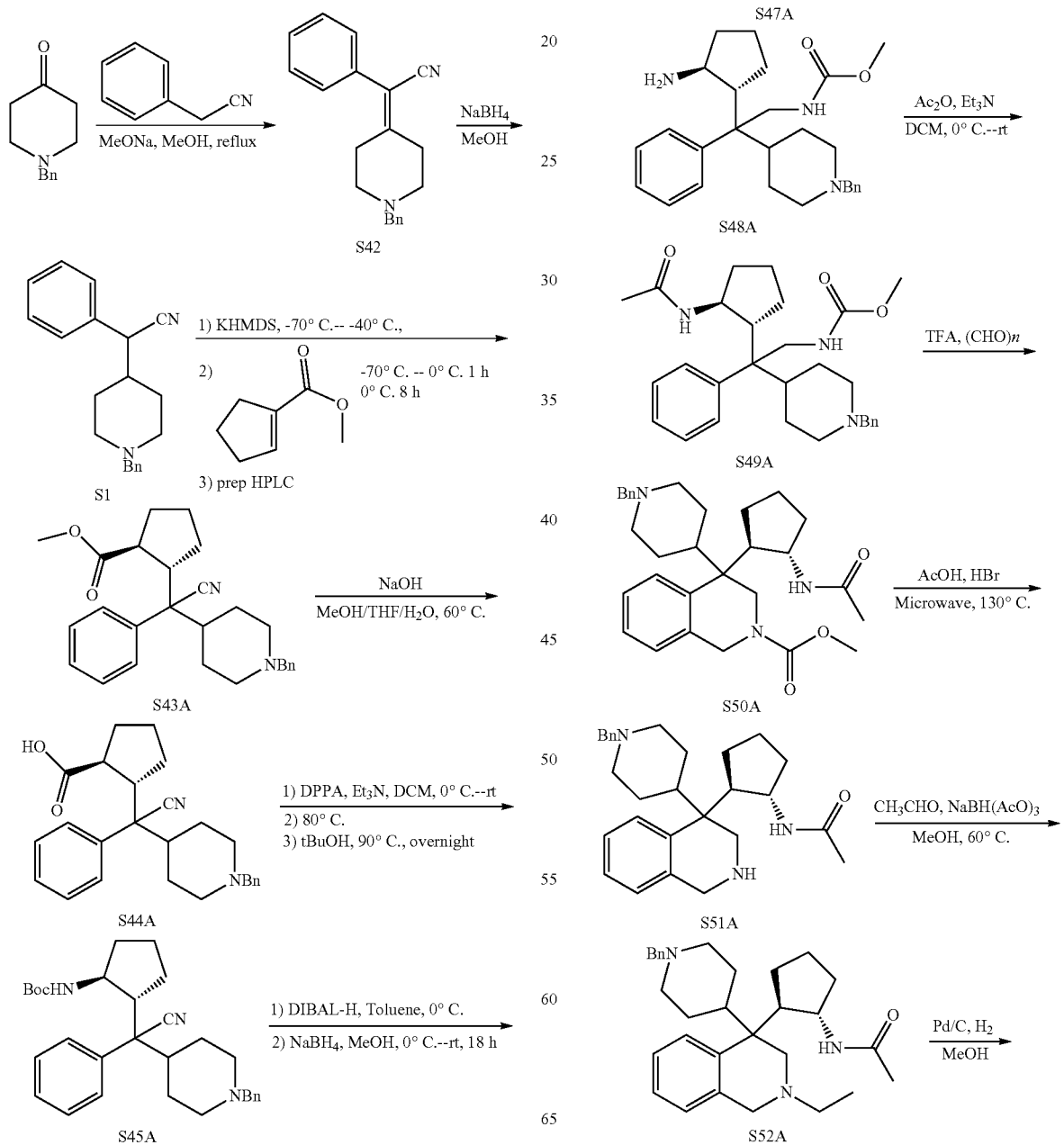

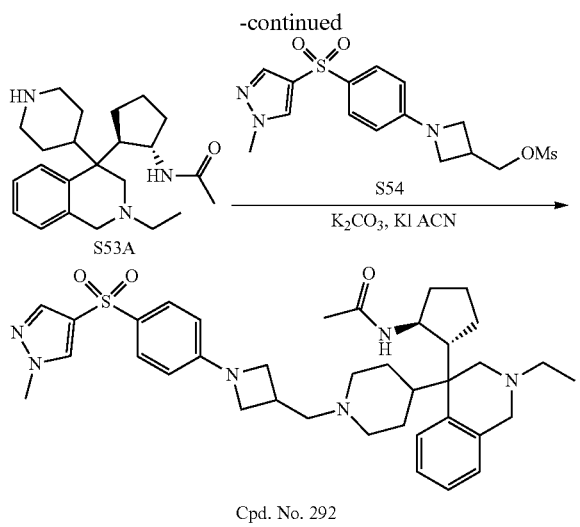

Cpd. No. 292

Step 1—Synthesis of 2-(1-benzylpiperidin-4-ylidene)-2-phenylacetonitrile (S42)

Sodium methoxide (25% wt. in MeOH) (46.8 mL, 205 mmol) was added to a solution of 1-benzylpiperidin-4-one (32.3 g, 171 mmol) and 2-phenylacetonitrile (20 g, 171 mmol) in anhydrous methanol (200 mL) under argon, and the mixture was stirred under reflux overnight. Then, the reaction mixture was cooled to room temperature and poured into ice (200 g). The resulting mixture was extracted with ethyl acetate. The separated organic layer was dried with Na$_2$SO$_4$, filtered and the solvent was evaporated in vacuum to yield the title product (48 g, 95%). MS (ESI) m/z 289.1 [M+H]$^+$.

Step 2—Synthesis of 2-(1-Benzylpiperidin-4-yl)-2-phenylacetonitrile (S1)

Sodium borohydride (12.6 g, 333 mmol) was added to a solution of S42 (48 g, 166 mmol) from STEP 1 in methanol (100 ml). The mixture was stirred under room temperature overnight. Then, a mixture of water and ice (200 ml) was added, the light yellow precipitate was formed and filtered. The residue was washed with water and dried in vacuum to yield the yellow product (38 g, 79%). MS (ESI) m/z 291.1 [M+H]$^+$.

Step 3—Synthesis of methyl rac-(1S,2S)-2-((1-benzylpiperidin-4-yl)(cyano)(phenyl)methyl)cyclopentane-1-carboxylate (S43A)

To a solution of S1 (1 g, 3.44 mmol) from STEP 2 in anhydrous toluene (15 mL) at −78° C. under argon was added potassium bis(trimethylsilyl)amide (0.5 M in toluene) (17.2 mL, 8.61 mmol). The mixture was stirred at −78° C. for 1 h, and then the corresponding methyl cyclopent-1-ene-1-carboxylate (3.48 g, 28 mmol) was added dropwise. The resulting mixture was stirred and warned to 0° C. for 1 h. The reaction was monitored by HPLC-Mass. Upon transformation of the starting material, the reaction was quenched with saturated aqueous NH$_4$Cl (5 mL). The mixture was extracted with dichloromethane (2×30 mL), dried (Na$_2$SO$_4$), and the solvent was evaporated. The diastereoisomeric mixture was purified by prep HPLC to give 350 mg (24%) of methyl rac-(1S,2S)-2-((1-benzylpiperidin-4-yl)(cyano)(phenyl)methyl)cyclopentane-1-carboxylate (S43A) and 450 mg (31%) of methyl rac-(1R,2R)-2-((1-benzylpiperidin-4-yl)(cyano)(phenyl)methyl)cyclopentane-1-carboxylate (S43B). MS (ESI) m/z 417.2 [M+H]$^+$.

Step 4—Synthesis of rac-(1S,2S)-2-((1-Benzylpiperidin-4-yl)(cyano)(phenyl)methyl)cyclopentane-1-carboxylic acid (S44A)

A solution of NaOH (33 mg, 0.84 mmol) in 10 mL of H$_2$O was added at room temperature to solution of S43A (0.21 g, 0.41 mmol) from STEP 3 in 10 mL of methanol. The resulting mixture was stirred at 60° C. overnight before being evaporated. The residue was partitioned between 2M HCl and ethyl acetate. The aqueous layer was back extracted twice with ethyl acetate. The combined organic layers were washed with brine, dried (Na$_2$SO$_4$), filtered, and evaporated to give the title product (310 mg, 89%). The product was used in the next step without purification. MS (ESI) m/z 403.2 [M+H]$^+$.

Step 5—Synthesis of tert-butyl rac-((1S,2R)-2-((1-benzylpiperidin-4-yl)(cyano)(phenyl)methyl)cyclopentyl)carbamate (S45A)

S44A (0.8 g, 2 mmol) from STEP 4, diphenylphosphoryl azide (0.51 mL, 2.4 mmol) and triethylamine (0.83 mL, 6 mmol) were dissolved in dichloromethane (25 mL). The mixture was stirred at room temperature for 5 h and then diluted with dichloromethane. The organic phase was washed with brine, and dried over anhydrous Na$_2$SO$_4$ and evaporated under reduced pressure. The residue was warmed without solvent at 80° C., until no further gas evolution occurred. The reaction mixture was then cooled, the resulting oil was dissolved in anhydrous t-BuOH (5 mL, 99.9% anhydrous packed under argon; Alfa Aesar), placed under and atmosphere of nitrogen, and refluxed in a 90° C. bath overnight. After this time, the reaction mixture was cooled and concentrated under reduced pressure to afford an oil crude product, which was then purified with flash column chromatography to afford the title compound (400 mg, 50.4%). MS (ESI) m/z 474.3 [M+H]$^+$.

Step 6—Synthesis of tert-butyl rac-((1S,2R)-2-(2-amino-1-(1-benzylpiperidin-4-yl)-1-phenylethyl)cyclopentyl)carbamate (S46A)

To an ice cold solution of S45A (256 mg, 0.54 mmol) from STEP 5 in toluene (3 mL) was added diisobutylaluminiumhydride (25% in toluene, 1.8 mL) under argon. The mixture was then allowed to warm to room temperature and stirred for 20 min. The mixture was cooled to 0° C. and quenched by careful addition of water (1 mL). The suspension was stirred for another 10 minutes, and filtered. The filtrate was extracted with ethyl acetate, dried over Na$_2$SO$_4$ and evaporated. The residue was dried in vacuum and then dissolved in methanol (10 mL). NaBH$_4$ (40 mg, 1 mmol) was added into the mixture, and the reaction mixture was stirred at room temperature overnight. The mixture was concentrated in vacuum and diluted with ethyl acetate and water. The mixture was extracted with ethyl acetate, dried (Na$_2$SO$_4$), and the solvent was evaporated. Then the residue was purified with prep HPLC to yield the title compound (200 mg, 77%). MS (ESI) m/z 478.3 [M+H]+.

Step 7—Synthesis of tert-butyl rac-((1S,2R)-2-(1-(1-benzylpiperidin-4-yl)-2-((methoxycarbonyl)amino)-1-phenylethyl)cyclopentyl)carbamate (S47A)

To a solution of S46A (213 mg, 0.45 mmol) from STEP 6 in dichloromethane (20 mL) was added methyl chloroformate (51 mg, 0.54 mmol) and triethylamine (90 mg, 0.89 mmol) in ice/water bath. Then, the ice/water bath was removed, the mixture was stirred at room temperature for 1 h. After this time, the reaction mixture was quenched with water, extracted with dichloromethane, dried ($Na_2SO_4$), and the solvent was evaporated to obtain the title compound (230 mg, 96%). The product was used in the next step without further purification. MS (ESI) m/z 536.3 [M+H]+.

Step 8—Synthesis of methyl rac-(2-((1R,2S)-2-aminocyclopentyl)-2-(1-benzylpiperidin-4-yl)-2-phenylethyl)carbamate (S48A)

To a solution of S47 (230 mg, 0.43 mmol) from STEP 7 in dichloromethane (5 mL) was added trifluoroacetic acid (0.5 mL). The reaction was stirred at room temperature for 2 h. The mixture was basified with saturated $NaHCO_3$, extracted with dichloromethane, dried ($Na_2SO_4$), and the solvent was evaporated to obtain the title compound (180 mg, 96%). The product was used in the next step without further purification. MS (ESI) m/z 436.3 [M+H]+.

Step 9—Synthesis of methyl rac-(2-((1R,2S)-2-acetamidocyclopentyl)-2-(1-benzylpiperidin-4-yl)-2-phenylethyl)carbamate (S49A)

To a solution of S48 A (192 mg, 0.44 mmol) from STEP 8 in dichloromethane (10 mL) was added acetic anhydride (67.5 mg, 0.66 mmol) and triethylamine (89 mg, 0.88 mmol). The reaction was stirred at room temperature for 2 h. The mixture was quenched with saturated $NaHCO_3$, extracted with dichloromethane, dried ($Na_2SO_4$), and the solvent was evaporated to obtain the title compound (195 mg, 93%). The product was used in the next step without further purification. MS (ESI) m/z 478.3 [M+H]+.

Step 10—Synthesis of methyl rac-4-((1R,2S)-2-acetamidocyclopentyl)-4-(1-benzylpiperidin-4-yl)-3,4-dihydroisoquinoline-2(1H)-carboxylate (S50A)

To a solution of the intermediate S49A (195 mg, 0.41 mmol) from STEP 9 in trifluoroacetic acid (2 mL) was added paraformaldehyde (123 mg, 4.1 mmol). The reaction was stirred at room temperature overnight. The mixture was quenched and basified with saturated $NaHCO_3$, extracted with dichloromethane, dried ($Na_2SO_4$), and the solvent was evaporated. The residue was purified with pre-HPLC to give the title compound (143 mg, 72%). MS (ESI) m/z 490.3 [M+H]+.

Step 11—Synthesis of rac-N-((1S,2R)-2-(4-(1-benzylpiperidin-4-yl)-1,2,3,4-tetrahydroisoquinolin-4-yl)cyclopentyl)acetamide (S51A)

To a solution of S50A (143 mg, 0.29 mmol) from STEP 10 in acetic acid (1 mL) was added HBr (40% wt. in $H_2O$) (0.5 mL). The reaction mixture was heated to 130° C. under microwave and stirred for 2 h. The mixture was basified carefully with saturated $NaHCO_3$ at 0° C., extracted with DCM, dried ($Na_2SO_4$), and the solvent was evaporated to obtain the title compound (110 mg, 87%). The product was used in the next step without further purification. MS (ESI) m/z 432.3 [M+H]+.

Step 12—Synthesis of rac-N-((1S,2R)-2-(4-(1-benzylpiperidin-4-yl)-2-ethyl-1,2,3,4-tetrahydroisoquinolin-4-yl)cyclopentyl)acetamide (S52A)

To a solution of the intermediate S51A (110 mg, 0.25 mmol) from STEP 11 in methanol (5 mL) was added acetaldehyde (108 mg, 0.51 mL) and sodium triacetoxyborohydride (22 mg, 0.51 mmol). The mixture was stirred overnight and evaporated to half its volume and partitioned between saturated $NaHCO_3$ and dichloromethane. The organic phase was washed with brine, dried ($Na_2SO_4$) and evaporated. The crude product was purified by pre-HPLC to obtain the title compound (74 mg, 63%). MS (ESI) m/z 460.3 [M+H]+.

Step 13—Synthesis of rac-N-((1S,2R)-2-(2-ethyl-4-(piperidin-4-yl)-1,2,3,4-tetrahydroisoquinolin-4-yl)cyclopentyl)acetamide (S53A)

To a solution of S52A (74 mg, 0.16 mmol) from STEP 12 in methanol (5 mL) was added 10% Pd/C (17 mg). The mixture was stirred for 4 h at room temperature under hydrogen atmosphere (normal pressure). After the Pd/C catalyst was filtered off, the solvent was removed by rotary evaporation to give the title compound (55 mg, 92%). The product was used in the next step without further purification. MS (ESI) m/z 370.3 [M+H]+.

Step 14—Synthesis of rac-N-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)acetamide (Cpd. No. 292)

To a solution of S53A (20 mg, 0.054 mmol) from STEP 13 in acetonitrile (2 mL) was added (1-(4-((1-methyl-1H-pyrazol-4-yl)sulfonyl)phenyl)azetidin-3-yl)methyl methanesulfonate (S54) (22 mg, 0.057 mmol), $K_2CO_3$ (15 mg, 0.11 mmol) and KI (1 mg, 0.005 mmol). The mixture was stirred at 80° C. overnight. Then, the mixture was extracted with ethyl acetate, washed with brine, dried ($Na_2SO_4$), and the solvent was evaporated. The residue was purified with pre-HPLC to give the title compound (20 mg, 56%). $^1$H NMR (400 MHz, MeOD, a mixture of rotamers) δ 8.09 (s, 1H), 8.02 (d, J=9.6 Hz, 0.5H) and 7.71 (d, J=8.4 Hz, 2.5H), 7.51 (d, J=8.0, 1H), 7.45 (t, J=6.8 Hz, 1H), 7.34-7.29 (m, 2H), 6.46 (d, J=8.8 Hz, 2H), 4.47 (d, J=12.8 Hz, 1H), 4.15-4.10 (m, 3H), 3.99-3.93 (m, 1H), 3.88 (s, 3H), 3.82-3.79 (m, 1H), 3.71-3.58 (m, 4H), 3.44-3.35 (m, 4H), 3.27-3.25 (m, 1H), 3.18-3.13 (m, 1H), 3.02-2.90 (m, 2H), 2.76-2.68 (m, 1H), 2.27-2.24 (m, 1H), 2.10-1.94 (m, 3H), 1.89-1.61 (m, 6H), 1.56 (t, J=7.2 Hz, 3H), 1.17 (s, 3H), 0.66-0.58 (m, 1H). MS (ESI) m/z 659.3 [M+H]+.

Example 11

Synthesis of rac-1-((1S,2R)-2-(2-ethyl-4-(1-((1-(4-((1-methyl-1H-pyrazol-4-yl)sulfonyl)phenyl)azetidin-3-yl)methyl)piperidin-4-yl)-1,2,3,4-tetrahydroisoquinolin-4-yl)cyclopentyl)-3-methylurea (Cpd. No. 291)

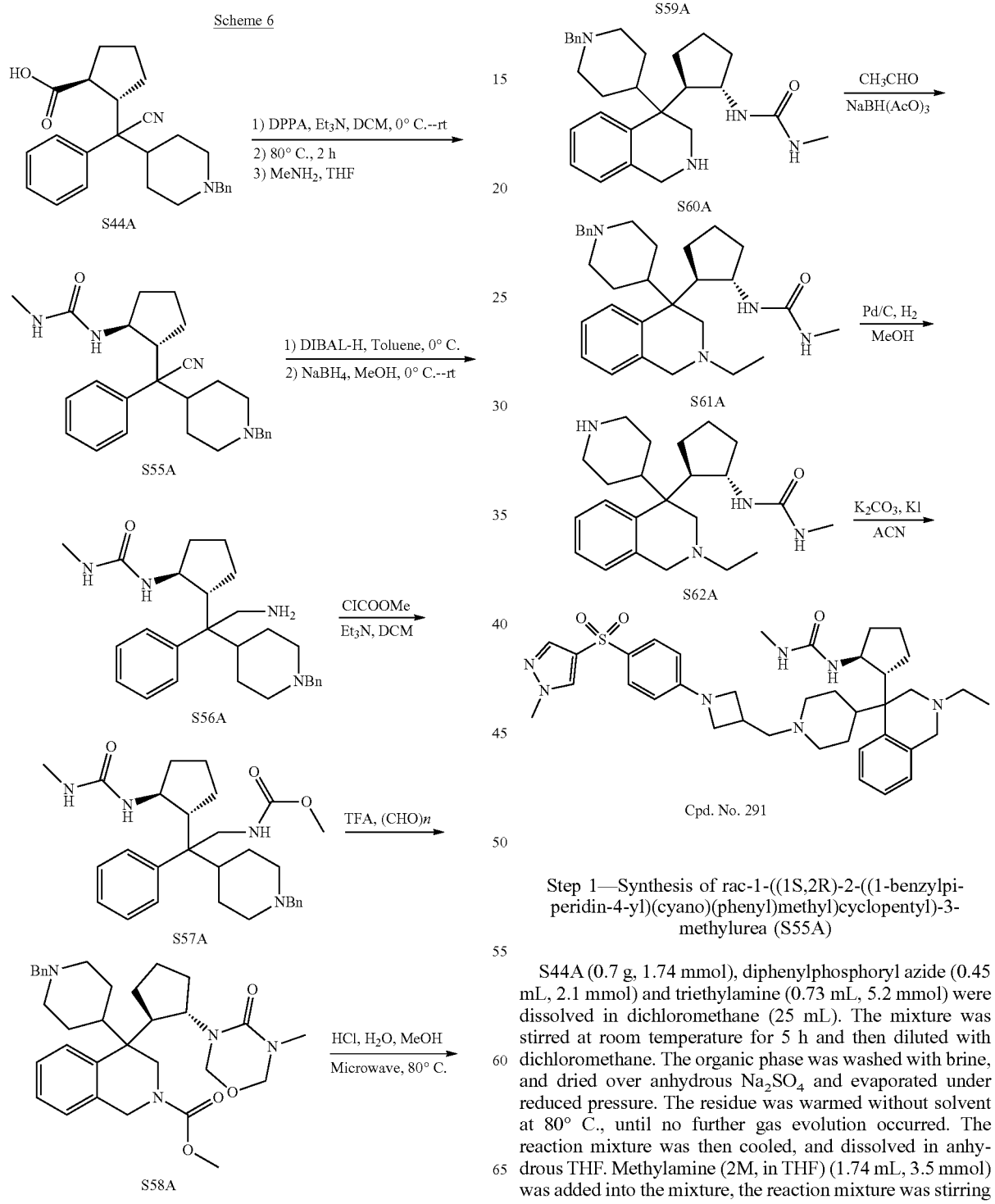

Step 1—Synthesis of rac-1-((1S,2R)-2-((1-benzylpiperidin-4-yl)(cyano)(phenyl)methyl)cyclopentyl)-3-methylurea (S55A)

S44A (0.7 g, 1.74 mmol), diphenylphosphoryl azide (0.45 mL, 2.1 mmol) and triethylamine (0.73 mL, 5.2 mmol) were dissolved in dichloromethane (25 mL). The mixture was stirred at room temperature for 5 h and then diluted with dichloromethane. The organic phase was washed with brine, and dried over anhydrous $Na_2SO_4$ and evaporated under reduced pressure. The residue was warmed without solvent at 80° C., until no further gas evolution occurred. The reaction mixture was then cooled, and dissolved in anhydrous THF. Methylamine (2M, in THF) (1.74 mL, 3.5 mmol) was added into the mixture, the reaction mixture was stirring at room temperature for 2 h. After this time, the reaction mixture was cooled and concentrated under reduced pressure to afford an oil crude product, which was then purified with prep HPLC to afford the title compound (597 mg, 80%). MS (ESI) m/z 431.3 [M+H]⁺.

S57A and S58A were prepared according to the methods for S47A and S50A.

Step 2—Synthesis of methyl rac-4-(1-benzylpiperidin-4-yl)-4-((1R,2S)-2-(3-methylureido)cyclopentyl)-3,4-dihydroisoquinoline-2(1H)-carboxylate (S59A)

To a solution of S58A (639 mg, 1.2 mmol) in methanol (3 mL) was added 0.2 mL of concentrated aqueous HCl (wt. 37%). The reaction mixture was heated to 80° C. under microwave and stirred for 2 h. The mixture was basified carefully with saturated NaHCO₃ at 0° C., extracted with DCM, dried (Na₂SO₄), and the solvent was evaporated to obtain the title compound (550 mg, 93%). The product was used in the next step without further purification. MS (ESI) m/z 505.5 [M+H]⁺.

S60A, S61A, S62A and Cpd. No. 291 were prepared according to the methods for S51A, S52A, S53A, and Cpd. No. 292, respectively.

Cpd. No. 291; ¹H NMR (400 MHz, MeOD) δ 8.09 (s, 1H), 7.72-7.69 (m, 3H), 7.50 (d, J=8.0 Hz, 1H), 7.39 (t, J=6.8 Hz, 1H), 7.32-7.25 (m, 2H), 6.46 (d, J=9.2, 2H), 4.40 (d, J=12.8, 1H), 4.13-4.08 (m, 3H), 3.88 (s, 3H), 3.82-3.75 (m, 2H), 3.71-3.66 (m, 2H), 3.60-3.53 (m, 2H), 3.42-3.34 (m, 4H), 3.17 (d, J=14.0 Hz, 2H), 3.01-2.90 (m, 2H), 2.74-2.67 (m, 1H), 2.27-2.24 (m, 1H), 2.20 (s, 3H), 2.04-1.67 (m, 8H), 1.55 (t, J=7.6 Hz, 3H). MS (ESI) m/z 674.3 [M+H]⁺.

Example 12

Synthesis of 1-(1-benzylpiperidin-4-yl)-1-cyclopentyl-1,2,3,4-tetrahydroisoquinoline (Cpd. No. 71)

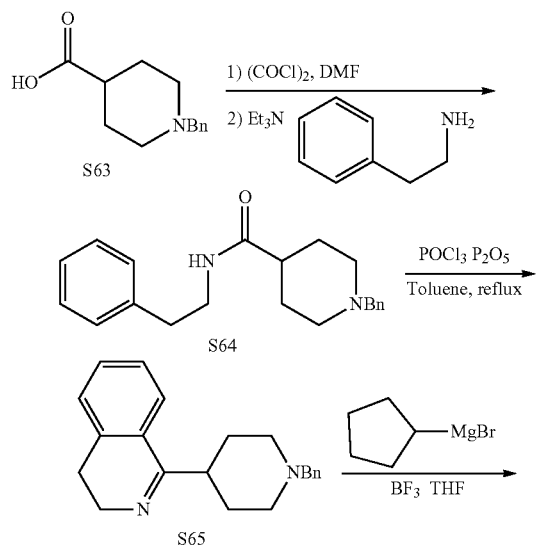

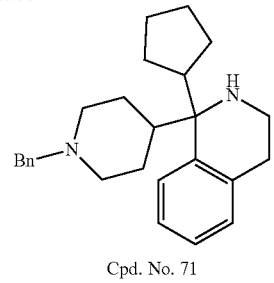

Cpd. No. 71

Step 1—Synthesis of 1-benzyl-N-phenethylpiperidine-4-carboxamide (S64)

To a suspension of 1-benzylpiperidine-4-carboxylic acid (15 g, 68.4 mmol) in dichloromethane (100 mL) was added DMF (1 drop) followed by oxalyl chloride (7 mL, 82 mmol) dropwise. The mixture was stirred for 4 h then concentrated under vacuum, affording acid chloride, rediluted with dichloromethane (100 mL). Triethylamine (23.8 mL, 171 mmol) was added into the mixture, followed by 2-phenylethan-1-amine (8.29 g, 68.4 mmol) at 0° C. The reaction mixture was stirred at room temperature overnight. The organic phase was washed with brine, dried (Na₂SO₄) and evaporated. The crude product was purified by recrystallization in dichloromethane to obtain the title compound (14.9 g, 68%). MS (ESI) m/z 323.2 [M+H]⁺.

Step 2—Synthesis of 1-(1-benzylpiperidin-4-yl)-3,4-dihydroisoquinoline (S65)

To a solution of S64 from STEP 1 in toluene (15 mL) were added phosphoryl chloride (3.3 mL, 35.4 mmol) and phosphorus pentoxide (3.35 g, 23.6 mmol). The reaction mixture was stirring under reflux overnight. The mixture was quenched and basified with saturated NaHCO₃, extracted with dichloromethane, dried (Na₂SO₄), and the solvent was evaporated to give the title compound (3.5 g, 97%). The product was used in the next step without further purification. MS (ESI) m/z 305.3 [M+H]⁺.

Step 3—Synthesis of 1-(1-benzylpiperidin-4-yl)-1-cyclopentyl-1,2,3,4-tetrahydroisoquinoline (Cpd. No. 71)

To a solution of S65 from STEP 2 was added boron trifluoride diethyl etherate (0.6 mL) at 0° C. under nitrogen atmosphere. After the mixture was stirring for 5 min, the cyclopentylmagnesium bromide solution (2M, in diethyl ether) (3.3 mL, 6.6 mmol) was added into the mixture dropwise at 0° C. The reaction mixture was stirred overnight, warming slowly to room temperature. The, the reaction was quenched with saturated aqueous NH₄Cl, extracted with dicloromethane, dried (Na₂SO₄), and the solvent was evaporated. The crude product was purified by prep HPLC to give the title compound (740 mg, 60%). MS (ESI) m/z 375.2 [M+H]⁺. ¹H NMR (400 MHz, CDCl₃) δ 7.48-7.35 (m, 5H), 7.32-7.28 (m, 2H), 7.21-7.13 (m, 2H), 4.11 (dd, J=25.6, 12.9 Hz, 2H), 3.65-3.37 (m, 4H), 3.16-2.91 (m, 2H), 2.86-2.75 (m, 2H), 2.69 (t, J=11.5 Hz, 1H), 2.40 (d, J=11.7 Hz, 1H), 2.27-2.12 (m, 2H), 1.96-1.80 (m, 2H), 1.75-1.57 (m, 4H), 1.46 (dd, J=33.9, 3.1 Hz, 2H), 1.37-1.25 (m, 1H), 1.22-1.09 (m, 1H).

Example 13

The following Compounds of the Disclosure, see Tables 1 and 2, were prepared using the illustrative methods described in Examples 1-12, and/or methods known to those skilled in the art in view of this disclosure, and characterized by ESI-MS and/or $^1$NMR as follows.

Cpd. No. 128; ESI-MS m/z 469.83 (M+H)$^+$.
Cpd. No. 130; ESI-MS m/z 456.83 (M+H)$^+$.
Cpd. No. 131; $^1$H-NMR (400 MHz, CD$_3$OD) δ ppm 7.66 (d, 2H, J=8.8 Hz), 7.47-7.41 (m, 1H), 7.40-7.29 (m, 3H), 6.97 (d, 2H, J=8.8 Hz), 5.00-4.93 (m, 1H), 3.97-3.84 (m, 1H), 3.63 (d, 1H, J=12.1 Hz), 3.59-3.44 (m, 3H), 3.16-3.01 (m, 2H), 2.97-2.71 (m, 6H), 2.69-2.51 (m, 3H), 2.26 (d, 1H, J=12.6 Hz), 2.02-1.88 (m, 2H), 1.88-1.73 (m, 3H), 1.73-1.40 (m, 6H), 1.26-1.10 (m, 1H); ESI-MS m/z 456.83 (M+H)$^+$.
Cpd. No. 132; ESI-MS m/z 508.83 (M+H)$^+$.
Cpd. No. 323; ESI-MS m/z 532.92 (M+H)$^+$.
Cpd. No. 324; ESI-MS m/z 532.83 (M+H)$^+$.
Cpd. No. 325; ESI-MS m/z 488.83 (M+H)$^+$.
Cpd. No. 326; ESI-MS m/z 488.83 (M+H)$^+$.
Cpd. No. 327; ESI-MS m/z 493.92 (M+H)$^+$.
Cpd. No. 328; ESI-MS m/z 493.83 (M+H)$^+$.
Cpd. No. 43; ESI-MS m/z 455.92 (M+H)$^+$.
Cpd. No. 44; ESI-MS m/z 511.50 (M+H)$^+$.
Cpd. No. 45; $^1$H-NMR (400 MHz, CD$_3$OD) δ ppm 7.58 (d, 1H, J=7.9 Hz), 7.51-7.43 (m, 3H), 7.36 (t, 1H, J=7.4 Hz), 7.29 (d, 1H, J=7.3 Hz), 6.47 (d, 2H, J=8.7 Hz), 4.46-4.23 (m, 3H), 4.17 (t, 2H, J=7.6 Hz), 3.78-3.72 (m, 2H), 3.52 (d, 2H, J=13.4 Hz), 3.43 (d, 3H, J=6.4 Hz), 3.15 (s, 3H), 3.08-2.90 (m, 3H), 2.17 (d, 1H, J=14.6 Hz), 1.93-1.80 (m, 3H), 1.73-1.44 (m, 8H), 1.36-1.21 (m, 2H); ESI-MS m/z 469.67 (M+H)$^+$.
Cpd. No. 46; ESI-MS m/z 482.17 (M+H)$^+$.
Cpd. No. 133; ESI-MS m/z 522.50 (M+H)$^+$.
Cpd. No. 134; ESI-MS m/z 536.67 (M+H)$^+$.
Cpd. No. 135; $^1$H-NMR (400 MHz, CD$_3$OD) δ ppm 7.66 (d, 2H, J=7.6 Hz), 7.48-7.42 (m, 1H), 7.39-7.29 (m, 3H), 6.52 (d, 2H, J=7.8 Hz), 4.19 (t, 2H, J=7.7 Hz), 3.81-3.73 (m, 2H), 3.64 (d, 1H, J=11.3 Hz), 3.61-3.42 (m, 7H), 3.16-2.98 (m, 5H), 2.85-2.72 (m, 1H), 2.67-2.52 (m, 2H), 2.25 (d, 1H, J=13.8 Hz), 2.01-1.90 (m, 2H), 1.86-1.41 (m, 9H), 1.34-1.18 (m, 1H), 1.18-1.12 (m, 2H), 1.03-0.96 (m, 2H); ESI-MS m/z 534.50 (M+H)$^+$.
Cpd. No. 329; ESI-MS m/z 458.58 (M+H)$^+$.
Cpd. No. 136; ESI-MS m/z 550.67 (M+H)$^+$.
Cpd. No. 137; ESI-MS m/z 562.67 (M+H)$^+$
Cpd. No. 330; ESI-MS m/z 487.83 (M+H)$^+$.
Cpd. No. 331; ESI-MS m/z 487.67 (M+H)$^+$.
Cpd. No. 138; ESI-MS m/z 469.50 (M+H)$^+$.
Cpd. No. 139; ESI-MS m/z 489.50 (M+H)$^+$.
Cpd. No. 140; $^1$H-NMR (400 MHz, CD$_3$OD) δ ppm 7.71 (d, 2H, J=8.6 Hz), 7.45 (m, 1H), 7.35 (m, 3H), 6.62 (d, 2H, J=8.7 Hz), 4.25 (m, 4H), 3.73 (m, 1H), 3.53 (m, 7H), 3.12 (m, 4H), 2.80 (m, 1H), 2.57 (m, 2H), 2.22 (d, 1H, J=13.7 Hz), 1.97 (m, 2H), 1.63 (m, 9H), 1.27 (m, 1H), 1.15 (m, 2H), 1.00 (m, 2H); ESI-MS m/z 552.67 (M+H)$^+$.
Cpd. No. 141; ESI-MS m/z 580.58 (M+H)$^+$.
Cpd. No. 47; ESI-MS m/z 580.58 (M+H)$^+$.
Cpd. No. 142; ESI-MS m/z 590.67 (M+H)$^+$.
Cpd. No. 143; ESI-MS m/z 576.58 (M+H)$^+$.
Cpd. No. 144; ESI-MS m/z 597.00 (M+H)$^+$.
Cpd. No. 145; ESI-MS m/z 590.67 (M+H)$^+$.
Cpd. No. 146; ESI-MS m/z 562.92 (M+H)$^+$.
Cpd. No. 147; ESI-MS m/z 598.58 (M+H)$^+$.
Cpd. No. 149; ESI-MS m/z 570.50 (M+H)$^+$.
Cpd. No. 151; $^1$H-NMR (400 MHz, CD$_3$OD) δ ppm 8.75 (d, 2H, J=5.7 Hz), 7.82 (dd, 2H, J=1.5 Hz, J=4.6 Hz), 7.76 (d, 2H, J=8.8 Hz), 7.47-7.41 (m, 1H), 7.41-7.28 (m, 3H), 6.51 (d, 2H, J=8.9 Hz), 4.19 (t, 2H, J=7.9 Hz), 3.81-3.73 (m, 2H), 3.67-3.39 (m, 8H), 3.19-2.96 (m, 4H) 2.89-2.73 (m, 1H), 2.67-2.52 (m, 1H), 2.24 (d, 1H, J=12.8 Hz), 2.04-1.88 (m, 2H), 1.88-1.37 (m, 8H), 1.37-1.13 (m, 1H); ESI-MS m/z 571.67 (M+H)$^+$.
Cpd. No. 152; ESI-MS m/z 599.58 (M+H)$^+$.
Cpd. No. 153; ESI-MS m/z 613.67 (M+H)$^+$.
Cpd. No. 154; ESI-MS m/z 613.67 (M+H)$^+$.
Cpd. No. 332; $^1$H-NMR (400 MHz, CD$_3$OD) δ ppm 7.66 (d, 2H, J=8.8 Hz), 7.50-7.30 (m, 5H), 6.53 (d, 2H, J=8.8 Hz), 4.17 (t, 1H, J=7.8 Hz), 3.77-3.69 (m, 2H), 3.54 (d, 3H, J=11.5 Hz), 3.49-3.37 (m, 6H), 3.24-2.96 (m, 2H), 2.61-2.47 (m, 2H), 2.46-2.35 (m, 1H), 2.32-2.17 (m, 2H), 2.08 (d, 1H, J=14.5 Hz), 2.00-1.88 (m, 1H), 1.88-1.71 (m, 4H), 1.63-1.46 (m, 1H), 1.41-1.27 (m, 1H), 1.19-1.11 (m, 2H), 1.03-0.95 (m, 2H); ESI-MS m/z 576.75 (M+H)$^+$.
Cpd. No. 333; $^1$H-NMR (400 MHz, CD$_3$OD) δ ppm 7.65 (d, 2H, J=8.8 Hz), 7.55-7.38 (m, 5H), 6.52 (d, 2H, J=8.8 Hz), 4.15 (t, 2H, J=7.9 Hz), 3.78 (s, 3H), 3.76-3.69 (m, 2H), 3.63-3.48 (m, 2H), 3.42 (d, 2H, J=7.1 Hz), 3.24-3.07 (m, 2H), 2.97-2.83 (m, 2H), 2.61-2.50 (m, 1H), 2.44-2.25 (m, 2H), 2.06 (d, 1H, J=14.6 Hz), 1.99-1.81 (m, 3H), 1.70-1.59 (m, 2H), 1.58-1.45 (m, 1H), 1.45-1.27 (m, 2H), 1.18-1.11 (m, 2H), 1.04-0.96 (m, 2H); ESI-MS m/z 576.42 (M+H)$^+$.
Cpd. No. 334; ESI-MS m/z 575.50 (M+H)$^+$.
Cpd. No. 335; ESI-MS m/z 589.58 (M+H)$^+$.
Cpd. No. 336; ESI-MS m/z 627.75 (M+H)$^+$.
Cpd. No. 337; ESI-MS m/z 627.58 (M+H)$^+$.
Cpd. No. 155; ESI-MS m/z 627.67 (M+H)$^+$.
Cpd. No. 338; ESI-MS m/z 583.67 (M+H)$^+$.
Cpd. No. 48; $^1$H-NMR (400 MHz, CD$_3$OD) δ ppm 8.76 (m, 2H), 7.83 (d, 2H, J=5.7 Hz), 7.76 (d, 2H, J=8.8 Hz), 7.56 (d, 1H, J=7.9 Hz), 7.46 (t, 1H, J=7.5 Hz), 7.40-7.29 (m, 2H), 6.49 (d, 2H, J=8.8 Hz), 4.46-4.25 (m, 2H), 4.24-4.11 (m, 2H), 3.87-3.70 (m, 4H), 3.56-3.37 (m, 5H), 3.09-2.89 (m, 2H), 2.24-2.04 (m, 2H), 1.93-1.78 (m, 2H), 1.78-1.59 (m, 6H), 1.51 (d, 6H, J=6.6 Hz), 1.38-1.06 (m, 2H); ESI-MS m/z 613.58 (M+H)$^+$.
Cpd. No. 49; ESI-MS m/z 625.58 (M+H)$^+$.
Cpd. No. 50; ESI-MS m/z 625.75 (M+H)$^+$.
Cpd. No. 156; ESI-MS m/z 627.58 (M+H)$^+$.
Cpd. No. 157; ESI-MS m/z 667.67 (M+H)$^+$.
Cpd. No. 339; ESI-MS m/z 627.25 (M+H)$^+$.
Cpd. No. 340; ESI-MS m/z 626.58 (M+H)$^+$.
Cpd. No. 158; ESI-MS m/z 650.50 (M+H)$^+$.
Cpd. No. 51; $^1$H-NMR (400 MHz, CD$_3$OD) δ ppm 8.76 (s, 2H), 7.83 (d, 2H, J=5.0 Hz), 7.76 (d, 2H, J=8.7 Hz), 7.55 (d, 1H, J=8.1 Hz), 7.43 (t, 1H, J=7.1 Hz), 7.37-7.25 (m, 2H), 6.50 (d, 2H, J=8.8 Hz), 4.33-4.22 (m, 2H), 4.18 (t, 2H, J=7.7 Hz), 3.79-3.72 (m, 2H), 3.60-3.47 (m, 4H), 3.47-3.39 (m, 4H), 3.08-2.90 (m, 2H), 2.62-2.49 (m, 1H), 2.32-2.19 (m, 1H), 2.15 (d, 1H, J=13.4 Hz), 1.90-1.72 (m, 4H), 1.69-1.44 (m, 8H), 1.35-1.22 (m, 1H), 1.19-1.02 (m, 1H); ESI-MS m/z 571.58 (M+H)$^+$.
Cpd. No. 52; ESI-MS m/z 641.93 (M+H)$^+$.
Cpd. No. 53; ESI-MS m/z 662.58 (M+H)$^+$.
Cpd. No. 54; ESI-MS m/z 684.50 (M+H)$^+$.
Cpd. No. 341; ESI-MS m/z 599.50 (M+H)$^+$.
Cpd. No. 342; ESI-MS m/z 599.50 (M+H)$^+$.
Cpd. No. 159; ESI-MS m/z 533.58 (M+H)$^+$.
Cpd. No. 160; ESI-MS m/z 649.75 (M+H)$^+$.

Cpd. No. 161; ¹H-NMR (400 MHz, CD₃OD) δ ppm 8.76 (d, 2H, J=4.8 Hz), 7.83 (d, 2H, J=4.7 Hz), 7.76 (d, 2H, J=7.6 Hz), 7.57 (d, 1H, J=8.1 Hz), 7.46 (t, 1H, J=7.3 Hz), 7.40-7.29 (m, 2H), 6.52 (d, 2H, J=8.0 Hz), 4.57-4.11 (m, 2H), 3.86 (d, 2H, J=7.9 Hz), 3.78 (d, 2H, J=7.9 Hz), 3.57-3.38 (m, 6H), 3.18-2.96 (m, 2H), 2.83-2.66 (m, 1H), 2.57-2.27 (m, 1H), 2.14 (d, 1H, J=13.6 Hz), 1.93-1.75 (m, 3H), 1.74-1.35 (m, 12H), 1.35-1.09 (m, 3H), 1.00-0.69 (m, 1H); ESI-MS m/z 613.58 (M+H)⁺.

Cpd. No. 343; ESI-MS m/z 578.42 (M+H)⁺.

Cpd. No. 344; ESI-MS m/z 451.75 (M+H)⁺.

Cpd. No. 162; ESI-MS m/z 636.50 (M+H)⁺.

Cpd. No. 163; ESI-MS m/z 520.50 (M+H)⁺.

Cpd. No. 347; ESI-MS m/z 627.75 (M+H)⁺.

Cpd. No. 348; ESI-MS m/z 627.50 (M+H)⁺.

Cpd. No. 351; ESI-MS m/z 671.83 (M+H)⁺.

Cpd. No. 352; ESI-MS m/z 671.42 (M+H)⁺.

Cpd. No. 164; ESI-MS m/z 642.58 (M+H)⁺.

Cpd. No. 392; ESI-MS m/z 686.67 (M+H)⁺.

Cpd. No. 393; ESI-MS m/z 619.42 (M+H)⁺.

Cpd. No. 394; ESI-MS m/z 645.50 (M+H)⁺.

Cpd. No. 395; ESI-MS m/z 625.50 (M+H)⁺.

Cpd. No. 396; ESI-MS m/z 645.75 (M+H)⁺.

Cpd. No. 397; ESI-MS m/z 649.58 (M+H)⁺.

Cpd. No. 398; ESI-MS m/z 645.50 (M+H)⁺.

Cpd. No. 399; ESI-MS m/z 670.42 (M+H)⁺.

Cpd. No. 400; ESI-MS m/z 512.58 (M+H)⁺.

Cpd. No. 401; ESI-MS m/z 555.58 (M+H)⁺.

Cpd. No. 402; ESI-MS m/z 487.58 (M+H)⁺.

Cpd. No. 404; ESI-MS m/z 495.67 (M+H)⁺.

Cpd. No. 405; ESI-MS m/z 602.58 (M+H)⁺.

Cpd. No. 1; MS (ESI) m/z: [M+H]⁺ calcd, 216.1; found, 217.4.

Cpd. No. 2; MS (ESI) m/z: [M+H]⁺ calcd, 286.1; found, 287.3.

Cpd. No. 3; MS (ESI) m/z: [M+H]⁺ calcd, 301.2; found, 302.4.

Cpd. No. 4; MS (ESI) m/z: [M+H]⁺ calcd, 375.2; found, 376.3.

Cpd. No. 5; MS (ESI) m/z: [M+H]⁺ calcd, 285.2; found, 286.3.

Cpd. No. 6; MS (ESI) m/z: [M+H]⁺ calcd, 355.2; found, 356.5.

Cpd. No. 7; MS (ESI) m/z: [M+H]⁺ calcd, 434.2; found, 435.5.

Cpd. No. 8; MS (ESI) m/z: [M+H]⁺ calcd, 433.3; found, 434.4.

Cpd. No. 9; MS (ESI) m/z: [M+H]⁺ calcd, 340.1; found, 341.4.

Cpd. No. 10; MS (ESI) m/z: [M+H]⁺ calcd, 464.1; found, 465.4.

Cpd. No. 11; MS (ESI) m/z: [M+H]⁺ calcd, 410.2; found, 411.4.

Cpd. No. 12; MS (ESI) m/z: [M+H]⁺ calcd, 489.2; found, 490.4.

Cpd. No. 13; MS (ESI) m/z: [M+H]⁺ calcd, 499.2; found, 500.3.

Cpd. No. 14; MS (ESI) m/z: [M+H]⁺ calcd, 623.2; found, 624.5.

Cpd. No. 15; MS (ESI) m/z: [M+H]⁺ calcd, 312.2; found, 313.3.

Cpd. No. 16; MS (ESI) m/z: [M+H]⁺ calcd, 285.2; found, 286.3.

Cpd. No. 17; MS (ESI) m/z: [M+H]⁺ calcd, 444.2; found, 445.3.

Cpd. No. 18; MS (ESI) m/z: [M+H]⁺ calcd, 443.3; found, 444.5.

Cpd. No. 19; ¹H NMR (400 MHz, MeOD) δ 7.73-7.63 (m, 2H), 7.58 (dt, J=11.2, 5.6 Hz, 1H), 7.48-7.40 (m, 1H), 7.40-7.26 (m, 2H), 7.13-7.02 (m, 2H), 4.43-4.22 (m, 2H), 4.17 (tt, J=14.2, 7.1 Hz, 2H), 3.75-3.52 (m, 3H), 3.48-3.37 (m, 1H), 3.31-3.25 (m, 1H), 3.02 (tdd, J=12.2, 11.4, 2.4 Hz, 2H), 2.65-2.52 (m, 1H), 2.36-2.22 (m, 3H), 2.22-2.13 (m, 1H), 1.93-1.75 (m, 4H), 1.71-1.47 (m, 6H), 1.40-1.26 (m, 1H), 1.21-1.05 (m, 1H). MS (ESI) m/z: [M+H]⁺ calcd, 443.3; found, 444.5.

Cpd. No. 20; ¹H NMR (400 MHz, MeOD) δ 7.66 (dd, J=9.2, 2.2 Hz, 2H), 7.54-7.43 (m, 4H), 7.40 (d, J=7.1 Hz, 1H), 7.06 (d, J=8.9 Hz, 2H), 4.16 (dd, J=13.4, 7.7 Hz, 2H), 3.73-3.56 (m, 2H), 3.30-3.20 (m, 2H), 3.18-2.98 (m, 2H), 2.93 (dd, J=16.1, 8.1 Hz, 1H), 2.43 (dd, J=16.9, 7.6 Hz, 1H), 2.31 (d, J=14.4 Hz, 1H), 2.20 (dt, J=15.8, 5.7 Hz, 2H), 2.14-1.95 (m, 2H), 1.86-1.68 (m, 2H), 1.68-1.53 (m, 4H), 1.53-1.37 (m, 2H), 1.28-1.14 (m, 1H). MS (ESI) m/z: [M+H]⁺ calcd, 427.3; found, 428.4.

Cpd. No. 21; ¹H NMR (400 MHz, MeOD) δ 8.05 (t, J=8.7 Hz, 1H), 7.67 (d, J=8.6 Hz, 2H), 7.63-7.55 (m, 1H), 7.53-7.45 (m, 1H), 7.41 (t, J=8.0 Hz, 1H), 7.06 (d, J=8.6 Hz, 2H), 4.15 (t, J=5.5 Hz, 2H), 3.64 (dd, J=25.6, 14.4 Hz, 4H), 3.31-3.20 (m, 2H), 3.02 (d, J=5.5 Hz, 2H), 2.91-2.74 (m, 1H), 2.67 (s, 1H), 2.25 (dt, J=14.7, 12.2 Hz, 3H), 2.08 (d, J=14.8 Hz, 1H), 1.91 (s, 2H), 1.81-1.39 (m, 6H), 1.17 (m, 2H). MS (ESI) m/z: [M+H]⁺ calcd, 457.3; found, 458.5.

Cpd. No. 22; MS (ESI) m/z: [M+H]⁺ calcd, 461.3; found, 462.4.

Cpd. No. 55; MS (ESI) m/z: [M+H]⁺ calcd, 468.3; found, 469.5.

Cpd. No. 56; MS (ESI) m/z: [M+H]⁺ calcd, 402.3; found, 403.5.

Cpd. No. 57; MS (ESI) m/z: [M+H]⁺ calcd, 346.2; found, 347.3.

Cpd. No. 58; MS (ESI) m/z: [M+H]⁺ calcd, 442.3; found, 443.5.

Cpd. No. 59; MS (ESI) m/z: [M+H]⁺ calcd, 443.3; found, 444.5.

Cpd. No. 60; ¹H NMR (400 MHz, MeOD) δ 7.68 (d, J=9.0 Hz, 2H), 7.59 (d, J=8.6 Hz, 1H), 7.55-7.44 (m, 2H), 7.40 (d, J=6.6 Hz, 1H), 7.06 (d, J=9.0 Hz, 2H), 4.36 (s, 2H), 4.09 (t, J=5.7 Hz, 2H), 3.86 (s, 1H), 3.69-3.57 (m, 1H), 3.41-3.36 (m, 2H), 3.28 (dt, J=3.3, 1.6 Hz, 1H), 3.20 (dd, J=18.2, 10.7 Hz, 2H), 3.13 (dd, J=13.6, 5.7 Hz, 3H), 2.87 (s, 1H), 2.02 (s, 2H), 1.91-1.79 (m, 2H), 1.77-1.51 (m, 4H), 1.20 (s, 1H). MS (ESI) m/z: [M+H]⁺ calcd, 415.3; found, 416.4.

Cpd. No. 61; MS (ESI) m/z: [M+H]⁺ calcd, 574.3; found, 575.4.

Cpd. No. 23; ¹H NMR (400 MHz, MeOD) δ 7.70-7.63 (m, 2H), 7.63-7.55 (m, 1H), 7.48 (t, J=7.7 Hz, 1H), 7.38 (t, J=7.5 Hz, 1H), 7.31 (d, J=7.6 Hz, 1H), 7.08 (d, J=8.8 Hz, 2H), 4.37 (s, 2H), 4.18 (t, J=5.4 Hz, 2H), 3.79-3.57 (m, 3H), 3.37 (dd, J=3.2, 1.6 Hz, 1H), 3.29 (dd, J=4.7, 3.1 Hz, 2H), 3.17 (s, 3H), 3.02 (dd, J=28.7, 15.3 Hz, 2H), 2.39-2.15 (m, 4H), 1.94-1.78 (m, 3H), 1.59 (d, J=6.8 Hz, 6H), 1.31 (s, 2H). MS (ESI) m/z: [M+H]⁺ calcd, 457.3; found, 458.5.

Cpd. No. 62; ¹H NMR (400 MHz, MeOD) δ 7.72-7.64 (m, 2H), 7.57 (d, J=7.0 Hz, 1H), 7.44 (dd, J=10.4, 6.0 Hz, 2H), 7.38 (t, J=7.1 Hz, 1H), 7.05 (d, J=8.9 Hz, 2H), 4.31 (s, 2H), 4.06 (t, J=5.8 Hz, 2H), 3.83 (s, 2H), 3.67-3.54 (m, 1H), 3.42-3.37 (m, 2H), 3.27 (dt, J=17.6, 8.0 Hz, 1H), 3.24-3.08 (m, 3H), 3.08-2.95 (m, 1H), 2.84 (s, 1H), 1.82 (s, 4H), 1.77-1.50 (m, 6H), 1.32 (s, 1H), 1.20 (s, 1H). MS (ESI) m/z: [M+H]⁺ calcd, 429.3; found, 430.4.

Cpd. No. 63; ¹H NMR (400 MHz, MeOD) δ 7.67 (dd, J=9.3, 2.3 Hz, 2H), 7.48-7.28 (m, 4H), 7.07 (dd, J=8.9, 7.1

Hz, 2H), 4.70-4.48 (m, 2H), 4.22-3.99 (m, 3H), 3.94-3.79 (m, 2H), 3.64 (s, 1H), 3.47 (dd, J=20.1, 8.5 Hz, 3H), 3.21-3.00 (m, 3H), 2.91 (d, J=12.0 Hz, 2H), 2.81 (s, 2H), 2.17 (s, 1H), 1.93 (d, J=5.9 Hz, 2H), 1.90-1.76 (m, 4H), 1.76-1.60 (m, 2H), 1.57 (d, J=19.4 Hz, 2H), 1.43-1.18 (m, 2H). MS (ESI) m/z: [M+H]$^+$ calcd, 457.3; found, 458.4.

Cpd. No. 64; MS (ESI) m/z: [M+H]$^+$ calcd, 521.3; found, 522.5.

Cpd. No. 165; MS (ESI) m/z: [M+H]$^+$ calcd, 383.2; found, 384.5.

Cpd. No. 166; MS (ESI) m/z: [M+H]$^+$ calcd, 327.3; found, 328.5.

Cpd. No. 167; MS (ESI) m/z: [M+H]$^+$ calcd, 325.3; found, 326.5.

Cpd. No. 168; MS (ESI) m/z: [M+H]$^+$ calcd, 466.3; found, 467.5.

Cpd. No. 169; MS (ESI) m/z: [M+H]$^+$ calcd, 505.2; found, 506.3.

Cpd. No. 170; MS (ESI) m/z: [M+H]$^+$ calcd, 530.3; found, 531.5.

Cpd. No. 171; MS (ESI) m/z: [M+H]$^+$ calcd, 477.3; found, 478.5.

Cpd. No. 65; MS (ESI) m/z: [M+H]$^+$ calcd, 525.4; found, 526.5.

Cpd. No. 66; MS (ESI) m/z: [M+H]$^+$ calcd, 452.3; found, 453.5.

Cpd. No. 67; MS (ESI) m/z: [M+H]$^+$ calcd, 452.3; found, 453.5.

Cpd. No. 24; $^1$H NMR (400 MHz, MeOD) δ 8.27 (d, J=7.7 Hz, 1H), 7.77 (dt, J=11.4, 7.2 Hz, 2H), 7.68 (d, J=8.9 Hz, 2H), 7.58 (t, J=7.3 Hz, 1H), 7.08 (d, J=8.9 Hz, 2H), 4.17 (t, J=5.7 Hz, 2H), 3.68 (d, J=11.7 Hz, 1H), 3.59 (d, J=10.5 Hz, 1H), 3.45-3.35 (m, 2H), 3.30-3.25 (m, 2H), 3.04 (dt, J=24.2, 12.4 Hz, 2H), 2.77 (dd, J=17.6, 7.6 Hz, 2H), 2.31-2.07 (m, 4H), 1.73 (dd, J=30.6, 13.0 Hz, 4H), 1.52 (d, J=7.9 Hz, 4H), 1.41-1.22 (m, 2H). MS (ESI) m/z: [M+H]$^+$ calcd, 457.3; found, 458.5.

Cpd. No. 68; MS (ESI) m/z: [M+H]$^+$ calcd, 510.3; found, 511.5.

Cpd. No. 172; MS (ESI) m/z: [M+H]$^+$ calcd, 445.3; found, 446.5.

Cpd. No. 25; MS (ESI) m/z: [M+H]$^+$ calcd, 611.3; found, 612.4.

Cpd. No. 26; MS (ESI) m/z: [M+H]$^+$ calcd, 487.3; found, 488.5.

Cpd. No. 173; MS (ESI) m/z: [M+H]$^+$ calcd, 429.3; found, 430.4.

Cpd. No. 69; MS (ESI) m/z: [M+H]$^+$ calcd, 535.3; found, 536.5.

Cpd. No. 70; $^1$H NMR (400 MHz, MeOD) δ 8.10-7.82 (m, 1H), 7.67 (d, J=8.7 Hz, 1H), 7.62-7.53 (m, 2H), 7.47 (d, J=6.5 Hz, 1H), 7.42-7.34 (m, 1H), 7.31 (d, J=6.2 Hz, 1H), 6.53 (d, J=8.7 Hz, 1H), 4.36 (s, 2H), 4.20 (s, 1H), 3.78 (s, 1H), 3.56 (s, 4H), 3.16 (s, 3H), 3.08-2.89 (m, 1H), 2.63-2.49 (m, 2H), 2.16 (s, 2H), 1.86 (s, 3H), 1.58 (s, 8H), 1.25 (dd, J=20.1, 17.7 Hz, 3H), 1.21-0.92 (m, 7H). MS (ESI) m/z: [M+H]$^+$ calcd, 547.3; found, 548.4.

Cpd. No. 174; MS (ESI) m/z: [M+H]$^+$ calcd, 457.3; found, 458.5.

Cpd. No. 175; MS (ESI) m/z: [M+H]$^+$ calcd, 457.3; found, 458.5.

Cpd. No. 176; $^1$H NMR (400 MHz, MeOD) δ 7.75-7.66 (m, 2H), 7.64-7.46 (m, 5H), 7.11 (dd, J=7.8, 6.0 Hz, 2H), 5.00 (s, 2H), 4.19 (d, J=5.5 Hz, 2H), 3.78-3.61 (m, 3H), 3.61-3.42 (m, 3H), 3.39-3.35 (m, 2H), 3.29 (dt, J=3.3, 1.7 Hz, 1H), 3.02-2.91 (m, 2H), 2.56 (s, 1H), 2.32 (d, J=5.5 Hz, 2H), 2.14 (s, 3H), 1.99 (ddd, J=43.6, 17.6, 11.4 Hz, 4H), 1.84-1.71 (m, 1H), 1.56-1.37 (m, 1H). MS (ESI) m/z: [M+H]$^+$ calcd, 457.3; found, 458.6.

Cpd. No. 177; MS (ESI) m/z: [M+H]$^+$ calcd, 457.3; found, 458.6.

Cpd. No. 178; MS (ESI) m/z: [M+H]$^+$ calcd, 507.3; found, 508.5.

Cpd. No. 179; MS (ESI) m/z: [M+H]$^+$ calcd, 507.3; found, 508.5.

Cpd. No. 180; MS (ESI) m/z: [M+H]$^+$ calcd, 521.3; found, 522.4.

Cpd. No. 181; MS (ESI) m/z: [M+H]$^+$ calcd, 521.3; found, 522.4.

Cpd. No. 182; MS (ESI) m/z: [M+H]$^+$ calcd, 569.2; found, 570.3.

Cpd. No. 183; MS (ESI) m/z: [M+H]$^+$ calcd, 549.3; found, 550.5.

Cpd. No. 184; MS (ESI) m/z: [M+H]$^+$ calcd, 549.3; found, 550.5.

Cpd. No. 185; $^1$H NMR (400 MHz, MeOD) δ 8.77 (s, 2H), 7.84 (dd, J=4.4, 1.7 Hz, 2H), 7.77 (dd, J=8.9, 2.6 Hz, 2H), 7.55-7.35 (m, 5H), 6.51 (dd, J=8.9, 2.6 Hz, 2H), 4.17 (t, J=8.0 Hz, 2H), 3.75 (d, J=5.8 Hz, 2H), 3.55 (t, J=11.4 Hz, 2H), 3.42 (d, J=6.9 Hz, 2H), 3.19 (m, 3H), 3.11-2.99 (m, 2H), 2.40 (d, J=11.9 Hz, 1H), 2.27 (d, J=10.6 Hz, 2H), 2.13-2.00 (m, 1H), 1.77 (m, 5H), 1.73-1.59 (m, 3H), 1.55 (d, J=12.4 Hz, 1H), 1.41 (d, J=12.4 Hz, 1H). MS (ESI) m/z: [M+H]$^+$ calcd, 612.3; found, 613.4.

Cpd. No. 186; MS (ESI) m/z: [M+H]$^+$ calcd, 612.3; found, 613.4.

Cpd. No. 187; $^1$H NMR (400 MHz, MeOD) δ 7.72-7.64 (m, 2H), 7.49 (q, J=7.2 Hz, 5H), 6.52 (d, J=8.5 Hz, 2H), 5.21 (s, 1H), 4.16 (t, J=7.8 Hz, 2H), 3.80-3.68 (m, 2H), 3.63-3.52 (m, 2H), 3.49-3.39 (m, 2H), 3.27-3.06 (m, 3H), 2.99 (t, J=11.9 Hz, 1H), 2.63-2.49 (m, 2H), 2.31 (d, J=14.6 Hz, 1H), 2.15-2.08 (m, 3H), 1.93 (dd, J=17.8, 12.2 Hz, 2H), 1.71 (m, 4H), 1.50 (m, 2H), 1.30 (dd, J=15.0, 5.4 Hz, 1H), 1.19-1.12 (m, 2H), 1.05-0.95 (m, 2H). MS (ESI) m/z: [M+H]$^+$ calcd, 575.3; found, 576.6.

Cpd. No. 188; MS (ESI) m/z: [M+H]$^+$ calcd, 575.3; found, 576.6.

Cpd. No. 189; MS (ESI) m/z: [M+H]$^+$ calcd, 535.3; found, 536.5.

Cpd. No. 190; MS (ESI) m/z: [M+H]$^+$ calcd, 554.3; found, 555.4

Cpd. No. 191; MS (ESI) m/z: [M+H]$^+$ calcd, 640.3; found, 641.5.

Cpd. No. 192; MS (ESI) m/z: [M+H]$^+$ calcd, 640.3; found, 641.5.

Cpd. No. 193; MS (ESI) m/z: [M+H]$^+$ calcd, 640.3; found, 641.4.

Cpd. No. 194; MS (ESI) m/z: [M+H]$^+$ calcd, 640.3; found, 641.5.

Cpd. No. 195; $^1$H NMR (400 MHz, MeOD) δ 8.65 (s, 2H), 7.72 (t, J=7.6 Hz, 2H), 7.64 (t, J=7.7 Hz, 2H), 7.43-7.31 (m, 5H), 6.39 (t, J=7.7 Hz, 2H), 5.08 (s, 1H), 4.05 (td, J=8.1, 1.9 Hz, 2H), 3.67-3.57 (m, 2H), 3.51-3.39 (m, 2H), 3.35-3.23 (m, 2H), 3.09 (dd, J=14.1, 7.2 Hz, 1H), 3.03-2.94 (m, 2H), 2.93-2.78 (m, 1H), 2.45 (t, J=12.2 Hz, 1H), 2.34-2.22 (m, 2H), 2.18 (d, J=14.4 Hz, 1H), 1.95-1.68 (m, 3H), 1.66-1.53 (m, 3H), 1.38 (dd, J=29.8, 15.6 Hz, 2H), 1.19 (ddd, J=12.9, 8.9, 5.2 Hz, 1H), 1.09-1.00 (m, 3H). MS (ESI) m/z: [M+H]$^+$ calcd, 626.3; found, 627.5.

Cpd. No. 196; MS (ESI) m/z: [M+H]$^+$ calcd, 626.3; found, 627.5.

Cpd. No. 197; $^1$H NMR (400 MHz, MeOD) δ 8.79 (s, 2H), 7.92-7.84 (m, 2H), 7.82-7.65 (m, 2H), 7.55-7.30 (m, 5H), 6.51 (d, J=8.9 Hz, 2H), 4.18 (t, J=8.1 Hz, 2H), 3.80-3.71 (m, 2H), 3.57 (dd, J=24.9, 11.1 Hz, 2H), 3.42 (d, J=7.1 Hz, 2H), 3.19 (ddd, J=11.8, 9.3, 5.0 Hz, 2H), 3.06 (dd, J=22.1, 10.8 Hz, 2H), 2.39 (d, J=11.3 Hz, 1H), 2.27 (d, J=11.0 Hz, 2H), 2.03 (d, J=18.9 Hz, 1H), 1.76 (d, J=30.7 Hz, 3H), 1.68 (dd, J=22.4, 12.6 Hz, 3H), 1.55 (d, J=12.9 Hz, 1H), 1.50-1.34 (m, 3H), 0.88-0.72 (m, 3H), 0.71-0.56 (m, 1H). MS (ESI) m/z: [M+H]$^+$ calcd, 638.3; found, 639.4.

Cpd. No. 198; MS (ESI) m/z: [M+H]$^+$ calcd, 638.3; found, 639.4.

Cpd. No. 199; MS (ESI) m/z: [M+H]$^+$ calcd, 598.3; found, 599.5.

Cpd. No. 200; MS (ESI) m/z: [M+H]$^+$ calcd, 626.3; found, 627.4.

Cpd. No. 201; $^1$H NMR (400 MHz, MeOD) δ 8.66 (d, J=5.4 Hz, 1H), 7.85 (s, 1H), 7.77 (t, J=5.8 Hz, 2H), 7.75 (d, J=5.4 Hz, 1H), 7.63 (d, J=7.7 Hz, 1H), 7.48 (t, J=7.3 Hz, 1H), 7.41 (t, J=7.5 Hz, 1H), 7.34 (d, J=7.6 Hz, 1H), 6.51 (d, J=8.9 Hz, 2H), 4.45 (s, 2H), 4.20 (t, J=8.0 Hz, 2H), 3.79 (s, 2H), 3.61 (s, 2H), 3.52 (d, J=13.7 Hz, 2H), 3.45 (d, J=6.6 Hz, 2H), 3.18 (s, 3H), 3.14 (d, J=8.1 Hz, 1H), 3.06 (d, J=12.2 Hz, 1H), 2.98 (d, J=10.8 Hz, 1H), 2.66 (s, 3H), 2.19-2.16 (m, 2H), 2.09-2.06 (m, 5H), 1.96 (s, 2H), 1.69 (s, 7H). MS (ESI) m/z: [M+H]$^+$ calcd, 656.3; found, 657.4.

Cpd. No. 202; MS (ESI) m/z: [M+H]$^+$ calcd, 656.3; found, 657.5.

Cpd. No. 203; MS (ESI) m/z: [M+H]$^+$ calcd, 605.3; found, 606.5.

Cpd. No. 204; MS (ESI) m/z: [M+H]$^+$ calcd, 605.3; found, 606.5.

Cpd. No. 205; MS (ESI) m/z: [M+H]$^+$ calcd, 596.3; found, 597.6.

Cpd. No. 206; $^1$H NMR (400 MHz, MeOD) δ 8.77 (d, J=5.6 Hz, 2H), 7.84 (dd, J=4.6, 1.6 Hz, 2H), 7.78 (d, J=8.8 Hz, 2H), 7.58 (d, J=7.7 Hz, 1H), 7.47 (t, J=7.6 Hz, 1H), 7.38 (t, J=7.5 Hz, 1H), 7.29 (d, J=7.5 Hz, 1H), 6.53 (t, J=12.2 Hz, 2H), 4.40 (s, 2H), 4.19 (t, J=8.1 Hz, 2H), 3.81-3.73 (m, 2H), 3.55 (d, J=11.8 Hz, 3H), 3.43 (d, J=7.0 Hz, 2H), 3.37 (dd, J=3.3, 1.7 Hz, 2H), 3.31-3.27 (m, 1H), 3.19 (d, J=15.5 Hz, 3H), 3.03-2.92 (m, 2H), 2.89 (s, 1H), 2.14 (s, 3H), 1.80 (s, 2H), 1.77 (m, 5H), 1.73-1.62 (m, 3H), 1.31 (s, 1H). MS (ESI) m/z: [M+H]$^+$ calcd, 642.3; found, 643.4.

Cpd. No. 207; MS (ESI) m/z: [M+H]$^+$ calcd, 612.3; found, 613.5.

Cpd. No. 208; $^1$H NMR (400 MHz, MeOD) δ 8.78 (s, 2H), 7.85 (d, J=4.5 Hz, 2H), 7.77 (d, J=8.5 Hz, 2H), 7.52-7.38 (m, 5H), 6.50 (d, J=8.5 Hz, 2H), 4.16 (t, J=7.7 Hz, 2H), 3.80-3.69 (m, 2H), 3.55 (s, 2H), 3.41 (d, J=6.8 Hz, 2H), 3.18 (d, J=10.2 Hz, 3H), 3.06 (d, J=11.5 Hz, 2H), 2.98-2.85 (m, 1H), 2.39 (s, 1H), 2.27 (s, 2H), 2.05 (dd, J=27.6, 8.6 Hz, 4H), 1.72 (dd, J=30.5, 20.9 Hz, 6H), 1.64 (s, 1H), 1.53 (d, J=11.5 Hz, 1H), 1.38 (d, J=12.3 Hz, 2H). MS (ESI) m/z: [M+H]$^+$ calcd, 652.3; found, 653.4.

Cpd. No. 209; MS (ESI) m/z: [M+H]$^+$ calcd, 652.3; found, 653.4.

Cpd. No. 211; $^1$H NMR (400 MHz, MeOD) δ 8.77 (d, J=5.6 Hz, 2H), 7.83 (dd, J=4.6, 1.5 Hz, 2H), 7.77 (d, J=8.8 Hz, 2H), 7.52-7.40 (m, 5H), 6.51 (d, J=8.9 Hz, 2H), 5.23 (d, J=6.9 Hz, 1H), 4.17 (td, J=8.1, 2.8 Hz, 2H), 3.79-3.70 (m, 2H), 3.55 (s, 2H), 3.41 (d, J=7.1 Hz, 2H), 3.16 (ddd, J=30.7, 19.7, 9.5 Hz, 4H), 2.93 (t, J=11.6 Hz, 1H), 2.50 (t, J=12.0 Hz, 1H), 2.29 (d, J=14.0 Hz, 1H), 2.17 (d, J=14.5 Hz, 1H), 2.08-1.93 (m, 1H), 1.80 (d, J=16.2 Hz, 3H), 1.75-1.61 (m, 2H), 1.43 (d, J=12.0 Hz, 2H), 1.34-1.19 (m, 1H). MS (ESI) m/z: [M+H]$^+$ calcd, 613.3; found, 614.6.

Cpd. No. 212; MS (ESI) m/z: [M+H]$^+$ calcd, 613.3; found, 614.6.

Cpd. No. 213; $^1$H NMR (400 MHz, MeOD) δ 8.79 (s, 2H), 7.86 (d, J=5.8 Hz, 2H), 7.82-7.74 (m, 2H), 7.44 (ddd, J=22.4, 18.2, 7.1 Hz, 5H), 6.51 (d, J=8.9 Hz, 2H), 4.17 (dd, J=8.0, 6.1 Hz, 2H), 3.79-3.69 (m, 2H), 3.56 (dd, J=23.5, 12.4 Hz, 2H), 3.42 (d, J=7.0 Hz, 2H), 3.20 (dd, J=20.0, 12.8 Hz, 2H), 3.12-2.93 (m, 5H), 2.43 (d, J=11.8 Hz, 1H), 2.32 (d, J=14.0 Hz, 1H), 2.21 (s, 1H), 1.99 (d, J=13.6 Hz, 1H), 1.72 (d, J=5.5 Hz, 5H), 1.54 (m, 3H), 1.03 (t, J=7.1 Hz, 3H). MS (ESI) m/z: [M+H]$^+$ calcd, 641.3; found, 642.4.

Cpd. No. 214; MS (ESI) m/z: [M+H]$^+$ calcd, 641.3; found, 642.4.

Cpd. No. 216; MS (ESI) m/z: [M+H]$^+$ calcd, 627.3; found, 628.4.

Cpd. No. 217; MS (ESI) m/z: [M+H]$^+$ calcd, 717.3; found, 718.5.

Cpd. No. 218; MS (ESI) m/z: [M+H]$^+$ calcd, 717.3; found, 718.5.

Cpd. No. 219; MS (ESI) m/z: [M+H]$^+$ calcd, 643.3; found, 644.5.

Cpd. No. 220; MS (ESI) m/z: [M+H]$^+$ calcd, 641.3; found, 642.5.

Cpd. No. 221; $^1$H NMR (400 MHz, MeOD) δ 8.77 (d, J=6.0 Hz, 2H), 7.83 (dd, J=4.6, 1.5 Hz, 2H), 7.78 (d, J=8.8 Hz, 2H), 7.58-7.42 (m, 5H), 6.53 (d, J=8.9 Hz, 2H), 4.18 (dd, J=7.8, 5.5 Hz, 2H), 3.87 (s, 2H), 3.78-3.71 (m, 2H), 3.60-3.49 (m, 3H), 3.43 (d, J=7.1 Hz, 2H), 3.20 (s, 1H), 3.12-3.00 (m, 3H), 2.44 (s, 2H), 2.33-2.17 (m, 3H), 1.98-1.9 (m, 2H), 1.60-1.80 (m, 5H), 1.30-1.49 (m, 3H). MS (ESI) m/z: [M+H]$^+$ calcd, 653.3; found, 654.4.

Cpd. No. 222; MS (ESI) m/z: [M+H]$^+$ calcd, 653.3; found, 654.4.

Cpd. No. 224; MS (ESI) m/z: [M+H]$^+$ calcd, 612.3; found, 613.5.

Cpd. No. 225; $^1$H NMR (400 MHz, MeOD) δ 7.90-7.81 (m, 2H), 7.73 (d, J=8.7 Hz, 2H), 7.59-7.38 (m, 8H), 6.57-6.39 (m, 2H), 4.14 (s, 2H), 3.70 (s, 2H), 3.54 (s, 2H), 3.39 (m, 3H), 3.23-2.98 (m, 3H), 2.89 (s, 1H), 2.74 (d, J=15.0 Hz, 2H), 2.58 (s, 3H), 2.46 (m, 2H), 1.96 (s, 1H), 1.69 (m, 4H), 1.49 (d, J=45.9 Hz, 1H), 1.31 (s, 1H). MS (ESI) m/z: [M+H]$^+$ calcd, 626.3; found, 627.4.

Cpd. No. 223; MS (ESI) m/z: [M+H]$^+$ calcd, 612.3; found, 613.5.

Cpd. No. 226; $^1$H NMR (400 MHz, MeOD) δ 7.72-7.63 (m, 2H), 7.54-7.37 (m, 5H), 6.52 (t, J=10.0 Hz, 2H), 4.18 (td, J=7.9, 2.6 Hz, 2H), 3.79-3.68 (m, 2H), 3.57 (dd, J=27.8, 11.5 Hz, 3H), 3.44 (t, J=7.1 Hz, 2H), 3.25-3.15 (m, 1H), 3.11 (d, J=36.0 Hz, 3H), 2.64-2.52 (m, 3H), 2.53-2.42 (m, 1H), 2.35 (d, J=13.2 Hz, 1H), 2.22 (s, 1H), 1.99 (d, J=14.3 Hz, 1H), 1.84-1.64 (m, 4H), 1.53 (dd, J=35.4, 22.4 Hz, 3H), 1.29-1.21 (m, 1H), 1.21-1.12 (m, 2H), 1.12-1.04 (m, 1H), 1.04-0.95 (m, 2H). MS (ESI) m/z: [M+H]$^+$ calcd, 590.3; found, 591.4.

Cpd. No. 227; MS (ESI) m/z: [M+H]$^+$ calcd, 590.3; found, 591.4.

Cpd. No. 228; $^1$H NMR (400 MHz, CDCl$_3$) δ 7.79 (d, J=8.7 Hz, 2H), 7.42 (t, J=17.0 Hz, 6H), 6.34 (d, J=8.6 Hz, 2H), 5.05 (s, 1H), 4.62 (s, 2H), 4.22-4.09 (m, 5H), 3.69 (s, 4H), 3.28 (s, 3H), 2.72 (d, J=37.7 Hz, 6H), 2.37 (s, 1H), 2.17 (d, J=13.0 Hz, 1H), 2.02 (s, 1H), 1.77 (s, 2H), 1.63 (s, 5H), 1.46 (s, 1H). MS (ESI) m/z: [M+H]$^+$ calcd, 708.2; found, 709.5.

Cpd. No. 229; MS (ESI) m/z: [M+H]$^+$ calcd, 708.2; found, 709.5.

Cpd. No. 230; $^1$H NMR (400 MHz, MeOD) δ 7.82-7.69 (m, 2H), 7.55-7.38 (m, 6H), 6.79 (d, J=2.0 Hz, 1H), 6.54 (dd, J=19.9, 8.8 Hz, 2H), 4.26-4.08 (m, 2H), 3.95 (s, 3H), 3.80-3.70 (m, 2H), 3.56 (dd, J=24.1, 12.0 Hz, 2H), 3.44 (d,

J=7.0 Hz, 2H), 3.33 (dt, J=3.1, 1.5 Hz, 3H), 3.28-3.18 (m, 1H), 3.06 (d, J=5.3 Hz, 3H), 2.55 (d, J=19.7 Hz, 2H), 2.46 (t, J=11.8 Hz, 1H), 2.33 (d, J=14.2 Hz, 1H), 2.20 (s, 1H), 1.98 (d, J=14.7 Hz, 1H), 1.83-1.65 (m, 4H), 1.65-1.40 (m, 3H). MS (ESI) m/z: [M+H]+ calcd, 630.3; found, 631.4.

Cpd. No. 231; MS (ESI) m/z: [M+H]+ calcd, 629.3; found, 630.5.

Cpd. No. 232; $^1$H NMR (400 MHz, CDCl$_3$) δ 11.72 (s, 1H), 7.57 (d, J=8.4 Hz, 2H), 7.50-7.30 (m, 5H), 6.89 (d, J=8.5 Hz, 2H), 5.07 (s, 1H), 4.72 (s, 1H), 4.06 (s, 2H), 3.74 (dd, J=35.4, 10.5 Hz, 2H), 3.19 (s, 2H), 2.92-2.59 (m, 6H), 2.42 (s, 1H), 2.26 (s, 3H), 2.04 (s, 2H), 1.78 (s, 2H), 1.59 (d, J=38.0 Hz, 4H), 1.49-1.20 (m, 1H). MS (ESI) m/z: [M+H]+ calcd, 500.3; found, 501.4.

Cpd. No. 233; $^1$H NMR (400 MHz, CDCl$_3$) δ 7.60 (d, J=8.8 Hz, 2H), 7.54-7.26 (m, 5H), 6.99 (d, J=8.7 Hz, 2H), 5.17 (s, 1H), 4.08 (t, J=5.2 Hz, 2H), 3.59 (t, J=12.2 Hz, 2H), 3.27 (d, J=1.2 Hz, 1H), 3.20 (dd, J=17.9, 10.3 Hz, 2H), 3.08 (d, J=11.7 Hz, 2H), 2.92-2.78 (m, 1H), 2.68 (d, J=15.1 Hz, 2H), 2.47 (dd, J=23.7, 11.6 Hz, 1H), 2.24 (d, J=14.5 Hz, 1H), 2.19-2.03 (m, 3H), 2.01-1.84 (m, 1H), 1.83-1.54 (m, 4H), 1.39 (d, J=6.4 Hz, 2H), 1.24 (dd, J=18.0, 8.9 Hz, 1H). MS (ESI) m/z: [M+H]+ calcd, 500.3; found, 501.4.

Cpd. No. 234; MS (ESI) m/z: [M+H]+ calcd, 640.3; found, 641.5.

Cpd. No. 235; MS (ESI) m/z: [M+H]+ calcd, 640.3; found, 641.5.

Cpd. No. 236; MS (ESI) m/z: [M+H]+ calcd, 681.3; found, 682.5.

Cpd. No. 237; MS (ESI) m/z: [M+H]+ calcd, 681.3; found, 682.5.

Cpd. No. 238; $^1$H NMR (400 MHz, MeOD) δ 8.82 (s, 1H), 8.11 (s, 1H), 7.77-7.71 (m, 3H), 7.68 (d, J=7.4 Hz, 2H), 7.53 (dd, J=14.7, 6.9 Hz, 3H), 7.43 (dd, J=16.3, 8.8 Hz, 2H), 6.48 (d, J=8.5 Hz, 2H), 4.15 (t, J=6.8 Hz, 2H), 3.95-3.87 (m, 3H), 3.72 (s, 2H), 3.63 (d, J=12.2 Hz, 1H), 3.41 (d, J=21.1 Hz, 4H), 3.25 (d, J=18.8 Hz, 2H), 3.13-3.01 (m, 1H), 2.94 (d, J=11.6 Hz, 1H), 2.85 (s, 1H), 2.71 (d, J=12.6 Hz, 3H), 2.55 (d, J=15.8 Hz, 1H), 2.29 (d, J=13.1 Hz, 1H), 1.99 (dd, J=35.5, 16.1 Hz, 2H), 1.75-1.57 (m, 2H), 1.57-1.36 (m, 4H), 1.12 (s, 1H), 0.90 (d, J=12.6 Hz, 1H). MS (ESI) m/z: [M+H]+ calcd, 685.3; found, 686.4.

Cpd. No. 239; MS (ESI) m/z: [M+H]+ calcd, 685.3; found, 686.4.

Cpd. No. 240; $^1$H NMR (400 MHz, MeOD) δ 8.11 (s, 1H), 7.72 (d, J=7.0 Hz, 2H), 7.66 (d, J=8.2 Hz, 1H), 7.56-7.32 (m, 5H), 6.70 (d, J=8.4 Hz, 1H), 6.47 (d, J=8.2 Hz, 1H), 5.22 (s, 1H), 4.13 (t, J=7.7 Hz, 1H), 3.98-3.84 (m, 3H), 3.70 (dd, J=12.7, 5.5 Hz, 2H), 3.63-3.51 (m, 2H), 3.42 (d, J=6.9 Hz, 1H), 3.24-3.06 (m, 4H), 2.98-2.84 (m, 1H), 2.79-2.68 (m, 3H), 2.50 (s, 1H), 2.28 (d, J=14.7 Hz, 2H), 2.12 (d, J=14.7 Hz, 1H), 1.97 (d, J=7.4 Hz, 1H), 1.77 (d, J=14.4 Hz, 2H), 1.66 (s, 2H), 1.46 (d, J=12.0 Hz, 2H), 1.33-1.19 (m, 1H). MS (ESI) m/z: [M+H]+ calcd, 630.3; found, 631.5.

Cpd. No. 241; MS (ESI) m/z: [M+H]+ calcd, 630.3; found, 631.5.

Cpd. No. 355; MS (ESI) m/z: [M+H]+ calcd, 609.3; found, 610.5.

Cpd. No. 356; MS (ESI) m/z: [M+H]+ calcd, 609.3; found, 610.5.

Cpd. No. 357; MS (ESI) m/z: [M+H]+ calcd, 613.3; found, 614.5.

Cpd. No. 358; MS (ESI) m/z: [M+H]+ calcd, 680.3; found, 681.4.

Cpd. No. 359; MS (ESI) m/z: [M+H]+ calcd, 680.3; found, 681.4.

Cpd. No. 360; MS (ESI) m/z: [M+H]+ calcd, 684.4; found, 685.5.

Cpd. No. 361; MS (ESI) m/z: [M+H]+ calcd, 684.4; found, 685.5.

Cpd. No. 362; $^1$H NMR (400 MHz, CDCl$_3$) δ 8.73 (s, 1H), 8.07 (d, J=8.3 Hz, 2H), 7.89 (d, J=8.3 Hz, 2H), 7.68 (d, J=8.7 Hz, 2H), 7.61 (s, 2H), 7.50-7.40 (m, 3H), 7.35 (dd, J=15.3, 8.6 Hz, 2H), 6.41 (d, J=8.2 Hz, 2H), 4.09 (s, 2H), 3.66 (s, 2H), 3.56 (s, 1H), 3.35 (s, 4H), 3.16 (s, 1H), 3.04-2.72 (m, 3H), 2.63 (d, J=9.3 Hz, 3H), 2.45 (s, 1H), 2.22 (s, 1H), 1.93 (s, 2H), 1.55 (s, 2H), 1.43 (s, 3H), 1.34-1.22 (m, 1H), 1.04 (s, 1H), 0.85 (s, 1H). MS (ESI) m/z: [M+H]+ calcd, 725.3; found, 726.5.

Cpd. No. 363; MS (ESI) m/z: [M+H]+ calcd, 725.3; found, 726.5.

Cpd. No. 364; MS (ESI) m/z: [M+H]+ calcd, 511.3; found, 512.5.

Cpd. No. 365; MS (ESI) m/z: [M+H]+ calcd, 566.3; found, 567.5.

Cpd. No. 367; MS (ESI) m/z: [M+H]+ calcd, 554.3; found, 555.5.

Cpd. No. 368; MS (ESI) m/z: [M+H]+ calcd, 554.3; found, 555.5.

Cpd. No. 369; MS (ESI) m/z: [M+H]+ calcd, 648.3; found, 649.5.

Cpd. No. 370; MS (ESI) m/z: [M+H]+ calcd, 648.3; found, 649.5.

Cpd. No. 371; MS (ESI) m/z: [M+H]+ calcd, 644.3; found, 645.5.

Cpd. No. 372; MS (ESI) m/z: [M+H]+ calcd, 644.3; found, 645.5.

Cpd. No. 373; MS (ESI) m/z: [M+H]+ calcd, 544.3; found, 545.5.

Cpd. No. 374; MS (ESI) m/z: [M+H]+ calcd, 544.3; found, 545.5.

Cpd. No. 27; $^1$H NMR (400 MHz, CDCl$_3$) δ 7.57 (d, J=8.4 Hz, 2H), 7.36-7.29 (m, 2H), 7.23-7.15 (m, 2H), 6.90 (d, J=8.5 Hz, 2H), 4.10 (s, 2H), 3.84-3.71 (m, 1H), 3.67-3.52 (m, 2H), 3.49-3.36 (m, 1H), 3.27-2.93 (m, 4H), 2.90-2.72 (m, 3H), 2.58-2.43 (m, 1H), 2.36-2.17 (m, 4H), 2.06-1.84 (m, 2H), 1.77-1.45 (m, 4H), 1.37-1.12 (m, 2H). MS (ESI) m/z 444.3 [M+H]+.

Cpd. No. 72; $^1$H NMR (400 MHz, DMSO) δ 7.43-7.38 (m, 1H), 7.34-7.26 (m, 3H), 3.49-3.41 (m, 1H), 3.30 (t, J=11.6 Hz, 3H), 3.00 (t, J=5.9 Hz, 2H), 2.96-2.89 (m, 1H), 2.86-2.74 (m, 2H), 2.41-2.30 (m, 1H), 1.98 (d, J=13.1 Hz, 1H), 1.89-1.79 (m, 1H), 1.70-1.39 (m, 7H), 1.35-1.18 (m, 3H). MS (ESI) m/z 285.2 [M+H]+.

Cpd. No. 242; MS (ESI) m/z 432.3 [M+H]+.

Cpd. No. 73; $^1$H NMR (400 MHz, CDCl$_3$) δ 7.35-7.29 (m, 2H), 7.24-7.17 (m, 2H), 3.72 (d, J=10.7 Hz, 1H), 3.62-3.53 (m, 2H), 3.47-3.39 (m, 3H), 3.15-2.93 (m, 4H), 2.90-2.63 (m, 3H), 2.51-2.39 (m, 1H), 2.35-2.17 (m, 2H), 2.06-1.87 (m, 4H), 1.78-1.45 (m, 6H), 1.37-1.24 (m, 1H), 1.23-1.08 (m, 1H). MS (ESI) m/z 357.3 [M+H]+.

Cpd. No. 74; $^1$H NMR (400 MHz, DMSO) δ 7.44-7.39 (m, 1H), 7.37-7.25 (m, 3H), 4.06 (s, 2H), 3.54-3.44 (m, 3H), 3.33 (t, J=6.8 Hz, 4H), 3.29-3.18 (m, 1H), 3.07-2.97 (m, 2H), 2.96-2.86 (m, 2H), 2.27-2.15 (m, 1H), 2.05-1.95 (m, 1H), 1.93-1.84 (m, 5H), 1.83-1.75 (m, 2H), 1.69-1.52 (m, 3H), 1.49-1.33 (m, 4H), 1.30-1.15 (m, 2H). MS (ESI) m/z 396.2 [M+H]+.

Cpd. No. 75; MS (ESI) m/z 299.2 [M+H]+.
Cpd. No. 76; MS (ESI) m/z 419.3 [M+H]+.
Cpd. No. 243; MS (ESI) m/z 466.2 [M+H]+.
Cpd. No. 244; MS (ESI) m/z 492.3 [M+H]+.
Cpd. No. 245; MS (ESI) m/z 446.3 [M+H]+.

Cpd. No. 246; $^1$H NMR (400 MHz, DMSO) δ 7.78 (d, J=8.5 Hz, 2H), 7.52-7.38 (m, 6H), 7.36 (d, J=8.2 Hz, 1H), 7.29 (d, J=7.5 Hz, 2H), 7.09 (d, J=8.6 Hz, 2H), 4.14 (t, J=5.9 Hz, 2H), 3.58 (t, J=8.6 Hz, 2H), 3.49-3.36 (m, 1H), 3.25-3.03 (m, 5H), 3.00-2.86 (m, 2H), 2.79-2.68 (m, 1H), 2.18-2.06 (m, 2H), 1.99-1.83 (m, 2H), 1.73 (d, J=14.5 Hz, 1H), 1.62-1.49 (m, 1H). MS (ESI) m/z 452.2 [M+H]$^+$.

Cpd. No. 77; $^1$H NMR (400 MHz, MeOD) δ 7.79-7.71 (m, 4H), 7.61 (d, J=8.8 Hz, 2H), 7.47 (d, J=7.0 Hz, 1H), 7.38-7.33 (m, 2H), 7.33-7.27 (m, 1H), 7.13 (d, J=8.9 Hz, 2H), 3.95 (d, J=12.1 Hz, 1H), 3.83 (d, J=12.7 Hz, 1H), 3.56-3.46 (m, 2H), 3.11-3.06 (m, 2H), 2.99-2.91 (m, 1H), 2.90-2.82 (m, 1H), 2.80-2.70 (m, 1H), 2.51 (t, J=11.8 Hz, 1H), 2.14 (d, J=12.5 Hz, 1H), 1.99-1.90 (m, 1H), 1.89-1.82 (m, 1H), 1.70-1.55 (m, 7H), 1.36-1.28 (m, 1H), 1.21-1.10 (m, 1H). MS (ESI) m/z 462.3 [M+H]$^+$.

Cpd. No. 247; $^1$H NMR (400 MHz, DMSO) δ 7.79 (d, J=8.2 Hz, 2H), 7.41-7.28 (m, 4H), 7.10 (d, J=8.4 Hz, 2H), 4.15 (t, J=5.8 Hz, 2H), 3.62 (d, J=11.8 Hz, 1H), 3.55-3.43 (m, 2H), 3.30-3.08 (m, 5H), 3.06-2.86 (m, 3H), 2.66-2.54 (m, 1H), 2.19-2.08 (m, 2H), 2.00-1.65 (m, 7H), 1.59-1.40 (m, 3H). MS (ESI) m/z 430.3 [M+H]$^+$.

Cpd. No. 78; $^1$H NMR (400 MHz, CDCl$_3$) δ 8.81 (d, J=5.2 Hz, 2H), 7.91 (d, J=5.4 Hz, 2H), 7.50-7.41 (m, 2H), 7.41-7.36 (m, 1H), 7.35-7.30 (m, 1H), 3.72-3.62 (m, 1H), 3.38-3.25 (m, 1H), 3.20-3.04 (m, 2H), 2.87 (d, J=16.7 Hz, 1H), 1.88-1.71 (m, 3H), 1.70-1.57 (m, 4H), 1.56-1.45 (m, 1H). MS (ESI) m/z 279.2 [M+H]$^+$.

Cpd. No. 79; MS (ESI) m/z 442.3 [M+H]$^+$.

Cpd. No. 80; MS (ESI) m/z 467.3 [M+H]$^+$.

Cpd. No. 81; MS (ESI) m/z 467.3 [M+H]$^+$.

Cpd. No. 248; MS (ESI) m/z 524.3 [M+H]$^+$.

Cpd. No. 28; MS (ESI) m/z 458.3 [M+H]$^+$.

Cpd. No. 249; $^1$H NMR (400 MHz, MeOD) δ 7.65 (d, J=8.9 Hz, 2H), 7.48-7.27 (m, 4H), 7.05 (d, J=8.9 Hz, 2H), 4.14 (t, J=5.8 Hz, 2H), 3.70 (d, J=11.3 Hz, 1H), 3.65-3.55 (m, 2H), 3.38-3.32 (m, 1H), 3.29-3.22 (m, 2H), 3.14-3.05 (m, 3H), 3.04-2.96 (m, 1H), 2.59 (t, J=11.6 Hz, 1H), 2.25-2.16 (m, 3H), 2.09 (d, J=14.1 Hz, 2H), 2.02-1.91 (m, 1H), 1.90-1.79 (m, 1H), 1.54-1.42 (m, 1H), 1.39-1.32 (m, 2H), 1.24-1.17 (m, 1H), 1.13 (t, J=7.4 Hz, 3H), 0.92 (t, J=7.4 Hz, 3H). MS (ESI) m/z 446.3 [M+H]$^+$.

Cpd. No. 250; $^1$H NMR (400 MHz, MeOD) δ 7.68 (d, J=8.2 Hz, 2H), 7.44-7.31 (m, 4H), 7.09 (d, J=8.2 Hz, 2H), 4.20 (t, J=5.7 Hz, 2H), 3.79 (d, J=12.5 Hz, 1H), 3.72-3.63 (m, 2H), 3.50-3.40 (m, 1H), 3.16-3.11 (m, 2H), 3.10-2.93 (m, 2H), 2.51 (t, J=11.6 Hz, 1H), 2.34-2.16 (m, 6H), 2.06-1.88 (m, 3H), 1.63-1.52 (m, 2H), 1.36-1.23 (m, 1H), 1.12-0.99 (m, 1H), 0.96-0.88 (m, 6H). MS (ESI) m/z 446.3 [M+H]$^+$.

Cpd. No. 251; $^1$H NMR (400 MHz, MeOD) δ 7.65 (d, J=8.8 Hz, 2H), 7.40-7.27 (m, 4H), 7.06 (d, J=8.8 Hz, 2H), 4.18 (t, J=5.7 Hz, 2H), 3.81-3.59 (m, 3H), 3.44-3.33 (m, 1H), 3.28-3.24 (m, 1H), 3.18-3.12 (m, 2H), 3.05-2.91 (m, 2H), 2.42 (d, J=12.9 Hz, 1H), 2.30-2.23 (m, 2H), 2.21-2.14 (m, 2H), 2.10-2.02 (m, 1H), 1.99-1.82 (m, 2H), 1.66 (t, J=13.3 Hz, 1H), 1.60-1.48 (m, 3H), 1.45-1.34 (m, 1H), 1.31-1.20 (m, 3H), 1.16-0.99 (m, 1H), 0.87-0.74 (m, 1H). MS (ESI) m/z 472.3 [M+H]$^+$.

Cpd. No. 252; $^1$H NMR (400 MHz, MeOD) δ 7.66 (d, J=8.4 Hz, 2H), 7.43-7.26 (m, 4H), 7.07 (d, J=8.5 Hz, 2H), 4.18 (t, J=5.7 Hz, 2H), 3.80 (d, J=11.8 Hz, 1H), 3.72-3.60 (m, 2H), 3.48-3.38 (m, 2H), 3.18-3.12 (m, 2H), 3.09-2.92 (m, 2H), 2.55 (t, J=11.9 Hz, 1H), 2.31-2.15 (m, 4H), 2.09-2.02 (m, 1H), 1.99-1.86 (m, 2H), 1.56-1.43 (m, 2H), 1.37-1.24 (m, 3H), 1.23-1.13 (m, 1H), 1.12-1.01 (m, 1H), 0.81 (t, J=7.3 Hz, 3H), 0.71 (t, J=7.3 Hz, 3H). MS (ESI) m/z 460.3 [M+H]$^+$.

Cpd. No. 82; MS (ESI) m/z 444.3 [M+H]$^+$.

Cpd. No. 83; $^1$H NMR (400 MHz, MeOD, a mixture of rotamers) δ 7.61-7.55 (m, 2H), 7.46 (d, J=7.0 Hz, 1H), 7.42-7.30 (m, 4H), 4.79 (s, 1.2H) and 4.66 (s, 0.8H), 4.28 (s, 2H), 3.83 (t, J=5.9 Hz, 1H), 3.74-3.56 (m, 4H), 3.51-3.37 (m, 2H), 3.17-3.08 (m, 3H), 3.01 (t, J=5.7 Hz, 1H), 2.94-2.90 (m, 1H), 2.90-2.83 (m, 1H), 2.60-2.46 (m, 1H), 2.22 (d, J=14.0 Hz, 1H), 2.05-1.90 (m, 3H), 1.79-1.61 (m, 5H), 1.60-1.52 (m, 1H), 1.44-1.27 (m, 2H). MS (ESI) m/z 483.3 [M+H]$^+$.

Cpd. No. 84; $^1$H NMR (400 MHz, MeOD) δ 8.09 (d, J=7.7 Hz, 1H), 7.63-7.57 (m, 1H), 7.49-7.43 (m, 2H), 7.40-7.30 (m, 4H), 4.74 (s, 1H), 4.17-4.12 (m, 1H), 4.02 (s, 1H), 3.77-3.67 (m, 2H), 3.64-3.55 (m, 1H), 3.53-3.43 (m, 2H), 3.22-3.14 (m, 2H), 3.14-3.05 (m, 3H), 3.01-2.94 (m, 1H), 2.90-2.82 (m, 1H), 2.64-2.53 (m, 1H), 2.28-2.17 (m, 1H), 2.06-1.87 (m, 4H), 1.79-1.61 (m, 6H), 1.59-1.52 (m, 1H), 1.47-1.38 (m, 1H), 1.35-1.24 (m, 1H). MS (ESI) m/z 458.3 [M+H]$^+$.

Cpd. No. 85; MS (ESI) m/z 548.3 [M+H]$^+$.

Cpd. No. 86; $^1$H NMR (400 MHz, MeOD) δ 7.63 (d, J=8.8 Hz, 2H), 7.46-7.41 (m, 1H), 7.40-7.34 (m, 2H), 7.34-7.29 (m, 1H), 6.51 (d, J=8.8 Hz, 2H), 4.18 (t, J=8.0 Hz, 2H), 3.81-3.74 (m, 2H), 3.65 (d, J=12.6 Hz, 1H), 3.59-3.42 (m, 6H), 3.21 (d, J=7.2 Hz, 2H), 3.13-3.00 (m, 3H), 2.85-2.70 (m, 1H), 2.69-2.54 (m, 2H), 2.25 (d, J=14.5 Hz, 1H), 2.02-1.92 (m, 4H), 1.92-1.83 (m, 2H), 1.82-1.71 (m, 6H), 1.69-1.56 (m, 4H), 1.55-1.45 (m, 1H), 1.30-1.14 (m, 1H). MS (ESI) m/z 562.3 [M+H]$^+$.

Cpd. No. 87; MS (ESI) m/z 550.3 [M+H]$^+$.

Cpd. No. 88; $^1$H NMR (400 MHz, MeOD) δ 7.57 (d, J=8.8 Hz, 2H), 7.47-7.42 (m, 1H), 7.40-7.35 (m, 2H), 7.34-7.29 (m, 1H), 6.52 (d, J=8.9 Hz, 2H), 4.17 (t, J=8.0 Hz, 2H), 3.79-3.73 (m, 2H), 3.65 (d, J=11.3 Hz, 1H), 3.60-3.43 (m, 5H), 3.28-3.21 (m, 1H), 3.15-3.00 (m, 4H), 2.81-2.75 (m, 1H), 2.69-2.64 (m, 1H), 2.61 (s, 6H), 2.25 (d, J=14.1 Hz, 1H), 2.04-1.91 (m, 2H), 1.85-1.73 (m, 3H), 1.72-1.56 (m, 4H), 1.54-1.44 (m, 1H), 1.27-1.14 (m, 1H). MS (ESI) m/z 537.3 [M+H]$^+$.

Cpd. No. 89; $^1$H NMR (400 MHz, MeOD) δ 7.82 (d, J=8.9 Hz, 2H), 7.47-7.41 (m, 1H), 7.39-7.35 (m, 2H), 7.34-7.29 (m, 1H), 7.05 (d, J=8.9 Hz, 2H), 4.74-4.64 (m, 1H), 3.65-3.52 (m, 3H), 3.50-3.40 (m, 2H), 3.14-3.07 (m, 2H), 3.06-2.99 (m, 2H), 2.96-2.86 (m, 2H), 2.85-2.76 (m, 1H), 2.65-2.56 (m, 1H), 2.47-2.35 (m, 2H), 2.25 (d, J=13.9 Hz, 1H), 2.00-1.84 (m, 3H), 1.78-1.54 (m, 6H), 1.50-1.39 (m, 1H), 1.32-1.23 (m, 1H), 1.22-1.16 (m, 2H), 1.06-0.99 (m, 2H). MS (ESI) m/z 535.3 [M+H]$^+$.

Cpd. No. 90; MS (ESI) m/z 535.3 [M+H]$^+$.

Cpd. No. 91; $^1$H NMR (400 MHz, MeOD) δ 7.66 (d, J=7.6 Hz, 2H), 7.44 (d, J=6.6 Hz, 1H), 7.41-7.35 (m, 2H), 7.32 (t, J=5.2 Hz, 1H), 6.51 (d, J=7.8 Hz, 2H), 4.22-4.11 (m, 2H), 3.77 (t, J=6.6 Hz, 2H), 3.64 (d, J=11.4 Hz, 1H), 3.60-3.43 (m, 5H), 3.29-3.21 (m, 1H), 3.16 (d, J=6.7 Hz, 2H), 3.12-3.01 (m, 4H), 2.82-2.73 (m, 1H), 2.65 (t, J=12.1 Hz, 1H), 2.25 (d, J=14.0 Hz, 1H), 2.16-2.07 (m, 1H), 2.04-1.90 (m, 3H), 1.86-1.75 (m, 6H), 1.71-1.56 (m, 6H), 1.56-1.44 (m, 4H), 1.30-1.15 (m, 3H). MS (ESI) m/z 576.3 [M+H]$^+$.

Cpd. No. 92; $^1$H NMR (400 MHz, MeOD) δ 7.61 (d, J=7.4 Hz, 2H), 7.45 (d, J=6.5 Hz, 1H), 7.41-7.29 (m, 3H), 6.52 (d, J=7.6 Hz, 2H), 4.19 (t, J=8.0 Hz, 2H), 3.78 (t, J=6.7 Hz, 2H), 3.65 (d, J=11.9 Hz, 1H), 3.60-3.44 (m, 5H), 3.29-3.22 (m, 1H), 3.16-3.01 (m, 4H), 2.98-2.87 (m, 1H), 2.84-2.73 (m, 1H), 2.70-2.58 (m, 1H), 2.25 (d, J=14.8 Hz, 1H), 2.06-1.91 (m, 4H), 1.89-1.73 (m, 5H), 1.72-1.60 (m, 4H), 1.58-1.43 (m, 2H), 1.38-1.19 (m, 5H), 1.19-1.05 (m, 1H). MS (ESI) m/z 576.4 [M+H]$^+$.

Cpd. No. 93; $^1$H NMR (400 MHz, MeOD) δ 7.66 (d, J=7.3 Hz, 2H), 7.45 (d, J=7.1 Hz, 1H), 7.40-7.29 (m, 3H), 6.52 (d, J=7.4 Hz, 4H), 4.18 (t, J=7.9 Hz, 2H), 3.84-3.74 (m, 2H), 3.64 (d, J=12.1 Hz, 1H), 3.59-3.42 (m, 5H), 3.29-3.19 (m, 1H), 3.15-3.04 (m, 3H), 3.00 (d, J=4.8 Hz, 2H), 2.84-2.73 (m, 1H), 2.65 (t, J=11.9 Hz, 1H), 2.26 (d, J=13.8 Hz, 1H), 2.07-1.92 (m, 2H), 1.87-1.73 (m, 6H), 1.72-1.56 (m, 7H), 1.55-1.40 (m, 2H), 1.31-1.14 (m, 4H), 1.11-0.98 (m, 2H). MS (ESI) m/z 590.3 [M+H]$^+$.

Cpd. No. 94; MS (ESI) m/z 576.3 [M+H]$^+$.

Cpd. No. 95; MS (ESI) m/z 576.3 [M+H]$^+$.

Cpd. No. 96; MS (ESI) m/z 576.3 [M+H]$^+$.

Cpd. No. 97; $^1$H NMR (400 MHz, MeOD) δ 7.64 (d, J=5.4 Hz, 2H), 7.48-7.41 (m, 1H), 7.41-7.30 (m, 3H), 6.54 (d, J=8.8 Hz, 2H), 4.21 (t, J=8.0 Hz, 2H), 4.03-3.93 (m, 2H), 3.82-3.75 (m, 2H), 3.68-3.49 (m, 4H), 3.46 (d, J=6.8 Hz, 2H), 3.39-3.34 (m, 2H), 3.28-3.19 (m, 2H), 3.14-2.99 (m, 4H), 2.85-2.74 (m, 1H), 2.66-2.55 (m, 1H), 2.24 (d, J=14.3 Hz, 1H), 2.00-1.92 (m, 2H), 1.85-1.72 (m, 5H), 1.70-1.54 (m, 7H), 1.51-1.40 (m, 1H), 1.33-1.16 (m, 1H). MS (ESI) m/z 578.3 [M+H]$^+$.

Cpd. No. 98; $^1$H NMR (400 MHz, MeOD) δ 7.65 (d, J=8.8 Hz, 2H), 7.47-7.42 (m, 1H), 7.40-7.34 (m, 2H), 7.34-7.29 (m, 1H), 6.88 (s, 1H), 6.84 (dd, J=4.0, 1.8 Hz, 1H), 6.48 (d, J=8.7 Hz, 2H), 6.13 (dd, J=3.9, 2.7 Hz, 1H), 4.17 (t, J=7.8 Hz, 2H), 3.75 (t, J=6.0 Hz, 2H), 3.65 (s, 3H), 3.63-3.47 (m, 4H), 3.44 (d, J=6.6 Hz, 2H), 3.28-3.19 (m, 1H), 3.15-2.96 (m, 4H), 2.85-2.71 (m, 1H), 2.68-2.54 (m, 1H), 2.24 (d, J=13.5 Hz, 1H), 2.02-1.90 (m, 2H), 1.87-1.40 (m, 8H), 1.31-1.12 (m, 1H). MS (ESI) m/z 573.3 [M+H]$^+$.

Cpd. No. 99; MS (ESI) m/z 541.3 [M+H]$^+$.

Cpd. No. 100; $^1$H NMR (400 MHz, MeOD) δ 7.88-7.74 (m, 2H), 7.57-7.21 (m, 7H), 7.16-6.97 (m, 2H), 4.73 (s, 2H), 4.00 (s, 2H), 3.86-3.71 (m, 2H), 3.49-3.41 (m, 1H), 3.28-3.11 (m, 3H), 2.90-2.74 (m, 3H), 2.69-2.58 (m, 1H), 2.00-1.87 (m, 1H), 1.81-1.60 (m, 5H), 1.57-1.45 (m, 2H), 1.25-1.16 (m, 2H), 1.08-1.00 (m, 2H). MS (ESI) m/z 555.2 [M+H]$^+$.

Cpd. No. 253; $^1$H NMR (400 MHz, MeOD) δ 9.09 (d, J=5.2 Hz, 2H), 8.59-8.45 (m, 2H), 7.93-7.77 (m, 2H), 7.64-7.36 (m, 5H), 7.06-6.82 (m, 2H), 4.61-4.16 (m, 2H), 3.93-3.59 (m, 4H), 3.56-3.36 (m, 3H), 3.27-2.97 (m, 4H), 2.81-2.72 (m, 3H), 2.70-2.56 (m, 1H), 2.52-2.32 (m, 1H), 2.28-2.01 (m, 2H), 2.00-1.52 (m, 9H), 1.51-1.36 (m, 1H). MS (ESI) m/z 663.2 [M+H]$^+$.

Cpd. No. 254; $^1$H NMR (400 MHz, MeOD) δ 9.10 (d, J=5.3 Hz, 2H), 8.52 (d, J=5.5 Hz, 2H), 7.81 (d, J=8.8 Hz, 2H), 7.57-7.36 (m, 5H), 6.89 (d, J=8.9 Hz, 2H), 4.75 (dd, J=34.7, 11.9 Hz, 2H), 4.59-4.25 (m, 2H), 3.75-3.59 (m, 4H), 3.46-3.35 (m, 2H), 3.25-3.09 (m, 3H), 3.10-2.98 (m, 3H), 2.88-2.55 (m, 3H), 2.31-2.20 (m, 1H), 2.00-1.80 (m, 3H), 1.77-1.62 (m, 3H), 1.59-1.40 (m, 3H), 1.32-1.12 (m, 1H). MS (ESI) m/z 663.2 [M+H]$^+$.

Cpd. No. 255; $^1$H NMR (400 MHz, MeOD) δ 8.79 (s, 2H), 7.85 (d, J=4.4 Hz, 2H), 7.80-7.76 (m, 2H), 7.60 (d, J=7.3 Hz, 2H), 7.54 (t, J=7.3 Hz, 2H), 7.50-7.42 (m, 1H), 6.55-6.49 (m, 2H), 4.17 (t, J=8.1 Hz, 2H), 3.79-3.70 (m, 2H), 3.55 (t, J=11.6 Hz, 2H), 3.42 (d, J=6.9 Hz, 2H), 3.26-3.16 (m, 1H), 3.07 (dd, J=25.3, 12.3 Hz, 2H), 2.94-2.80 (m, 1H), 2.63 (d, J=14.3 Hz, 1H), 2.50-2.43 (m, 1H), 2.42 (s, 3H), 2.31-2.06 (m, 4H), 1.94-1.58 (m, 6H), 1.39-1.22 (m, 1H). MS (ESI) m/z 647.3 [M+H]$^+$.

Cpd. No. 256; $^1$H NMR (400 MHz, MeOD) δ 8.78 (d, J=4.4 Hz, 2H), 7.84 (d, J=4.7 Hz, 2H), 7.78 (d, J=8.6 Hz, 2H), 7.57-7.38 (m, 5H), 6.53 (d, J=8.7 Hz, 2H), 4.19 (t, J=7.0 Hz, 2H), 3.81-3.73 (m, 2H), 3.63 (d, J=10.7 Hz, 1H), 3.53-3.43 (m, 4H), 3.39-3.35 (m, 1H), 3.26-3.18 (m, 1H), 3.17-3.09 (m, 1H), 3.05 (s, 3H), 3.01 (d, J=10.6 Hz, 1H), 2.92-2.85 (m, 1H), 2.69-2.54 (m, 2H), 2.38 (d, J=14.5 Hz, 1H), 2.01 (d, J=14.8 Hz, 1H), 1.94-1.79 (m, 2H), 1.77-1.53 (m, 4H), 1.49-1.29 (m, 2H). MS (ESI) m/z 647.3 [M+H]$^+$.

Cpd. No. 257; $^1$H NMR (400 MHz, MeOD) δ 8.77 (d, J=6.0 Hz, 2H), 7.83 (d, J=6.1 Hz, 2H), 7.78 (d, J=8.9 Hz, 2H), 7.55 (d, J=7.3 Hz, 2H), 7.49 (t, J=7.6 Hz, 2H), 7.45-7.39 (m, 1H), 6.52 (d, J=8.9 Hz, 2H), 4.18 (t, J=7.8 Hz, 2H), 3.77-3.70 (m, 2H), 3.54 (d, J=11.6 Hz, 2H), 3.41 (d, J=7.1 Hz, 2H), 3.23-3.13 (m, 2H), 3.12-3.00 (m, 3H), 2.69 (dd, J=13.2, 8.2 Hz, 1H), 2.43 (t, J=12.3 Hz, 1H), 2.29 (d, J=14.3 Hz, 1H), 2.19-2.06 (m, 2H), 1.95-1.87 (m, 1H), 1.84-1.75 (m, 1H), 1.74-1.53 (m, 5H), 1.40-1.20 (m, 2H). MS (ESI) m/z 585.3 [M+H]$^+$.

Cpd. No. 258; $^1$H NMR (400 MHz, MeOD) δ 8.75 (d, J=4.9 Hz, 2H), 7.81 (d, J=4.6 Hz, 2H), 7.76 (d, J=7.4 Hz, 2H), 7.52-7.34 (m, 5H), 6.51 (d, J=7.4 Hz, 2H), 4.16 (t, J=8.4 Hz, 2H), 3.80-3.69 (m, 2H), 3.59 (d, J=6.0 Hz, 2H), 3.57-3.45 (m, 3H), 3.40 (d, J=6.7 Hz, 2H), 3.23-3.15 (m, 1H), 3.15-3.04 (m, 1H), 3.01-2.91 (m, 1H), 2.86-2.77 (m, 1H), 2.56-2.47 (m, 1H), 2.35 (d, J=13.5 Hz, 1H), 2.30-2.21 (m, 1H), 2.16 (d, J=13.0 Hz, 1H), 1.86-1.75 (m, 1H), 1.71-1.43 (m, 6H), 1.40-1.24 (m, 3H). MS (ESI) m/z 585.3 [M+H]$^+$.

Cpd. No. 259; MS (ESI) m/z 615.3 [M+H]$^+$.

Cpd. No. 260; MS (ESI) m/z 615.2 [M+H]$^+$.

Cpd. No. 261; $^1$H NMR (400 MHz, MeOD) δ 7.68 (d, J=7.4 Hz, 2H), 7.55 (d, J=7.2 Hz, 2H), 7.50 (t, J=7.4 Hz, 2H), 7.45 (d, J=7.0 Hz, 1H), 6.54 (d, J=7.5 Hz, 2H), 4.18 (t, J=8.0 Hz, 2H), 3.77-3.71 (m, 2H), 3.63-3.53 (m, 4H), 3.44 (d, J=7.0 Hz, 2H), 3.25-3.17 (m, 1H), 3.16-3.03 (m, 2H), 2.77 (dd, J=13.8, 8.1 Hz, 1H), 2.62-2.53 (m, 1H), 2.44 (t, J=11.8 Hz, 1H), 2.29-2.03 (m, 4H), 1.97 (s, 3H), 1.87-1.55 (m, 6H), 1.37-1.23 (m, 1H), 1.21-1.12 (m, 2H), 1.07-0.94 (m, 2H). MS (ESI) m/z 590.3 [M+H]$^+$.

Cpd. No. 262; $^1$H NMR (400 MHz, MeOD) δ 7.66 (d, J=7.5 Hz, 2H), 7.55-7.36 (m, 5H), 6.52 (d, J=7.5 Hz, 2H), 4.26 (dd, J=11.0, 4.3 Hz, 1H), 4.17 (t, J=7.2 Hz, 2H), 4.01-3.94 (m, 1H), 3.77-3.70 (m, 2H), 3.64-3.58 (m, 1H), 3.54 (d, J=12.8 Hz, 1H), 3.45 (d, J=7.1 Hz, 2H), 3.25-3.02 (m, 3H), 2.76 (dd, J=13.7, 8.0 Hz, 1H), 2.61-2.51 (m, 2H), 2.42-2.31 (m, 1H), 2.10 (s, 3H), 2.04-1.94 (m, 1H), 1.88-1.78 (m, 1H), 1.68-1.50 (m, 5H), 1.48-1.29 (m, 2H), 1.20-1.10 (m, 2H), 1.04-0.94 (m, 2H). MS (ESI) m/z 590.2 [M+H]$^+$.

Cpd. No. 263; $^1$H NMR (400 MHz, MeOD) δ 8.75 (d, J=6.1 Hz, 2H), 7.82 (d, J=6.2 Hz, 2H), 7.76 (d, J=8.8 Hz, 2H), 7.53 (d, J=7.5 Hz, 2H), 7.45 (t, J=7.4 Hz, 2H), 7.39 (d, J=7.1 Hz, 1H), 6.51 (d, J=8.9 Hz, 2H), 4.24-4.13 (m, 3H), 3.74 (t, J=6.2 Hz, 2H), 3.61-3.48 (m, 2H), 3.42 (d, J=7.2 Hz, 2H), 3.24-3.15 (m, 1H), 3.08-2.98 (m, 2H), 2.88-2.79 (m, 1H), 2.54 (t, J=12.3 Hz, 1H), 2.25 (d, J=14.7 Hz, 1H), 2.21-2.11 (m, 1H), 1.94 (d, J=14.9 Hz, 1H), 1.79-1.67 (m, 2H), 1.65 (s, 3H), 1.62-1.42 (m, 4H), 1.38-1.26 (m, 1H). MS (ESI) m/z 612.3 [M+H]$^+$.

Cpd. No. 264; $^1$H NMR (400 MHz, MeOD) δ 8.76 (d, J=4.2 Hz, 2H), 7.82 (d, J=4.6 Hz, 2H), 7.76 (d, J=7.3 Hz, 2H), 7.53-7.36 (m, 4H), 7.31-7.01 (m, 1H), 6.55-6.44 (m, 2H), 4.38-4.33 (m, 1H), 4.15 (t, J=8.1 Hz, 2H), 3.76-3.69 (m, 2H), 3.53 (dd, J=21.5, 12.3 Hz, 2H), 3.40 (d, J=6.9 Hz, 2H), 3.24-3.13 (m, 1H), 3.08 (t, J=12.6 Hz, 1H), 2.93-2.81 (m, 2H), 2.65 (t, J=11.6 Hz, 1H), 2.28 (d, J=14.4 Hz, 1H), 2.00 (s, 3H), 1.94 (d, J=10.1 Hz, 2H), 1.89-1.80 (m, 1H), 1.75-1.57 (m, 3H), 1.52-1.36 (m, 2H), 1.35-1.23 (m, 1H). MS (ESI) m/z 612.3 [M+H]⁺.

Cpd. No. 265; ¹H NMR (400 MHz, MeOD) δ 7.66 (d, J=7.5 Hz, 2H), 7.57-7.38 (m, 5H), 6.53 (d, J=7.6 Hz, 2H), 4.17 (t, J=7.9 Hz, 2H), 3.77-3.71 (m, 2H), 3.60-3.51 (m, 2H), 3.43 (d, J=7.2 Hz, 2H), 3.24-3.11 (m, 2H), 3.09 (d, J=1.2 Hz, 3H), 3.06-3.00 (m, 1H), 2.95-2.86 (m, 2H), 2.77-2.68 (m, 1H), 2.60-2.52 (m, 1H), 2.49-2.39 (m, 1H), 2.30 (d, J=14.2 Hz, 1H), 2.18-1.94 (m, 3H), 1.83-1.70 (m, 1H), 1.68-1.53 (m, 5H), 1.40-1.26 (m, 2H), 1.19-1.11 (m, 2H), 1.04-0.96 (m, 2H). MS (ESI) m/z 562.3 [M+H]⁺.

Cpd. No. 266; MS (ESI) m/z 562.3 [M+H]⁺.

Cpd. No. 101; ¹H NMR (400 MHz, MeOD) δ 7.66 (d, J=8.8 Hz, 2H), 7.58 (d, J=8.0 Hz, 1H), 7.47 (t, J=7.2 Hz, 1H), 7.39-7.31 (m, 2H), 7.25-7.24 (m, 1H), 6.71 (t, J=2.8 Hz, 1H), 6.45 (d, J=8.8 Hz, 2H), 6.31-6.29 (m, 1H), 4.52-4.36 (m, 1H), 4.35-4.22 (m, 1H), 4.13 (t, J=7.2 Hz, 2H), 3.73-3.69 (m, 2H), 3.67 (s, 3H), 3.57-3.47 (m, 6H), 3.27-3.21 (m, 1H), 3.08-2.95 (m, 2H), 2.87-2.68 (m, 1H), 2.48-2.38 (m, 1H), 2.18-2.15 (m, 1H), 2.11-1.94 (m, 2H), 1.89-1.83 (m, 1H), 1.81-1.52 (m, 8H), 1.48 (t, J=7.2 Hz, 3H), 1.36-1.22 (m, 1H), 1.12-0.83 (m, 1H). MS (ESI) m/z 601.3 [M+H]⁺.

Cpd. No. 102; MS (ESI) m/z 602.3 [M+H]⁺.

Cpd. No. 103; ¹H NMR (400 MHz, MeOD) δ 8.15 (s, 1H), 7.77-7.71 (m, 3H), 7.57 (d, J=8.0 Hz, 1H), 7.46 (t, J=7.6 Hz, 1H), 7.38-7.30 (m, 2H), 6.47 (d, J=7.6 Hz, 2H), 4.50-4.37 (m, 1H), 4.34-4.25 (m, 1H), 4.21-4.13 (m, 4H), 3.79-3.69 (m, 3H), 3.53-3.42 (m, 6H), 3.24-3.13 (m, 1H), 3.02-2.96 (m, 2H), 2.84-2.67 (m, 1H), 2.51-2.32 (m, 1H), 2.16 (d, J=13.2 Hz, 1H), 1.93-1.81 (m, 2H), 1.78-1.52 (m, 8H), 1.50-1.41 (m, 6H), 1.34-1.23 (m, 1H), 1.15-0.79 (m, 1H). MS (ESI) m/z 616.3 [M+H]⁺.

Cpd. No. 267; ¹H NMR (400 MHz, MeOD) δ 8.77 (s, 2H), 7.84 (d, J=4.6 Hz, 2H), 7.79-7.73 (m, 2H), 7.62 (d, J=7.9 Hz, 2H), 7.49 (t, J=7.4 Hz, 2H), 7.45-7.38 (m, 1H), 6.53-6.49 (m, 2H), 4.24-4.14 (m, 2H), 3.81-3.71 (m, 2H), 3.66 (d, J=11.7 Hz, 1H), 3.52-3.43 (m, 4H), 3.27-3.19 (m, 1H), 3.15-2.88 (m, 4H), 2.83-2.78 (m, 1H), 2.76 (s, 3H), 2.59 (d, J=14.0 Hz, 1H), 2.09-1.98 (m, 1H), 1.88-1.71 (m, 3H), 1.67-1.55 (m, 2H), 1.45-1.20 (m, 2H). MS (ESI) m/z 648.3 [M+H]⁺.

Cpd. No. 268; ¹H NMR (400 MHz, MeOD) δ 8.75 (d, J=5.1 Hz, 2H), 7.81 (d, J=6.1 Hz, 2H), 7.75 (d, J=8.8 Hz, 2H), 7.51-7.37 (m, 5H), 6.49 (d, J=8.9 Hz, 2H), 4.19-4.09 (m, 2H), 4.04 (dd, J=13.2, 6.6 Hz, 1H), 3.75-3.65 (m, 2H), 3.52 (d, J=11.9 Hz, 1H), 3.39 (d, J=7.1 Hz, 2H), 3.23-3.12 (m, 1H), 3.06 (s, 3H), 3.04-2.96 (m, 3H), 2.88 (t, J=12.4 Hz, 1H), 2.36 (d, J=14.2 Hz, 1H), 2.29-2.16 (m, 2H), 1.83-1.65 (m, 4H), 1.42-1.19 (m, 3H). MS (ESI) m/z 648.2 [M+H]⁺.

Cpd. No. 269; ¹H NMR (400 MHz, MeOD) δ 8.75 (d, J=6.1 Hz, 2H), 7.82 (d, J=6.3 Hz, 2H), 7.77 (d, J=8.7 Hz, 2H), 7.59 (d, J=7.5 Hz, 2H), 7.46 (t, J=7.5 Hz, 2H), 7.41 (d, J=7.1 Hz, 1H), 6.52 (d, J=8.8 Hz, 2H), 4.23-4.09 (m, 3H), 3.75 (dd, J=8.2, 5.7 Hz, 2H), 3.65-3.58 (m, 1H), 3.50-3.43 (m, 3H), 3.23-3.17 (m, 1H), 3.10-2.95 (m, 2H), 2.80-2.65 (m, 2H), 2.60 (s, 3H), 2.36 (d, J=13.9 Hz, 1H), 2.11-2.06 (m, 1H), 1.90-1.79 (m, 1H), 1.73-1.42 (m, 5H), 1.33-1.23 (m, 2H). MS (ESI) m/z 627.2 [M+H]⁺.

Cpd. No. 270; ¹H NMR (400 MHz, MeOD) δ 8.75 (dd, J=4.6, 1.6 Hz, 2H), 7.81 (dd, J=4.6, 1.7 Hz, 2H), 7.76 (d, J=8.8 Hz, 2H), 7.47-7.43 (m, 4H), 7.42-7.38 (m, 1H), 6.50 (d, J=8.9 Hz, 2H), 4.30 (d, J=19.5 Hz, 1H), 4.15 (d, J=19.2 Hz, 1H), 3.72 (d, J=21.3 Hz, 1H), 3.51 (d, J=32.3 Hz, 1H), 3.39 (d, J=11.4 Hz, 1H), 3.15 (d, J=36.3 Hz, 1H), 2.92 (s, 1H), 2.73 (s, 1H), 2.64 (s, 1H), 2.30 (d, J=25.8 Hz, 1H), 2.03 (d, J=45.8 Hz, 1H), 1.81 (d, J=38.3 Hz, 1H), 1.62 (d, J=42.0 Hz, 2H), 1.30 (d, J=82.4 Hz, 3H). MS (ESI) m/z 627.2 [M+H]⁺.

Cpd. No. 271; ¹H NMR (400 MHz, MeOD) δ 8.75 (d, J=5.2 Hz, 2H), 7.81 (d, J=5.2 Hz, 2H), 7.75 (d, J=8.0 Hz, 2H), 7.51 (d, J=8.0 Hz, 1H), 7.45 (t, J=7.2 Hz, 1H), 7.35 (t, J=7.6 Hz, 1H), 7.25 (d, J=8.0 Hz, 1H), 6.49 (d, J=8.4 Hz, 2H), 4.37-4.22 (m, 2H), 4.14 (t, J=8.4 Hz, 2H), 4.03-4.01 (m, 1H), 3.84 (d, J=14.0 Hz, 1H), 3.73-3.69 (m, 2H), 3.60-3.57 (m, 1H), 3.42-3.34 (m, 3H), 3.25-3.23 (m, 1H), 3.21 (s, 3H), 3.10-2.90 (m, 2H), 2.74-2.67 (m, 1H), 2.26 (d, J=13.2 Hz, 1H), 2.07-1.94 (m, 3H), 1.88-1.81 (m, 3H), 1.73-1.60 (m, 3H), 1.33-1.29 (m, 1H), 1.18 (s, 3H). MS (ESI) m/z 642.3 [M+H]⁺.

Cpd. No. 272; ¹H NMR (400 MHz, MeOD) δ 8.78-8.77 (m, 2H), 7.85-7.83 (m, 2H), 7.78 (d, J=8.8 Hz, 2H), 7.63-7.56 (m, 1H), 7.48-7.40 (m, 2H), 7.34-7.32 (m, 1H), 6.53 (d, J=9.2 Hz, 2H), 4.71 (d, J=15.6 Hz, 1H), 4.33-4.30 (m, 1H), 4.24-4.20 (m, 2H), 3.82-3.77 (m, 2H), 3.67-3.59 (m, 3H), 3.53-3.51 (m, 1H), 3.49-3.46 (m, 2H), 3.44-3.39 (m, 1H), 3.13 (s, 3H), 3.08-2.91 (m, 2H), 2.59-2.47 (m, 2H), 2.20-2.02 (m, 3H), 1.99 (s, 3H), 1.85-1.52 (m, 5H), 1.39-1.36 (m, 2H), 1.00-0.87 (m, 1H). MS (ESI) m/z 642.3 [M+H]⁺.

Cpd. No. 273; ¹H NMR (400 MHz, MeOD) δ 7.68-7.59 (m, 4H), 7.51-7.40 (m, 3H), 6.81-6.71 (m, 1H), 6.55-6.50 (m, 1H), 4.64-4.55 (m, 1H), 4.22-4.12 (m, 1H), 3.83-3.66 (m, 3H), 3.55-3.41 (m, 3H), 3.23-3.13 (m, 2H), 3.11-3.02 (m, 2H), 3.00-2.95 (m, 3H), 2.94-2.86 (m, 1H), 2.84 (s, 3H), 2.59-2.53 (m, 1H), 2.40-2.33 (m, 1H), 2.26-2.11 (m, 1H), 2.08-1.51 (m, 7H), 1.45-1.23 (m, 2H), 1.17-1.09 (m, 2H), 1.05-0.98 (m, 2H). MS (ESI) m/z 625.3 [M+H]⁺.

Cpd. No. 274; ¹H NMR (400 MHz, MeOD) δ 7.68-7.39 (m, 7H), 6.77-6.50 (m, 2H), 4.64-4.59 (m, 1H), 4.15 (t, J=8.0 Hz, 1H), 3.77-3.69 (m, 2H), 3.60-3.49 (m, 2H), 3.42 (d, J=7.2 Hz, 2H), 3.24-3.14 (m, 3H), 3.05-3.01 (m, 1H), 2.98-2.95 (m, 6H), 2.88-2.80 (m, 1H), 2.58-2.52 (m, 1H), 2.24 (d, J=14.0 Hz, 1H), 2.12 (d, J=14.8 Hz, 1H), 2.01-1.94 (m, 2H), 1.84-1.70 (m, 3H), 1.43-1.24 (m, 4H), 1.19-1.14 (m, 2H), 0.99-0.96 (m, 2H). MS (ESI) m/z 625.3 [M+H]⁺.

Cpd. No. 275; ¹H NMR (400 MHz, MeOD) δ 8.77 (s, 2H), 7.83 (d, J=6.0 Hz, 2H), 7.76 (d, J=8.8 Hz, 2H), 7.56 (d, J=7.2 Hz, 2H), 7.44-7.38 (m, 3H), 6.51 (d, J=8.8 Hz, 2H), 4.19-4.14 (m, 3H), 3.75-3.72 (m, 2H), 3.59 (d, J=12.0 Hz, 1H), 3.51 (d, J=12.8 Hz, 1H), 3.42 (d, J=7.6 Hz, 2H), 3.23-3.18 (m, 1H), 3.07-2.92 (m, 2H), 2.71 (s, 6H), 2.56 (t, J=11.6 Hz, 1H), 2.28 (d, J=14.4 Hz, 1H), 2.14-2.10 (m, 1H), 1.92 (d, J=15.2 Hz, 1H), 1.82-1.46 (m, 6H), 1.38-1.29 (m, 1H). MS (ESI) m/z 641.3 [M+H]⁺.

Cpd. No. 276; ¹H NMR (400 MHz, MeOD) δ 8.76 (d, J=5.2 Hz, 2H), 7.83-7.81 (m, 2H), 7.75 (d, J=8.8 Hz, 2H), 7.45-7.37 (m, 5H), 6.49 (d, J=8.8 Hz, 2H), 4.28 (q, J=7.2 Hz, 1H), 4.17-4.12 (m, 2H), 3.74-3.69 (m, 2H), 3.54 (t, J=12.0, 2H), 3.40 (d, J=6.8 Hz, 2H), 3.21-3.08 (m, 2H), 3.04-2.99 (m, 1H), 2.94 (s, 6H), 2.77 (t, J=11.2 Hz, 1H), 2.58 (t, J=11.6 Hz, 1H), 2.27 (d, J=14.4 Hz, 1H), 2.03-1.97 (m, 2H), 1.86-1.78 (m, 1H), 1.71-1.39 (m, 5H), 1.33-1.24 (m, 1H). MS (ESI) m/z 641.3 [M+H]⁺.

Cpd. No. 277; ¹H NMR (400 MHz, MeOD) δ 8.78 (s, 2H), 7.86 (d, J=6.0 Hz, 2H), 7.75 (d, J=8.8 Hz, 2H), 7.50 (d, J=8.0 Hz, 1H), 7.37 (t, J=7.2 Hz, 1H), 7.28 (t, J=7.6 Hz, 1H), 7.21 (d, J=7.2 Hz, 1H), 6.48 (d, J=8.8 Hz, 2H), 4.30-4.18 (m, 2H), 4.13 (t, J=8.0 Hz, 2H), 3.91-3.84 (m, 1H), 3.79 (d, J=14.4 Hz, 1H), 3.73-3.68 (m, 2H), 3.58 (d, J=12.0 Hz, 1H), 3.41-3.35 (m, 3H), 3.26-3.19 (m, 2H), 3.17 (s, 3H), 3.00-2.90 (m, 2H), 2.72-2.65 (m, 1H), 2.25 (s, 1H), 2.20 (s, 3H), 2.01-1.53 (m, 9H), 0.69-0.60 (m, 1H). MS (ESI) m/z 657.3 [M+H]⁺.

Cpd. No. 278; ¹H NMR (400 MHz, MeOD) δ 8.77 (s, 2H), 7.84 (d, J=8.8 Hz, 2H), 7.76 (d, J=8.4 Hz, 2H), 7.56 (s, 1H), 7.42-7.36 (m, 2H), 7.30 (d, J=7.2 Hz, 1H), 6.50 (d, J=8.0 Hz, 2H), 4.65 (d, J=15.2 Hz, 1H), 4.28 (d, J=14.4 Hz, 1H), 4.19 (t, J=8.0 Hz, 2H), 3.80-3.75 (m, 2H), 3.62 (d, J=12.8 Hz, 2H), 3.49-3.43 (m, 5H), 3.08-2.94 (m, 5H), 2.71 (s, 3H), 2.60-2.54 (m, 1H), 2.48-2.37 (m, 1H), 2.22-2.06 (m, 2H), 2.04-1.91 (m, 1H), 2.93-1.31 (m, 7H), 1.12-0.95 (m, 1H). MS (ESI) m/z 657.3 [M+H]⁺.

Cpd. No. 279; ¹H NMR (400 MHz, MeOD) δ 8.76 (s, 2H), 7.82 (d, J=4.8 Hz, 2H), 7.79-7.74 (m, 2H), 7.55 (d, J=7.2 Hz, 2H), 7.46-7.40 (m, 3H), 6.50 (d, J=7.6 Hz, 2H), 4.64 (d, J=8.4 Hz, 1H), 4.52 (d, J=7.2 Hz, 1H), 4.43 (d, J=6.8 Hz, 1H), 4.26-4.14 (m, 4H), 3.75-3.72 (m, 2H), 3.58-3.51 (m, 2H), 3.42 (d, J=7.2 Hz, 2H), 3.28 (d, J=8.4 Hz, 1H), 3.24-3.18 (m, 1H), 3.07-2.93 (m, 2H), 2.70 (s, 3H), 2.52 (t, J=12.0, 1H), 2.23 (d, J=14.4 Hz, 1H), 2.16-2.10 (m, 1H), 1.98 (d, J=14.0 Hz, 1H), 1.84-1.56 (m, 5H), 1.47-1.29 (m, 2H). MS (ESI) m/z 668.3 [M+H]⁺.

Cpd. No. 280; ¹H NMR (400 MHz, MeOD) δ 8.77 (s, 2H), 7.84 (d, J=5.6 Hz, 2H), 7.75 (d, J=8.8 Hz, 2H), 7.51 (d, J=7.6 Hz, 2H), 7.45 (t, J=7.2 Hz, 2H), 7.41-7.37 (m, 1H), 6.49 (d, J=8.8 Hz, 2H), 5.07 (d, J=8.8 Hz, 1H), 4.97 (d, J=9.2 Hz, 1H), 4.83-4.78 (m, 2H), 4.74-4.68 (m, 1H), 4.14 (t, J=8.0 Hz, 2H), 3.74-3.69 (m, 2H), 3.57-3.52 (m, 2H), 3.40 (d, J=7.2 Hz, 2H), 3.23-3.18 (m, 2H), 3.11-3.05 (m, 1H), 2.88 (s, 3H), 2.74-2.68 (m, 1H), 2.60-2.54 (m, 1H), 2.26 (d, J=14.4 Hz, 1H), 2.02 (d, J=14.0 Hz, 1H), 1.97-1.80 (m, 2H), 1.78-1.55 (m, 3H), 1.46-1.29 (m, 3H). MS (ESI) m/z 668.3 [M+H]⁺.

Cpd. No. 281; ¹H NMR (400 MHz, MeOD) δ 7.66 (d, J=8.8 Hz, 2H), 7.53 (d, J=7.6 Hz, 2H), 7.45 (t, J=7.2 Hz, 2H), 7.40-7.37 (m, 1H), 6.52 (d, J=9.2 Hz, 2H), 4.21-4.14 (m, 3H), 3.73 (t, J=6.0 Hz, 2H), 3.60-3.52 (m, 2H), 3.43 (d, J=7.2 Hz, 2H), 3.24-3.17 (m, 1H), 3.04 (t, J=12.8 Hz, 2H), 2.88-2.82 (m, 1H), 2.59-2.49 (m, 2H), 2.24 (d, J=14.4 Hz, 1H), 2.19-2.13 (m, 1H), 1.96 (d, J=14.4 Hz, 1H), 1.78-1.68 (m, 3H), 1.64 (s, 3H), 1.62-1.46 (m, 4H), 1.17-1.12 (m, 2H), 1.02-0.96 (m, 2H). MS (ESI) m/z 574.2 [M+H]⁺.

Cpd. No. 282; ¹H NMR (400 MHz, MeOD) δ 7.66 (d, J=8.8 Hz, 2H), 7.49-7.45 (m, 4H), 7.43-7.39 (m, 1H), 7.29-7.05 (m, 1H), 6.52 (d, J=8.8 Hz, 2H), 4.39 (m, 1H), 4.18-4.13 (m, 2H), 3.75-3.71 (m, 2H), 3.59-3.51 (m, 2H), 3.43 (d, J=6.8 Hz, 2H), 3.22-3.16 (m, 1H), 3.13-3.07 (m, 1H), 2.92-2.85 (m, 2H), 2.69-2.63 (m, 1H), 2.59-2.52 (m, 1H), 2.29 (d, J=14.4 Hz, 1H), 2.01 (s, 3H), 1.97-1.82 (m, 3H), 1.74-1.58 (m, 3H), 1.53-1.39 (m, 2H), 1.34-1.25 (m, 1H), 1.17-1.13 (m, 2H), 1.02-0.97 (m, 2H). MS (ESI) m/z 574.2 [M+H]⁺.

Cpd. No. 283; ¹H NMR (400 MHz, MeOD) δ 7.65 (d, J=8.8 Hz, 2H), 7.51 (d, J=8.0 Hz, 1H), 7.39 (t, J=7.2 Hz, 1H), 7.30 (t, J=7.6 Hz, 1H), 7.22 (d, J=7.2 Hz, 1H), 6.51 (d, J=8.8 Hz, 2H), 4.29 (d, J=16.0 Hz, 1H), 4.20 (d, J=14.8 Hz, 1H), 4.16-4.12 (m, 2H), 3.92-3.86 (m, 1H), 3.81 (d, J=15.0 Hz, 1H), 3.73-3.69 (m, 2H), 3.60 (d, J=12.4 Hz, 1H), 3.43-3.38 (m, 3H), 3.22 (d, J=15.0 Hz, 1H), 3.18 (s, 3H), 3.02-2.91 (m, 2H), 2.74-2.66 (m, 2H), 2.59-2.52 (m, 1H), 2.27-2.24 (m, 1H), 2.21 (s, 3H), 2.03-1.54 (m, 9H), 1.16-1.12 (m, 2H), 1.01-0.96 (m, 2H), 0.70-0.61 (m, 1H). MS (ESI) m/z 620.3 [M+H]⁺.

Cpd. No. 284; ¹H NMR (400 MHz, MeOD) δ 8.08 (s, 1H), 7.71-7.69 (m, 3H), 7.50 (d, J=8.0 Hz, 1H), 7.36 (t, J=7.2 Hz, 1H), 7.30-7.22 (m, 2H), 6.45 (d, J=8.8 Hz, 2H), 4.23-4.09 (m, 4H), 4.00-3.93 (m, 1H), 3.87 (s, 3H), 3.77 (d, J=14.4 Hz, 1H), 3.70-3.65 (m, 2H), 3.58 (d, J=13.2 Hz, 1H), 3.40-3.34 (m, 3H), 3.20-3.12 (m, 2H), 3.00-2.88 (m, 2H), 2.71-2.63 (m, 1H), 2.25-2.22 (m, 1H), 2.19 (s, 3H), 2.07-1.97 (m, 2H), 1.96-1.51 (m, 9H), 0.69-0.60 (m, 1H). MS (ESI) m/z 646.3 [M+H]⁺.

Cpd. No. 285; ¹H NMR (400 MHz, MeOD) δ 7.64 (d, J=7.6 Hz, 2H), 7.50 (d, J=8.0 Hz, 1H), 7.37 (t, J=7.2 Hz, 1H), 7.30-7.22 (m, 2H), 6.51 (d, J=8.0 Hz, 2H), 4.23-4.18 (m, 2H), 4.14 (t, J=8.0 Hz, 2H), 4.01-3.93 (m, 1H), 3.77 (d, J=14.4 Hz, 1H), 3.72-3.68 (m, 2H), 3.59 (d, J=11.2 Hz, 1H), 3.41-3.37 (m, 3H), 3.21-3.14 (m, 2H), 3.01-2.89 (m, 2H), 2.71-2.64 (m, 1H), 2.57-2.51 (m, 1H), 2.24 (d, J=12.4 Hz, 1H), 2.19 (s, 3H), 2.06-2.02 (m, 2H), 1.96-1.51 (m, 8H), 1.15-1.11 (m, 2H), 1.00-0.95 (m, 2H), 0.70-0.61 (m, 1H). MS (ESI) m/z 606.3 [M+H]⁺.

Cpd. No. 286; ¹H NMR (400 MHz, MeOD) δ 8.09 (s, 1H), 7.89 (d, J=9.6 Hz, 1H), 7.72-7.70 (m, 2H), 7.52 (d, J=8.4 Hz, 1H), 7.43 (t, J=7.6 Hz, 1H), 7.33 (t, J=7.6 Hz, 1H), 7.27 (d, J=8.0 Hz, 1H), 6.47 (d, J=7.2 Hz, 2H), 4.27-4.17 (m, 2H), 4.12 (t, J=8.0 Hz, 2H), 3.88 (s, 3H), 3.80 (d, J=14.4 Hz, 1H), 3.71-3.66 (m, 2H), 3.59 (d, J=11.2 Hz, 1H), 3.41-3.36 (m, 3H), 3.23 (d, J=14.4, 1H), 3.17-3.14 (m, 1H), 3.01-2.89 (m, 2H), 2.73-2.66 (m, 1H), 2.25 (d, J=14.4 Hz, 1H), 2.09-2.06 (m, 1H), 1.94-1.58 (m, 8H), 1.33-1.29 (m, 1H), 1.17 (s, 3H), 0.68-0.59 (m, 1H). MS (ESI) m/z 631.3 [M+H]⁺.

Cpd. No. 287; ¹H NMR (400 MHz, MeOD) δ 8.10 (s, 1H), 7.73-7.70 (m, 3H), 7.57 (d, J=7.6 Hz, 1H), 7.44-7.31 (m, 3H), 6.47 (d, J=8.8 Hz, 2H), 4.49 (d, J=15.6 Hz, 1H), 4.30 (d, J=15.6 Hz, 1H), 4.18-4.13 (m, 2H), 3.88 (s, 3H), 3.76-3.72 (m, 3H), 3.63-3.43 (m, 6H), 3.25-3.24 (m, 1H), 3.07 (t, J=10.4 Hz, 1H), 2.95 (t, J=12.4 Hz, 1H), 2.53 (t, J=12.0 Hz, 1H), 2.44-2.41 (m, 1H), 2.13 (d, J=14.0 Hz, 1H), 2.05-2.00 (m, 1H), 1.96 (s, 3H), 1.90-1.80 (m, 1H), 1.75-1.56 (m, 5h), 1.39 (d, J=12.8 Hz, 1H), 1.10-1.00 (m, 1H). MS (ESI) m/z 631.3 [M+H]⁺.

Cpd. No. 288; ¹H NMR (400 MHz, MeOD) δ 7.65 (d, J=8.8 Hz, 2H), 7.50 (d, J=8.0 Hz, 1H), 7.38 (t, J=7.6 Hz, 1H), 7.32-7.26 (m, 2H), 6.51 (d, J=8.8 Hz, 2H), 4.30-4.12 (m, 4H), 3.91-3.86 (m, 1H), 3.82-3.75 (m, 1H), 3.74-3.67 (m, 2H), 3.64-3.59 (m, 2H), 3.42-3.38 (m, 3H), 3.23-3.19 (m, 2H), 3.02-2.91 (m, 2H), 2.76-2.69 (m, 1H), 2.58-2.52 (m, 1H), 2.27-2.24 (m, 1H), 2.19 (s, 3H), 2.08-1.68 (m, 9H), 1.57 (t, J=6.8 Hz, 6H), 1.34-1.29 (m, 1H), 1.16-1.13 (m, 2H), 1.00-0.97 (m, 2H), 0.69-0.63 (m, 1H). MS (ESI) m/z 648.3 [M+H]⁺.

Cpd. No. 289; ¹H NMR (400 MHz, MeOD) δ 7.65 (d, J=8.8 Hz, 2H), 7.51 (d, J=8.0 Hz, 1H), 7.40 (t, J=7.2 Hz, 1H), 7.33-7.26 (m, 2H), 6.51 (d, J=8.8 Hz, 2H), 4.40 (d, J=13.2 Hz, 1H), 4.17-4.09 (m, 3H), 3.85-3.69 (m, 4H), 3.62-3.55 (m, 2H), 3.43-3.38 (m, 4H), 3.18 (d, J=13.2 Hz, 2H), 3.03-2.91 (m, 2H), 2.75-2.67 (m, 1H), 2.57-2.53 (m, 1H), 2.28-2.24 (m, 1H), 2.20 (s, 3H), 2.07-1.68 (m, 8H), 1.64-1.59 (m, 1H), 1.55 (t, J=7.2 Hz, 3H), 1.15-1.13 (m, 2H), 1.00-0.98 (m, 2H), 0.70-0.60 (m, 1H). MS (ESI) m/z 634.3 [M+H]⁺.

Cpd. No. 290; ¹H NMR (400 MHz, MeOD) δ 7.85 (d, J=7.2 Hz, 2H), 7.71 (d, J=8.8 Hz, 2H), 7.59-7.49 (m, 4H), 7.38 (t, J=6.8 Hz, 1H), 7.32-7.25 (m, 2H), 6.46 (d, J=8.8 Hz, 2H), 4.39 (d, J=12.8 Hz, 1H), 4.13-4.08 (m, 3H), 3.87-3.75 (m, 2H), 3.70-3.65 (m, 2H), 3.59-3.52 (m, 2H), 3.42-3.35 (m, 4H), 3.17 (d, J=13.2 Hz, 2H), 3.00-2.89 (m, 2H), 2.73-2.66 (m, 1H), 2.26-2.23 (m, 1H), 2.20 (s, 3H), 2.03-1.67 (m, 8H), 1.62-1.59 (m, 1H), 1.54 (t, J=7.2 Hz, 3H). MS (ESI) m/z 670.3 [M+H]⁺.

Cpd. No. 375; ¹H NMR (400 MHz, MeOD) δ 7.66 (d, J=8.8 Hz, 2H), 7.50 (d, J=8.0 Hz, 1H), 7.39 (t, J=7.2 Hz, 1H), 7.32-7.23 (m, 3H), 6.71 (t, J=2.6 Hz, 1H), 6.44 (d, J=8.8 Hz, 2H), 6.30-6.29 (m, 1H), 4.40 (d, J=12.8, 1H), 4.12-4.08 (m, 3H), 3.87-3.75 (m, 2H), 3.67 (s, 3H), 3.65-3.63 (m, 1H), 3.60-3.53 (m, 2H), 3.42-3.35 (m, 4H), 3.21-3.13 (m, 2H), 3.01-2.90 (m, 2H), 2.74-2.67 (m, 1H), 2.25 (d, J=13.2 Hz, 1H), 2.20 (s, 3H), 2.04-1.67 (m, 8H), 1.55 (t, J=7.2 Hz, 3H), 0.69-0.59 (m, 1H). MS (ESI) m/z 673.4 [M+H]$^+$.

Cpd. No. 376; $^1$H NMR (400 MHz, MeOD) δ 8.76 (s, 1H), 8.10 (s, 1H), 7.73-7.71 (m, 3H), 7.65 (d, J=7.6 Hz, 2H), 7.53 (t, J=7.8 Hz, 2H), 7.48 (s, 1H), 7.43 (t, J=7.4 Hz, 1H), 7.36 (s, 1H), 6.47 (d, J=8.8 Hz, 2H), 5.15 (d, J=15.2, 1H), 4.95 (d, J=15.6 Hz, 1H), 4.33-4.28 (m, 1H), 4.14 (t, J=8.0, 2H), 3.88 (s, 3H), 3.73-3.68 (m, 2H), 3.62 (d, J=12.4 Hz, 1H), 3.46 (d, J=13.6 Hz, 1H), 3.41 (d, J=7.2 Hz, 2H), 3.24-3.19 (m, 1H), 3.11-3.05 (m, 1H), 2.93 (s, 6H), 2.89-2.85 (m, 1H), 2.78-2.71 (m, 1H), 2.46 (t, J=11.8 Hz, 1H), 2.22 (d, J=13.6 Hz, 1H), 2.05-2.00 (m, 1H), 1.91-1.84 (m, 1H), 1.72-1.41 (m, 4H), 1.16-1.03 (m, 2H), 0.90-0.82 (m, 1H). MS (ESI) m/z 699.4 [M+H]$^+$.

Cpd. No. 377; $^1$H NMR (400 MHz, MeOD) δ 8.90 (s, 1H), 8.10 (s, 1H), 7.73-7.71 (m, 3H), 7.66 (d, J=8.0 Hz, 2H), 7.56 (s, 1H), 7.53-7.48 (m, 3H), 7.42-7.38 (m, 1H), 6.47 (d, J=8.8 Hz, 2H), 5.14 (d, J=15.6 Hz, 1H), 4.95 (d, J=14.4 Hz, 1H), 4.32-4.27 (m, 1H), 4.17-4.12 (m, 2H), 3.88 (s, 3H), 3.73-3.68 (m, 2H), 3.60 (d, J=12.0 Hz, 1H), 3.45-3.38 (m, 2H), 3.23-3.18 (m, 1H), 3.03 (t, J=12.0 Hz, 1H), 2.89-2.83 (m, 2H), 2.77 (s, 6H), 2.63-2.57 (s, 1H), 2.27 (d, J=12.8 Hz, 1H), 1.97-1.85 (m, 2H), 1.59-1.34 (m, 4H), 1.22-1.15 (m, 1H), 1.08-0.98 (m, 2H). MS (ESI) m/z 699.3 [M+H]$^+$.

Cpd. No. 378; $^1$H NMR (400 MHz, MeOD) δ 8.46 (s, 1H), 8.16 (s, 1H), 7.57 (d, J=8.0 Hz, 2H), 7.49-7.45 (m, 4H), 7.34 (t, J=7.2 Hz, 1H), 6.47 (d, J=8.8 Hz, 2H), 4.37 (m, 1H), 4.19-4.14 (m, 2H), 4.11-4.06 (m, 1H), 3.95 (d, J=15.0 Hz, 2H), 3.72 (q, J=6.0 Hz, 2H), 3.61 (d, J=11.6 Hz, 1H), 3.46-3.42 (m, 3H), 3.23-3.18 (m, 1H), 3.0 (t, J=11.2 Hz, 1H), 2.88 (t, J=11.6, 1H), 2.73-2.70 (m, 1H), 2.68 (s, 3H), 2.37-2.31 (m, 2H), 1.91-1.88 (m, 2H), 1.84-1.74 (m, 1H), 1.68-1.59 (m, 1H), 1.48-1.29 (m, 5H), 1.09-1.01 (m, 1H). MS (ESI) m/z 610.3 [M+H]$^+$.

Cpd. No. 379; $^1$H NMR (400 MHz, MeOD) δ 8.46 (s, 1H), 8.16 (s, 1H), 7.54 (d, J=8.0 Hz, 2H), 7.49-7.44 (m, 4H), 7.34 (t, J=6.8 Hz, 1H), 6.47 (d, J=8.0 Hz, 2H), 4.19-4.12 (m, 4H), 3.75-3.70 (m, 2H), 3.59 (d, J=11.2 Hz, 1H), 3.45-3.41 (m, 3H), 3.36-3.35 (m, 1H), 3.23-3.18 (m, 1H), 3.08 (t, J=12.0 Hz, 1H), 2.95 (t, J=12.0 Hz, 1H), 2.71 (s, 3H), 2.50-2.42 (m, 2H), 2.26 (d, J=6.8 Hz, 1H), 2.03 (s, 1H), 1.98-1.85 (m, 2H), 1.75-1.46 (m, 4H), 1.41-1.34 (m, 3H). MS (ESI) m/z 610.2 [M+H]$^+$.

Cpd. No. 380; $^1$H NMR (400 MHz, MeOD) δ 8.74 (d, J=26.3 Hz, 1H), 7.70-7.60 (m, 4H), 7.54-7.45 (m, 3H), 7.44-7.33 (m, 4H), 5.03-4.93 (m, 2H), 4.64-4.37 (m, 1H), 4.02-3.73 (m, 1H), 2.99 (t, J=11.8 Hz, 1H), 2.85-2.77 (m, 1H), 2.74-2.69 (m, 1H), 2.68 (s, 3H), 2.58-2.42 (m, 2H), 2.39-2.33 (m, 1H), 2.32-2.22 (m, 1H), 2.13-2.05 (m, 1H), 2.02-1.93 (m, 1H), 1.91-1.77 (m, 2H), 1.71 (d, J=12.5 Hz, 1H), 1.64-1.28 (m, 5H), 1.25-1.05 (m, 2H), 0.30-0.17 (m, 1H). MS (ESI) m/z 567.3 [M+H]$^+$.

Cpd. No. 29; $^1$H NMR (400 MHz, CDCl$_3$) δ 11.76 (brs, 1H), 8.73 (brs, 3H), 7.51 (d, J=8.8 Hz, 2H), 7.25 (dd, J=14.0, 8.1 Hz, 1H), 7.02 (t, J=8.4 Hz, 1H), 6.96 (d, J=8.0 Hz, 1H), 6.83 (d, J=8.8 Hz, 2H), 4.04 (s, 2H), 3.71 (d, J=9.8 Hz, 1H), 3.35 (dd, J=15.5, 7.0 Hz, 2H), 3.22-3.01 (m, 3H), 2.96-2.61 (m, 4H), 2.43 (m, 1H), 2.36-2.12 (m, 4H), 2.01-1.78 (m, 2H), 1.74-1.39 (m, 6H), 1.28-1.09 (m, 2H). MS (ESI) m/z 462.2 [M+H]$^+$.

Cpd. No. 30; $^1$H NMR (400 MHz, CDCl$_3$) δ 7.58-7.51 (m, 2H), 7.20 (dd, J=8.8, 5.7 Hz, 1H), 6.96-6.88 (m, 2H), 6.85 (td, J=8.6, 2.9 Hz, 1H), 6.76 (dd, J=9.3, 2.8 Hz, 1H), 4.02 (t, J=6.4 Hz, 2H), 3.12-2.94 (m, 3H), 2.90 (d, J=10.9 Hz, 1H), 2.66 (dd, J=11.3, 6.0 Hz, 2H), 2.43 (t, J=7.3 Hz, 2H), 2.39-2.29 (m, 1H), 2.01-1.88 (m, 3H), 1.88-1.74 (m, 2H), 1.73-1.59 (m, 2H), 1.50-1.37 (m, 6H), 1.36-1.27 (m, 2H), 1.22-1.08 (m, 2H), 0.93-0.79 (m, 1H). MS (ESI) m/z 462.2 [M+H]$^+$.

Cpd. No. 31; MS (ESI) m/z 476.3 [M+H]$^+$.

Cpd. No. 32; $^1$H NMR (400 MHz, CDCl$_3$) δ 10.18 (brs, 2H), 8.50 (brs, 1H), 7.51 (d, J=8.8 Hz, 2H), 7.23 (d, J=5.3 Hz, 1H), 6.84 (d, J=8.8 Hz, 2H), 6.76 (d, J=5.3 Hz, 1H), 4.04 (s, 2H), 3.76 (d, J=10.5 Hz, 1H), 3.65-3.53 (m, 2H), 3.48 (s, 1H), 3.16 (s, 2H), 3.01 (s, 2H), 2.84-2.58 (m, 3H), 2.46-2.30 (m, 1H), 2.27-2.18 (m, 3H), 2.04 (s, 1H), 1.82 (s, 1H), 1.67 (s, 1H), 1.60-1.37 (m, 6H), 1.25-1.08 (m, 1H). MS (ESI) m/z 450.2 [M+H]$^+$ Cpd. No. 33; $^1$H NMR (400 MHz, MeOD) δ 7.48 (d, J=8.7 Hz, 2H), 7.44-7.38 (m, 2H), 7.25-7.05 (m, 3H), 6.47 (d, J=8.7 Hz, 2H), 4.54-4.27 (m, 2H), 4.18 (td, J=8.0, 2.4 Hz, 2H), 3.77 (dd, J=9.9, 3.8 Hz, 2H), 3.69-3.58 (m, 2H), 3.53 (d, J=12.2 Hz, 1H), 3.51-3.41 (m, 2H), 3.14 (s, 3H), 3.09-2.91 (m, 2H), 2.91-2.77 (m, 1H), 2.71-2.53 (m, 1H), 2.30-2.11 (m, 1H), 2.05-1.82 (m, 3H), 1.77-1.58 (m, 4H), 1.53-1.40 (m, 1H), 1.41-1.27 (m, 1H), 1.24-1.07 (m, 1H). MS (ESI) m/z 487.2 [M+H]$^+$.

Cpd. No. 34; MS (ESI) m/z 492.2 [M+H]$^+$.
Cpd. No. 35; MS (ESI) m/z 445.2 [M+H]$^+$.
Cpd. No. 37; MS (ESI) m/z 433.3 [M+H]$^+$.
Cpd. No. 38; MS (ESI) m/z 535.3 [M+H]$^+$.

Cpd. No. 39; $^1$H NMR (400 MHz, MeOD) δ 7.66 (d, J=8.9 Hz, 2H), 7.55-7.45 (m, 2H), 7.43-7.33 (m, 3H), 7.06 (d, J=8.9 Hz, 2H), 4.16 (t, J=5.8 Hz, 2H), 3.71 (d, J=12.6 Hz, 1H), 3.61 (d, J=11.4 Hz, 1H), 3.57 (s, 2H), 3.28 (s, 2H), 3.13-2.95 (m, 1H), 2.57-2.44 (m, 1H), 2.33 (t, J=12.3 Hz, 1H), 2.24 (dt, J=16.0, 5.7 Hz, 2H), 2.14 (d, J=14.1 Hz, 1H), 1.98 (d, J=14.5 Hz, 1H), 1.84-1.66 (m, 3H), 1.66-1.46 (m, 5H), 1.37-1.14 (m, 1H). MS (ESI) m/z 432.3 [M+H]$^+$

Cpd. No. 40; MS (ESI) m/z 474.3 [M+H]$^+$.
Cpd. No. 41; MS (ESI) m/z 497.3 [M+H]$^+$.

Cpd. No. 42; $^1$H NMR (400 MHz, MeOD) δ 7.65 (d, J=8.7 Hz, 1H), 7.53-7.35 (m, 3H), 7.30 (d, J=2.0 Hz, 1H), 6.93 (d, J=1.9 Hz, 1H), 6.49 (d, J=8.7 Hz, 1H), 4.64 (q, J=15.4 Hz, 2H), 4.14 (t, J=8.0 Hz, 1H), 3.73 (dd, J=7.8, 5.8 Hz, 1H), 3.58 (d, J=12.1 Hz, 1H), 3.51 (d, J=12.0 Hz, 1H), 3.43 (d, J=7.0 Hz, 1H), 3.24 (dt, J=13.2, 6.5 Hz, 1H), 3.17-2.98 (m, 1H), 2.74-2.52 (m, 1H), 2.49 (t, J=12.3 Hz, 1H), 2.42 (s, 1H), 2.09 (t, J=14.5 Hz, 1H), 1.96-1.63 (m, 2H), 1.59 (s, 2H), 1.52-1.36 (m, 1H), 1.34-1.20 (m, 1H), 1.19-1.07 (m, 2H), 1.05-0.94 (m, 2H). MS (ESI) m/z 587.3 [M+H]$^+$.

Cpd. No. 104; MS (ESI) m/z 458.3 [M+H]$^+$.
Cpd. No. 105; MS (ESI) m/z 444.2 [M+H]$^+$.
Cpd. No. 106; MS (ESI) m/z 389.2 [M+H]$^+$.
Cpd. No. 107; MS (ESI) m/z 299.2 [M+H]$^+$.
Cpd. No. 108; MS (ESI) m/z 430.3 [M+H]$^+$.
Cpd. No. 109; MS (ESI) m/z 456.2 [M+H]$^+$.
Cpd. No. 110; MS (ESI) m/z 456.2 [M+H]$^+$.
Cpd. No. 111; MS (ESI) m/z 432.2 [M+H]$^+$.
Cpd. No. 112; MS (ESI) m/z 453.2 [M+H]$^+$.
Cpd. No. 113; MS (ESI) m/z 469.3 [M+H]$^+$.
Cpd. No. 114; MS (ESI) m/z 439.2 [M+H]$^+$.
Cpd. No. 115; MS (ESI) m/z 483.3 [M+H]$^+$.
Cpd. No. 116; MS (ESI) m/z 554.2 [M+H]$^+$.
Cpd. No. 117; MS (ESI) m/z 582.3 [M+H]$^+$.
Cpd. No. 118; MS (ESI) m/z 467.2 [M+H]$^+$.

Cpd. No. 119; $^1$H NMR (400 MHz, MeOD) δ 7.94-7.82 (m, 1H), 7.62 (d, J=7.6 Hz, 2H), 7.41 (dd, J=14.3, 7.4 Hz, 1H), 7.30 (d, J=8.5 Hz, 1H), 7.16 (t, J=8.6 Hz, 1H), 6.47 (d,

J=7.7 Hz, 2H), 4.14 (t, J=7.8 Hz, 2H), 3.73 (t, J=6.5 Hz, 2H), 3.69-3.49 (m, 4H), 3.45 (d, J=6.0 Hz, 2H), 3.26 (dd, J=12.9, 7.4 Hz, 1H), 3.16-2.99 (m, 4H), 2.86-2.72 (m, 1H), 2.71-2.60 (m, 1H), 2.45 (d, J=1.2 Hz, 3H), 2.24 (d, J=13.7 Hz, 1H), 2.10-1.90 (m, 2H), 1.87-1.74 (m, 2H), 1.72-1.41 (m, 4H), 1.31-1.12 (m, 1H). MS (ESI) m/z 541.3 [M+H]$^+$.

Cpd. No. 120; MS (ESI) m/z 442.3 [M+H]$^+$.
Cpd. No. 121; MS (ESI) m/z 456.3 [M+H]$^+$.
Cpd. No. 122; MS (ESI) m/z 576.2 [M+H]$^+$.
Cpd. No. 123; MS (ESI) m/z 562.2 [M+H]$^+$.
Cpd. No. 124; MS (ESI) m/z 415.2 [M+H]$^+$.
Cpd. No. 125; MS (ESI) m/z 414.2 [M+H]$^+$.
Cpd. No. 126; MS (ESI) m/z 543.2 [M+H]$^+$.
Cpd. No. 127; MS (ESI) m/z 442.2 [M+H]$^+$.
Cpd. No. 293; MS (ESI) m/z 416.2 [M+H]$^+$.
Cpd. No. 294; MS (ESI) m/z 442.2 [M+H]$^+$.
Cpd. No. 295; MS (ESI) m/z 511.2 [M+H]$^+$.
Cpd. No. 296; MS (ESI) m/z 497.2 [M+H]$^+$.

Cpd. No. 297; $^1$H NMR (400 MHz, MeOD) δ 7.79 (d, J=7.8 Hz, 1H), 7.66 (d, J=8.8 Hz, 2H), 7.58-7.52 (m, 1H), 7.45 (t, J=7.2 Hz, 1H), 7.38-7.30 (m, 1H), 7.08 (d, J=8.6 Hz, 2H), 4.33-4.25 (m, 1H), 4.19 (t, J=5.6 Hz, 2H), 4.06-3.96 (m, 1H), 3.85-3.73 (m, 1H), 3.64-3.53 (m, 2H), 3.18-3.07 (m, 3H), 3.04 (s, 3H), 2.74 (t, J=12.4 Hz, 1H), 2.28 (s, 1H), 2.15 (s, 3H), 1.86-1.65 (m, 4H), 1.43-1.28 (m, 2H), 1.10 (s, 1H). MS (ESI) m/z 515.3 [M+H]$^+$.

Cpd. No. 298; $^1$H NMR (400 MHz, MeOD) δ 7.65 (d, J=8.6 Hz, 2H), 7.46-7.27 (m, 4H), 7.05 (d, J=6.9 Hz, 2H), 4.15 (t, J=5.7 Hz, 2H), 3.66 (t, J=13.6 Hz, 2H), 3.56-3.45 (m, 1H), 3.35 (d, J=5.9 Hz, 1H), 3.26 (d, J=7.9 Hz, 1H), 3.12-2.97 (m, 4H), 2.61 (t, J=11.5 Hz, 1H), 2.30 (t, J=11.7 Hz, 1H), 2.22 (dt, J=15.9, 5.9 Hz, 2H), 2.12 (d, J=14.3 Hz, 1H), 2.06-1.83 (m, 4H), 1.76 (dd, J=27.9, 13.3 Hz, 2H), 1.56 (d, J=12.4 Hz, 1H), 1.51-1.27 (m, 4H), 1.26-1.06 (m, 3H). MS (ESI) m/z 458.3 [M+H]$^+$.

Cpd. No. 299; MS (ESI) m/z 543.3 [M+H]$^+$.
Cpd. No. 300; MS (ESI) m/z 543.3 [M+H]$^+$.
Cpd. No. 301; MS (ESI) m/z 571.3 [M+H]$^+$.
Cpd. No. 302; MS (ESI) m/z 543.3 [M+H]$^+$.
Cpd. No. 303; MS (ESI) m/z 466.2 [M+H]$^+$.
Cpd. No. 304; MS (ESI) m/z 494.2 [M+H]$^+$.
Cpd. No. 305; MS (ESI) m/z 376.2 [M+H]$^+$.
Cpd. No. 306; MS (ESI) m/z 471.2 [M+H]$^+$.
Cpd. No. 307; MS (ESI) m/z 485.3 [M+H]$^+$.
Cpd. No. 308; MS (ESI) m/z 504.2 [M+H]$^+$.
Cpd. No. 309; MS (ESI) m/z 504.2 [M+H]$^+$.
Cpd. No. 310; MS (ESI) m/z 594.3 [M+H]$^+$.
Cpd. No. 311; MS (ESI) m/z 594.3 [M+H]$^+$.

Cpd. No. 312; $^1$H NMR (400 MHz, MeOD) δ 7.86 (d, J=7.2 Hz, 2H), 7.71 (d, J=8.7 Hz, 2H), 7.58 (t, J=7.2 Hz, 1H), 7.52 (t, J=7.3 Hz, 2H), 7.49-7.44 (m, 1H), 7.34 (d, J=7.8 Hz, 1H), 7.26 (d, J=10.4 Hz, 1H), 7.16 (t, J=8.4 Hz, OH), 6.47 (d, J=8.6 Hz, 2H), 4.13 (t, J=7.9 Hz, 2H), 3.70 (t, J=8.0 Hz, 2H), 3.54 (t, J=11.2 Hz, 2H), 3.40 (d, J=7.1 Hz, 2H), 3.23-3.09 (m, 2H), 3.09-2.99 (m, 2H), 2.40 (t, J=11.8 Hz, 1H), 2.31-2.18 (m, 2H), 2.05 (d, J=14.4 Hz, 1H), 1.90-1.74 (m, 5H), 1.73-1.59 (m, 2H), 1.52 (dd, J=24.7, 11.2 Hz, 1H), 1.44-1.27 (m, 1H). MS (ESI) m/z 630.2 [M+H]$^+$.

Cpd. No. 313; MS (ESI) m/z 630.2 [M+H]$^+$.
Cpd. No. 314; MS (ESI) m/z 534.3 [M+H]$^+$.
Cpd. No. 315; MS (ESI) m/z 534.3 [M+H]$^+$.

Cpd. No. 316; $^1$H NMR (400 MHz, MeOD) δ 7.66 (d, J=8.8 Hz, 2H), 7.41-7.29 (m, 2H), 7.23-7.10 (m, 1H), 6.52 (d, J=8.8 Hz, 2H), 5.08 (s, 1H), 4.46-4.30 (m, 1H), 4.18 (t, J=8.0 Hz, 2H), 3.76 (dd, J=7.8, 5.5 Hz, 2H), 3.64-3.52 (m, 2H), 3.44 (d, J=7.0 Hz, 2H), 3.05-2.80 (m, 2H), 2.64-2.50 (m, 1H), 2.23-2.09 (m, 2H), 2.01-1.59 (m, 5H), 1.51 (d, J=14.7 Hz, 1H), 1.44-1.27 (m, 1H), 1.20-1.11 (m, 2H), 1.04-0.95 (m, 2H). MS (ESI) m/z 624.3 [M+H]$^+$.

Cpd. No. 317; MS (ESI) m/z 624.3 [M+H]$^+$.
Cpd. No. 318; MS (ESI) m/z 500.3 [M+H]$^+$.

Cpd. No. 320; $^1$H NMR (400 MHz, MeOD) δ 7.66 (d, J=8.6 Hz, 2H), 7.52-7.34 (m, 5H), 6.52 (d, J=8.8 Hz, 2H), 4.25-4.04 (m, 3H), 3.80-3.68 (m, 5H), 3.63-3.52 (m, 2H), 3.43 (d, J=7.0 Hz, 2H), 3.23-3.06 (m, 2H), 2.96-2.83 (m, 2H), 2.72-2.51 (m, 1H), 2.30 (d, J=14.1 Hz, 1H), 2.09-1.89 (m, 2H), 1.86-1.77 (m, 1H), 1.70-1.56 (m, 2H), 1.50-1.39 (m, 1H), 1.32-1.24 (m, 1H), 1.19-1.10 (m, 2H), 1.05-0.94 (m, 2H). MS (ESI) m/z 591.3 [M+H]$^+$.

Cpd. No. 319; MS (ESI) m/z 591.3 [M+H]$^+$.

Cpd. No. 321; $^1$H NMR (400 MHz, MeOD) δ 7.96-7.79 (m, 2H), 7.70 (d, J=8.7 Hz, 2H), 7.61-7.43 (m, 3H), 7.42-7.22 (m, 5H), 6.55-6.33 (m, 2H), 4.29-4.00 (m, 2H), 3.85-3.56 (m, 4H), 3.51 (d, J=12.5 Hz, 1H), 3.45-3.39 (m, 2H), 3.21-3.04 (m, 2H), 3.01-2.96 (m, 1H), 2.93 (d, J=9.8 Hz, 1H), 2.87 (d, J=11.6 Hz, 1H), 2.83-2.75 (m, 1H), 2.22 (s, 1H), 2.14 (d, J=14.9 Hz, 1H), 1.95 (d, J=14.0 Hz, 1H), 1.88 (s, 1H), 1.73 (s, 1H), 1.67-1.44 (m, 2H), 1.32 (d, J=25.5 Hz, 1H), 0.94 (s, 1H). MS (ESI) m/z 630.3 [M+H]$^+$.

Cpd. No. 322; $^1$H NMR (400 MHz, MeOD) δ 7.86 (d, J=7.6 Hz, 2H), 7.72 (d, J=8.4 Hz, 2H), 7.60-7.44 (m, 7H), 7.37 (t, J=7.2 Hz, 1H), 6.47 (d, J=8.8 Hz, 2H), 4.16 (t, J=8.0, 2H), 3.97-3.91 (m, 2H), 3.77-3.72 (m, 2H), 3.64 (d, J=12 Hz, 1H), 3.54 (d, J=12 Hz, 1H), 3.48-3.42 (m, 3H), 3.06 (t, J=11.2 Hz, 1H), 2.96 (t, J=12 Hz, 1H), 2.73 (s, 3H), 2.50-2.38 (m, 2H), 2.08 (t, J=16.4 Hz, 2H), 1.88-1.77 (m, 2H), 1.69-1.63 (m, 2H), 1.53-1.51 (m, 1H), 1.36 (m, 4H). MS (ESI) m/z 630.3 [M+H]$^+$.

Cpd. No. 381; MS (ESI) m/z 666.3 [M+H]$^+$.
Cpd. No. 382; MS (ESI) m/z 496.3 [M+H]$^+$.
Cpd. No. 383; MS (ESI) m/z 496.3 [M+H]$^+$.
Cpd. No. 384; MS (ESI) m/z 532.2 [M+H]$^+$.
Cpd. No. 385; MS (ESI) m/z 532.2 [M+H]$^+$.
Cpd. No. 386; MS (ESI) m/z 466.2 [M+H]$^+$.
Cpd. No. 387; MS (ESI) m/z 466.2 [M+H]$^+$.
Cpd. No. 388; MS (ESI) m/z 516.2 [M+H]$^+$.
Cpd. No. 389; MS (ESI) m/z 516.2 [M+H]$^+$.

Cpd. No. 390; $^1$H NMR (400 MHz, MeOD) δ 8.85 (s, 1H), 7.72-7.35 (m, 7H), 7.21 (t, J=7.4 Hz, 1H), 6.48 (d, J=8.8 Hz, 2H), 5.01 (q, J=15.6 Hz, 2H), 4.17 (td, J=8.0, 2.0 Hz, 2H), 3.74 (ddd, J=8.3, 5.7, 3.0 Hz, 2H), 3.62 (d, J=11.6 Hz, 1H), 3.51-3.41 (m, 3H), 3.26-3.21 (m, 1H), 3.07 (t, J=12.3 Hz, 1H), 3.02-2.86 (m, 2H), 2.69 (s, 2H), 2.45 (t, J=11.1 Hz, 1H), 2.30-2.17 (m, 1H), 2.13-1.93 (m, 2H), 1.75-1.37 (m, 6H), 1.20-1.09 (m, 1H), 1.07-0.97 (m, 1H). MS (ESI) m/z 585.3 [M+H]$^+$.

Cpd. No. 391; $^1$H NMR (400 MHz, MeOD) δ 8.98 (s, 1H), 8.04 (d, J=9.2 Hz, 1H), 7.98 (dd, J=6.8, 0.8 Hz, 1H), 7.72 (d, J=6.9 Hz, 1H), 7.41 (d, J=7.5 Hz, 2H), 7.36 (t, J=7.5 Hz, 2H), 7.33-7.26 (m, 1H), 7.03 (dd, J=9.1, 2.2 Hz, 1H), 6.63 (d, J=2.1 Hz, 1H), 4.87-4.80 (m, 1H), 4.31 (t, J=7.9 Hz, 3H), 4.01-3.79 (m, 3H), 3.48 (t, J=11.9 Hz, 2H), 3.39 (d, J=7.3 Hz, 2H), 3.10-2.89 (m, 4H), 2.33 (t, J=12.0 Hz, 2H), 2.24-2.07 (m, 3H), 1.97 (d, J=14.5 Hz, 1H), 1.78-1.63 (m, 7H), 1.62-1.50 (m, 3H), 1.46 (dd, J=13.4, 2.5 Hz, 1H), 1.39-1.26 (m, 2H). MS (ESI) m/z 523.2 [M+H]$^+$.

Cpd. No. 406; $^1$H NMR (400 MHz, MeOD) δ 7.59 (d, J=7.5 Hz, 2H), 7.54-7.46 (m, 4H), 7.44 (t, J=7.3 Hz, 1H), 7.30 (s, 1H), 6.94 (s, 1H), 6.46 (d, J=8.8 Hz, 2H), 5.00 (s, 1H), 4.76 (d, J=15.5 Hz, 1H), 4.61 (d, J=15.5 Hz, 1H), 4.15 (td, J=8.0, 2.4 Hz, 2H), 3.77-3.70 (m, 2H), 3.66 (d, J=11.5 Hz, 1H), 3.51-3.41 (m, 3H), 3.25-3.16 (m, 1H), 3.06 (t, J=11.7 Hz, 1H), 2.95 (t, J=11.7 Hz, 1H), 2.90-2.82 (m, 1H), 2.72 (s, 3H), 2.70-2.61 (m, 1H), 2.59 (s, 3H), 2.33 (d, J=13.8 Hz, 1H), 2.09-1.94 (m, 2H), 1.73-1.35 (m, 5H), 1.16-0.98 (m, 2H). MS (ESI) m/z 581.4 [M+H]⁺.

Cpd. No. 407; ¹H NMR (400 MHz, MeOD) δ 8.80 (s, 1H), 7.67 (d, J=7.9 Hz, 2H), 7.56-7.48 (m, 3H), 7.46-7.35 (m, 2H), 7.14 (d, J=8.8 Hz, 2H), 6.42 (d, J=8.8 Hz, 2H), 5.07-4.96 (m, 2H), 4.08-3.99 (m, 2H), 3.65-3.53 (m, 3H), 3.46-3.37 (m, 3H), 3.21-3.10 (m, 1H), 3.03 (t, J=11.5 Hz, 1H), 2.93 (t, J=11.6 Hz, 1H), 2.88-2.81 (m, 1H), 2.68 (s, 3H), 2.57-2.46 (m, 1H), 2.27 (d, J=13.4 Hz, 1H), 2.06-1.88 (m, 3H), 1.68-1.56 (m, 2H), 1.55-1.40 (m, 3H), 1.15-1.05 (m, 1H), 0.95-0.83 (m, 1H). MS (ESI) m/z 576.3 [M+H]⁺.

Cpd. No. 408; ¹H NMR (400 MHz, MeOD) δ 7.60 (d, J=7.7 Hz, 2H), 7.56-7.41 (m, 5H), 7.32 (s, 1H), 6.95 (s, 1H), 6.46 (d, J=8.8 Hz, 2H), 4.99 (s, 1H), 4.78 (d, J=11.7 Hz, 1H), 4.64 (d, J=15.4 Hz, 1H), 4.15 (td, J=8.0, 2.2 Hz, 2H), 3.78-3.68 (m, 2H), 3.65 (d, J=11.5 Hz, 1H), 3.53-3.41 (m, 3H), 3.26-3.17 (m, 1H), 3.06 (t, J=11.6 Hz, 1H), 3.01-2.86 (m, 4H), 2.72 (s, 3H), 2.61 (d, J=11.0 Hz, 1H), 2.33 (d, J=13.7 Hz, 1H), 2.00 (dd, J=25.4, 21.6 Hz, 1H), 1.72-1.45 (m, 3H), 1.39 (t, J=7.5 Hz, 2H), 1.12-0.96 (m, 1H). MS (ESI) m/z 595.3 [M+H]⁺.

Cpd. No. 409; ¹H NMR (400 MHz, MeOD) δ 7.52-7.46 (m, 4H), 7.44-7.32 (m, 4H), 7.07 (s, 1H), 6.47 (d, J=8.8 Hz, 2H), 5.26 (s, 1H), 4.71 (d, J=16.4 Hz, 1H), 4.59 (d, J=15.2 Hz, 1H), 4.16 (t, J=8.0 Hz, 2H), 3.74 (dd, J=7.9, 5.7 Hz, 2H), 3.57 (s, 2H), 3.45 (d, J=7.1 Hz, 2H), 3.27-3.18 (m, 1H), 3.12-3.01 (m, 2H), 2.84-2.74 (m, 1H), 2.70 (s, 3H), 2.68-2.60 (m, 1H), 2.46 (d, J=11.5 Hz, 2H), 2.19 (d, J=14.3 Hz, 1H), 2.06-1.97 (m, 2H), 1.76-1.55 (m, 5H), 1.43-1.33 (m, 2H), 1.28 (t, J=7.3 Hz, 3H). MS (ESI) m/z 595.3 [M+H]⁺.

Cpd. No. 410; ¹H NMR (400 MHz, MeOD) δ 8.10 (s, 1H), 7.78-7.67 (m, 3H), 7.57-7.45 (m, 1H), 7.38 (d, J=2.0 Hz, 1H), 7.28-7.10 (m, 3H), 7.07 (s, 1H), 6.48 (d, J=8.9 Hz, 2H), 5.13 (s, 1H), 4.73 (d, J=16.1 Hz, 1H), 4.61 (d, J=15.5 Hz, 1H), 4.15 (t, J=8.0 Hz, 2H), 3.88 (s, 3H), 3.72 (dd, J=7.9, 5.7 Hz, 2H), 3.62-3.51 (m, 3H), 3.43 (d, J=7.1 Hz, 2H), 3.27-3.19 (m, 1H), 3.06 (t, J=11.6 Hz, 2H), 2.78-2.72 (m, 1H), 2.70 (s, 3H), 2.52-2.47 (m, 1H), 2.45 (s, 3H), 2.15 (d, J=14.5 Hz, 1H), 2.09-1.93 (m, 2H), 1.74-1.51 (m, 5H), 1.40-1.23 (m, 2H). MS (ESI) m/z 718.4 [M+H]⁺.

Cpd. No. 411; ¹H NMR (400 MHz, MeOD) δ 8.10 (s, 1H), 7.76-7.68 (m, 3H), 7.57-7.51 (m, 1H), 7.44 (d, J=8.0 Hz, 1H), 7.38 (d, J=11.8 Hz, 1H), 7.34 (s, 1H), 7.21 (t, J=8.1 Hz, 1H), 6.96 (s, 1H), 6.47 (d, J=8.9 Hz, 2H), 4.94 (s, 1H), 4.71 (dd, J=28.9, 15.8 Hz, 2H), 4.15 (td, J=8.0, 1.9 Hz, 2H), 3.88 (s, 3H), 3.75-3.68 (m, 2H), 3.64 (d, J=11.4 Hz, 1H), 3.51-3.46 (m, 1H), 3.43 (d, J=6.4 Hz, 2H), 3.25-3.17 (m, 1H), 3.06 (t, J=12.0 Hz, 1H), 2.99-2.88 (m, 2H), 2.71 (s, 3H), 2.63 (s, 3H), 2.59-2.50 (m, 1H), 2.30 (d, J=14.3 Hz, 1H), 2.11-1.96 (m, 2H), 1.70-1.50 (m, 4H), 1.47-1.27 (m, 1H), 1.17-0.97 (m, 2H). MS (ESI) m/z 718.4 [M+H]⁺.

Cpd. No. 412; ¹H NMR (400 MHz, MeOD) δ 8.79 (s, 1H), 7.72-7.64 (m, 4H), 7.57-7.50 (m, 3H), 7.44 (d, J=7.4 Hz, 1H), 7.41 (d, J=8.0 Hz, 1H), 6.53 (d, J=8.9 Hz, 2H), 4.99 (s, 2H), 4.79-4.74 (m, 3H), 4.62-4.52 (m, 1H), 4.18 (td, J=8.0, 2.4 Hz, 2H), 3.80-3.72 (m, 2H), 3.62 (d, J=10.5 Hz, 1H), 3.51-3.40 (m, 3H), 3.24-3.18 (m, 1H), 3.04 (t, J=12.6 Hz, 1H), 2.96 (t, J=11.9 Hz, 1H), 2.92-2.84 (m, 1H), 2.68 (s, 3H), 2.57-2.42 (m, 1H), 2.27 (d, J=14.7 Hz, 1H), 2.07-1.93 (m, 2H), 1.69-1.43 (m, 6H), 1.38-1.27 (m, 1H), 1.16-1.04 (m, 1H), 0.97-0.85 (m, 1H). MS (ESI) m/z 662.3 [M+H]⁺.

Cpd. No. 413; ¹H NMR (400 MHz, MeOD) δ 7.55 (dd, J=14.5, 7.8 Hz, 1H), 7.44 (d, J=7.8 Hz, 1H), 7.39 (d, J=11.2 Hz, 1H), 7.33 (d, J=1.8 Hz, 1H), 7.24-7.18 (m, 1H), 7.17-7.11 (m, 1H), 6.96 (s, 1H), 6.46-6.38 (m, 2H), 4.95 (s, 1H), 4.71 (dd, J=35.2, 15.6 Hz, 2H), 4.03 (td, J=7.5, 2.2 Hz, 2H), 3.64 (d, J=11.7 Hz, 1H), 3.62-3.53 (m, 2H), 3.50-3.44 (m, 1H), 3.41 (d, J=6.3 Hz, 2H), 3.20-3.11 (m, 1H), 3.06 (t, J=12.1 Hz, 1H), 2.99-2.86 (m, 2H), 2.71 (s, 3H), 2.64 (s, 3H), 2.62-2.50 (m, 1H), 2.31 (d, J=14.0 Hz, 1H), 2.09-1.98 (m, 2H), 1.70-1.51 (m, 3H), 1.45-1.29 (m, 1H), 1.17-0.98 (m, 2H). MS (ESI) m/z 608.3 [M+H]⁺.

Cpd. No. 414; ¹H NMR (400 MHz, MeOD) δ 7.58-7.49 (m, 1H), 7.38 (d, J=2.0 Hz, 1H), 7.26 (d, J=7.3 Hz, 1H), 7.20 (td, J=8.2, 2.2 Hz, 1H), 7.16-7.12 (m, 3H), 7.11-7.02 (m, 1H), 6.46-6.39 (m, 2H), 5.12 (s, 1H), 4.73 (d, J=15.7 Hz, 1H), 4.61 (d, J=15.6 Hz, 1H), 4.04 (t, J=7.6 Hz, 2H), 3.64-3.51 (m, 4H), 3.42 (d, J=7.1 Hz, 2H), 3.21-3.13 (m, 1H), 3.05 (t, J=11.5 Hz, 2H), 2.78-2.73 (m, 1H), 2.71 (s, 3H), 2.45 (s, 3H), 2.43-2.32 (m, 1H), 2.15 (d, J=14.0 Hz, 1H), 2.09-1.97 (m, 2H), 1.73-1.47 (m, 5H), 1.40-1.22 (m, 2H). MS (ESI) m/z 608.3 [M+H]⁺.

Cpd. No. 415; MS (ESI) m/z 515.2 [M+H]⁺.
Cpd. No. 416; MS (ESI) m/z 515.2 [M+H]⁺.
Cpd. No. 417; ¹H NMR (400 MHz, MeOD) δ 7.85 (d, J=7.7 Hz, 1H), 7.77 (d, J=6.6 Hz, 1H), 7.71 (t, J=7.8 Hz, 1H), 7.56-7.46 (m, 1H), 6.54-6.45 (m, 1H), 4.16 (td, J=8.0, 2.3 Hz, 1H), 3.73 (ddd, J=7.5, 5.8, 1.3 Hz, 1H), 3.58 (d, J=12.3 Hz, 1H), 3.44 (d, J=7.2 Hz, 1H), 3.26-3.23 (m, OH), 3.22-3.17 (m, 1H), 3.16-3.03 (m, 1H), 2.52-2.40 (m, 1H), 2.37-2.27 (m, 1H), 2.20-2.10 (m, 1H), 1.93-1.77 (m, 2H), 1.75 (s, 2H), 1.72-1.64 (m, 1H), 1.52-1.40 (m, 1H), 1.38-1.24 (m, 1H). MS (ESI) m/z 565.3 [M+H]⁺.

Cpd. No. 418; MS (ESI) m/z 565.3 [M+H]⁺.
Cpd. No. 419; MS (ESI) m/z 572.3 [M+H]⁺.
Cpd. No. 420; MS (ESI) m/z 572.3 [M+H]⁺.
Cpd. No. 421; MS (ESI) m/z 610.3 [M+H]⁺.
Cpd. No. 422; MS (ESI) m/z 543.3 [M+H]⁺.
Cpd. No. 423; MS (ESI) m/z 543.3 [M+H]⁺.
Cpd. No. 424; MS (ESI) m/z 624.3 [M+H]⁺.
Cpd. No. 425; MS (ESI) m/z 624.3 [M+H]⁺.

The following Compounds of the Disclosure, see Table 5, were prepared using the illustrative methods described in Examples 1-12, and/or methods known to those skilled in the art in view of this disclosure, and characterized by ESI-MS as provided in Table 6.

TABLE 6

| Cpd. No. | MS (ESI) m/z [M + H]⁺ |
| --- | --- |
| 426 | 517.75 |
| 427 | 624.75 |
| 428 | 624.67 |
| 429 | 649.83 |
| 430 | 599.92 |
| 431 | 599.92 |
| 432 | 613.92 |
| 433 | 656.92 |
| 434 | 692.45 |
| 435 | 720.39 |
| 436 | 706.51 |
| 437 | 728.46 |
| 438 | 568.3 |
| 439 | 568.2 |
| 440 | 594.2 |
| 441 | 609.3 |
| 442 | 599.2 |
| 443 | 600.3 |
| 444 | 643.1 |
| 445 | 600.3 |
| 446 | 642.2 |
| 447 | 668.1 |
| 448 | 668.3 |
| 449 | 690.2 |
| 450 | 617.1 |
| 451 | 600.3 |
| 452 | 617.3 |

TABLE 6-continued

| Cpd. No. | MS (ESI) m/z [M + H]+ |
|---|---|
| 453 | 613.3 |
| 454 | 588.2 |
| 455 | 613.1 |
| 456 | 613.2 |
| 457 | 613.3 |
| 458 | 613.2 |
| 459 | 617.1 |
| 460 | 580.2 |
| 461 | 580.3 |
| 462 | 627.2 |
| 463 | 627.1 |
| 464 | 613.3 |
| 465 | 631.2 |
| 466 | 631.3 |
| 467 | 649.1 |
| 468 | 529.2 |
| 469 | 649.3 |
| 470 | 692.1 |
| 471 | 720.3 |
| 472 | 747.2 |
| 473 | 661.1 |
| 474 | 710.3 |
| 475 | 562.3 |
| 476 | 562.2 |
| 477 | 534.1 |
| 478 | 534.3 |
| 479 | 612.2 |
| 480 | 713.2 |
| 481 | 670.3 |
| 482 | 706.3 |
| 483 | 649.3 |
| 484 | 645.2 |
| 485 | 645.1 |
| 486 | 645.2 |
| 487 | 623.3 |
| 488 | 651.1 |
| 489 | 630.2 |
| 490 | 497.3 |
| 491 | 497.2 |
| 492 | 439.3 |
| 493 | 511.1 |
| 494 | 525.2 |
| 495 | 469.3 |
| 496 | 469.3 |
| 497 | 483.2 |
| 498 | 515.3 |
| 499 | 515.3 |
| 500 | 565.3 |
| 501 | 565.3 |
| 502 | 572.3 |
| 503 | 572.3 |
| 504 | 574.3 |
| 505 | 574.3 |
| 506 | 628.3 |
| 507 | 603.3 |
| 508 | 568.3 |
| 509 | 615.3 |
| 510 | 615.3 |
| 511 | 617.3 |
| 512 | 633.3 |
| 513 | 586.3 |
| 514 | 661.3 |
| 515 | 613.4 |
| 516 | 613.4 |
| 517 | 631.5 |
| 518 | 631.5 |
| 519 | 629.3 |
| 520 | 629.3 |
| 521 | 635.3 |
| 522 | 665.3 |

Example 14

Menin Binding Affinity

A fluorescence polarization (FP) competitive binding assay was used to determine the binding affinities of representative menin inhibitors. A FAM labeled fluorescent probe was designed and synthesized based on a MLL1 peptide (FAM-MM2). Equilibrium dissociation constant ($K_d$) value of FAM-MM2 to menin protein was determined from protein saturation experiments by monitoring the total fluorescence polarization of mixtures composed with the fluorescent probe at a fixed concentration and the protein with increasing concentrations up to full saturation. Serial dilutions of the protein were mixed with FAM-MM2 to a final volume of 200 µl in the assay buffer (PBS with 0.02% Bovine γ-Globulin and 4% DMSO. 0.01% Triton X-100 was added right before assays). Final FAM-MM2 concentration was 2 nM. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, v-bottom plates (Thermo Scientific, Waltham, Mash.) at an excitation wavelength of 485 nm and an emission wavelength of 530 nm. $K_d$ value of FAM-MM2, which was calculated by fitting the sigmoidal dose-dependent FP increases as a function of protein concentrations using Graphpad Prism 6.0 software (Graphpad Software, San Diego, Calif.), is determined as 1.4 nM.

The $IC_{50}$, see Table 3, and $K_i$ values of representative Compounds of the Disclosure were determined in a competitive binding experiment. Mixtures of 5 µl of the tested compounds in DMSO and 195 µl of preincubated protein/probe complex solution in the assay buffer were added into assay plates which were incubated at room temperature for 30 minutes with gentle shaking. Final concentration of the menin protein was 4 nM, and final probe concentration is 2 nM. Negative controls containing protein/probe complex only (equivalent to 0% inhibition), and positive controls containing only free probes (equivalent to 100% inhibition), were included in each assay plate. FP values were measured as described above. $IC_{50}$ values were determined by non-linear regression fitting of the competition curves.

TABLE 3

| Cpd. No. | Menin Binding Affinity $IC_{50}$ (µM) |
|---|---|
| 19 | 0.061 |
| 20 | 1.3 |
| 21 | 1.1 |
| 22 | 0.473 |
| 23 | 0.054 |
| 24 | 0.416 |
| 25 | 2.7 |
| 26 | No inhibition |
| 27 | 0.071 |
| 28 | 0.379 |
| 29 | 0.091 |
| 30 | 0.439 |
| 31 | 0.037 |
| 32 | 0.059 |
| 33 | 0.019 |
| 34 | 1.8 |
| 35 | 3.2 |
| 37 | 0.449 |
| 38 | 0.304 |
| 39 | 0.124 |
| 40 | 0.817 |

TABLE 3-continued

| Cpd. No. | Menin Binding Affinity IC$_{50}$ (μM) |
|---|---|
| 41 | 0.166 |
| 42 | 0.029 |
| 43 | 0.026 |
| 44 | 0.910 |
| 45 | 0.027 |
| 46 | 0.023 |
| 47 | 0.137 |
| 48 | 0.007 |
| 49 | 0.009 |
| 50 | 0.007 |
| 51 | 0.008 |
| 52 | 0.025 |
| 53 | 1.1 |
| 54 | 0.011 |
| 55 | 0.669 |
| 56 | 18.2 |
| 57 | No inhibition |
| 58 | 0.241 |
| 59 | 2.3 |
| 60 | No inhibition |
| 61 | No inhibition |
| 62 | 36.2 |
| 63 | 6.0 |
| 64 | 0.061 |
| 65 | 2.8 |
| 66 | 1.1 |
| 67 | 1.2 |
| 68 | 0.181 |
| 69 | 0.030 |
| 70 | 0.012 |
| 71 | 190 |
| 72 | 609.8 |
| 73 | 9.9 |
| 74 | 3.1 |
| 75 | 142.4 |
| 76 | 1.3 |
| 77 | 2581 |
| 78 | No inhibition |
| 79 | 0.7 |
| 80 | 11.6 |
| 81 | 1.9 |
| 82 | 6.2 |
| 83 | 0.847 |
| 84 | 8.2 |
| 85 | 0.036 |
| 86 | 0.055 |
| 87 | 0.122 |
| 88 | 0.075 |
| 89 | 13.1 |
| 90 | 2.4 |
| 91 | 0.042 |
| 92 | 0.019 |
| 93 | 0.052 |
| 94 | 0.029 |
| 95 | 0.024 |
| 96 | 0.587 |
| 97 | 0.049 |
| 98 | 0.021 |
| 99 | 0.802 |
| 100 | 4.7 |
| 101 | 0.010 |
| 102 | 0.011 |
| 103 | 0.012 |
| 104 | 32.7 |
| 105 | 20.2 |
| 106 | 84.1 |
| 107 | 298.7 |
| 108 | 56.5 |
| 109 | 0.825 |
| 110 | 575.4 |
| 111 | 46.2 |
| 112 | 41.6 |
| 113 | 0.067 |
| 114 | 32.6 |
| 115 | 4.0 |
| 116 | 6.0 |
| 117 | 7.2 |
| 118 | 21.8 |
| 119 | 0.015 |
| 120 | 5.7 |
| 121 | 13.1 |
| 122 | 57.5 |
| 123 | No inhibition |
| 124 | No inhibition |
| 125 | No inhibition |
| 126 | 58.4 |
| 127 | 293.9 |
| 128 | 4.1 |
| 129 | 0.036 |
| 130 | 10.6 |
| 131 | 1.1 |
| 132 | 0.077 |
| 133 | 0.030 |
| 134 | 0.067 |
| 135 | 0.025 |
| 136 | 0.009 |
| 137 | 0.008 |
| 138 | 0.099 |
| 139 | 0.073 |
| 140 | 0.104 |
| 141 | 0.028 |
| 142 | 0.008 |
| 143 | 0.028 |
| 144 | 0.023 |
| 145 | 0.015 |
| 146 | 0.013 |
| 147 | 0.009 |
| 148 | 0.006 |
| 149 | 0.012 |
| 151 | 0.015 |
| 152 | 0.009 |
| 153 | 0.007 |
| 154 | 0.006 |
| 155 | 0.016 |
| 156 | 0.008 |
| 157 | 0.016 |
| 158 | 0.008 |
| 159 | No inhibition |
| 160 | No inhibition |
| 161 | 0.021 |
| 162 | No inhibition |
| 163 | No inhibition |
| 164 | 0.008 |
| 165 | 2993 |
| 166 | 1412 |
| 167 | 172 |
| 168 | 5.6 |
| 169 | 49.9 |
| 170 | 47.6 |
| 171 | No test |
| 172 | 11.2 |
| 173 | 3.0 |
| 174 | 24.6 |
| 175 | 8.8 |
| 176 | 140.1 |
| 177 | 3.6 |
| 178 | 6.5 |
| 179 | 3.8 |
| 180 | 9.7 |
| 181 | 18.1 |
| 182 | 23.7 |
| 183 | 0.073 |
| 184 | 2.6 |
| 185 | 0.007 |
| 186 | 1.0 |
| 187 | 0.018 |
| 188 | 1.7 |
| 189 | 20.5 |
| 190 | 2.0 |
| 191 | 0.623 |
| 192 | 28.0 |
| 193 | 0.237 |
| 194 | 164.6 |
| 195 | 0.010 |

TABLE 3-continued

| Cpd. No. | Menin Binding Affinity IC$_{50}$ (μM) |
|---|---|
| 196 | 1.0 |
| 197 | 0.018 |
| 198 | 0.853 |
| 199 | 9.0 |
| 200 | 0.017 |
| 201 | 0.005 |
| 202 | 0.113 |
| 203 | 0.009 |
| 204 | 0.122 |
| 205 | 0.088 |
| 206 | 0.003 |
| 207 | 2.8 |
| 208 | 0.435 |
| 209 | 0.111 |
| 210 | 0.004 |
| 211 | 0.009 |
| 212 | 0.454 |
| 213 | 0.170 |
| 214 | 3.4 |
| 215 | 0.006 |
| 216 | 0.396 |
| 217 | 11.6 |
| 218 | No inhibition |
| 219 | 0.003 |
| 220 | 0.261 |
| 221 | 0.075 |
| 222 | 2.0 |
| 223 | 0.014 |
| 224 | 0.331 |
| 225 | 0.009 |
| 226 | 0.014 |
| 227 | 0.498 |
| 228 | 0.004 |
| 229 | 0.160 |
| 230 | 0.007 |
| 231 | 0.068 |
| 232 | 0.020 |
| 233 | 0.178 |
| 234 | 0.050 |
| 235 | 6.2 |
| 236 | 0.012 |
| 237 | 0.042 |
| 238 | 0.008 |
| 239 | 0.046 |
| 240 | 0.009 |
| 241 | 0.849 |
| 242 | 2.1 |
| 243 | 4.2 |
| 244 | 2.3 |
| 245 | 3.3 |
| 246 | 35.6 |
| 247 | 1.1 |
| 248 | 0.8 |
| 249 | 1.9 |
| 250 | 4.7 |
| 251 | 7.1 |
| 252 | 1.2 |
| 253 | 14.4 |
| 254 | 23.2 |
| 255 | 4.7 |
| 256 | 3.3 |
| 257 | 4.6 |
| 258 | 0.563 |
| 259 | 10.3 |
| 260 | 17.0 |
| 261 | 9.3 |
| 262 | 6.9 |
| 263 | 0.010 |
| 264 | 0.555 |
| 265 | 4.9 |
| 266 | 4.5 |
| 267 | 0.437 |
| 268 | 4.7 |
| 269 | 0.009 |
| 270 | 0.881 |
| 271 | 0.005 |
| 272 | 0.180 |
| 273 | 37.6 |
| 274 | 19.2 |
| 275 | 0.012 |
| 276 | 1.2 |
| 277 | 0.008 |
| 278 | 0.296 |
| 279 | 0.065 |
| 280 | 1.4 |
| 281 | 0.029 |
| 282 | 3.3 |
| 283 | 0.010 |
| 284 | 0.011 |
| 285 | 0.009 |
| 286 | 0.004 |
| 287 | 0.247 |
| 288 | 0.012 |
| 289 | 0.004 |
| 290 | 0.009 |
| 291 | 0.007 |
| 292 | 0.011 |
| 293 | 2.8 |
| 294 | 11.1 |
| 295 | 1.9 |
| 296 | 0.4 |
| 297 | 2.1 |
| 298 | 0.3 |
| 299 | 16.8 |
| 300 | 56.5 |
| 301 | 34.8 |
| 302 | 6.5 |
| 303 | 75.3 |
| 304 | 10.7 |
| 305 | 42.1 |
| 306 | 40.0 |
| 307 | 30.6 |
| 308 | 0.066 |
| 309 | 11.4 |
| 310 | 0.045 |
| 311 | 5.7 |
| 312 | 0.013 |
| 313 | 13.8 |
| 314 | 0.031 |
| 315 | 0.131 |
| 316 | 0.003 |
| 317 | 0.161 |
| 318 | 20.9 |
| 319 | 0.031 |
| 320 | 5.1 |
| 321 | 0.004 |
| 322 | 0.108 |
| 323 | 10.4 |
| 324 | 9.6 |
| 325 | 1.8 |
| 326 | 2.7 |
| 327 | 485.2 |
| 328 | 119.4 |
| 329 | 19 |
| 330 | 111.4 |
| 331 | 23.3 |
| 332 | 0.261 |
| 333 | 5.1 |
| 334 | 3.2 |
| 335 | 5.6 |
| 336 | 29.4 |
| 337 | 25.8 |
| 338 | 10.2 |
| 339 | 5.2 |
| 340 | 2.9 |
| 340 | 1.5 |
| 342 | 0.897 |
| 343 | 8.8 |
| 344 | 180.5 |
| 345 | 0.011 |
| 346 | 0.569 |
| 347 | 0.014 |
| 348 | 0.819 |
| 349 | 0.015 |

TABLE 3-continued

| Cpd. No. | Menin Binding Affinity IC$_{50}$ (µM) |
|---|---|
| 350 | 1.2 |
| 351 | 0.015 |
| 352 | 2.7 |
| 353 | 0.006 |
| 354 | 0.062 |
| 355 | 0.045 |
| 356 | 0.022 |
| 357 | 0.032 |
| 358 | 0.221 |
| 359 | 0.012 |
| 360 | 1.4 |
| 361 | 0.063 |
| 362 | 0.008 |
| 363 | 0.027 |
| 364 | 3.1 |
| 365 | 0.281 |
| 366 | 0.009 |
| 367 | 0.030 |
| 368 | 0.506 |
| 369 | 0.068 |
| 370 | 3.6 |
| 371 | 2.1 |
| 372 | 0.048 |
| 373 | 0.112 |
| 374 | 4.7 |
| 375 | 0.011 |
| 376 | 0.006 |
| 377 | 1.129 |
| 378 | 0.032 |
| 379 | 3.8 |
| 380 | 0.798 |
| 381 | 0.013 |
| 382 | 0.102 |
| 383 | 2.5 |
| 384 | 4.6 |
| 385 | 0.013 |
| 386 | No inhibition |
| 387 | No inhibition |
| 388 | 15.1 |
| 389 | 6.5 |
| 390 | 0.005 |
| 392 | 0.007 |
| 393 | 0.008 |
| 394 | 0.015 |
| 395 | 0.016 |
| 396 | 0.012 |
| 397 | 0.186 |
| 398 | 0.167 |
| 399 | 0.007 |
| 400 | 0.029 |
| 401 | 0.089 |
| 402 | 2.4 |
| 403 | 0.007 |
| 404 | 0.212 |
| 405 | 0.174 |
| 406 | 0.003 |
| 407 | 0.005 |
| 408 | 0.003 |
| 409 | 0.116 |
| 410 | 0.049 |
| 411 | 0.003 |
| 412 | 0.004 |
| 413 | 0.006 |
| 414 | 0.539 |
| 415 | 0.016 |
| 416 | 3.28 |
| 417 | 1.61 |
| 418 | 923.13 |
| 419 | 0.293 |
| 420 | 11.6 |
| 421 | 0.004 |
| 422 | 0.028 |
| 423 | 0.776 |

Example 15

Cell Growth Inhibition

Cell growth inhibitory activity of representative menin inhibitors was determined using CellTiter-Glo® Luminescent Cell Viability Assay. Cells were seeded in 384-well white opaque cell culture plates at a density of 2,000 cells/well with serially diluted compounds and incubated at 37° C. in an atmosphere of 95% air and 5% $CO_2$ for 4 days. Cell viability was determined using the CellTiter-Glo® Luminescent Cell Viability Assay Kit (Promega, Madison, Wis.) according to the manufacture's instruction. Briefly, a volume of CellTiter-Glo® Reagent equal to the volume of cell culture medium was added to each well, and then the plates were incubated at room temperature for 10-20 minutes. The luminescent signal was measured using a Tecan Infinite M1000 multimode microplate reader (Tecan, Morrisville, N.C.). The half maximal inhibitory concentration (IC$_{50}$) was calculated using the GraphPad Prism 5 software (GraphPad Software, La Jolla, Calif.).

TABLE 4

| | Cell Growth Inhibition IC$_{50}$ (µM) | |
|---|---|---|
| Cpd. No. | MV4; 11 | MOLM13 |
| 19 | 1.6 ± 0.1 | 7.3 |
| 23 | 1.0 ± 0.4 | 5.0 |
| 27 | 0.9 | 3.6 |
| 43 | 0.896 ± 0.056 | 2.1 |
| 45 | 0.845 ± 0.436 | 5.0 |
| 46 | 0.972 ± 0.558 | 5.1 ± 0.2 |
| 48 | 0.908 | 2.8 |
| 49 | 0.898 | 4 |
| 51 | 0.67 | 1.46 |
| 70 | 2.2 | 3.5 |
| 85 | 1.6 | 4.2 |
| 86 | 0.864 ± 0.017 | 1.2 ± 0.5 |
| 91 | 1.3 ± 0.3 | 1.7 ± 0.004 |
| 92 | 0.961 ± 0.384 | 1.6 ± 0.1 |
| 93 | 0.779 ± 0.068 | 1.1 ± 0.7 |
| 94 | 2.0 | 2.3 |
| 95 | 1.8 | 1.9 |
| 101 | 0.3 | 0.73 |
| 102 | 0.2668 | 0.7075 |
| 103 | 0.49 | 2.26 |
| 111 | 14.4 | 96.2 |
| 113 | 1.6 | 2.4 |
| 119 | 1.8 | 1.3 |
| 133 | 1.7 ± 1.0 | 2.9 ± 0.8 |
| 134 | 1.1 | 3.8 |
| 135 | 1.3 ± 0.4 | 2.1 ± 1.0 |
| 136 | 1.2 | 3.8 |
| 137 | 1.0 ± 0.2 | 1.9 ± 0.7 |
| 141 | 4.7 | 54.7 |
| 142 | 0.979 ± 0.335 | 3.2 ± 0.3 |
| 143 | 1.2 ± 1.0 | 3.4 ± 0.5 |
| 144 | 1.6 ± 1.1 | 4.0 ± 0.7 |
| 145 | 1.6 ± 0.8 | 3.3 ± 0.5 |
| 146 | 0.785 ± 0.247 | 1.9 ± 1.2 |
| 147 | 0.956 ± 0.727 | 1.6 ± 0.8 |
| 148 | 0.810 ± 0.364 | 1.5 ± 0.9 |
| 149 | 0.493 | 0.331 |
| 151 | 1.3 | 0.627 |
| 152 | 0.46 | 0.49 |
| 153 | 0.79 | 0.77 |
| 156 | 0.654 | 1.8 |
| 157 | 1.8 | 4.4 |
| 158 | 0.8 | 1.56 |
| 164 | 0.27 | 0.72 |
| 185 | 0.624 ± 0.165 | 0.783 ± 0.474 |
| 187 | 1.2 ± 0.3 | 1.9 ± 0.7 |
| 195 | 0.991 | 1.5 |

TABLE 4-continued

| Cpd. No. | Cell Growth Inhibition IC$_{50}$ (μM) | |
|---|---|---|
| | MV4; 11 | MOLM13 |
| 201 | 0.090 ± 0.051 | 0.399 ± 0.153 |
| 203 | 0.234 | 0.687 |
| 206 | 0.119 ± 0.048 | 0.411 ± 0.300 |
| 210 | 0.023 ± 0.016 | 0.135 ± 0.093 |
| 211 | 0.3017 | 0.5457 |
| 215 | 0.173 ± 0.048 | 0.415 ± 0.208 |
| 219 | 0.074 ± 0.011 | 0.236 |
| 223 | 0.29 | 0.49 |
| 225 | 0.24 | 0.82 |
| 228 | 0.18 | 0.25 |
| 230 | 0.092 | 0.25 |
| 232 | 0.3 | 0.94 |
| 234 | 1.11 | 6.41 |
| 238 | 0.027 | 0.16 |
| 240 | 0.2 | 0.54 |
| 263 | 0.254 | 1.4 |
| 269 | 0.2728 | 1.729 |
| 271 | 0.123 ± 0.043 | 0.717 ± 0.002 |
| 272 | 4.294 ± 1.446 | 2.971 |
| 275 | 0.45 | 0.41 |
| 277 | 0.12 | 0.43 |
| 278 | 2.27 | 2.12 |
| 281 | 0.55 | 2.35 |
| 283 | 0.21 | 0.53 |
| 284 | 2.59 | >10 |
| 285 | 2.48 | 12.39 |
| 286 | 0.48 | 5.69 |
| 288 | 0.35 | 48.75 |
| 289 | 0.17 | 0.32 |
| 290 | 0.11 | 0.32 |
| 291 | 0.2 | 0.71 |
| 292 | 0.13 | 1.34 |
| 314 | 2.97 | >10 |
| 316 | 0.3 | 1.8 |
| 319 | 0.33 | 2.77 |
| 321 | 0.73 | 1.25 |
| 345 | 0.54 | 0.71 |
| 347 | 0.36 | 0.44 |
| 349 | 0.44 | 0.87 |
| 351 | 3.02 | 16.05 |
| 353 | 0.075 | 0.25 |
| 354 | 1.3 | 4.7 |
| 356 | 0.71 | 0.69 |
| 359 | 0.43 | 1.46 |
| 362 | 4.79 | >10 |
| 363 | 0.56 | 2.64 |
| 366 | 0.035 | 0.14 |
| 367 | 1.66 | 2.96 |
| 369 | 3.5 | 7.71 |
| 372 | 2.03 | 5.01 |
| 375 | 0.39 | 1.73 |
| 376 | 10.46 ± 2.08 | >10 |
| 381 | 0.14 | 0.67 |
| 390 | 0.021 | 0.082 |
| 392 | 0.084 ± 0.032 | 0.76 ± 0.32 |
| 393 | 0.25 | 0.88 |
| 394 | 0.43 | 1.94 |
| 395 | 0.65 | 2.29 |
| 396 | 0.46 | 1.46 |
| 397 | 4.54 | >10 |
| 398 | 4.57 | >10 |
| 399 | 0.11 | 1.63 |
| 400 | 0.83 | 6.11 |
| 403 | 0.19 | 1.3 |
| 404 | >10 | >10 |
| 406 | 0.004 ± 0.002 | 0.009 ± 0.0004 |
| 407 | 0.41 ± 0.28 | 0.69 ± 0.089 |
| 408 | 0.005 ± 0.002 | 0.017 ± 0.007 |
| 409 | 1.7 | 1.6 |
| 410 | 2.7 | 3.1 |
| 411 | 0.003 | 0.016 |

Example 16

Mechanism of Action Studies

MOLM-13 or MV4-11 cells were seeded in a 6-well plate at a density of 500,000 cells/well in 2 ml of culture medium and treated with either Cpd. No. 210 or Cpd. No. 366 at the concentrations as indicated. About 4 days after the treatments, cells were harvested and the expression of each gene was measured with qPCR.

In MOLM-13 cells, Cpd. No. 210 and Cpd. No. 366 reduced MEIS1 after 4 days of treatment. These compounds also reduced HOX7 and HOX10 in a dose dependent manner. Cpd. No. 366 may reduce MYB gene at high concentration. MYB encodes the protein that plays an essential role in the regulation of hematopoiesis. See FIG. 1.

In MV4-11 cells, Cpd. No. 210 and Cpd. No. 366 reduced MEIS1 after 4 days of treatment. These compounds also reduced HOX10 at a dose dependent manner. Since the level of HOX7 in MV4-11 cells is low, the effect of these compounds on HOX7 is not as robust as those of HOX10. There is no effect of Cpd. No. 210 and Cpd. No. 366 on MYB after 4 days of treatment at the concentration tested. See FIG. 2.

Example 17

Mechanism of Action Studies

MOLM-13 cells were seeded in a 6-well plate at a density of 500,000 cells/well in 2 ml of culture medium and treated with either Cpd. No. 366 or Cpd. No. 238 at the concentrations as indicated. About 66 hours after the treatment, cells were harvested and the expression of each gene was measured with qPCR.

In MOLM-13 cells, Cpd. No. 366 or Cpd. No. 238 reduced MEIS1 after 66 hours of treatment. The compounds also reduced HOX7 and HOX10 aint a dose dependent manner. The compounds had not effect on ITGAM, a gene coding for CD11b. See FIG. 3.

Example 18

Mechanism of Action Studies

MOLM-13 or MV4-11 cells were seeded in a 6-well plate at a density of 500,000-800,000 cells/well in 2 ml of culture medium and treated with either Cpd. No. 366 or Cpd. No. 215 at the concentrations as indicated. About 40 hours after the treatment, cells were harvested and the expression of each gene was measured with qPCR.

In MOLM-13 cells, Cpd. No. 366 reduced MEIS1 after 40 hours of treatment. Cpd. No. 366 also reduces all the tested HOX genes at a dose dependent manner. Cpd. No. 215 has a similar effect, except on HOX9 gene. See FIG. 4.

In MV4-11 cells, Cpd. No. 366 reduced MEIS1 after 40 hours of treatment. Cpd. No. 366 also significantly reduced HOX10 and HOX11 genes. Neither Cpd. No. 366 nor Cpd. No. 215 showed an effect on HOX7 gene at the concentrations tested and after 40 hours of treatment. See FIG. 5.

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications and publications cited herein are fully incorporated by reference herein in their entirety.

What is claimed is:

1. A compound, or a pharmaceutically acceptable salt, hydrate, or solvate thereof, having Formula VIi:

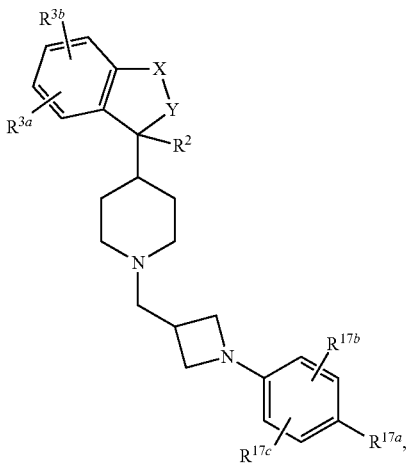

wherein:

X—Y is selected from the group consisting of
—N(R$^{1a}$)—C(=O)—;
—C(=O)—O—;
—C(=O)—N(R$^{1b}$)—;
—CH$_2$N(R$^{1c}$)—CH$_2$—;
—C(=O)N(R$^{1d}$)—CH$_2$—;
—CH$_2$CH$_2$—N(R$^{1e}$)—;
—CH$_2$N(R$^{1f}$)—C(=O)—; and
—CH$_2$O—CH$_2$—;

R$^{1a}$ is selected from the group consisting of hydrogen and alkyl;

R$^{1b}$ is selected from the group consisting of hydrogen, alkyl, and aralkyl;

R$^{1c}$ is selected from the group consisting of hydrogen, alkyl, haloalkyl, optionally substituted cycloalkyl, optionally substituted heterocyclo, (cycloalkyl)alkyl, (heterocycloalkyl)alkyl, aralkyl, (heteroaryl)alkyl, alkylcarbonyl, arylcarbonyl, and alkoxycarbonyl;

R$^{1d}$ is selected from the group consisting of hydrogen, alkyl, and aralkyl;

R$^{1e}$ is selected from the group consisting of hydrogen, alkyl, and (aryloxy)alkyl;

R$^{1f}$ is selected from the group consisting of hydrogen and alkyl;

R$^2$ is selected from the group consisting of hydrogen, alkyl, alkenyl, optionally substituted cycloalkyl, optionally substituted aryl, optionally substituted heterocyclo, optionally substituted heteroaryl, and aralkyl;

R$^{3a}$ and R$^{3b}$ are each independently selected from the group consisting of hydrogen, alkyl, halo, hydroxy, cyano, amino, alkylamino, dialkylamino, haloalkyl, alkoxy, and haloalkoxy;

R$^{17a}$ is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl; and R$^{17b}$ and R$^{17c}$ are independently selected from the group consisting of hydrogen, alkyl, halo, hydroxy, cyano, amino, alkylamino, dialkylamino, haloalkyl, alkoxy, and haloalkoxy.

2. The compound of claim 1, or a pharmaceutically acceptable salt, hydrate, or solvate thereof, wherein:

R$^{17a}$ is selected from the group consisting of alkylsulfonyl, cycloalkylsulfonyl, arylsulfonyl, and heteroarylsulfonyl; and R$^{17b}$ and R$^{17c}$ are hydrogen.

3. The compound of claim 1, or a pharmaceutically acceptable salt, hydrate, or solvate thereof, wherein R$^2$ is selected from the group consisting of alkyl, alkenyl, optionally substituted cycloalkyl, optionally substituted aryl, optionally substituted heterocyclo, optionally substituted heteroaryl, and aralkyl.

4. The compound of claim 3, or a pharmaceutically acceptable salt, hydrate, or solvate thereof, wherein R$^2$ is optionally substituted cycloalkyl.

5. The compound of claim 4, or a pharmaceutically acceptable salt, hydrate, or solvate thereof, wherein R$^2$ is substituted cycloalkyl having Formula VII:

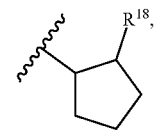

wherein:

R$^{18}$ is selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N(R$^{19a}$)C(=O)—R$^{19b}$, and —N(R$^{20a}$)SO$_2$—R$^{20b}$;

R$^{19a}$ is selected from the group consisting of hydrogen and alkyl;

R$^{19b}$ is selected from the group consisting of amino, alkoxy, alkyl, and optionally substituted aryl;

R$^{20a}$ is selected from the group consisting of hydrogen and alkyl; and

R$^{20b}$ is selected from the group consisting of amino, alkyl, and optionally substituted aryl.

6. The compound of claim 5, or a pharmaceutically acceptable salt, hydrate, or solvate thereof, wherein R$^{18}$ is selected from the group consisting of —OC(=O)-amino and —NHC(=O)—R$^{19b}$.

7. The compound of claim 3, or a pharmaceutically acceptable salt, hydrate, or solvate thereof, wherein $R^2$ is selected from the group consisting of:
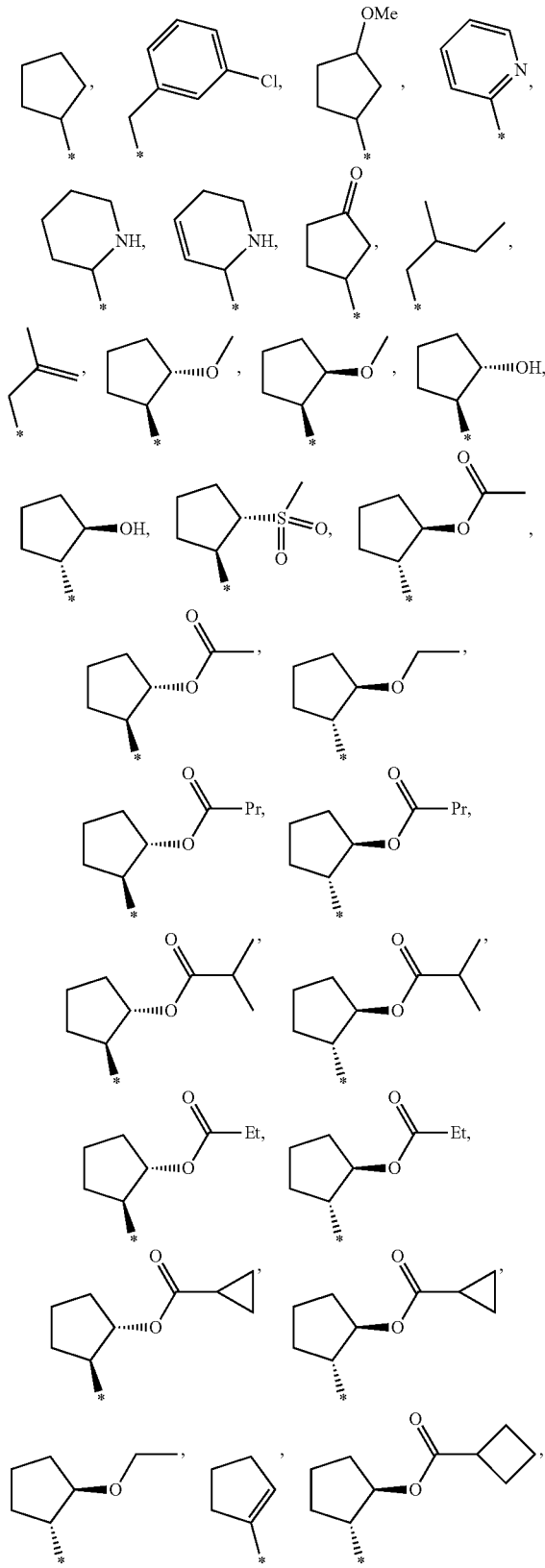
-continued
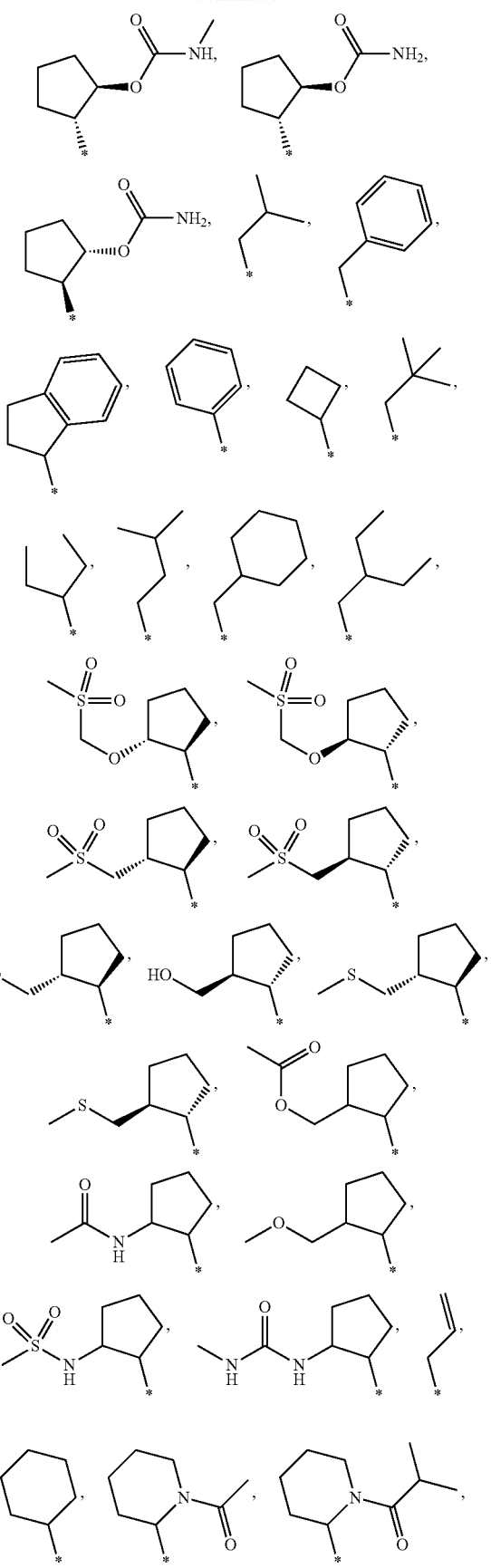

-continued

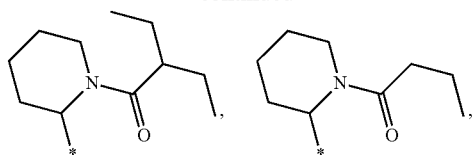

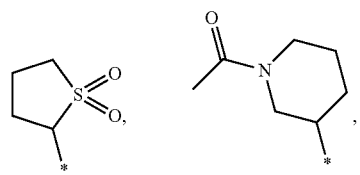

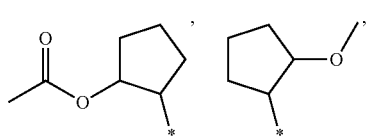

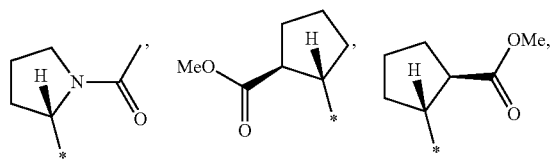

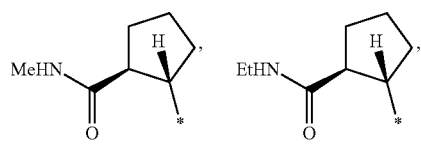

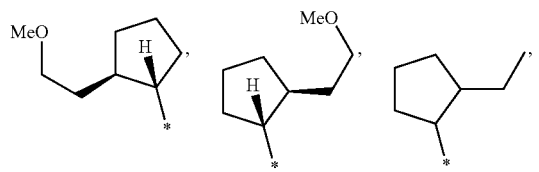

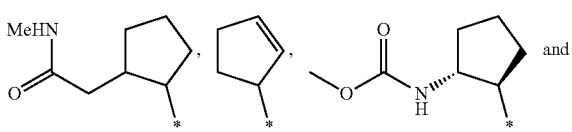

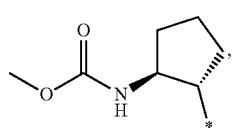

wherein "*" indicates the point of attachment to the remainder of the molecule.

8. The compound of claim 1, or a pharmaceutically acceptable salt, hydrate, or solvate thereof, wherein X—Y is selected from the group consisting of —N(R$^{1a}$)—C(=O)—; —C(=O)—O—; —C(=O)—N(R$^{1b}$)—; —CH$_2$N(R$^{1c}$)—CH$_2$—; —C(=O)N(R$^{1d}$)—CH$_2$—; —CH$_2$CH$_2$—N(R$^{1e}$); CH$_2$N(R$^{1f}$)—C(=O)—; and —CH$_2$O—CH$_2$—.

9. The compound of claim 8, or a pharmaceutically acceptable salt, hydrate, or solvate thereof, wherein X—Y is —CH$_2$N(R$^{1c}$)—CH$_2$—.

10. The compound of claim 8, or a pharmaceutically acceptable salt, hydrate, or solvate thereof, wherein X—Y is —CH$_2$CH$_2$—N(R$^{1e}$)—.

11. The compound of claim 8, or a pharmaceutically acceptable salt, hydrate, or solvate thereof, wherein X—Y is —CH$_2$N(R$^{1f}$)—C(=O)—.

12. The compound of claim 8, or a pharmaceutically acceptable salt, hydrate, or solvate thereof, wherein X—Y is —CH$_2$O—CH$_2$—.

13. The compound of claim 1, or a pharmaceutically acceptable salt, hydrate, or solvate thereof, having Formula IX:

IX

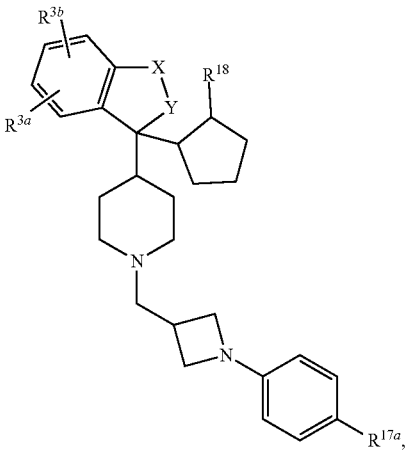

wherein:

X—Y is —CH$_2$N(R$^{1c}$)—CH$_2$—;

R$^{1c}$ is C$_{1-3}$ alkyl;

R$^{3a}$ and R$^{3b}$ are each independently selected from the group consisting of hydrogen, alkyl, halo, hydroxy, cyano, amino, alkylamino, dialkylamino, haloalkyl, alkoxy, and haloalkoxy;

R$^{17a}$ is selected from the group consisting of chloro, cyano, alkylsulfonyl, haloalkylsulfonyl, cycloalkylsulfonyl, arylsulfonyl, and heteroarylsulfonyl;

R$^{18}$ is selected from the group consisting of —OC(=O)-amino and —NHC(=O)—R$^{19b}$; and R$^{19b}$ is selected from the group consisting of amino, alkoxy, alkyl, and optionally substituted aryl.

14. The compound of claim 1, or a pharmaceutically acceptable salt, hydrate, or solvate thereof, wherein:

X—Y is —CH$_2$N(R$^{1c}$)—CH$_2$—; and

R$^{1c}$ is selected from the group consisting of hydrogen and C$_{1-6}$ alkyl.

15. A compound, or a pharmaceutically acceptable salt, hydrate, or solvate thereof, selected from one or more of:
25
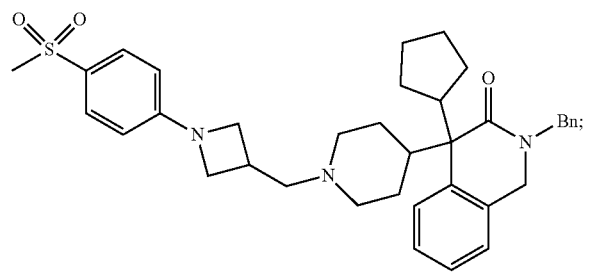
33
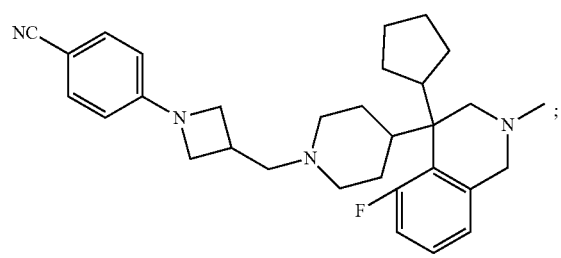
38
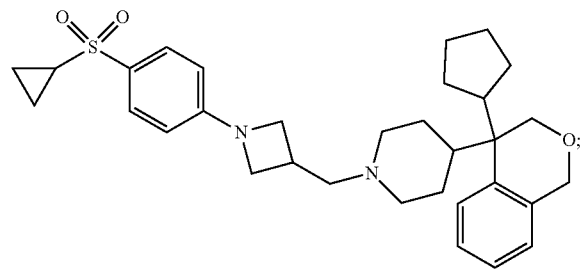
42
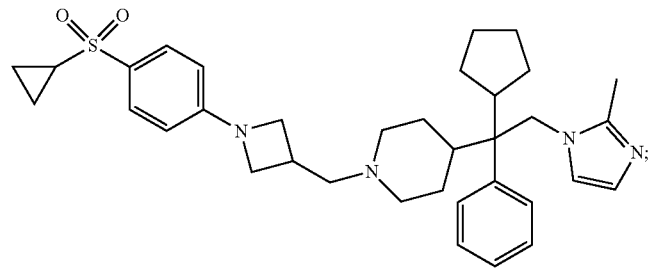
43
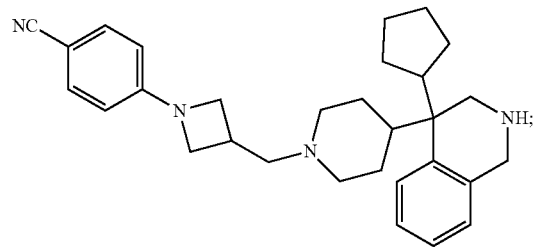

-continued
44
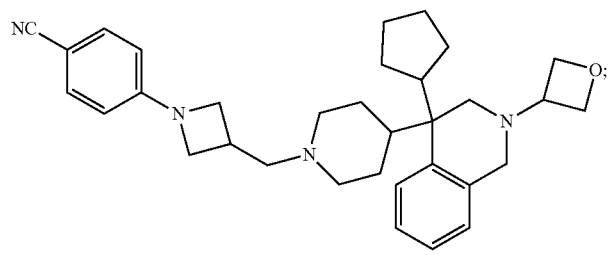
45
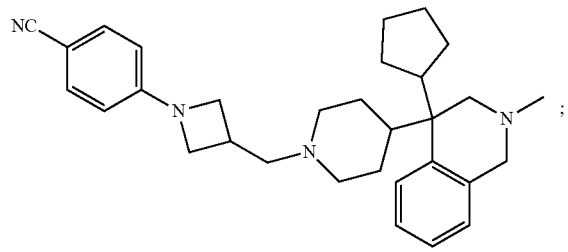
46
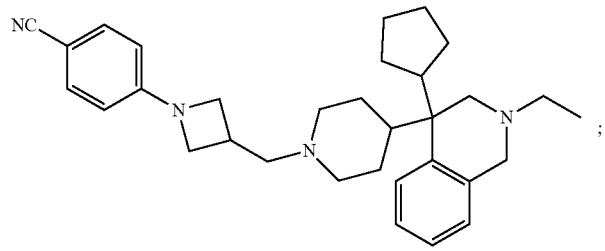
47
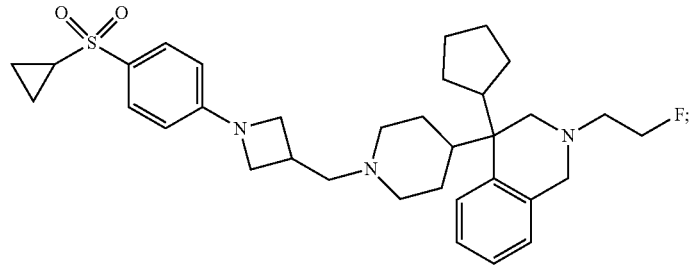
48
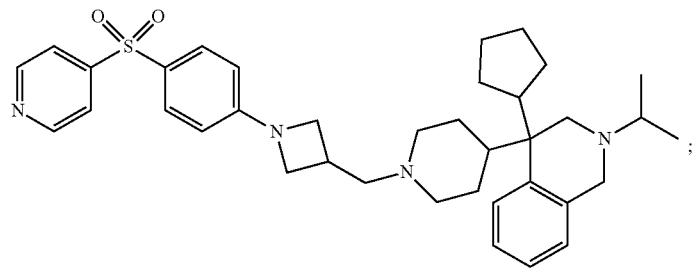
49
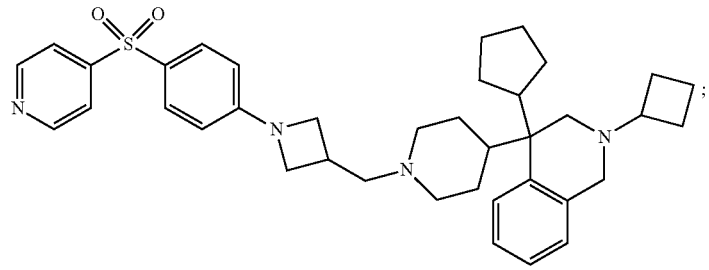

-continued
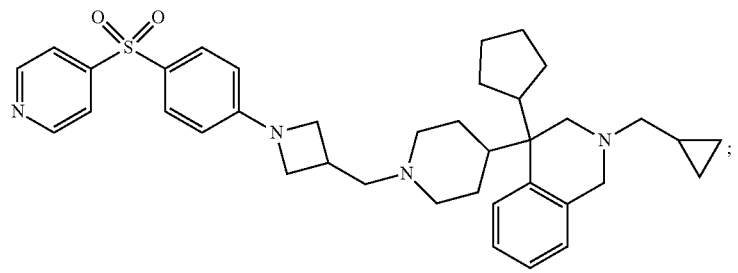
50
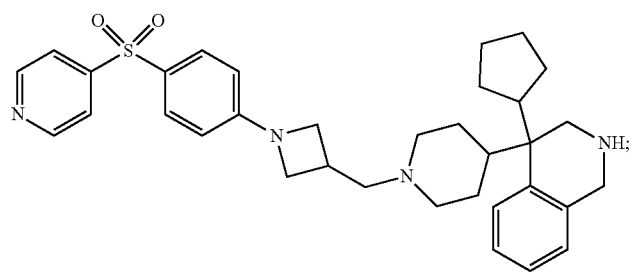
51
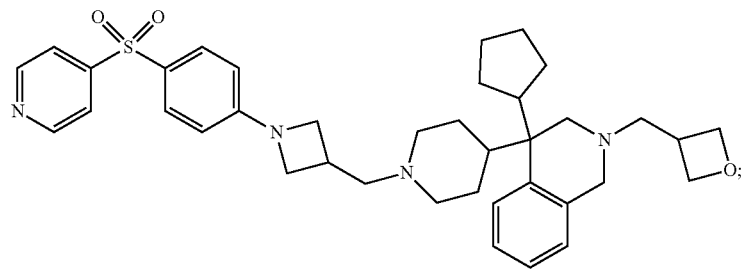
52
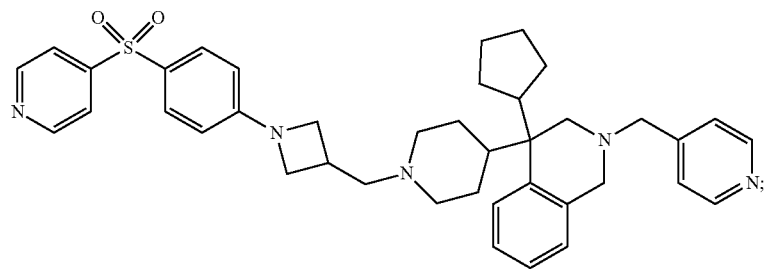
53
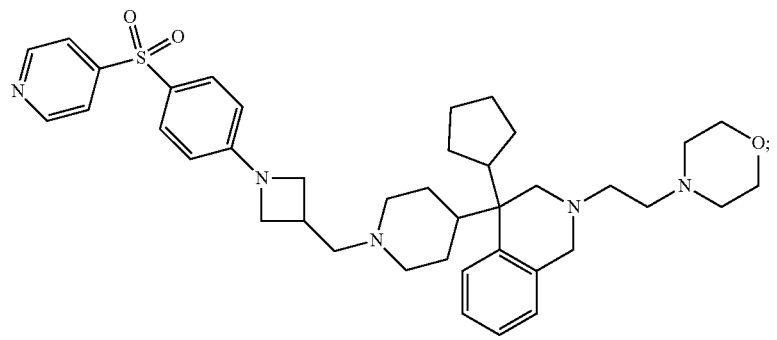
54

64
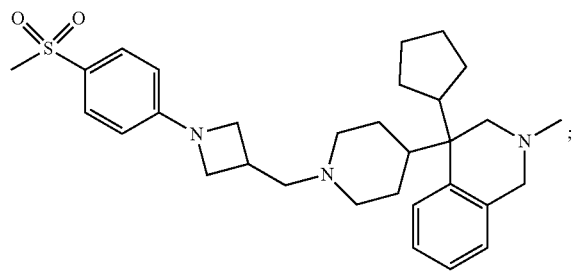
69
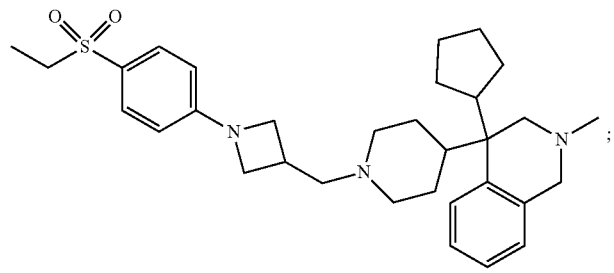
70
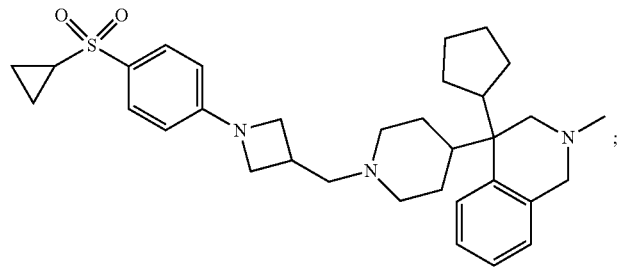
85
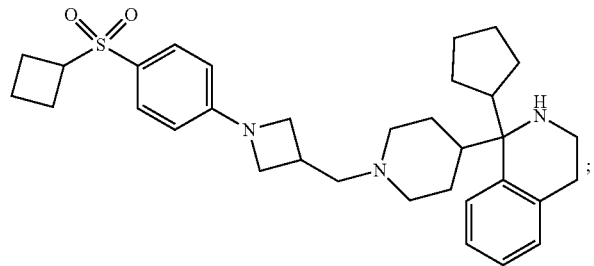
86
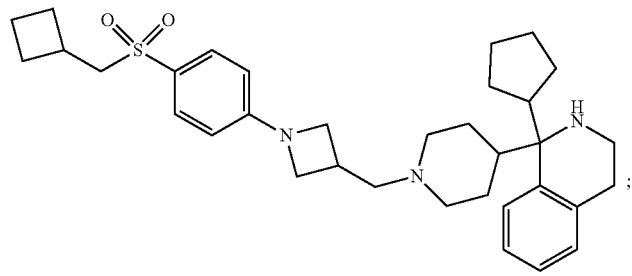

87
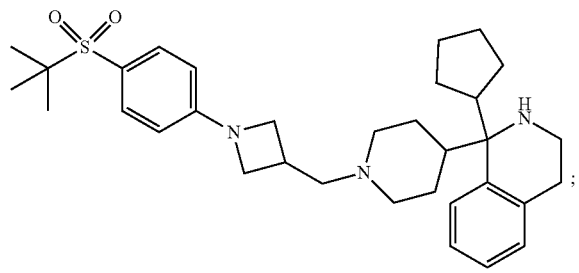
88
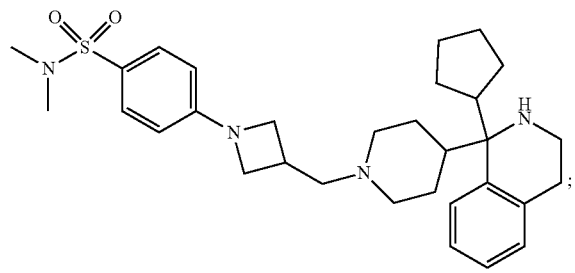
91
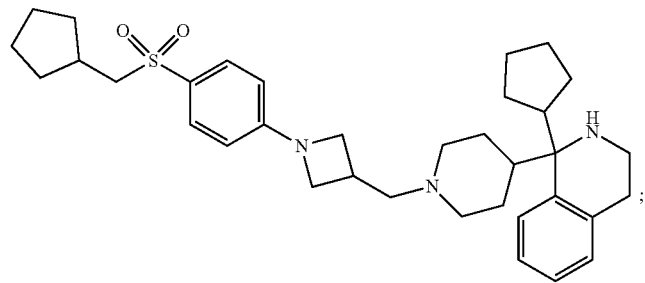
92
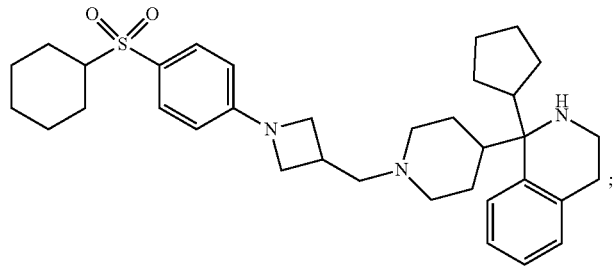
93
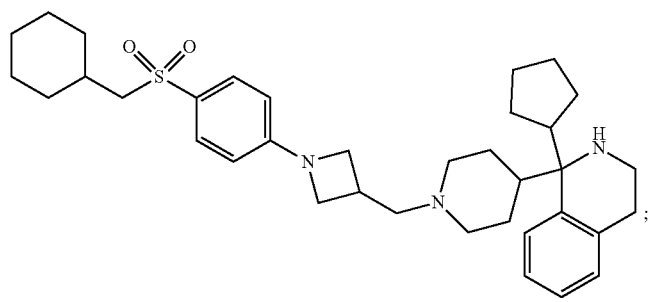

-continued
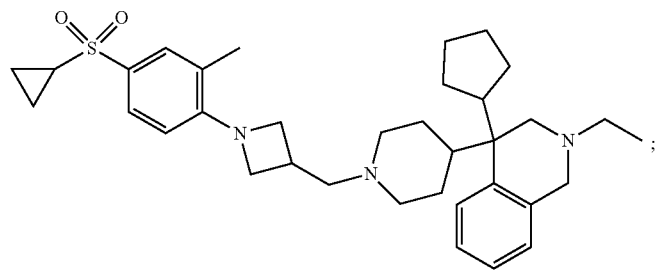
96
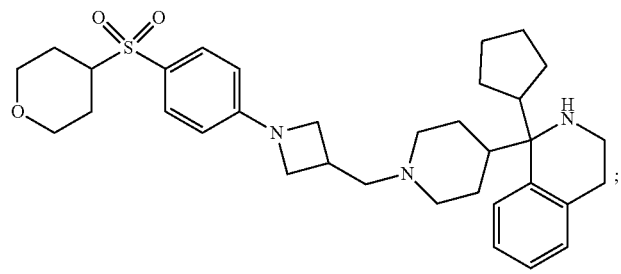
97
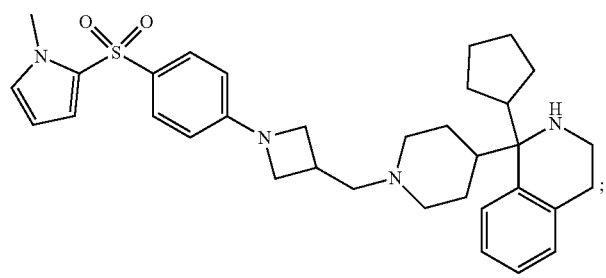
98
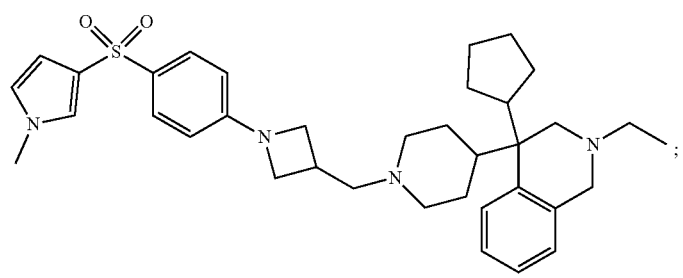
101
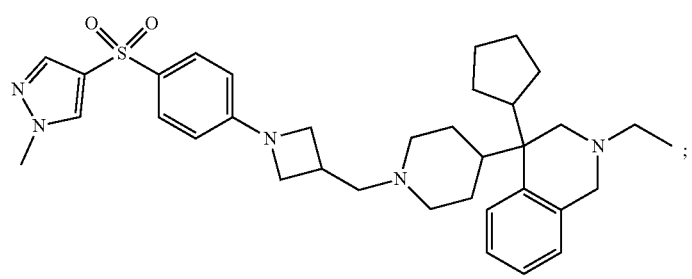
102
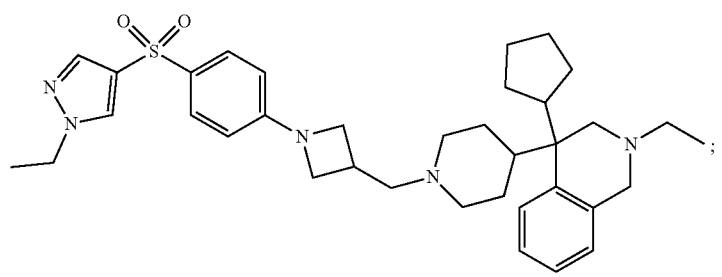
103

109
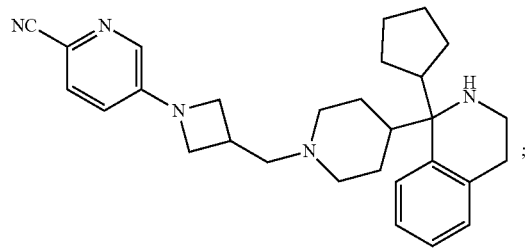
110
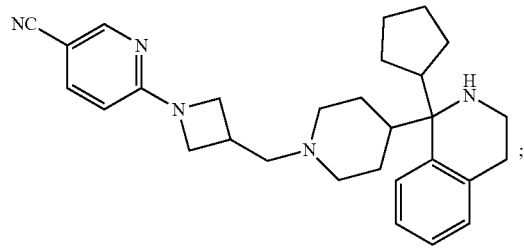
111
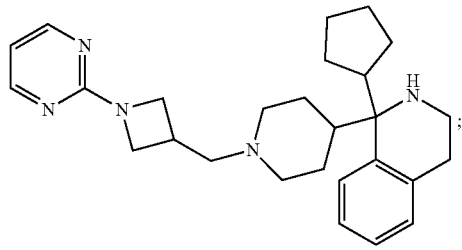
119
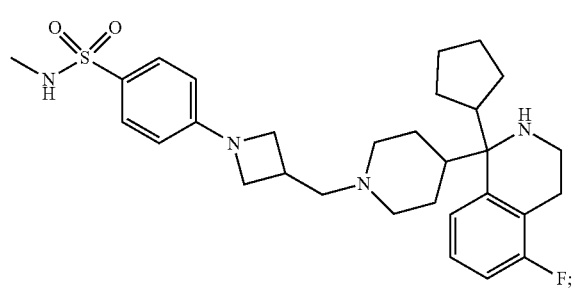
129
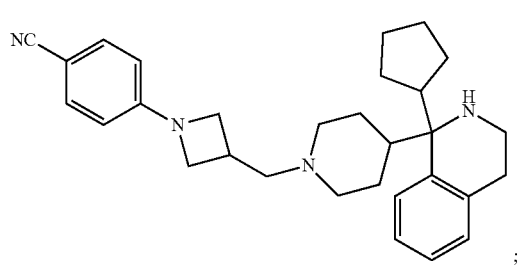
132
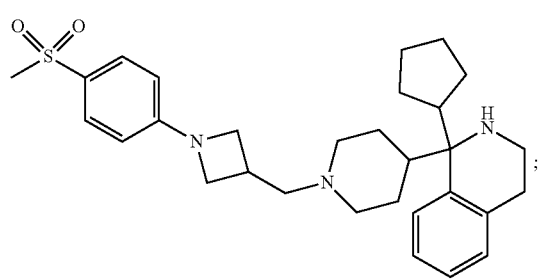
133
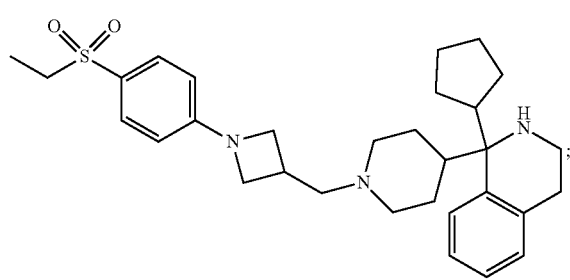
134
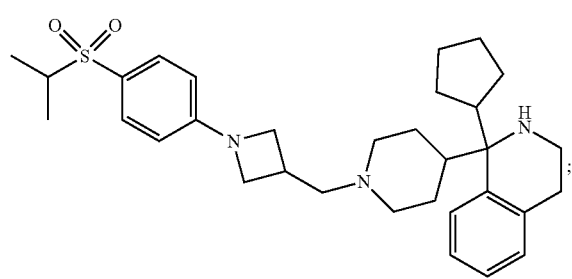
135
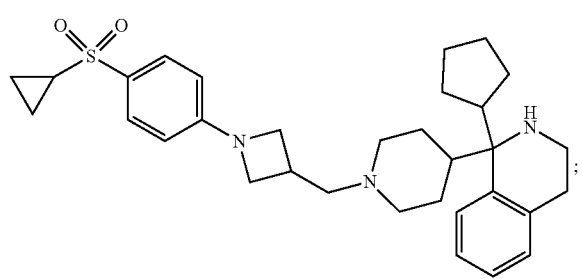

-continued
136
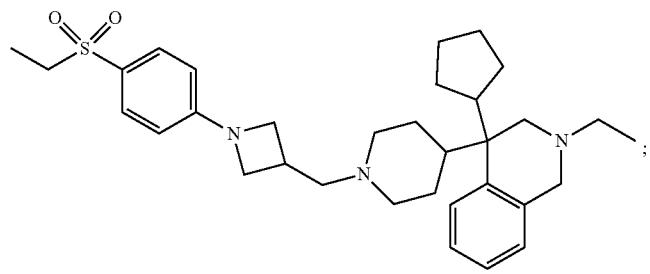
137
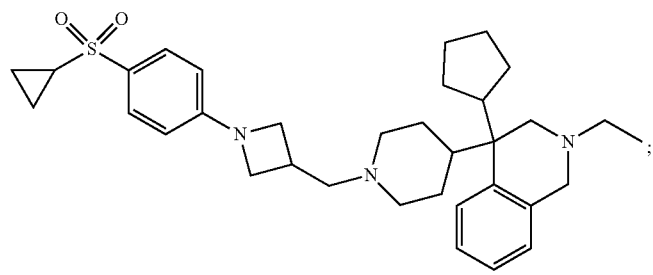
138
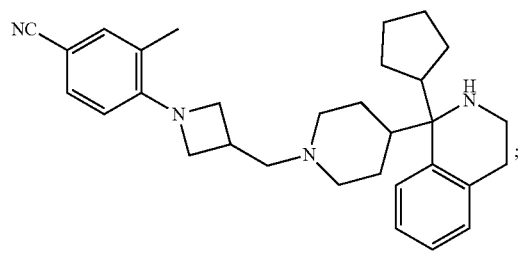
139
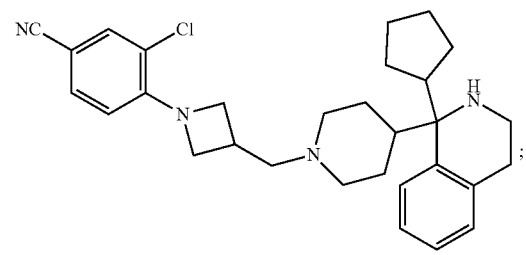
142
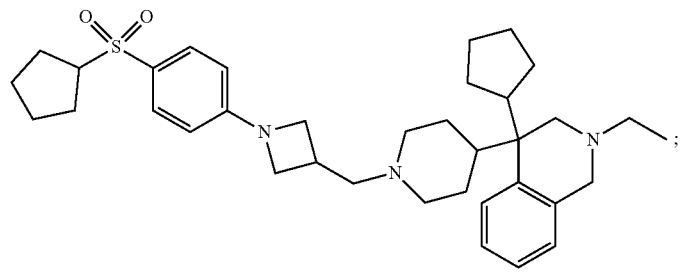
143
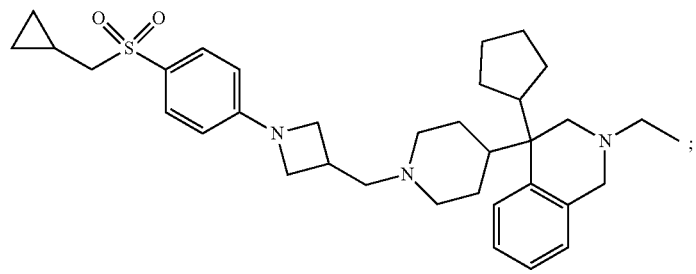
144
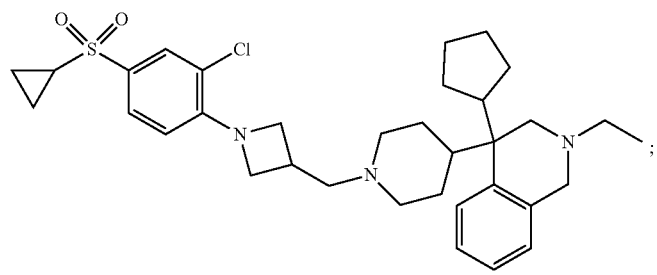

-continued
145
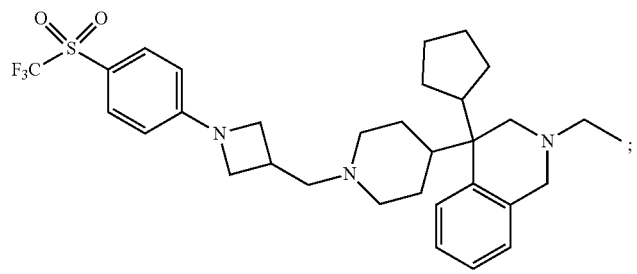
146
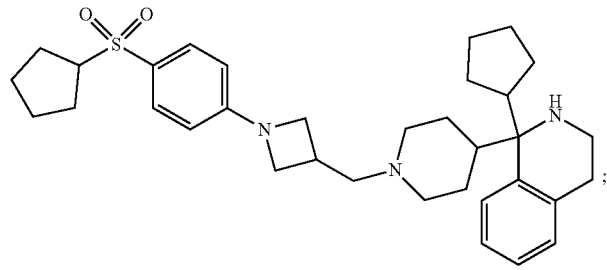
147
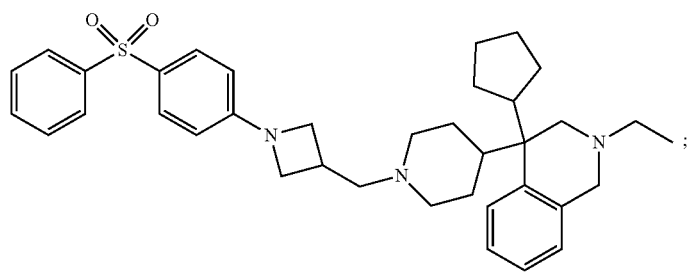
148
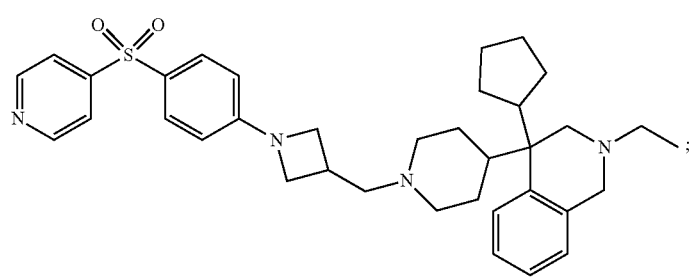
149
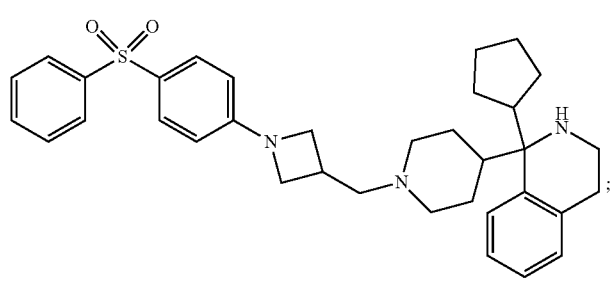
151
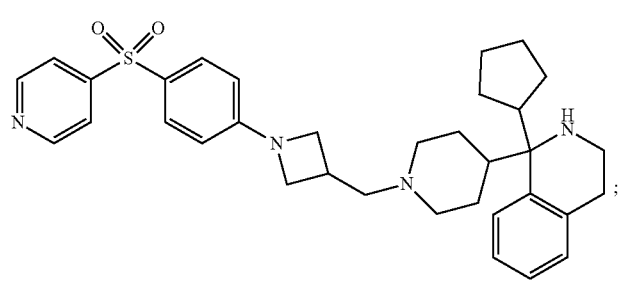

-continued
152
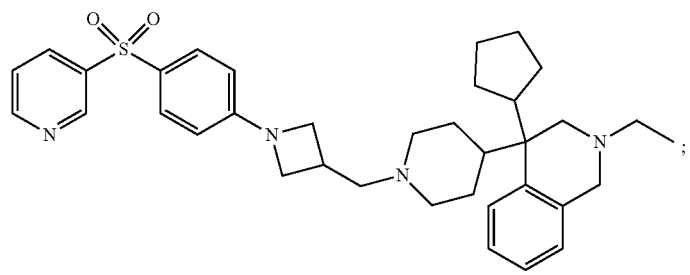
153
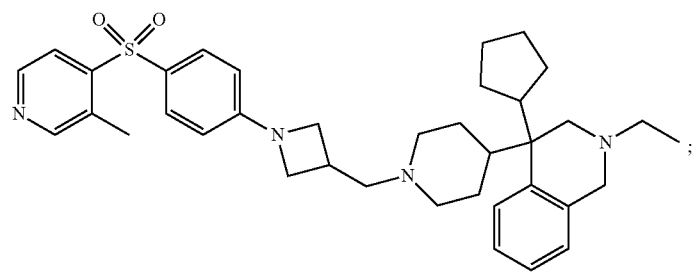
154
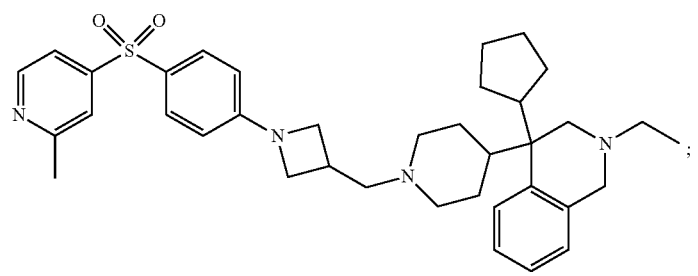
155
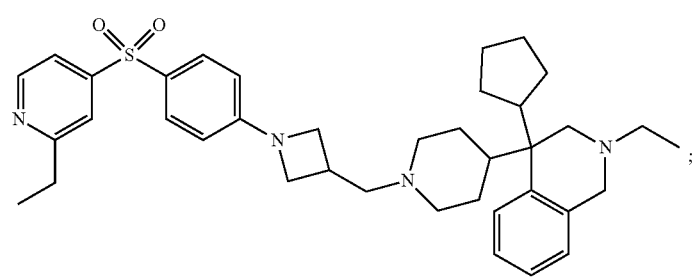
156
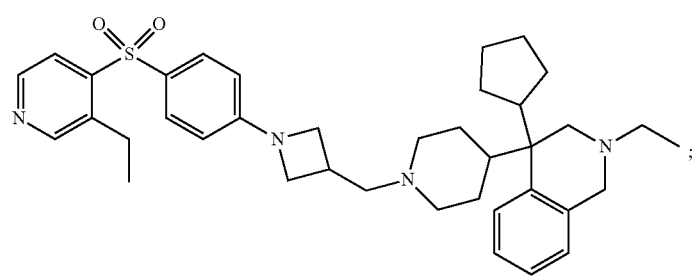
157
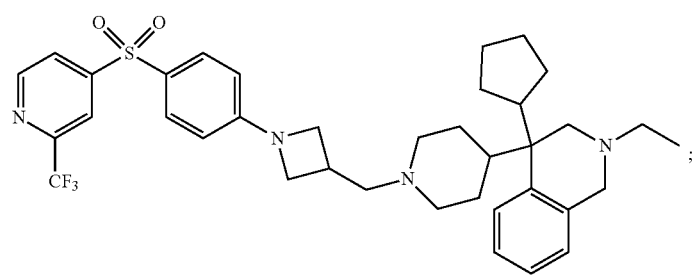

-continued
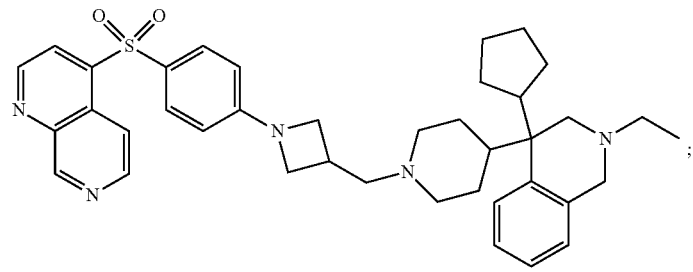
158
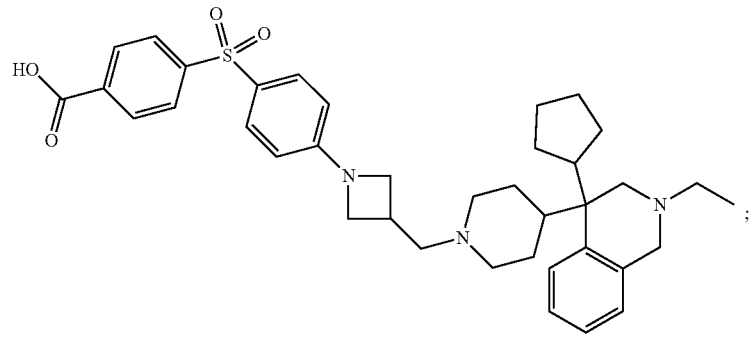
164
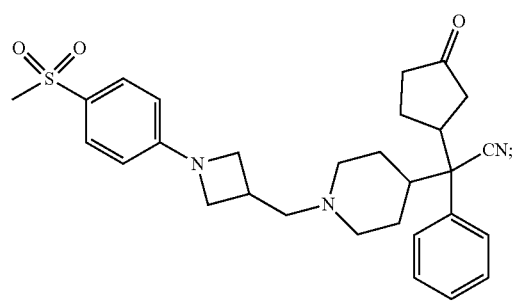
169
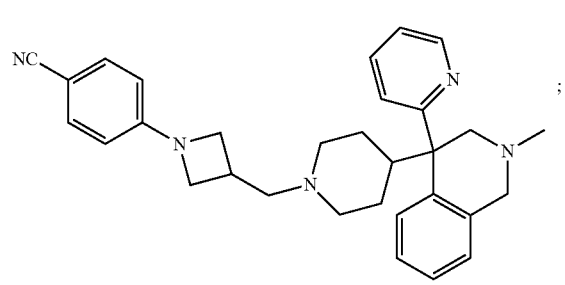
170
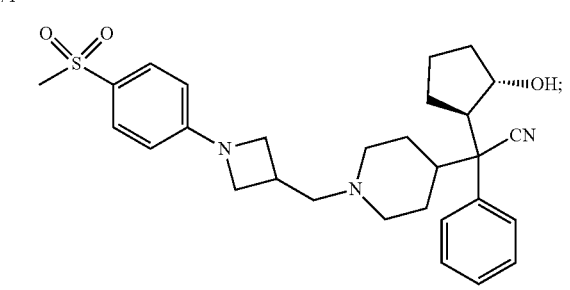
171
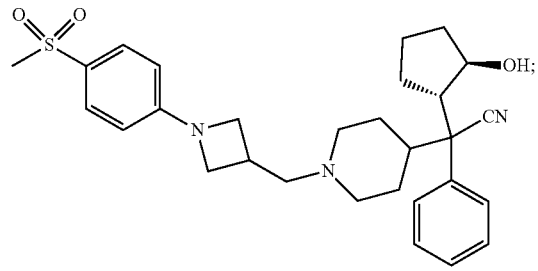
178
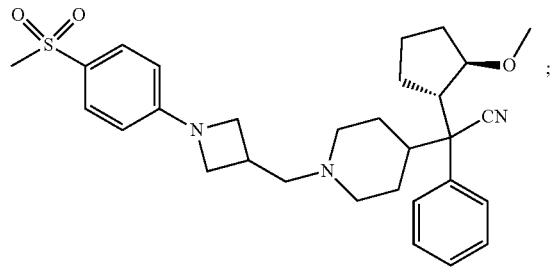
179 180

-continued
181
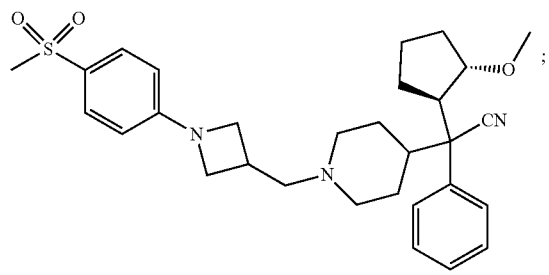
182
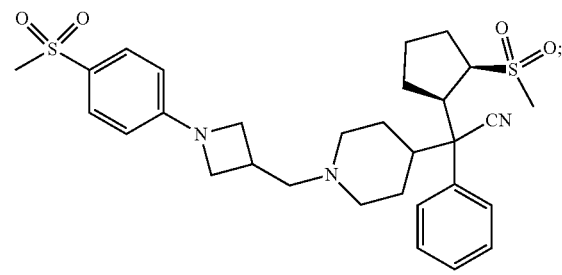
183
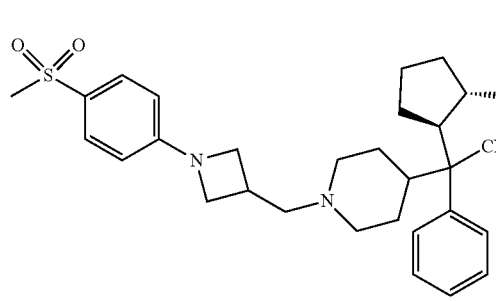
184
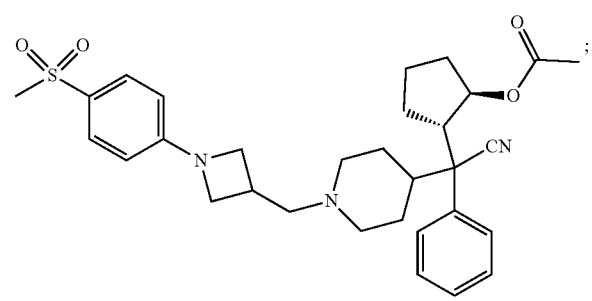
185
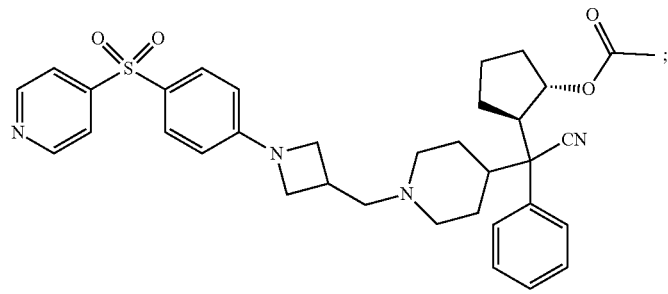
186
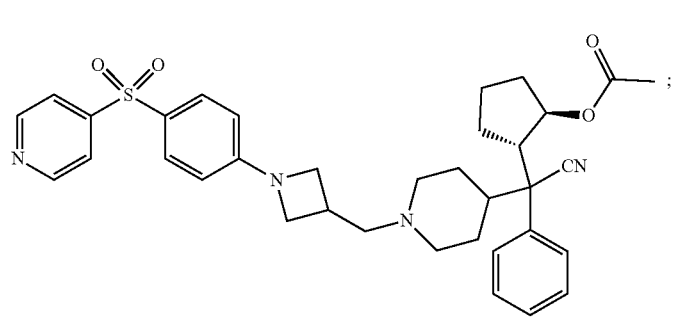
187
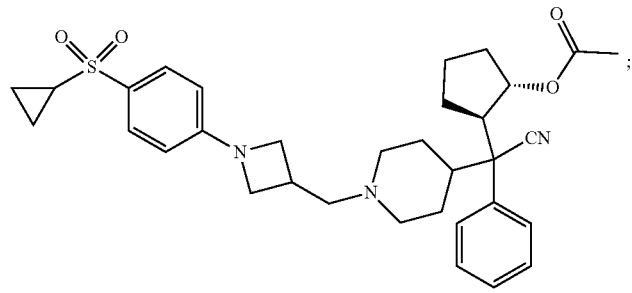

-continued
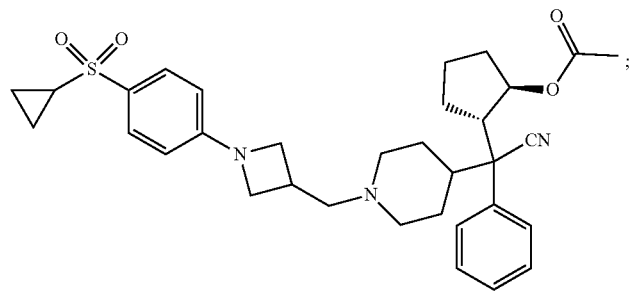
188
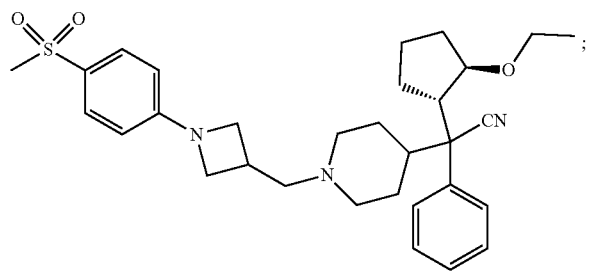
189
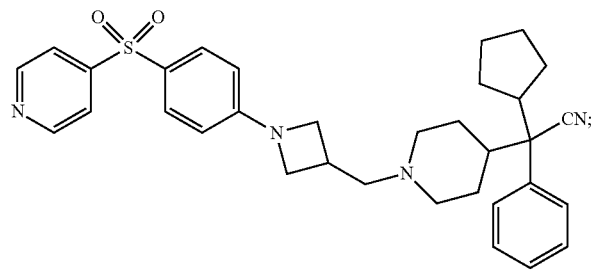
190
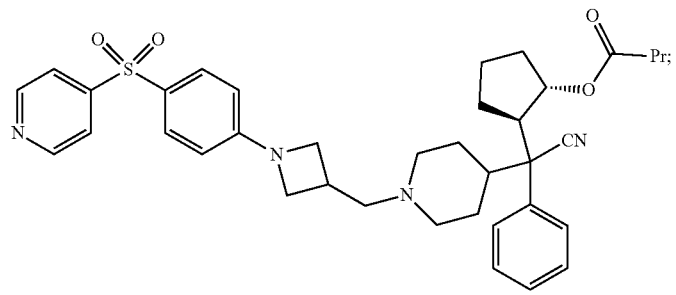
191
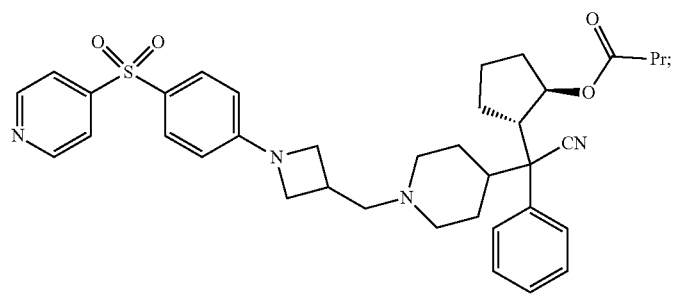
192

-continued
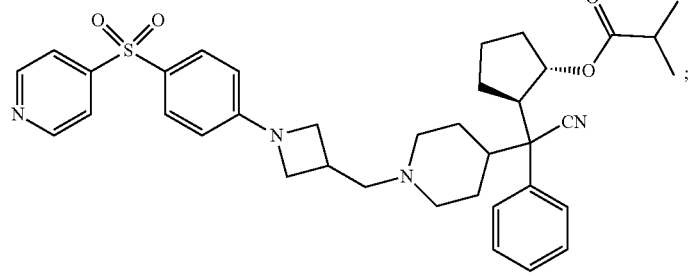
193
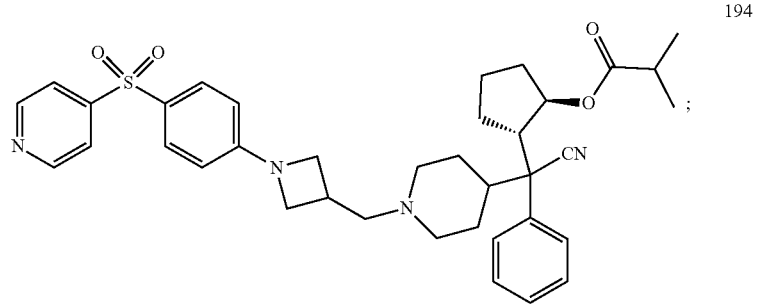
194
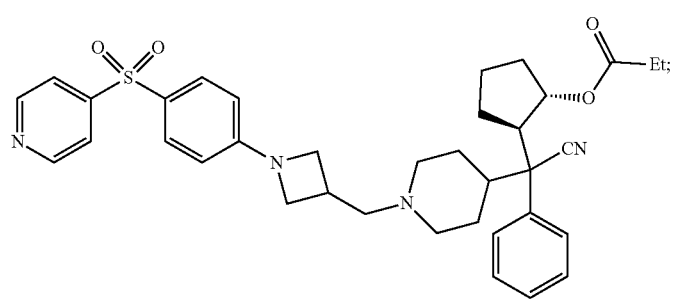
195
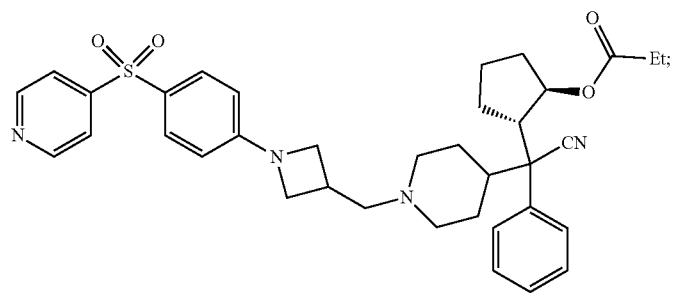
196
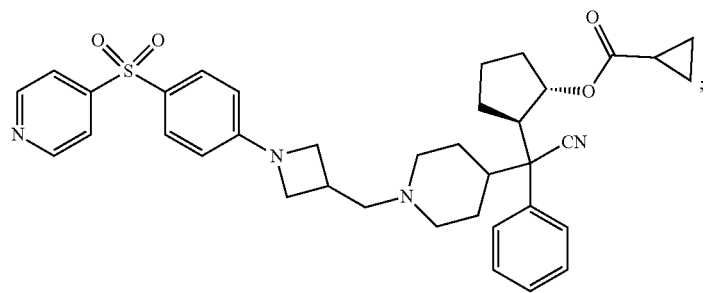
197

-continued
198
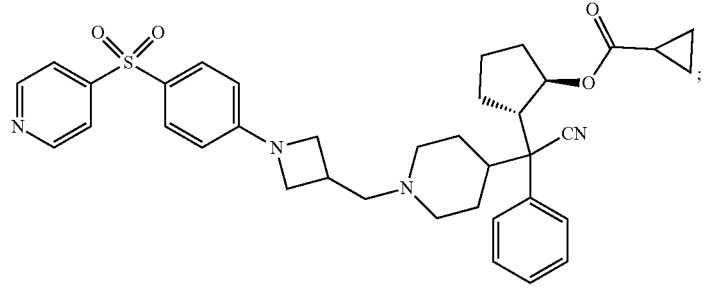
199
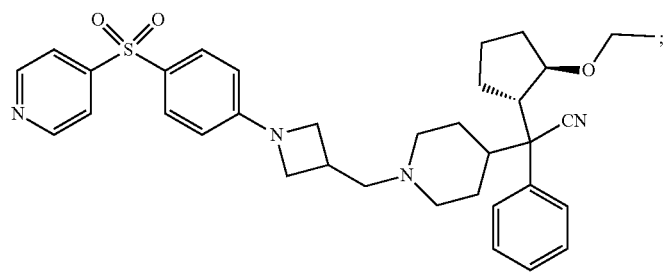
200
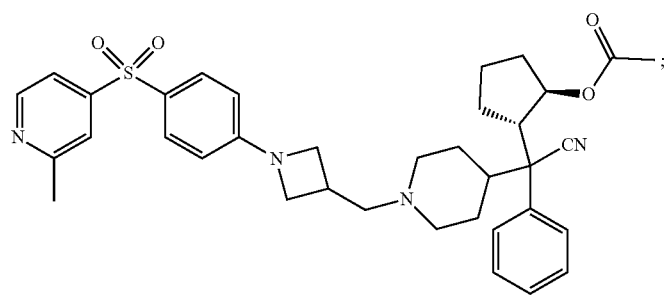
201
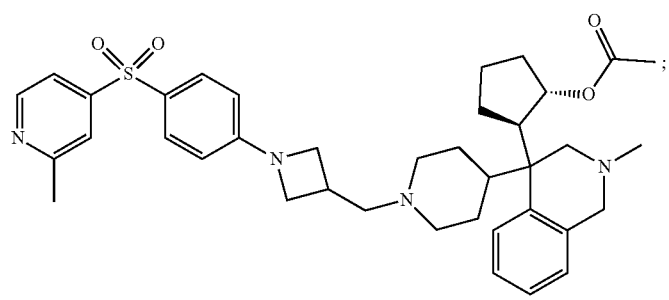
202
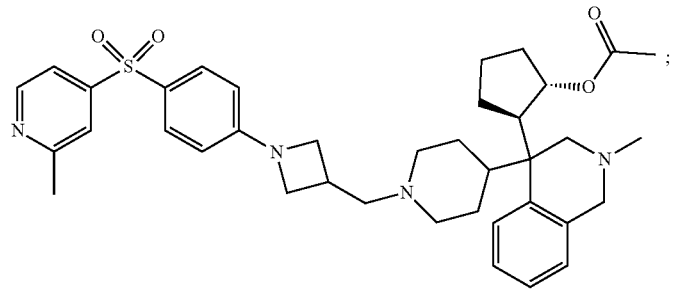

-continued
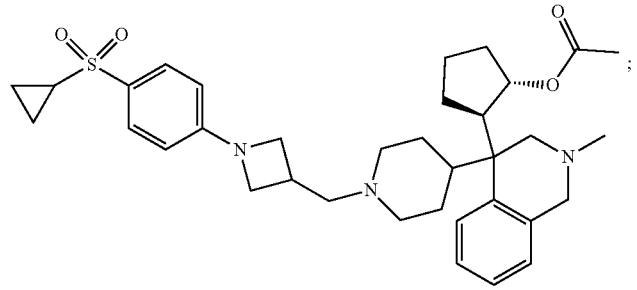
203
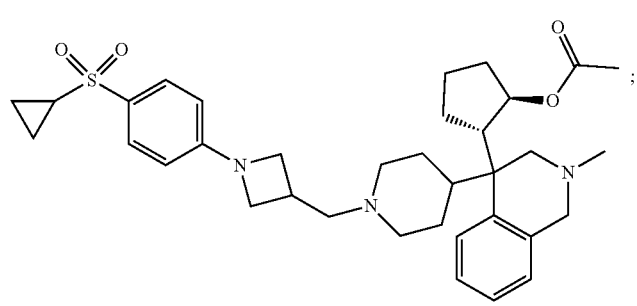
204
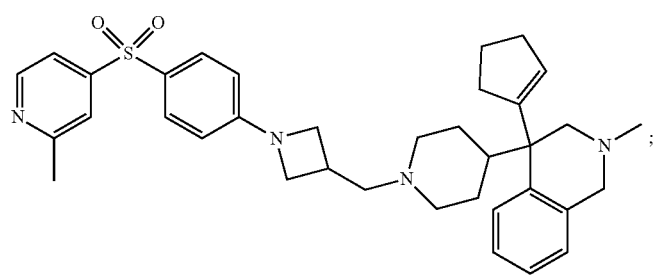
205
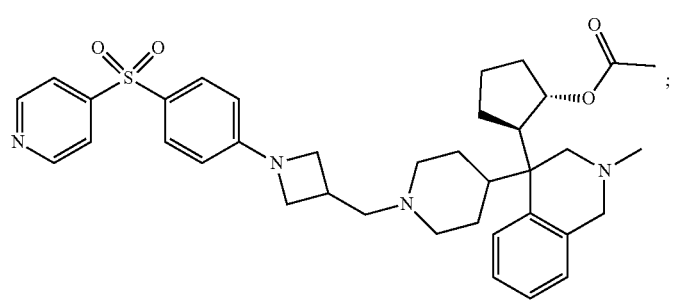
206
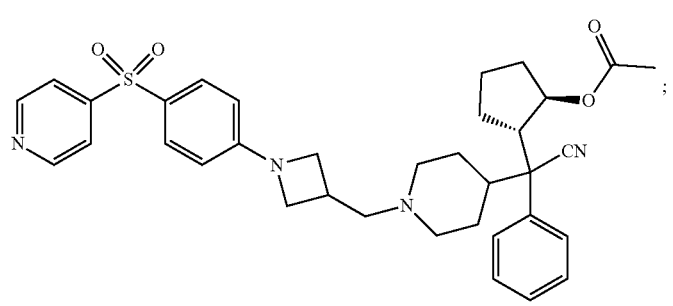
207

-continued
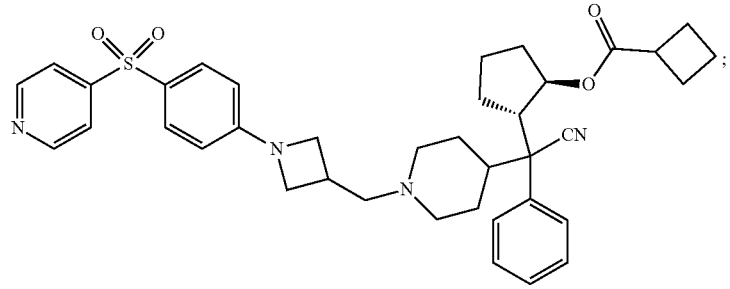
208
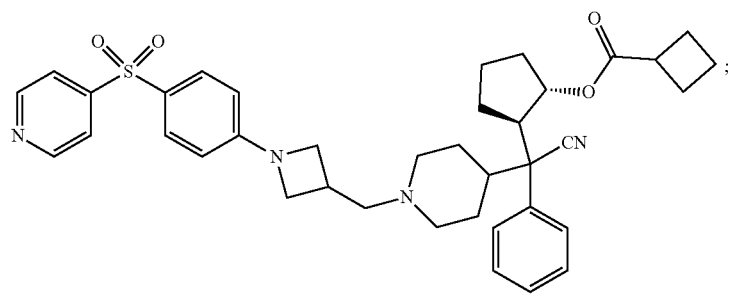
209
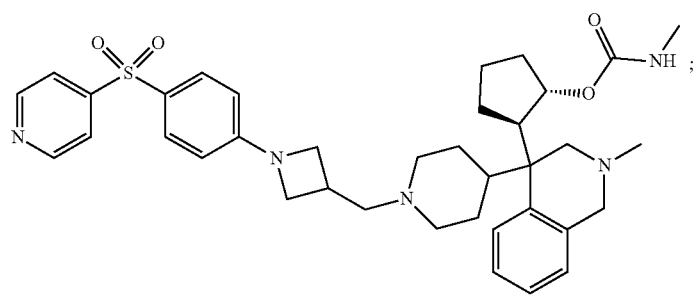
210
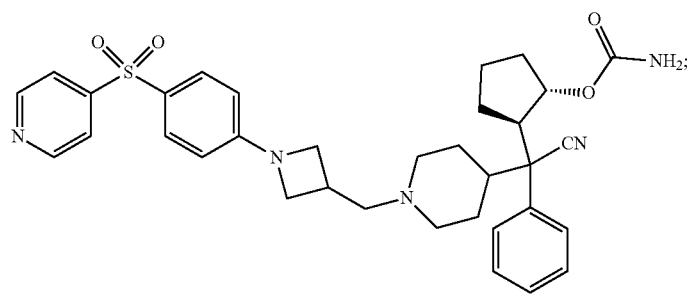
211
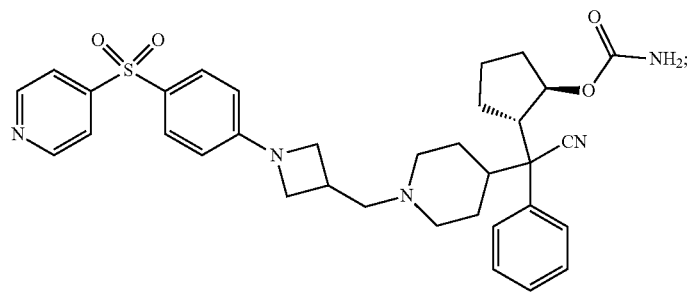
212

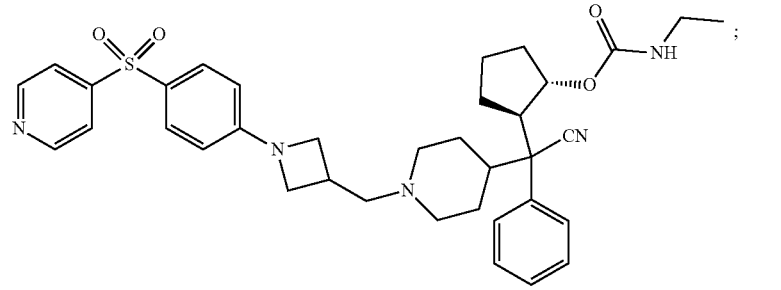
213
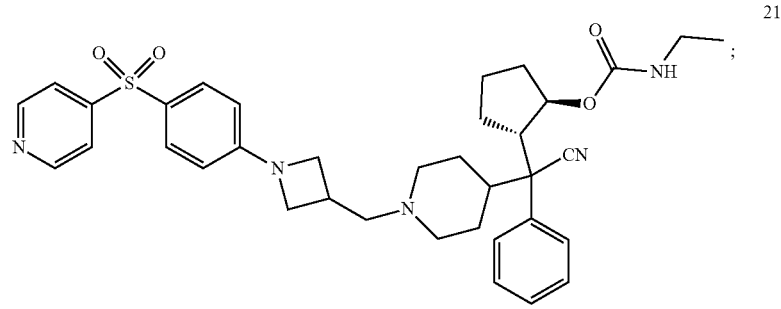
214
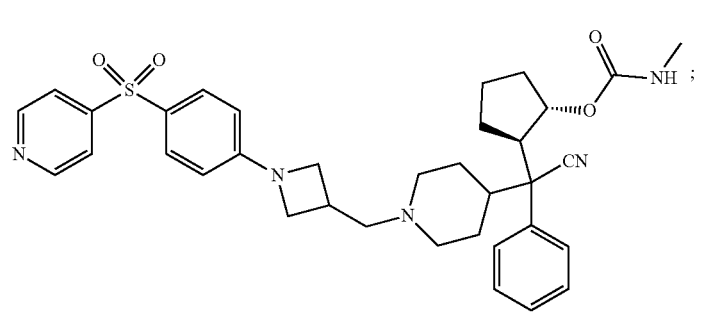
215
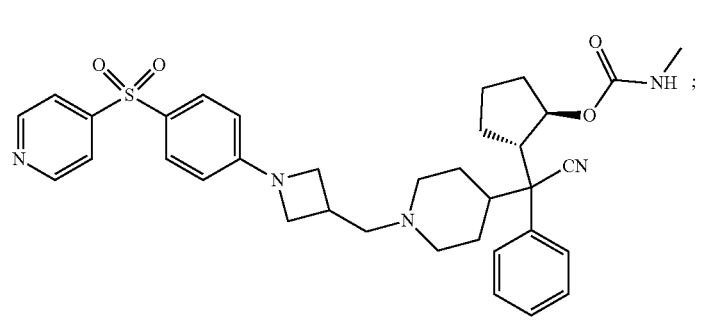
216
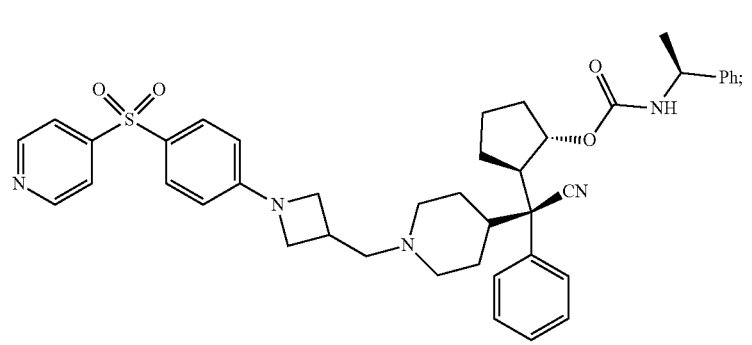
217

-continued
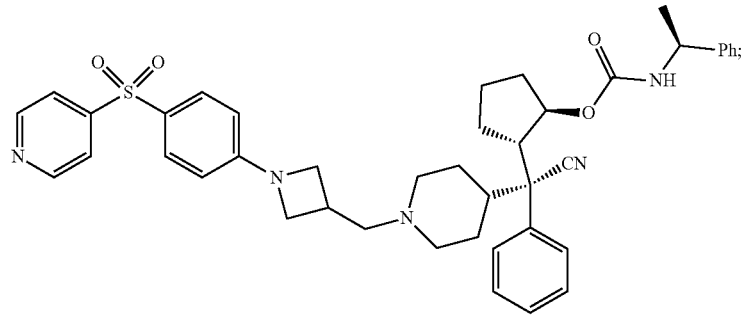
218
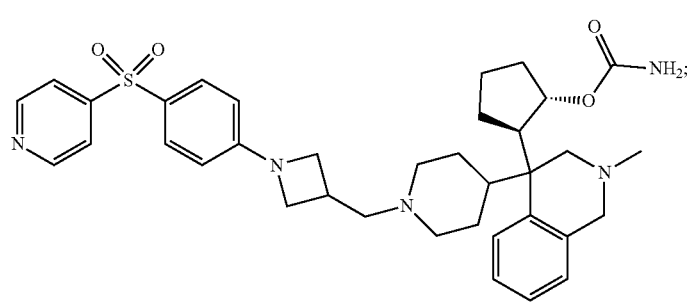
219
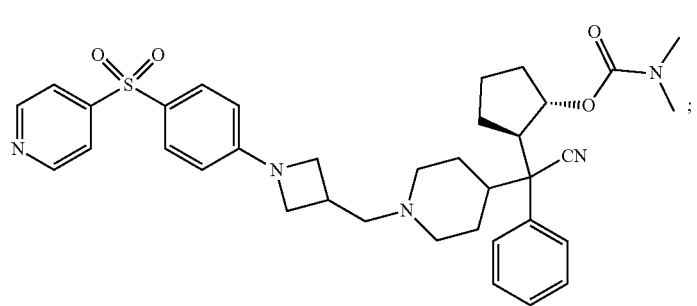
220
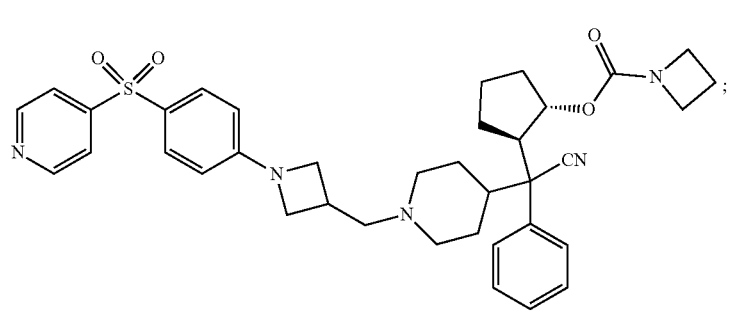
221
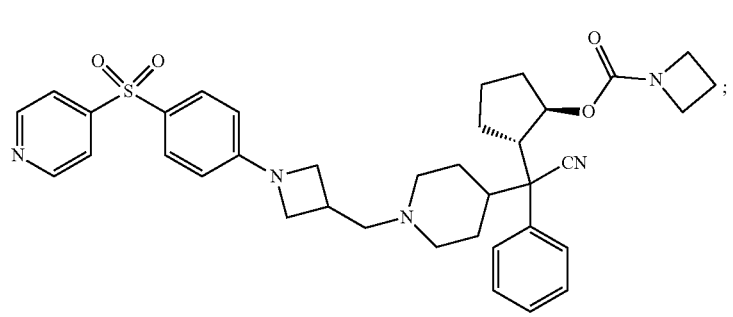
222

-continued
223
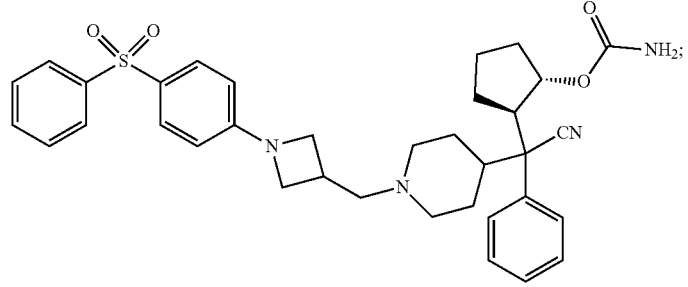
224
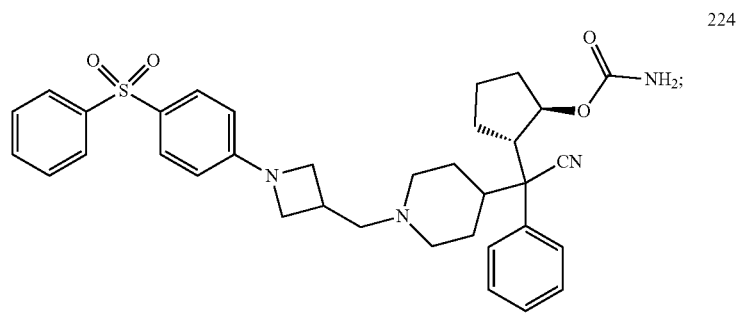
225
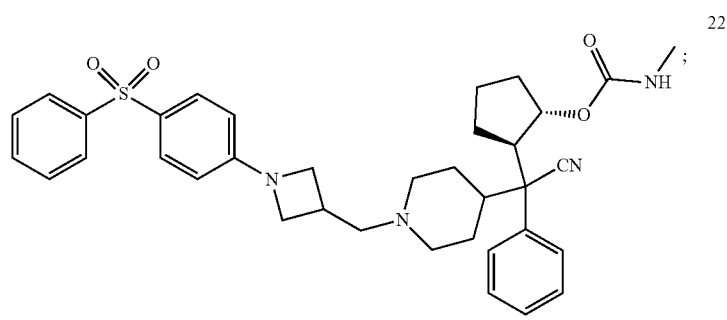
226
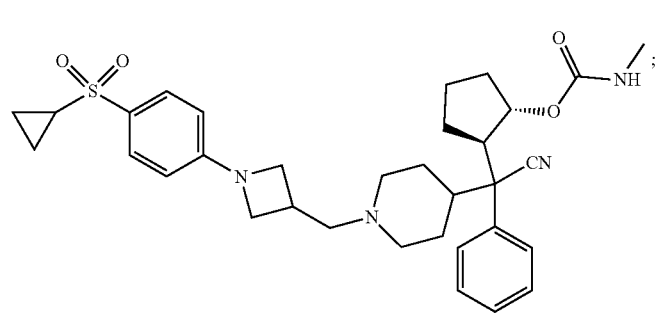
227
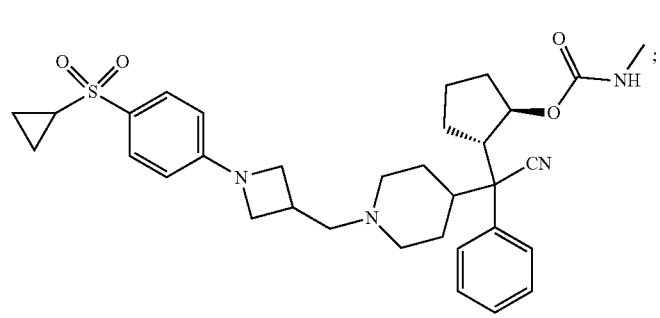

-continued
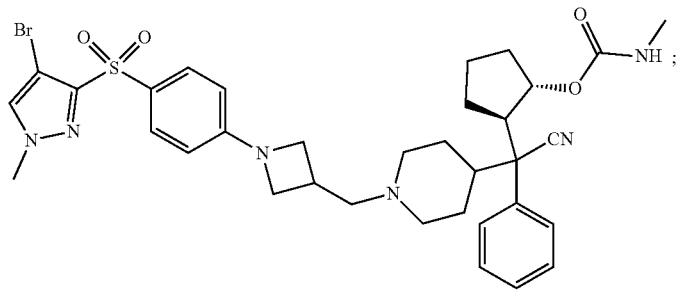
228
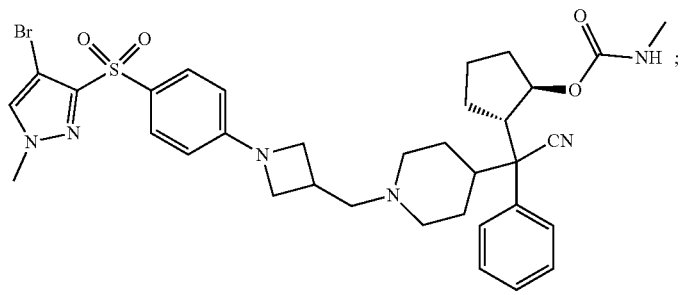
229
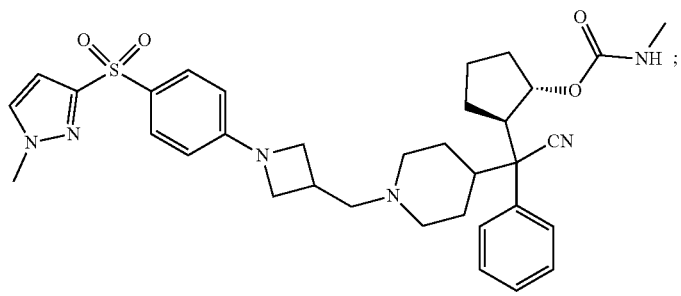
230
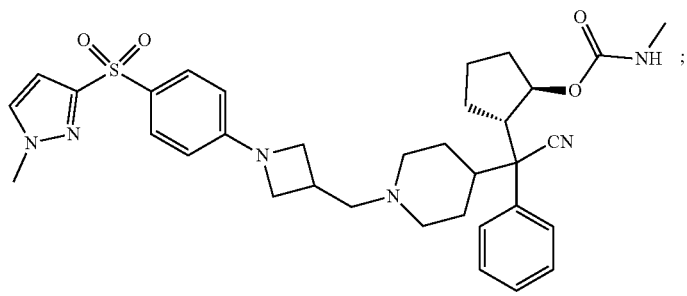
231
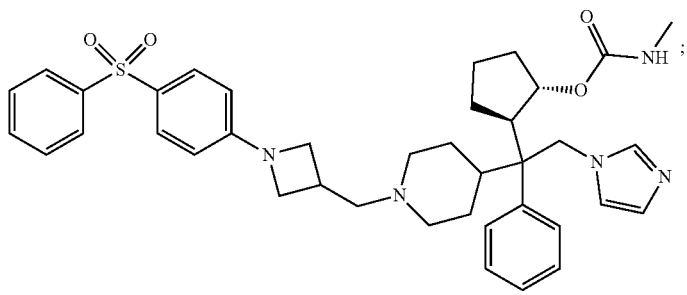
236

-continued
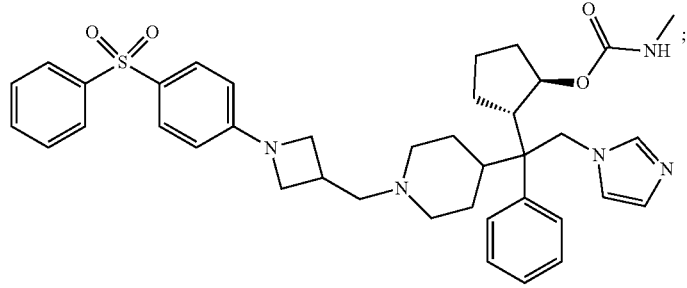
237
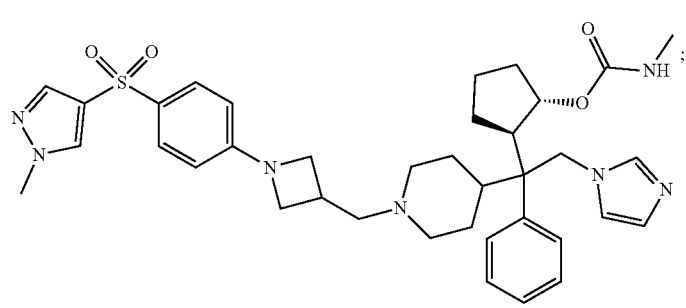
238
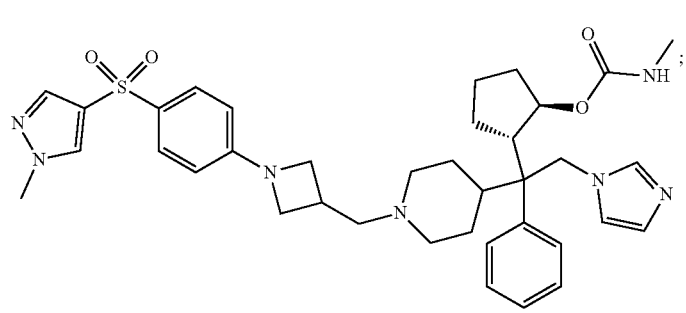
239
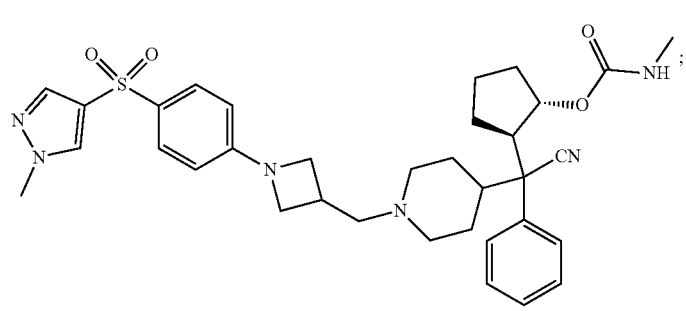
240
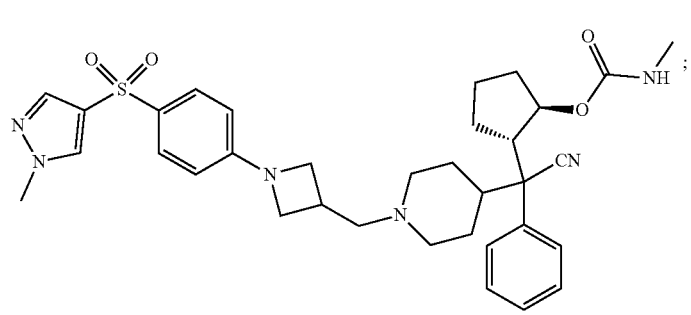
241

248
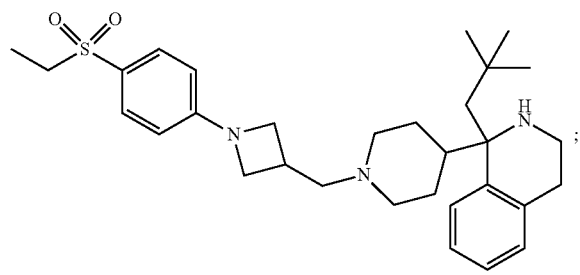
253
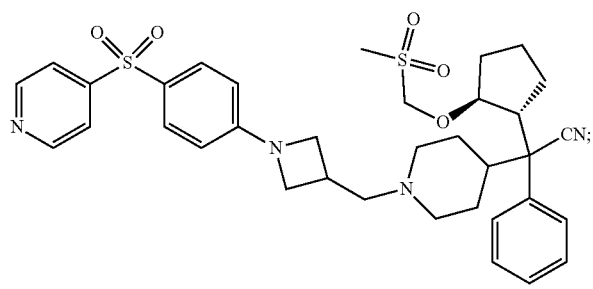
254
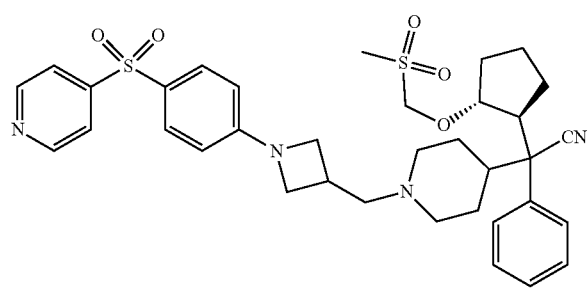
255
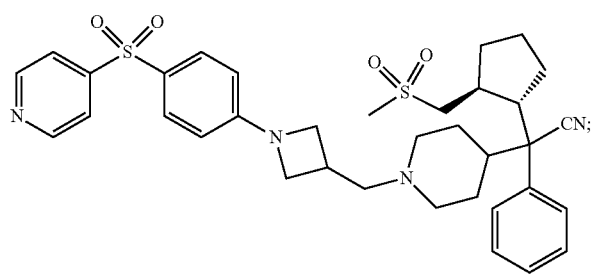
256
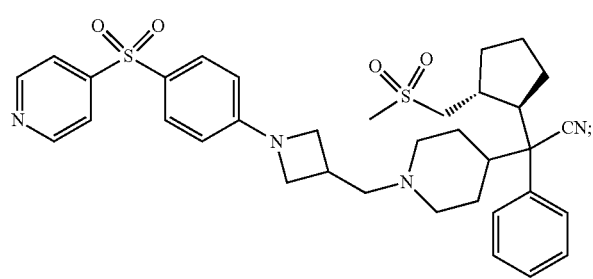
257
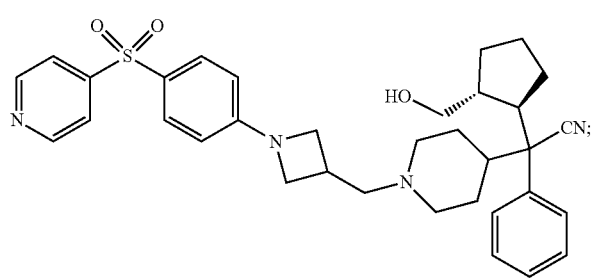
258
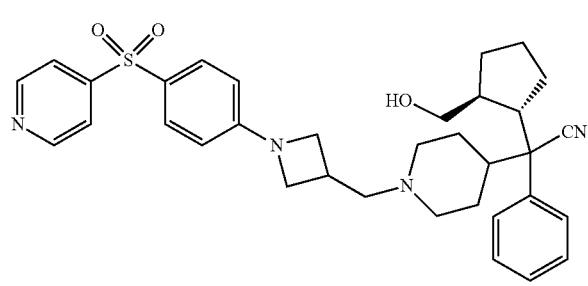
259
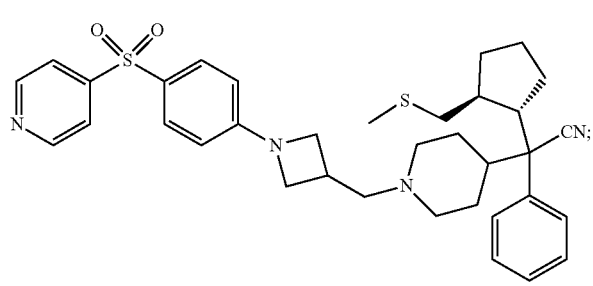
260
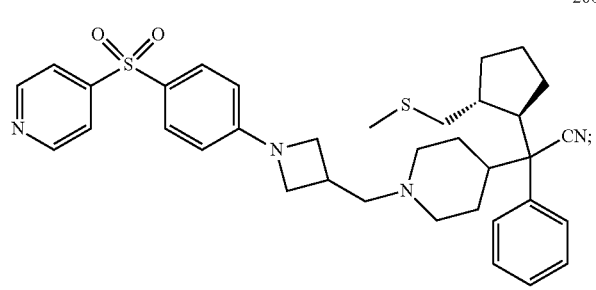
261
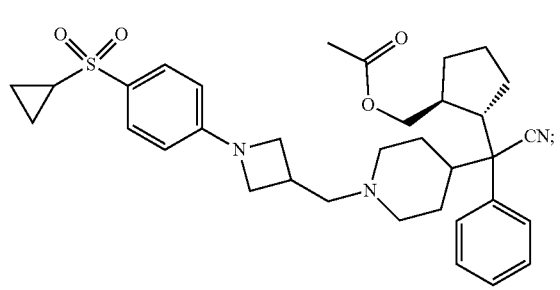

-continued
262
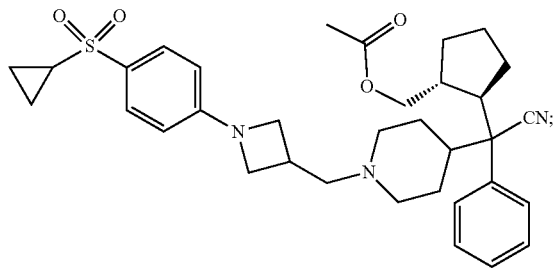
263
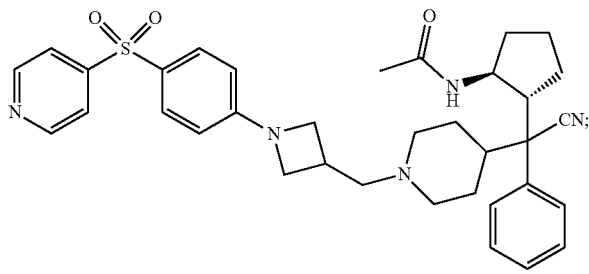
264
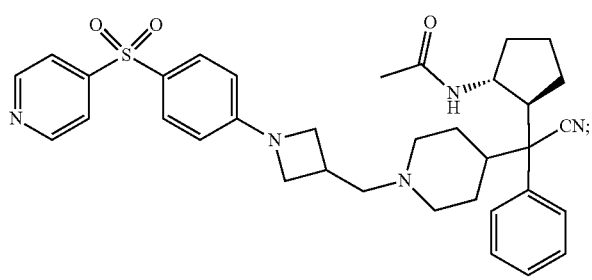
265
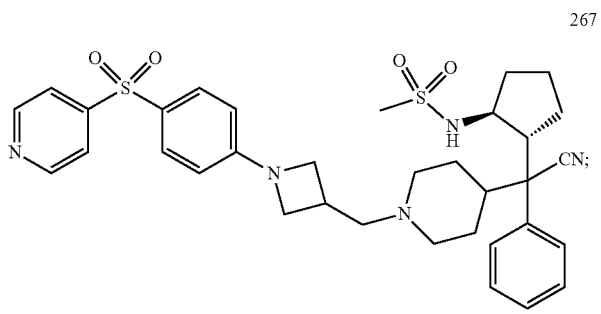
266
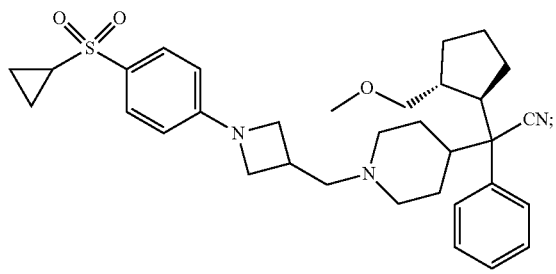
267
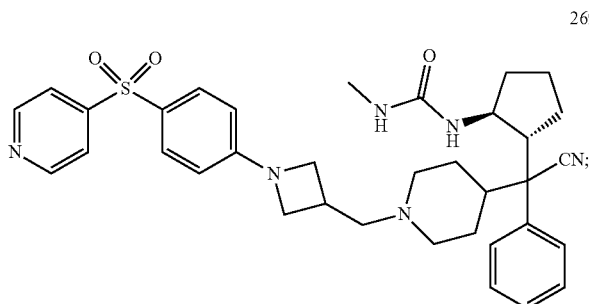
268
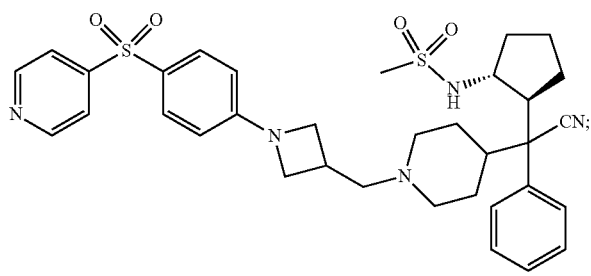
269
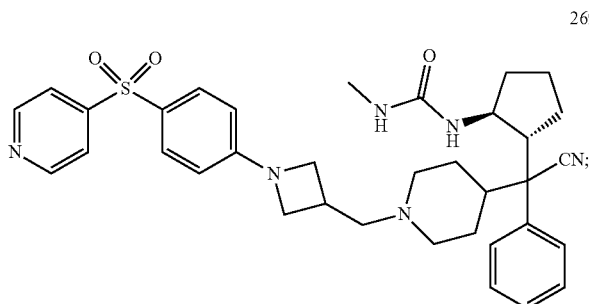
270
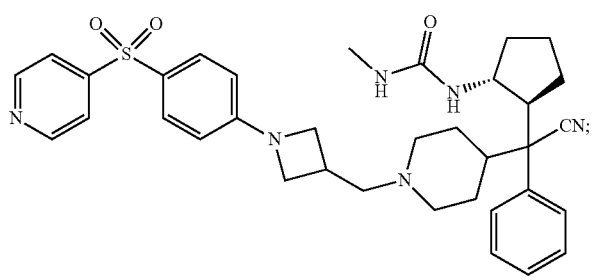

-continued
271
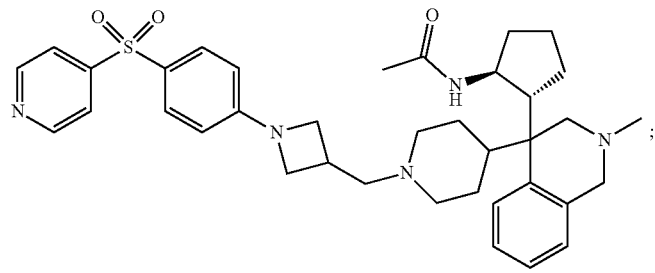
272
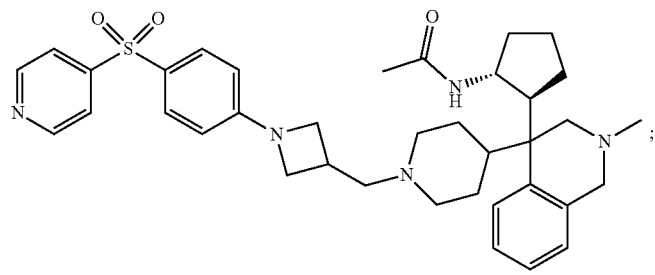
273
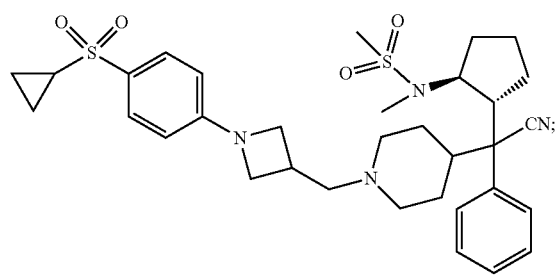
274
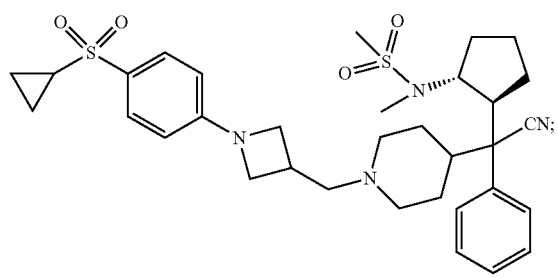
275
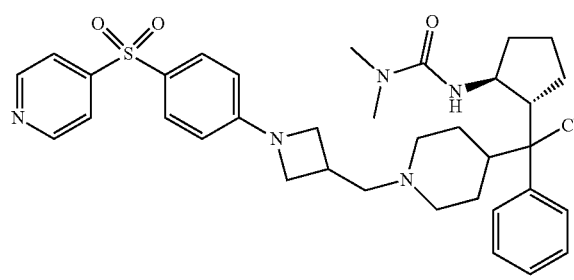
276
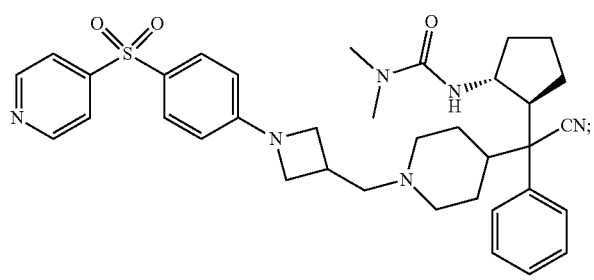
277
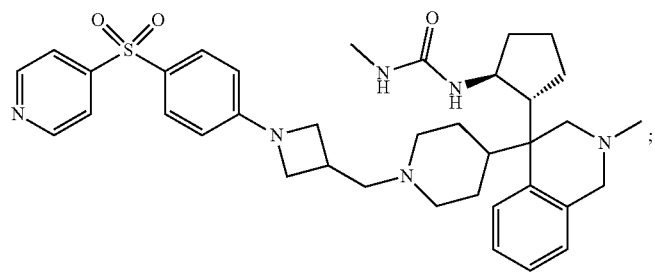

-continued
278
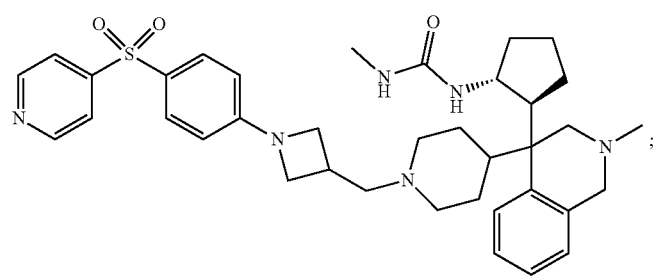
279
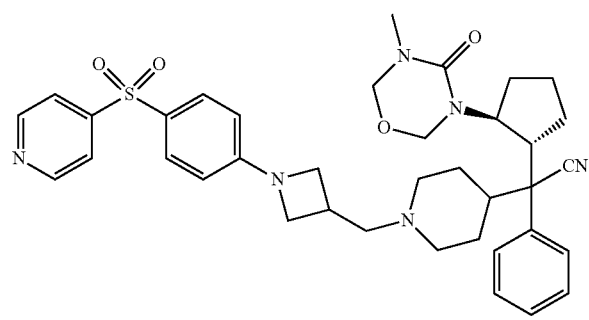
280
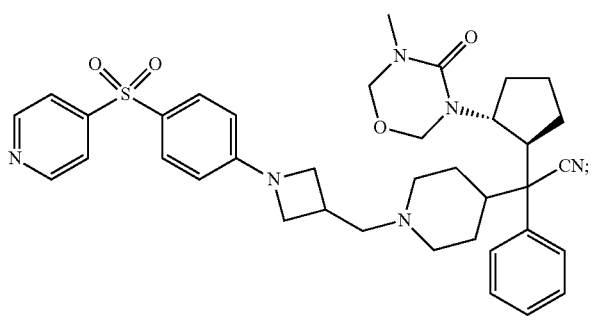
281
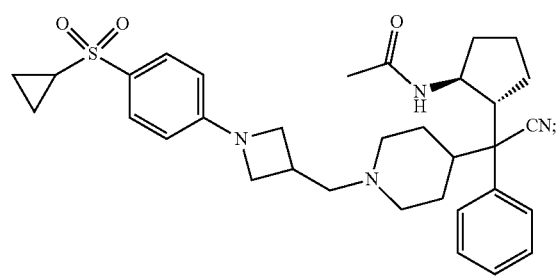
282
283
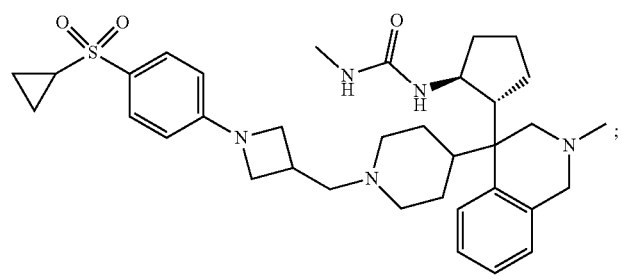
284
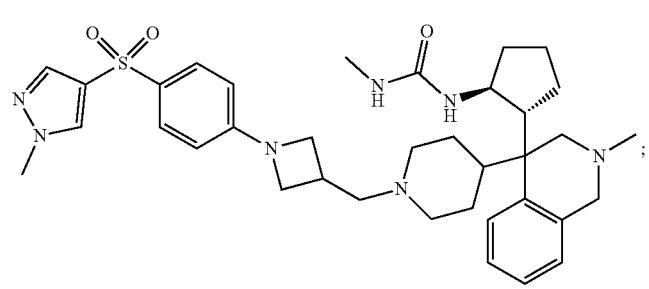

-continued
285
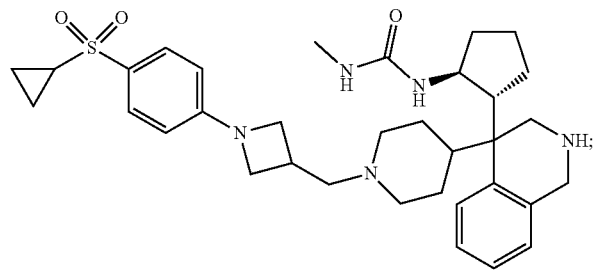
286
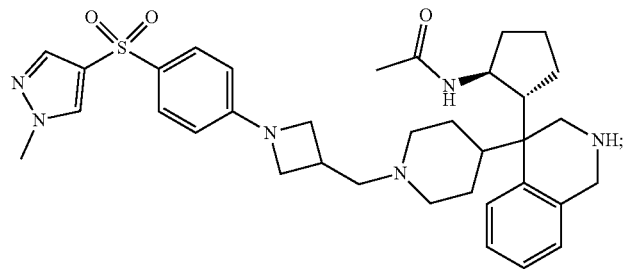
287
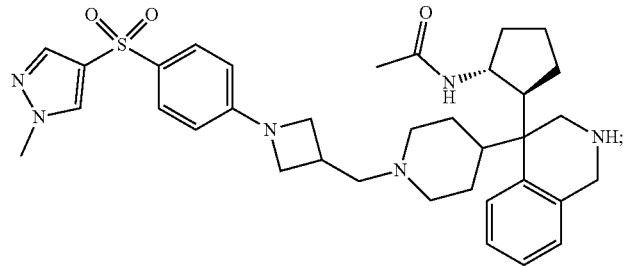
288
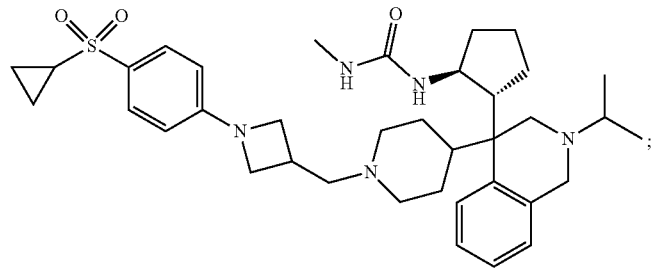
289
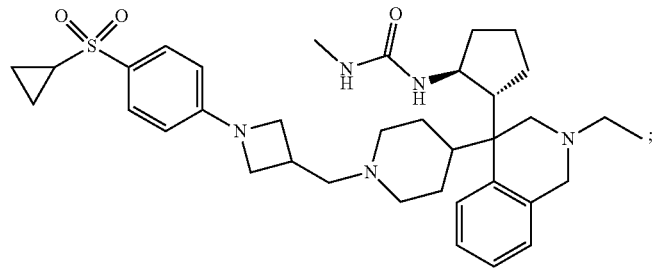

-continued
290
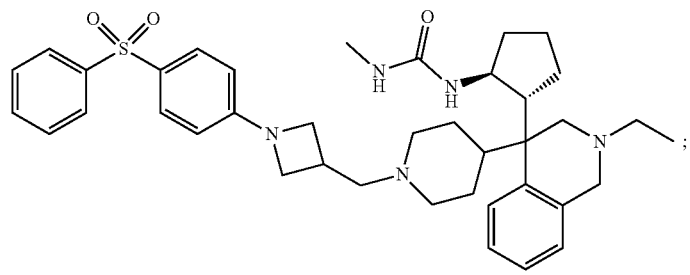
291
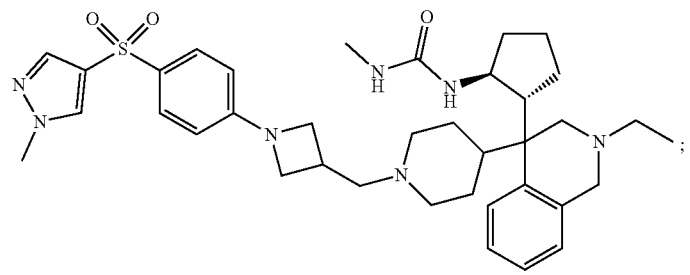
292
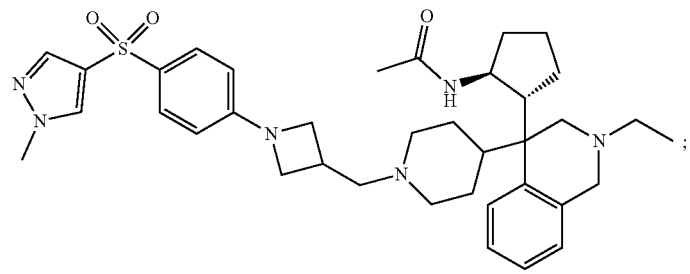
310 311
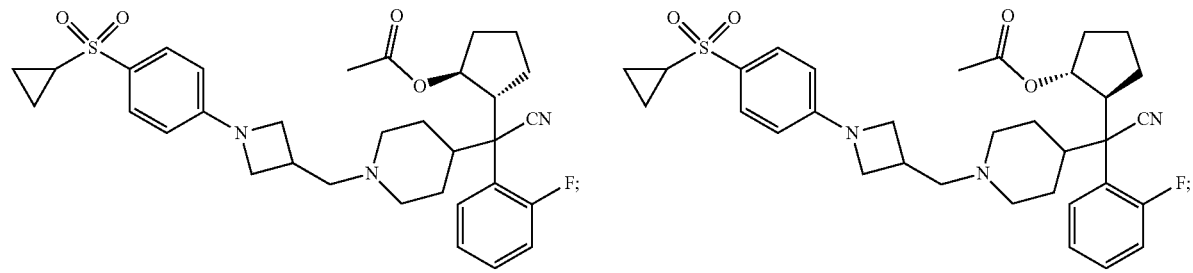
312
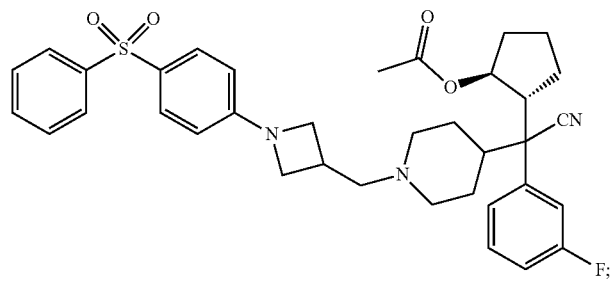

-continued
313
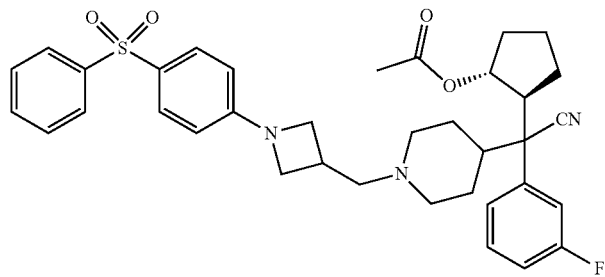
316
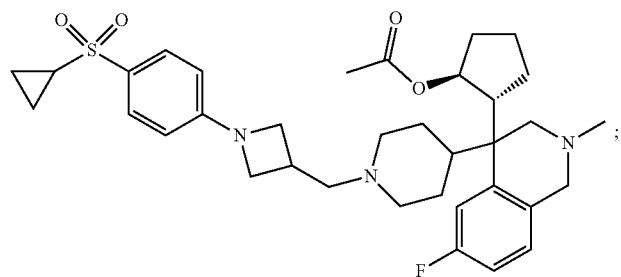
317
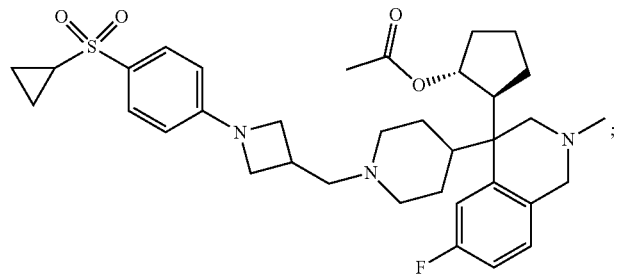
319
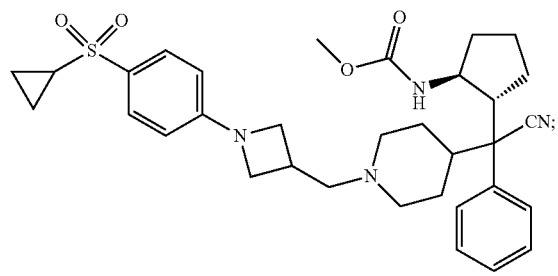
320
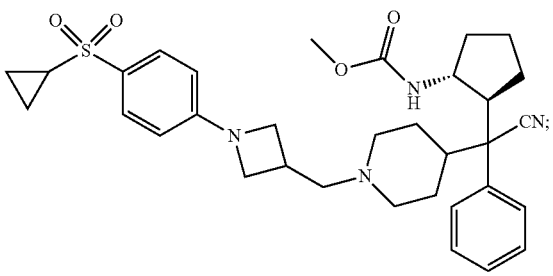
321
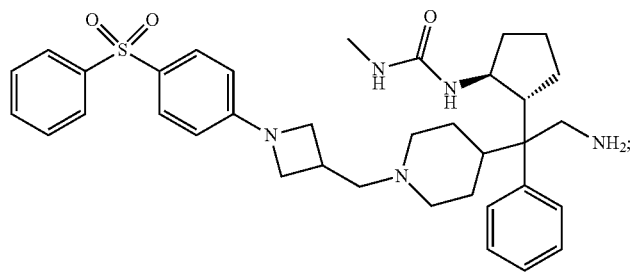

-continued
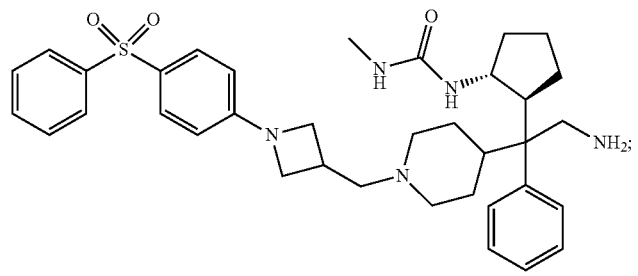
322
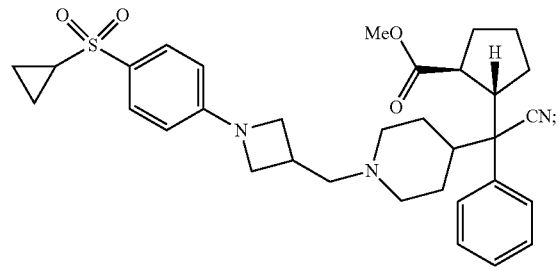
332
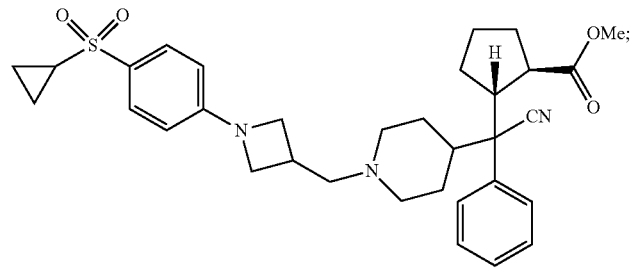
333
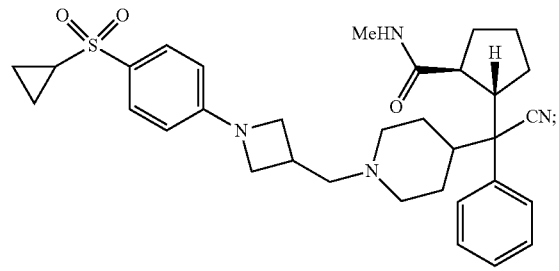
334
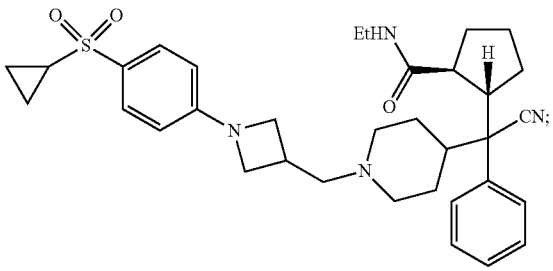
335
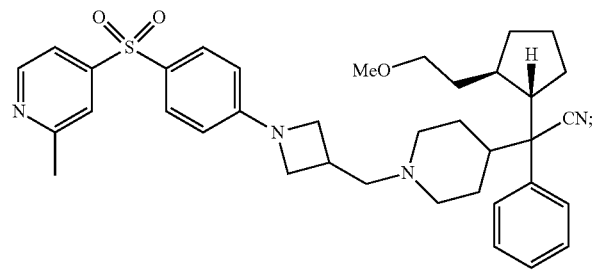
336

337
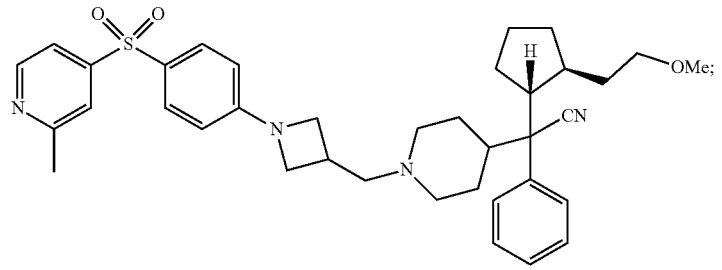
338
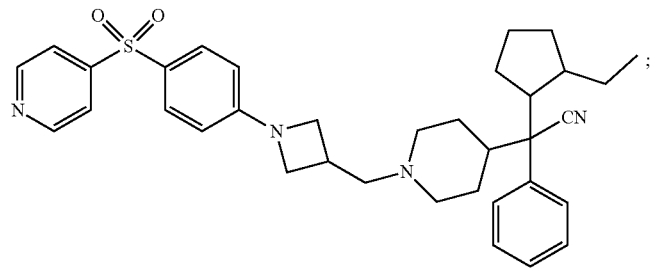
339 340
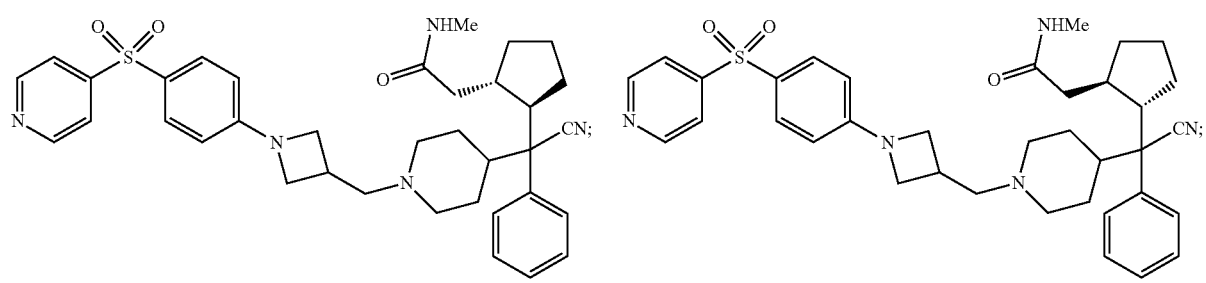
341
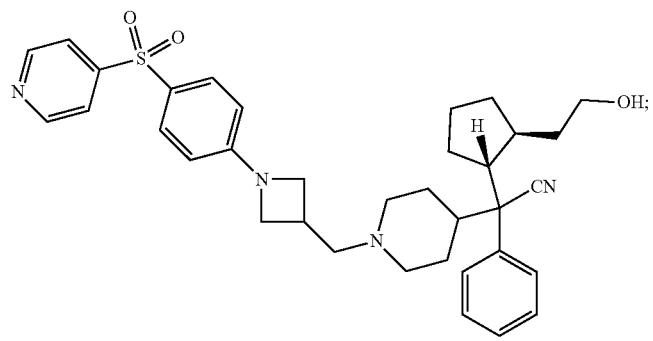
342
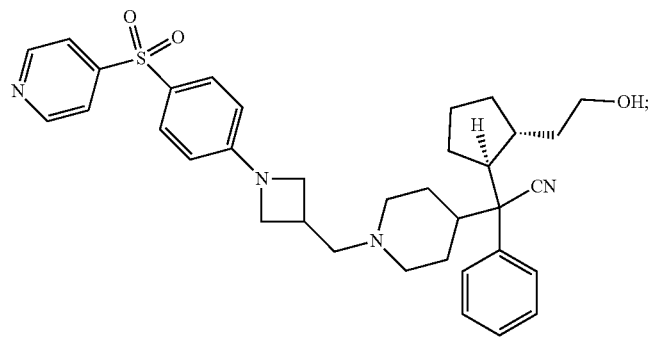

343
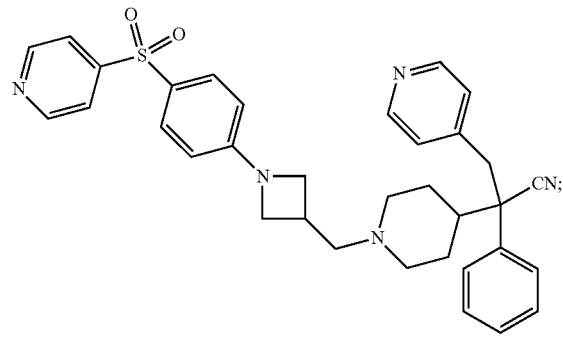
345
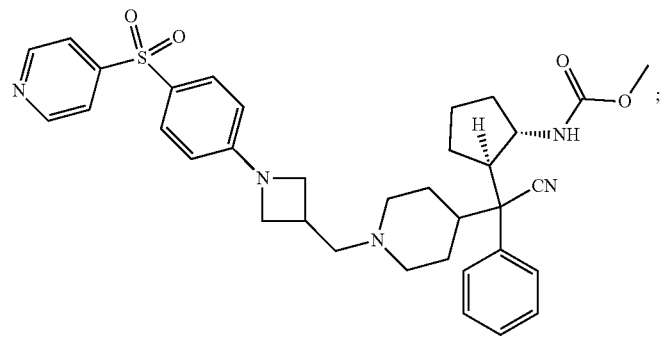
346
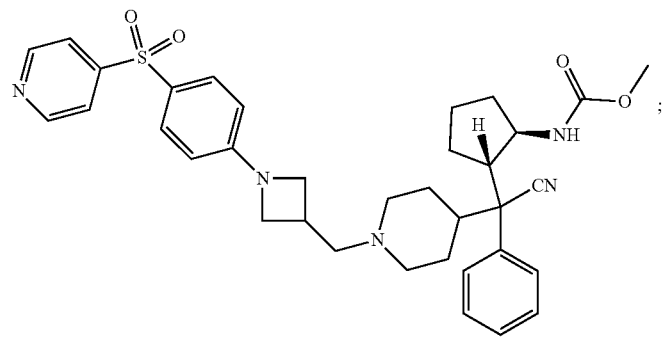
347
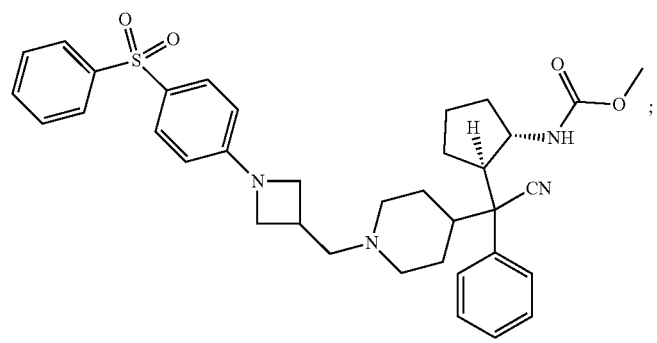

-continued
348
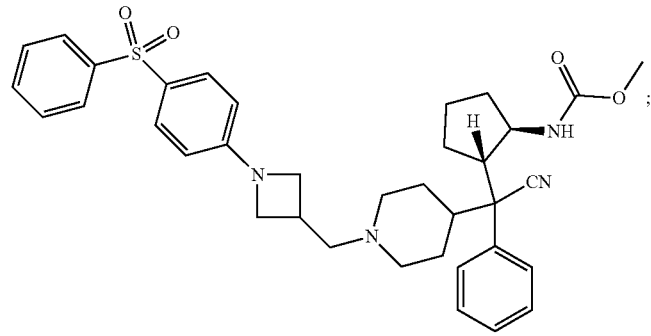
349
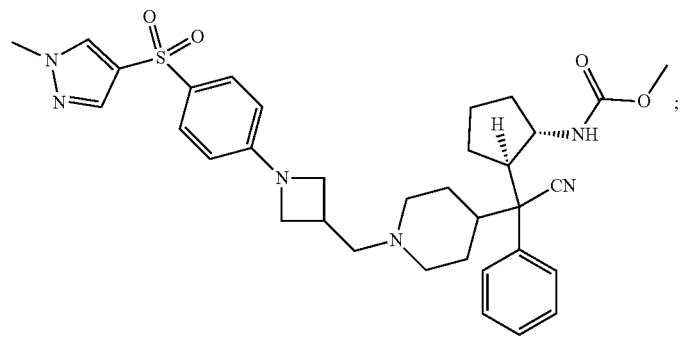
350
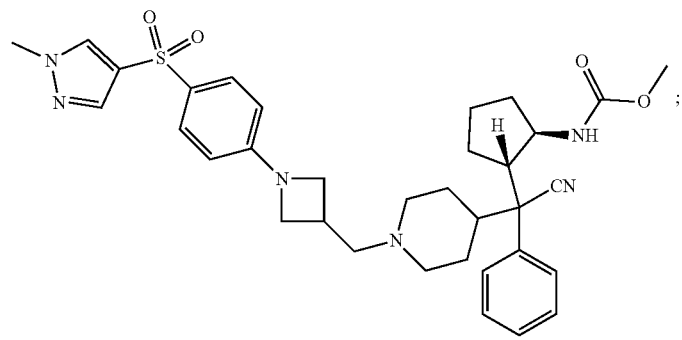
351
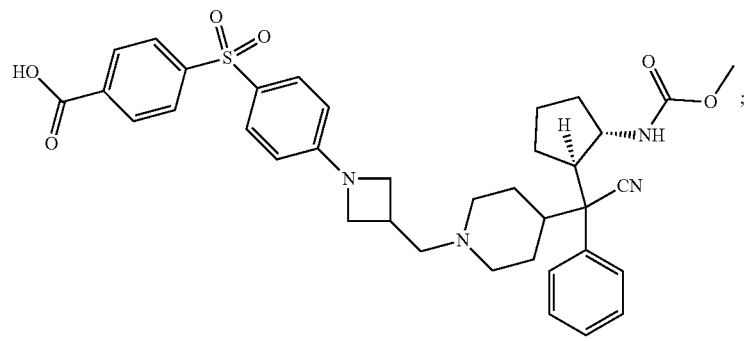

-continued
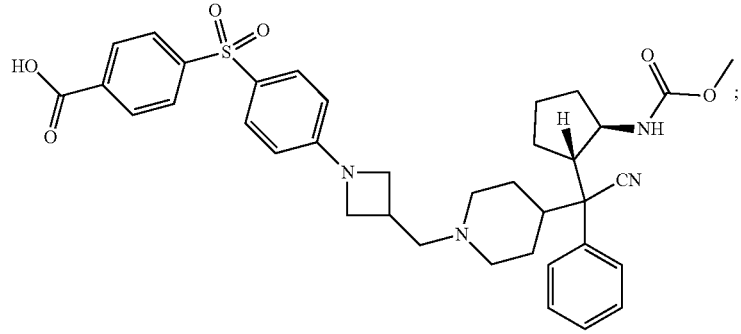
352
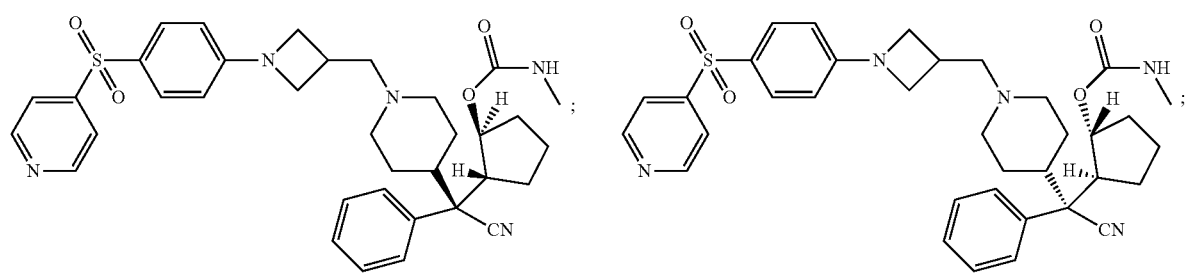
353 354
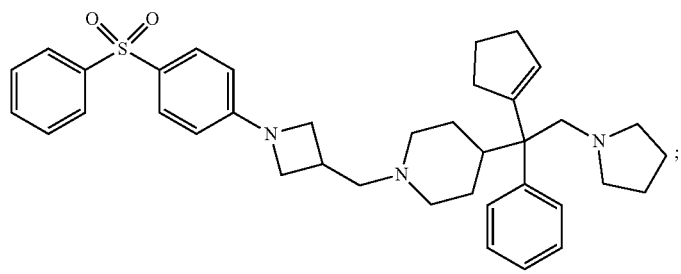
355
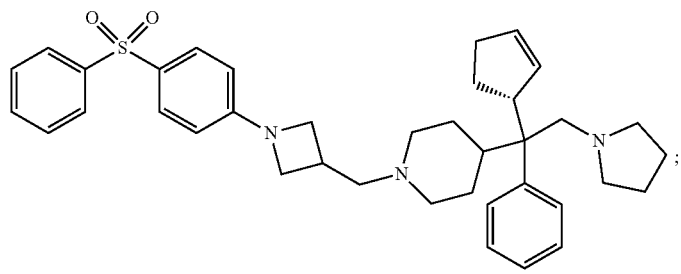
356
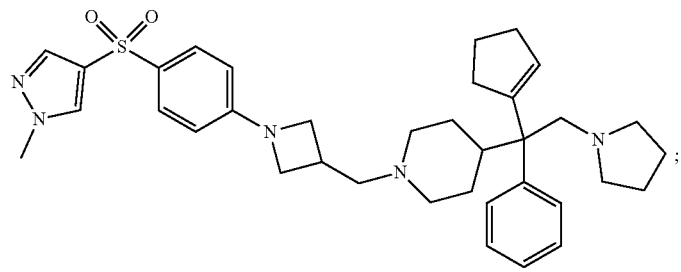
357

-continued
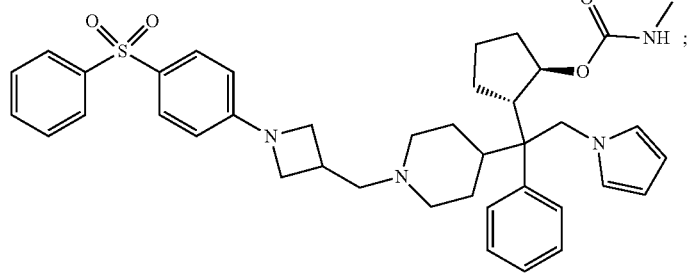
358
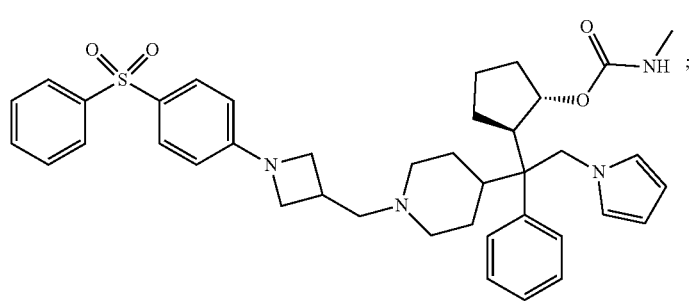
359
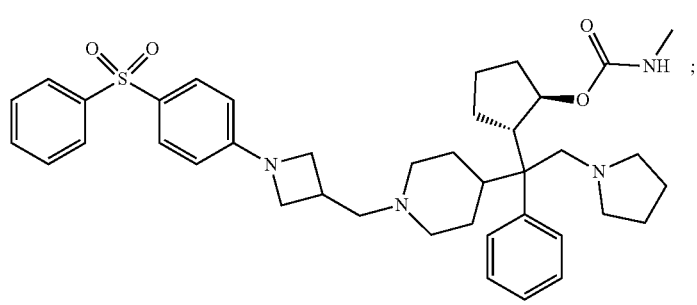
360
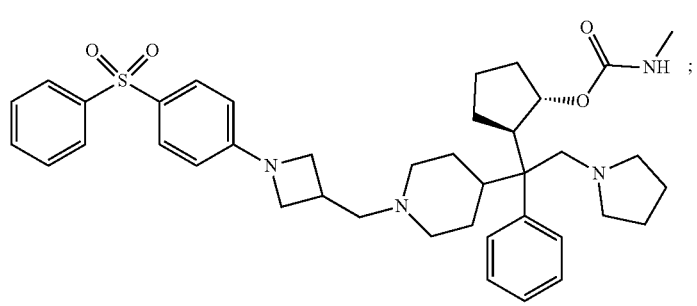
361
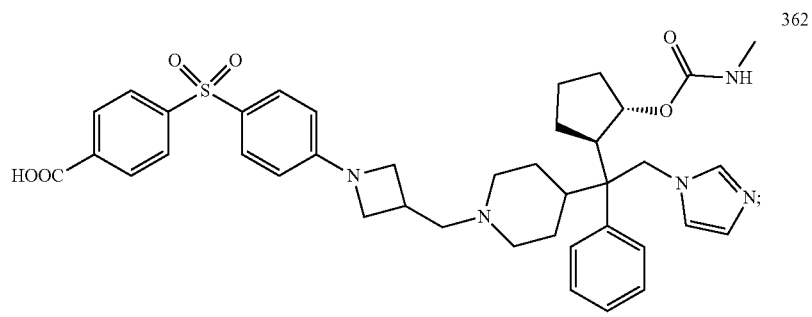
362

-continued
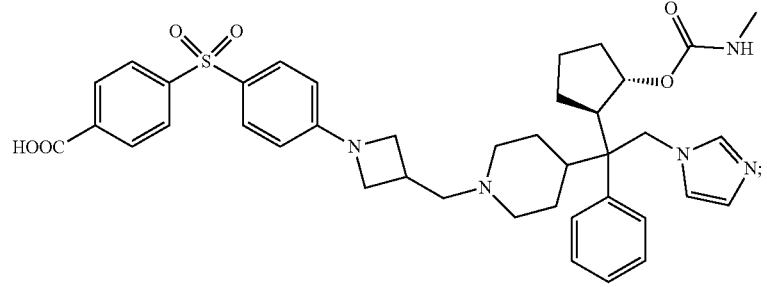
363
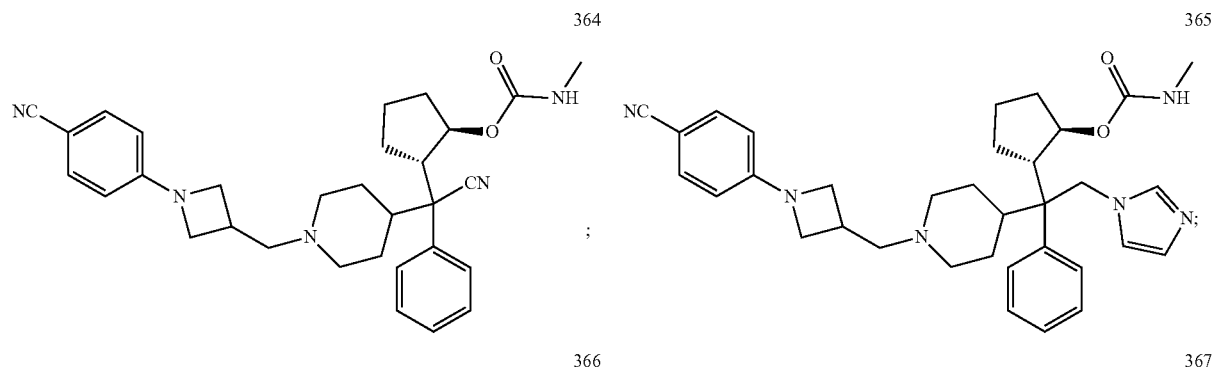
364
365
366
367
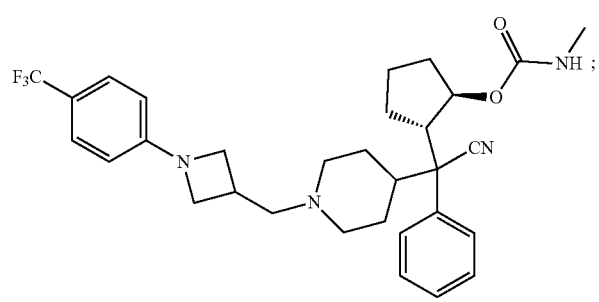
368
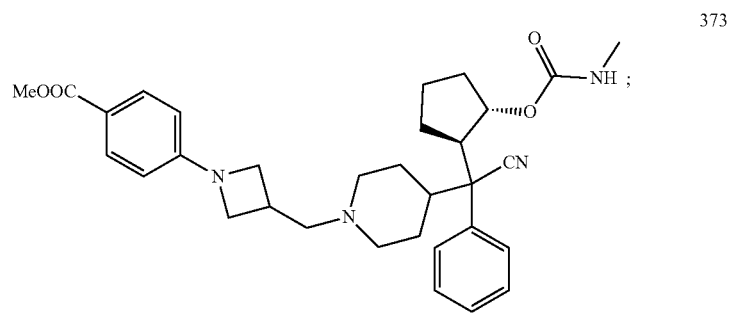
373

-continued
374
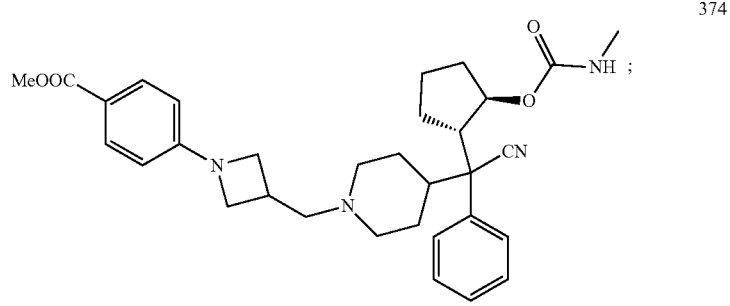
375
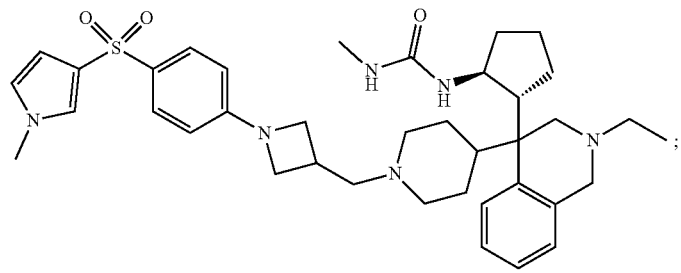
376
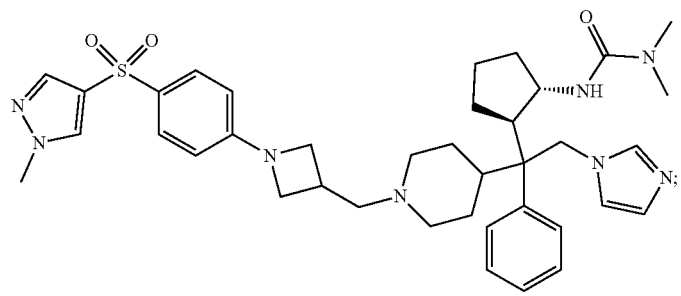
377
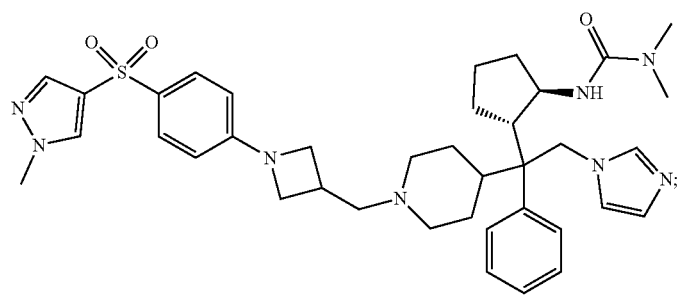
378
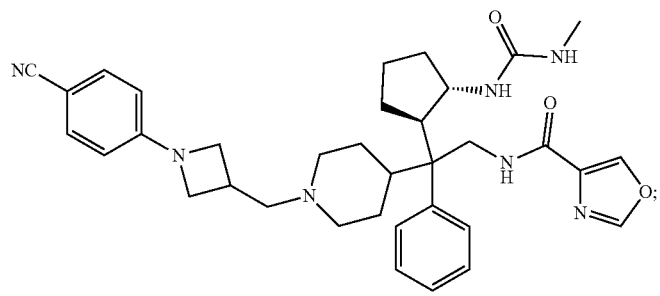

-continued
379
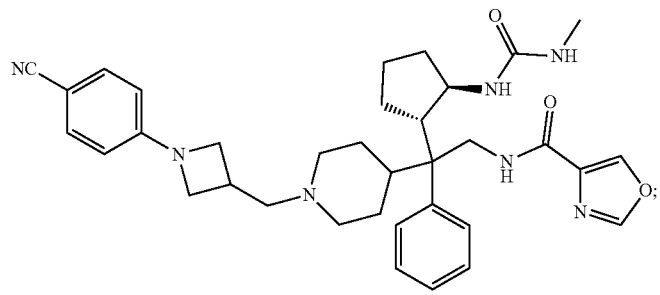
381
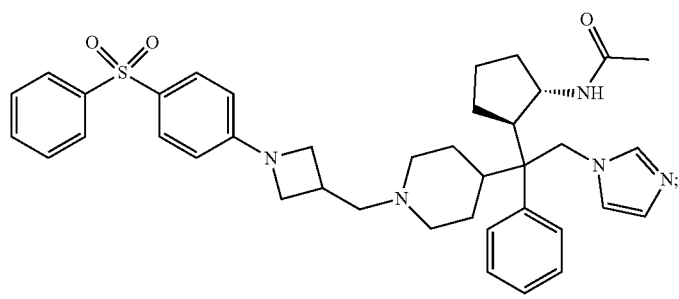
382
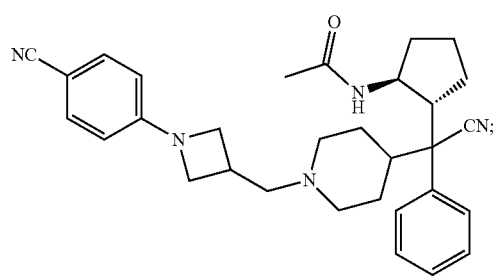
383
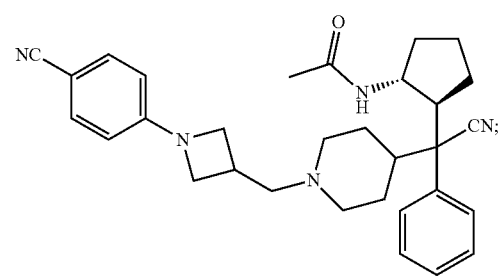
384
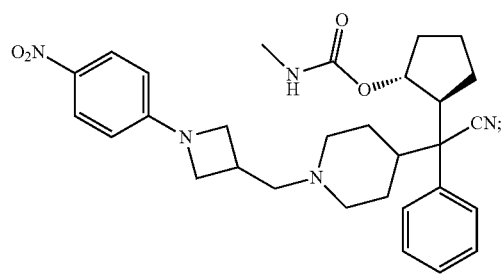
385
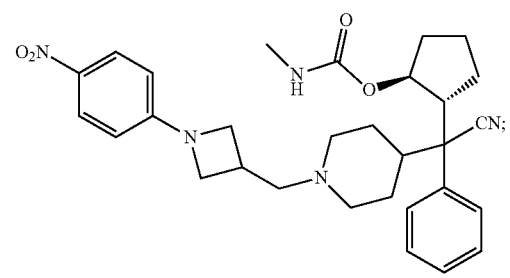
388
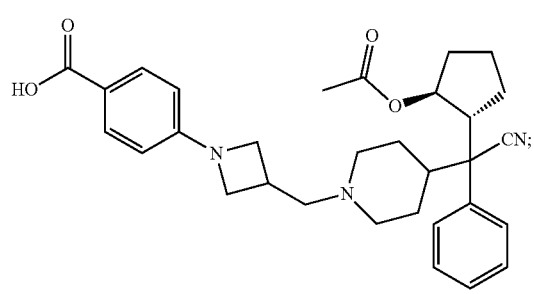
389
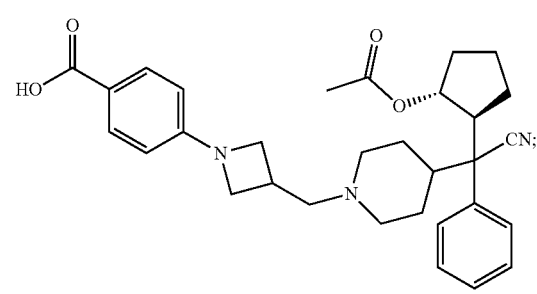

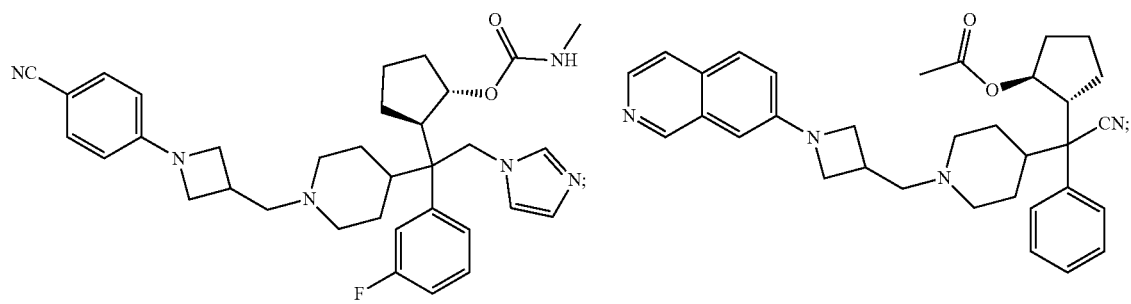
390
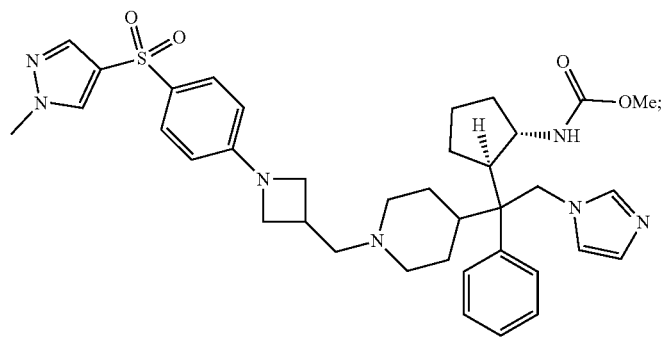
391
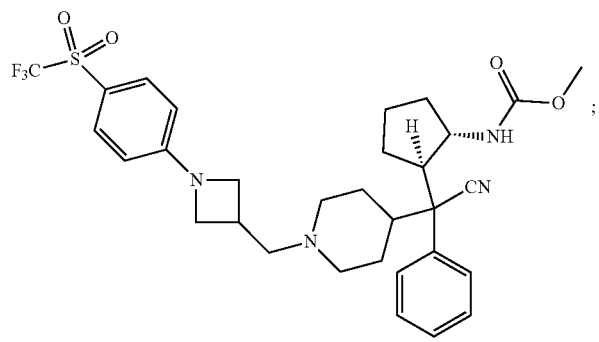
392
393
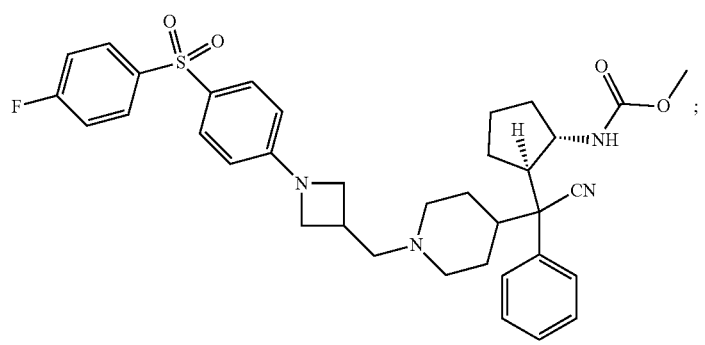
394

-continued
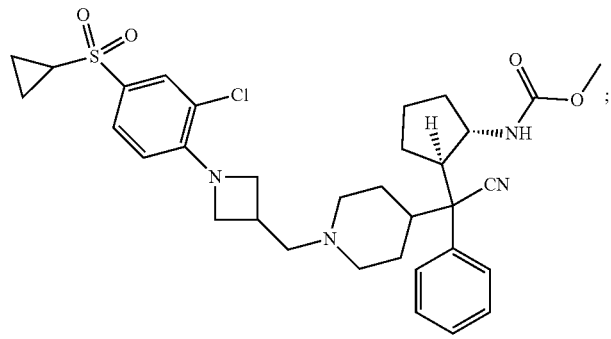
395
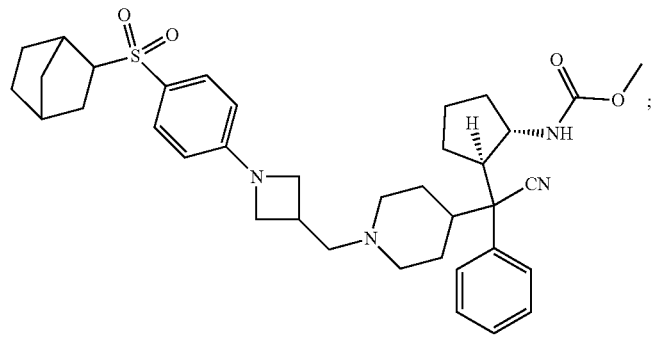
396
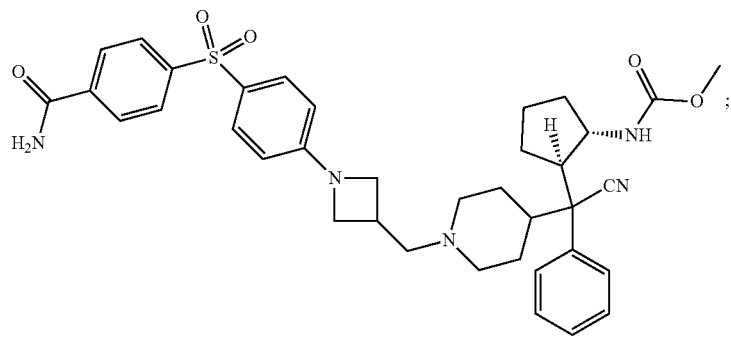
399
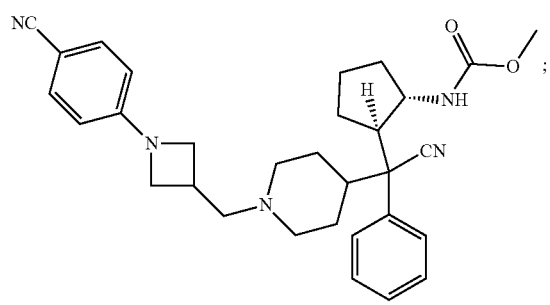
400
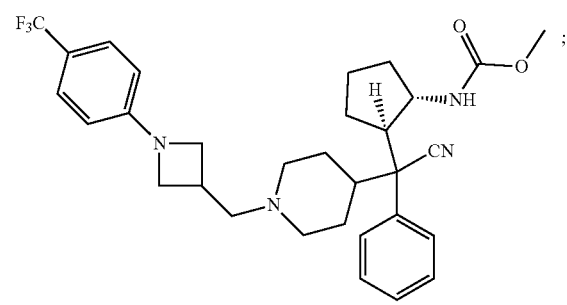
401

-continued
402
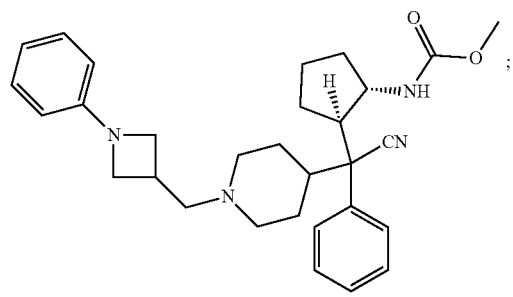
403
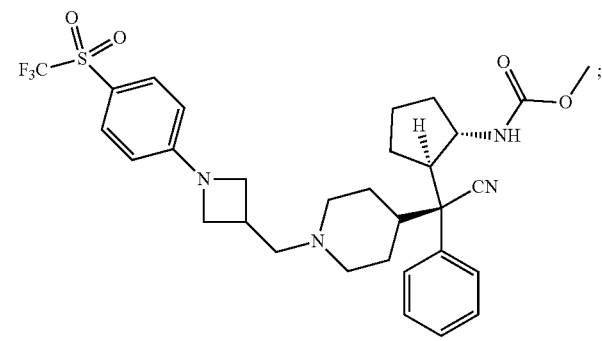
406
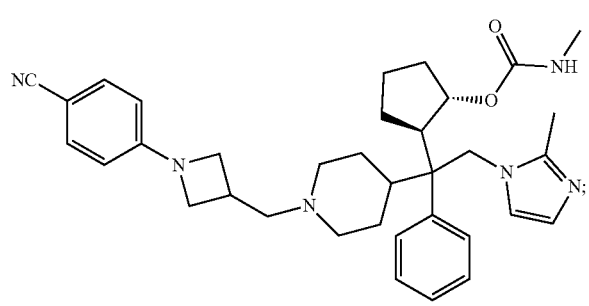
407
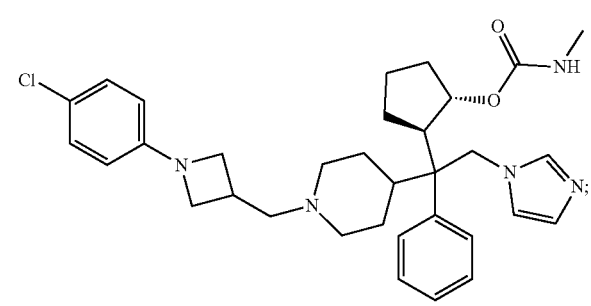
408
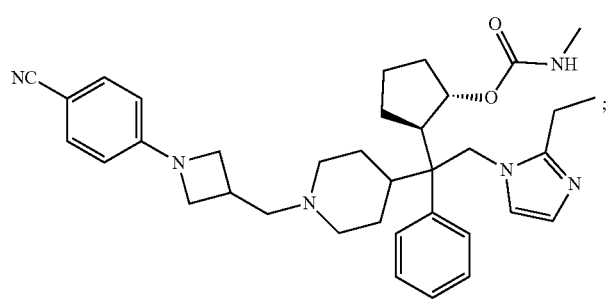
409
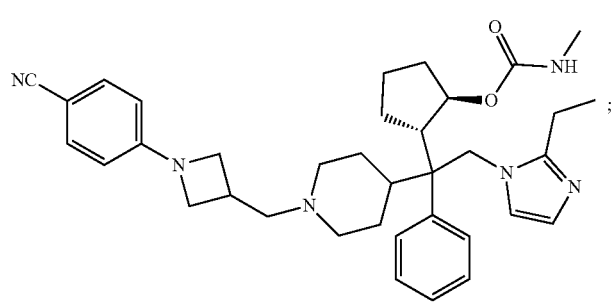
410
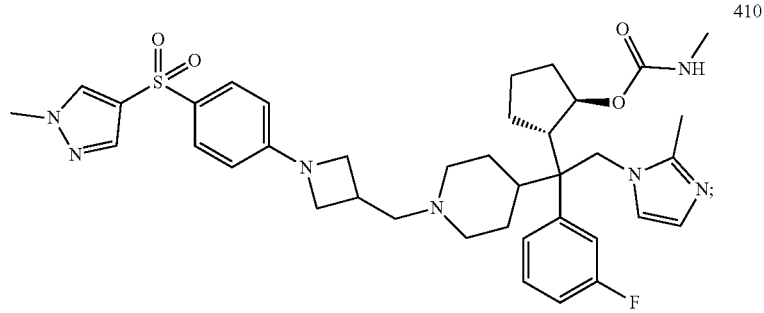

-continued
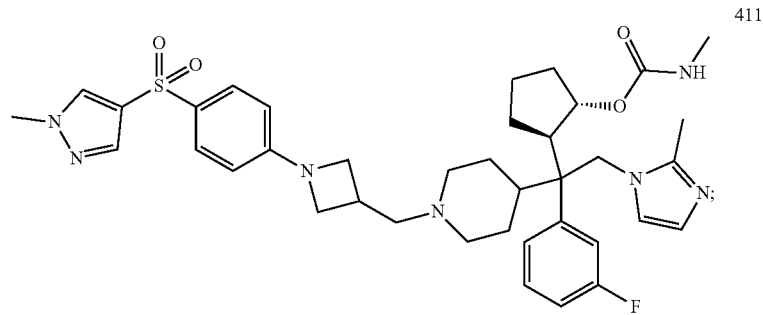
411
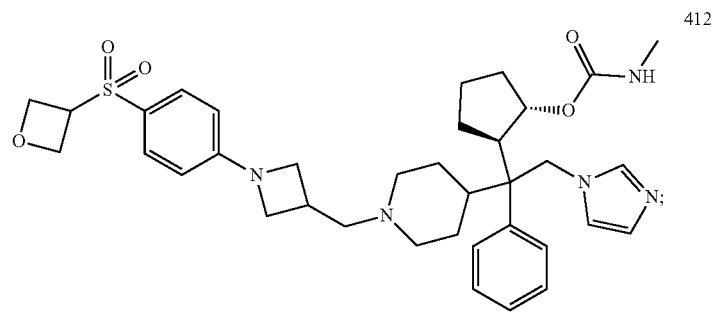
412
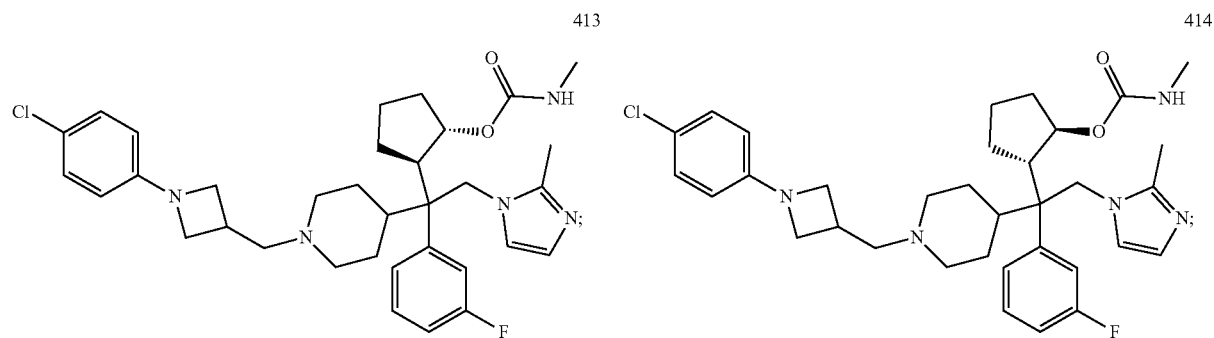
413   414
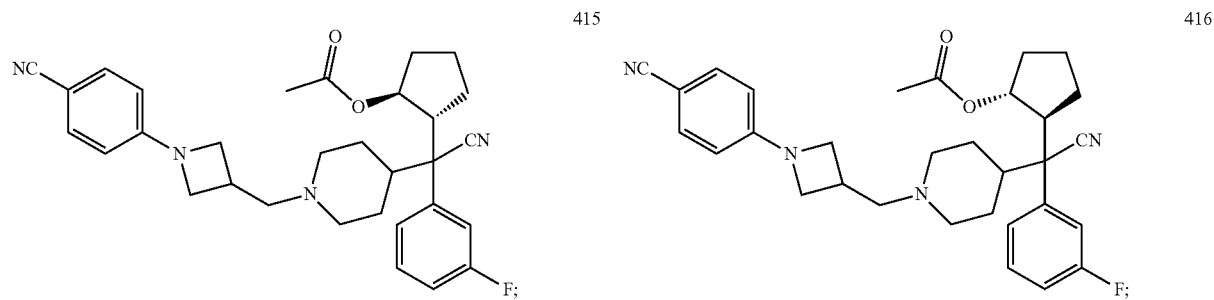
415   416
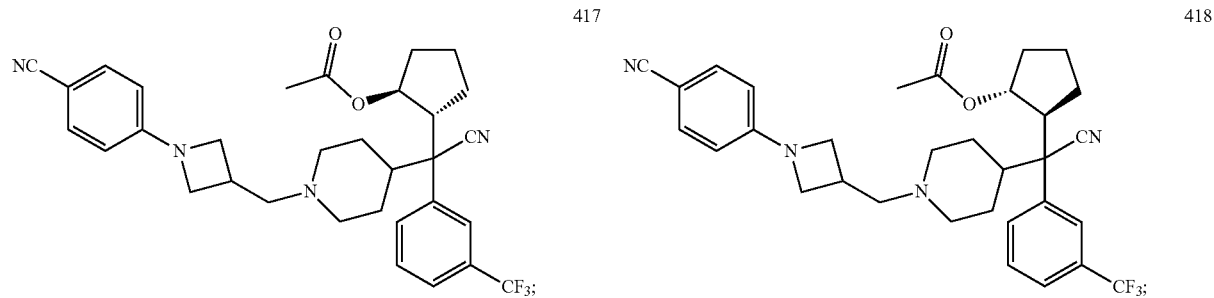
417   418

-continued
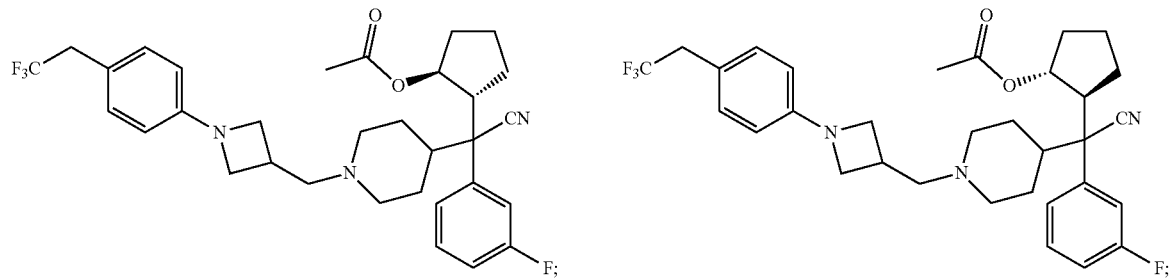
419
420
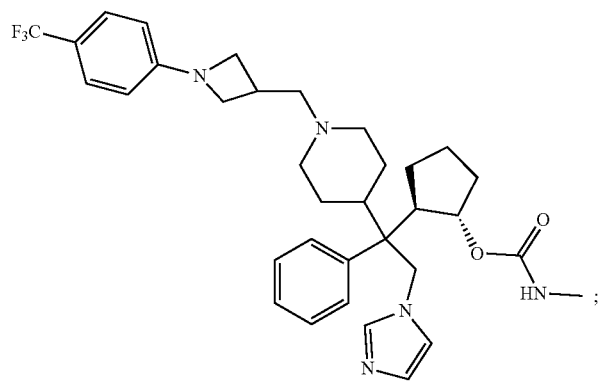
421
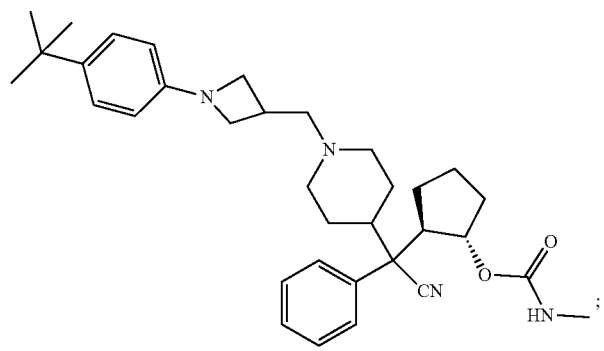
422
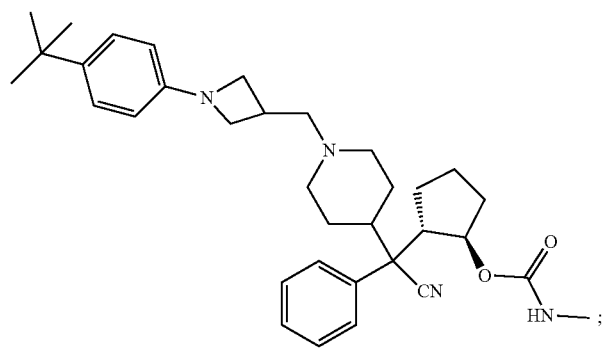
423

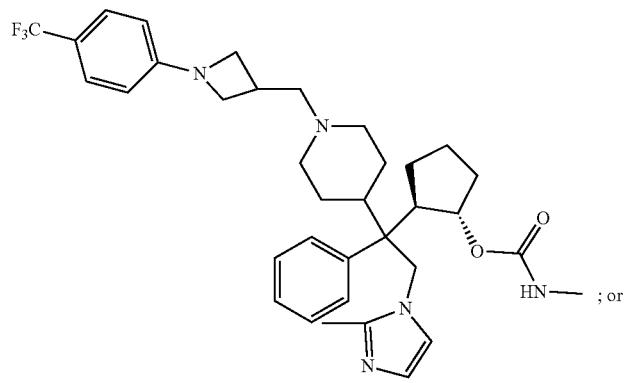
424
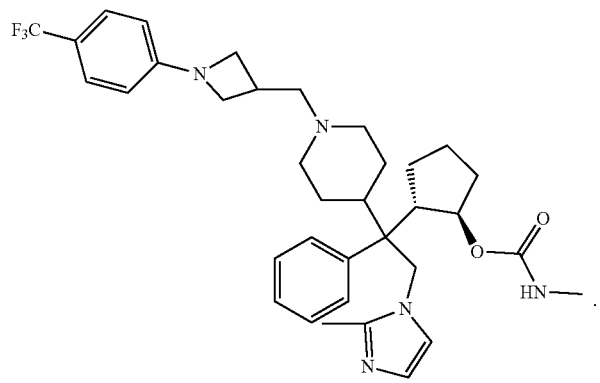
425
16. A compound, or a pharmaceutically acceptable salt, hydrate, or solvate thereof, selected from one or more of:
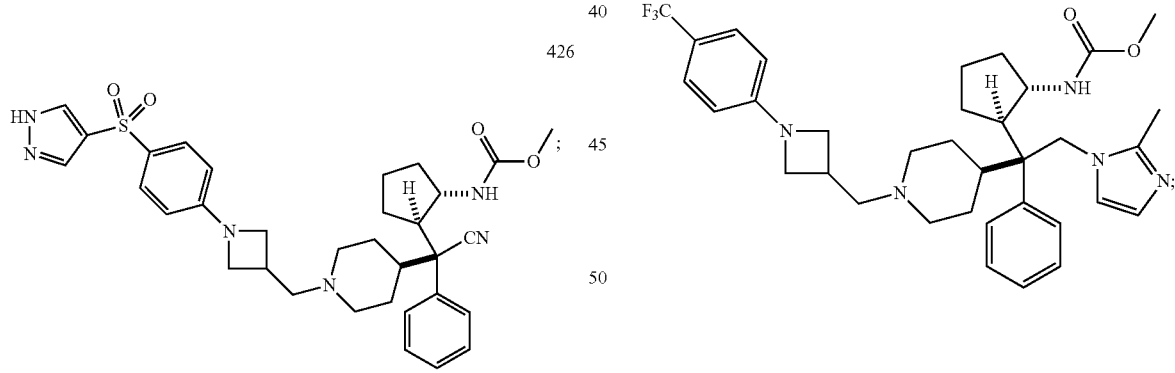
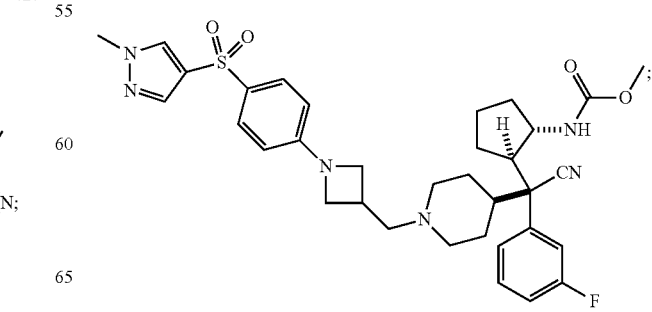

445
-continued
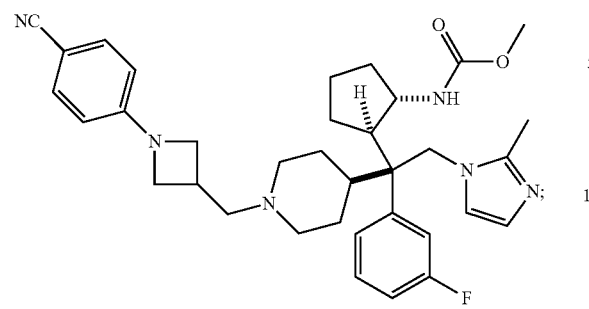
430
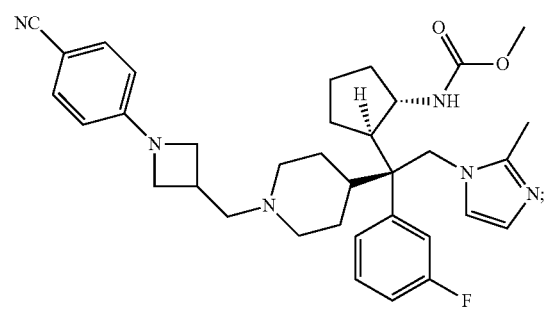
431
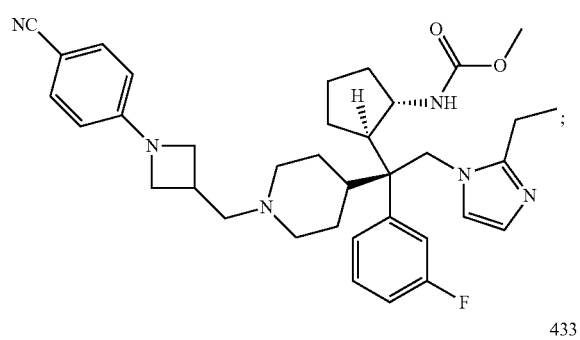
432
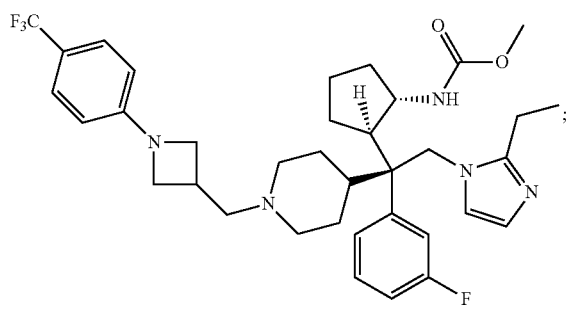
433
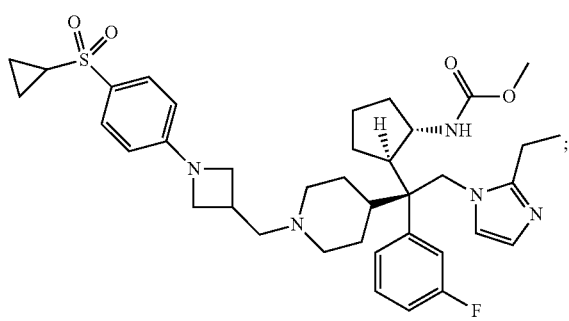
434
446
-continued
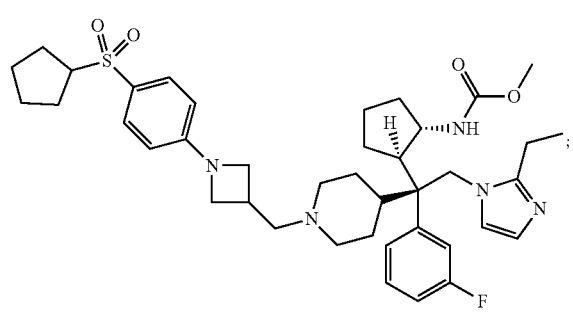
435
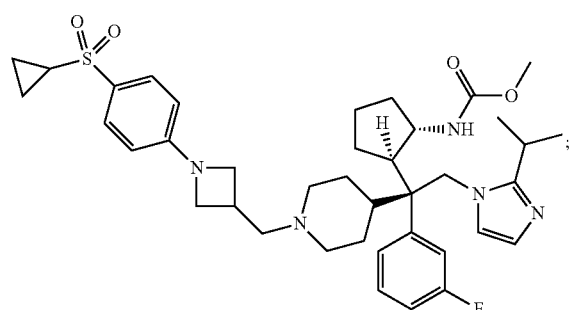
436
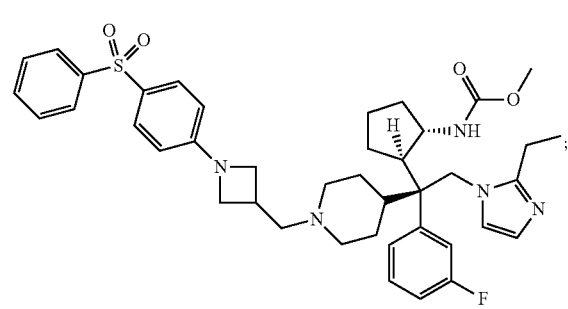
437
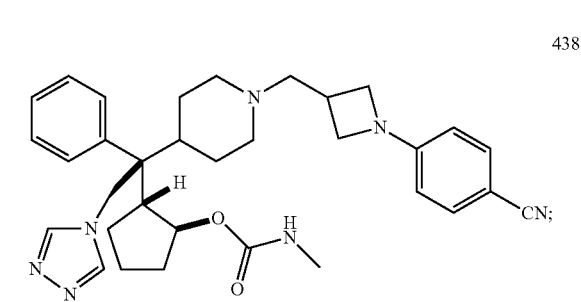
438
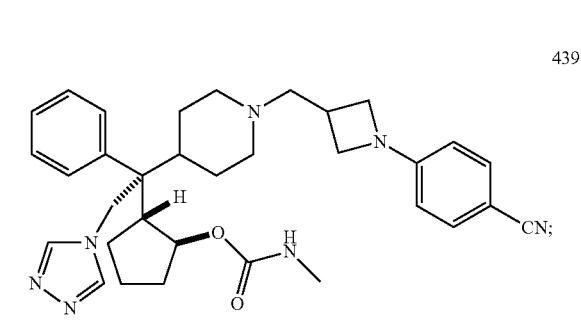
439

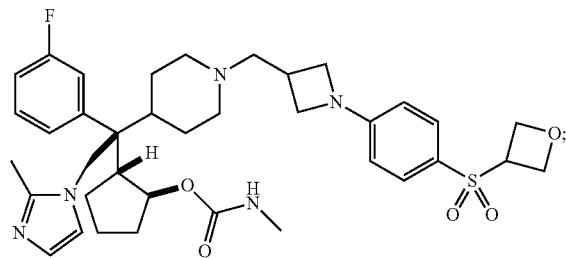
440
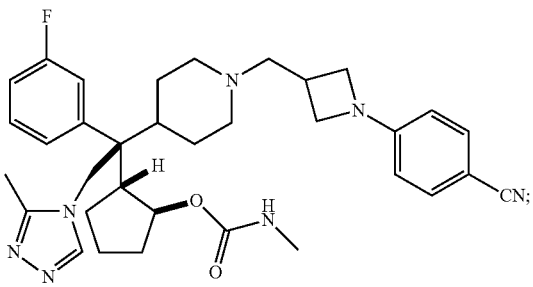
445
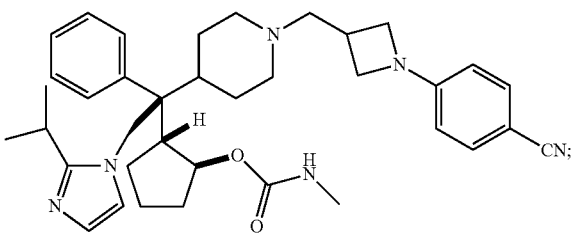
441
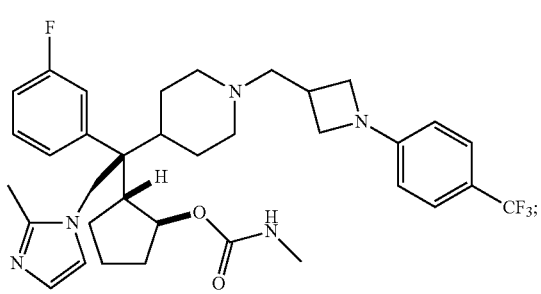
446
442
447
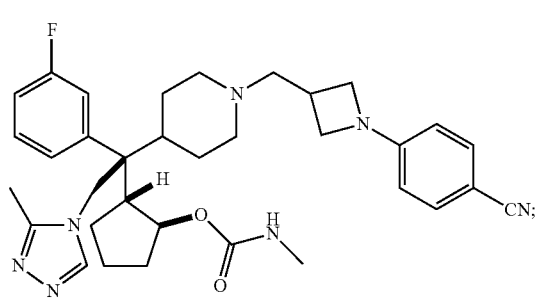
443
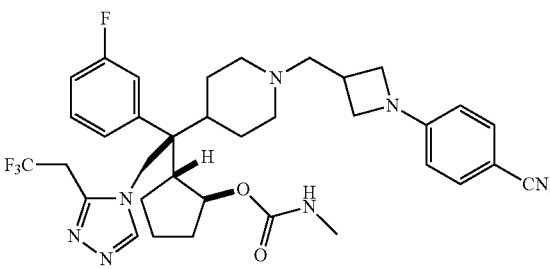
448
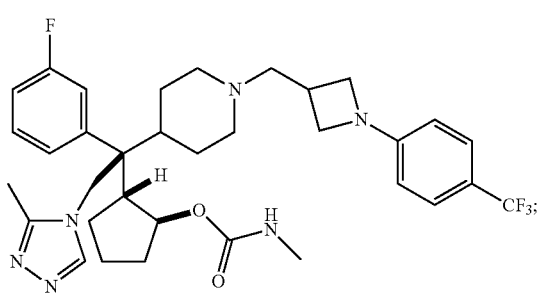
444
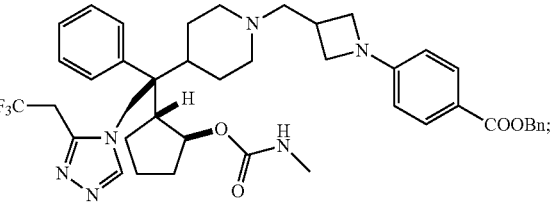
449

449
-continued
450
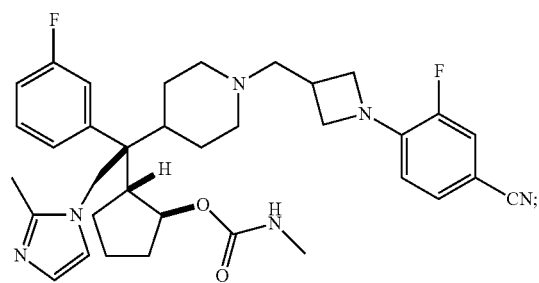
451
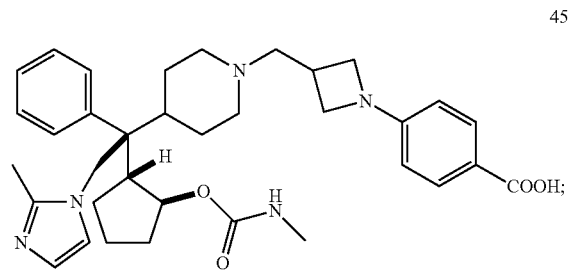
452
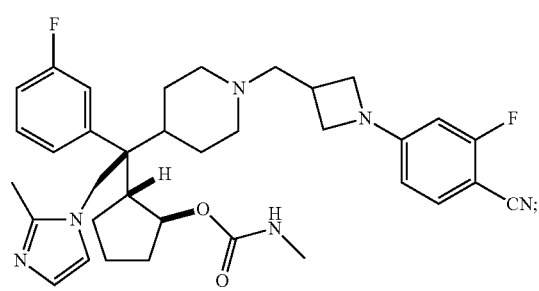
453
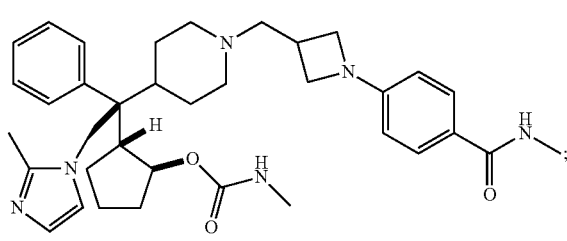
455
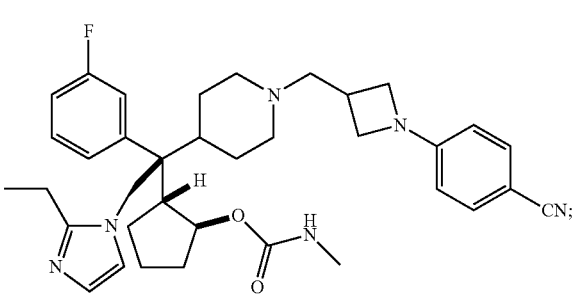
450
-continued
456
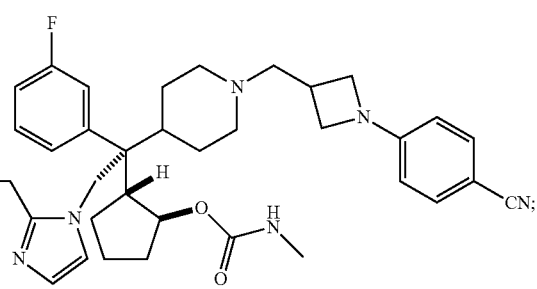
457
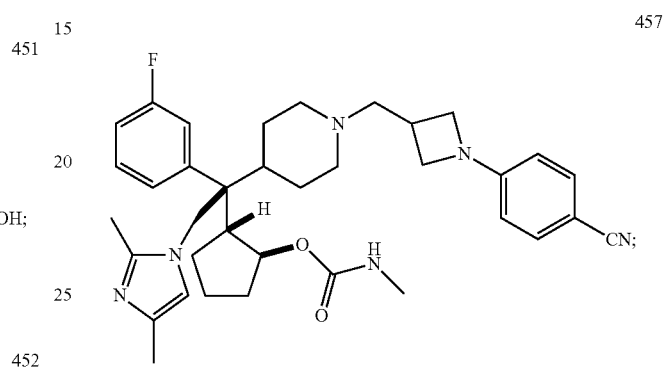
458
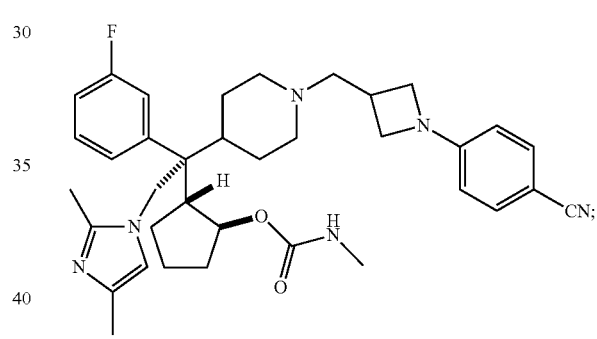
459
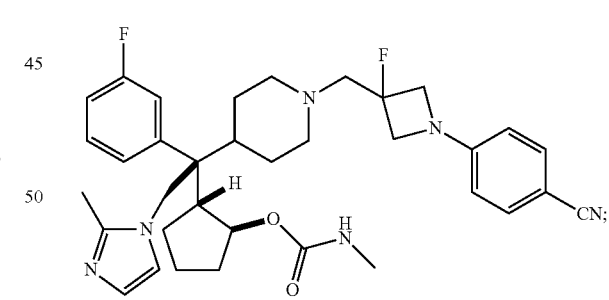
460
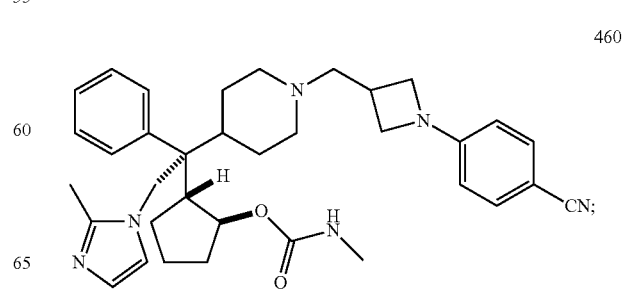

461
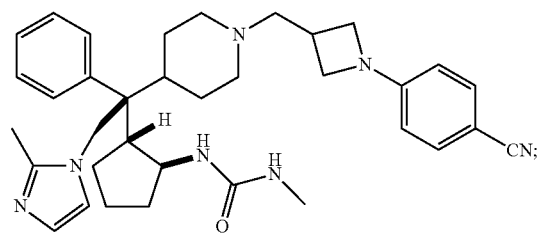
466
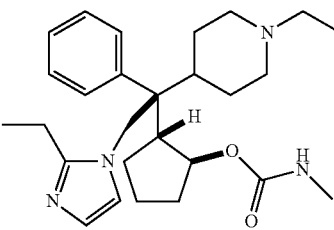
462
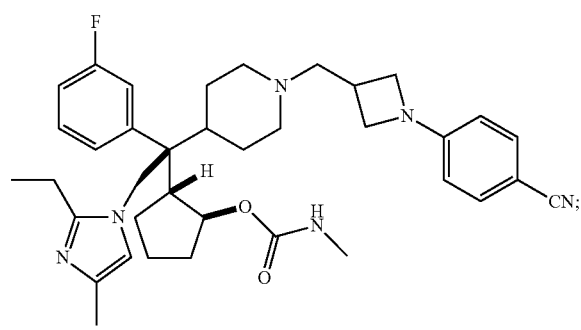
467
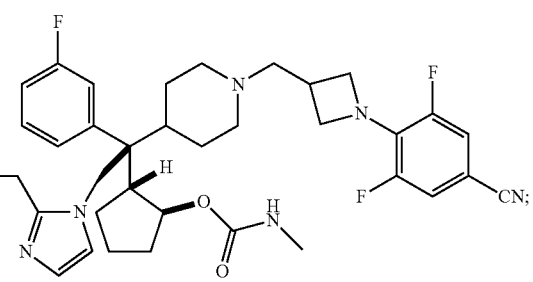
463
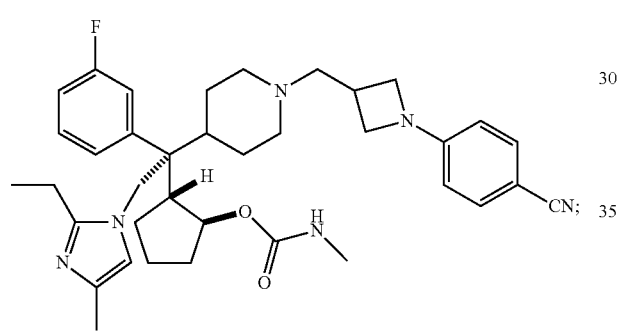
468
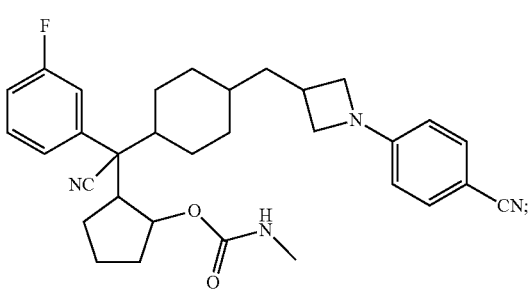
464
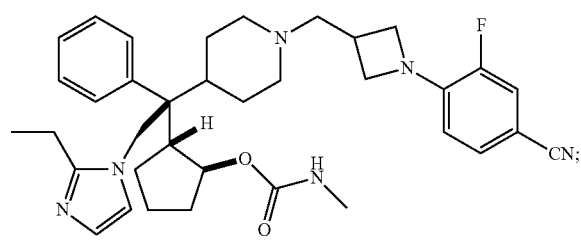
469
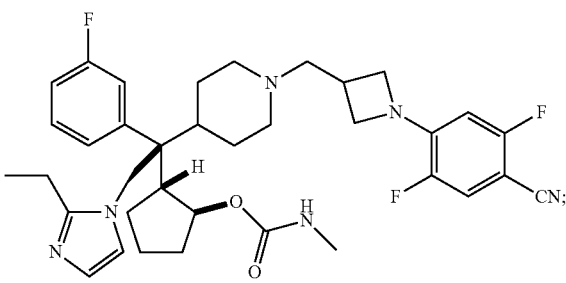
465
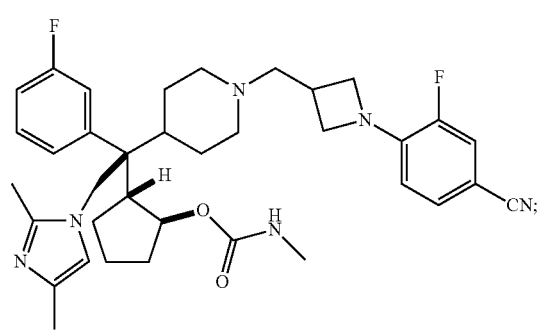
470
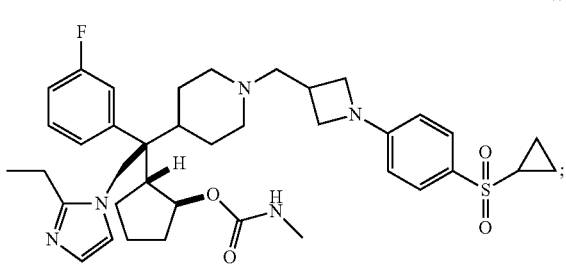

453
-continued
471
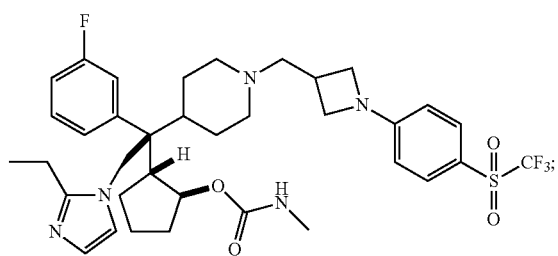
472
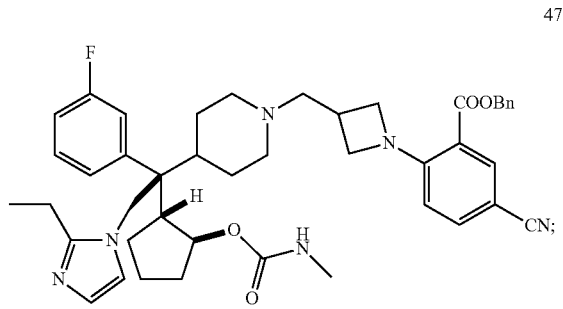
473
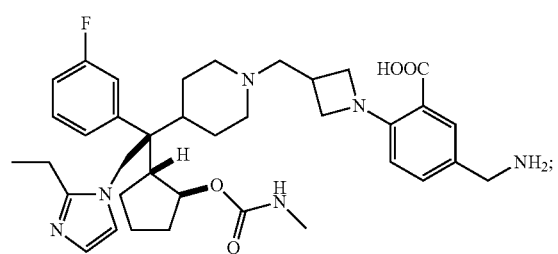
475
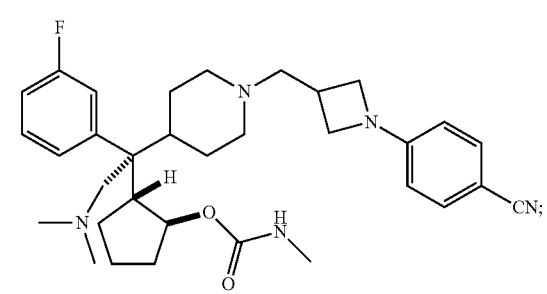
476
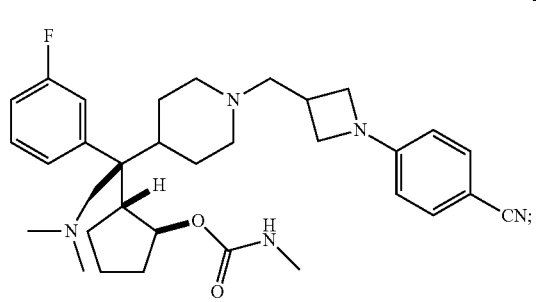
454
-continued
477
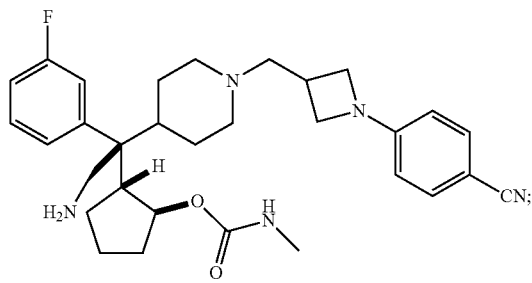
478
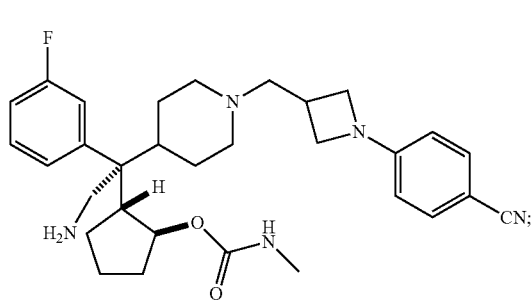
479
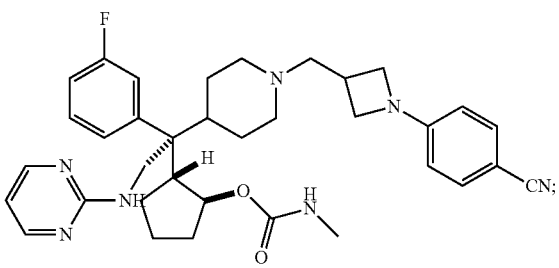
480
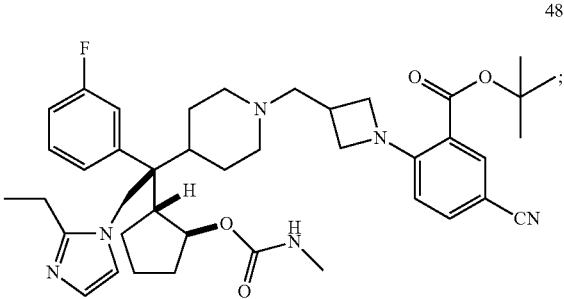
481
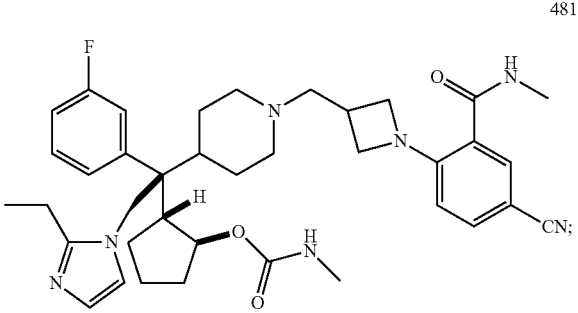

482
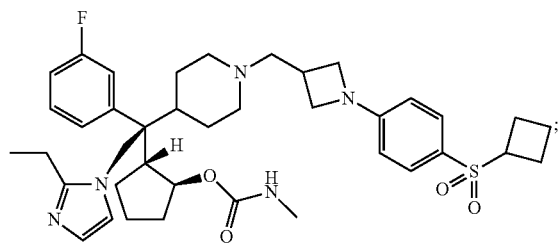
483
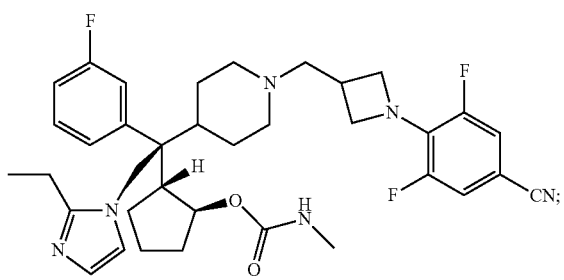
484
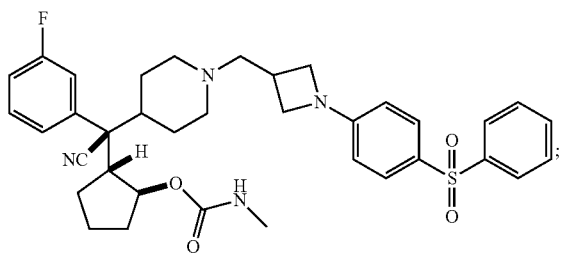
485
486
487
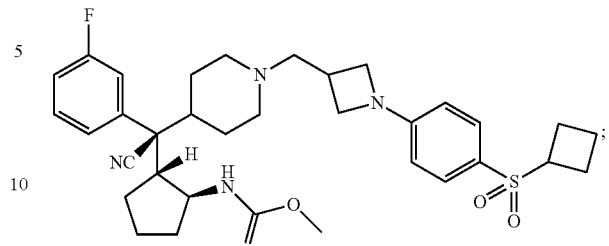
488
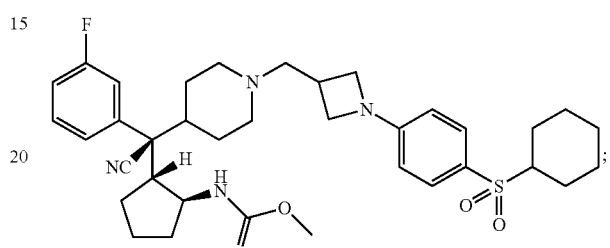
489
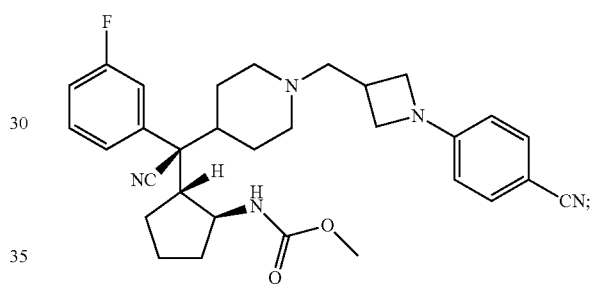
490
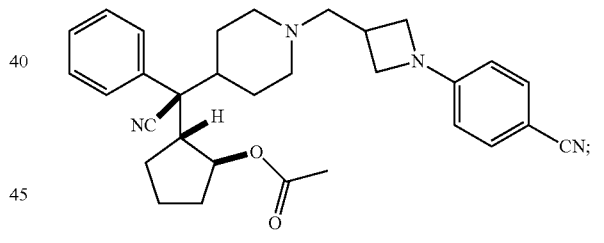
491
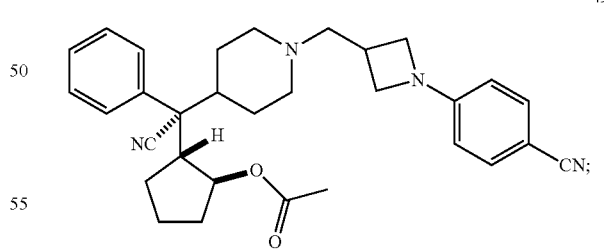
492
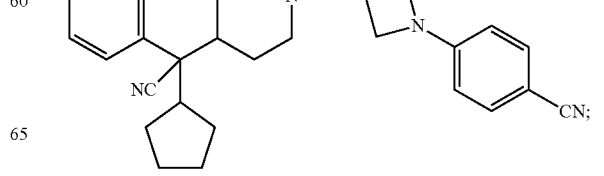

457
-continued
493
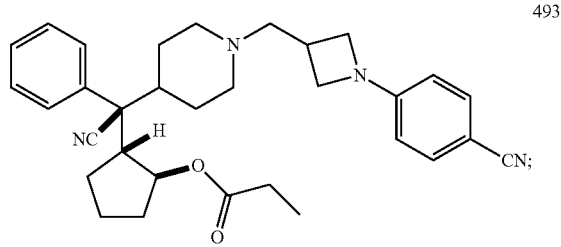
494
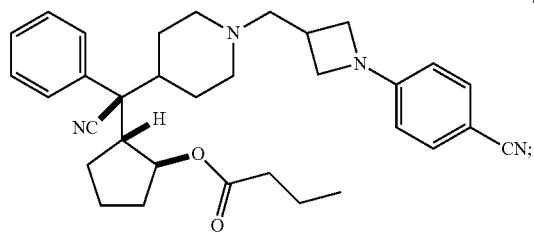
495
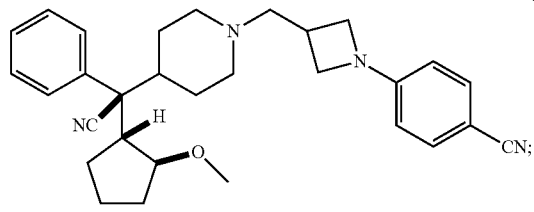
496
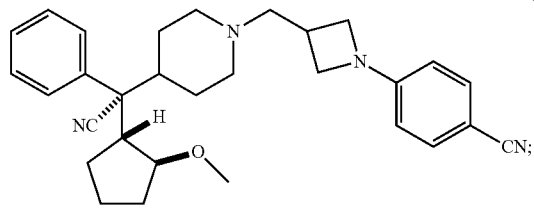
497
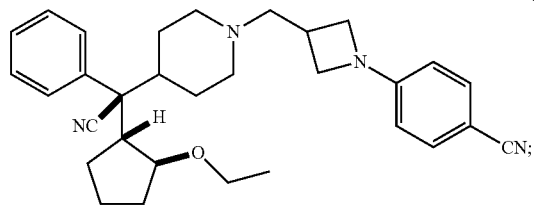
498
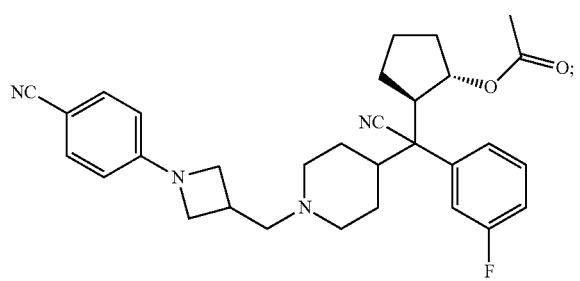
458
-continued
499
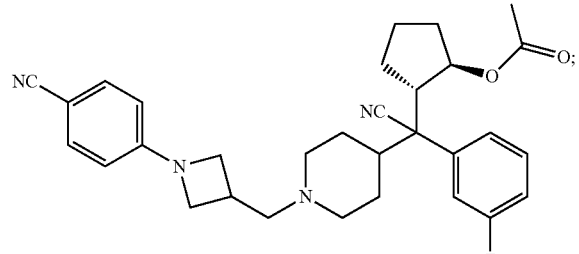
500
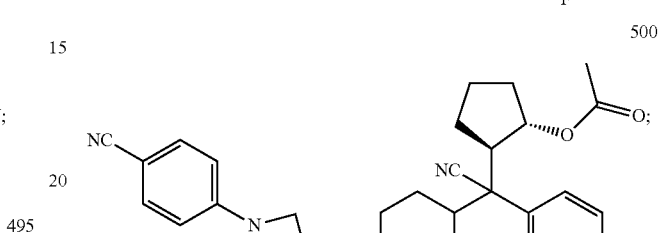
501
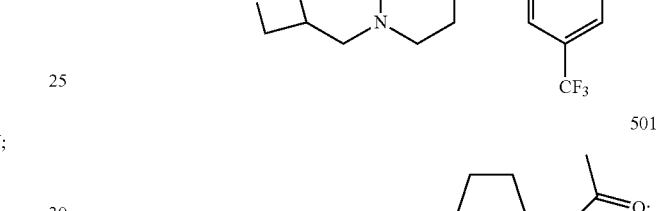
502
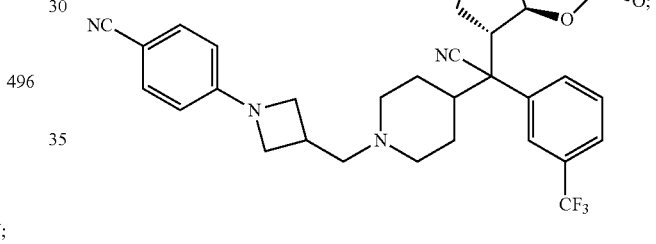
503
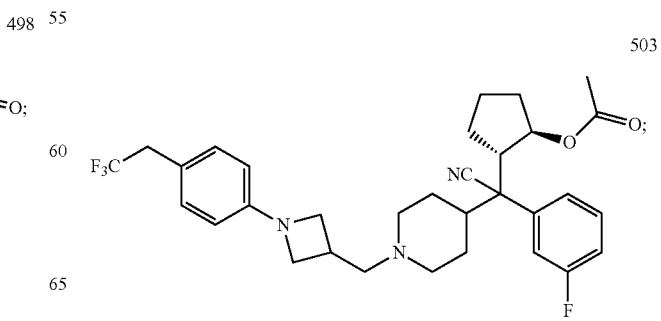

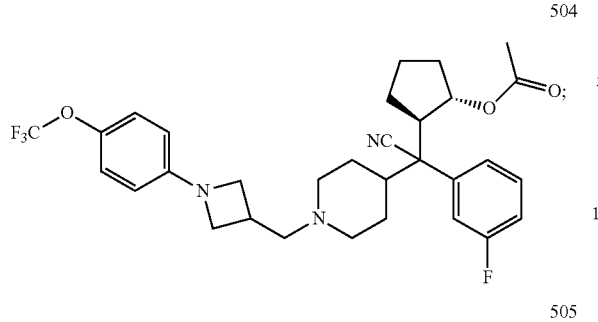
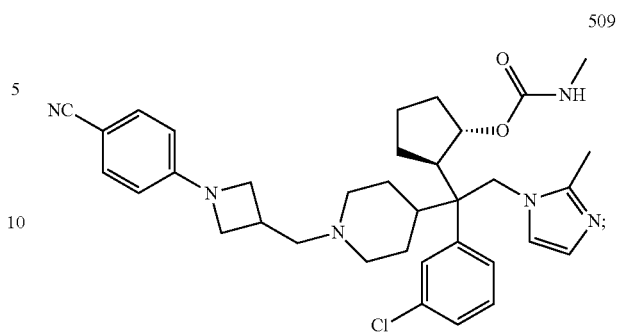
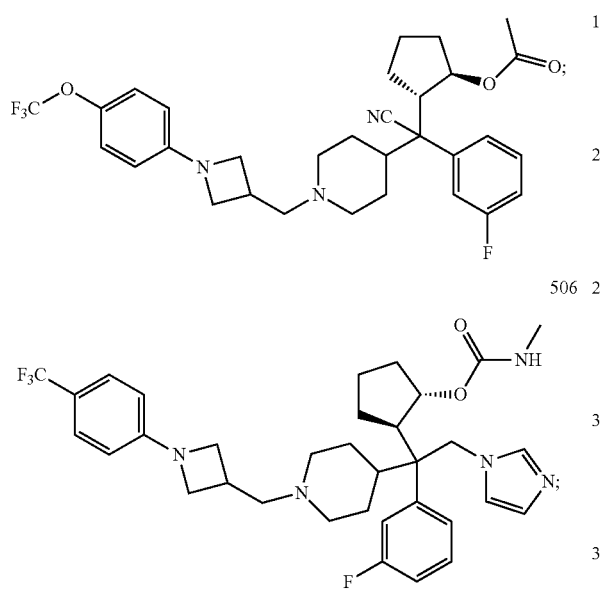
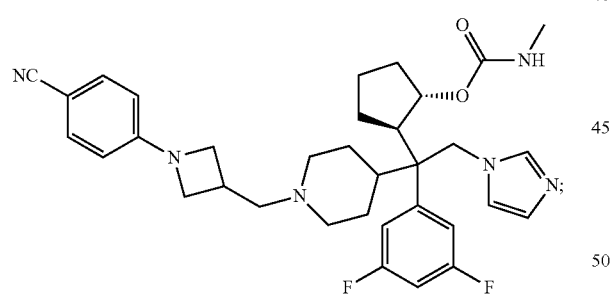
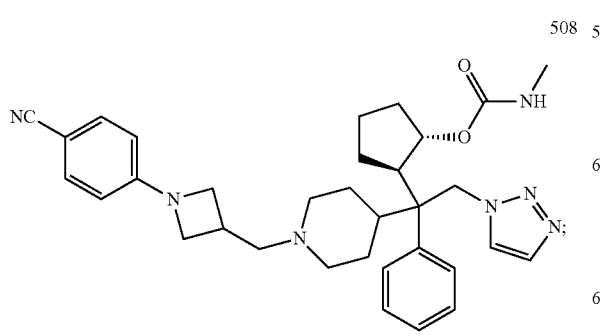

461
-continued

514

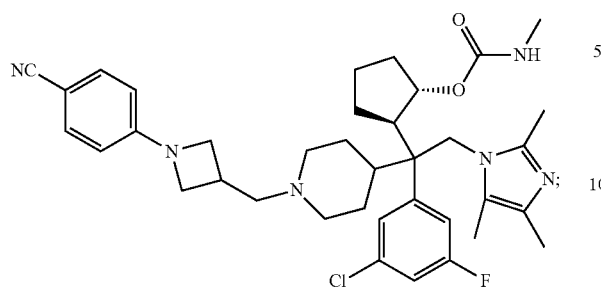

517

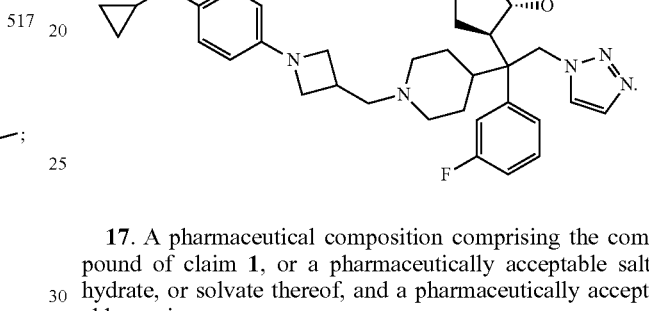

518

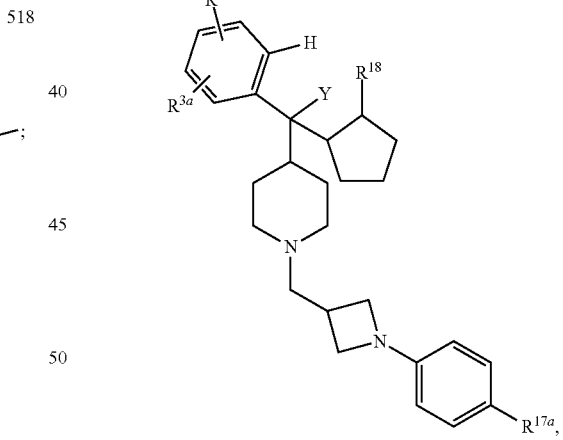

519

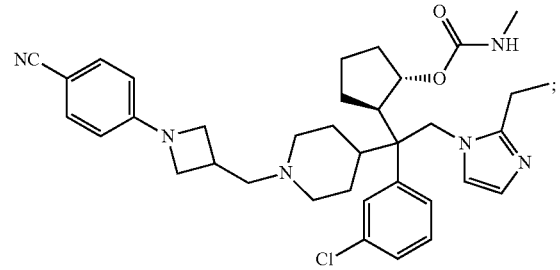

462
-continued

520

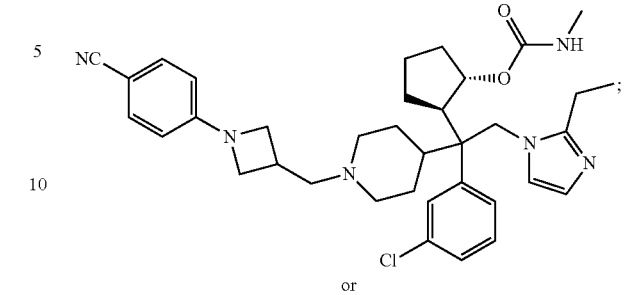

or

522

17. A pharmaceutical composition comprising the compound of claim 1, or a pharmaceutically acceptable salt, hydrate, or solvate thereof, and a pharmaceutically acceptable carrier.

18. A compound, or a pharmaceutically acceptable salt, hydrate, or solvate thereof, having Formula X:

X wherein:
Y is selected from the group consisting of cyano, hydroxy, and —CH$_2$—R$^{12}$;
R$^{3a}$ and R$^{3b}$ are each independently selected from the group consisting of hydrogen, alkyl, halo, hydroxy, cyano, amino, alkylamino, dialkylamino, haloalkyl, alkoxy, and haloalkoxy;
R$^{12}$ is selected from the group consisting of hydroxy, amino, optionally substituted heteroaryl, optionally substituted heterocyclo, and —NHC(=O)—R$^{16}$;
R$^{16}$ is selected from the group consisting of alkyl, optionally substituted aryl, optionally substituted heteroaryl, and optionally substituted cycloalkyl;

R[17a] is selected from the group consisting of hydrogen, alkyl, halo, hydroxy, cyano, amino, alkylamino, dialkylamino, haloalkyl, alkoxy, haloalkoxy, alkylsulfonyl, haloalkylsulfonyl, cycloalkylsulfonyl, (cycloalkyl)alkylsulfonyl, arylsulfonyl, heteroarylsulfonyl, heterocyclosulfonyl, sulfonamido, optionally substituted heteroaryl, optionally substituted heterocyclo, carboxamido, alkylcarbonyl, arylcarbonyl, alkoxycarbonyl, carboxy, and carboxyalkyl;

R[18] is selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N(R[19a])C(=O)—R[19b], and N(R[20a])SO$_2$—R[20b];

R[19a] is selected from the group consisting of hydrogen and alkyl;

R[19b] is selected from the group consisting of amino, alkoxy, alkyl, and optionally substituted aryl;

R[20a] is selected from the group consisting of hydrogen and alkyl; and

R[20b] is selected from the group consisting of amino, alkyl, and optionally substituted aryl.

19. The compound of claim 18, or a pharmaceutically acceptable salt, hydrate, or solvate thereof, wherein Y is —CH$_2$—R[12].

20. The compound of claim 19, or a pharmaceutically acceptable salt, hydrate, or solvate thereof, wherein R[12] is a 5-membered heteroaryl.

21. The compound of claim 19, or a pharmaceutically acceptable salt, hydrate, or solvate thereof, wherein R[12] is optionally substituted imidazol-1-yl.

22. The compound of claim 21, or a pharmaceutically acceptable salt, hydrate, or solvate thereof, wherein R[12] is

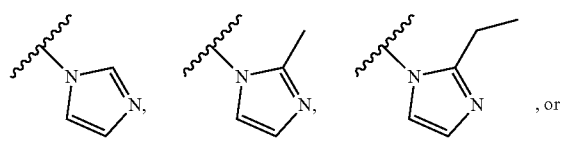, or

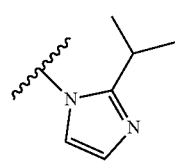.

23. The compound of claim 18, or a pharmaceutically acceptable salt, hydrate, or solvate thereof, wherein:

Y is selected from the group consisting of cyano and —CH$_2$—R[12];

R[12] is selected from the group consisting of amino and heteroaryl;

R[17a] is selected from the group consisting of chloro, cyano, alkylsulfonyl, haloalkylsulfonyl, cycloalkylsulfonyl, arylsulfonyl, and heteroarylsulfonyl;

R[18] is selected from the group consisting of —OC(=O)-amino and —NHC(=O)—R[19b]; and R[19b] is selected from the group consisting of amino, alkoxy, alkyl, and optionally substituted aryl.

24. A compound, or a pharmaceutically acceptable salt, hydrate, or solvate thereof, having Formula Xi:

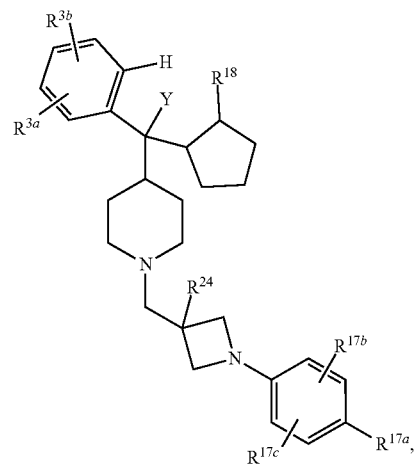

wherein:

Y is selected from the group consisting of cyano and —CH$_2$—R[12];

R[3a] and R[3b] are each independently selected from the group consisting of hydrogen, alkyl, halo, hydroxy, cyano, amino, alkylamino, dialkylamino, haloalkyl, alkoxy, and haloalkoxy;

R[12] is selected from the group consisting of amino and heteroaryl;

R[17a] is selected from the group consisting of chloro, cyano, alkylsulfonyl, haloalkylsulfonyl, cycloalkylsulfonyl, arylsulfonyl, and heteroarylsulfonyl;

R[17b] and R[17c] are independently selected from the group consisting of hydrogen and halo;

R[18] is selected from the group consisting of —OC(=O)-amino and —NHC(=O)—R[19b];

R[19b] is selected from the group consisting of amino, alkoxy, alkyl, and optionally substituted aryl; and R[24] is selected from the group consisting of hydrogen and fluoro.

25. A compound, or a pharmaceutically acceptable salt, hydrate, or solvate thereof, having Formula Xi:

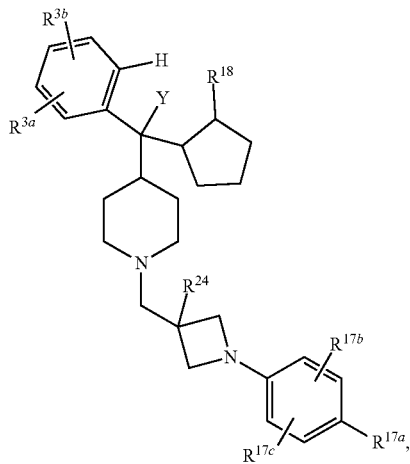

wherein:
Y is selected from the group consisting of cyano and —CH$_2$—R$^{12}$;
R$^{3a}$ and R$^{3b}$ are each independently selected from the group consisting of hydrogen, alkyl, halo, hydroxy, cyano, amino, alkylamino, dialkylamino, haloalkyl, alkoxy, and haloalkoxy;
R$^{12}$ is optionally substituted 5-membered heteroaryl;
R$^{17a}$ is selected from the group consisting of chloro, cyano, alkylsulfonyl, haloalkylsulfonyl, cycloalkylsulfonyl, arylsulfonyl, and heteroarylsulfonyl;
R$^{17b}$ and R$^{17c}$ are independently selected from the group consisting of hydrogen and halo;
R$^{18}$ is selected from the group consisting of —OC(=O)-amino and —NHC(=O)—R$^{19b}$;
R$^{19b}$ is selected from the group consisting of amino, alkoxy, alkyl, and optionally substituted aryl; and
R$^{24}$ is selected from the group consisting of hydrogen and fluoro.

26. The compound of claim 25, or a pharmaceutically acceptable salt, hydrate, or solvate thereof, wherein R$^{12}$ is optionally substituted imidazole-1-yl.

27. The compound of claim 25, or a pharmaceutically acceptable salt, hydrate, or solvate thereof, wherein R$^{12}$ is optionally substituted 1,3,4-triazole.

28. The compound of claim 25, or a pharmaceutically acceptable salt, hydrate, or solvate thereof, wherein R$^{12}$ is optionally substituted 1,2,3-triazole.

29. A pharmaceutical composition comprising the compound of claim 18, or a pharmaceutically acceptable salt, hydrate, or solvate thereof, and a pharmaceutically acceptable carrier.

* * * * *

UNITED STATES PATENT AND TRADEMARK OFFICE
CERTIFICATE OF CORRECTION

PATENT NO. : 10,899,738 B2
APPLICATION NO. : 16/098147
DATED : January 26, 2021
INVENTOR(S) : Shaomeng Wang et al.

Page 1 of 3

It is certified that error appears in the above-identified patent and that said Letters Patent is hereby corrected as shown below:

In the Claims

Column 356, Lines 5-6, Claim 8 "—CH$_2$CH$_2$—N(R$^{1e}$);CH$_2$N(R$^{1f}$)—C(=O)—;"
should be -- —CH$_2$CH$_2$—N(R$^{1e}$) —; —CH$_2$N(R$^{1f}$)—C(=O)—;" --.

Column 385, structure 202, Claim 15 " 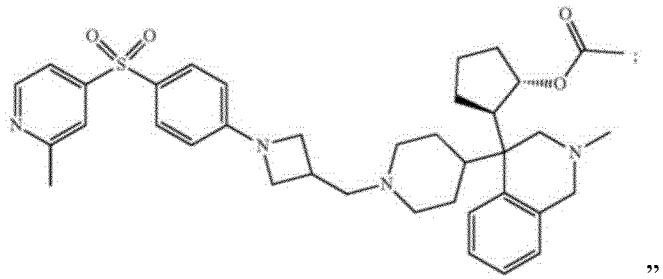 "

should be -- 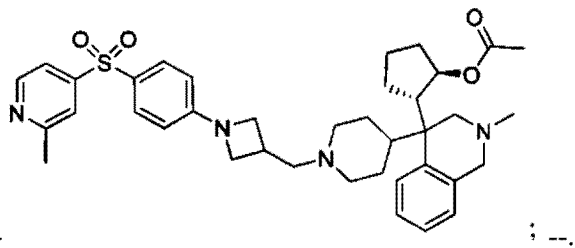 ; --.

Column 448, structure 449, Claim 16 " 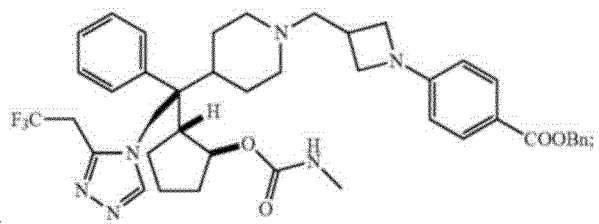 "

Signed and Sealed this
Eighteenth Day of January, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,899,738 B2 should be -- 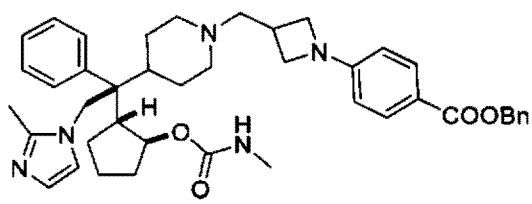 .

Column 450, in structure 460, Claim 16 " 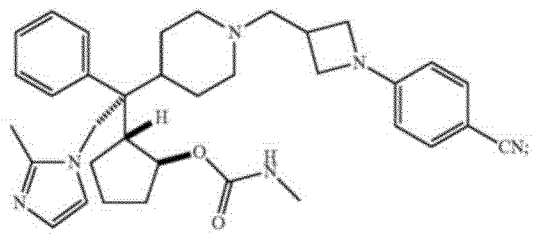 "

should be -- 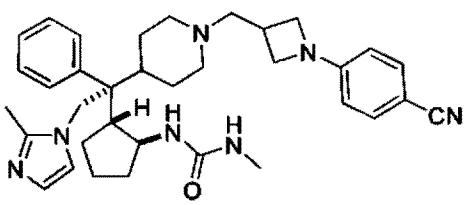 .

Column 454, structure 479, Claim 16 " 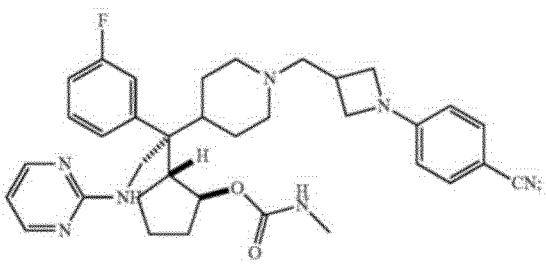 "

should be -- 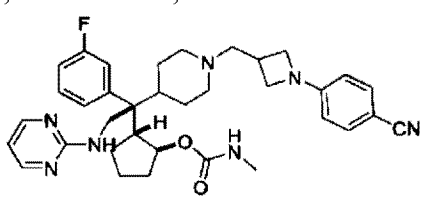 .

Column 455, structure 483, Claim 16 " 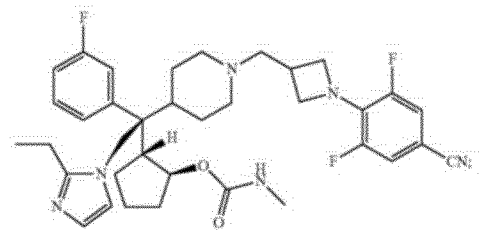 "

CERTIFICATE OF CORRECTION (continued)
U.S. Pat. No. 10,899,738 B2 should be -- 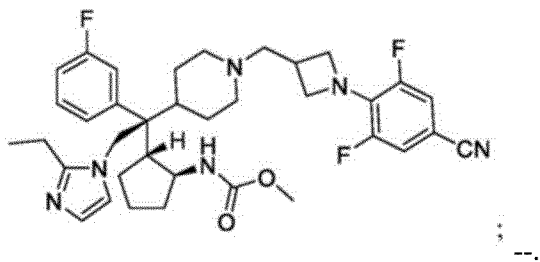 --.

Column 460, in structure 512, Claim 16 " 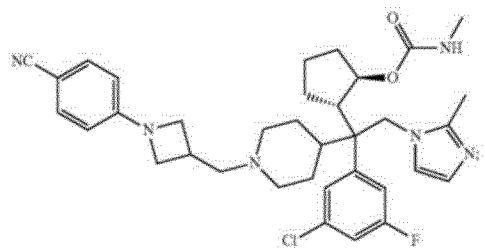 "

should be -- 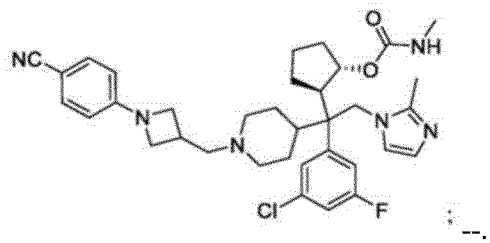 --.